(12) United States Patent
Homma et al.

(10) Patent No.: US 9,388,195 B2
(45) Date of Patent: *Jul. 12, 2016

(54) HETEROCYCLIC COMPOUND

(71) Applicant: Takeda Pharmaceutical Company Limited, Osaka-shi, Osaka (JP)

(72) Inventors: Misaki Homma, Kanagawa (JP); Toru Miyazaki, Kanagawa (JP); Yuya Oguro, Kanagawa (JP); Osamu Kurasawa, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/566,157

(22) Filed: Dec. 10, 2014

(65) Prior Publication Data

US 2015/0158882 A1    Jun. 11, 2015

Related U.S. Application Data

(63) Continuation of application No. 14/223,329, filed on Mar. 24, 2014, now Pat. No. 8,933,069, which is a continuation of application No. 13/578,959, filed as application No. PCT/JP2011/053303 on Feb. 16, 2011, now Pat. No. 8,722,660.

(30) Foreign Application Priority Data

Feb. 17, 2010    (JP) .................................. 2010-031899
Jun. 9, 2010    (JP) .................................. 2010-131950

(51) Int. Cl.
  *C07D 495/04*    (2006.01)
  *C07D 498/20*    (2006.01)
(52) U.S. Cl.
  CPC ............ *C07D 495/04* (2013.01); *C07D 498/20* (2013.01)
(58) Field of Classification Search
  CPC .......................... C07D 495/04; C07D 498/20
  See application file for complete search history.

(56) References Cited

U.S. PATENT DOCUMENTS

| | | | |
|---|---|---|---|
| 6,503,914 B1 | 1/2003 | Benish et al. | |
| 7,618,984 B2 | 11/2009 | Yamada et al. | |
| 7,989,433 B2 | 8/2011 | Washburn et al. | |
| 8,148,384 B2 | 4/2012 | Penning et al. | |
| 8,193,332 B2 | 6/2012 | Takagi et al. | |
| 8,318,184 B2 | 11/2012 | Monn et al. | |
| 2003/0096813 A1 | 5/2003 | Cao et al. | |
| 2005/0032869 A1 | 2/2005 | Berta et al. | |
| 2005/0043323 A1 | 2/2005 | Vanotti et al. | |
| 2005/0059687 A1 | 3/2005 | Makings et al. | |
| 2005/0256121 A1 | 11/2005 | Jefferson et al. | |
| 2005/0256140 A1 | 11/2005 | Luke et al. | |
| 2007/0142414 A1 | 6/2007 | Vanotti et al. | |
| 2007/0142415 A1 | 6/2007 | Vanotti et al. | |
| 2008/0102068 A1 | 5/2008 | Coleman et al. | |
| 2008/0161559 A1 | 7/2008 | Penning et al. | |
| 2008/0221107 A1 | 9/2008 | Giordanetto et al. | |
| 2009/0023735 A1 | 1/2009 | Heino et al. | |
| 2009/0028861 A1 | 1/2009 | Takagi et al. | |
| 2009/0030196 A1 | 1/2009 | Wang et al. | |
| 2009/0118276 A1 | 5/2009 | Gopalsamy et al. | |
| 2009/0298794 A1 | 12/2009 | Washburn et al. | |
| 2011/0098288 A1 | 4/2011 | Major et al. | |
| 2011/0152334 A1 | 6/2011 | Monn et al. | |
| 2011/0182881 A1 | 7/2011 | Chin et al. | |
| 2012/0040981 A1 | 2/2012 | Oguro et al. | |
| 2012/0225928 A1 | 9/2012 | Takagi et al. | |
| 2012/0238533 A1 | 9/2012 | Cleve et al. | |
| 2012/0251551 A1 | 10/2012 | Lucking et al. | |

FOREIGN PATENT DOCUMENTS

| | | |
|---|---|---|
| EP | 1 329 454 | 7/2003 |
| JP | 2002-105081 | 4/2002 |
| WO | 98/55449 | 12/1998 |
| WO | 02/26745 | 4/2002 |
| WO | 02/057271 | 7/2002 |

(Continued)

OTHER PUBLICATIONS

Vanotti, et al., "Cdc7 Kinase Inhibitors: Pyrrolopyridinones as Potential Antitumor Agents. 1. Synthesis and Structure—Activity Relationships", J. Med. Chem., 2008, vol. 51, No. 3, pp. 487-501.

(Continued)

*Primary Examiner* — Wu-Cheng Winston Shen
*Assistant Examiner* — Christopher R Stone
(74) *Attorney, Agent, or Firm* — Hamre, Schumann, Mueller & Larson, P.C.

(57) ABSTRACT

Provided is a compound useful for the prophylaxis or treatment of cancer.

The present invention relates to a compound represented by formula (I):

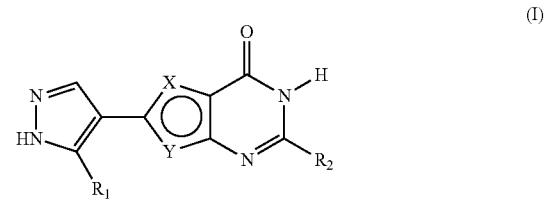

wherein each symbol in the formula is as defined in the specification, or a salt thereof or a prodrug thereof, which is useful for the prophylaxis or treatment of cancer.

16 Claims, No Drawings

(56) References Cited

FOREIGN PATENT DOCUMENTS

| WO | 02/085909 | 10/2002 |
| WO | 2004/013141 | 2/2004 |
| WO | 2004/111014 | 12/2004 |
| WO | 2005/005414 | 1/2005 |
| WO | 2005/014572 | 2/2005 |
| WO | 2005/095386 | 10/2005 |
| WO | 2005/097189 | 10/2005 |
| WO | 2006/078574 | 7/2006 |
| WO | 2007/011284 | 1/2007 |
| WO | 2007/026664 | 3/2007 |
| WO | 2007/034035 | 3/2007 |
| WO | 2007/068728 | 6/2007 |
| WO | 2007/071621 | 6/2007 |
| WO | 2007/102679 | 9/2007 |
| WO | 2008/082839 | 7/2008 |
| WO | 2008/094909 | 8/2008 |
| WO | 2009/001214 | 12/2008 |
| WO | 2009/059272 | 5/2009 |
| WO | 2009/112490 | 9/2009 |
| WO | 2009/146365 | 12/2009 |
| WO | 2009/158620 | 12/2009 |
| WO | 2010/101302 | 9/2010 |
| WO | 2010/126002 | 11/2010 |
| WO | 2011/029537 | 3/2011 |

OTHER PUBLICATIONS

Bonte, et al., "Cdc7-Dbf4 Kinase Overexpression in Multiple Cancers and Tumor Cell Lines is Correlated with p53 Inactivation", Neoplasia, vol. 10, No. 9, Sep. 2008, pp. 920-931.

SEQUENCE LISTING

<160> NUMBER OF SEQ ID NOS: 4

<210> SEQ ID NO 1
<211> LENGTH: 51
<212> TYPE: DNA
<213> ORGANISM: Artificial
<220> FEATURE:
<223> OTHER INFORMATION: synthetic DNA for His Tag

<400> SEQUENCE: 1
tatgcatcat catcatcatc acggatccca tcatcatcat catcactgag c            51

<210> SEQ ID NO 2

-continued

```
<211> LENGTH: 53
<212> TYPE: DNA
<213> ORGANISM: Artificial
<220> FEATURE:
<223> OTHER INFORMATION: synthetic DNA for His Tag

<400> SEQUENCE: 2
ggccgctcag tgatgatgat gatgatggga tccgtgatga tgatgatgat gca        53

<210> SEQ ID NO 3
<211> LENGTH: 29
<212> TYPE: DNA
<213> ORGANISM: Artificial
<220> FEATURE:
<223> OTHER INFORMATION: primer

<400> SEQUENCE: 3
cgcggatcca tggcatccag cccggccca                                   29

<210> SEQ ID NO 4
<211> LENGTH: 39
<212> TYPE: DNA
<213> ORGANISM: Artificial
<220> FEATURE:
<223> OTHER INFORMATION: primer

<400> SEQUENCE: 4
attcttatgc ggccgctcac agctcctcca ccagaggca                        39
```

HETEROCYCLIC COMPOUND

TECHNICAL FIELD

The present invention relates to heterocyclic compounds and use thereof. More particularly, the present invention relates to fused heterocyclic compounds having a strong cell division cycle 7 (Cdc7) inhibitory activity, which is useful for the prophylaxis or treatment of cancer, and the like, and use thereof.

BACKGROUND OF THE INVENTION

A characteristic of cancer is an abnormal cell proliferation with a broken control mechanism. Most cancer cells grow more rapidly than cells of normal tissues. In the cell division cycle, chromosome duplication is essential and replication of DNA in S phase is tightly regulated. Inhibition of DNA replication has been confirmed to be an effective therapy for cancer treatment and, for example, DNA replication inhibitors such as hydroxyurea (HU), gemcitabine and active metabolites of 5-fluorouracil, and the like are widely used as therapeutic agents for cancer in clinical practice.

Cdc7 is an evolutionally well-conserved serine/threonine kinase and plays an important role in the initiation of DNA replication (non-patent document 1). The kinase activity of Cdc7 is controlled by binding with its activating partner thereof. From the late stage of Gi phase to S phase, Cdc7 forms a complex with Dbf4 (also known as ASK) and phosphorylates Cdc7 substrate to control transition from the Gi phase to the S phase (non-patent document 2). Furthermore, recent studies have reported that Cdc7 plays important roles in both DNA replication and DNA damage signaling pathways (non-patent document 3).

In recent years, Cdc7 kinase is getting a lot of attentions as an attractive target in cancer treatments. Overexpression of Cdc7 is observed in clinical tumors such as breast cancer, colorectal cancer, lung cancer and the like, and many cancer cell lines (non-patent document 4). In some cancer cell lines, an increase in chromosomal copy number of an activating factor, Dbf4, is found. Interestingly, a cancer cell line and an untransformed fibroblast cell line show different responses to suppression of Cdc7 expression using siRNA. The suppression of Cdc7 expression using siRNA causes the S phase arrest in cancer cell lines and induces apoptosis, whereas in normal cells it induces the G1 phase arrest in a p53 activity-dependent manner (non-patent document 5). Furthermore, Cdc7 kinase is activated in the cells under replication stress, and apoptosis induced by hydroxyurea and etoposide increases in the Cdc7 down-regulated cells (non-patent document 6). Thus, a Cdc7 inhibitor, as a single agent or in combination with other chemotherapeutic agents, is useful for a selective cancer treatment.

Patent document 1 describes, as a compound having a Pim kinase inhibitory activity, a compound represented by the formula

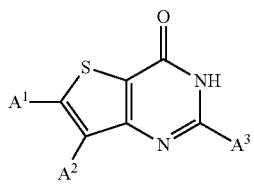

wherein $A^1$ and $A^2$ are each independently a hydrogen atom, $R^1$, $R^2$, $R^3$, $R^4$ or hydroxy and the like; $A^3$ is a hydrogen atom, $R^{12}$, $R^{13}$, $R^{14}$ or $R^{15}$ and the like; $R^1$ is phenyl and the like; $R^2$ is heteroarene and the like; $R^3$ is cycloalkyl and the like; $R^4$ and $R^{15}$ are alkyl and the like; $R^{12}$ is phenyl and the like; $R^{13}$ is heteroarene and the like; $R^{14}$ is cycloalkyl and the like; and $R^{15}$ is alkyl and the like.

Patent document 2 describes, as a compound useful for the treatment of diseases relating to Src family tyrosine kinase, a compound represented by the formula

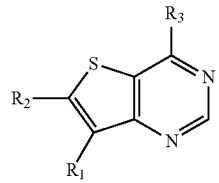

wherein $R_1$ is a hydrogen atom or alkyl and the like; $R_2$ is a hydrogen atom or alkyl and the like; and $R_3$ is a hydrogen atom, alkyl, a hydrogen bond donor or hydrazone crosslinking bound to a hydrogen bond receptor.

Patent document 3 describes, as a protein kinase inhibitor, a compound represented by the formula

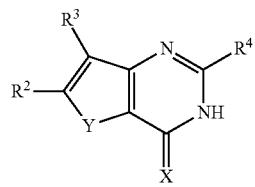

wherein X is an oxygen atom or a sulfur atom; Y is an oxygen atom, a sulfur atom or $-NR^1-$; $R^1$ is R, $CO_2R$ and the like; R is a hydrogen atom or a $C_{1-6}$ aliphatic group and the like; $R^2$ is R, $N(R)_2$ and the like; $R^3$ is R or CN and the like; and $R^4$ is R, $N(R)_2$ and the like.

Patent document 4 describes, as a compound having B-Raf kinase inhibitory activity and useful for the treatment of cancer, a compound represented by the formula

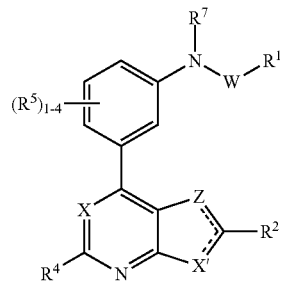

wherein $R^1$ is phenyl or a heterocycle and the like; $R^2$ is a hydrogen atom or heteroaryl and the like; $R^4$ is a hydrogen atom or $C_{1-8}$ alkyl and the like; $R^5$ is a hydrogen atom or a nitro group and the like; $R^7$ is $C_{1-8}$ alkyl and the like; X is a nitrogen atom and the like; X' is a sulfur atom or $=C(R^3)-$ and the like, and Z is a sulfur atom or $=C(R^3)-$, and only one of X' and Z is $=C(R^3)-$; and --- is a single bond or a double bond, and further describes a compound represented by the formula

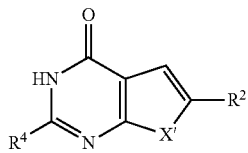

wherein each symbol is as defined above.

Patent document 5 describes, as a compound having an IKB kinase β inhibitory activity and useful for the treatment of diseases such as cancer and the like, a compound represented by the formula

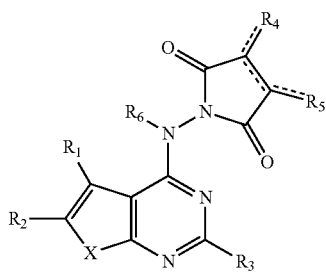

wherein X is a sulfur atom and the like; $R_1$ is a hydrogen atom or $C_{1-10}$ alkyl and the like; $R_2$ is a hydrogen atom or $C_{5-20}$ heteroaryl and the like; $R_3$ is a hydrogen atom or $C_{1-10}$ alkyl and the like; $R_4$ and $R_6$ are each a hydrogen atom or $C_{1-5}$ alkyl and the like; $R_6$ is a hydrogen atom or $C_{1-5}$ alkyl and the like; and ---- is a single bond or a double bond, and further describes a compound represented by the formula

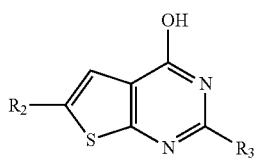

wherein each symbol is as defined above.

Patent document 6 describes, as a compound having an inhibitory activity on Tie2 receptor tyrosine kinase, and valuable for the treatment of disease states such as cancer and the like, a compound represented by the formula

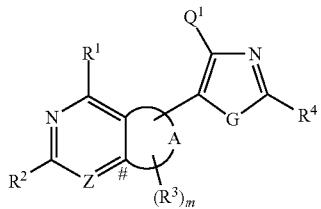

wherein A forms, together with the carbon atom bonded thereto, a fused 5-membered heteroaryl ring, wherein the aforementioned heteroaryl ring contains 1 or 2 hetero atoms selected from O, N and S; a 5-membered ring containing G is bonded to the ring formed by A at a meta-position relative to the bridgehead carbon marked with # in the formula; G is selected from 0, S and $NR^5$; Z is N and the like; $Q^1$ is aryl, heteroaryl and the like; $R^1$ is a hydrogen atom or a halogen atom and the like; $R^2$ is a hydrogen atom or amino- and the like; $R^3$ is as independently defined for $R^4$ and $R^6$, provided when $R^3$ is not hydrogen and bonded to a nitrogen atom for A, $R^3$ is not halogeno; $R^5$ is as independently defined for $R^4$ and $R^6$, provided $R^5$ is not halogeno; and $R^4$ and $R^6$ are the same or different and each is hydrogen, halogeno, trifluoromethyl, trifluoromethoxy, cyano and the like.

Patent document 7 describes, as a compound effective for the treatment of cell proliferative disorders at least partly mediated by CDC7, PKA and/or Akt, a compound represented by the formula

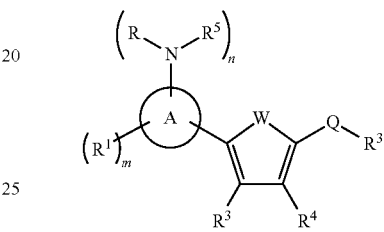

wherein ring A is nitrogen-containing heteroaryl containing 5 or 6 ring atoms, and 1-4 ring atoms are nitrogen atoms; n is an integer selected from 0 or 1; m is an integer equal to 0, 1 or 2; R is a hydrogen atom, hydroxy and the like; $R^1$ is halo or cyano and the like; $R^2$ and $R^4$ are each independently hydrogen, cycloalkyl and the like; $R^3$ is a hydrogen atom or $C_1$-$C_5$ alkyl and the like; Q is —C(X')$NR^6$— and the like, wherein X' is selected from the group consisting of oxygen and sulfur, $R^6$ is hydrogen, $C_1$-$C_3$ alkyl, $C_1$-$C_3$ substituted alkyl and the like, or $R^6$ forms, together with Q, a carbon atom to which Q is bonded, $R^4$ or a carbon atom to which $R^4$ is bonded, heterocyclyl or substituted heterocyclyl and the like.

Patent document 8 describes, as a compound effective for the prophylaxis and/or treatment of inflammatory diseases, a compound represented by the formula

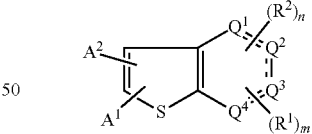

wherein $A^1$ is a nitrogen-containing heteroaryl group optionally having substituent(s); $A^2$ is an aryl group optionally having substituent(s) or a cycloalkyl group optionally having substituent(s); $R^1$ and $R^2$ are each independently a lower alkyl group optionally having substituent(s), an acyl group optionally having substituent(s), an acyloxy group optionally having substituent(s) and the like; m and n are each an integer of 0-2; $Q^1$, $Q^2$, $Q^3$ and $Q^4$ are each selected from C, CH, $CH_2$, C=O, O, N and NH, and one or two of $Q^1$ to $Q^4$ is/are N or NH; and ---- is a double bond or a single bond.

Patent document 9 describes, as a medicament having a cGMP specific phosphodiesterase inhibitory action and the like, a compound represented by the formula

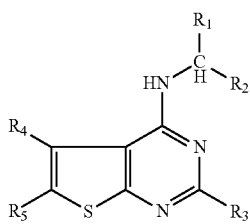

wherein $R_1$ is a hydrogen atom or a $C_{1-6}$ alkyl group; $R_2$ is an optionally substituted $C_{3-8}$ cycloalkyl group, an optionally substituted phenyl group and the like; $R_3$ is a saturated or unsaturated heterocyclic group containing 1 to 4 optionally substituted N, O or S and the like; $R_4$ is a hydrogen atom, a $C_{1-6}$ alkyl group, a hydroxy group, a $C_{1-6}$ alkoxy group, halogen, a $C_{1-6}$ haloalkyl group, a nitro group or a cyano group; and $R_5$ is a cyano group, an optionally substituted phenyl group, a saturated or unsaturated heterocyclic group containing 1 to 4 optionally substituted N, O or S and the like.

DOCUMENT LIST

Patent Documents patent document 1: US2009/0030196
patent document 2: WO02/057271
patent document 3: US2003/0096813
patent document 4: WO2009/059272
patent document 5: WO2007/102679
patent document 6: WO2004/013141
patent document 7: WO2005/095386
patent document 8: JP-A-2002-105081
patent document 9: WO02/026745

Non-Patent Documents non-patent document 1: EMBO J. 1999, 18(20), p. 5703-5713
non-patent document 2: J Cell Physiol. 2002, 190(3), p. 287-296
non-patent document 3: Oncogene. 2008, 27(24), p. 3475-3482
non-patent document 4: Neoplasia. 2008, 10(9), p. 920-931
non-patent document 5: Cancer Res. 2004, 64(19), p. 7110-7116
non-patent document 6: J Biol Chem. 2007, 282(1), p. 208-215

SUMMARY OF THE INVENTION

Problems to be Solved by the Invention

A Cdc7 inhibitor superior in the efficacy expression, pharmacokinetics, solubility, interaction with other pharmaceutical products, safety and stability is expected to show a therapeutically superior effect. Accordingly, it is an object of the present invention to provide a low-toxic compound having a Cdc7 inhibitory activity and sufficiently satisfactory as a pharmaceutical product.

Means of Solving the Problems

The present inventors have found that the following compound represented by the formula (I) has a superior Cdc7 inhibitory action, and conducted further studies and completed the present invention. Accordingly, the present invention relates to the following.

[1] A compound represented by formula:

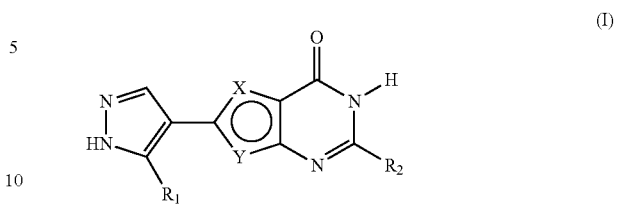

wherein
one of X and Y is a sulfur atom, and the other is CH,
$R_1$ is a $C_{1-6}$ alkyl group optionally substituted by halogen atom(s),
$R_2$ is a substituent,
or a salt thereof.
[2] The compound of the above-mentioned [1], wherein X is a sulfur atom; and
Y is CH, or a salt thereof.
[3] The compound of the above-mentioned [1], wherein $R_2$ is a hydrocarbon group optionally having substituent(s),
a heterocyclic group optionally having substituent(s), or a non-aromatic heterocyclyl-carbonyl group optionally having substituent(s), or a salt thereof.
[4] The compound of the above-mentioned [1], wherein $R_2$ is
(1) a $C_{1-6}$ alkyl group optionally substituted by 1 to 3 substituents selected from
  (a) a non-aromatic heterocyclic group optionally substituted by 1 to 3 substituents selected from
    (i) a halogen atom,
    (ii) a hydroxy group,
    (iii) a $C_{1-6}$ alkyl group optionally substituted by 1 to 3 substituents selected from
      (aa) a halogen atom,
      (bb) a hydroxy group,
      (cc) a $C_{1-6}$ alkoxy group, and
      (dd) a $C_{6-14}$ aryl group optionally substituted by 1 to 3 $C_{1-6}$ alkyl groups,
    (iv) a $C_{1-6}$ alkoxy group,
    (v) a $C_{6-14}$ aryl group optionally substituted by 1 to 3 halogen atoms,
    (vi) a $C_{6-14}$ aryloxy group,
    (vii) a $C_{1-6}$ alkoxy-carbonyl group,
    (viii) a $C_{1-6}$ alkyl-carbonyl group,
    (ix) a cyano group,
    (x) a $C_{6-14}$ arylsulfonyl group,
    (xi) a carboxy group,
    (xii) an amino group optionally mono- or di-substituted by a $C_{1-6}$ alkyl group,
    (xiii) a non-aromatic heterocyclic group optionally substituted by an oxo group, and
    (xiv) an oxo group,
  (b) a $C_{1-6}$ alkoxy group,
  (c) an amino group optionally mono- or di-substituted by substituent(s) selected from
    (i) a $C_{1-6}$ alkyl group optionally substituted by 1 to 3 substituents selected from
      (aa) a $C_{6-14}$ aryl group optionally substituted by 1 to 3 $C_{1-6}$ alkoxy groups,
      (bb) a $C_{1-6}$ alkoxy-carbonyl group,
      (cc) an aromatic heterocyclic group,
      (dd) a $C_{3-8}$ cycloalkyl group optionally substituted by an aromatic heterocyclic group, and
      (ee) a hydroxy group, (ii) a non-aromatic heterocyclic group optionally substituted by 1 to 3 $C_{7-13}$ aralkyl groups,
(iii) a $C_{6-14}$ aryl group optionally substituted by 1 to 3 $C_{1-6}$ alkoxy groups, and
(iv) a $C_{3-8}$ cycloalkyl group,
(d) a 5- or 6-membered aromatic heterocyclic group,
(e) a $C_{6-14}$ aryl group, and
(f) a $C_{3-8}$ cycloalkyl group optionally substituted by an amino group;
(2) a $C_{6-14}$ aryl group optionally substituted by 1 to 3 halogen atoms;
(3) a non-aromatic heterocyclic group optionally substituted by 1 to 3 substituents selected from
(a) a halogen atom,
(b) a $C_{1-6}$ alkyl group optionally substituted by 1 to 3 substituents selected from
(i) a hydroxy group,
(ii) a $C_{1-6}$ alkoxy-carbonyl group, and
(iii) a carbamoyl group,
(c) a $C_{6-14}$ aryloxy group,
(d) a $C_{1-6}$ alkoxy-carbonyl group,
(e) a $C_{1-6}$ alkyl-carbonyl group,
(f) a $C_{6-14}$ aryl group optionally substituted by a $C_{1-6}$ alkyl-sulfonyl group,
(g) a $C_{7-13}$ aralkyl group optionally substituted by 1 to 3 halogen atoms,
(h) a hydroxy group,
(i) a carbamoyl group, and
(j) a non-aromatic heterocyclic group;
(4) a $C_{2-6}$ alkenyl group optionally substituted by 1 to 3 $C_{6-14}$ aryl groups;
(5) a 5- or 6-membered aromatic heterocyclic group;
(6) a non-aromatic heterocyclyl-carbonyl group; or
(7) a $C_{3-8}$ cycloalkyl group optionally substituted by an amino group, or a salt thereof.
[5] The compound of the above-mentioned [1], wherein $R_2$ is
(1) a 4- to 6-membered non-aromatic heterocyclyl-$C_{1-6}$ alkyl group optionally substituted by 1 to 3 halogen atoms;
(2) a $C_{6-14}$ aryl group optionally substituted by 1 to 3 halogen atoms; or
(3) a non-aromatic heterocyclic group optionally substituted by 1 to 3 substituents selected from
(a) a halogen atom, and
(b) a $C_{1-6}$ alkyl group,
or a salt thereof.
[6] The compound of the above-mentioned [4], wherein X is a sulfur atom;
Y is CH; and
$R_1$ is a $C_{1-6}$ alkyl group,
or a salt thereof.
[7] The compound of the above-mentioned [1], wherein $R_1$ is a $C_1$-6 alkyl group, or a salt thereof.
[8] 6-(5-Methyl-1H-pyrazol-4-yl)-2-[(2S)-pyrrolidin-2-yl]thieno[3,2-d]pyrimidin-4 (3H)-one, or a salt thereof.
[9] 6-(5-Methyl-1H-pyrazol-4-yl)-2-[(2S)-piperidin-2-yl]thieno[3,2-d]pyrimidin-4 (3H)-one, or a salt thereof.
[10] 2-(7-Azabicyclo[2.2.1]hept-1-yl)-6-(5-methyl-1H-pyrazol-4-yl)thieno[3,2-d]pyrimidin-4 (3H)-one, or a salt thereof.
[11] 6-(5-Methyl-1H-pyrazol-4-yl)-2-[(2S)-1,2,3,6-tetrahydropyridin-2-yl]thieno[3,2-d]pyrimidin-4 (3H)-one, or a salt thereof.
[12] 2-[(2S)-Piperidin-2-yl]-6-[5-(trifluoromethyl)-1H-pyrazol-4-yl]thieno[3,2-d]pyrimidin-4 (3H)-one, or a salt thereof.
[13] 2-[(2S)-1-Azabicyclo[2.2.2]oct-2-yl]-6-(5-methyl-1H-pyrazol-4-yl)thieno[3,2-d]pyrimidin-4 (3H)-one, or a salt thereof.
[14] A medicament comprising the compound of the above-mentioned [1] or a salt thereof.
[15] The medicament of the above-mentioned [14], which is a cell division cycle 7 inhibitor.
[16] The medicament of the above-mentioned [14], which is an agent for the prophylaxis or treatment of cancer.
[17] A method of inhibiting a cell division cycle 7 in a mammal, which comprises administering an effective amount of the compound of the above-mentioned [1] or a salt thereof to the mammal.
[18] A method for the prophylaxis or treatment of cancer in a mammal, which comprises administering an effective amount of the compound of the above-mentioned [1] or a salt thereof to the mammal.
[19] Use of the compound of the above-mentioned [1] or a salt thereof for the production of a cell division cycle 7 inhibitor.
[20] Use of the compound of the above-mentioned [1] or a salt thereof for the production of an agent for the prophylaxis or treatment of cancer.

Effect of the Invention

The compound of the present invention is low toxic, shows a strong Cdc7 inhibitory action, and is useful since it provides an agent for the prophylaxis or treatment of cancer, a cancer growth inhibitor or a cancer metastasis suppressive agent.

DETAILED DESCRIPTION OF THE INVENTION

The definition of each symbol in the formula (I) is explained in detail in the following.

Unless otherwise specified, the "halogen atom" in the present specification means a fluorine atom, a chlorine atom, a bromine atom or an iodine atom.

Examples of the "$C_{1-6}$ alkyl (group)" in the present specification include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

Examples of the "$C_{6-14}$ aryl (group)" in the present specification include phenyl, naphthyl, anthryl, phenanthryl, acenaphthylenyl and biphenylyl.

Examples of the "$C_{2-6}$ alkenyl (group)" in the present specification include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

Examples of the "$C_{2-6}$ alkynyl (group)" in the present specification include ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl and 5-hexynyl.

Examples of the "$C_{1-6}$ alkoxy (group)" in the present specification include methoxy, ethoxy, propoxy, isopropoxy, butoxy, isobutoxy, sec-butoxy, tert-butoxy, pentoxy, isopentoxy and hexoxy.

Examples of the "$C_{1-6}$ alkyl-carbonyl (group)" in the present specification include acetyl, ethylcarbonyl, propylcarbonyl, isopropylcarbonyl, butylcarbonyl, isobutylcarbonyl, sec-butylcarbonyl, tert-butylcarbonyl, pentylcarbonyl and hexylcarbonyl.

Examples of the "$C_{1-6}$ alkoxy-carbonyl (group)" in the present specification include methoxycarbonyl, ethoxycarbonyl, propoxycarbonyl, isopropoxycarbonyl, butoxycarbonyl, isobutoxycarbonyl and tert-butoxycarbonyl.

Examples of the "$C_{3-8}$ cycloalkyl (group)" in the present specification include cyclopropyl, cyclobutyl, cyclopentyl, cyclohexyl, cycloheptyl and cyclooctyl.

Examples of the "$C_{3-8}$ cycloalkane (group)" in the present specification include cyclopropane, cyclobutane, cyclopentane, cyclohexane, cycloheptane and cyclooctane.

Examples of the "$C_{3-6}$ cycloalkane (group)" in the present specification include cyclopropane, cyclobutane, cyclopentane and cyclohexane.

Examples of the "$C_{3-8}$ cycloalkenyl (group)" in the present specification include cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl) and cyclohexenyl (e.g., 2-cyclohexen-1-yl, 3-cyclohexen-1-yl).

Examples of the "$C_{7-13}$ aralkyl (group)" in the present specification include benzyl, phenethyl and naphthylmethyl.

Examples of the "$C_{4-10}$ cycloalkadienyl (group)" in the present specification include a cyclopentadienyl group.

Examples of the "heterocyclic group" in the present specification include an aromatic heterocyclic group and a non-aromatic heterocyclic group.

Examples of the "aromatic heterocyclic group" in the present specification include a 4- to 7-membered (preferably 5- or 6-membered) monocyclic aromatic heterocyclic group containing, as a ring-constituting atom besides carbon atoms, 1 to 4 hetero atoms selected from an oxygen atom, a sulfur atom (the sulfur atom is optionally oxidized) and a nitrogen atom, and a fused aromatic heterocyclic group. Examples of the fused aromatic heterocyclic group include a group derived from a fused ring wherein a ring corresponding to the 4- to 7-membered monocyclic aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed.

Preferable examples of the aromatic heterocyclic group include
monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like; and
fused aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

Examples of the "non-aromatic heterocyclic group" in the present specification include a 4- to 7-membered (preferably 4- to 6-membered) monocyclic non-aromatic heterocyclic group containing, as a ring-constituting atom besides carbon atoms, 1 to 4 hetero atoms selected from an oxygen atom, a sulfur atom (the sulfur atom is optionally oxidized) and a nitrogen atom, and a fused non-aromatic heterocyclic group. Examples of the fused non-aromatic heterocyclic group include a group derived from a fused ring wherein a ring corresponding to the 4- to 7-membered monocyclic non-aromatic heterocyclic group and 1 or 2 rings selected from a 5- or 6-membered aromatic heterocycle containing 1 or 2 nitrogen atoms (e.g., pyrrole, imidazole, pyrazole, pyrazine, pyridine, pyrimidine), a 5-membered aromatic heterocycle containing one sulfur atom (e.g., thiophene) and a benzene ring are condensed, and a group wherein the above-mentioned group is partially saturated.

Preferable examples of the non-aromatic heterocyclic group include monocyclic non-aromatic heterocyclic groups such as oxetanyl (e.g., 2-oxetanyl, 3-oxetanyl), pyrrolidinyl (e.g., pyrrolidin-1-yl, pyrrolidin-2-yl), piperidyl (e.g., piperidino, piperidin-2-yl, piperidin-3-yl, piperidin-4-yl), morpholinyl (e.g., morpholino), thiomorpholinyl (e.g., thiomorpholino), piperazinyl (e.g., piperazin-1-yl, piperazin-2-yl, piperazin-3-yl), hexamethyleniminyl (e.g., hexamethylenimine-1-yl), oxazolidinyl (e.g., oxazolidin-2-yl, oxazolidin-5-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), 2-thioxo-1,3-oxazolidin-5-yl, pyranyl (e.g., 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxide tetrahydrothiopyranyl (e.g., 1-oxide tetrahydrothiopyran-4-yl), 1,1-dioxide tetrahydrothiopyranyl (e.g., 1,1-dioxide tetrahydrothiopyran-4-yl), tetrahydrofuryl (e.g., tetrahydrofuran-3-yl, tetrahydrofuran-2-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-1,2,3-triazol-1-yl), tetrahydrotriazolyl (e.g., 2,3,4,5-tetrahydro-1H-1,2,3-triazol-1-yl), azepanyl (e.g., azepan-3-yl, azepane-2-yl), azetidinyl (e.g., azetidin-1-yl, azetidin-2-yl), dihydropyridyl (e.g., 3,6-dihydropyridin-1-yl, 3,6-dihydropyridin-2-yl), tetrahydropyridyl (e.g., 1,2,3,6-tetrahydropyridin-2-yl), oxotetrahydropyrimidinyl (e.g., oxotetrahydropyrimidin-1-yl) and the like;
fused non-aromatic heterocyclic groups such as dihydroindolyl (e.g., 2,3-dihydro-1H-indol-1-yl), dihydroisoindolyl (e.g., 1,3-dihydro-2H-isoindol-2-yl), dihydrobenzofuryl (e.g., 2,3-dihydro-1-benzofuran-5-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), tetrahydrobenzofuryl (e.g., 4,5,6,7-tetrahydro-1-benzofuran-3-yl), chromenyl (e.g., 4H-chromen-2-yl, 2H-chromen-3-yl), dihydroquinolyl (e.g., 1,2-dihydroquinolin-4-yl), tetrahydroquinolyl (e.g., 1,2,3,4-tetrahydroquinolin-4-yl), dihydroisoquinolyl (e.g., 1,2-dihydroisoquinolin-4-yl, 3,4-dihydroisoquinolin-2-yl), tetrahydroisoquinolyl (e.g., 1,2,3,4-tetrahydroisoquinolin-4-yl), dihydrophthalazinyl (e.g., 1,4-dihydrophthalazin-4-yl), octahydroindolizinyl (e.g., octahydroindolizin-3-yl, octahydroindolizin-5-yl), octahydroquinolizinyl (e.g., octahydro-2H-quinolizin-4-yl), octahydropyrrolopyrazinyl (e.g., octahydropyrrolo[1,2-a]pyrazin-3-yl), octahydroindolyl (e.g., octahydro-1H-indol-2-yl), octahydrocyclopenta[b]pyrrolyl, decahydroisoquinolyl (e.g., decahydroisoquinolin-1-yl) and the like.

In addition, the "non-aromatic heterocyclic group" in the present specification may be bridged non-aromatic heterocyclic group, or a spiro cyclic non-aromatic heterocyclic group.

Examples of the bridged non-aromatic heterocyclic group include azabicyclo[2.1.1]hexanyl (e.g., 2-azabicyclo[2.1.1]hex-1-yl), azabicyclo[3.1.0]hexanyl (e.g., 3-azabicyclo[3.1.0]hex-2-yl, 3-azabicyclo[3.1.0]hex-3-yl, 2-azabicyclo[3.1.0]hex-3-yl, 2-azabicyclo[3.1.0]hex-1-yl), azabicyclo[2.2.1]heptanyl (e.g., 2-azabicyclo[2.2.1]hept-3-yl, 7-azabicyclo[2.2.1]hept-1-yl), azabicyclo[2.2.2]octanyl (e.g., 2-azabicyclo[2.2.2]oct-3-yl, 1-azabicyclo[2.2.2]oct-2-yl), azabicyclo[2.2.1]hexanyl (e.g., 2-azabicyclo[2.2.1]hex-1-yl), azabicyclo[4.1.0]heptanyl (e.g., 3-azabicyclo[4.1.0]hept-4-yl) and the like.

Examples of the spiro cyclic non-aromatic heterocyclic group include 1,4-dioxa-7-azaspiro[4.4]non-7-yl, tetrahydro-5H-spiro[1,3-oxazolo[3,4-a]pyrazine-1,4'-piperidin]-1'-yl, 4-azaspiro[2.4]hept-5-yl and the like.

When compound (I) has a tautomer, each isomer is also encompassed in compound (I).

For example, compound (I) wherein a partial structure of the formula

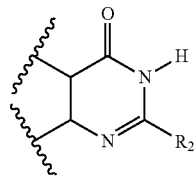

wherein each symbol is as defined above, is the formula

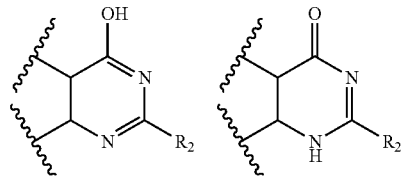

wherein each symbol is as defined above, is also encompassed in compound (I).

In addition, for example, compound (I) wherein a partial structure of the formula

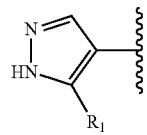

wherein each symbol is as defined above, is the formula

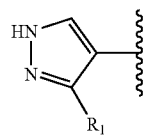

wherein each symbol is as defined above, is also encompassed in compound (I).

One of X and Y is a sulfur atom, and the other is CH.

Preferably, X is a sulfur atom, and Y is CH.

$R_1$ is a $C_{1-6}$ alkyl group optionally substituted by halogen atom(s).

$R_1$ is preferably a methyl group, an ethyl group, a trifluoromethyl group and the like.

$R_1$ is more preferably a methyl group, a trifluoromethyl group and the like.

$R_1$ is even more preferably a methyl group and the like.

$R_2$ is a substituent.

Examples of the "substituent" for $R_2$ include a hydrocarbon group optionally having substituent(s), a heterocyclic group optionally having substituent(s), and groups of (5)-(30) in the below-mentioned Substituent Group A.

Examples of the "hydrocarbon group" of the aforementioned "hydrocarbon group optionally having substituent(s)" include a $C_{1-6}$ alkyl group, a $C_{2-6}$ alkenyl group, a $C_{2-6}$ alkynyl group, a $C_{3-8}$ cycloalkyl group, a $C_{3-8}$ cycloalkenyl group, a $C_{4-10}$ cycloalkadienyl group and a $C_{6-14}$ aryl group.

The aforementioned $C_{3-8}$ cycloalkyl group, $C_{3-8}$ cycloalkenyl group and $C_{4-10}$ cycloalkadienyl group may be each condensed with a benzene ring. Examples of the fused ring group include indanyl, dihydronaphthyl, tetrahydronaphthyl and fluorenyl. In addition, a bridged hydrocarbon group such as norbornanyl, adamantyl and the like is also encompassed in the aforementioned hydrocarbon group.

The hydrocarbon group of the aforementioned "hydrocarbon group optionally having substituent(s)" is preferably a $C_{1-6}$ alkyl group (e.g., methyl, ethyl), a $C_{3-8}$ cycloalkyl group (particularly, cyclopentyl, cyclohexyl), a $C_{2-6}$ alkenyl group (e.g., ethenyl), or a $C_{6-14}$ aryl group (e.g., phenyl). Particularly preferred is a $C_{1-6}$ alkyl group (e.g., methyl, ethyl) and a $C_{6-14}$ aryl group (e.g., phenyl).

The $C_{1-6}$ alkyl group, $C_{2-6}$ alkenyl group and $C_{2-6}$ alkynyl group exemplified as the aforementioned "hydrocarbon group" may have 1 to 5 (preferably 1 to 3) substituents at substitutable position(s).

Examples of the substituent include the following Substituent Group A. When the number of the substituents is not less than 2, the respective substituents may be the same or different.

(Substituent Group A)

(1) a $C_{3-8}$ cycloalkyl group (e.g., cyclopropyl, cyclopentyl, cyclohexyl) optionally substituted by an amino group;

(2) a $C_{6-14}$ aryl group (e.g., phenyl, naphthyl) optionally substituted by 1 to 3 substituents selected from (a) a $C_{3-8}$ alkyl group optionally substituted by 1 to 3 halogen atoms, (b) a hydroxy group,
(c) a $C_{1-6}$ alkoxy group optionally substituted by 1 to 3 halogen atoms,
(d) a halogen atom (e.g., fluorine atom), and
(e) a $C_{1-6}$ alkylsulfonyl group (e.g., methylsulfonyl);
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl, pyrrolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(4) a non-aromatic heterocyclic group (e.g., tetrahydrofuryl, morpholinyl, thiomorpholinyl, piperidyl, pyrrolidinyl, piperazinyl, azetidinyl, 3,4-dihydroisoquinolyl, tetrahydroisoquinolyl, dihydropyridyl, tetrahydropyridyl, 1,3-dihydro-2H-isoindolyl, 1,4-dioxa-7-azaspiro[4.4]non-7-yl, tetrahydro-5H-spiro[1,3-oxazolo[3,4-a]pyrazine-1,4'-piperidine]-1'-yl, azabicyclo[3.1.0]hex-3-yl) optionally substituted by 1 to 3 substituents selected from
  (a) a $C_{1-6}$ alkyl group (e.g., methyl) optionally substituted by 1 to 3 substituents selected from
    (i) a halogen atom (e.g., a fluorine atom),
    (ii) a hydroxy group, and
    (iii) a $C_{6-14}$ aryl group (e.g., phenyl) optionally substituted by
      (aa) a halogen atom (e.g., a fluorine atom),
      (bb) a hydroxy group,
      (cc) a $C_{1-6}$ alkoxy group (e.g., methoxy), and
      (dd) 1 to 3 $C_{1-6}$ alkyl groups (e.g., methyl),
  (b) a hydroxy group,
  (c) a $C_{1-6}$ alkoxy group (e.g., methoxy) optionally substituted by 1 to 3 halogen atoms,
  (d) a halogen atom (e.g., a fluorine atom),
  (e) an oxo group,
  (f) a $C_{6-14}$ aryl group (e.g., phenyl) optionally substituted by 1 to 3 halogen atoms (e.g., a fluorine atom),
  (g) a $C_{6-14}$ aryloxy group (e.g., phenoxy),
  (h) a $C_{1-6}$ alkoxy-carbonyl group (e.g., ethoxycarbonyl) or a $C_{1-6}$ alkyl-carbonyl group (e.g., acetyl),
  (i) a cyano group,
  (j) a $C_{6-14}$ arylsulfonyl group (e.g., phenylsulfonyl),
  (k) a carboxy group,
  (l) an amino group optionally mono- or di-substituted by $C_{1-6}$ alkyl group(s) (e.g., methyl), and
  (m) a non-aromatic heterocyclic group (e.g., pyrrolidinyl, tetrahydropyrimidinyl) optionally substituted by an oxo group;
(5) an amino group optionally mono- or di-substituted by substituent(s) selected from
  (a) a $C_{1-6}$ alkyl group (e.g., methyl, ethyl, isopropyl) optionally substituted by 1 to 3 substituents selected from
    (i) a halogen atom,
    (ii) a $C_{6-14}$ aryl group (e.g., phenyl) optionally substituted by 1 to 3 $C_{1-6}$ alkoxy groups (e.g., methoxy),
    (iii) a $C_{1-6}$ alkoxy-carbonyl group (e.g., ethoxycarbonyl),
    (iv) an aromatic heterocyclic group (e.g., pyridyl),
    (v) a $C_{3-8}$ cycloalkyl group (e.g., cyclopropyl) optionally substituted by 1 to 3 aromatic heterocyclic groups (e.g., thienyl), and
    (vi) a hydroxy group,
  (b) a $C_{1-6}$ alkyl-carbonyl group optionally substituted by 1 to 3 halogen atoms,
  (c) a $C_{1-6}$ alkoxy-carbonyl group optionally substituted by 1 to 3 halogen atoms,
  (d) a $C_{1-6}$ alkylsulfonyl group (e.g., methylsulfonyl) optionally substituted by 1 to 3 halogen atoms,
  (e) a carbamoyl group optionally mono- or di-substituted by $C_{1-6}$ alkyl group(s) optionally substituted by 1 to 3 halogen atoms,
  (f) an aromatic heterocyclic group (e.g., thienyl, furyl, pyridyl, pyrazolyl, imidazolyl, tetrazolyl, oxazolyl, thiazolyl, oxadiazolyl, thiadiazolyl),
  (g) a non-aromatic heterocyclic group (e.g., pyrrolidinyl) optionally substituted by 1 to 3 $C_{7-13}$ aralkyl groups (e.g., benzyl),
  (h) a $C_{6-14}$ aryl group (e.g., phenyl) optionally substituted by 1 to 3 $C_{1-6}$ alkoxy groups (e.g., methoxy), and
  (i) a $C_{3-8}$ cycloalkyl group (e.g., cyclopentyl);
(6) a $C_{1-6}$ alkyl-carbonyl group optionally substituted by 1 to 3 halogen atoms;
(7) a $C_{1-6}$ alkoxy-carbonyl group (e.g., tert-butoxycarbonyl) optionally substituted by 1 to 3 substituents selected from
  (a) a halogen atom,
  (b) a $C_{1-6}$ alkoxy group,
  (c) a $C_{6-14}$ aryl group (e.g., phenyl), and
  (d) a heterocyclic group (e.g., tetrahydrofuryl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by $C_{1-6}$ alkyl group(s) optionally substituted by 1 to 3 halogen atoms; (10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group (e.g., ethoxy) optionally substituted by 1 to 3 substituents selected from
  (a) a halogen atom,
  (b) a carboxy group,
  (c) a $C_{1-6}$ alkoxy group,
  (d) a $C_{1-6}$ alkoxy-carbonyl group optionally substituted by 1 to 3 $C_{6-14}$ aryl groups (e.g., phenyl),
  (e) an amino group optionally mono- or di-substituted by substituent(s) selected from a $C_{1-6}$ alkyl group and a $C_{1-6}$ alkoxy-carbonyl group,
  (f) a heterocyclic group (e.g., tetrahydrofuryl), and
  (g) a $C_{3-8}$ cycloalkyl group;
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenoxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
  (a) a halogen atom, and
  (b) a $C_{1-6}$ alkyl group optionally substituted by 1 to 3 halogen atoms;
(20) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;

(21) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(22) a $C_{7-13}$ aralkyloxy-carbonyl group (e.g., benzyloxycarbonyl);
(23) a mercapto group;
(24) a $C_{1-6}$ alkylthio group (e.g., methylthio, ethylthio) optionally substituted by 1 to 3 substituents selected from
   (a) a halogen atom, and
   (b) a $C_{1-6}$ alkoxy-carbonyl group;
(25) a $C_{7-13}$ aralkylthio group (e.g., benzylthio);
(26) a $C_{6-14}$ arylthio group (e.g., phenylthio, naphthylthio);
(27) a cyano group;
(28) a nitro group;
(29) a halogen atom (e.g., a chlorine atom);
(30) a $C_{3-10}$ cycloalkyloxy group (e.g., cyclopropyloxy, cyclopentyloxy) optionally substituted by 1 to 3 substituents selected from
   (a) a halogen atom (e.g., a fluorine atom), and
   (b) a $C_{1-6}$ alkoxy group (e.g., methoxy); and
(31) an oxo group.

The aforementioned $C_{3-10}$ cycloalkyl group, $C_{3-10}$ cycloalkenyl group, $C_{4-10}$ cycloalkadienyl group and $C_{6-14}$ aryl group exemplified as the aforementioned "hydrocarbon group" optionally have 1 to 5 (preferably 1 to 3) substituents at substitutable positions.

Examples of the substituent include the following Substituent Group B. When the number of the substituents is not less than 2, respective substituents may be the same or different.

(Substituent Group B)
(1) the groups exemplified as the aforementioned Substituent Group A;
(2) a $C_{1-6}$ alkyl group optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group,
   (f) an amino group optionally mono- or di-substituted by $C_{1-6}$ alkyl group(s), and
   (g) a carbamoyl group;
(3) a $C_{2-6}$ alkenyl group (e.g., ethenyl, 1-propenyl) optionally substituted by 1 to 3 substituents selected from
   (a) a halogen atom,
   (b) a carboxy group,
   (c) a hydroxy group,
   (d) a $C_{1-6}$ alkoxy-carbonyl group,
   (e) a $C_{1-6}$ alkoxy group, and
   (f) an amino group optionally mono- or di-substituted by $C_{1-6}$ alkyl group(s); and
(4) a $C_{7-13}$ aralkyl group (e.g., benzyl) optionally substituted by 1 to 3 substituents selected from
   (a) a $C_{1-6}$ alkyl group optionally substituted by 1 to 3 halogen atoms,
   (b) a hydroxy group,
   (c) a $C_{1-6}$ alkoxy group, and
   (d) a halogen atom.

Preferable examples of the substituent of the aforementioned "hydrocarbon group optionally having substituent(s)" include
(1) a halogen atom (e.g., a chlorine atom),
(2) a $C_{1-6}$ alkoxy group (e.g., methoxy, ethoxy),
(3) a non-aromatic heterocyclic group (e.g., pyrrolidinyl, piperidyl, morpholinyl, thiomorphonyl, piperazinyl, azetidinyl, tetrahydroisoquinolyl, dihydropyridyl, tetrahydropyridyl, tetrahydrofuryl, 1,3-dihydro-2H-isoindolyl, 1,4-dioxa-7-azaspiro[4.4]non-7-yl, tetrahydro-5H-spiro[1,3-oxazolo[3,4-a]pyrazine-1,4'-piperidin]-1'-yl, azabicyclo[3.1.0]hex-3-yl) optionally substituted by 1 to 4 substituents selected from
   (a) a halogen atom (e.g., a fluorine atom),
   (b) a hydroxy group,
   (c) a $C_{1-6}$ alkyl group (e.g., methyl) optionally substituted by 1 to 3 substituents selected from a halogen atom (e.g., a fluorine atom) and a hydroxy group,
   (d) a $C_{1-6}$ alkoxy group (e.g., methoxy),
   (e) a $C_{6-14}$ aryl group (e.g., phenyl) optionally substituted by 1 to 3 halogen atoms (e.g., a fluorine atom),
   (f) a $C_{6-14}$ aryloxy group (e.g., phenoxy),
   (g) a $C_{1-6}$ alkoxy-carbonyl group (e.g., ethoxycarbonyl)
   (h) a $C_{1-6}$ alkyl-carbonyl group (e.g., acetyl),
   (i) a cyano group,
   (j) a $C_{6-14}$ arylsulfonyl group (e.g., phenylsulfonyl),
   (k) a carboxy group,
   (l) an amino group optionally mono- or di-substituted by $C_{1-6}$ alkyl group(s) (e.g., methyl),
   (m) a non-aromatic heterocyclic group (e.g., pyrrolidinyl, tetrahydropyrimidinyl) optionally substituted by an oxo group, and
   (n) an oxo group,
(4) an amino group optionally mono- or di-substituted by substituent(s) selected from
   (a) a $C_{1-6}$ alkyl group (e.g., methyl, ethyl, isopropyl) optionally substituted by 1 to 3 substituents selected from
      (i) a $C_{6-14}$ aryl group (e.g., phenyl) optionally substituted by a $C_{1-6}$ alkoxy group (e.g., methoxy),
      (ii) a $C_{1-6}$ alkoxy-carbonyl group (e.g., ethoxycarbonyl),
      (iii) an aromatic heterocyclic group (e.g., pyridyl), and
      (iv) a $C_{3-8}$ cycloalkyl group (e.g., cyclopropyl) optionally substituted by 1 to 3 aromatic heterocyclic groups (e.g., thienyl),
   (b) a non-aromatic heterocyclic group (e.g., pyrrolidinyl) optionally substituted by 1 to 3 $C_{7-13}$ aralkyl groups (e.g., benzyl), and
   (c) a $C_{6-14}$ aryl group (e.g., phenyl) optionally substituted by 1 to 3 $C_{1-6}$ alkoxy groups (e.g., methoxy),
(5) an oxo group, and
(6) a 5- or 6-membered aromatic heterocyclic group (e.g., imidazolyl).

More preferable examples of the substituent of the aforementioned "hydrocarbon group optionally having substituent(s)" include
(1) a halogen atom (e.g., a chlorine atom),
(2) a 4- to 6-membered non-aromatic heterocyclic group (e.g., pyrrolidinyl, piperidyl, morpholinyl, piperazinyl, azetidinyl, tetrahydrofuryl, dihydropyridyl) optionally substituted by 1 to 3 substituents selected from
   (a) a halogen atom (e.g., a fluorine atom),
   (b) a hydroxy group,
   (c) a $C_{1-6}$ alkyl group (e.g., methyl) optionally substituted by 1 to 3 substituents selected from a halogen atom (e.g., a fluorine atom) and a hydroxy group,
   (d) a $C_{1-6}$ alkoxy group (e.g., methoxy), and
   (e) a $C_{6-14}$ aryl group (e.g., phenyl), and
(3) a $C_{1-6}$ alkoxy group (e.g., ethoxy).

Particularly preferable examples of the substituent of the aforementioned "hydrocarbon group optionally having substituent(s)" include (1) a halogen atom (e.g., a chlorine atom), and
(2) a 4- to 6-membered non-aromatic heterocyclic group (e.g., pyrrolidinyl, dihydropyridyl) optionally substituted by 1 to 3 halogen atoms (e.g., a fluorine atom, a chlorine atom).

Preferable examples of the heterocyclic group of the aforementioned "heterocyclic group optionally having substituent(s)" include a non-aromatic heterocyclic group. The non-aromatic heterocyclic group may be a monocyclic non-aromatic heterocyclic group or a fused non-aromatic heterocyclic group.

Preferable examples of the aforementioned monocyclic non-aromatic heterocyclic group include a 4- to 7-membered monocyclic non-aromatic heterocyclic group (e.g., pyrrolidinyl, morpholinyl, piperidyl, piperazinyl, tetrahydrofuryl, tetrahydropyridyl, azetidinyl, azepanyl, thiazolidinyl).

The aforementioned monocyclic non-aromatic heterocyclic group is preferably a 5- or 6-membered monocyclic non-aromatic heterocyclic group (e.g., pyrrolidinyl, piperidyl, piperazinyl, morpholinyl). The 5- or 6-membered monocyclic non-aromatic heterocyclic group is more preferably pyrrolidinyl, piperidyl, morphonyl and the like. Other preferable examples of the 5- or 6-membered monocyclic non-aromatic heterocyclic group include pyrrolidinyl, piperidyl and tetrahydropyridyl.

Preferable examples of the aforementioned fused non-aromatic heterocyclic group include a 8- to 10-membered fused non-aromatic heterocyclic group (e.g., octahydroindolizinyl, octahydroquinolizinyl, octahydropyrrolopyrazinyl, octahydroindolyl, octahydrocyclopenta[b]pyrrolyl, tetrahydroquinolyl, tetrahydroisoquinolyl, decahydroisoquinolyl).

The aforementioned non-aromatic heterocyclic group may be a bridged non-aromatic heterocyclic group or a Spiro cyclic non-aromatic heterocyclic group.

Preferable examples of the bridged non-aromatic heterocyclic group include azabicyclo[3.1.0]hexanyl (e.g., 3-azabicyclo[3.1.0]hex-2-yl, 2-azabicyclo[3.1.0]hex-3-yl), azabicyclo[2.2.2]octanyl (e.g., 2-azabicyclo[2.2.2]oct-3-yl), azabicyclo[2.2.1]heptanyl (e.g., 2-azabicyclo[2.2.1]hept-3-yl, 7-azabicyclo[2.2.1]hept-1-yl), azabicyclo[2.2.1]hexanyl (e.g., 2-azabicyclo[2.2.1]hex-1-yl), azabicyclo[2.2.2]octanyl (e.g., 1-azabicyclo[2.2.2]oct-2-yl) and azabicyclo[2.1.1]hexanyl (e.g., 2-azabicyclo[2.1.1]hex-1-yl). More preferable examples of the bridged non-aromatic heterocyclic group include azabicyclo[2.2.2]octanyl (e.g., 2-azabicyclo[2.2.2]oct-3-yl, 2-azabicyclo[2.2.2]oct-2-yl), azabicyclo[2.2.1]heptanyl (e.g., 2-azabicyclo[2.2.1]hept-3-yl, 2-azabicyclo[2.2.1]hept-1-yl) and the like.

Preferable examples of the spiro cyclic non-aromatic heterocyclic group include azaspiro[2.4]heptyl(4-azaspiro[2.4]hept-5-yl) and the like.

The heterocyclic group of the aforementioned "heterocyclic group optionally having substituent(s)" is preferably a 4- to 7-membered monocyclic non-aromatic heterocyclic group (e.g., pyrrolidinyl, piperidyl, morpholinyl, azetidinyl, azepanyl), a 8- to 10-membered fused non-aromatic heterocyclic group (e.g., octahydroindolinyl) or a bridged non-aromatic heterocyclic group (e.g., azabicyclo[3.1.0]hexanyl, azabicyclo[2.2.1]heptanyl, azabicyclo[2.2.2]octanyl).

The "heterocyclic group" of the "heterocyclic group optionally having substituent(s)" for $R_2$ may have 1 to 5 (preferably 1 to 3) substituents at substitutable position(s).

Examples of such substituent include the groups exemplified as the above-mentioned Substituent Group B. When the number of the substituents is two or more, the respective substituents may be the same or different.

Preferable examples of the substituent of the aforementioned "heterocyclic group optionally having substituent(s)" include
(1) a halogen atom (e.g., a fluorine atom),
(2) a $C_{1-6}$ alkyl group (e.g., methyl, ethyl) optionally substituted by 1 to 3 substituents selected from
 (a) a hydroxy group,
 (b) a $C_{1-6}$ alkoxy-carbonyl group (e.g., ethoxycarbonyl, tert-butoxycarbonyl), and
 (c) a carbamoyl group,
(3) a $C_{1-6}$ alkoxy group (e.g., methoxy),
(4) a $C_{6-14}$ aryl group (e.g., phenyl),
(5) a $C_{6-14}$ aryloxy group (e.g., phenoxy),
(6) a $C_{7-13}$ aralkyloxy group (e.g., benzyloxy),
(7) a $C_{1-6}$ alkoxy-carbonyl group (e.g., tert-butoxycarbonyl),
(8) a $C_{6-14}$ aryl group (e.g., phenyl) optionally substituted by a $C_{1-6}$ alkylsulfonyl group (e.g., methylsulfonyl),
(9) a $C_{1-6}$ alkyl-carbonyl group (e.g., acetyl),
(10) a $C_{7-13}$ aralkyl group (e.g., benzyl) optionally substituted by 1 to 3 halogen atoms (e.g., fluorine atom),
(11) a hydroxy group,
(12) a carbamoyl group, and
(13) a non-aromatic heterocyclic group (e.g., piperidyl).

More preferable examples of the substituent of the aforementioned "heterocyclic group optionally having substituent(s)" include
(1) a halogen atom (e.g., a fluorine atom),
(2) a $C_{6-14}$ aryloxy group (e.g., phenoxy), and
(3) a $C_{1-6}$ alkyl group (e.g., methyl).

$R_2$ is preferably a hydrocarbon group optionally having substituent(s), a heterocyclic group optionally having substituent(s), or a non-aromatic heterocyclyl-carbonyl group optionally having substituent(s). Of these, a hydrocarbon group optionally having substituent(s) or a heterocyclic group optionally having substituent(s) is preferable. Examples of the aforementioned "non-aromatic heterocyclyl-carbonyl group optionally having substituent(s)" include the group of (21) in the aforementioned Substituent Group A.

$R_2$ is more preferably a $C_{1-6}$ alkyl group optionally having substituent(s) (particularly, methyl, ethyl, isopropyl, isobutyl), a $C_{6-14}$ aryl group (particularly, phenyl) optionally having substituent(s), or a 5- or 6-membered non-aromatic heterocyclic group (particularly, pyrrolidinyl, morpholinyl) optionally having substituent(s). Of these,
(1) a 4- to 6-membered non-aromatic heterocyclyl-$C_{1-6}$ alkyl group optionally substituted by 1 to 3 halogen atoms;
(2) a $C_{6-14}$ aryl group optionally substituted by 1 to 3 halogen atoms; or
(3) a non-aromatic heterocyclic group optionally substituted by 1 to 3 substituents selected from
 (a) a halogen atom, and
 (b) a $C_{1-6}$ alkyl group
is preferable.

Specifically preferable examples of $R_2$ include
(1) a $C_{1-6}$ alkyl group (particularly, methyl, ethyl, isopropyl, isobutyl) optionally having substituent(s),
(2) a $C_{6-14}$ aryl group (particularly, phenyl) optionally having substituent(s),
(3) a non-aromatic heterocyclic group (particularly, pyrrolidinyl, morpholinyl, piperazinyl, piperidyl, tetrahydrofuryl, tetrahydropyridyl, tetrahydroquinolyl, tetrahydroisoquinolyl, decahydroisoquinolyl, azetidinyl, azepanyl, octahydropyrrolopyrazinyl, octahydroindolyl, octahydrocyclopenta[b]pyrrolyl, thiazolidinyl, azabicyclo[3.1.0]hexanyl, azabicyclo[2.1.1]hexanyl, azabicyclo[2.2.1]heptanyl, azabicyclo[4.1.0]heptanyl, azabicyclo[2.2.2]octanyl, azaspiro[2.4]heptyl) optionally having substituent(s),
(4) a $C_{2-6}$ alkenyl group (particularly, ethenyl) optionally having substituent(s),
(5) a 5- or 6-membered aromatic heterocyclic group (particularly, pyridyl, pyrazolyl, thiazolyl) optionally having substituent(s),
(6) a non-aromatic heterocyclyl-carbonyl group (particularly, pyrrolidinylcarbonyl) optionally having substituent(s), and
(7) a $C_{3-8}$ cycloalkyl group (particularly, cyclopentyl, cyclohexyl) optionally having substituent(s).

More specifically preferable examples of $R_2$ include
(1) a $C_{1-6}$ alkyl group (particularly, methyl, ethyl, isopropyl, isobutyl) optionally substituted by 1 to 3 substituents selected from
 (a) a non-aromatic heterocyclic group (particularly, pyrrolidinyl, piperidyl, morpholinyl, thiomorphonyl, piperazinyl, azetidinyl, tetrahydroisoquinolyl, tetrahydropyridyl, 1,3-dihydro-2H-isoindolyl, 1,4-dioxa-7-azaspiro[4.4]non-7-yl, tetrahydro-5H-spiro[1,3-oxazolo[3,4-a]pyrazine-1,4'-piperidine]-1'-yl, azabicyclo[3.1.0]hexanyl) optionally substituted by 1 to 3 substituents selected from
  (i) a halogen atom (particularly, a fluorine atom),
  (ii) a hydroxy group,
  (iii) a $C_{1-6}$ alkyl group (particularly, methyl) optionally substituted by 1 to 3 substituents selected from
   (aa) a halogen atom (particularly, a fluorine atom),
   (bb) a hydroxy group,
   (cc) a $C_{1-6}$ alkoxy group (particularly, methoxy), and
   (dd) a $C_{6-14}$ aryl group (particularly, phenyl) optionally substituted by 1 to 3 $C_{1-6}$ alkyl groups (particularly, methyl),
  (iv) a $C_{1-6}$ alkoxy group (particularly, methoxy),
  (v) a $C_{6-14}$ aryl group (particularly, phenyl) optionally substituted by 1 to 3 halogen atoms (particularly, a fluorine atom),
  (vi) a $C_{6-14}$ aryloxy group (particularly, phenoxy),
  (vii) a $C_{1-6}$ alkoxy-carbonyl group (particularly, ethoxycarbonyl),
  (viii) a $C_{1-6}$ alkyl-carbonyl group (particularly, acetyl),
  (ix) a cyano group,
  (x) a $C_{6-14}$ arylsulfonyl group (particularly, phenylsulfonyl),
  (xi) a carboxy group,
  (xii) an amino group optionally mono- or di-substituted by $C_{1-6}$ alkyl group(s) (particularly, methyl),
  (xiii) a non-aromatic heterocyclic group (particularly, pyrrolidinyl, tetrahydropyrimidinyl) optionally substituted by an oxo group, and
  (xiv) an oxo group,
 (b) a $C_{1-6}$ alkoxy group (particularly, ethoxy),
 (c) an amino group optionally mono- or di-substituted by substituent(s) selected from
  (i) a $C_{1-6}$ alkyl group (particularly, methyl, ethyl, isopropyl) optionally substituted by 1 to 3 substituents selected from
   (aa) a $C_{6-14}$ aryl group (particularly, phenyl) optionally substituted by 1 to 3 $C_{1-6}$ alkoxy groups (particularly, methoxy),
   (bb) a $C_{1-6}$ alkoxy-carbonyl group (particularly, ethoxycarbonyl),
   (cc) an aromatic heterocyclic group (particularly, pyridyl),
   (dd) a $C_{3-8}$ cycloalkyl group (particularly, cyclopropyl) optionally substituted by an aromatic heterocyclic group (particularly, thienyl), and
   (ee) a hydroxy group,
  (ii) a non-aromatic heterocyclic group (particularly, pyrrolidinyl) optionally substituted by 1 to 3 $C_{7-13}$ aralkyl groups (particularly, benzyl),
  (iii) a $C_{6-14}$ aryl group (particularly, phenyl) optionally substituted by 1 to 3 $C_{1-6}$ alkoxy groups (particularly, methoxy), and
  (iv) a $C_{3-8}$ cycloalkyl group (particularly, cyclopentyl),
 (d) a 5- or 6-membered aromatic heterocyclic group (particularly, imidazolyl, pyrrolyl),
 (e) a $C_{6-14}$ aryl group (particularly, phenyl), and
 (f) a $C_{3-8}$ cycloalkyl group (particularly, cyclopropyl, cyclopentyl, cyclohexyl) optionally substituted by an amino group,
(2) a $C_{6-14}$ aryl group (particularly, phenyl) optionally substituted by 1 to 3 halogen atoms (particularly, a chlorine atom),
(3) a non-aromatic heterocyclic group (particularly, pyrrolidinyl, morpholinyl, piperazinyl, piperidyl, tetrahydrofuryl, tetrahydropyridyl, tetrahydroquinolyl, tetrahydroisoquinolyl, decahydroisoquinolyl, azetidinyl, azepanyl, octahydropyrrolopyrazinyl, octahydroindolyl, octahydrocyclopenta[b]pyrrolyl, thiazolidinyl, azabicyclo[3.1.0]hexanyl, azabicyclo[2.1.1]hexanyl, azabicyclo[2.2.1]heptanyl, azabicyclo[4.1.0]heptanyl, azabicyclo[2.2.2]octanyl, azaspiro[2.4]heptyl) optionally substituted by 1 to 3 substituents selected from
 (a) a halogen atom (particularly, a fluorine atom),
 (b) a $C_{1-6}$ alkyl group (particularly, methyl, propyl) optionally substituted by 1 to 3 substituents selected from
  (i) a hydroxy group,
  (ii) a $C_{1-6}$ alkoxy-carbonyl group (particularly, ethoxycarbonyl, tert-butoxycarbonyl), and
  (iii) a carbamoyl group,
 (c) a $C_{6-14}$ aryloxy group (particularly, phenoxy),
 (d) a $C_{1-6}$ alkoxy-carbonyl group (particularly, tert-butoxycarbonyl),
 (e) a $C_{1-6}$ alkyl-carbonyl group (particularly, acetyl),
 (f) a $C_{6-14}$ aryl group (particularly, phenyl) optionally substituted by a $C_{1-6}$ alkylsulfonyl group (particularly, methylsulfonyl),
 (g) a $C_{7-13}$ aralkyl group (particularly, benzyl) optionally substituted by 1 to 3 halogen atoms (particularly, a fluorine atom),
 (h) a hydroxy group,
 (i) a carbamoyl group, and
 (j) a non-aromatic heterocyclic group (particularly, piperidyl),
(4) a $C_{2-6}$ alkenyl group (particularly, ethenyl) optionally substituted by 1 to 3 $C_{6-14}$ aryl groups (particularly, phenyl),
(5) a 5- or 6-membered aromatic heterocyclic group (particularly, pyridyl, pyrazolyl, thiazolyl),
(6) a non-aromatic heterocyclyl-carbonyl group (particularly, pyrrolidinylcarbonyl), and
(7) a $C_{3-8}$ cycloalkyl group (particularly, cyclopentyl, cyclohexyl) optionally substituted by an amino group.

More specifically preferable examples of $R_2$ include
(1) an aminomethyl group optionally substituted by 1 or 2 $C_{1-6}$ alkyl groups (particularly, a methyl group),
(2) a 5- or 6-membered non-aromatic heterocyclyl-methyl group (particularly, pyrrolidinylmethyl, dihydropyridylmethyl) optionally substituted by a $C_{1-6}$ alkyl group (particularly, a methyl group), or (3) a non-aromatic heterocyclic group (particularly, pyrrolidinyl, morpholinyl, piperidyl, 1,2,3,6-tetrahydropyridyl, azepanyl, 3-azabicyclo[3.1.0]hexanyl, 7-azabicyclo[2.2.1]heptanyl, 2-azabicyclo[2.2.1]heptanyl, 1-azabicyclo[2.2.2]octanyl, 2-azabicyclo[2.2.2]octanyl) optionally substituted by 1 to 3 halogen atoms (particularly, a fluorine atom).

Other specifically preferable examples of $R_2$ include
(1) a 5- or 6-membered non-aromatic heterocyclyl-methyl group (particularly, pyrrolidinylmethyl), or
(2) a non-aromatic heterocyclic group (particularly, pyrrolidinyl, piperidinyl, 1,2,3,6-tetrahydropyridyl, 7-azabicyclo[2.2.1]heptanyl, 2-azabicyclo[2.2.1]heptanyl, 1-azabicyclo[2.2.2]octanyl) optionally substituted by 1 to 3 halogen atoms (particularly, a fluorine atom).

Other more specifically preferable examples of $R_2$ include a non-aromatic heterocyclic group (particularly, pyrrolidinyl, morpholinyl, piperidyl, 1,2,3,6-tetrahydropyridyl, azepanyl, 3-azabicyclo[3.1.0]hexanyl, 7-azabicyclo[2.2.1]heptanyl, 2-azabicyclo[2.2.1]heptanyl, 1-azabicyclo[2.2.2]octanyl, 2-azabicyclo[2.2.2]octanyl) optionally substituted by 1 to 3 halogen atoms (particularly, a fluorine atom). Of these, pyrrolidin-2-yl, piperidin-2-yl, 1,2,3,6-tetrahydropyridin-2-yl, 7-azabicyclo[2.2.1]hept-1-yl, 2-azabicyclo[2.2.1]hept-3-yl, or 1-azabicyclo[2.2.2]oct-2-yl is preferable, each of which is optionally substituted by 1 to 3 halogen atoms (particularly, a fluorine atom).

Preferable examples of compound (I) include the following compounds.

[Compound A-2]
A compound wherein
X is a sulfur atom;
Y is CH;
$R_1$ is a $C_{1-6}$ alkyl group (particularly, methyl, ethyl, isopropyl, isobutyl) optionally substituted by halogen atom(s); and $R_2$ is
(1) a $C_{1-6}$ alkyl group (particularly, methyl, ethyl) optionally having substituent(s),
(2) a $C_{6-14}$ aryl group (particularly, phenyl) optionally having substituent(s),
(3) a non-aromatic heterocyclic group (particularly, pyrrolidinyl, morpholinyl, piperazinyl, piperidyl, tetrahydrofuryl, tetrahydropyridyl, tetrahydroquinolyl, tetrahydroisoquinolyl, decahydroisoquinolyl, azetidinyl, azepanyl, octahydropyrrolopyrazinyl, octahydroindolyl, octahydrocyclopenta[b]pyrrolyl, thiazolidinyl, azabicyclo[3.1.0]hexanyl, azabicyclo[2.1.1]hexanyl, azabicyclo[2.2.1]heptanyl, azabicyclo[4.1.0]heptanyl, azabicyclo[2.2.2]octanyl, azaspiro[2.4]heptyl) optionally having substituent(s),
(4) a $C_{2-6}$ alkenyl group (particularly, ethenyl) optionally having substituent(s),
(5) a 5- or 6-membered aromatic heterocyclic group (particularly, pyridyl, pyrazolyl, thiazolyl) optionally having substituent(s),
(6) a non-aromatic heterocyclyl-carbonyl group (particularly, pyrrolidinylcarbonyl) optionally having substituent(s), or
(7) a $C_{3-8}$ cycloalkyl group (particularly, cyclopentyl, cyclohexyl) optionally having substituent(s),
or a salt thereof.

[Compound A-1]
A compound wherein
X is a sulfur atom;
Y is CH;
$R_1$ is a $C_{1-6}$ alkyl group (particularly, methyl); and $R_2$ is
(1) a $C_{1-6}$ alkyl group (particularly, methyl, ethyl) optionally having substituent(s),
(2) a $C_{6-14}$ aryl group (particularly, phenyl) optionally having substituent(s),
(3) a non-aromatic heterocyclic group (particularly, pyrrolidinyl, morpholinyl, piperidyl, tetrahydrofuryl, azetidinyl, azepanyl, octahydropyrrolopyrazinyl, octahydroindolyl, thiazolidinyl, azabicyclo[3.1.0]hex-2-yl, azabicyclo[2.2.1]hept-3-yl, azabicyclo[2.2.2]oct-3-yl) optionally having substituent(s),
(4) a $C_{2-6}$ alkenyl group (particularly, ethenyl) optionally having substituent(s), or
(5) a 5- or 6-membered aromatic heterocyclic group (particularly, pyridyl) optionally having substituent(s),
or a salt thereof.

[Compound A]
A compound wherein
X is a sulfur atom;
Y is CH;
$R_1$ is a $C_{1-6}$ alkyl group (particularly, methyl); and
$R_2$ is a $C_{1-6}$ alkyl group (particularly, methyl, ethyl) optionally having substituent(s), a $C_{6-14}$ aryl group (particularly, phenyl) optionally having substituent(s), or a 5- or 6-membered non-aromatic heterocyclic group (particularly, pyrrolidinyl, morpholinyl) optionally having substituent(s),
or a salt thereof.

[Compound B-2]
A compound wherein
X is a sulfur atom;
Y is CH;
$R_1$ is a $C_{1-6}$ alkyl group (particularly, methyl, ethyl) optionally substituted by halogen atom(s) (particularly, a fluorine atom); and
$R_2$ is
(1) a $C_{1-6}$ alkyl group (particularly, methyl, ethyl, isopropyl, isobutyl) optionally substituted by 1 to 3 substituents selected from
  (a) a non-aromatic heterocyclic group (particularly, pyrrolidinyl, piperidyl, morpholinyl, thiomorphonyl, piperazinyl, azetidinyl, tetrahydroisoquinolyl, tetrahydropyridyl, 1,3-dihydro-2H-isoindolyl, 1,4-dioxa-7-azaspiro[4.4]non-7-yl, tetrahydro-5H-spiro[1,3-oxazolo[3,4-a]pyrazine-1,4'-piperidine]-1'-yl, azabicyclo[3.1.0]hexanyl) optionally substituted by 1 to 3 substituents selected from
    (i) a halogen atom (particularly, a fluorine atom),
    (ii) a hydroxy group,
    (iii) a $C_{1-6}$ alkyl group (particularly, methyl) optionally substituted by 1 to 3 substituents selected from
      (aa) a halogen atom (particularly, a fluorine atom),
      (bb) a hydroxy group,
      (cc) a $C_{1-6}$ alkoxy group (particularly, methoxy), and
      (dd) a $C_{6-14}$ aryl group (particularly, phenyl) optionally substituted by 1 to 3 $C_{1-6}$ alkyl groups (particularly, methyl),
    (iv) a $C_{1-6}$ alkoxy group (particularly, methoxy),
    (v) a $C_{6-14}$ aryl group (particularly, phenyl) optionally substituted by 1 to 3 halogen atoms (particularly, fluorine atom),
    (vi) a $C_{6-14}$ aryloxy group (particularly, phenoxy),
    (vii) a $C_{1-6}$ alkoxy-carbonyl group (particularly, ethoxycarbonyl),
    (viii) a $C_{1-6}$ alkyl-carbonyl group (particularly, acetyl),
    (ix) a cyano group,
    (x) a $C_{6-14}$ arylsulfonyl group (particularly, phenylsulfonyl),
    (xi) a carboxy group, (xii) an amino group optionally mono- or di-substituted by $C_{1-6}$ alkyl group(s) (particularly, methyl), (xiii) a non-aromatic heterocyclic group (particularly, pyrrolidinyl, tetrahydropyrimidinyl) optionally substituted by an oxo group, and (xiv) an oxo group, (b) a $C_{1-6}$ alkoxy group (particularly, ethoxy), (c) an amino group optionally mono- or di-substituted by substituent(s) selected from (i) a $C_{1-6}$ alkyl group (particularly, methyl, ethyl, isopropyl) optionally substituted by 1 to 3 substituents selected from (aa) a $C_{6-14}$ aryl group (particularly, phenyl) optionally substituted by 1 to 3 $C_{1-6}$ alkoxy groups (particularly, methoxy), (bb) a $C_{1-6}$ alkoxy-carbonyl group (particularly, ethoxycarbonyl), (cc) an aromatic heterocyclic group (particularly, pyridyl), (dd) a $C_{3-8}$ cycloalkyl group (particularly, cyclopropyl) optionally substituted by an aromatic heterocyclic group (particularly, thienyl), and (ee) a hydroxy group, (ii) a non-aromatic heterocyclic group (particularly, pyrrolidinyl) optionally substituted by 1 to 3 $C_{7-13}$ aralkyl groups (particularly, benzyl), (iii) a $C_{6-14}$ aryl group (particularly, phenyl) optionally substituted by 1 to 3 $C_{1-6}$ alkoxy groups (particularly, methoxy), and (iv) a $C_{3-8}$ cycloalkyl group (particularly, cyclopentyl), (d) a 5- or 6-membered aromatic heterocyclic group (particularly, imidazolyl, pyrrolyl), (e) a $C_{6-14}$ aryl group (particularly, phenyl), and (f) a $C_{3-8}$ cycloalkyl group (particularly, cyclopropyl, cyclopentyl, cyclohexyl) optionally substituted by an amino group, (2) a $C_{6-14}$ aryl group (particularly, phenyl) optionally substituted by 1 to 3 halogen atoms (particularly, a chlorine atom), (3) a non-aromatic heterocyclic group (particularly, pyrrolidinyl, morpholinyl, piperazinyl, piperidyl, tetrahydrofuryl, tetrahydropyridyl, tetrahydroquinolyl, tetrahydroisoquinolyl, decahydroisoquinolyl, azetidinyl, azepanyl, octahydropyrrolopyrazinyl, octahydroindolyl, octahydrocyclopenta[b]pyrrolyl, thiazolidinyl, azabicyclo[3.1.0]hexanyl, azabicyclo[2.1.1]hexanyl, azabicyclo[2.2.1]heptanyl, azabicyclo[4.1.0]heptanyl, azabicyclo[2.2.2]octanyl, azaspiro[2.4]heptyl) optionally substituted by 1 to 3 substituents selected from (a) a halogen atom (particularly, a fluorine atom), (b) a $C_{1-6}$ alkyl group (particularly, methyl, propyl) optionally substituted by 1 to 3 substituents selected from (i) a hydroxy group, (ii) a $C_{1-6}$ alkoxy-carbonyl group (particularly, ethoxycarbonyl, tert-butoxycarbonyl), and (iii) a carbamoyl group, (c) a $C_{6-14}$ aryloxy group (particularly, phenoxy), (d) a $C_{1-6}$ alkoxy-carbonyl group (particularly, tert-butoxycarbonyl), (e) a $C_{1-6}$ alkyl-carbonyl group (particularly, acetyl), (f) a $C_{6-14}$ aryl group (particularly, phenyl) optionally substituted by a $C_{1-6}$ alkylsulfonyl group (particularly, methylsulfonyl), (g) a $C_{7-13}$ aralkyl group (particularly, benzyl) optionally substituted by 1 to 3 halogen atoms (particularly, a fluorine atom), (h) a hydroxy group, (i) a carbamoyl group, and (j) a non-aromatic heterocyclic group (particularly, piperidyl), (4) a $C_{2-6}$ alkenyl group (particularly, ethenyl) optionally substituted by 1 to 3 $C_{6-14}$ aryl groups (particularly, phenyl), (5) a 5- or 6-membered aromatic heterocyclic group (particularly, pyridyl, pyrazolyl, thiazolyl), (6) a non-aromatic heterocyclyl-carbonyl group (particularly, pyrrolidinylcarbonyl), or (7) a $C_{3-8}$ cycloalkyl group (particularly, cyclopentyl, cyclohexyl) optionally substituted by an amino group, or a salt thereof.

[Compound B-1]

A compound wherein

X is a sulfur atom;

Y is CH;

$R_1$ is a $C_{1-6}$ alkyl group (particularly, methyl); and $R_2$ is (1) a $C_{1-6}$ alkyl group (particularly, methyl, ethyl) optionally substituted by 1 to 3 substituents selected from (a) a non-aromatic heterocyclic group (particularly, pyrrolidinyl, piperidyl, morpholinyl, thiomorphonyl, piperazinyl, azetidinyl, 3,4-dihydroisoquinolyl, dihydropyridyl, 1,3-dihydro-2H-isoindolyl, 1,4-dioxa-7-azaspiro[4.4]non-7-yl, tetrahydro-5H-spiro[1,3-oxazolo[3,4-a]pyrazine-1,4'-piperidine]-1'-yl, azabicyclo[3.1.0]hex-3-yl) optionally substituted by 1 to 3 substituents selected from (i) a halogen atom (particularly, a fluorine atom), (ii) a hydroxy group, (iii) a $C_{1-6}$ alkyl group (particularly, methyl) optionally substituted by 1 to 3 substituents selected from (aa) a halogen atom (particularly, a fluorine atom), (bb) a hydroxy group, (cc) $C_{1-6}$ alkoxy (particularly, methoxy), and (dd) a $C_{6-14}$ aryl group (particularly, phenyl) optionally substituted by 1 to 3 $C_{1-6}$ alkyl groups (particularly, methyl), (iv) a $C_{1-6}$ alkoxy group (particularly, methoxy), (v) a $C_{6-14}$ aryl group (particularly, phenyl) optionally substituted by 1 to 3 halogen atoms (particularly, a fluorine atom), (vi) a $C_{6-14}$ aryloxy group (particularly, phenoxy), (vii) a $C_{1-6}$ alkoxy-carbonyl group (particularly, ethoxycarbonyl) or a $C_{1-6}$ alkyl-carbonyl group (particularly, acetyl), (viii) a cyano group, (ix) a $C_{6-14}$ arylsulfonyl group (particularly, phenylsulfonyl), (x) a carboxy group, (xi) an amino group optionally mono- or di-substituted by $C_{1-6}$ alkyl group(s) (particularly, methyl), (xii) a non-aromatic heterocyclic group (particularly, pyrrolidinyl, tetrahydropyrimidinyl) optionally substituted by an oxo group, and (xiii) an oxo group, (b) a $C_{1-6}$ alkoxy group (particularly, ethoxy), (c) an amino group optionally mono- or di-substituted by substituent(s) selected from (i) a $C_{1-6}$ alkyl group (particularly, methyl, ethyl, isopropyl) optionally substituted by 1 to 3 substituents selected from (aa) a $C_{6-14}$ aryl group (particularly, phenyl) optionally substituted by 1 to 3 $C_{1-6}$ alkoxy groups (particularly, methoxy), (bb) a $C_{1-6}$ alkoxy-carbonyl group (particularly, ethoxycarbonyl),
(cc) an aromatic heterocyclic group (particularly, pyridyl), and
(dd) a $C_{3-8}$ cycloalkyl group (particularly, cyclopropyl) optionally substituted by an aromatic heterocyclic group (particularly, thienyl),
(ii) a non-aromatic heterocyclic group (particularly, pyrrolidinyl) optionally substituted by 1 to 3 $C_{7-13}$ aralkyl groups (particularly, benzyl), and
(iii) a $C_{6-14}$ aryl group (particularly, phenyl) optionally substituted by 1 to 3 $C_{1-6}$ alkoxy groups (particularly, methoxy),
(d) a 5- or 6-membered aromatic heterocyclic group (particularly, imidazolyl), and
(e) a $C_{6-14}$ aryl group (particularly, phenyl);
(2) a $C_{6-14}$ aryl group (particularly, phenyl) optionally substituted by 1 to 3 halogen atoms (particularly, a chlorine atom);
(3) a non-aromatic heterocyclic group (particularly, pyrrolidinyl, morpholinyl, piperidyl, tetrahydrofuryl, azetidinyl, azepanyl, octahydropyrrolopyrazinyl, octahydroindolyl, thiazolidinyl, azabicyclo[3.1.0]hex-2-yl, azabicyclo[2.2.1]hept-3-yl, azabicyclo[2.2.2]oct-3-yl) optionally substituted by 1 to 3 substituents selected from
(a) a halogen atom (particularly, a fluorine atom),
(b) a $C_{1-6}$ alkyl group (particularly, methyl),
(c) a $C_{6-14}$ aryloxy group (particularly, phenoxy),
(d) a $C_{1-6}$ alkoxy-carbonyl group (particularly, tert-butoxycarbonyl),
(e) a $C_{6-14}$ aryl group (particularly, phenyl) optionally substituted by a $C_{1-6}$ alkylsulfonyl group (particularly, methylsulfonyl), and
(f) a $C_{7-13}$ aralkyl group (particularly, benzyl) optionally substituted by 1 to 3 halogen atoms (particularly, a fluorine atom);
(4) a $C_{2-6}$ alkenyl group (particularly, ethenyl) optionally substituted by 1 to 3 $C_{6-14}$ aryl groups (particularly, phenyl); or
(5) a 5- or 6-membered aromatic heterocyclic group (particularly, pyridyl),
or a salt thereof.

[Compound B]
A compound wherein
X is a sulfur atom;
Y is CH;
$R_1$ is a $C_{1-6}$ alkyl group (particularly, methyl); and
$R_2$ is
(1) a $C_{1-6}$ alkyl group (particularly, methyl, ethyl) optionally substituted by 1 to 3 substituents selected from
(a) a 4- to 6-membered non-aromatic heterocyclic group (particularly, pyrrolidinyl, piperidyl, morpholinyl, piperazinyl, azetidinyl, tetrahydrofuryl) optionally substituted by 1 to 3 substituents selected from
(i) a halogen atom (particularly, a fluorine atom),
(ii) a hydroxy group,
(iii) a $C_{1-6}$ alkyl group (e.g., methyl) optionally substituted by 1 to 3 substituents selected from a halogen atom (particularly, a fluorine atom) and a hydroxy group,
(iv) a $C_{1-6}$ alkoxy group (particularly, methoxy), and
(v) a $C_{6-14}$ aryl group (particularly, phenyl), and
(b) a $C_{1-6}$ alkoxy group (particularly, ethoxy),
(2) a $C_{6-14}$ aryl group (particularly, phenyl) optionally substituted by 1 to 3 halogen atoms (particularly, a chlorine atom), or
(3) a 5- or 6-membered non-aromatic heterocyclic group (particularly, pyrrolidinyl, morpholinyl) optionally substituted by 1 to 3 substituents selected from
(a) a halogen atom (particularly, a fluorine atom), and
(b) a $C_{6-14}$ aryloxy group (particularly, phenoxy),
or a salt thereof.

[Compound C-1]
A compound wherein
X is a sulfur atom;
Y is CH;
$R_1$ is a $C_{1-6}$ alkyl group (particularly, methyl); and
$R_2$ is
(1) a 4- to 6-membered non-aromatic heterocyclyl-$C_{1-6}$ alkyl group (particularly, pyrrolidinylmethyl, dihydropyridylmethyl) optionally substituted by 1 to 3 halogen atoms (particularly, a fluorine atom),
(2) a $C_{6-14}$ aryl group (particularly, phenyl) optionally substituted by 1 to 3 halogen atoms (particularly, a chlorine atom), or
(3) a non-aromatic heterocyclic group (particularly, pyrrolidinyl, morpholinyl, piperidyl, azetidinyl, azepanyl, octahydroindolyl, azabicyclo[3.1.0]hex-2-yl, azabicyclo[2.2.1]hept-3-yl, azabicyclo[2.2.2]oct-3-yl) optionally substituted by 1 to 3 substituents selected from
(a) a halogen atom (particularly, a fluorine atom), and
(b) a $C_{1-6}$ alkyl group (particularly, methyl),
or a salt thereof.

[Compound D-2]
A compound wherein
X is a sulfur atom;
Y is CH;
$R_1$ is a $C_{1-6}$ alkyl group (particularly, a methyl group) optionally substituted by 1 to 3 halogen atoms (particularly, a fluorine atom); and
$R_2$ is
(1) an aminomethyl group optionally substituted by 1 or 2 $C_{1-6}$ alkyl groups (particularly, a methyl group),
(2) a 5- or 6-membered non-aromatic heterocyclyl-methyl group (particularly, pyrrolidinylmethyl, dihydropyridylmethyl) optionally substituted by a $C_{1-6}$ alkyl group (particularly, a methyl group), or
(3) a non-aromatic heterocyclic group (particularly, pyrrolidinyl, morpholinyl, piperidyl, 1,2,3,6-tetrahydropyridyl, azepanyl, 3-azabicyclo[3.1.0]hexanyl, 7-azabicyclo[2.2.1]heptanyl, 2-azabicyclo[2.2.1]heptanyl, 1-azabicyclo[2.2.2]octanyl, 2-azabicyclo[2.2.2]octanyl) optionally substituted by 1 to 3 halogen atoms (particularly, a fluorine atom),
or a salt thereof.

[Compound E-2]
A compound wherein
X is a sulfur atom;
Y is CH;
$R_1$ is a $C_{1-6}$ alkyl group (particularly, a methyl group) optionally substituted by 1 to 3 halogen atoms (particularly, a fluorine atom); and
$R_2$ is
(1) a 5- or 6-membered non-aromatic heterocyclyl-methyl group (particularly, pyrrolidinylmethyl), or
(2) a non-aromatic heterocyclic group (particularly, pyrrolidinyl, piperidinyl, 1,2,3,6-tetrahydropyridyl, 7-azabicyclo[2.2.1]heptanyl, 2-azabicyclo[2.2.1]heptanyl, 1-azabicyclo[2.2.2]octanyl) optionally substituted by 1 to 3 halogen atoms (particularly, a fluorine atom),
or a salt thereof.

[Compound F-2]

6-(5-methyl-1H-pyrazol-4-yl)-2-[(2S)-pyrrolidin-2-yl]thieno[3,2-d]pyrimidin-4 (3H)-one (Example 11); 6-(5-methyl-1H-pyrazol-4-yl)-2-[(2S)-piperidin-2-yl]thieno[3,2-d]pyrimidin-4 (3H)-one (Example 83); 2-(7-azabicyclo[2.2.1]hept-1-yl)-6-(5-methyl-1H-pyrazol-4-yl)thieno[3,2-d]pyrimidin-4 (3H)-one (Example 116); 6-(5-methyl-1H-pyrazol-4-yl)-2-[(2S)-1,2,3,6-tetrahydropyridin-2-yl]thieno[3,2-d]pyrimidin-4 (3H)-one (Example 145); 2-[(2S)-piperidin-2-yl]-6-[5-(trifluoromethyl)-1H-pyrazol-4-yl]thieno[3,2-d]pyrimidin-4 (3H)-one (Example 161); 2-[(2S)-1-azabicyclo[2.2.2]oct-2-yl]-6-(5-methyl-1H-pyrazol-4-yl)thieno[3,2-d]pyrimidin-4 (3H)-one (Example 170)

or a salt thereof.

The salt of compound (I) is preferably a pharmacologically acceptable salt, and examples thereof include salts with inorganic bases, salts with organic bases, salts with inorganic acids, salts with organic acids, and salts with basic or acidic amino acids.

Preferable examples of the salt with inorganic base include alkali metal salts such as a sodium salt, a potassium salt and the like; alkaline earth metal salts such as a calcium salt, a magnesium salt and the like; an aluminum salt and an ammonium salt.

Preferable examples of the salt with organic base include a salt with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine or N,N-dibenzylethylenediamine.

Preferable examples of the salt with inorganic acid include a salt with hydrochloric acid, hydrobromic acid, nitric acid, sulfuric acid or phosphoric acid.

Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid.

Preferable examples of the salt with basic amino acid include a salt with arginine, lysine or ornithine.

Preferable examples of the salt with acidic amino acid include a salt with aspartic acid or glutamic acid.

Among the above-mentioned salts, a salt with inorganic acid (preferably hydrochloric acid) or organic acid (preferably trifluoroacetic acid) is preferable.

The production methods of compound (I) are explained in the following.

The compounds in the following reaction schemes may form salts, and examples of such salt include those similar to the salts of compound (I).

While the compounds obtained in respective steps can be used for the next reaction in the form of a reaction mixture as a crude product, they can also be isolated from the reaction mixture by a known separation means such as recrystallization, distillation, chromatography and the like.

Compound (I) can be obtained, for example, according to the method shown in following reaction scheme, or a method analogous thereto.

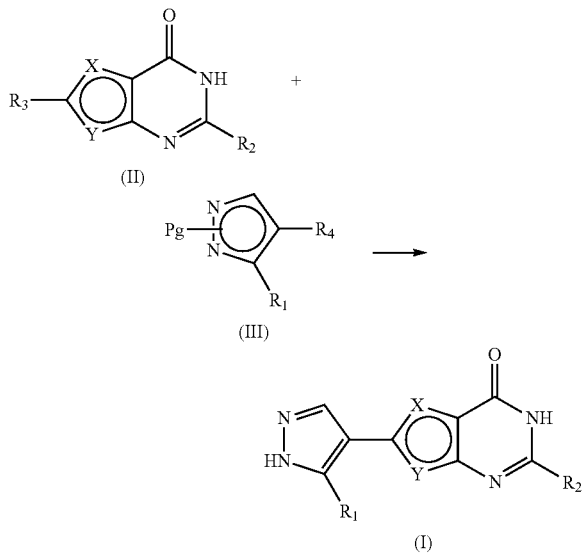

(Reaction scheme 1)

wherein Pg is a protecting group of pyrazole nitrogen. Examples of the protecting group include a tert-butoxycarbonyl group and an N,N-dimethylaminosulfonyl group. $R_3$ is a halogen atom (for example, a bromine atom, a chlorine atom or an iodine atom), $R_4$ is boric acid, borate (e.g., 4,4,5,5-tetramethyl-1,3,2-dioxaborolan-2-yl), a trifluoromethanesulfonyl group, or a stannyl group having a substituent (e.g., tributylstannyl), and other symbols are each as defined above.

In this reaction, compound (II) is subjected to a reaction generally known as Suzuki reaction or Stille reaction or a method similar thereto, and the compound is subjected to a deprotection to remove a protecting group where necessary, whereby compound (I) can be produced.

This reaction is preferably performed in the presence of a palladium catalyst.

The amount of compound (III) to be used is about 1-3 equivalents relative to compound (II).

This reaction can be performed in the presence of a base. Examples of the base include sodium carbonate, potassium carbonate and cesium carbonate. The amount of the base to be used is about 2 to 20 equivalents, relative to compound (II).

Examples of the palladium catalyst include [1,1'-bis(diphenylphosphino)ferrocene]dichloropalladium(II) dichloromethane complex and tetrakis(triphenylphosphine)palladium(0). The amount of the palladium catalyst to be used is about 0.01 to 1 equivalents, relative to compound (II).

This reaction is preferably performed in a solvent. Examples of the solvent include aromatic hydrocarbons (e.g., benzene, toluene, xylene), ethers (e.g., tetrahydrofuran, dioxane, 1,2-dimethoxyethane), acetone, acetonitrile, ethyl acetate, N,N-dimethylformamide, N,N-dimethylacetamide, 1-methyl-2-pyrrolidone, dimethyl sulfoxide, water, and a mixed solvent thereof.

This reaction can be performed at room temperature (about 15 to 30° C.) or under heating (about 40 to 150° C.). The reaction time is generally about 1 to 50 hr, preferably about 1 to 20 hr.

Compound (III) may be a commercially available product, or can be produced according to a method known per se.

Compound (II) is obtained according to, for example, the method shown in the following reaction scheme or a method analogous thereto.

(Reaction scheme 2)

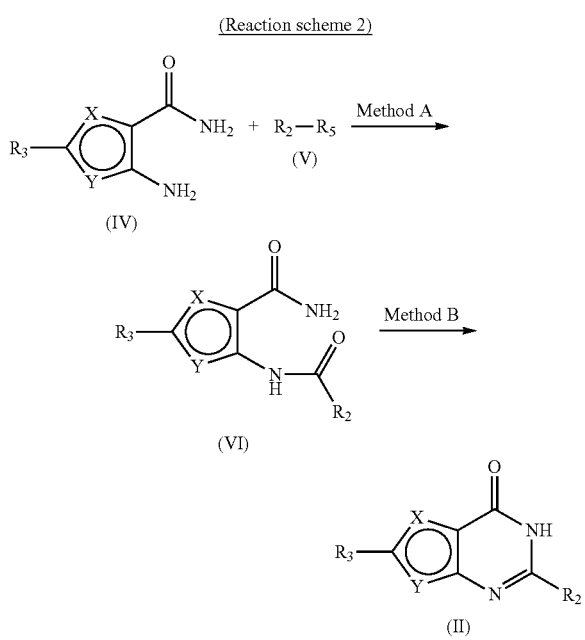

wherein $R_5$ is a carbonyl chloride group or a carboxy group, and other symbols are each as defined above.

(Method A)

In this reaction, compound (VI) can be produced by reacting compound (IV) with compound (V).

The amount of compound (V) to be used in this reaction is generally 1-10 equivalents, preferably 1-5 equivalents, relative to compound (IV).

This reaction is preferably performed in a solvent. Examples of the solvent include ethers (e.g., tetrahydrofuran, dioxane, 1,2-dimethoxyethane), acetonitrile, amides (e.g., N,N-dimethylformamide, N,N-dimethylacetamide, N-methylpyrrolidone) and a mixed solvent thereof.

When compound (V) wherein $R_5$ is a carbonyl chloride group is used, this reaction is preferably performed in the presence of a base. Examples of the base include pyridine, N,N-dimethylpyridine-4-amine, triethylamine and N-methyl-N-(1-methylethyl)propane-2-amine. The amount of the base to be used is 1-100 equivalents, preferably 1-10 equivalents, relative to compound (IV). When compound (V) wherein $R_5$ is a carboxy group is used, this reaction can be performed under known condensation reaction conditions. Examples of the known condensation reaction conditions include a condition in which N,N-dimethylformamide is co-present with O-(7-azabenzotriazol-1-yl)-N,N,N',N'-tetramethyluronium hexafluorophosphate and N-ethyl-N-(1-methylethyl)propane-2-amine, and a condition generally known as a mixed acid anhydride method, for example, a condition in which 2-methylpropyl chlorocarbonate, triethylamine and tetrahydrofuran are co-present.

This reaction can be performed at room temperature (about 15-30° C.) or under heating (about 40-150° C.). The reaction time is generally about 1-50 hr, preferably about 1-5 hr.

Compound (IV) and compound (V) may be commercially available products or can be produced by applying a means known per se.

(Method B)

In this reaction, compound (II) is obtained by cyclizing compound (VI) in the presence of a base.

Examples of the base in this reaction include sodium hydroxide. The amount of the base to be used is 1-100 equivalents, preferably 1-10 equivalents, relative to compound (VI).

This reaction is preferably performed in a solvent. Examples of the solvent include organic solvents such as alcohols (methanol, ethanol and the like); ethers (tetrahydrofuran, dioxane, 1,2-dimethoxyethane and the like); and the like, water, and a mixed solvent thereof.

This reaction can be performed at room temperature (about 15-30° C.) or under heating (about 40-120° C.). The reaction time is generally about 1-20 hr, preferably about 1-4 hr.

Compound (II) wherein $R_2$ is a methyl group substituted by an amino group optionally mono- or di-substituted by substituent(s) selected from (a) a $C_{1-6}$ alkyl group optionally substituted by 1 to 3 halogen atoms, (b) a $C_{1-6}$ alkyl-carbonyl group optionally substituted by 1 to 3 halogen atoms, (c) a $C_{1-6}$ alkoxy-carbonyl group optionally substituted by 1 to 3 halogen atoms, (d) a $C_{1-6}$ alkylsulfonyl group (e.g., methylsulfonyl) optionally substituted by 1 to 3 halogen atoms, (e) a carbamoyl group optionally mono- or di-substituted by a $C_{1-6}$ alkyl group optionally substituted by 1 to 3 halogen atoms, and (f) an aromatic heterocyclic group (e.g., thienyl, furyl, pyridyl, pyrazolyl, imidazolyl, tetrazolyl, oxazolyl, thiazolyl, oxadiazolyl, thiadiazolyl)

can be produced according to, for example, the method shown in the following reaction scheme or a method analogous thereto.

(Reaction scheme 3)

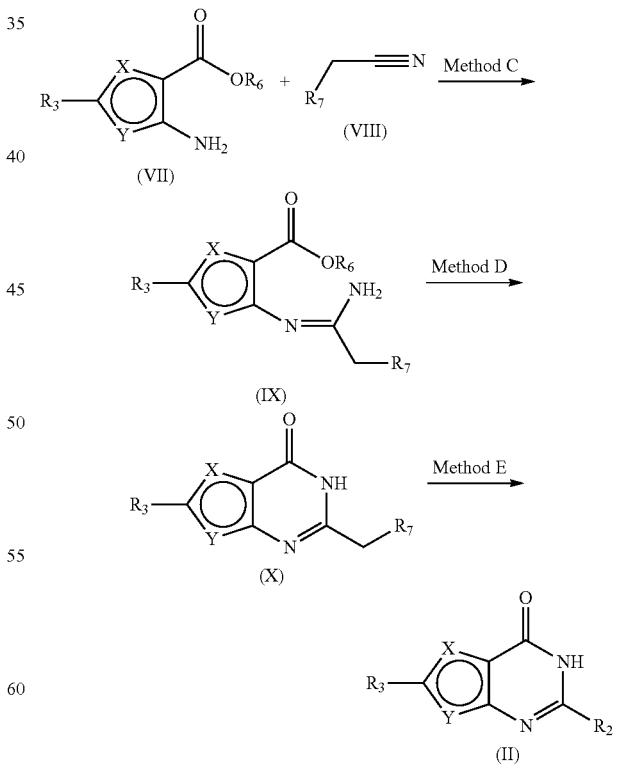

wherein $R_6$ is a $C_{1-6}$ alkyl group, $R_7$ is a halogen atom (for example, a chlorine atom), and other symbols are each as defined above.

(Method C)

In this reaction, compound (IX) can be produced by reacting compound (VII) with compound (VIII) in the presence of an acid.

The amount of compound (VIII) to be used in this reaction is generally 1-10 equivalents, preferably 1-5 equivalents, relative to compound (VII). Examples of the acid in this reaction include hydrochloric acid/cyclopentylmethylether solution. The amount of the acid to be used is generally 1-100 equivalents, preferably 1-10 equivalents, relative to compound (VII).

This reaction is preferably performed in a solvent. Examples of the solvent include ethers (e.g., diethyl ether, tetrahydrofuran, dioxane, 1,2-dimethoxyethane).

This reaction can be performed at room temperature (about 15-30° C.) or under heating (about 40-120° C.). The reaction time is generally about 1-20 hr, preferably about 1-4 hr.

(Method D)

In this reaction, compound (X) can be produced by heating compound (IX) under reduced pressure.

This reaction can be performed under heating (about 40-100° C.). The reaction time is generally about 1-8 hr, preferably about 1-4 hr. The reaction is performed under reduced pressure (about 4-10 Torr). Compound (VII) and compound (VIII) may be commercially available products or can be produced by applying a means known per se.

(Method E)

In this reaction, compound (II) can be produced by substituting $R_7$ of compound (X) by primary amine, secondary amine, amide, carbamate, sulfonamide or urea corresponding to an amino group optionally mono- or di-substituted by substituent(s) selected from (a) a $C_{1-6}$ alkyl group optionally substituted by 1 to 3 halogen atoms,
(b) a $C_{1-6}$ alkyl-carbonyl group optionally substituted by 1 to 3 halogen atoms,
(c) a $C_{1-6}$ alkoxy-carbonyl group optionally substituted by 1 to 3 halogen atoms,
(d) a $C_{1-6}$ alkylsulfonyl group (e.g., methylsulfonyl) optionally substituted by 1 to 3 halogen atoms,
(e) a carbamoyl group optionally mono- or di-substituted by a $C_{1-6}$ alkyl group optionally substituted by 1 to 3 halogen atoms, and
(f) an aromatic heterocyclic group (e.g., thienyl, furyl, pyridyl, pyrazolyl, imidazolyl, tetrazolyl, oxazolyl, thiazolyl, oxadiazolyl, thiadiazolyl).

The amount of the primary amine, secondary amine, amide, carbamate, sulfonamide or urea to be used in this reaction is generally 1-10 equivalents, preferably 1-3 equivalents, relative to compound (X).

The reaction can be performed in the presence of a base.

Examples of the base include potassium carbonate. The amount of the base to be used is generally 1-10 equivalents, preferably 1-5 equivalents, relative to compound (X).

This reaction is preferably performed in a solvent. Examples of the solvent include ethers (e.g., tetrahydrofuran, dioxane, 1,2-dimethoxyethane), acetonitrile, ethyl acetate, N,N-dimethylformamide, N,N-dimethylacetamide, 1-methyl-2-pyrrolidone, dimethyl sulfoxide, and a mixed solvent thereof.

The reaction can be performed at room temperature (about 15-30° C.) or under heating (about 40-120° C.). The reaction time is generally about 0.5-20 hr, preferably about 0.5-4 hr.

Compound (II) can be also produced according to, for example, the method shown in the following reaction scheme or a method analogous thereto.

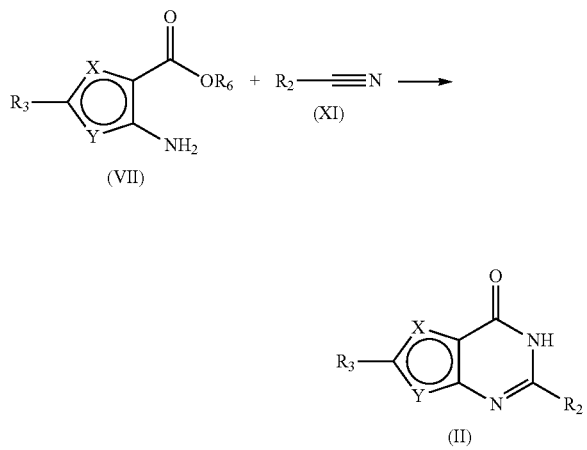

(Reaction scheme 4)

wherein each symbol is as defined above.

In this reaction, compound (II) can be produced by reacting compound (VII) with compound (XI) in the presence of an acid.

The amount of compound (XI) to be used in this reaction is generally 1-10 equivalents, preferably 1-5 equivalents, relative to compound (VII). Examples of the acid in this reaction include hydrochloric acid/cyclopentylmethylether solution. The amount of the acid to be used is generally 1-100 equivalents, preferably 1-10 equivalents, relative to compound (VII). The reaction is preferably performed in a solvent. Examples of the solvent in the reaction include ethers (e.g., diethyl ether, tetrahydrofuran, dioxane, 1,2-dimethoxyethane).

This reaction can be performed at room temperature (about 15-30° C.) or under heating (about 40-120° C.). The reaction time is generally about 1-20 hr, preferably about 1-4 hr.

Compound (XI) may be a commercially available product, or can be produced by applying a means known per se.

Compound (I) can be produced according to, for example, a method shown in the following reaction scheme or a method analogous thereto.

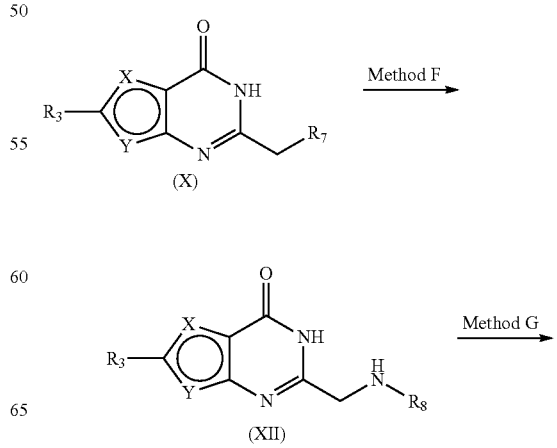

(Reaction scheme 5)

-continued

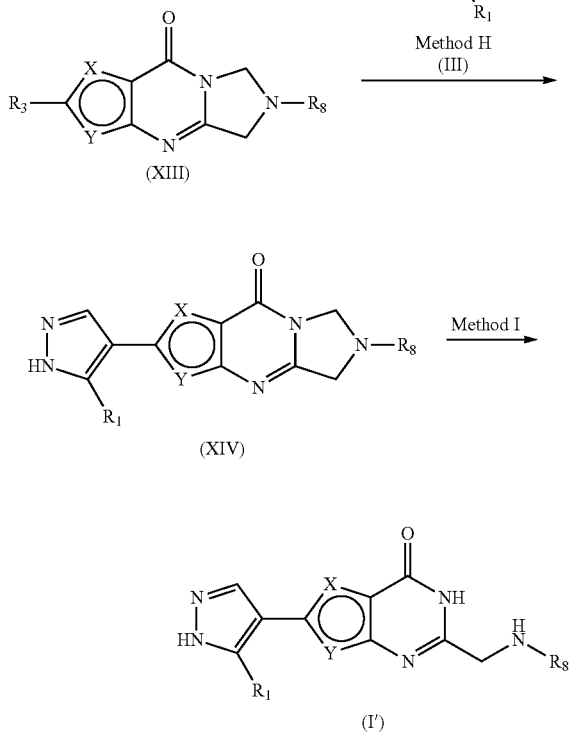

wherein
$R_8$ is a $C_{1-6}$ alkyl group (e.g., a methyl group, an ethyl group) optionally substituted by 1 to 3 substituents selected from
(i) a $C_{6-14}$ aryl group (e.g., phenyl) optionally substituted by 1 to 3 $C_{1-6}$ alkoxy groups (e.g., methoxy),
(ii) an aromatic heterocyclic group (e.g., pyridyl), and
(iii) a $C_{3-8}$ cycloalkyl group (e.g., cyclopropyl) optionally substituted by an aromatic heterocyclic group (e.g., thienyl), and
other symbols are each as defined above.

(Method F)

In this reaction, compound (XII) can be produced by substituting $R_7$ of compound (X) by primary amine in the same manner as in method E shown in reaction scheme 3. Examples of the primary amine include benzylamine.

(Method G)

In this reaction, compound (XIII) can be produced by reacting compound (XII) with, for example, formaldehyde. Examples of the formaldehyde include 37% aqueous formaldehyde solution.

The amount of the formaldehyde to be used in this reaction is generally 10-1000 equivalents, relative to compound (XII).

This reaction is desirably performed in a solvent. Examples of the solvent in the reaction include aromatic hydrocarbons (e.g., benzene, toluene, xylene), ethers (e.g., tetrahydrofuran, dioxane, 1,2-dimethoxyethane), and a mixed solvent thereof.

This reaction can be performed at room temperature (about 15-30° C.) or under heating (about 40-150° C.). The reaction time is generally about 1-50 hr, preferably about 1-20 hr.

(Method H)

In this reaction, compound (XIV) can be produced from compound (XIII) and compound (III) in the same manner as in the method shown in reaction scheme 1.

(Method I)

In this reaction, compound (I') can be produced by heating compound (XIV) in trifluoroacetic acid in the presence of alcohol. Examples of the alcohol include methanol, ethanol, and a mixed solvent thereof.

The amount of the trifluoroacetic acid to be used in this reaction is generally 10-1000 equivalents, relative to compound (XIV).

The reaction can be performed under heating (about 40-80° C.). The reaction time is generally about 1-20 hr, preferably about 1-10 hr.

Compound (I) can be produced according to, for example, the method shown in the following reaction scheme or a method analogous thereto.

(Reaction scheme 6)

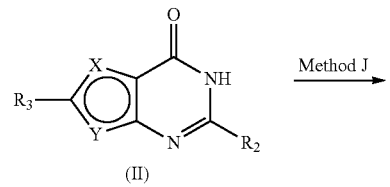

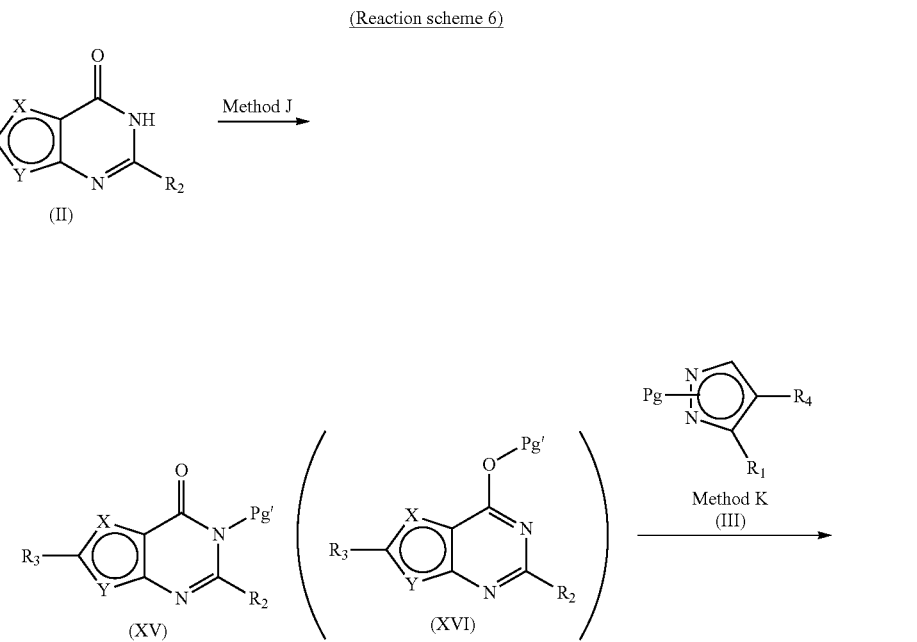

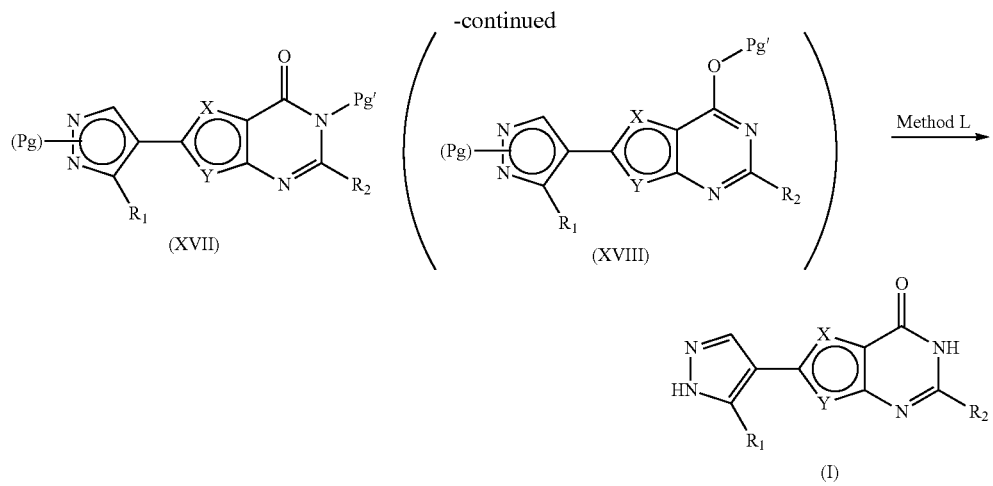

wherein Pg' is a protecting group of lactam moiety. Examples of the protecting group include a [2-(trimethylsilyl)ethoxy]methyl group and a 2,4-dimethoxybenzyl group. Other symbols are each as defined above.

(Method J)

In this reaction, compound (XV), compound (XVI), or a mixture of compound (XV) and compound (XVI) can be produced by introducing a protecting group into the lactam moiety of compound (II).

In one embodiment of method J, namely, when a [2-(trimethylsilyl)ethoxy]methyl group is introduced into the lactam moiety, compound (XV), compound (XVI), or a mixture of compound (XV) and compound (XVI) can be produced by, for example, reacting compound (II) with [2-(chloromethoxy)ethyl](trimethyl)silane in the presence of a base.

Examples of the base in this reaction include sodium hydride. The amount of the base to be used is generally 1-5 equivalents, preferably 1-2 equivalents, relative to compound (II).

The amount of the [2-(chloromethoxy)ethyl](trimethyl)silane to be used in this reaction is generally 1-5 equivalents, preferably 1-2 equivalents, relative to compound (II). The reaction can be performed under cooling (about 0-10° C.), at room temperature (about 15-30° C.) or under heating (about 40-80° C.). The reaction time is generally about 1-20 hr, preferably about 1-3 hr. This reaction is desirably performed in a solvent. Examples of the solvent in the reaction include ethers (e.g., tetrahydrofuran, dioxane, 1,2-dimethoxyethane).

In another embodiment of method J, namely, when a 2,4-dimethoxybenzyl group is introduced into the lactam moiety, compound (XV), compound (XVI), or a mixture of compound (XV) and compound (XVI) can be produced by, for example, subjecting compound (II) and (2,4-dimethoxyphenyl)methanol to a reaction generally known as Mitsunobu reaction, for example, reaction with triphenylphosphine and diethyl (E)-diazene-1,2-dicarboxylate in a solvent.

The amount of the triphenylphosphine to be used in this reaction is about 1-5 equivalents relative to compound (II).

The amount of the diethyl (E)-diazene-1,2-dicarboxylate to be used in this reaction is about 1-5 equivalents relative to compound (II).

The amount of the (2,4-dimethoxyphenyl)methanol to be used in this reaction is about 1-5 equivalents relative to compound (II).

Examples of the solvent in this reaction include ethers (e.g., tetrahydrofuran, dioxane, 1,2-dimethoxyethane).

The reaction can be performed under cooling (about 0-10° C.), at room temperature (about 15-30° C.) or under heating (about 40-80° C.). The reaction time is generally about 1-20 hr, preferably about 1-8 hr.

(Method K)

In this reaction, compound (XVII) can be produced from compound (XV) and compound (III) in the same manner as in the method shown in reaction scheme 1. In addition, compound (XVII) can be produced from compound (XVI) and compound (III) in the same manner. Moreover, in the same manner, compound (XVII), compound (XVIII), or a mixture of compound (XVII) and compound (XVIII) can be produced from a mixture of compound (XV) and compound (XVI), and compound (III). The protecting group on pyrazole nitrogen of compound (XVII) and compound (XVIII) is sometimes removed during this reaction.

(Method L)

In this reaction, compound (I) can be produced by removing a protecting group of compound (XVII), compound (XVIII), or a mixture of compound (XVII) and compound (XVIII) according to a conventional method.

In one embodiment of method L, namely, when the protecting group on the pyrazole nitrogen is a t-butoxycarbonyl group, the t-butoxycarbonyl group can be deprotected by reacting compound (XVII), compound (XVIII), or a mixture of compound (XVII) and compound (XVIII) with an acid.

Examples of the acid in this reaction include trifluoroacetic acid, 10% hydrochloric acid/methanol solution, and 4M hydrochloric acid/ethyl acetate solution. The amount of the acid to be used is about 10-5000 equivalents, relative to compound (XVII), compound (XVIII), or a mixture of compound (XVII) and compound (XVIII).

A solvent may be used for this reaction. Examples of the solvent include alcohols (e.g., methanol, ethanol). The reaction can be performed at room temperature or under heating (about 40-80° C.). The reaction time is generally about 0.5-20 hr, preferably about 0.5-3 hr.

In another embodiment of method L, namely, when the protecting group of the lactam moiety is a [2-(trimethylsilyl)ethoxy]methyl group, the [2-(trimethylsilyl)ethoxy]methyl group can be deprotected by subjecting compound (XVII), compound (XVIII), or a mixture of compound (XVII) and compound (XVIII) to a fluoride-containing solvent, or a reaction with an acid.

Examples of the fluoride-containing solvent in this reaction include 1M N,N,N-tributylbutan-1-aminium fluoride/ tetrahydrofuran solution. The amount of the fluoride to be used is about 5-50 equivalents, relative to compound (XVII), compound (XVIII), or a mixture of compound (XVII) and compound (XVIII). The reaction is desirably performed under heating (about 40-80° C.). The reaction time is generally about 1-20 hr, preferably about 1-8 hr. Examples of the acid in this reaction include trifluoroacetic acid, 10% hydrochloric acid/methanol solution, and 4M hydrochloric acid/ethyl acetate solution. The amount of the acid to be used is about 10-5000 equivalents relative to compound (XVII), compound (XVIII) or a mixture of compound (XVII) and compound (XVIII). The reaction can be performed at room temperature or under heating (about 40-80° C.). The reaction time is generally about 1-20 hr, preferably about 1-3 hr.

In still another embodiment of method L, namely, when the protecting group of the lactam moiety is a 2,4-dimethoxybenzyl group, the 2,4-dimethoxybenzyl group can be deprotected by reaction with an acid. Examples of the acid in this reaction include trifluoroacetic acid. The amount of the acid to be used is about 10-5000 equivalents, relative to compound (XVII), compound (XVIII), or a mixture of compound (XVII) and compound (XVIII). A solvent may be used for this reaction. Examples of the solvent include dichloromethane and water. The reaction can be performed under heating (about 40-100° C.). The reaction time is generally about 1-20 hr, preferably about 1-8 hr.

Compound (I) can be produced according to, for example, the method shown in the following reaction scheme or a method analogous thereto.

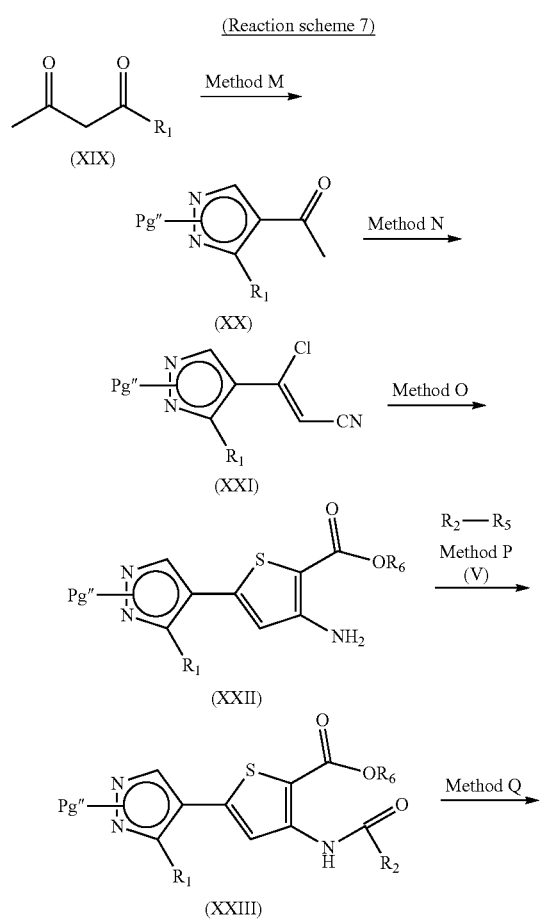

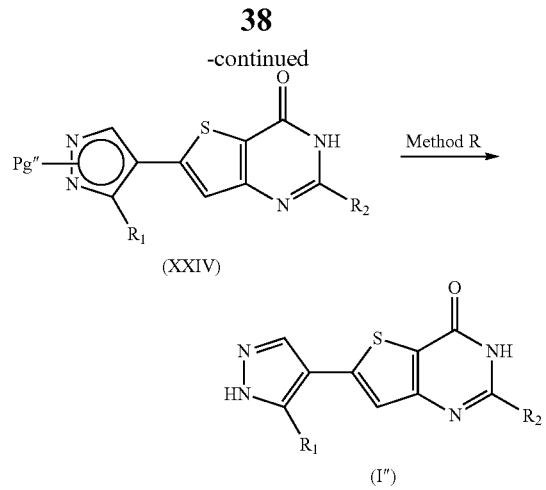

wherein Pg" is a protecting group on pyrazole nitrogen. Examples of the protecting group include a benzyl group, a tert-butyl group and a 4-methoxybenzyl group. Other symbols are each as defined above.

(Method M)

In this reaction, compound (XIX) is reacted with 1,1-dimethoxy-N,N-dimethylmethanamine (method M-1), and thereafter reacted with hydrazine having a Pg" group or a salt thereof (method M-2) to give compound (XX). Compound (XIX), 1,1-dimethoxy-N,N-dimethylmethanamine, and hydrazine having a Pg" group or a salt thereof may be commercially available products, or can be produced by applying a means known per se.

(Method M-1)

The amount of the 1,1-dimethoxy-N,N-dimethylmethanamine to be used in this reaction is generally 1-10 equivalents, preferably 1-2 equivalents, relative to compound (XIX). The reaction can be performed under heating (about 60-100° C.). The reaction time is generally about 1-50 hr, preferably about 1-5 hr.

(Method M-2)

The amount of hydrazine having a Pg" group or a salt thereof to be used in this reaction is generally 1-5 equivalents, preferably 1-2 equivalents, relative to compound (XIX). The reaction is preferably performed in a solvent. Examples of the solvent include ethers (e.g., tetrahydrofuran, dioxane, 1,2-dimethoxyethane). This reaction can be performed under cooling (about 0-10° C.), at room temperature (about 15-30° C.) or under heating (about 40-100° C.). The reaction time is generally about 30 min-5 hr, preferably about 30 min-1 hr.

(Method N)

In this reaction, compound (XX) is reacted with a Vilsmeier reagent (method N-1), and thereafter reacted with hydroxylamine hydrochloride (method N-2) to give compound (XXI). The protecting group on pyrazole nitrogen may be removed during the reaction in method N-2. In the case, compound (XXI) can be produced by reaction with halide having a Pg" group in the presence of a base (method N-3).

(Method N-1)

The amount of the Vilsmeier reagent to be used in this reaction is generally 1-10 equivalents, preferably 1-5 equivalents, relative to compound (XX). The Vilsmeier reagent can be produced from N,N-dimethylformamide and phosphorus oxychloride under a condition generally known. For example, phosphorus oxychloride is added to N,N-dimethylformamide under ice-cooling and the mixture is stirred at room temperature for 30 min-1 hr.

The reaction can be performed at room temperature or under heating (about 40-60° C.). The reaction time is generally about 30 min-2 hr, preferably about 30 min-1 hr.
(Method N-2)

The amount of the hydroxylamine hydrochloride to be used in this reaction is generally 5-20 equivalents, preferably 5-10 equivalents, relative to compound (XX). The protecting group on pyrazole nitrogen may be removed during this reaction. The reaction can be performed under heating (about 50-80° C.). The reaction time is generally about 0.5-8 hr, preferably about 0.5-2 hr.
(Method N-3)

Examples of the halides having a Pg" group in this reaction include (bromomethyl)benzene and 1-(chloromethyl)-4-methoxybenzene. The amount of the halides having a Pg" group to be used is generally 1-3 equivalents, preferably 1-2 equivalents, relative to compound (XX). Examples of the base in this reaction include potassium carbonate. The amount of the potassium carbonate to be used is generally 1-5 equivalents, preferably 1-3 equivalents. This reaction is preferably performed in a solvent. Examples of the solvent include N,N-dimethylformamide, N,N-dimethylacetamide, 1-methyl-2-pyrrolidone, and a mixed solvent thereof. The reaction can be performed at room temperature (about 15-30° C.) or under heating (about 40-120° C.). The reaction time is generally about 2-48 hr, preferably about 6-24 hr.
(Method O)

In this reaction, compound (XXI) is reacted with sulfanylacetate having an $R_6$ group in the presence of a base to give compound (XXII).

The amount of the sulfanylacetate having an $R_6$ group to be used in this reaction is generally 1-3 equivalents, preferably 1-2 equivalents, relative to compound (XXI). The sulfanylacetate having an $R_6$ group may be a commercially available product, or can be produced by applying a means known per se. Examples of the base in this reaction include inorganic bases (e.g., sodium hydride, potassium carbonate, cesium carbonate) and organic bases (e.g., triethylamine, N-ethyl-N-(1-methylethyl)propan-2-amine). This reaction is preferably performed in a solvent. Examples of the solvent include N,N-dimethylformamide. The reaction can be performed under cooling (about 0-10° C.), at room temperature (about 15-30° C.) or under heating (about 40-100° C.). The reaction time is generally about 30 min-5 hr, preferably about 30 min-2 hr.
(Method P)

In this reaction, compound (XXIII) can be produced from compound (XXII) and compound (V) in the same manner as in method A shown in reaction scheme 2.
(Method Q)

In this reaction, compound (XXIV) can be produced from compound (XXIII) in the same manner as in method B shown in reaction scheme 2.
(Method R)

In this reaction, compound (I") can be produced by subjecting compound (XXIV) to deprotection of a Pg" group. For example, compound (XXIV) having a benzyl group as a Pg" group is reacted with palladium hydroxide-carbon in formic acid under a hydrogen atmosphere to give compound (I"). The amount of the palladium hydroxide-carbon to be used in this reaction is catalytic amount—equivalent amount, relative to compound (XXIV). The hydrogen atmosphere in this reaction is 1-3 atm. The reaction can be performed at room temperature (about 15-30° C.) or under heating (about 40-100° C.). The reaction time is generally about 2-120 hr, preferably about 8-24 hr.

In addition, for example, compound (XXIV) having a 4-methoxybenzyl group as a Pg" group is heated in trifluoroacetic acid in the presence of methoxybenzene to give compound (I"). The amount of the methoxybenzene to be used in the reaction is 1-5 equivalents. The reaction can be performed under heating (about 40-100° C.). The reaction time is generally about 8-48 hr, preferably about 8-24 hr.

Compound (I) can be produced according to, for example, the method shown in the following reaction scheme or a method analogous thereto.

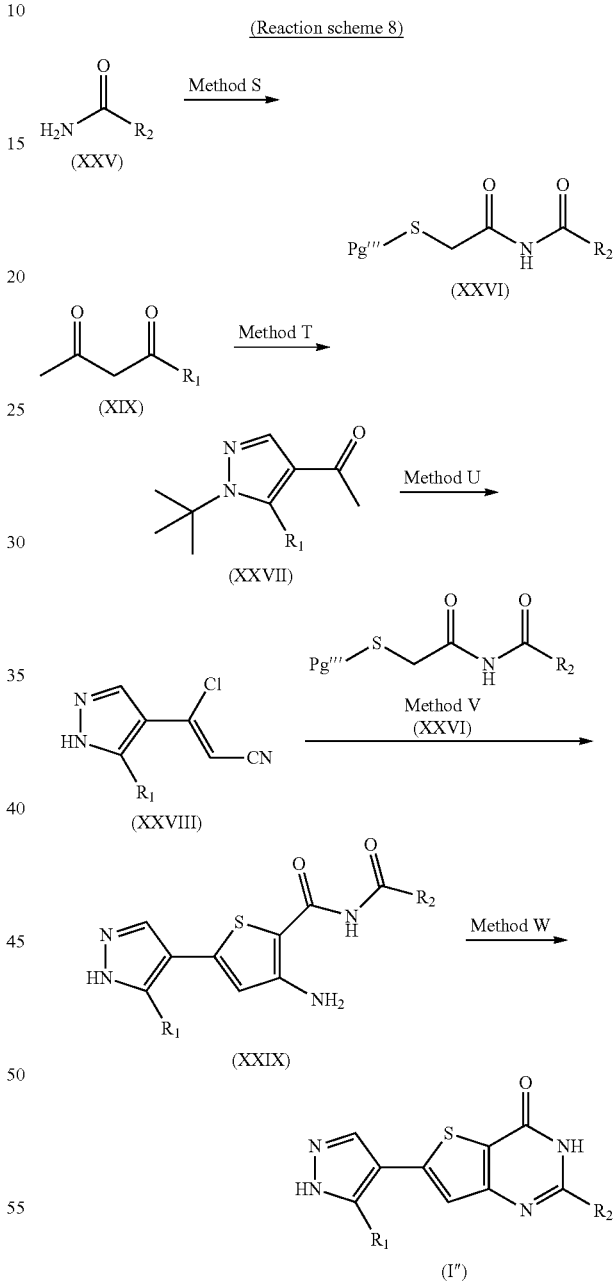

(Reaction scheme 8)

wherein Pg''' is a protecting group on a sulfur atom. Examples of the protecting group include an acetyl group. Other symbols are each as defined above.
(Method S)

In this reaction, compound (XXV) is reacted with chloroacetyl chloride (method S-1), and thereafter reacted with thiol having a Pg''' group in the presence of a base (method S-2) to give compound (XXVI).

(Method S-1)

The amount of the chloroacetyl chloride to be used in this reaction is generally 2-10 equivalents, preferably 2-4 equivalents, relative to compound (XXV). The reaction can be performed at room temperature (about 15-30° C.) or under heating (about 40-120° C.). The reaction time is generally about 3-24 hr, preferably about 12-18 hr.

(Method S-2)

The amount of the thiol having a Pg''' group to be used in this reaction is generally 1-2 equivalents, preferably 1-1.1 equivalents, relative to compound (XXV). The amount of the base (e.g., potassium carbonate, triethylamine) to be used in this reaction is generally 1-2 equivalents, preferably 1-1.1 equivalents, relative to compound (XXV). The reaction is preferably performed in a solvent. Examples of the solvent include tetrahydrofuran. The reaction can be performed under ice-cooling (about −5-5° C.) or at room temperature (about 15-30° C.). The reaction time is generally about 0.1-1 hr, preferably about 0.1-0.5 hr.

Compound (XXV) and chloroacetyl chloride may be commercially available products, or can be produced by applying a means known per se.

(Method T)

In this reaction, compound (XIX) is reacted with 1,1-dimethoxy-N,N-dimethylmethanamine (method T-1), and thereafter reacted with tert-butylhydrazine or a salt thereof (method T-2) to give compound (XXVII). Compound (XIX) and tert-butylhydrazine or a salt thereof may be commercially available products.

(Method T-1)

The amount of the 1,1-dimethoxy-N,N-dimethylmethanamine to be used in this reaction is generally 1-10 equivalents, preferably 1-2 equivalents, relative to compound (XIX). The reaction can be performed under heating (about 60-100° C.). The reaction time is generally about 1-50 hr, preferably about 1-5 hr.

(Method T-2)

The amount of the tert-butylhydrazine or a salt thereof to be used in this reaction is generally 1-5 equivalents, preferably 1-2 equivalents, relative to compound (XIX). The reaction is preferably performed in a solvent. Examples of the solvent include ethers (e.g., tetrahydrofuran, dioxane, 1,2-dimethoxyethane). The reaction can be performed under cooling (about 0-10° C.), at room temperature (about 15-30° C.) or under heating (about 40-100° C.). The reaction time is generally about 30 min-5 hr, preferably about 30 min-1 hr.

(Method U)

In this reaction, compound (XXVII) is reacted with a Vilsmeier reagent (method U-1), and thereafter reacted with hydroxylamine hydrochloride (method U-2) to give compound (XXVIII).

(Method U-1)

The amount of the Vilsmeier reagent to be used in this reaction is generally 1-10 equivalents, preferably 1-5 equivalents, relative to compound (XXVII). The Vilsmeier reagent can be prepared from N,N-dimethylformamide and phosphorus oxychloride under a condition generally known (e.g., phosphorus oxychloride is added to N,N-dimethylformamide under ice-cooling, and the mixture is stirred at room temperature for 30 min-1 hr).

This reaction can be performed at room temperature or under heating (about 40-60° C.). The reaction time is generally about 30 min-2 hr, preferably about 30 min-1 hr.

(Method U-2)

The amount of the hydroxylamine hydrochloride to be used in this reaction is generally 5-20 equivalents, preferably 5-10 equivalents, relative to compound (XXVII). This reaction can be performed under heating (about 40-60° C.). The reaction time is generally about 30 min-2 hr, preferably about 30 min-1 hr.

(Method V)

In this reaction, compound (XXIX) can be produced by reacting compound (XXVIII) with compound (XXVI) in the presence of a base.

The amount of compound (XXVI) to be used in this reaction is generally 1-1.5 equivalents, preferably 1-1.1 equivalents, relative to compound (XXVIII). The amount of the base (e.g., potassium carbonate, cesium carbonate) to be used in this reaction is generally 1-2 equivalents, preferably 1-1.2 equivalents, relative to compound (XXVIII). This reaction is preferably performed in a solvent. Examples of the solvent include tetrahydrofuran, N,N-dimethylformamide, and a mixed solvent thereof. This reaction can be performed under ice-cooling (about −5-5° C.) or at room temperature (about 15-30° C.). The reaction time is generally about 0.5-5 hr, preferably about 0.5-2 hr.

(Method W)

In this reaction, compound (I″) can be produced by reacting compound (XXIX) with acid or base.

Examples of the acid in this reaction include diluted hydrochloric acid and trifluoroacetic acid. The amount of the acid to be used is generally 2-20 equivalents, preferably 5-10 equivalents, relative to compound (XXIX). Examples of the base in this reaction include aqueous sodium hydroxide solution, potassium carbonate and sodium hydride. The amount of the base to be used is generally 1-10 equivalents, preferably 2-5 equivalents, relative to compound (XXIX). This reaction is preferably performed in a solvent. Examples of the solvent include methanol, N,N-dimethylformamide, and a mixed solvent thereof. This reaction can be performed at room temperature (about 15-30° C.) or under heating (about 40-120° C.). The reaction time is generally about 0.2-72 hr, preferably about 0.2-5 hr.

A compound within the scope of the present invention can also be produced by applying means known per se to compound (I) for conversion of substituent (i.e., introduction of substituent and conversion of functional group).

For the conversion of substituent, a known conventional method can be used. Examples thereof include conversion to carboxy group by hydrolysis of ester, conversion to carbamoyl group by amidation of carboxy group, conversion to hydroxymethyl group by reduction of carboxy group, conversion to alcohol compound by reduction or alkylation of carbonyl group, reductive amination of carbonyl group, oximation of carbonyl group, acylation of amino group, ureation of amino group, sulfonylation of amino group, alkylation of amino group, substitution or amination of active halogen by amine, alkylation of hydroxy group, substitution or amination of hydroxy group.

When a reactive moiety that causes non-objective reaction is present during the introduction of substituents and conversion of functional groups, a protecting group is introduced in advance as necessary into the reactive moiety by a means known per se, and the protecting group is removed by a means known per se after the objective reaction, whereby the compound within the scope of the present invention can be also produced.

For example, when the starting compound or the intermediate has an amino group, a carboxyl group or a hydroxy group as a substituent, these groups may be protected by a protecting group generally used in the peptide chemistry and the like. In this case, the object compound can be obtained by removing the protecting group as necessary after the reaction.

Examples of the amino-protecting group include a formyl group; a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl) and a $C_{2-6}$ alkenyl group (e.g., 1-allyl). These groups are optionally substituted by 1 to 3 substituents selected from a halogen atom, a $C_{1-6}$ alkoxy group and a nitro group.

Examples of the carboxy-protecting group include a $C_{1-6}$ alkyl group, a $C_{7-11}$ aralkyl group (e.g., benzyl), a phenyl group, a trityl, a substituted silyl group (e.g., trimethylsilyl, triethylsilyl, dimethylphenylsilyl, tert-butyldimethylsilyl, tert-butyldiethylsilyl) and a $C_{2-6}$ alkenyl group (e.g., 1-allyl). These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuryl group, a substituted silyl group (e.g., trimethylsilyl, triethylsilyl, dimethylphenylsilyl, tert-butyldimethylsilyl, tert-butyldiethylsilyl) and a $C_{2-6}$ alkenyl group (e.g., 1-allyl). These groups are optionally substituted by 1 to 3 substituents selected from a halogen atom, a $C_{1-6}$ alkyl group, a $C_{1-6}$ alkoxy group and a nitro group. For removal of the above-mentioned protecting group, a method known per se, for example, a method described in Protective Groups in Organic Synthesis, John Wiley and Sons (1980) can be employed. For example, employed is a method using acid, base, UV light, hydrazine, phenyl hydrazine, sodium N-methyldithiocarbamate, tetrabutylammonium fluoride, palladium acetate, trialkylsilyl halide (e.g., trimethylsilyl iodide, trimethylsilyl bromide) and the like, reduction and the like.

Depending on the kind of the substituent of the starting compound, a starting compound having a different substituent can be produced by the aforementioned conversion of substituent from, as a starting material, a compound produced by the aforementioned production method.

Compound (I), which is a product of the aforementioned reaction, may be produced as a single compound or as a mixture.

Thus-obtained compound (I) can be isolated and purified by a separation means known per se, such as concentration, concentration under reduced pressure, solvent extraction, crystallization, recrystallization, phase transfer, chromatography and the like.

When compound (I) is obtained as a free form, it can be converted to a desired salt by a method known per se or a method analogous thereof; conversely, when compound (I) is obtained as a salt, it can be converted to a free form or other desired salt by a method known per se or a method analogous thereof.

When compound (I) has an isomer such as an optical isomer, a stereoisomer, a regioisomer, a rotamer and the like, such isomer and a mixture thereof are also encompassed in compound (I). For example, when compound (I) has an optical isomer, an optical isomer resolved from a racemate is also encompassed in compound (I). These isomers can be obtained as single products by synthetic techniques and separation techniques known per se (e.g., concentration, solvent extraction, column chromatography, recrystallization).

Compound (I) may be in the form of a crystal, and the crystal form of the crystal may be single or plural, both of which are encompassed in the compound (I). The crystal can be produced by a crystallization method known per se.

In addition, compound (I) may be a pharmaceutically acceptable cocrystal or a cocrystal salt. Here, the cocrystal or cocrystal salt means a crystalline substance, which is constituted from two or more kinds of specific solids each having different physical properties (e.g., structure, melting point, heat of fusion, hygroscopicity and stability) at room temperature. The cocrystal and cocrystal salt can be produced according to a cocrystallization method known per se.

Compound (I) may be a hydrate, a non-hydrate, a solvate or a non-solvate, all of which are encompassed in compound (I).

A compound labeled with an isotope (e.g., $^{2}H$, $^{3}H$, $^{11}C$, $^{14}C$, $^{18}F$, $^{35}S$, $^{125}I$) and the like is also encompassed in compound (I).

A prodrug of the compound (I) of the present invention means a compound which is converted to compound (I) by a reaction due to an enzyme, gastric acid, etc. under the physiological conditions in the living body, that is, a compound which is converted to compound (I) by oxidation, reduction, hydrolysis, etc.; a compound which is enzymatically converted to compound (I) by hydrolysis etc. due to gastric acid, etc. A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any of these compounds can be produced from compound (I) by a method known per se.

A prodrug of compound (I) may also be one which is converted to compound (I) under physiological conditions, such as those described in IYAKUHIN no KAIHATSU (Development of Pharmaceuticals), Vol. 7, Design of Molecules, pp. 163-198, Published by HIROKAWA SHOTEN (1990).

Compound (I) or a prodrug thereof (in the specification, sometimes to be abbreviated as "the compound of the present invention") possesses a Cdc7 inhibitory activity, which is an agent for the prophylaxis or treatment of cancer, a cancer growth inhibitor and a cancer metastasis suppressive agent.

Since the compound of the present invention shows a strong inhibitory activity on Cdc7, and is also superior in the efficacy expression, pharmacokinetics (e.g., absorption, distribution, metabolism, excretion), solubility (e.g., water-solubility), interaction with other pharmaceutical products (e.g., drug-metabolizing enzyme inhibitory action), safety (e.g., acute toxicity, chronic toxicity, genetic toxicity, reproductive toxicity, cardiotoxicity, carcinogenicity) and stability (e.g., chemical stability, stability to enzyme etc.), it is useful as a medicament.

Since the compound of the present invention shows low inhibitory activity against protein kinases other than Cdc7, it is useful as an agent for the prophylaxis or treatment of cancer, which has reduced toxicity to normal cells.

Accordingly, the compound of the present invention can be used for inhibiting excessive (abnormal) Cdc7 action on mammals (e.g., mouse, rat, hamster, rabbit, cat, dog, bovine, sheep, monkey, human).

The compound of the present invention is used as a medicament such as an agent for the prophylaxis or treatment of diseases possibly influenced by Cdc7, for example, cancer [for example, colorectal cancer (e.g., colorectal cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophagus cancer, gastric cancer (e.g., papillary adenocarcinoma, mucinous adenocarcinoma, adenosquamous carcinoma), duodenal cancer, small intestinal cancer, breast cancer (e.g., infiltrating intraductal carcinoma, noninfiltrating intraductal carcinoma, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer), liver cancer (e.g., hepatocellular cancer, primary liver cancer, Extrahepatic Bile Duct Cancer), thyroid cancer (e.g., medullary thyroid carcinoma), kidney cancer (e.g., renal cell carcinoma, transitional cell carcinoma of renal pelvis and urinary duct), uterine cancer (e.g., cervical cancer, cancer of uterine body, uterus sarcoma), brain tumor (e.g., medulloblastoma, glioma, pineal astrocytoma, pilocytic astrocytoma, diffuse astrocytoma, anaplastic astrocytoma, pituitary adenoma), retinoblastoma, skin cancer (e.g., basal cell tumor, malignant melanoma), sarcoma (e.g., rhabdomyosarcoma, leiomyosarcoma, soft tissue sarcoma), malignant bone tumor, urinary bladder cancer, hematologic cancer (e.g., multiple myeloma, leukemia, malignant lymphoma, Hodgkin's disease, chronic bone marrow proliferative disease), unknown primary cancer], a cancer growth inhibitor, a cancer metastasis suppressive agent, apoptosis promoter, and the like.

Particularly, the compound of the present invention is effective for hematologic cancer, breast cancer, colorectal cancer, lung cancer, pancreatic cancer and the like.

The compound of the present invention can be administered, as a medicament, orally or parenterally as it is or in a mixture with a pharmacologically acceptable carrier to the aforementioned mammal.

The medicament comprising the compound of the present invention (sometimes to be abbreviated as "the medicament of the present invention") is explained in detail in the following.

Examples of the dosage form of the medicament of the present invention for oral administration of the compound of the present invention include oral preparations such as tablet (including sugar-coated tablet, film-coated tablet, sublingual tablet, buccal tablet, fast disintegration oral tablet), pill, granule, powder, capsule (including soft capsule, microcapsule), syrup, emulsion, suspension and films (e.g., oral mucosal adhesive film). Examples of the dosage form of the medicament of the present invention for parenteral administration include injection, impregnant, drip infusion, transdermal agent (e.g., iontophoresis transdermal agent) and suppository. It is also effective to prepare a sustained-release preparation by combining the compound of the present invention with a suitable base (e.g., butyric acid polymer, glycolic acid polymer, butyric acid-glycolic acid copolymer, a mixture of butyric acid polymer and glycolic acid polymer, polyglycerol fatty acid ester).

The medicament of the present invention can be produced by a known production method generally used in the technical field of pharmaceutical preparations (e.g., the method described in the Japanese Pharmacopoeia). In addition, the medicament of the present invention can appropriately contain, where necessary, appropriate amounts of additives generally used in the pharmaceutical field, such as excipient, binder, disintegrant, lubricant, sweetener, surfactant, suspending agent, emulsifier, colorant, preservative, aromatic, corrigent, stabilizer, thickener and the like.

Examples of the aforementioned pharmacologically acceptable carrier include these additives.

For example, tablet can be produced by using excipient, binder, disintegrant, lubricant and the like, and pill and granule can be produced by using excipient, binder and disintegrant. In addition, powder and capsule can be produced by using excipient and the like, syrup can be produced by using sweetener and the like, and emulsion and suspension can be produced by using suspending agent, surfactant, emulsifier and the like.

Examples of the excipient include lactose, refined sugar, glucose, starch, sucrose, crystalline cellulose, powdered glycyrrhiza, mannitol, sodium hydrogen carbonate, calcium phosphate and calcium sulfate.

Examples of the binder include 5-10 wt % starch liquid paste, 10-20 wt % gum arabic solution or gelatin solution, 1-5 wt % tragacanth solution, carboxymethyl cellulose solution, sodium alginate solution and glycerin.

Examples of the disintegrant include starch and calcium carbonate.

Examples of the lubricant include magnesium stearate, stearic acid, calcium stearate and purified talc.

Examples of the sweetener include glucose, fructose, invert sugar, sorbitol, xylitol, glycerin and simple syrup.

Examples of the surfactant include sodium lauryl sulfate, polysorbate 80, sorbitan monofatty acid ester and polyoxyl 40 stearate.

Examples of the suspending agent include gum arabic, sodium alginate, sodium carboxymethyl cellulose, methyl cellulose and bentonite.

Examples of the emulsifier include gum arabic, tragacanth, gelatin, polysorbate 80.

For example, when the medicament of the present invention is in the form of a tablet, the tablet can be produced according to a method known per se, by adding, for example, excipient (e.g., lactose, refined sugar, starch), disintegrant (e.g., starch, calcium carbonate), binder (e.g., starch, gum arabic, carboxymethylcellulose, polyvinylpyrrolidone, hydroxypropylcellulose) or lubricant (e.g., talc, magnesium stearate, polyethylene glycol 6000) to the compound of the present invention, compression molding the mixture, and then, where necessary, applying a coating by a method known per se for the purpose of masking taste, enteric coating or sustainability. Examples of the coating agent used for coating include hydroxypropylmethylcellulose, ethylcellulose, hydroxymethylcellulose, hydroxypropylcellulose, polyoxyethyleneglycol, Tween 80, pluronic F68, cellulose acetate phthalate, hydroxypropylmethylcellulose phthalate, hydroxymethylcellulose acetate succinate, Eudragit (manufactured by Rohm, Germany, methacrylic acid-acrylic acid copolymer) and dye (e.g., red iron oxide, titanium dioxide). The thus-obtained tablet may be any of immediate-release preparation and sustained-release preparation.

Examples of the aforementioned injection include intravenous injection as well as subcutaneous injection, intracutaneous injection, intramuscular injection, instillation and the like.

Such injections are prepared by methods known per se, or by dissolving, suspending or emulsifying the compound of the present invention in a sterilized aqueous or oily liquid. Examples of the aqueous liquid include isotonic solution containing saline, glucose and other auxiliary agents (e.g., D-SORBITOL, D-mannitol, sodium chloride) and the like. The aqueous liquid may contain suitable solubilizing agents, for example, alcohol (e.g., ethanol), polyalcohol (e.g., propylene glycol, polyethylene glycol), and non-ionic surfactant (e.g., polysorbate 80, HCO-50). Examples of the oil liquid include sesame oil, soybean oil and the like. The oil liquid may contain suitable solubilizing agents. Examples of the solubilizing agents include benzyl benzoate, benzyl alcohol and the like. In addition, the injection may contain buffering agents (e.g., phosphate buffer, sodium acetate buffer), soothing agents (e.g., benzalkonium chloride, procaine hydrochloride), stabilizers (e.g., human serum albumin, polyethylene glycol), preservatives (e.g., benzyl alcohol, phenol) and the like. A prepared injection is generally filled in an ampoule.

While the content of the compound of the present invention in the medicament of the present invention varies depending on the form of the pharmaceutical preparation, it is generally about 0.01 to 100 wt %, preferably about 2 to 85 wt %, more preferably about 5 to 70 wt %, relative to the entire preparation.

While the content of the additive in the medicament of the present invention varies depending on the form of the pharmaceutical preparation, it is generally about 1 to 99.9 wt %, preferably about 10 to 90 wt %, relative to the entire preparation.

The compound of the present invention is stable and low toxic, and can be used safely. While the daily dose varies depending on the condition and body weight of patients, the kind of compound, administration route and the like, in the case of, for example, oral administration to patients for the treatment of cancer, the daily dose to an adult (body weight about 60 kg) is about 1 to 1000 mg, preferably about 3 to 300 mg, more preferably about 10 to 200 mg, as the compound of the present invention, which can be given in a single administration or administered in 2 or 3 portions a day.

When the compound of the present invention is administered parenterally, it is generally administered in the form of a liquid (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, relative to 1 kg body weight, which is preferably intravenous injection.

The compound of the present invention can be used concurrently with other drugs. To be specific, the compound of the present invention can be used together with medicaments such as hormonal therapeutic agents, chemotherapeutic agents, immunotherapeutic agents, drugs inhibiting the action of cell growth factors or receptors thereof, and the like. In the following, the drugs that can be used in combination with the compound of the present invention are abbreviated as concomitant drugs.

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate), pill preparations, mepitiostane, testrolactone, aminoglutethimide, LH-RH agonists (e.g., goserelin acetate, buserelin, leuprorelin), droloxifene, epitiostanol, ethinylestradiol sulfonate, aromatase inhibitors (e.g., fadrozole hydrochloride, anastrozole, retrozole, exemestane, vorozole, formestane), anti-androgens (e.g., flutamide, bicartamide, nilutamide), 5α-reductase inhibitors (e.g., finasteride, epristeride), adrenocortical hormone drugs (e.g., dexamethasone, prednisolone, betamethasone, triamcinolone), androgen synthesis inhibitors (e.g., abiraterone), retinoid and drugs that retard retinoid metabolism (e.g., liarozole), thyroid hormone, and DDS (Drug Delivery System) preparations thereof.

Examples of the "chemotherapeutic agents" include alkylating agents, antimetabolites, anticancer antibiotics, and plant-derived anticancer agents.

Examples of the "alkylating agents" include nitrogen mustard, nitrogen mustard N-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and DDS preparations thereof.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, capecitabine), aminopterine, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, bendamustine, and DDS preparations thereof.

Examples of the "anticancer antibiotics" include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and DDS preparations thereof.

Examples of the "plant-derived anticancer agents" include etoposide, etoposide phosphate, vinblastine sulfate, vincristine sulfate, vindesine sulfate, teniposide, paclitaxel, docetaxel, vinorelbine, and DDS preparations thereof.

Examples of the "immunotherapeutic agents" include picibanil, krestin, sizofiran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole and anti-CTLA4 antibody.

Examples of the "cell growth factor" in the "drugs inhibiting the action of cell growth factors or receptors thereof" include any substances that promote cell proliferation, which are normally peptides having a molecular weight of not more than 20,000 that are capable of exhibiting their activity at low concentrations by binding to a receptor, and specific examples thereof include (1) EGF (epidermal growth factor) or substances possessing substantially the same activity as it [e.g., TGF-α], (2) insulin or substances possessing substantially the same activity as it [e.g., insulin, IGF (insulin-like growth factor)-1, IGF-2], (3) FGF (fibroblast growth factor) or substances possessing substantially the same activity as it [e.g., acidic FGF, basic FGF, KGF (keratinocyte growth factor), FGF-10], and (4) other cell growth factors [e.g., CSF (colony stimulating factor), EPO (erythropoietin), IL-2 (interleukin-2), NGF (nerve growth factor), PDGF (platelet-derived growth factor), TGF β (transforming growth factor β), HGF (hepatocyte growth factor), VEGF (vascular endothelial growth factor), heregulin, angiopoietin].

Examples of the "cell growth factor receptors" include any receptors capable of binding to the aforementioned cell growth factors, and specific thereof include EGF receptor, heregulin receptor (HER3, etc.), insulin receptor, IGF receptor-1, IGF receptor-2, FGF receptor-1 or FGF receptor-2, VEGF receptor, angiopoietin receptor (Tie2 etc.), PDGF receptor, and the like.

Examples of the "drugs inhibiting the action of cell growth factors or receptors thereof" include EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor inhibitor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Trk inhibitor, Ret inhibitor, mTOR inhibitor, Aurora inhibitor, PLK inhibitor, MEK (MEK1/2) inhibitor, MET inhibitor, CDK inhibitor, Akt inhibitor, ERK inhibitor and the like. More specific examples thereof include anti-VEGF antibody (e.g., Bevacizumab), anti-HER2 antibody (e.g., Trastuzumab, Pertuzumab), anti-EGFR antibody (e.g., Cetuximab, Panitumumab, Matuzumab, Nimotuzumab), anti-VEGFR antibody, anti-HGF antibody, Imatinib mesylate, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino) pyridine-3-carboxamide (AMG-706), Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), 2-[N-[3-[4-[5-[N-(3-fluorophenyl) carbamoylmethyl]-1H-pyrazol-3-ylamino]quinazoline-7-yloxy]propyl]-N-ethylamino]ethyl phosphate (AZD-1152), 4-[9-chloro-7-(2,6-difluorophenyl)-5H-primido[5,4-d][2] benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 2-hydroxyethyl 5-(4-bromo-2-chlorophenylamino)-4-fluoro-1-methyl-1H-benzimidazole-6-carbohydroxamate (AZD-6244), N-[2(R), 3-dihydroxypropoxy]-3,4-difluoro-2-(2-fluoro-4-iodophenylamino)benzamide (PD-0325901), everolimus (RAD001) and the like.

In addition to the aforementioned drugs, L-asparaginase, aceglatone, procarbazine hydrochloride, protoporphyrin-cobalt complex salt, mercuric hematoporphyrin-sodium, topoisomerase I inhibitor (e.g., irinotecan, topotecan), topoisomerase II inhibitor (e.g., sobuzoxane), differentiation inducer (e.g., retinoid, vitamin D), other angiogenesis inhibitor (e.g., fumagillin, shark extract, COX-2 inhibitor), α-blocker (e.g., tamsulosin hydrochloride), bisphosphonic acid (e.g., pamidronate, zoledronate), thalidomide, 5-azacytidine, decitabine, proteasome inhibitor (e.g., bortezomib), antitumor antibody such as anti-CD20 antibody and the like, toxin labeled antibody and the like can also be used as concomitant drugs.

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer,
(4) a sustained treatment effect can be designed,
(5) a synergistic effect can be afforded by a combined use of the compound of the present invention and a concomitant drug, and the like, can be achieved.

Hereinafter, the compound of the present invention and a concomitant drug used in combination are referred to as the "combination agent of the present invention".

For use of the combination agent of the present invention, the administration time of the compound of the present invention and the concomitant drug is not restricted, and the compound of the present invention and the concomitant drug can be administered to the administration subject simultaneously, or may be administered at different times. For administration in a staggered manner, the time difference varies depending on the active ingredient to be administered, dosage form and administration method. For example, when a concomitant drug is administered first, the compound of the present invention can be administered in 1 min to 3 days, preferably 10 min to 1 day, more preferably 15 min to 1 hr, after administration of the concomitant drug. When the compound of the present invention is administered first, the concomitant drug can be administered in 1 min to 1 day, preferably 10 min to 6 hr, more preferably 15 min to 1 hr, after administration of the compound of the present invention. The dosage of the concomitant drug may be determined according to the dose clinically used, and can be appropriately selected depending on the administration subject, administration route, disease, combination and the like.

Examples of the administration mode of the compound of the present invention and the concomitant drug include the following:
(1) administration of a single preparation obtained by simultaneously processing the compound of the present invention and the concomitant drug,
(2) simultaneous administration of two kinds of preparations of the compound of the present invention and the concomitant drug, which have been separately produced, by the same administration route,
(3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes,
(5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug is appropriately determined in accordance with its clinical dose. The ratio of the compound of the present invention and the concomitant drug is appropriately determined depending on the administration subject, administration route, target disease, symptom, combination, and the like. For example, when the administration subject is human, the concomitant drug is used in 0.01 to 100 (parts by weight), relative to 1 part by weight of the compound of the present invention.

The combination drug of the present invention is low toxic and can be safely administered orally or parenterally (e.g., topical, rectal, intravenous), for example, after admixing the compound of the present invention and/or the aforementioned concomitant drug with a pharmacologically acceptable carrier to give a pharmaceutical composition such as tablets (including sugar-coated tablets and film-coated tablets), powders, granules, capsules (including soft capsules), liquids, injections, suppositories and sustained-release agents, according to a method known per se, to a mammal (e.g., mouse, rat, hamster, rabbit, cat, dog, bovine, sheep, monkey, human). Injection can be administered by intravenous, intramuscular, subcutaneous or intraorgan administration or directly to the lesion.

Examples of the pharmacologically acceptable carrier which is used for preparing the combination agent of the present invention include those similar to the aforementioned pharmacologically acceptable carriers that are used for the preparation of the medicament of the present invention.

The mixing ratio of the compound of the present invention and the concomitant drug in the combination drug of the present invention can be appropriately determined according to the subject of administration, administration route, disease and the like.

For example, the content of the compound of the present invention in the combination drug of the present invention varies depending on the form of preparation, and is usually from about 0.01% by weight to 100% by weight, preferably from about 0.1% by weight to 50% by weight, more preferably from about 0.5% by weight to 20% by weight, relative to the total of the preparation.

The content of the concomitant drug in the combination drug of the present invention varies depending on the form of preparation, and is usually from about 0.01% by weight to 90% by weight, preferably from about 0.1% by weight to 50% by weight, more preferably from about 0.5% by weight to 20% by weight, relative to the total of the preparation.

The content of additive in the combination drug of the present invention varies depending on the form of preparation, and is usually from about 1% by weight to 99.99% by weight, preferably from about 10% by weight to 90% by weight, to the total of the preparation.

When the compound of the present invention and the concomitant drug are formulated separately, the same contents may be adopted.

The combination drug of the present invention can be produced by a method known per se, which is generally used in the technical field of pharmaceutical preparations.

The compound of the present invention is preferably molded into an oral administration preparation such as a solid preparation (e.g., powder, granule, tablet, capsule) and the like, or molded into a rectal administration preparation such as a suppository. Particularly, an oral administration preparation is preferable.

The concomitant drug can be made into the above-mentioned dosage form depending on the kind of the drug.

The dose of the combination drug of the present invention differs depending on the kind of the compound of the present invention; age, body weight, condition of the patient; dosage form, administration method, administration period etc., and for example, for a cancer patient (adult, body weight: about 60 kg), the combination drug is administered intravenously, at a dose of about 0.01 to about 1,000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times a day in divided portions. Of course, since the dose as described above varies depending on various conditions, it may be sometimes sufficient to administer smaller amounts than the above-mentioned dosage, and further, it may be sometimes necessary to administer greater amounts than that.

The amount of the concomitant drug can be set at any value unless side effects are problematical. The daily dosage in terms of the combination drug differs depending on the severity of symptoms, age, sex, body weight, sensitivity difference of the subject, administration time and interval, property, prescription, and kind of the pharmaceutical preparation, kind of effective ingredient, etc., and not particularly limited; for example, in the case of oral administration, the dose of the drug is usually from about 0.001 mg to 2,000 mg, preferably from about 0.01 mg to 500 mg, further preferably from about 0.1 mg to 100 mg, per 1 kg body weight of a mammal, which is usually administered once to four times a day in divided portions.

Furthermore, the compound of the present invention or the combination agent of the present invention can be used concurrently with a non-drug therapy. To be precise, the compound of the present invention or the combination agent of the present invention can be combined with a non-drug therapy such as (1) surgery, (2) hypertensive chemotherapy using angiotensin II etc., (3) gene therapy, (4) thermotherapy, (5) cryotherapy, (6) laser cauterization and (7) radiotherapy.

For example, by using the compound of the present invention or the combination agent of the present invention before and after the aforementioned operation and the like, or by using before and after a treatment combining two or three kinds thereof, effects of prevention of resistance expression, elongation of Disease-Free Survival, suppression of cancer metastasis or recurrence, apothanasia and the like can be obtained.

In addition, a treatment with the compound of the present invention or the combination agent of the present invention can be combined with a supporting therapy [(i) administration of antibiotic (e.g., β-lactams such as pansporin and the like, macrolides such as clarithromycin and the like) for complication with various infectious diseases, (ii) administration of high-calorie infusion, amino acid preparation or general vitamin preparation for malnutrition improvement, (iii) administration of morphine for pain mitigation, (iv) administration of medicament for ameliorating side effects such as nausea, vomiting, anorexia, diarrhea, leucopenia, thrombocytopenia, hemoglobin concentration decrease, hair loss, hepatopathy, renopathy, DIC, fever and the like, and (v) administration of medicament for suppressing multiple drug resistance of cancer etc.].

Preferably, the compound of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described supporting therapy is conducted.

In the case of administration of the compound of the present invention or the combination agent of the present invention before the surgery, etc., for example, the compound of the present invention or the combination agent of the present invention can be administrated once about 30 min to 24 hr before the surgery, etc., or once to three times in divided portions about 3 to 6 months before the surgery, etc. In this way, the surgery, etc. can be conducted easily because, for example, a cancer tissue can be reduced by administering the compound of the present invention or the combination agent of the present invention before the surgery, and the like.

In the case of administration of the compound of the present invention or the combination agent of the present invention after the surgery and the like, for example, it can be administrated repeatedly about 30 min to 24 hr after the surgery, and the like in a unit of several weeks to 3 months. In this way, the effect of the surgery and the like can be enhanced by administering the compound of the present invention or the combination agent of the present invention after the surgery and the like.

EXAMPLES

The present invention is explained in more detail in the following by referring to Examples, Experimental Examples and Formulation Examples, which are not to be construed as limitative, and the invention may be changed within the scope of the present invention.

In the following Examples, the "room temperature" generally shows about 10° C. to about 35° C. The ratios for mixed solvents show, unless otherwise specified, volume mixing ratios. Unless otherwise specified, % shows wt %.

In silica gel column chromatography, basic silica gel column chromatography means use of aminopropylsilane-bound silica gel. $^1$H-NMR (proton nuclear magnetic resonance spectrum) was measured by Fourier transform NMR. Very mild peaks of protons in hydroxyl group, an amino group and the like are not described.

The abbreviations in the Examples and Experimental Examples follow general examples currently used in this technical field and mean, for example, the following.

s: singlet
d: doublet
t: triplet
q: quartet
dd: double doublet
m: multiplet
brs: broad singlet
J: coupling constant
DMSO: dimethyl sulfoxide
Hz: hertz
CDCl$_3$: deuteriochloroform
$^1$H-NMR: proton nuclear magnetic resonance
SDS: sodium dodecyl sulfate
PAGE: polyacrylamide gel electrophoresis
PVDF: polyvinylidene fluoride
HRP: Horseradish Peroxidase SEQ ID NOs in the Sequence Listing of the present specification shows the following sequences.
(SEQ ID NO: 1) base sequence of primer used in Experimental Example 1
(SEQ ID NO: 2) base sequence of primer used in Experimental Example 1
(SEQ ID NO: 3) base sequence of primer used in Experimental Example 1
(SEQ ID NO: 4) base sequence of primer used in Experimental Example 1

Example 1

Production of 2-(2-chlorophenyl)-6-(5-methyl-1H-pyrazol-4-yl)thieno[3,2-d]pyrimidin-4 (3H)-one A) Production of methyl 3-[(trifluoroacetyl)amino]thiophene-2-carboxylate To a solution of methyl 3-aminothiophene-2-carboxylate (50 g) in acetonitrile (650 mL) were added pyridine (31 mL) and trifluoroacetic anhydride (58.6 mL) while stirring under ice-cooling, and the mixture was stirred at 0° C. for 5 min. After stirring, the reaction system was allowed to warm to room temperature and, 10 min later, poured into ice water (6 L). After stirring for 20 min, the precipitate was collected by filtration and washed with water to give the title compound (80 g) as a pale-brown solid.

$^1$H-NMR (DMSO-d$_6$) δ 3.86 (3H, s), 7.72 (1H, d, J=5.4 Hz), 8.03 (1H, d, J=5.4 Hz), 11.17 (1H, brs).

B) Production of methyl 5-bromo-3-[(trifluoroacetyl)amino]thiophene-2-carboxylate To a solution of diisopropylamine (20 mL) in tetrahydrofuran (200 mL) was added 1.6M n-butyllithium/hexane solution (82.4 mL) while stirring under ice-cooling, and the mixture was stirred at 0° C. for 15 min. After stirring, the reaction system was cooled to −78° C., and a solution of methyl 3-[(trifluoroacetyl)amino]thiophene-2-carboxylate (10 g) in tetrahydrofuran (50 mL) was added dropwise. After the completion of the dropwise addition, the mixture was stirred at the same temperature for 1 hr, and 1,2-dibromoethane (20.6 mL) was added. After stirring at the same temperature for 30 min, the reaction system was allowed to warm to room temperature, and further stirred for 30 min. The reaction system was poured into saturated aqueous sodium hydrogen carbonate (600 mL), and the mixture was extracted with ethyl acetate, washed with brine, and dried over anhydrous sodium sulfate. Insoluble material was removed by filtration, and the filtrate was concentrated under reduced pressure. The residue was purified by silica gel column chromatography (ethyl acetate/hexane) to give the title compound (5.3 g) as a yellow solid.

$^1$H-NMR (CDCl$_3$) δ 3.94 (3H, s), 8.11 (1H, s), 11.15 (1H, brs).

C) Production of methyl 3-amino-5-bromothiophene-2-carboxylate

A mixture of methyl 5-bromo-3-[(trifluoroacetyl)amino]thiophene-2-carboxylate (5.3 g), potassium carbonate (10 g), methanol (100 mL) and water (25 mL) was stirred at room temperature for 2 hr. The reaction system was concentrated under reduced pressure, and ethyl acetate and water were poured thereinto. The mixture was extracted with ethyl acetate, washed with brine, and dried over anhydrous sodium sulfate. Insoluble material was removed by filtration, and the filtrate was concentrated under reduced pressure. The residue was purified by silica gel column chromatography (ethyl acetate/hexane) to give the title compound (3.3 g) as a yellow solid.

$^1$H-NMR (DMSO-$d_6$) δ 3.70 (3H, s), 6.68 (2H, brs), 6.75 (1H, s).

D) Production of 3-amino-5-bromothiophene-2-carboxamide

A mixture of methyl 3-amino-5-bromothiophene-2-carboxylate (5.76 g), sodium hydroxide (2.94 g), water (25 mL) and methanol (100 mL) was stirred at 70° C. overnight. The reaction system was ice-cooled, 6M hydrochloric acid (8.17 mL) was added, and the mixture was concentrated under reduced pressure. Ammonium chloride (26.3 g), triethylamine (49.7 g) and N,N-dimethylformamide (230 mL) were added to the residue, and the mixture was stirred at room temperature for 5 min. To the reaction system were added 1-ethyl-3-(3-dimethylaminopropyl)carbodiimide hydrochloride (28.2 g) and 1-hydroxybenzotriazole (19.9 g), and the mixture was stirred at room temperature for 5 days. The reaction system was poured into saturated aqueous sodium hydrogen carbonate (700 mL), and the mixture was extracted with ethyl acetate (700 mL), washed with saturated aqueous sodium hydrogen carbonate, and dried over anhydrous magnesium sulfate. Insoluble material was removed by filtration, and the filtrate was concentrated under reduced pressure. The residue was purified by silica gel column chromatography (ethyl acetate/hexane) to give the title compound (4.1 g) as a yellow solid.

$^1$H-NMR (300 MHz, DMSO-$d_6$) δ 6.56 (2H, brs), 6.70 (1H, s), 6.91 (2H, brs).

E) Production of 6-bromo-2-(2-chlorophenyl)thieno [3,2-d]pyrimidin-4 (3H)-one

A mixture of 3-amino-5-bromothiophene-2-carboxamide (100 mg), 2-chlorobenzoylchloride (57 μL), N,N-dimethylpyridin-4-amine (55 mg), pyridine (1.0 mL) and N,N-dimethylformamide (2.0 mL) was stirred at 70° C. for 1.5 hr. The reaction system was concentrated under reduced pressure, 2M aqueous sodium hydroxide solution was added to the residue, and the mixture was heated to 120° C. After 1 hr, insoluble material was removed by filtration, and the filtrate was neutralized with 1M hydrochloric acid. The precipitate was collected by filtration and washed with water to give the title compound (120 mg) as a dark orange solid.

$^1$H-NMR (DMSO-$d_6$) δ 7.44-7.67 (4H, m), 7.69 (1H, s), 13.04 (1H, brs).

F) Production of 2-(2-chlorophenyl)-6-(5-methyl-1H-pyrazol-4-yl)thieno[3,2-d]pyrimidin-4 (3H)-one 6-Bromo-2-(2-chlorophenyl)thieno[3.2-d]pyrimidin-4 (3H)-one (157 mg), tert-butyl 3-methyl-4-(4,4,5,5-tetramethyl-1,3,2-dioxaborolan-2-yl)-1H-pyrazole-1-carboxylate (425 mg), sodium carbonate (138 mg), 1,2-dimethoxyethane (4.0 mL) and water (2.0 mL) were placed in a flask, and the atmosphere in the flask was purged with argon. [1,1'-Bis(diphenylphosphino)ferrocene]palladium(II) dichloride-dichloromethane complex (1:1) (38 mg) was added, and the atmosphere in the flask was purged again with argon. The reaction system was stirred at 100° C. for 1 hr, 8M aqueous sodium hydroxide solution (1 mL) was added, and the mixture was stirred at 100° C. for 30 min. After stirring, the mixture was extracted with ethyl acetate/tetrahydrofuran mixture, and the extract was concentrated under reduced pressure. The residue was purified by silica gel column chromatography (ethyl acetate/hexane), and the obtained pale-yellow solid was crystallized from methanol/ethyl acetate to give the title compound (43 mg) as a yellow solid.

$^1$H-NMR (DMSO-$d_6$) δ 2.43 (3H, brs), 7.43-7.69 (5H, m), 7.92 (0.6H, brs), 8.30 (0.4H, brs), 12.78 (1H, brs), 13.03 (1H, brs).

Example 2

Production of 6-(5-methyl-1H-pyrazol-4-yl)-2-(pyrrolidin-1-ylmethyl)thieno[3,2-d]pyrimidin-4 (3H)-one A) Production of 6-bromo-2-(chloromethyl)thieno[3,2-d]pyrimidin-4 (3H)-one A mixture of methyl 3-amino-5-bromothiophene-2-carboxylate (15 g) produced in Example 1, step C, chloroacetonitrile (12 mL) and 4M hydrochloric acid/cyclopentylmethylether solution (100 mL) was stirred at room temperature for 2 hr, and stirred at 70° C. for 1 hr. The reaction system was concentrated under reduced pressure, and saturated aqueous sodium hydrogen carbonate was added to the residue. The precipitate was collected by filtration and washed with water. The obtained solid was dried at 80° C. for 8 hr under reduced pressure to give the title compound (18 g) as a pale-brown solid.

$^1$H-NMR (DMSO-$d_6$) δ 4.51 (2H, s), 7.56 (1H, s), 13.00 (1H, brs).

B) Production of 6-bromo-2-(pyrrolidin-1-ylmethyl)thieno[3,2-d]pyrimidin-4 (3H)-one To a mixture of pyrrolidine (2.2 mL), potassium carbonate (2.5 g), sodium iodide (134 mg) and N,N-dimethylformamide (40 mL) was added 6-bromo-2-(chloromethyl)thieno[3,2-d]pyrimidin-4 (3H)-one (2.5 g), and the mixture was stirred at 70° C. for 30 min. Insoluble material was removed by filtration, the filtrate was concentrated under reduced pressure, and the residue was washed with a small amount of ethyl acetate to give the title compound (1.5 g) as a pale-yellow solid. The filtrate was purified by basic silica gel column chromatography (methanol/ethyl acetate) to give the title compound (0.87 g) as a pale-yellow solid. The total yield of the title compound was 2.37 g.

$^1$H-NMR (DMSO-$d_6$) δ 1.65-1.77 (4H, m), 2.52-2.60 (4H, m), 3.57 (2H, s), 7.60 (1H, s), 12.24 (1H, brs).

C) Production of 6-(5-methyl-1H-pyrazol-4-yl)-2-(pyrrolidin-1-ylmethyl)thieno[3,2-d]pyrimidin-4 (3H)-one 6-Bromo-2-(pyrrolidin-1-ylmethyl)thieno[3,2-d]pyrimidin-4 (3H)-one (100 mg), tert-butyl 3-methyl-4-(4,4,5,5-tetramethyl-1,3,2-dioxaborolan-2-yl)-1H-pyrazole-1-carboxylate (294 mg), sodium carbonate (95 mg), 1,2-dimethoxyethane (3.0 mL) and water (1.5 mL) were placed in a flask, and the atmosphere in the flask was purged with argon. [1,1'-Bis(diphenylphosphino)ferrocene]palladium(II) dichloride-dichloromethane complex (1:1) (26 mg) was added, and the atmosphere in the flask was purged again with argon. The reaction system was stirred at 100° C. for 3 hr, 8M aqueous sodium hydroxide solution (1 mL) was added, and the mixture was stirred at 100° C. for 30 min. After stirring, the mixture was extracted with ethyl acetate/tetrahydrofuran mixture, and the extract was dried over anhydrous sodium sulfate. Insoluble material was removed by filtration, and the filtrate was concentrated under reduced pressure. The residue was purified by basic silica gel column chromatography (ethyl acetate/hexane and methanol/ethyl acetate), and the obtained pale-yellow solid was crystallized from methanol/ethyl acetate to give the title compound (44 mg) as a pale-yellow solid.

$^1$H-NMR (DMSO-$d_6$) δ 1.65-1.78 (4H, m), 2.45 (3H, s), 2.53-2.59 (4H, m), 3.57 (2H, s), 7.37 (1H, s), 8.00 (1H, brs), 11.84-13.16 (2H, m).
MS(ESI+): [M+H]$^+$316.
MS(ESI+), found: 316.

Example 3

Production of 6-(5-methyl-1H-pyrazol-4-yl)-2-phenylthieno[3,2-d]pyrimidin-4 (3H)-one A) Production of 6-bromo-2-phenylthieno[3,2-d]pyrimidin-4 (3H)-one In the same manner as in Example 1, step E, the title compound (111 mg) was obtained as a yellow solid from 3-amino-5-bromothiophene-2-carboxamide (120 mg) and benzoyl chloride (0.063 mL), N,N-dimethylpyridine-4-amine (66 mg), pyridine (1.0 mL) and N,N-dimethylformamide (2.0 mL).

$^1$H-NMR (DMSO-$d_6$) δ 7.50-7.61 (3H, m), 7.70 (1H, s), 8.07-8.14 (2H, m), 12.87 (1H, brs).

B) Production of 6-(5-methyl-1H-pyrazol-4-yl)-2-phenylthieno[3,2-d]pyrimidin-4 (3H)-one In the same manner as in Example 1, step F, the title compound (51 mg) was obtained as a pale-yellow solid from 6-bromo-2-phenylthieno[3,2-d]pyrimidin-4 (3H)-one (110 mg) and tert-butyl 3-methyl-4-(4,4,5,5-tetramethyl-1,3,2-dioxaborolan-2-yl)-1H-pyrazole-1-carboxylate (331 mg), sodium carbonate (107 mg), 1,2-dimethoxyethane (3.0 mL) and water (1.5 mL) and [1,1'-bis(diphenylphosphino)ferrocene]palladium(II) dichloride-dichloromethane complex (1:1) (29 mg).

$^1$H-NMR (DMSO-$d_6$) δ 2.49 (3H, brs), 7.49 (1H, s), 7.51-7.65 (3H, m), 7.94 (0.6H, brs), 8.10-8.20 (2H, m), 8.29 (0.4H, brs), 12.65 (1H, brs), 13.02 (1H, brs).

Example 4

Production of 2-{[(3S)-3-fluoropyrrolidin-1-yl]methyl}-6-(5-methyl-1H-pyrazol-4-yl)thieno[3,2-d]pyrimidin-4 (3H)-one A) Production of 6-bromo-2-{[(3S)-3-fluoropyrrolidin-1-yl]methyl}thieno[3,2-d]pyrimidin-4 (3H)-one In the same manner as in Example 2, step B, the title compound (197 mg) was obtained as a pale-yellow solid from 6-bromo-2-(chloromethyl)thieno[3,2-d]pyrimidin-4 (3H)-one (200 mg) produced in Example 2, step A, (3S)-3-fluoropyrrolidine hydrochloride (270 mg), potassium carbonate (494 mg), sodium iodide (10 mg) and N,N-dimethylformamide (4.0 mL).

$^1$H-NMR (DMSO-$d_6$) δ 1.75-2.28 (2H, m), 2.44-2.54 (1H, m), 2.67-2.98 (3H, m), 3.61 (2H, s), 4.96-5.48 (1H, m), 7.62 (1H, s), 12.42 (1H, brs).

B) Production of 2-{[(3S)-3-fluoropyrrolidin-1-yl]methyl}-6-(5-methyl-1H-pyrazol-4-yl)thieno[3,2-d]pyrimidin-4 (3H)-one In the same manner as in Example 2, step C, the title compound (93 mg) was obtained as a pale-yellow solid from 6-bromo-2-{[(3S)-3-fluoropyrrolidin-1-yl]methyl}thieno[3,2-d]pyrimidin-4 (3H)-one (192 mg) and tert-butyl 3-methyl-4-(4,4,5,5-tetramethyl-1,3,2-dioxaborolan-2-yl)-1H-pyrazole-1-carboxylate (392 mg), sodium carbonate (139 mg), 1,2-dimethoxyethane (4.0 mL) and water (2.0 mL) and [1,1'-bis(diphenylphosphino)ferrocene]palladium(II) dichloride-dichloromethane complex (1:1) (47 mg).

$^1$H-NMR (DMSO-$d_6$) δ 1.75-2.30 (2H, m), 2.45 (3H, brs), 2.48-2.55 (1H, m), 2.69-3.04 (3H, m), 3.61 (2H, s), 4.97-5.45 (1H, m), 7.38 (1H, s), 7.89 (1H, brs), 12.19 (1H, brs), 12.99 (1H, brs).

Example 5

Production of 2-{[(3R)-3-fluoropyrrolidin-1-yl]methyl}-6-(5-methyl-1H-pyrazol-4-yl)thieno[3,2-d]pyrimidin-4 (3H)-one A) Production of 6-bromo-2-{[(3R)-3-fluoropyrrolidin-1-yl]methyl}thieno[3,2-d]pyrimidin-4 (3H)-one In the same manner as in Example 2, step B, the title compound (192 mg) was obtained as a pale-yellow solid from 6-bromo-2-(chloromethyl)thieno[3,2-d]pyrimidin-4 (3H)-one (200 mg) produced in Example 2, step A, (3R)-3-fluoropyrrolidine hydrochloride (270 mg), potassium carbonate (494 mg), sodium iodide (10 mg) and N,N-dimethylformamide (4.0 mL).

$^1$H-NMR (DMSO-$d_6$) δ 1.75-2.26 (2H, m), 2.41-2.51 (1H, m), 2.67-2.97 (3H, m), 3.60 (2H, s), 5.03-5.37 (1H, m), 7.61 (1H, s), 12.44 (1H, brs).

B) Production of 2-{[(3R)-3-fluoropyrrolidin-1-yl]methyl}-6-(5-methyl-1H-pyrazol-4-yl)thieno[3,2-d]pyrimidin-4 (3H)-one In the same manner as in Example 2, step C, the title compound (68 mg) was obtained as a pale-yellow solid from 6-bromo-2-{[(3R)-3-fluoropyrrolidin-1-yl]methyl}thieno[3,2-d]pyrimidin-4 (3H)-one (192 mg) and tert-butyl 3-methyl-4-(4,4,5,5-tetramethyl-1,3,2-dioxaborolan-2-yl)-1H-pyrazole-1-carboxylate (392 mg), sodium carbonate (139 mg), 1,2-dimethoxyethane (4.0 mL) and water (2.0 mL) and [1,1'-bis(diphenylphosphino)ferrocene]palladium(II) dichloride-dichloromethane complex (1:1) (47 mg).

$^1$H-NMR (DMSO-$d_6$) δ 1.75-2.27 (2H, m), 2.45 (3H, brs), 2.48-2.57 (1H, m), 2.69-3.01 (3H, m), 3.61 (2H, s), 5.03-5.38 (1H, m), 7.38 (1H, s), 7.97 (1H, brs), 12.17 (1H, brs), 12.98 (1H, brs).

Example 6

Production of 2-{[(3R)-3-hydroxypyrrolidin-1-yl]methyl}-6-(5-methyl-1H-pyrazol-4-yl)thieno[3,2-d]pyrimidin-4 (3H)-one A) Production of 6-bromo-2-{[(3R)-3-hydroxypyrrolidin-1-yl]methyl}thieno[3,2-d]pyrimidin-4 (3H)-one In the same manner as in Example 2, step B, the title compound (129 mg) was obtained as a pale-yellow solid from 6-bromo-2-(chloromethyl)thieno[3,2-d]pyrimidin-4 (3H)-one (180 mg) produced in Example 2, step A, (3R)-pyrrolidin-3-ol (0.16 mL), potassium carbonate (178 mg), sodium iodide (9.7 mg) and N,N-dimethylformamide (3.0 mL).

$^1$H-NMR (DMSO-$d_6$) δ 1.40-1.67 (1H, m), 1.88-2.11 (1H, m), 2.39-2.49 (2H, m), 2.65-2.80 (2H, m), 3.58 (2H, s), 4.11-4.22 (1H, m), 4.85 (1H, brs), 7.60 (1H, s), 12.27 (1H, brs).

B) Production of 2-{[(3R)-3-hydroxypyrrolidin-1-yl]methyl}-6-(5-methyl-1H-pyrazol-4-yl)thieno[3,2-d]pyrimidin-4 (3H)-one In the same manner as in Example 2, step C, the title compound (20 mg) was obtained as a brown solid from 6-bromo-2-{[(3R)-3-hydroxypyrrolidin-1-yl]methyl}thieno[3,2-d]pyrimidin-4 (3H)-one (125 mg) and tert-butyl 3-methyl-4-(4,4,5,5-tetramethyl-1,3,2-dioxaborolan-2-yl)-1H-pyrazole-1-carboxylate (257 mg), sodium carbonate (91 mg), 1,2-dimethoxyethane (3.0 mL) and water (1.5 mL) and [1,1'-bis(diphenylphosphino)ferrocene]palladium(II) dichloride-dichloromethane complex (1:1) (31 mg).

$^1$H-NMR (DMSO-$d_6$) δ 1.48-1.65 (1H, m), 1.92-2.12 (1H, m), 2.41-2.49 (5H, m), 2.68-2.82 (2H, m), 3.58 (2H, s), 4.11-4.25 (1H, m), 7.35 (1H, s), 8.02 (1H, brs), 12.22-13.36 (2H, m).

Example 7

Production of 2-{[(3S)-3-hydroxypyrrolidin-1-yl]methyl}-6-(5-methyl-1H-pyrazol-4-yl)thieno[3,2-d]pyrimidin-4 (3H)-one

A) Production of 6-bromo-2-{[(3S)-3-hydroxypyrrolidin-1-yl]methyl}thieno[3,2-d]pyrimidin-4 (3H)-one In the same manner as in Example 2, step B, the title compound (99 mg) was obtained as a pale-yellow solid from 6-bromo-2-(chloromethyl)thieno[3,2-d]pyrimidin-4 (3H)-one (180 mg) produced in Example 2, step A, (3S)-pyrrolidin-3-ol (0.16 mL), potassium carbonate (178 mg), sodium iodide (9.7 mg) and N,N-dimethylformamide (3.0 mL).

$^1$H-NMR (DMSO-$d_6$) δ 1.49-1.66 (1H, m), 1.90-2.11 (1H, m), 2.39-2.49 (2H, m), 2.65-2.82 (2H, m), 3.59 (2H, s), 4.10-4.24 (1H, m), 4.85 (1H, brs), 7.60 (1H, s), 12.11 (1H, brs).

B) Production of 2-{[(3S)-3-hydroxypyrrolidin-1-yl]methyl}-6-(5-methyl-1H-pyrazol-4-yl)thieno[3,2-d]pyrimidin-4 (3H)-one In the same manner as in Example 2, step C, the title compound (36 mg) was obtained as a brown solid from 6-bromo-2-{[(3S)-3-hydroxypyrrolidin-1-yl]methyl}thieno[3,2-d]pyrimidin-4 (3H)-one (95 mg) and tert-butyl 3-methyl-4-(4,4,5,5-tetramethyl-1,3,2-dioxaborolan-2-yl)-1H-pyrazole-1-carboxylate (195 mg), sodium carbonate (69 mg), 1,2-dimethoxyethane (2.0 mL) and water (1.0 mL) and [1,1'-bis(diphenylphosphino)ferrocene]palladium(II) dichloride-dichloromethane complex (1:1) (24 mg).

$^1$H-NMR (DMSO-$d_6$) δ 1.46-1.67 (1H, m), 1.92-2.09 (1H, m), 2.40-2.48 (5H, m), 2.69-2.83 (2H, m), 3.57 (2H, s), 4.11-4.25 (1H, m), 7.33 (1H, s), 8.00 (1H, brs), 12.49-13.20 (2H, m).

Example 8

Production of 2-[(3,3-difluoropyrrolidin-1-yl)methyl]-6-(5-methyl-1H-pyrazol-4-yl)thieno[3,2-d]pyrimidin-4 (3H)-one

A) Production of 6-bromo-2-[(3,3-difluoropyrrolidin-1-yl)methyl]thieno[3,2-d]pyrimidin-4 (3H)-one In the same manner as in Example 2, step B, the title compound (162 mg) was obtained as a pale-yellow solid from 6-bromo-2-(chloromethyl)thieno[3,2-d]pyrimidin-4 (3H)-one (180 mg) produced in Example 2, step A, 3,3-difluoropyrrolidine hydrochloride (277 mg), potassium carbonate (445 mg), sodium iodide (9.7 mg) and N,N-dimethylformamide (3.0 mL).

$^1$H-NMR (DMSO-$d_6$) δ 2.13-2.36 (2H, m), 2.83 (2H, t, J=7.0 Hz), 3.04 (2H, t, J=13.5 Hz), 3.62 (2H, s), 7.62 (1H, s), 12.51 (1H, brs).

B) Production of 2-[(3,3-difluoropyrrolidin-1-yl)methyl]-6-(5-methyl-1H-pyrazol-4-yl)thieno[3,2-d]pyrimidin-4 (3H)-one In the same manner as in Example 2, step C, the title compound (103 mg) was obtained as a pale-yellow solid from 6-bromo-2-[(3,3-difluoropyrrolidin-1-yl)methyl]thieno[3,2-d]pyrimidin-4 (3H)-one (162 mg) and tert-butyl 3-methyl-4-(4,4,5,5-tetramethyl-1,3,2-dioxaborolan-2-yl)-1H-pyrazole-1-carboxylate (314 mg), sodium carbonate (111 mg), 1,2-dimethoxyethane (3.0 mL) and water (1.5 mL) and [1,1'-bis(diphenylphosphino)ferrocene]palladium(II) dichloride-dichloromethane complex (1:1) (38 mg).

$^1$H-NMR (DMSO-$d_6$) δ 2.18-2.35 (2H, m), 2.46 (3H, brs), 2.85 (2H, t, J=6.9 Hz), 3.06 (2H, t, J=13.4 Hz), 3.63 (2H, s), 7.39 (1H, s), 7.90 (0.6H, brs), 8.26 (0.4H, brs), 12.25 (1H, brs), 12.98 (1H, brs).

Example 9

Production of 6-(5-methyl-1H-pyrazol-4-yl)-2-(piperidin-1-ylmethyl)thieno[3,2-d]pyrimidin-4 (3H)-one

A) Production of 6-bromo-2-(piperidin-1-ylmethyl)thieno[3,2-d]pyrimidin-4 (3H)-one In the same manner as in Example 2, step B, the title compound (175 mg) was obtained as a pale-yellow solid from 6-bromo-2-(chloromethyl)thieno[3,2-d]pyrimidin-4 (3H)-one (180 mg) produced in Example 2, step A, piperidine (0.19 mL), potassium carbonate (178 mg), sodium iodide (9.7 mg) and N,N-dimethylformamide (3.0 mL).

$^1$H-NMR (DMSO-$d_6$) δ 1.31-1.42 (2H, m), 1.45-1.56 (4H, m), 2.35-2.46 (4H, m), 3.40 (2H, s), 7.61 (1H, s), 12.20 (1H, brs).

B) Production of 6-(5-methyl-1H-pyrazol-4-yl)-2-(piperidin-1-ylmethyl)thieno[3,2-d]pyrimidin-4 (3H)-one In the same manner as in Example 2, step C, the title compound (56 mg) was obtained as a pale-brown solid from 6-bromo-2-(piperidin-1-ylmethyl)thieno[3,2-d]pyrimidin-4 (3H)-one (175 mg) and tert-butyl 3-methyl-4-(4,4,5,5-tetramethyl-1,3,2-dioxaborolan-2-yl)-1H-pyrazole-1-carboxylate (361 mg), sodium carbonate (128 mg), 1,2-dimethoxyethane (4.0 mL) and water (2.0 mL) and [1,1'-bis (diphenylphosphino)ferrocene]palladium(II) dichloride-dichloromethane complex (1:1) (44 mg).

$^1$H-NMR (DMSO-d$_6$) δ 1.30-1.44 (2H, m), 1.44-1.60 (4H, m), 2.40-2.48 (7H, m), 3.42 (2H, s), 7.38 (1H, s), 8.04 (1H, brs), 12.61 (2H, brs).

Example 10

Production of 6-(5-methyl-1H-pyrazol-4-yl)-2-(morpholin-4-ylmethyl)thieno[3,2-d]pyrimidin-4 (3H)-one A) Production of 6-bromo-2-(morpholin-4-ylmethyl)thieno[3,2-d]pyrimidin-4 (3H)-one In the same manner as in Example 2, step B, the title compound (110 mg) was obtained as a white solid from 6-bromo-2-(chloromethyl)thieno[3,2-d]pyrimidin-4 (3H)-one (180 mg) produced in Example 2, step A, morpholine (0.17 mL), potassium carbonate (178 mg), sodium iodide (9.7 mg) and N,N-dimethylformamide (3.0 mL).

$^1$H-NMR (DMSO-d$_6$) δ 2.44-2.49 (4H, m), 3.44 (2H, s), 3.54-3.64 (4H, m), 7.61 (1H, s), 12.40 (1H, brs).

B) Production of 6-(5-methyl-1H-pyrazol-4-yl)-2-(morpholin-4-ylmethyl)thieno[3,2-d]pyrimidin-4 (3H)-one In the same manner as in Example 2, step C, the title compound (34 mg) was obtained as a colorless solid from 6-bromo-2-(morpholin-4-ylmethyl)thieno[3,2-d]pyrimidin-4 (3H)-one (110 mg) and tert-butyl 3-methyl-4-(4,4,5,5-tetramethyl-1,3,2-dioxaborolan-2-yl)-1H-pyrazole-1-carboxylate (226 mg), sodium carbonate (80 mg), 1,2-dimethoxyethane (3.0 mL) and water (1.5 mL) and [1,1'-bis(diphenylphosphino)ferrocene]palladium(II) dichloride-dichloromethane complex (1:1) (27 mg).

$^1$H-NMR (DMSO-d$_6$) δ 2.39-2.48 (7H, m), 3.45 (2H, s), 3.54-3.64 (4H, m), 7.38 (1H, s), 7.88 (0.6H, brs), 8.23 (0.4H, brs), 12.11 (1H, brs), 12.96 (1H, brs).

Example 11

Production of 6-(5-methyl-1H-pyrazol-4-yl)-2-[(2S)-pyrrolidin-2-yl]thieno[3,2-d]pyrimidin-4 (3H)-one monotrifluoroacetate A) Production of tert-butyl(2S)-2-(6-bromo-4-oxo-3,4-dihydrothieno[3,2-d]pyrimidin-2-yl)pyrrolidine-1-carboxylate A solution of 3-amino-5-bromothiophene-2-carboxamide (300 mg) produced in Example 1, step D, 1-(tert-butoxycarbonyl)-L-proline (700 mg), O-(7-azabenzotriazol-1-yl)-N,N,N',N'-tetramethyluronium hexafluorophosphate (1.55 g) and N-ethyl-N-(1-methylethyl)propan-2-amine (0.713 mL) in N,N-dimethylformamide (8 mL) was stirred at 90° C. for 16 hr. Ethyl acetate (40 mL) and aqueous sodium hydrogen carbonate (20 mL) were added to the reaction mixture, and the separated aqueous layer was extracted with ethyl acetate (10 mL). The combined organic layers were washed with brine (10 mL), and dried over anhydrous sodium sulfate. Insoluble material was filtered off, and the filtrate was concentrated under reduced pressure. The residue was purified by silica gel column chromatography (ethyl acetate/hexane) to give an inseparable mixture of tert-butyl(2S)-2-[(5-bromo-2-carbamoylthiophen-3-yl)carbamoyl]pyrrolidine-1-carboxylate and 3-amino-5-bromothiophene-2-carboxamide (starting material) as a yellow oil. To a solution of the mixture of tert-butyl(2S)-2-[(5-bromo-2-carbamoylthiophen-3-yl)carbamoyl]pyrrolidine-1-carboxylate and 3-amino-5-bromothiophene-2-carboxamide produced above in ethanol (6 mL) was added 2M aqueous sodium hydroxide solution (2.04 mL), and the mixture was stirred at 70° C. for 4 hr. 6M Hydrochloric acid (1 mL), ethyl acetate (20 mL) and aqueous sodium hydrogen carbonate (10 mL) were added to the reaction mixture, and the separated aqueous layer was extracted with ethyl acetate (5 mL×2). The combined organic layers were washed with brine (5 mL) and dried over anhydrous sodium sulfate. Insoluble material was filtered off, and the filtrate was concentrated under reduced pressure. The residue was purified by silica gel column chromatography (ethyl acetate/hexane) to give the title compound (175 mg) as a colorless solid.

$^1$H-NMR (DMSO-d$_6$) δ 1.12 (9H, s, major), 1.37 (9H, s, minor), 1.73-2.04 (3H, m), 2.18-2.36 (1H, m), 3.32-3.43 (1H, m), 3.48-3.59 (1H, m), 4.56 (1H, dd, J=7.6, 4.8 Hz, major), 4.60-4.66 (1H, m, minor), 7.60 (1H, s, minor), 7.63 (1H, s, major), 12.63 (1H, brs, minor), 12.72 (1H, brs, major). The ratio of the observed isomers was 2:1.

B) Production of 6-(5-methyl-1H-pyrazol-4-yl)-2-[(2S)-pyrrolidin-2-yl]thieno[3,2-d]pyrimidin-4 (3H)-one monotrifluoroacetate tert-Butyl(2S)-2-(6-bromo-4-oxo-3,4-dihydrothieno[3,2-d]pyrimidin-2-yl)pyrrolidine-1-carboxylate (173 mg), tert-butyl 3-methyl-4-(4,4,5,5-tetramethyl-1,3,2-dioxaborolan-2-yl)-1H-pyrazole-1-carboxylate (266 mg), cesium carbonate (282 mg), 1,2-dimethoxyethane (5 mL) and water (0.5 mL) were placed in a flask, and the atmosphere in the flask was purged with argon. [1,1'-Bis(diphenylphosphino)ferrocene]palladium(II) dichloride-dichloromethane complex (1:1, 71 mg) was added, the atmosphere in the flask was purged again with argon, and the mixture was stirred at 80° C. for 2 hr. Ethyl acetate (20 mL) and water (5 mL) were added to the reaction mixture, and the separated aqueous layer was extracted with ethyl acetate (5 mL×2). The combined organic layers were washed with brine (5 mL) and dried over anhydrous sodium sulfate. Insoluble material was filtered off, and the filtrate was concentrated under reduced pressure. The residue was purified by silica gel column chromatography (ethyl acetate/hexane), and the object fraction was concentrated under reduced pressure to give a mixture of tert-butyl 4-{2-[(2S)-1-(tert-butoxycarbonyl)pyrrolidin-2-yl]-4-oxo-3,4-dihydrothieno[3,2-d]pyrimidin-6-yl}-3-methyl-1H-pyrazole-1-carboxylate and tert-butyl(2S)-2-[6-(5-methyl-1H-pyrazol-4-yl)-4-oxo-3,4-dihydrothieno[3,2-d]pyrimidin-2-yl]pyrrolidine-1-carboxylate. A solution of the mixture of tert-butyl 4-{2-[(2S)-1-(tert-butoxycarbonyl)pyrrolidin-2-yl]-4-oxo-3,4-dihydrothieno[3,2-d]pyrimidin-6-yl}-3-methyl-1H-pyrazole-1-carboxylate and tert-butyl(2S)-2-[6-(5-methyl-1H-pyrazol-4-yl)-4-oxo-3,4-dihydrothieno[3,2-d]pyrimidin-2-yl]pyrrolidine-1-carboxylate produced above in trifluoroacetic acid (10 mL) was stirred at room temperature for 1 hr, and the mixture was concentrated under reduced pressure. The residue was crystallized from methanol/ethyl acetate (1 mL/4 mL) to give the title compound (129 mg) as a pale-brown solid.

$^1$H-NMR (DMSO-d$_6$) δ 1.93-2.15 (3H, m), 2.38-2.44 (1H, m), 2.46 (3H, brs), 3.35-3.50 (2H, m), 4.66 (1H, t, J=7.2 Hz), 7.37 (1H, s), 7.85-8.48 (1H, m), 8.99 (1H, brs), 9.52 (1H, brs), 12.80 (1H, brs), 13.06 (1H, brs).

MS(ESI+): [M+H]$^+$302.

MS(ESI+), found: 302.

Example 12

Production of 6-(5-methyl-1H-pyrazol-4-yl)-2-[(2R)-pyrrolidin-2-yl]thieno[3,2-d]pyrimidin-4 (3H)-one monotrifluoroacetate A) Production of tert-butyl(2R)-2-(6-bromo-4-oxo-3,4-dihydrothieno[3,2-d]pyrimidin-2-yl)pyrrolidine-1-carboxylate In the same manner as in Example 11, step A, the title compound (176 mg) was obtained as a white solid from 3-amino-5-bromothiophene-2-carboxamide (300 mg) produced in Example 1, step D and 1-(tert-butoxycarbonyl)-D-proline (878 mg) and O-(7-azabenzotriazol-1-yl)-N,N,N',N'-tetramethyluronium hexafluorophosphate (2.06 g) and N-ethyl-N-(1-methylethyl)propan-2-amine (0.95 mL) and N,N-dimethylformamide (8 mL).

$^1$H-NMR (DMSO-d$_6$) δ 1.12 (9H, s, major), 1.37 (9H, s, minor), 1.77-2.02 (3H, m), 2.19-2.34 (1H, m), 3.34-3.43 (1H, m), 3.47-3.59 (1H, m), 4.56 (1H, dd, J=7.6, 4.8 Hz, major), 4.62 (1H, dd, J=7.7, 3.4 Hz, minor), 7.59 (1H, s, minor), 7.62 (1H, s, major), 12.70 (1H, brs). The ratio of the observed isomers was 2:1.

B) Production of 6-(5-methyl-1H-pyrazol-4-yl)-2-[(2R)-pyrrolidin-2-yl]thieno[3,2-d]pyrimidin-4 (3H)-one monotrifluoroacetate In the same manner as in Example 11, step B, the title compound (121 mg) was obtained as a white solid from tert-butyl(2R)-2-(6-bromo-4-oxo-3,4-dihydrothieno[3,2-d]pyrimidin-2-yl)pyrrolidine-1-carboxylate (173 mg) and tert-butyl 3-methyl-4-(4,4,5,5-tetramethyl-1,3,2-dioxaborolan-2-yl)-1H-pyrazole-1-carboxylate (266 mg) and cesium carbonate (282 mg) and 1,2-dimethoxyethane (5 mL) and water (0.5 mL) and [1,1'-bis(diphenylphosphino)ferrocene]palladium(II) dichloride-dichloromethane complex (1:1) (71 mg).

$^1$H-NMR (DMSO-d$_6$) δ 1.94-2.15 (3H, m), 2.39-2.47 (1H, m), 2.46 (3H, s), 3.27-3.43 (2H, m), 4.66 (1H, t, J=7.1 Hz), 7.37 (1H, s), 8.09 (1H, brs), 8.98 (1H, brs), 9.55 (1H, brs), 12.80 (1H, brs).

Example 13

Production of 6-(5-methyl-1H-pyrazol-4-yl)-2-(2-pyrrolidin-1-ylethyl)thieno[3,2-d]pyrimidin-4 (3H)-one A) Production of 6-bromo-2-(2-pyrrolidin-1-ylethyl)thieno[3,2-d]pyrimidin-4 (3H)-one To a mixture of 3-amino-5-bromothiophene-2-carboxamide (120 mg) produced in Example 1, step D, triethylamine (0.083 mL) and tetrahydrofuran (3.0 mL) was added 3-chloropropanoyl chloride (0.057 mL) with stirring at room temperature. After 10 min, pyrrolidine (0.23 mL) was added, and the mixture was stirred at room temperature for 10 min. The reaction system was concentrated under reduced pressure, 2M aqueous sodium hydroxide solution (1.0 mL) was added to the residue, and the mixture was stirred with heating at 120° C. for 1 hr. The mixture was extracted with ethyl acetate, washed with brine and dried over anhydrous sodium sulfate. Insoluble material was removed by filtration, and the filtrate was concentrated under reduced pressure to give the title compound (131 mg) as a pale-yellow solid.

$^1$H-NMR (DMSO-d$_6$) δ 1.63-1.70 (4H, m), 2.43-2.49 (4H, m), 2.78-2.82 (4H, m), 7.57 (1H, s), 12.61 (1H, brs).

B) Production of 6-(5-methyl-1H-pyrazol-4-yl)-2-(2-pyrrolidin-1-ylethyl)thieno[3,2-d]pyrimidin-4 (3H)-one In the same manner as in Example 1, step F, the title compound (66 mg) was obtained as a pale-yellow solid from 6-bromo-2-(2-pyrrolidin-1-ylethyl)thieno[3,2-d]pyrimidin-4 (3H)-one (125 mg) and tert-butyl 3-methyl-4-(4,4,5,5-tetramethyl-1,3,2-dioxaborolan-2-yl)-1H-pyrazole-1-carboxylate (352 mg), sodium carbonate (114 mg), 1,2-dimethoxyethane (3.0 mL) and water (1.5 mL) and [1,1'-bis(diphenylphosphino)ferrocene]palladium(II) dichloride-dichloromethane complex (1:1) (31 mg).

$^1$H-NMR (DMSO-d$_6$) δ 1.51-1.78 (4H, m), 2.40-2.49 (7H, m), 2.75-2.89 (4H, m), 7.34 (1H, s), 8.02 (1H, brs), 11.93-13.36 (2H, m).

Example 14

Production of 6-(5-methyl-1H-pyrazol-4-yl)-2-[(4-phenylpiperazin-1-yl)methyl]thieno[3,2-d]pyrimidin-4 (3H)-one A) Production of 6-bromo-2-[(4-phenylpiperazin-1-yl)methyl]thieno[3,2-d]pyrimidin-4 (3H)-one In the same manner as in Example 2, step B, the title compound (180 mg) was obtained as a pale-yellow solid from 6-bromo-2-(chloromethyl)thieno[3,2-d]pyrimidin-4 (3H)-one (180 mg) produced in Example 2, step A, 1-phenylpiperazine (0.29 mL), potassium carbonate (178 mg), sodium iodide (9.7 mg) and N,N-dimethylformamide (3.0 mL).

$^1$H-NMR (DMSO-d$_6$) δ 2.60-2.70 (4H, m), 3.05-3.19 (4H, m), 3.52 (2H, s), 6.72-6.81 (1H, m), 6.92 (2H, d, J=7.9 Hz), 7.13-7.26 (2H, m), 7.63 (1H, s), 12.36 (1H, brs).

B) Production of 6-(5-methyl-1H-pyrazol-4-yl)-2-[(4-phenylpiperazin-1-yl)methyl]thieno[3,2-d]pyrimidin-4 (3H)-one In the same manner as in Example 2, step C, the title compound (86 mg) was obtained as a white solid from 6-bromo-2-[(4-phenylpiperazin-1-yl)methyl]thieno[3,2-d]pyrimidin-4 (3H)-one (180 mg) and tert-butyl 3-methyl-4-(4,4,5,5-tetramethyl-1,3,2-dioxaborolan-2-yl)-1H-pyrazole-1-carboxylate (410 mg), sodium carbonate (133 mg), 1,2-dimethoxyethane (3.0 mL) and water (1.5 mL) and [1,1'-bis(diphenylphosphino)ferrocene]palladium(II) dichloride-dichloromethane complex (1:1) (36 mg).

$^1$H-NMR (DMSO-d$_6$) δ 2.39-2.48 (3H, m), 2.60-2.70 (4H, m), 3.08-3.23 (4H, m), 3.53 (2H, s), 6.77 (1H, t, J=7.2 Hz), 6.92 (2H, d, J=7.2 Hz), 7.12-7.26 (2H, m), 7.40 (1H, s), 7.89 (0.6H, brs), 8.26 (0.4H, brs), 12.18 (1H, brs), 13.00 (1H, brs).

Example 15

Production of 6-(5-methyl-1H-pyrazol-4-yl)-2-[(4-phenylpiperidin-1-yl)methyl]thieno[3,2-d]pyrimidin-4 (3H)-one A) Production of 6-bromo-2-[(4-phenylpiperidin-1-yl)methyl]thieno[3,2-d]pyrimidin-4 (3H)-one In the same manner as in Example 2, step B, the title compound (241 mg) was obtained as a pale-yellow solid from 6-bromo-2-(chloromethyl)thieno[3,2-d]pyrimidin-4 (3H)-one (240 mg) produced in Example 2, step A, 4-phenylpiperidine (415 mg), potassium carbonate (237 mg), sodium iodide (13 mg) and N,N-dimethylformamide (4.0 mL).

$^1$H-NMR (DMSO-d$_6$) δ 1.53-1.82 (4H, m), 2.14-2.32 (2H, m), 2.43-2.48 (1H, m), 2.93-3.03 (2H, m), 3.50 (2H, s), 7.10-7.35 (5H, m), 7.62 (1H, s), 12.24 (1H, brs).

B) Production of 6-(5-methyl-1H-pyrazol-4-yl)-2-[(4-phenylpiperidin-1-yl)methyl]thieno[3,2-d]pyrimidin-4 (3H)-one In the same manner as in Example 2, step C, the title compound (138 mg) was obtained as a pale-yellow solid from 6-bromo-2-[(4-phenylpiperidin-1-yl)methyl]thieno[3,2-d]pyrimidin-4 (3H)-one (240 mg) and tert-butyl 3-methyl-4-(4,4,5,5-tetramethyl-1,3,2-dioxaborolan-2-yl)-1H-pyrazole-1-carboxylate (549 mg), sodium carbonate (178 mg), 1,2-dimethoxyethane (4.0 mL) and water (2.0 mL) and [1,1'-bis(diphenylphosphino)ferrocene]palladium(II) dichloride-dichloromethane complex (1:1) (49 mg).

$^1$H-NMR (DMSO-d$_6$) δ 1.61-1.83 (4H, m), 2.14-2.33 (2H, m), 2.40-2.50 (4H, m), 2.90-3.08 (2H, m), 3.50 (2H, s), 7.10-7.34 (5H, m), 7.39 (1H, s), 7.96 (1H, brs), 12.08 (1H, brs), 12.97 (1H, brs).

Example 16

Production of 2-{[(2S)-2-(hydroxymethyl)pyrrolidin-1-yl]methyl}-6-(5-methyl-1H-pyrazol-4-yl)thieno[3,2-d]pyrimidin-4 (3H)-one dihydrochloride A) Production of 6-bromo-2-{[(2S)-2-(hydroxymethyl)pyrrolidin-1-yl]methyl}thieno[3,2-d]pyrimidin-4 (3H)-one In the same manner as in Example 2, step B, the title compound (112 mg) was obtained as a pale-yellow solid from 6-bromo-2-(chloromethyl)thieno[3,2-d]pyrimidin-4 (3H)-one (180 mg) produced in Example 2, step A, (2S)-pyrrolidin-2-ylmethanol (0.19 mL), potassium carbonate (178 mg), sodium iodide (9.7 mg) and N,N-dimethylformamide (3.0 mL).

$^1$H-NMR (DMSO-d$_6$) δ 1.49-1.92 (4H, m), 2.21-2.41 (1H, m), 2.59-2.72 (1H, m), 2.82-3.00 (1H, m), 3.19-3.54 (3H, m), 4.01 (1H, d, J=14.7 Hz), 4.74 (1H, brs), 7.60 (1H, s), 12.04 (1H, brs).

B) Production of 2-{[(2S)-2-(hydroxymethyl)pyrrolidin-1-yl]methyl}-6-(5-methyl-1H-pyrazol-4-yl)thieno[3,2-d]pyrimidin-4 (3H)-one dihydrochloride In the same manner as in Example 2, step C, the title compound (90 mg) was obtained as a pale-yellow solid from 6-bromo-2-{[(2S)-2-(hydroxymethyl)pyrrolidin-1-yl]methyl}thieno[3,2-d]pyrimidin-4 (3H)-one (112 mg) and tert-butyl 3-methyl-4-(4,4,5,5-tetramethyl-1,3,2-dioxaborolan-2-yl)-1H-pyrazole-1-carboxylate (300 mg), sodium carbonate (78 mg), 1,2-dimethoxyethane (3.0 mL) and water (1.5 mL) and [1,1'-bis(diphenylphosphino)ferrocene]palladium(II) dichloride-dichloromethane complex (1:1) (27 mg).

$^1$H-NMR (DMSO-d$_6$) δ 1.67-2.22 (4H, m), 2.47 (3H, s), 3.33-3.50 (1H, m), 3.63-3.91 (4H, m), 4.37-4.51 (1H, m), 4.65-4.78 (1H, m), 7.41 (1H, s), 8.10 (1H, s), 10.27 (1H, brs), 12.77 (1H, brs).

Example 17

Production of 2-{[(2R)-2-(hydroxymethyl)pyrrolidin-1-yl]methyl}-6-(5-methyl-1H-pyrazol-4-yl)thieno[3,2-d]pyrimidin-4 (3H)-one dihydrochloride A) Production of 6-bromo-2-{[(2R)-2-(hydroxymethyl)pyrrolidin-1-yl]methyl}thieno[3,2-d]pyrimidin-4 (3H)-one In the same manner as in Example 2, step B, the title compound (122 mg) was obtained as a colorless solid from 6-bromo-2-(chloromethyl)thieno[3,2-d]pyrimidin-4 (3H)-one (180 mg) produced in Example 2, step A, (2R)-pyrrolidin-2-ylmethanol (0.19 mL), potassium carbonate (178 mg), sodium iodide (9.7 mg) and N,N-dimethylformamide (3.0 mL).

$^1$H-NMR (DMSO-d$_6$) δ 1.53-1.91 (4H, m), 2.23-2.38 (1H, m), 2.61-2.71 (1H, m), 2.83-2.98 (1H, m), 3.20-3.55 (3H, m), 4.01 (1H, d, J=14.7 Hz), 4.33-5.67 (1H, m), 7.60 (1H, s), 11.13-12.68 (1H, m).

B) Production of 2-{[(2R)-2-(hydroxymethyl)pyrrolidin-1-yl]methyl}-6-(5-methyl-1H-pyrazol-4-yl)thieno[3,2-d]pyrimidin-4 (3H)-one dihydrochloride In the same manner as in Example 2, step C, the title compound (96 mg) was obtained as a pale-yellow solid from 6-bromo-2-{[(2R)-2-(hydroxymethyl)pyrrolidin-1-yl]methyl}thieno[3,2-d]pyrimidin-4 (3H)-one (122 mg) and tert-butyl 3-methyl-4-(4,4,5,5-tetramethyl-1,3,2-dioxaborolan-2-yl)-1H-pyrazole-1-carboxylate (327 mg), sodium carbonate (85 mg), 1,2-dimethoxyethane (3.0 mL) and water (1.5 mL) and [1,1'-bis(diphenylphosphino)ferrocene]palladium(II) dichloride-dichloromethane complex (1:1) (29 mg).

$^1$H-NMR (DMSO-d$_6$) δ 1.69-2.23 (4H, m), 2.47 (3H, s), 3.31-3.52 (1H, m), 3.63-3.94 (4H, m), 4.35-4.54 (1H, m), 4.62-4.82 (1H, m), 7.40 (1H, s), 8.09 (1H, s), 10.29 (1H, brs), 12.76 (1H, brs).

Example 18

Production of 2-{[(3S)-3-methoxypyrrolidin-1-yl]methyl}-6-(5-methyl-1H-pyrazol-4-yl)thieno[3,2-d]pyrimidin-4 (3H)-one A) Production of 6-bromo-2-{[(3S)-3-methoxypyrrolidin-1-yl]methyl}thieno[3,2-d]pyrimidin-4 (3H)-one In the same manner as in Example 2, step B, the title compound (152 mg) was obtained as a pale-yellow solid from 6-bromo-2-(chloromethyl)thieno[3,2-d]pyrimidin-4 (3H)-one (180 mg) produced in Example 2, step A, (3S)-3-methoxypyrrolidine hydrochloride (265 mg), potassium carbonate (445 mg), sodium iodide (9.7 mg) and N,N-dimethylformamide (3.0 mL).

$^1$H-NMR (DMSO-d$_6$) δ 1.59-1.76 (1H, m), 1.90-2.07 (1H, m), 2.52-2.59 (2H, m), 2.60-2.71 (1H, m), 2.75-2.85 (1H, m), 3.15 (3H, s), 3.55 (2H, s), 3.82-3.95 (1H, m), 7.61 (1H, s), 12.36 (1H, brs).

B) Production of 2-{[(3S)-3-methoxypyrrolidin-1-yl]methyl}-6-(5-methyl-1H-pyrazol-4-yl)thieno[3,2-d]pyrimidin-4 (3H)-one In the same manner as in Example 2, step C, the title compound (56 mg) was obtained as a pale-yellow solid from 6-bromo-2-{[(3S)-3-methoxypyrrolidin-1-yl]methyl}thieno[3,2-d]pyrimidin-4 (3H)-one (150 mg) and tert-butyl 3-methyl-4-(4,4,5,5-tetramethyl-1,3,2-dioxaborolan-2-yl)-1H-pyrazole-1-carboxylate (403 mg), sodium carbonate (105 mg), 1,2-dimethoxyethane (4.0 mL) and water (2.0 mL) and [1,1'-bis(diphenylphosphino)ferrocene]palladium(II) dichloride-dichloromethane complex (1:1) (36 mg).

$^1$H-NMR (DMSO-d$_6$) δ 1.60-1.74 (1H, m), 1.92-2.07 (1H, m), 2.45 (3H, s), 2.52-2.61 (2H, m), 2.63-2.73 (1H, m), 2.77-2.87 (1H, m), 3.16 (3H, s), 3.56 (2H, s), 3.81-4.02 (1H, m), 7.38 (1H, s), 7.97 (1H, brs), 12.10 (1H, brs), 12.96 (1H, brs).

Example 19

Production of 2-{[(3R)-3-methoxypyrrolidin-1-yl]methyl}-6-(5-methyl-1H-pyrazol-4-yl)thieno[3,2-d]pyrimidin-4 (3H)-one A) Production of 6-bromo-2-{[(3R)-3-methoxypyrrolidin-1-yl]methyl}thieno[3,2-d]pyrimidin-4 (3H)-one In the same manner as in Example 2, step B, the title compound (150 mg) was obtained as a pale-yellow solid from 6-bromo-2-(chloromethyl)thieno[3,2-d]pyrimidin-4 (3H)-one (180 mg) produced in Example 2, step A, (3R)-3-methoxypyrrolidine hydrochloride (265 mg), potassium carbonate (445 mg), sodium iodide (9.7 mg) and N,N-dimethylformamide (3.0 mL).

$^1$H-NMR (DMSO-d$_6$) δ 1.57-1.74 (1H, m), 1.91-2.07 (1H, m), 2.52-2.59 (2H, m), 2.61-2.71 (1H, m), 2.75-2.85 (1H, m), 3.15 (3H, s), 3.55 (2H, s), 3.81-3.96 (1H, m), 7.61 (1H, s), 12.36 (1H, brs).

B) Production of 2-{[(3R)-3-methoxypyrrolidin-1-yl]methyl}-6-(5-methyl-1H-pyrazol-4-yl)thieno[3,2-d]pyrimidin-4 (3H)-one In the same manner as in Example 2, step C, the title compound (71 mg) was obtained as a pale-yellow solid from 6-bromo-2-{[(3R)-3-methoxypyrrolidin-1-yl]methyl}thieno[3,2-d]pyrimidin-4 (3H)-one (150 mg) and tert-butyl 3-methyl-4-(4,4,5,5-tetramethyl-1,3,2-dioxaborolan-2-yl)-1H-pyrazole-1-carboxylate (403 mg), sodium carbonate (105 mg), 1,2-dimethoxyethane (4.0 mL) and water (2.0 mL) and [1,1'-bis(diphenylphosphino)ferrocene]palladium(II) dichloride-dichloromethane complex (1:1) (36 mg).

$^1$H-NMR (DMSO-d$_6$) δ 1.60-1.74 (1H, m), 1.92-2.07 (1H, m), 2.45 (3H, s), 2.52-2.61 (2H, m), 2.62-2.72 (1H, m), 2.77-2.86 (1H, m), 3.16 (3H, s), 3.56 (2H, s), 3.81-3.97 (1H, m), 7.38 (1H, s), 8.00 (1H, brs), 12.21 (1H, brs), 12.92 (1H, brs).

Example 20

Production of 6-(5-methyl-1H-pyrazol-4-yl)-2-(1-pyrrolidin-1-ylethyl)thieno[3,2-d]pyrimidin-4 (3H)-one A) Production of 6-bromo-2-(1-pyrrolidin-1-ylethyl)thieno[3,2-d]pyrimidin-4 (3H)-one To a mixture of 3-amino-5-bromothiophene-2-carboxamide (221 mg) produced in Example 1, step D, triethylamine (0.15 mL) and tetrahydrofuran (5.0 mL) was added 2-bromopropanoylchloride (0.11 mL) with stirring at room temperature. After 10 min, pyrrolidine (0.42 mL) was added, and the mixture was stirred at 70° C. for 1 hr. The reaction system was concentrated under reduced pressure, 2M aqueous sodium hydroxide solution (1.0 mL) was added to the residue, and the mixture was stirred with heating at 120° C. for 2 hr. The mixture was extracted with ethyl acetate and dried over anhydrous sodium sulfate. Insoluble material was removed by filtration, and the filtrate was concentrated under reduced pressure. The residue was purified by basic silica gel column chromatography (ethyl acetate/hexane and methanol/ethyl acetate) to give the title compound (276 mg) as a pale-yellow solid.

$^1$H-NMR (DMSO-d$_6$) δ 1.38 (3H, d, J=6.8 Hz), 1.69 (4H, brs), 2.40-2.48 (2H, m), 2.55-2.66 (2H, m), 3.49 (1H, q, J=6.8 Hz), 7.59 (1H, s), 12.14 (1H, brs).

B) Production of 6-(5-methyl-1H-pyrazol-4-yl)-2-(1-pyrrolidin-1-ylethyl)thieno[3,2-d]pyrimidin-4 (3H)-one In the same manner as in Example 2, step C, the title compound (145 mg) was obtained as a pale-brown solid from 6-bromo-2-(1-pyrrolidin-1-ylethyl)thieno[3,2-d]pyrimidin-4 (3H)-one (270 mg) and tert-butyl 3-methyl-4-(4,4,5,5-tetramethyl-1,3,2-dioxaborolan-2-yl)-1H-pyrazole-1-carboxylate (761 mg), sodium carbonate (198 mg), 1,2-dimethoxyethane (6.0 mL) and water (3.0 mL) and [1,1'-bis(diphenylphosphino)ferrocene]palladium(II) dichloride-dichloromethane complex (1:1) (67 mg).

$^1$H-NMR (DMSO-d$_6$) δ 1.39 (3H, d, J=6.8 Hz), 1.64-1.75 (4H, m), 2.40-2.48 (5H, m), 2.55-2.65 (2H, m), 3.49 (1H, q, J=6.8 Hz), 7.37 (1H, s), 8.02 (1H, brs), 12.00-13.09 (2H, m).

Example 21

Production of 6-(5-ethyl-1H-pyrazol-4-yl)-2-(pyrrolidin-1-ylmethyl)thieno[3,2-d]pyrimidin-4 (3H)-one dihydrochloride A) Production of N,N-dimethyl-1H-pyrazole-1-sulfonamide Sodium hydride (50%, 8.46 g) was added to a solution of pyrazole (12 g) in tetrahydrofuran (200 mL) while stirring at 0° C. After 20 min, dimethylsulfamoyl chloride (17 mL) was added dropwise, and the mixture was stirred at the same temperature for 1 hr and allowed to warm to room temperature over 1 hr. The reaction system was poured into saturated aqueous sodium hydrogen carbonate, and the mixture was extracted with ethyl acetate, and dried over anhydrous magnesium sulfate. Insoluble material was removed by filtration, and the filtrate was concentrated under reduced pressure. The residue was purified by silica gel column chromatography (ethyl acetate/hexane) to give the title compound (25.3 g) as a colorless oil.

$^1$H-NMR (300 MHz, CDCl$_3$) δ 2.95 (6H, s), 6.40 (1H, m), 7.75 (1H, m), 7.99 (1H, d, J=2.7 Hz).

B) Production of 5-ethyl-N,N-dimethyl-1H-pyrazole-1-sulfonamide 1.6M n-Butyllithium/hexane solution (99 mL) was added dropwise to a stirring solution (200 mL) of N,N-dimethyl-1H-pyrazole-1-sulfonamide (25.3 g) in tetrahydrofuran at −78° C. After 30 min from the completion of the dropwise addition, iodoethane (12.8 mL) was added dropwise. The mixture was stirred at the same temperature for 30 min, and the reaction system was allowed to warm to room temperature. After 1 hr, tetrahydrofuran (200 mL) was added to facilitate stirring of the reaction system, and the mixture was further stirred for 2 hr. The reaction system was poured into saturated aqueous sodium hydrogen carbonate (600 mL), and the mixture was extracted with ethyl acetate (400 mL×2), and dried over anhydrous magnesium sulfate. Insoluble material was removed by filtration, and the filtrate was concentrated under reduced pressure. The residue was subjected to silica gel column chromatography (ethyl acetate/hexane), and the object fraction was concentrated under reduced pressure to give the title compound (19.8 g) as a colorless oil.

$^1$H-NMR (300 MHz, CDCl$_3$) δ 1.30 (3H, t, J=7.8 Hz), 2.94 (2H, dd, J=15.0, 7.5 Hz), 3.03 (6H, s), 6.13 (1H, brs), 7.55 (1H, brs).

C) Production of 4-bromo-5-ethyl-N,N-dimethyl-1H-pyrazole-1-sulfonamide

1-Bromopyrrolidine-2,5-dione (20.8 g) was added to a stirring solution (300 mL) of 5-ethyl-N,N-dimethyl-1H-pyrazole-1-sulfonamide (19.8 g) in tetrahydrofuran at room temperature. The reaction system was heated to 50° C., stirred for 2 hr and concentrated under reduced pressure. The residue was poured into saturated aqueous sodium hydrogen carbonate, and the mixture was extracted with ethyl acetate, and dried over anhydrous magnesium sulfate. Insoluble material was removed by filtration, and the filtrate was concentrated under reduced pressure. The residue was purified by silica gel column chromatography (ethyl acetate/hexane) to give the title compound (26.2 g) as a yellow oil.

$^1$H-NMR (300 MHz, CDCl$_3$) δ 1.24 (3H, t, J=7.5 Hz), 2.97 (2H, dd, J=15.0 Hz, 7.8 Hz), 3.06 (6H, s), 7.54 (1H, s).

D) Production of 5-ethyl-N,N-dimethyl-4-(4,4,5,5-tetramethyl-1,3,2-dioxaborolan-2-yl)-1H-pyrazole-1-sulfonamide 4-Bromo-5-ethyl-N,N-dimethyl-1H-pyrazole-1-sulfonamide(13.0 g), 4,4,4',4',5,5,5',5'-octamethyl-2,2'-bi-1,3,2-dioxaborolane (12.3 g), potassium acetate (13.6 g) and 1,2-dimethoxyethane (300 mL) were placed in a flask, and the atmosphere in the flask was purged with argon. [1,1'-Bis (diphenylphosphino)ferrocene]palladium(II) dichloride-dichloromethane complex (1:1, 3.76 g) was added, the atmosphere in the flask was purged again with argon, and the mixture was stirred at 90° C. overnight. The reaction system was allowed to cool to room temperature. Insoluble material was removed by filtration, and the filtrate was concentrated under reduced pressure. A mixture of ethyl acetate and hexane (1:1) was added to the residue, the insoluble material was removed again by filtration, and the filtrate was concentrated under reduced pressure. The residue was purified by silica gel column chromatography (ethyl acetate/hexane) to give the title compound (6.32 g) as a white solid.

$^1$H-NMR (300 MHz, CDCl$_3$) δ 1.25 (3H, t, J=7.5 Hz), 1.31 (12H, s), 3.03 (6H, s), 3.17 (2H, dd, J=15.0, 7.5 Hz), 7.75 (1H, s).

E) Production of 6-(5-ethyl-1H-pyrazol-4-yl)-2-(pyrrolidin-1-ylmethyl)thieno[3,2-d]pyrimidin-4 (3H)-one dihydrochloride 6-Bromo-2-(pyrrolidin-1-ylmethyl)thieno[3,2-d]pyrimidin-4 (3H)-one (100 mg), 5-ethyl-N,N-dimethyl-4-(4,4,5,5-tetramethyl-1,3,2-dioxaborolan-2-yl)-1H-pyrazole-1-sulfonamide(210 mg), cesium carbonate (311 mg), 1,2-dimethoxyethane (5 mL) and water (1 mL) were placed in a flask, and the atmosphere in the flask was purged with argon. [1,1'-Bis(diphenylphosphino)ferrocene]palladium(II) dichloride-dichloromethane complex (1:1) (26.0 mg) was added, the atmosphere in the flask was purged again with argon, and the mixture was stirred at 90° C. for 3 hr. The reaction system was allowed to cool to room temperature, and sodium carbonate (169 mg), 5-ethyl-N,N-dimethyl-4-(4,4,5,5-tetramethyl-1,3,2-dioxaborolan-2-yl)-1H-pyrazole-1-sulfonamide (210 mg), water (1 mL) and [1,1'-bis(diphenylphosphino)ferrocene]palladium(II) dichloride-dichloromethane complex (1:1) (26.0 mg) were added. The atmosphere in the flask was purged again with argon, and the mixture was stirred at 90° C. overnight. The reaction system was poured into brine, and the mixture was extracted with a mixture of ethyl acetate and tetrahydrofuran (3:1), and dried over anhydrous magnesium sulfate. Insoluble material was removed by filtration, and the filtrate was concentrated under reduced pressure. The residue was subjected to basic silica gel column chromatography (methanol/ethyl acetate), and the object fraction was concentrated under reduced pressure. 1M Hydrochloric acid/diethylether solution (5 mL) and methanol (5 mL) were added to the residue, and the mixture was stirred at 60° C. for 2 hr. The reaction system was allowed to cool to room temperature, and the precipitate was collected by filtration to give the title compound (95.9 mg) as a white solid.

$^1$H-NMR (DMSO-d$_6$) δ 1.26 (3H, t, J=7.5 Hz), 1.99 (4H, m), 2.84-2.92 (2H, m), 3.17-3.25 (2H, m), 3.64-3.77 (2H, m), 4.51 (2H, s), 7.38 (1H, s), 8.09 (1H, s), 10.61 (1H, brs), 12.80 (1H, brs).

Example 22

Production of 2-[(2S)-4,4-difluoropyrrolidin-2-yl]-6-(5-methyl-1H-pyrazol-4-yl)thieno[3,2-d]pyrimidin-4 (3H)-one dihydrochloride

A) Production of tert-butyl(2S)-2-(6-bromo-4-oxo-3,4-dihydrothieno[3,2-d]pyrimidin-2-yl)-4,4-difluoropyrrolidine-1-carboxylate In the same manner as in Example 11, step A, the title compound (286 mg) was obtained as a pale-yellow solid from 3-amino-5-bromothiophene-2-carboxamide (250 mg) produced in Example 1, step D and 1-(tert-butoxycarbonyl)-4,4-difluoro-L-proline (568 mg) and O-(7-azabenzotriazol-1-yl)-N,N,N',N'-tetramethyluronium hexafluorophosphate (1.29 g) and N-ethyl-N-(1-methylethyl)propan-2-amine (0.592 mL) and N,N-dimethylformamide (5 mL).

$^1$H-NMR (DMSO-d$_6$) δ 1.14 (9H, s, major), 1.39 (9H, s, minor), 2.55-2.71 (1H, m), 2.86-2.97 (1H, m), 3.80-4.03 (2H, m), 4.74-4.90 (1H, m), 7.60 (1H, s, minor), 7.63 (1H, s, major), 12.84 (1H, brs). The ratio of the observed isomer was 3:2.

B) Production of 2-[(2S)-4,4-difluoropyrrolidin-2-yl]-6-(5-methyl-1H-pyrazol-4-yl)thieno[3,2-d]pyrimidin-4 (3H)-one dihydrochloride In the same manner as in Example 11, step B, the title compound (163 mg) was obtained as a white solid from tert-butyl(2S)-2-(6-bromo-4-oxo-3,4-dihydrothieno[3,2-d] pyrimidin-2-yl)-4,4-difluoropyrrolidine-1-carboxylate (286 mg) and tert-butyl 3-methyl-4-(4,4,5,5-tetramethyl-1,3,2-dioxaborolan-2-yl)-1H-pyrazole-1-carboxylate (404 mg) and cesium carbonate (427 mg) and 1,2-dimethoxyethane (7 mL)

and water (0.7 mL) and [1,1'-bis(diphenylphosphino)ferrocene]palladium(II) dichloride-dichloromethane complex (1:1) (107 mg).

$^1$H-NMR (DMSO-d$_6$) δ 2.46 (3H, s), 2.75-2.95 (1H, m), 3.01-3.21 (1H, m), 3.89 (2H, t, J=12.3 Hz), 5.05 (1H, t, J=8.5 Hz), 7.41 (1H, s), 8.11 (1H, s), 10.32 (1H, brs), 12.87 (1H, brs).

Example 23

Production of 2-[(2S,4R)-4-fluoropyrrolidin-2-yl]-6-(5-methyl-1H-pyrazol-4-yl)thieno[3,2-d]pyrimidin-4 (3H)-one dihydrochloride A) Production of tert-butyl(2S,4R)-2-(6-bromo-4-oxo-3,4-dihydrothieno[3,2-d]pyrimidin-2-yl)-4-fluoropyrrolidine-1-carboxylate In the same manner as in Example 11, step A, the title compound (239 mg) was obtained as a pale-yellow solid from 3-amino-5-bromothiophene-2-carboxamide (250 mg) produced in Example 1, step D and (4R)-1-(tert-butoxycarbonyl)-4-fluoro-L-proline (568 mg) and O-(7-azabenzotriazol-1-yl)-N,N,N',N'-tetramethyluronium hexafluorophosphate (1.29 g) and N-ethyl-N-(1-methylethyl)propan-2-amine (0.592 mL) and N,N-dimethylformamide (5 mL).

$^1$H-NMR (DMSO-d$_6$) δ 1.11 (9H, s, major), 1.37 (9H, s, minor), 2.09-2.35 (1H, m), 2.54-2.67 (1H, m), 3.63-3.86 (2H, m), 4.64-4.76 (1H, m), 5.38 (1H, d, J=53.4 Hz), 7.58 (1H, s, minor), 7.61 (1H, s, major), 12.79 (1H, brs). The ratio of the observed isomers was 2:1.

B) Production of 2-[(2S,4R)-4-fluoropyrrolidin-2-yl]-6-(5-methyl-1H-pyrazol-4-yl)thieno[3,2-d]pyrimidin-4 (3H)-one dihydrochloride In the same manner as in Example 11, step B, the title compound (139 mg) was obtained as a colorless solid from tert-butyl(2S,4R)-2-(6-bromo-4-oxo-3,4-dihydrothieno[3,2-d]pyrimidin-2-yl)-4-fluoropyrrolidine-1-carboxylate (237 mg) and tert-butyl 3-methyl-4-(4,4,5,5-tetramethyl-1,3,2-dioxaborolan-2-yl)-1H-pyrazole-1-carboxylate (348 mg) and cesium carbonate (368 mg) and 1,2-dimethoxyethane (5 mL) and water (0.5 mL) and [1,1'-bis(diphenylphosphino)ferrocene]palladium(II) dichloride-dichloromethane complex (1:1) (92.3 mg).

$^1$H-NMR (DMSO-d$_6$) δ 2.29-2.45 (1H, m), 2.46 (3H, s), 2.76-2.93 (1H, m), 3.50-3.70 (2H, m), 4.80-4.96 (1H, m), 5.45-5.69 (1H, m), 7.37 (1H, s), 8.10 (1H, s), 9.38 (1H, brs), 10.44 (1H, brs), 12.85 (1H, brs).

Example 24

Production of 2-[(2S,4S)-4-fluoropyrrolidin-2-yl]-6-(5-methyl-1H-pyrazol-4-yl)thieno[3,2-d]pyrimidin-4 (3H)-one dihydrochloride A) Production of tert-butyl(2S,4S)-2-(6-bromo-4-oxo-3,4-dihydrothieno[3,2-d]pyrimidin-2-yl)-4-fluoropyrrolidine-1-carboxylate In the same manner as in Example 11, step A, the title compound (106 mg) was obtained as a colorless solid from 3-amino-5-bromothiophene-2-carboxamide (250 mg) produced in Example 1, step D and (4S)-1-(tert-butoxycarbonyl)-4-fluoro-L-proline (568 mg) and O-(7-azabenzotriazol-1-yl)-N,N,N',N'-tetramethyluronium hexafluorophosphate (1.29 g) and N-ethyl-N-(1-methylethyl)propan-2-amine (0.592 mL) and N,N-dimethylformamide (5 mL).

$^1$H-NMR (DMSO-d$_6$) δ 1.18 (9H, s, major), 1.42 (9H, s, minor), 2.19-2.38 (1H, m), 2.55-2.82 (1H, m), 3.57-3.83 (2H, m), 4.71-4.86 (1H, m), 5.16-5.41 (1H, m), 7.59 (1H, s, minor), 7.62 (1H, s, major), 12.61 (1H, brs). The ratio of the observed isomers was 2:1.

B) Production of 2-[(2S,4S)-4-fluoropyrrolidin-2-yl]-6-(5-methyl-1H-pyrazol-4-yl)thieno[3,2-d]pyrimidin-4 (3H)-one dihydrochloride In the same manner as in Example 11, step B, the title compound (102 mg) was obtained as a colorless solid from tert-butyl(2S,4S)-2-(6-bromo-4-oxo-3,4-dihydrothieno[3,2-d]pyrimidin-2-yl)-4-fluoropyrrolidine-1-carboxylate (180 mg) and tert-butyl 3-methyl-4-(4,4,5,5-tetramethyl-1,3,2-dioxaborolan-2-yl)-1H-pyrazole-1-carboxylate (265 mg) and cesium carbonate (281 mg) and 1,2-dimethoxyethane (5 mL) and water (0.5 mL) and [1,1'-bis(diphenylphosphino)ferrocene]palladium(II) dichloride-dichloromethane complex (1:1) (70.3 mg).

$^1$H-NMR (DMSO-d$_6$) δ 2.46 (3H, s), 2.71-2.96 (1H, m), 3.47-3.77 (3H, m), 4.87 (1H, brs), 5.37-5.61 (1H, m), 7.37 (1H, s), 8.10 (1H, s), 9.40 (1H, brs), 10.34 (1H, brs), 12.87 (1H, brs).

Example 25

Production of 2-[(3,3-difluoroazetidin-1-yl)methyl]-6-(5-methyl-1H-pyrazol-4-yl)thieno[3,2-d]pyrimidin-4 (3H)-one In the same manner as in Example 2, step B and step C, the title compound (93 mg) was obtained as a white solid from 6-bromo-2-(chloromethyl)thieno[3,2-d]pyrimidin-4 (3H)-one (160 mg) produced in Example 2, step A and 3,3-difluoroazetidinehydrochloride (200 mg) and potassium carbonate (158 mg) and sodium iodide (8.6 mg) and N,N-dimethylacetamide (4.0 mL) and tert-butyl 3-methyl-4-(4,4,5,5-tetramethyl-1,3,2-dioxaborolan-2-yl)-1H-pyrazole-1-carboxylate (353 mg) and cesium carbonate (373 mg) and 1,2-dimethoxyethane (4.0 mL) and water (1 mL) and [1,1'-bis(diphenylphosphino)ferrocene]palladium(II) dichloride-dichloromethane complex (1:1) (26 mg).

$^1$H-NMR (DMSO-d$_6$) δ 2.42-2.47 (3H, m), 3.71-3.82 (6H, m), 7.36-7.38 (1H, m), 7.88 (0.6H, brs), 8.25 (0.4H, brs), 12.28 (1H, brs), 12.97 (1H, brs).

Example 26

Production of 6-(5-methyl-1H-pyrazol-4-yl)-2-{[(3R)-3-methylpyrrolidin-1-yl]methyl}thieno[3,2-d]pyrimidin-4 (3H)-one A) Production of 6-bromo-2-{[(3R)-3-methylpyrrolidin-1-yl]methyl}thieno[3,2-d]pyrimidin-4 (3H)-one In the same manner as in Example 2, step B, the title compound (171 mg) was obtained as a pale-yellow solid from 6-bromo-2-(chloromethyl)thieno[3,2-d]pyrimidin-4 (3H)-one (180 mg) produced in Example 2, step A, (3R)-3-methylpyrrolidine hydrochloride (235 mg), potassium carbonate (445 mg), sodium iodide (9.7 mg) and N,N-dimethylformamide (3.0 mL).

$^1$H-NMR (DMSO-d$_6$) δ 0.98 (3H, d, J=6.6 Hz), 1.17-1.37 (1H, m), 1.85-2.02 (1H, m), 2.03-2.26 (2H, m), 2.53-2.61 (1H, m), 2.62-2.71 (1H, m), 2.77-2.86 (1H, m), 3.55 (2H, s), 7.59 (1H, s), 12.30 (1H, brs).

B) Production of 6-(5-methyl-1H-pyrazol-4-yl)-2-{[(3R)-3-methylpyrrolidin-1-yl]methyl}thieno[3,2-d]pyrimidin-4 (3H)-one In the same manner as in Example 2, step C, the title compound (36 mg) was obtained as a pale-brown solid from 6-bromo-2-{[(3R)-3-methylpyrrolidin-1-yl]methyl}thieno [3,2-d]pyrimidin-4 (3H)-one (170 mg) and tert-butyl 3-methyl-4-(4,4,5,5-tetramethyl-1,3,2-dioxaborolan-2-yl)-1H-pyrazole-1-carboxylate (479 mg), sodium carbonate (124 mg), 1,2-dimethoxyethane (4.0 mL) and water (2.0 mL) and [1,1'-bis(diphenylphosphino)ferrocene]palladium(II) dichloride-dichloromethane complex (1:1) (42 mg).

$^1$H-NMR (DMSO-d$_6$) δ 0.98 (3H, d, J=6.6 Hz), 1.21-1.37 (1H, m), 1.87-2.02 (1H, m), 2.06-2.26 (2H, m), 2.45 (3H, brs), 2.53-2.61 (1H, m), 2.62-2.73 (1H, m), 2.77-2.89 (1H, m), 3.55 (2H, s), 7.37 (1H, s), 8.03 (1H, brs), 12.13-12.91 (2H, m).

Example 27

Production of 6-(5-methyl-1H-pyrazol-4-yl)-2-{[(3S)-3-methylpyrrolidin-1-yl]methyl}thieno[3,2-d]pyrimidin-4 (3H)-one A) Production of 6-bromo-2-{[(3S)-3-methylpyrrolidin-1-yl]methyl}thieno[3,2-d]pyrimidin-4 (3H)-one In the same manner as in Example 2, step B, the title compound (186 mg) was obtained as a pale-yellow solid from 6-bromo-2-(chloromethyl)thieno[3,2-d]pyrimidin-4 (3H)-one (180 mg) produced in Example 2, step A, (3S)-3-methylpyrrolidine hydrochloride (235 mg), potassium carbonate (445 mg), sodium iodide (9.7 mg) and N,N-dimethylformamide (3.0 mL).

$^1$H-NMR (DMSO-d$_6$) δ 0.98 (3H, d, J=6.6 Hz), 1.21-1.36 (1H, m), 1.86-2.03 (1H, m), 2.05-2.25 (2H, m), 2.53-2.61 (1H, m), 2.61-2.74 (1H, m), 2.76-2.88 (1H, m), 3.55 (2H, s), 7.59 (1H, s), 12.19 (1H, brs).

B) Production of 6-(5-methyl-1H-pyrazol-4-yl)-2-{[(3S)-3-methylpyrrolidin-1-yl]methyl}thieno[3,2-d]pyrimidin-4 (3H)-one In the same manner as in Example 2, step C, the title compound (37 mg) was obtained as a pale-brown solid from 6-bromo-2-{[(3S)-3-methylpyrrolidin-1-yl]methyl}thieno [3,2-d]pyrimidin-4 (3H)-one (180 mg) and tert-butyl 3-methyl-4-(4,4,5,5-tetramethyl-1,3,2-dioxaborolan-2-yl)-1H-pyrazole-1-carboxylate (507 mg), sodium carbonate (132 mg), 1,2-dimethoxyethane (4.0 mL) and water (2.0 mL) and [1,1'-bis(diphenylphosphino)ferrocene]palladium(II) dichloride-dichloromethane complex (1:1) (45 mg).

$^1$H-NMR (DMSO-d$_6$) δ 0.98 (3H, d, J=6.6 Hz), 1.20-1.37 (1H, m), 1.88-2.03 (1H, m), 2.05-2.25 (2H, m), 2.45 (3H, s), 2.53-2.62 (1H, m), 2.62-2.72 (1H, m), 2.78-2.86 (1H, m), 3.55 (2H, s), 7.37 (1H, s), 8.02 (1H, brs), 11.97-13.06 (2H, m).

Example 28

Production of 6-(5-methyl-1H-pyrazol-4-yl)-2-{[3-(trifluoromethyl)pyrrolidin-1-yl]methyl}thieno[3,2-d]pyrimidin-4 (3H)-one A) Production of 6-bromo-2-{[3-(trifluoromethyl)pyrrolidin-1-yl]methyl}thieno[3,2-d]pyrimidin-4 (3H)-one In the same manner as in Example 2, step B, the title compound (220 mg) was obtained as a pale-brown solid from 6-bromo-2-(chloromethyl)thieno[3,2-d]pyrimidin-4 (3H)-one (200 mg) produced in Example 2, step A and 3-trifluoromethylpyrrolidine hydrochloride (377 mg) and triethylamine (0.595 mL) and sodium iodide (10.7 mg) and N,N-dimethylformamide (4.0 mL).

$^1$H-NMR (DMSO-d$_6$) δ 1.70-1.84 (1H, m), 1.95-2.10 (1H, m), 2.55-2.72 (3H, m), 2.91 (1H, t, J=9.3 Hz), 3.02-3.19 (1H, m), 3.58 (2H, s), 7.58 (1H, s), 12.37 (1H, brs).

B) Production of 6-(5-methyl-1H-pyrazol-4-yl)-2-{[3-(trifluoromethyl)pyrrolidin-1-yl]methyl}thieno [3,2-d]pyrimidin-4 (3H)-one In the same manner as in Example 2, step C, the title compound (57.3 mg) was obtained as a colorless solid from 6-bromo-2-{[3-(trifluoromethyl)pyrrolidin-1-yl] methyl}thieno[3,2-d]pyrimidin-4 (3H)-one (218 mg) and tert-butyl 3-methyl-4-(4,4,5,5-tetramethyl-1,3,2-dioxaborolan-2-yl)-1H-pyrazole-1-carboxylate (351 mg), cesium carbonate (371 mg), 1,2-dimethoxyethane (5.0 mL) and water (0.5 mL) and [1,1'-bis(diphenylphosphino)ferrocene]palladium(II) dichloride-dichloromethane complex (1:1) (93 mg).

$^1$H-NMR (DMSO-d$_6$) δ 1.71-1.86 (1H, m), 1.96-2.12 (1H, m), 2.45 (3H, s), 2.57-2.78 (3H, m), 2.93 (1H, t, J=9.2 Hz), 3.01-3.21 (1H, m), 3.60 (2H, s), 7.38 (1H, s), 7.70-8.39 (1H, m), 12.16 (1H, brs), 12.97 (1H, brs).

Example 29

Production of 6-(5-methyl-1H-pyrazol-4-yl)-2-{[2-(trifluoromethyl)pyrrolidin-1-yl]methyl}thieno[3,2-d]pyrimidin-4 (3H)-one A) Production of 6-bromo-2-{[2-(trifluoromethyl)pyrrolidin-1-yl]methyl}thieno[3,2-d]pyrimidin-4 (3H)-one In the same manner as in Example 2, step B, the title compound (35.8 mg) was obtained as a pale-yellow solid from 6-bromo-2-(chloromethyl)thieno[3,2-d]pyrimidin-4 (3H)-one (200 mg) produced in Example 2, step A and 2-trifluoromethylpyrrolidine (0.247 mL) and triethylamine (0.298 mL) and sodium iodide (10.7 mg) and N,N-dimethylformamide (4.0 mL).

$^1$H-NMR (DMSO-d$_6$) δ 1.68-1.89 (3H, m), 2.02-2.17 (1H, m), 2.75-2.86 (1H, m), 3.03-3.13 (1H, m), 3.78-3.85 (1H, m), 3.87 (2H, d, J=3.8 Hz), 7.57 (1H, s), 12.42 (1H, brs).

B) Production of 6-(5-methyl-1H-pyrazol-4-yl)-2-{[2-(trifluoromethyl)pyrrolidin-1-yl]methyl}thieno [3,2-d]pyrimidin-4 (3H)-one In the same manner as in Example 2, step C, the title compound (8.3 mg) was obtained as a white solid from 6-bromo-2-{[2-(trifluoromethyl)pyrrolidin-1-yl]

methyl}thieno[3,2-d]pyrimidin-4 (3H)-one (34 mg) and tert-butyl 3-methyl-4-(4,4,5,5-tetramethyl-1,3,2-dioxaborolan-2-yl)-1H-pyrazole-1-carboxylate (54.8 mg), cesium carbonate (58.0 mg), 1,2-dimethoxyethane (3.0 mL) and water (0.3 mL) and [1,1'-bis(diphenylphosphino)ferrocene] palladium(II) dichloride-dichloromethane complex (1:1) (14.5 mg).

$^1$H-NMR (DMSO-d$_6$) δ 1.66-1.92 (3H, m), 2.06-2.23 (1H, m), 2.46 (3H, s), 2.75-2.87 (1H, m), 3.06-3.16 (1H, m), 3.80-3.89 (1H, m), 3.90 (2H, s), 7.39 (1H, s), 7.85-8.32 (1H, m), 12.16 (1H, brs), 12.99 (1H, brs).

Example 30

Production of 6-(5-methyl-1H-pyrazol-4-yl)-2-[(2S, 4R)-4-phenoxypyrrolidin-2-yl]thieno[3,2-d]pyrimidin-4 (3H)-one dihydrochloride A) Production of tert-butyl(2S,4R)-2-(6-bromo-4-oxo-3,4-dihydrothieno[3,2-d]pyrimidin-2-yl)-4-phenoxypyrrolidine-1-carboxylate A solution of (4R)-1-(tert-butoxycarbonyl)-4-phenoxy-L-proline (1.04 g), O-(7-azabenzotriazol-1-yl)-N,N,N',N'-tetramethyluronium hexafluorophosphate (1.29 g) and N-ethyl-N-(1-methylethyl)propan-2-amine (0.692 mL) in N,N-dimethylformamide (5 mL) was stirred at room temperature for 30 min. To the reaction mixture was added 3-amino-5-bromothiophene-2-carboxamide (250 mg) produced in Example 1, step D, and the mixture was stirred at 90° C. for 1.5 hr. The reaction mixture was concentrated under reduced pressure, ethyl acetate (20 mL) and aqueous sodium hydrogen carbonate (10 mL) were added to the obtained residue, and the separated aqueous layer was extracted with ethyl acetate (5 mL). The combined organic layers were washed with brine (5 mL) and dried over anhydrous sodium sulfate. Insoluble material was filtered off, and the filtrate was concentrated under reduced pressure. The residue was purified by silica gel column chromatography (ethyl acetate/hexane) to give an inseparable mixture of tert-butyl(2S,4R)-2-[(5-bromo-2-carbamoylthiophen-3-yl)carbamoyl]-4-phenoxy-pyrrolidine-1-carboxylate and impurity having an undetermined structure as a pale-yellow solid. To a solution of the inseparable mixture of tert-butyl(2S,4R)-2-[(5-bromo-2-carbamoylthiophen-3-yl)carbamoyl]-4-phenoxypyrrolidine-1-carboxylate produced above and impurity having an undetermined structure in ethanol (5 mL) was added 2M aqueous sodium hydroxide solution (1.70 mL), and the mixture was stirred at 70° C. for 2 hr. 6M Hydrochloric acid (0.60 mL) was added to the reaction mixture, and the precipitated solid was collected by filtration, and washed successively with water (5 mL), ethanol (5 mL) and diethyl ether (5 mL) to give the title compound (440 mg) as a colorless solid.

$^1$H-NMR (DMSO-d$_6$) δ 1.11 (9H, s, major), 1.34 (9H, s, minor), 2.24-2.37 (1H, m), 2.43-3.58 (1H, m), 3.56-3.67 (1H, m), 3.79-3.91 (1H, m), 4.67-4.81 (1H, m), 5.07-5.15 (1H, m), 6.93-7.02 (3H, m), 7.27-7.37 (2H, m), 7.60 (1H, s, minor), 7.63 (1H, s, major), 12.77 (1H, brs). The ratio of the observed isomer was 2:1.

B) Production of 6-(5-methyl-1H-pyrazol-4-yl)-2-[(2S,4R)-4-phenoxypyrrolidin-2-yl]thieno[3,2-d]pyrimidin-4 (3H)-one dihydrochloride In the same manner as in Example 11, step B, the title compound (310 mg) was obtained as a colorless solid from tert-butyl(2S,4R)-2-(6-bromo-4-oxo-3,4-dihydrothieno[3,2-d]pyrimidin-2-yl)-4-phenoxypyrrolidine-1-carboxylate (450 mg) and tert-butyl 3-methyl-4-(4,4,5,5-tetramethyl-1,3,2-dioxaborolan-2-yl)-1H-pyrazole-1-carboxylate (564 mg), cesium carbonate (596 mg), 1,2-dimethoxyethane (10 mL) and water (1.0 mL) and [1,1'-bis(diphenylphosphino)ferrocene]palladium(II) dichloride-dichloromethane complex (1:1) (149 mg).

$^1$H-NMR (DMSO-d$_6$) δ 2.36-2.46 (1H, m), 2.47 (3H, s), 2.79 (1H, dd, J=14.0, 6.8 Hz), 3.42-3.54 (1H, m), 3.78-3.92 (1H, m), 4.84-4.97 (1H, m), 5.28 (1H, t, J=4.5 Hz), 6.99-7.08 (3H, m), 7.32-7.38 (2H, m), 7.39 (1H, s), 8.11 (1H, s), 9.42 (1H, brs), 10.67 (1H, brs), 12.83 (1H, brs).

Example 31

Production of 6-(5-methyl-1H-pyrazol-4-yl)-2-morpholin-4-ylthieno[3,2-d]pyrimidin-4 (3H)-one A) Production of 6-bromo-2-morpholin-4-ylthieno[3,2-d]pyrimidin-4 (3H)-one A mixture of methyl 3-amino-5-bromothiophene-2-carboxylate (200 mg) produced in Example 1, step C, morpholine-4-carbonitrile (0.17 mL) and 4M hydrochloric acid/cyclopentylmethylether solution (3.0 mL) was stirred at 110° C. for 4 hr. The reaction system was concentrated under reduced pressure, and saturated aqueous sodium hydrogen carbonate was added to the residue. The precipitate was collected by filtration and washed with water. The obtained pale-brown solid was washed with a mixed solvent of ethyl acetate/hexane (1:1) to give the title compound (144 mg) as a pale-yellow solid.

$^1$H-NMR (DMSO-d$_6$) δ 3.51-3.60 (4H, m), 3.61-3.71 (4H, m), 7.29 (1H, s), 11.50 (1H, brs).

B) Production of 6-(5-methyl-1H-pyrazol-4-yl)-2-morpholin-4-ylthieno[3,2-d]pyrimidin-4 (3H)-one In the same manner as in Example 2, step C, the title compound (81 mg) was obtained as a pale-brown solid from 6-bromo-2-morpholin-4-ylthieno[3,2-d]pyrimidin-4 (3H)-one (140 mg) and tert-butyl 3-methyl-4-(4,4,5,5-tetramethyl-1,3,2-dioxaborolan-2-yl)-1H-pyrazole-1-carboxylate (410 mg), sodium carbonate (106 mg), 1,2-dimethoxyethane (3.0 mL) and water (1.5 mL) and [1,1'-bis(diphenylphosphino) ferrocene]palladium(II) dichloride-dichloromethane complex (1:1) (36 mg).

$^1$H-NMR (DMSO-d$_6$) δ 2.33-2.47 (3H, m), 3.50-3.61 (4H, m), 3.61-3.72 (4H, m), 7.11 (1H, s), 7.83 (0.6H, brs), 8.19 (0.4H, brs), 11.35 (1H, brs), 12.79-13.07 (1H, m).

Example 32

Production of 6-(5-methyl-1H-pyrazol-4-yl)-2-(tetrahydrofuran-2-yl)thieno[3,2-d]pyrimidin-4 (3H)-one A) Production of tetrahydrofuran-2-carbonylchloride A mixture of tetrahydrofuran-2-carboxylic acid (0.19 mL) and ethanedioyldichloride (0.42 mL) was stirred at room temperature for 18 hr. The reaction system was concentrated under reduced pressure to give the title compound (241 mg) as a pale-yellow liquid.

$^1$H-NMR (CDCl$_3$) δ 2.14-2.46 (2H, m), 3.50-3.63 (1H, m), 3.77-4.06 (3H, m), 4.06-4.16 (1H, m).

B) Production of 6-bromo-2-(tetrahydrofuran-2-yl) thieno[3,2-d]pyrimidin-4 (3H)-one To a mixture of 3-amino-5-bromothiophene-2-carboxamide (120 mg) produced in Example 1, step D, triethylamine (0.083 mL) and tetrahydrofuran (3.0 mL) was added tetrahydrofuran-2-carbonylchloride (80 mg) with stirring at room temperature. The reaction mixture was stirred for 10 min, and the reaction system was concentrated under reduced pressure. 2M Aqueous sodium hydroxide solution (1.0 mL) was added to the residue, and the mixture was stirred with heating at 120° C. for 2 hr. The mixture was extracted with ethyl acetate, washed with brine and dried over anhydrous sodium sulfate. Insoluble material was removed by filtration, and the filtrate was concentrated under reduced pressure to give the title compound (160 mg) as a pale-yellow solid.

$^1$H-NMR (DMSO-$d_6$) δ 2.04-2.33 (2H, m), 3.22-3.34 (1H, m), 3.67-3.89 (3H, m), 3.93-4.01 (1H, m), 7.32 (1H, s).

C) Production of 6-(5-methyl-1H-pyrazol-4-yl)-2-(tetrahydrofuran-2-yl)thieno[3,2-d]pyrimidin-4 (3H)-one In the same manner as in Example 2, step C, the title compound (59 mg) was obtained as a pale-brown solid from 6-bromo-2-(tetrahydrofuran-2-yl)thieno[3,2-d]pyrimidin-4 (3H)-one (160 mg) and tert-butyl 3-methyl-4-(4,4,5,5-tetramethyl-1,3,2-dioxaborolan-2-yl)-1H-pyrazole-1-carboxylate (491 mg), sodium carbonate (128 mg), 1,2-dimethoxyethane (3.0 mL) and water (1.5 mL) and [1,1'-bis(diphenylphosphino)ferrocene]palladium(II) dichloride-dichloromethane complex (1:1) (43 mg).

$^1$H-NMR (DMSO-$d_6$) δ 2.18-2.31 (2H, m), 2.38-2.48 (3H, m), 3.38-3.52 (1H, m), 3.72-3.94 (3H, m), 3.99-4.06 (1H, m), 7.38 (1H, s), 7.89 (0.6H, brs), 8.25 (0.4H, brs), 12.38 (1H, brs), 12.87-13.06 (1H, m).

Example 33

Production of 6-(5-methyl-1H-pyrazol-4-yl)-2-{[(2R)-2-methylpyrrolidin-1-yl]methyl}thieno[3,2-d]pyrimidin-4 (3H)-one

A) Production of 6-bromo-2-{[(2R)-2-methylpyrrolidin-1-yl]methyl}thieno[3,2-d]pyrimidin-4 (3H)-one In the same manner as in Example 2, step B, the title compound (205 mg) was obtained as a yellow solid from 6-bromo-2-(chloromethyl)thieno[3,2-d]pyrimidin-4 (3H)-one (180 mg) produced in Example 2, step A, (2R)-2-methylpyrrolidine hydrochloride (235 mg), potassium carbonate (445 mg), sodium iodide (9.7 mg) and N,N-dimethylformamide (3.0 mL).

$^1$H-NMR (DMSO-$d_6$) δ 1.04 (3H, d, J=6.0 Hz), 1.28-1.42 (1H, m), 1.56-1.74 (2H, m), 1.80-1.97 (1H, m), 2.21-2.35 (1H, m), 2.52-2.57 (1H, m), 2.88-3.04 (1H, m), 3.32 (1H, d, J=14.2 Hz), 3.81 (1H, d, J=14.2 Hz), 7.61 (1H, s), 12.18 (1H, brs).

B) Production of 6-(5-methyl-1H-pyrazol-4-yl)-2-{[(2R)-2-methylpyrrolidin-1-yl]methyl}thieno[3,2-d]pyrimidin-4 (3H)-one In the same manner as in Example 2, step C, the title compound (13 mg) was obtained as a yellow solid from 6-bromo-2-{[(2R)-2-methylpyrrolidin-1-yl]methyl}thieno[3,2-d]pyrimidin-4 (3H)-one (200 mg) and tert-butyl 3-methyl-4-(4,4,5,5-tetramethyl-1,3,2-dioxaborolan-2-yl)-1H-pyrazole-1-carboxylate (564 mg), sodium carbonate (146 mg), 1,2-dimethoxyethane (4.0 mL) and water (2.0 mL) and [1,1'-bis(diphenylphosphino)ferrocene]palladium(II) dichloride-dichloromethane complex (1:1) (50 mg).

$^1$H-NMR (DMSO-$d_6$) δ 1.06 (3H, d, J=6.0 Hz), 1.27-1.47 (1H, m), 1.57-1.76 (2H, m), 1.85-2.00 (1H, m), 2.24-2.37 (1H, m), 2.45 (3H, s), 2.52-2.60 (1H, m), 2.93-3.04 (1H, m), 3.33 (1H, d, J=14.0 Hz), 3.81 (1H, d, J=14.0 Hz), 7.37 (1H, s), 8.03 (1H, brs), 11.92-13.20 (2H, m).

Example 34

Production of 2-(ethoxymethyl)-6-(5-methyl-1H-pyrazol-4-yl)thieno[3,2-d]pyrimidin-4 (3H)-one

A) Production of ethoxyacetylchloride

A mixture of ethoxyacetic acid (0.19 mL) and ethanedioyldichloride (0.42 mL) was stirred at room temperature for 18 hr. The reaction system was concentrated under reduced pressure to give the title compound (220 mg) as a pale-yellow liquid.

$^1$H-NMR (CDCl$_3$) δ 1.26 (3H, t, J=7.0 Hz), 3.65 (2H, q, J=7.0 Hz), 4.41 (2H, s).

B) Production of 6-bromo-2-(ethoxymethyl)thieno[3,2-d]pyrimidin-4 (3H)-one

In the same manner as in Example 32, step B, the title compound (140 mg) was obtained as a pale-yellow solid from 3-amino-5-bromothiophene-2-carboxamide (120 mg) produced in Example 1, step D, and triethylamine (0.083 mL) and tetrahydrofuran (3.0 mL) and ethoxyacetylchloride (74 mg).

$^1$H-NMR (DMSO-$d_6$) δ 1.14 (3H, t, J=7.0 Hz), 3.53 (2H, q, J=7.0 Hz), 4.30 (2H, s), 7.48 (1H, s), 12.60 (1H, brs).

C) 2-(ethoxymethyl)-6-(5-methyl-1H-pyrazol-4-yl) thieno[3,2-d]pyrimidin-4 (3H)-one In the same manner as in Example 2, step C, the title compound (59 mg) was obtained as a pale-brown solid from 6-bromo-2-(ethoxymethyl)thieno[3,2-d]pyrimidin-4 (3H)-one (140 mg) and tert-butyl 3-methyl-4-(4,4,5,5-tetramethyl-1,3,2-dioxaborolan-2-yl)-1H-pyrazole-1-carboxylate (448 mg), sodium carbonate (116 mg), 1,2-dimethoxyethane (3.0 mL) and water (1.5 mL) and [1,1'-bis(diphenylphosphino)ferrocene]palladium(II) dichloride-dichloromethane complex (1:1) (40 mg).

$^1$H-NMR (DMSO-$d_6$) δ 1.17 (3H, t, J=7.0 Hz), 2.38-2.50 (3H, m), 3.56 (2H, q, J=7.0 Hz), 4.38 (2H, s), 7.39 (1H, s), 7.89 (0.6H, brs), 8.26 (0.4H, brs), 12.34 (1H, brs), 12.77-13.18 (1H, m).

Example 35

Production of 6-(5-methyl-1H-pyrazol-4-yl)-2-{[(2S)-2-methylpyrrolidin-1-yl]methyl}thieno[3,2-d] pyrimidin-4 (3H)-one dihydrochloride In the same manner as in Example 2, step B and step C, the title compound (104 mg) was obtained as a white solid from 6-bromo-2-(chloromethyl)thieno[3,2-d]pyrimidin-4 (3H)-one (140 mg) produced in Example 2, step A and (S)-2-methylpyrrolidine hydrochloride (182 mg) and potassium carbonate (276 mg) and sodium iodide (7.5 mg) and N,N- dimethylacetamide (4.0 mL) and tert-butyl 3-methyl-4-(4,4,5,5-tetramethyl-1,3,2-dioxaborolan-2-yl)-1H-pyrazole-1-carboxylate (308 mg) and sodium carbonate (265 mg) and 1,2-dimethoxyethane (4.0 mL) and water (1 mL) and [1,1'-bis(diphenylphosphino)ferrocene]palladium(II) dichloride-dichloromethane complex (1:1) (26 mg).

$^1$H-NMR (DMSO-$d_6$) δ 1.41-1.43 (3H, m), 1.62-1.74 (1H, m), 1.93-2.03 (2H, m), 2.17-2.27 (1H, m), 2.46 (3H, s), 3.28-3.38 (3H, m), 4.25-4.64 (2H, m), 7.40 (1H, s), 8.10 (1H, s), 10.24 (1H, brs), 12.80 (1H, brs).

Example 36

Optical resolution of 6-(5-methyl-1H-pyrazol-4-yl)-2-(1-pyrrolidin-1-ylethyl)thieno[3,2-d]pyrimidin-4 (3H)-one 6-(5-Methyl-1H-pyrazol-4-yl)-2-(1-pyrrolidin-1-ylethyl)thieno[3,2-d]pyrimidin-4 (3H)-one (106 mg) was fractionated by high performance liquid chromatography (column: CHIRALPAK AD (50 mm i.d.×500 mm L, manufactured by DAICEL CHEMICAL INDUSTRIES, LTD.), mobile phase: hexane/ethanol/diethylamine (500/500/1), flow rate: 60 mL/min, column temperature: 30° C.). Under the above-mentioned high performance liquid chromatography conditions, the fraction solution containing an optically active form having a shorter retention time was concentrated to give an optically active form of 6-(5-methyl-1H-pyrazol-4-yl)-2-(1-pyrrolidin-1-ylethyl)thieno[3,2-d]pyrimidin-4 (3H)-one (53 mg, retention time 10.6 min, 99.3% ee).

$^1$H-NMR (DMSO-$d_6$) δ 1.39 (3H, d, J=6.6 Hz), 1.63-1.77 (4H, m), 2.38-2.48 (5H, m), 2.55-2.65 (2H, m), 3.49 (1H, q, J=6.6 Hz), 7.37 (1H, s), 8.02 (1H, brs), 12.09-12.93 (2H, m).

In addition, the fraction solution containing an optically active form having a longer retention time was concentrated to give an optically active form of 6-(5-methyl-1H-pyrazol-4-yl)-2-(1-pyrrolidin-1-ylethyl)thieno[3,2-d]pyrimidin-4 (3H)-one (39 mg, retention time 12.1 min, >99.9% ee).

$^1$H-NMR (DMSO-$d_6$) δ 1.39 (3H, d, J=6.8 Hz), 1.60-1.75 (4H, m), 2.37-2.48 (5H, m), 2.54-2.66 (2H, m), 3.49 (1H, q, J=6.8 Hz), 7.37 (1H, s), 8.02 (1H, brs), 12.12-13.00 (2H, m).

The analysis was performed by high performance liquid chromatography (column: CHIRALPAK AD (4.6 mm i.d.× 250 mm L, manufactured by DAICEL CHEMICAL INDUSTRIES, LTD.), mobile phase: hexane/ethanol/diethylamine (500/500/1), flow rate: 0.5 mL/min, column temperature: 30° C., detection 220 nm).

Example 37

Production of 6-(5-methyl-1H-pyrazol-4-yl)-2-[(2S)-pyrrolidin-2-yl]thieno[3,2-d]pyrimidin-4 (3H)-one dihydrochloride In the same manner as in the below-mentioned Example 83, step C, the title compound (1.39 g) was obtained as a colorless solid from tert-butyl(2S)-2-(6-bromo-4-oxo-3,4-dihydrothieno[3,2-d]pyrimidin-2-yl)pyrrolidine-1-carboxylate (2.27 g) produced in Example 11, step A, tert-butyl 3-methyl-4-(4,4,5,5-tetramethyl-1,3,2-dioxaborolan-2-yl)-1H-pyrazole-1-carboxylate (2.94 g), cesium carbonate (3.11 g), [1,1'-bis(diphenylphosphino)ferrocene]palladium(II) dichloride-dichloromethane complex (1:1) (779 mg), 1,2-dimethoxyethane (50 mL), water (5 mL), 4M hydrochloric acid/ethyl acetate solution (10 mL) and methanol (50 mL).

$^1$H-NMR (DMSO-$d_6$) δ 1.93-2.16 (3H, m), 2.37-2.47 (1H, m), 2.46 (3H, s), 3.23-3.48 (2H, m), 4.61-4.74 (1H, m), 7.37 (1H, s), 8.10 (1H, s), 8.98 (1H, brs), 10.05 (1H, brs), 12.85 (1H, brs).

Example 38

Production of 6-(5-methyl-1H-pyrazol-4-yl)-2-[(3-phenoxypyrrolidin-1-yl)methyl]thieno[3,2-d]pyrimidin-4 (3H)-one A) Production of 6-bromo-2-[(3-phenoxypyrrolidin-1-yl)methyl]thieno[3,2-d]pyrimidin-4 (3H)-one In the same manner as in Example 2, step B, the title compound (212 mg) was obtained as a colorless solid from 6-bromo-2-(chloromethyl)thieno[3,2-d]pyrimidin-4 (3H)-one (180 mg) produced in Example 2, step A, 3-phenoxypyrrolidine hydrochloride (385 mg), potassium carbonate (445 mg), sodium iodide (9.7 mg) and N,N-dimethylformamide (3.0 mL).

$^1$H-NMR (DMSO-$d_6$) δ 1.72-1.88 (1H, m), 2.20-2.37 (1H, m), 2.54-2.64 (1H, m), 2.69-2.77 (1H, m), 2.77-2.87 (1H, m), 2.96-3.06 (1H, m), 3.54-3.67 (2H, m), 4.83-4.93 (1H, m), 6.82-6.95 (3H, m), 7.19-7.33 (2H, m), 7.61 (1H, s), 12.45 (1H, brs).

B) Production of 6-(5-methyl-1H-pyrazol-4-yl)-2-[(3-phenoxypyrrolidin-1-yl)methyl]thieno[3,2-d]pyrimidin-4 (3H)-one In the same manner as in Example 2, step C, the title compound (46 mg) was obtained as a colorless solid from 6-bromo-2-[(3-phenoxypyrrolidin-1-yl)methyl]thieno[3,2-d]pyrimidin-4 (3H)-one (210 mg) and tert-butyl 3-methyl-4-(4,4,5,5-tetramethyl-1,3,2-dioxaborolan-2-yl)-1H-pyrazole-1-carboxylate (478 mg), sodium carbonate (124 mg), 1,2-dimethoxyethane (3.0 mL) and water (1.5 mL) and [1,1'-bis(diphenylphosphino)ferrocene]palladium(II) dichloride-dichloromethane complex (1:1) (42 mg).

$^1$H-NMR (DMSO-$d_6$) δ 1.73-1.88 (1H, m), 2.22-2.37 (1H, m), 2.45 (3H, brs), 2.55-2.67 (1H, m), 2.70-2.79 (1H, m), 2.79-2.90 (1H, m), 2.96-3.11 (1H, m), 3.53-3.69 (2H, m), 4.81-4.98 (1H, m), 6.80-6.97 (3H, m), 7.20-7.33 (2H, m), 7.38 (1H, s), 7.90 (0.6H, brs), 8.22 (0.4H, brs), 12.20 (1H, brs), 12.97 (1H, brs).

Example 39

Production of 2-(1,4-dioxa-7-azaspiro[4.4]non-7-ylmethyl)-6-(5-methyl-1H-pyrazol-4-yl)thieno[3,2-d]pyrimidin-4 (3H)-one A) Production of benzyl 1,4-dioxa-7-azaspiro[4.4]nonane-7-carboxylate A mixture of benzyl 3-oxopyrrolidine-1-carboxylate (2.00 g), ethane-1,2-diol (2.85 mL), p-toluenesulfonic acid monohydrate (10 mg) and toluene (20 mL) was stirred with heating in a Dean-Stark apparatus at 120° C. for 6 hr. The mixture was allowed to cool to room temperature, diluted with ethyl acetate (10 mL), washed successively with water (5 mL×2) and brine (5 mL), and dried over anhydrous sodium sulfate. Insoluble material was removed by filtration, and the filtrate was concentrated under reduced pressure. The residue was purified by silica gel column chromatography (ethyl acetate/hexane) to give the title compound (2.1 g) as a pale-yellow liquid.

$^1$H-NMR (CDCl$_3$) δ 2.00-2.13 (2H, m), 3.42-3.49 (2H, m), 3.51-3.62 (2H, m), 3.93-4.02 (4H, m), 5.13 (2H, s), 7.28-7.41 (5H, m).

B) Production of 1,4-dioxa-7-azaspiro[4.4]nonane

To a solution of benzyl 1,4-dioxa-7-azaspiro[4.4]nonane-7-carboxylate (1.1 g) in methanol (30 mL) was added palladium(II) hydroxide (100 mg) at room temperature. The mixture was stirred for 2.5 hr under a hydrogen atmosphere (0.4 MPa). Insoluble material was removed by filtration, and the filtrate was concentrated under reduced pressure to give the title compound (540 mg) as a dark orange liquid.

$^1$H-NMR (DMSO-d$_6$) δ 1.76 (2H, t, J=7.1 Hz), 2.71 (2H, s), 2.81 (2H, t, J=7.1 Hz), 3.81 (4H, s).

C) Production of 6-bromo-2-(1,4-dioxa-7-azaspiro[4.4]non-7-ylmethyl)thieno[3,2-d]pyrimidin-4 (3H)-one In the same manner as in Example 2, step B, the title compound (422 mg) was obtained as a pale-yellow solid from 6-bromo-2-(chloromethyl)thieno[3,2-d]pyrimidin-4 (3H)-one (390 mg) produced in Example 2, step A, 1,4-dioxa-7-azaspiro[4.4]nonane (540 mg), potassium carbonate (384 mg), sodium iodide (21 mg) and N,N-dimethylformamide (3.0 mL).

$^1$H-NMR (DMSO-d$_6$) δ 1.87-1.97 (2H, m), 2.63-2.71 (4H, m), 3.53 (2H, s), 3.73-3.87 (4H, m), 7.61 (1H, s), 11.63 (1H, brs).

D) Production of 2-(1,4-dioxa-7-azaspiro[4.4]non-7-ylmethyl)-6-(5-methyl-1H-pyrazol-4-yl)thieno[3,2-d]pyrimidin-4 (3H)-one In the same manner as in Example 2, step C, the title compound (203 mg) was obtained as a pale-brown solid from 6-bromo-2-(1,4-dioxa-7-azaspiro[4.4]non-7-ylmethyl)thieno[3,2-d]pyrimidin-4 (3H)-one (422 mg) and tert-butyl 3-methyl-4-(4,4,5,5-tetramethyl-1,3,2-dioxaborolan-2-yl)-1H-pyrazole-1-carboxylate (1.05 g), sodium carbonate (271 mg), 1,2-dimethoxyethane (5.0 mL) and water (2.5 mL) and [1,1'-bis(diphenylphosphino)ferrocene]palladium(II) dichloride-dichloromethane complex (1:1) (92 mg).

$^1$H-NMR (DMSO-d$_6$) δ 1.94 (2H, t, J=6.9 Hz), 2.45 (3H, brs), 2.63-2.75 (4H, m), 3.54 (2H, s), 3.74-3.88 (4H, m), 7.38 (1H, s), 7.89 (0.6H, brs), 8.19 (0.4H, brs), 12.17 (1H, brs), 12.98 (1H, brs).

Example 40

Production of 6-(5-methyl-1H-pyrazol-4-yl)-2-[(2S,5R)-5-phenylpyrrolidin-2-yl]thieno[3,2-d]pyrimidin-4 (3H)-one monohydrochloride A) Production of tert-butyl(2S,5R)-2-[(5-bromo-2-carbamoylthiophen-3-yl)carbamoyl]-5-phenylpyrrolidine-1-carboxylate In the same manner as in Example 11, step A, the title compound (434 mg) was obtained as a colorless solid from 3-amino-5-bromothiophene-2-carboxamide (250 mg) produced in Example 1, step D and (5R)-1-(tert-butoxycarbonyl)-5-phenyl-L-proline (988 mg) and O-(7-azabenzotriazol-1-yl)-N,N,N',N'-tetramethyluronium hexafluorophosphate (1.28 g) and N-ethyl-N-(1-methylethyl)propan-2-amine (0.692 mL) and N,N-dimethylformamide (5 mL).

$^1$H-NMR (DMSO-d$_6$) δ 1.11 (9/2H, brs), 1.24 (9/2H, brs), 1.69-1.86 (1H, m), 2.01 (1H, brs), 2.13-2.42 (2H, m), 4.28-4.45 (1H, m), 4.64-4.96 (1H, m), 7.16-7.25 (1H, m), 7.25-7.34 (2H, m), 7.56 (2H, d, J=7.4 Hz), 7.74 (2H, brs), 8.13 (1H, s), 11.51 (1H, brs).

* observed as a 1:1 mixture of rotamers.

B) Production of tert-butyl(2S,5R)-2-(6-bromo-4-oxo-3,4-dihydrothieno[3,2-d]pyrimidin-2-yl)-5-phenylpyrrolidine-1-carboxylate To a solution of tert-butyl(2S,5R)-2-[(5-bromo-2-carbamoylthiophen-3-yl)carbamoyl]-5-phenylpyrrolidine-1-carboxylate (430 mg) produced above in ethanol (5 mL) was added 2M aqueous sodium hydroxide solution (1.31 mL), and the mixture was stirred at 70° C. for 2.5 hr. The reaction mixture was neutralized with 6M hydrochloric acid (0.45 mL) under ice-cooling, and water (4 mL) was added dropwise at room temperature. The precipitated solid was collected by filtration to give the title compound (342 mg) as a white solid.

$^1$H-NMR (DMSO-d$_6$) δ 0.94-1.22 (9H, m), 1.78-2.12 (2H, m), 2.17-2.41 (2H, m), 4.62-4.98 (2H, m), 7.17-7.27 (1H, m), 7.37 (2H, t, J=7.6 Hz), 7.68 (1H, brs), 7.74-7.86 (2H, m), 12.76 (1H, brs).

C) Production of 6-(5-methyl-1H-pyrazol-4-yl)-2-[(2S,5R)-5-phenylpyrrolidin-2-yl]thieno[3,2-d]pyrimidin-4 (3H)-one monohydrochloride In the same manner as in the below-mentioned Example 83, step C, tert-butyl 4-{2-[(2S,5R)-1-(tert-butoxycarbonyl)-5-phenylpyrrolidin-2-yl]-4-oxo-3,4-dihydrothieno[3,2-d]pyrimidin-6-yl}-3-methyl-1H-pyrazole-1-carboxylate was obtained as a colorless solid from tert-butyl(2S,5R)-2-(6-bromo-4-oxo-3,4-dihydrothieno[3,2-d]pyrimidin-2-yl)-5-phenylpyrrolidine-1-carboxylate (340 mg) produced above, tert-butyl 3-methyl-4-(4,4,5,5-tetramethyl-1,3,2-dioxaborolan-2-yl)-1H-pyrazole-1-carboxylate (440 mg), cesium carbonate (466 mg), [1,1'-bis(diphenylphosphino)ferrocene]palladium(II) dichloride-dichloromethane complex (1:1) (117 mg), 1,2-dimethoxyethane (5 mL), and water (0.5 mL). To a solution of tert-butyl 4-{2-[(2S,5R)-1-(tert-butoxycarbonyl)-5-phenylpyrrolidin-2-yl]-4-oxo-3,4-dihydrothieno[3,2-d]pyrimidin-6-yl}-3-methyl-1H-pyrazole-1-carboxylate produced above in methanol (10 mL) was added 4M hydrochloric acid/ethyl acetate solution (2 mL), and the mixture was stirred at 50° C. for 1.5 hr. The reaction mixture was concentrated under reduced pressure, and the obtained residue was crystallized from methanol/water (10 mL/10 mL) to give the title compound (126 mg) as a colorless solid.

$^1$H-NMR (DMSO-d$_6$) δ 2.20-2.47 (3H, m), 2.47 (3H, brs), 2.53-2.62 (1H, m), 4.79 (1H, dd, J=10.8, 6.6 Hz), 4.88 (1H, dd, J=8.5, 4.2 Hz), 7.42 (1H, s), 7.43-7.56 (3H, m), 7.62-7.70 (2H, m), 7.86-8.44 (1H, m), 8.80 (1/2H, brs), 10.91 (1/2H, brs), 12.46-13.35 (2H, m).

Example 41

Production of 2-[(dimethylamino)methyl]-6-(5-methyl-1H-pyrazol-4-yl)thieno[3,2-d]pyrimidin-4 (3H)-one dihydrochloride In the same manner as in Example 2, step B and step C, the title compound (66 mg) was obtained as a white solid from 6-bromo-2-(chloromethyl)thieno[3,2-d]pyrimidin-4 (3H)-one (140 mg) produced in Example 2, step A and N-methylmethanamine hydrochloride (203 mg) and N,N-dimethylformamide (3.0 mL) and tert-butyl 3-methyl-4-(4,4,5,5-tetramethyl-1,3,2-dioxaborolan-2-yl)-1H-pyrazole-1-carboxylate (380 mg) and sodium carbonate (265 mg) and 1,2-dimethoxyethane (4.0 mL) and water (2 mL) and [1,1'-bis(diphenylphosphino)ferrocene]palladium(II) dichloride-dichloromethane complex (1:1) (41 mg).

$^1$H-NMR (DMSO-d$_6$) δ 2.47 (3H, s), 2.95 (6H, s), 4.40 (2H, s), 7.40 (1H, s), 8.10 (1H, s), 10.40 (1H, brs), 12.82 (1H, brs).

Example 42

Production of 2-[(diethylamino)methyl]-6-(5-methyl-1H-pyrazol-4-yl)thieno[3,2-d]pyrimidin-4 (3H)-one 0.57M Diethylamine/N,N-dimethylacetamide solution (0.7 mL), 0.15M sodium iodide/N,N-dimethylacetamide solution (0.2 mL), and 0.12 M 6-bromo-2-(chloromethyl)thieno[3,2-d]pyrimidin-4 (3H)-one/N,N-dimethylacetamide solution (1.0 mL) were successively added to potassium carbonate (33.2 mg), and the mixture was stirred at 70° C. for 2.5 hr. Insoluble material was removed by filtration, and the filtrate was purified by high performance liquid chromatography {column: YMC CombiPrep Pro C18 RS (20 mm i.d.×50 mm L), mobile phase: acetonitrile/10% aqueous ammonium formate solution}. The obtained compound was dissolved in 1,2-dimethoxyethane (0.5 mL), 0.48M tert-butyl 3-methyl-4-(4,4,5,5-tetramethyl-1,3,2-dioxaborolan-2-yl)-1H-pyrazole-1-carboxylate/DME solution (0.5 mL), 0.96M aqueous calcium carbonate solution (0.5 mL), and [1,1'-bis(diphenylphosphino)ferrocene]palladium(II) dichloride-dichloromethane complex (1:1) (10 mg) were added, and the mixture was stirred at 100° C. for 4 hr under a nitrogen atmosphere. Insoluble material was removed by filtration, and the filtrate was purified by high performance liquid chromatography {column: YMC CombiPrep Pro C18 RS (20 mm i.d.×50 mm L), mobile phase: acetonitrile/10% aqueous ammonium formate solution} to give the title compound (8.5 mg).

MS(ESI+): [M+H]$^+$318.
MS(ESI+), found: 318.

Example 43

Production of 2-[(4-hydroxypiperidin-1-yl)methyl]-6-(5-methyl-1H-pyrazol-4-yl)thieno[3,2-d]pyrimidin-4 (3H)-one In the same manner as in Example 42 except that a 0.57M piperidin-4-ol/N,N-dimethylacetamide solution (0.7 mL) was used instead of the 0.57M diethylamine/N,N-dimethylacetamide solution (0.7 mL), the title compound (12 mg) was obtained.

MS(ESI+): [M+H]$^+$346.
MS(ESI+), found: 346.

Example 44

Production of 2-[(3-hydroxypiperidin-1-yl)methyl]-6-(5-methyl-1H-pyrazol-4-yl)thieno[3,2-d]pyrimidin-4 (3H)-one In the same manner as in Example 42 except that a 0.57M piperidin-3-ol/N,N-dimethylacetamide solution (0.7 mL) was used instead of the 0.57 M diethylamine/N,N-dimethylacetamide solution (0.7 mL), the title compound (20.5 mg) was obtained.

MS(ESI+): [M+H]$^+$346.
MS(ESI+), found: 346.

Example 45

Production of 6-(5-methyl-1H-pyrazol-4-yl)-2-(thiomorpholin-4-ylmethyl)thieno[3,2-d]pyrimidin-4 (3H)-one In the same manner as in Example 42 except that a 0.57M thiomorpholine/N,N-dimethylacetamide solution (0.7 mL) was used instead of the 0.57 M diethylamine/N,N-dimethylacetamide solution (0.7 mL), the title compound (9.7 mg) was obtained.

MS(ESI+): [M+11]$^+$348.
MS(ESI+), found: 348.

Example 46

Production of 2-{[(2R)-2-(methoxymethyl)pyrrolidin-1-yl]methyl}-6-(5-methyl-1H-pyrazol-4-yl)thieno[3,2-d]pyrimidin-4 (3H)-one In the same manner as in Example 42 except that a 0.57M (2R)-2-(methoxymethyl)pyrrolidine/N,N-dimethylacetamide solution (0.7 mL) was used instead of the 0.57 M diethylamine/N,N-dimethylacetamide solution (0.7 mL), the title compound (17.6 mg) was obtained.

MS(ESI+): [M+H]$^+$360.
MS(ESI+), found: 360.

Example 47

Production of 2-{[(2S)-2-(methoxymethyl)pyrrolidin-1-yl]methyl}-6-(5-methyl-1H-pyrazol-4-yl)thieno[3,2-d]pyrimidin-4 (3H)-one In the same manner as in Example 42 except that a 0.57M (2S)-2-(methoxymethyl)pyrrolidine/N,N-dimethylacetamide solution (0.7 mL) was used instead of the 0.57M diethylamine/N,N-dimethylacetamide solution (0.7 mL), the title compound (17.6 mg) was obtained.

MS(ESI+): [M+H]$^+$360.
MS(ESI+), found: 360.

Example 48

Production of 2-(1,3-dihydro-2H-isoindol-2-ylmethyl)-6-(5-methyl-1H-pyrazol-4-yl)thieno[3,2-d]pyrimidin-4 (3H)-one In the same manner as in Example 42 except that a 0.57M 2,3-dihydro-1H-isoindole/N,N-dimethylacetamide solution (0.7 mL) was used instead of the 0.57M diethylamine/N,N-dimethylacetamide solution (0.7 mL), the title compound (12.5 mg) was obtained.

MS(ESI+): [M+H]$^+$364.
MS(ESI+), found: 364.

Example 49

Production of 2-{[benzyl(methyl)amino]methyl}-6-(5-methyl-1H-pyrazol-4-yl)thieno[3,2-d]pyrimidin-4 (3H)-one In the same manner as in Example 42 except that a 0.57M N-methyl-1-phenylmethanamine/N,N-dimethylacetamide solution (0.7 mL) was used instead of the 0.57M diethylamine/N,N-dimethylacetamide solution (0.7 mL), the title compound (14.1 mg) was obtained.
MS(ESI+): [M+H]$^+$366.
MS(ESI+), found: 366.

Example 50

Production of 2-(3,4-dihydroisoquinolin-2 (1H)-ylmethyl)-6-(5-methyl-1H-pyrazol-4-yl)thieno[3,2-d]pyrimidin-4 (3H)-one In the same manner as in Example 42 except that a 0.57M 1,2,3,4-tetrahydroisoquinoline/N,N-dimethylacetamide solution (0.7 mL) was used instead of the 0.57M diethylamine/N,N-dimethylacetamide solution (0.7 mL), the title compound (3.6 mg) was obtained.
MS(ESI+): [M+H]$^+$378.
MS(ESI+), found: 378.

Example 51

Production of ethyl 1-{[6-(5-methyl-1H-pyrazol-4-yl)-4-oxo-3,4-dihydrothieno[3,2-d]pyrimidin-2-yl]methyl}piperidine-3-carboxylate In the same manner as in Example 42 except that a 0.57M ethyl piperidine-3-carboxylate/N,N-dimethylacetamide solution (0.7 mL) was used instead of the 0.57M diethylamine/N,N-dimethylacetamide solution (0.7 mL), the title compound (23.8 mg) was obtained.
MS(ESI+): [M+H]$^+$402.
MS(ESI+), found: 402.

Example 52

Production of 1-{[6-(5-methyl-1H-pyrazol-4-yl)-4-oxo-3,4-dihydrothieno[3,2-d]pyrimidin-2-yl]methyl}-4-phenylpiperidine-4-carbonitrile In the same manner as in Example 42 except that a 0.57M 4-phenylpiperidine-4-carbonitrile monohydrochloride/N,N-dimethylacetamide solution (0.7 mL) was used instead of the 0.57M diethylamine/N,N-dimethylacetamide solution (0.7 mL), the title compound (1.4 mg) was obtained.
MS(ESI+): [M+H]$^+$431.
MS(ESI+), found: 431.

Example 53

Production of 2-[(4-acetyl-4-phenylpiperidin-1-yl)methyl]-6-(5-methyl-1H-pyrazol-4-yl)thieno[3,2-d]pyrimidin-4 (3H)-one In the same manner as in Example 42 except that a 0.57M 1-(4-phenylpiperidin-4-yl)ethanone monohydrochloride/N,N-dimethylacetamide solution (0.7 mL) was used instead of the 0.57M diethylamine/N,N-dimethylacetamide solution (0.7 mL), the title compound (13.1 mg) was obtained.
MS(ESI+): [M+H]$^+$448.
MS(ESI+), found: 448.

Example 54

Production of 1-{[6-(5-methyl-1H-pyrazol-4-yl)-4-oxo-3,4-dihydrothieno[3,2-d]pyrimidin-2-yl]methyl}-L-proline In the same manner as in Example 42 except that a 0.57M benzyl L-prolinate monohydrochloride/N,N-dimethylacetamide solution (0.7 mL) was used instead of the 0.57M diethylamine/N,N-dimethylacetamide solution (0.7 mL), the title compound (20.6 mg) was obtained.
MS(ESI+): [M+H]$^+$360.
MS(ESI+), found: 360.

Example 55

Production of 2-{[3-(dimethylamino)pyrrolidin-1-yl]methyl}-6-(5-methyl-1H-pyrazol-4-yl)thieno[3,2-d]pyrimidin-4 (3H)-one In the same manner as in Example 42 except that a 0.57M N,N-dimethylpyrrolidin-3-amine/N,N-dimethylacetamide solution (0.7 mL) was used instead of the 0.57M diethylamine/N,N-dimethylacetamide solution (0.7 mL), the title compound (10.3 mg) was obtained.
MS(ESI+): [M+H]$^+$359.
MS(ESI+), found: 359.

Example 56

Production of 6-(5-methyl-1H-pyrazol-4-yl)-2-[(4-(pyrrolidin-1-yl)piperidin-1-yl)methyl]thieno[3,2-d]pyrimidin-4 (3H)-one In the same manner as in Example 42 except that a 0.57M 4-(pyrrolidin-1-yl)piperidine/N,N-dimethylacetamide solution (0.7 mL) was used instead of the 0.57M diethylamine/N,N-dimethylacetamide solution (0.7 mL), the title compound (22.2 mg) was obtained.
MS(ESI+): [M+H]$^+$399.
MS(ESI+), found: 399.

Example 57

Production of 2-{[(1-benzylpyrrolidin-3-yl)(methyl)amino]methyl}-6-(5-methyl-1H-pyrazol-4-yl)thieno[3,2-d]pyrimidin-4 (3H)-one In the same manner as in Example 42 except that a 0.57M 1-benzyl-N-methylpyrrolidin-3-amine/N,N-dimethylacetamide solution (0.7 mL) was used instead of the 0.57M diethylamine/N,N-dimethylacetamide solution (0.7 mL), the title compound (16.2 mg) was obtained.
MS(ESI+): [M+H]$^+$435.
MS(ESI+), found: 435.

Example 58

Production of 2-{[4-(2-fluorophenyl)piperazin-1-yl]methyl}-6-(5-methyl-1H-pyrazol-4-yl)thieno[3,2-d]pyrimidin-4 (3H)-one In the same manner as in Example 42 except that a 0.57M 1-(2-fluorophenyl)piperazine/N,N-dimethylacetamide solution (0.7 mL) was used instead of the 0.57M diethylamine/N,N-dimethylacetamide solution (0.7 mL), the title compound (1 mg) was obtained.
MS(ESI+): [M+H]$^+$425.
MS(ESI+), found: 425.

Example 59

Production of ethyl N-{[6-(5-methyl-1H-pyrazol-4-yl)-4-oxo-3,4-dihydrothieno[3,2-d]pyrimidin-2-yl]methyl}-N-(pyridin-2-ylmethyl)glycinate In the same manner as in Example 42 except that a 0.57M ethyl N-(pyridin-2-ylmethyl)glycinate/N,N-dimethylacetamide solution (0.7 mL) was used instead of the 0.57M diethylamine/N,N-dimethylacetamide solution (0.7 mL), the title compound (1.1 mg) was obtained.
MS(ESI+): [M+H]$^+$439.
MS(ESI+), found: 439.

Example 60

Production of 2-{[bis(pyridin-3-ylmethyl)amino]methyl}-6-(5-methyl-1H-pyrazol-4-yl)thieno[3,2-d]pyrimidin-4 (3H)-one In the same manner as in Example 42 except that a 0.57M 1-(pyridin-3-yl)-N-(pyridin-3-ylmethyl)methanamine/N,N-dimethylacetamide solution (0.7 mL) was used instead of the 0.57M diethylamine/N,N-dimethylacetamide solution (0.7 the title compound (4.5 mg) was obtained.
MS(ESI+): [M+H]$^+$444.
MS(ESI+), found: 444.

Example 61

Production of 2-{[4-(diphenylmethyl)piperazin-1-yl]methyl}-6-(5-methyl-1H-pyrazol-4-yl)thieno[3,2-d]pyrimidin-4 (3H)-one In the same manner as in Example 42 except that a 0.57M 1-(diphenylmethyl)piperazine/N,N-dimethylacetamide solution (0.7 mL) was used instead of the 0.57M diethylamine/N,N-dimethylacetamide solution (0.7 mL), the title compound (7.3 mg) was obtained.
MS(ESI+): [M+H]$^+$497.
MS(ESI+), found: 497.

Example 62

Production of 2-{[(3,5-dimethoxyphenyl)amino]methyl}-6-(5-methyl-1H-pyrazol-4-yl)thieno[3,2-d]pyrimidin-4 (3H)-one In the same manner as in Example 42 except that a 0.57M 3,5-dimethoxyaniline/N,N-dimethylacetamide solution (0.7 mL) was used instead of the 0.57M diethylamine/N,N-dimethylacetamide solution (0.7 mL), the title compound (1.4 mg) was obtained.
MS(ESI+): [M+H]$^+$398.
MS(ESI+), found: 398.

Example 63

Production of 2-{[(2,4-dimethoxyphenyl)amino]methyl}-6-(5-methyl-1H-pyrazol-4-yl)thieno[3,2-d]pyrimidin-4 (3H)-one In the same manner as in Example 42 except that a 0.57M 2,4-dimethoxyaniline/N,N-dimethylacetamide solution (0.7 mL) was used instead of the 0.57M diethylamine/N,N-dimethylacetamide solution (0.7 mL), the title compound (2.1 mg) was obtained.
MS(ESI+): [M+H]$^+$398.
MS(ESI+), found: 398.

Example 64

Production of 6-(5-methyl-1H-pyrazol-4-yl)-2-[(2-phenylthiomorpholin-4-yl)methyl]thieno[3,2-d]pyrimidin-4 (3H)-one In the same manner as in Example 42 except that a 0.57M 2-phenylthiomorpholine/N,N-dimethylacetamide solution (0.7 mL) was used instead of the 0.57M diethylamine/N,N-dimethylacetamide solution (0.7 mL), the title compound (10.8 mg) was obtained.
MS(ESI+): [M+H]$^+$424.
MS(ESI+), found: 424.

Example 65

Production of 6-(5-methyl-1H-pyrazol-4-yl)-2-[(2-phenylpyrrolidin-1-yl)methyl]thieno[3,2-d]pyrimidin-4 (3H)-one In the same manner as in Example 42 except that a 0.57M 2-phenylpyrrolidine/N,N-dimethylacetamide solution (0.7 mL) was used instead of the 0.57M diethylamine/N,N-dimethylacetamide solution (0.7 mL), the title compound (10.8 mg) was obtained.
MS(ESI+): [M+H]$^+$392.
MS(ESI+), found: 392.

Example 66

Production of 2-{[3-(4-methylbenzyl)pyrrolidin-1-yl]methyl}-6-(5-methyl-1H-pyrazol-4-yl)thieno[3,2-d]pyrimidin-4 (3H)-one In the same manner as in Example 42 except that a 0.57M 3-(4-methylbenzyl)pyrrolidine monohydrochloride/N,N-dimethylacetamide solution (0.7 mL) was used instead of the 0.57M diethylamine/N,N-dimethylacetamide solution (0.7 mL), the title compound (3.5 mg) was obtained.
MS(ESI+): [M+H]$^+$420.
MS(ESI+), found: 420.

Example 67

Production of 6-(5-methyl-1H-pyrazol-4-yl)-2-{[4-(2-oxotetrahydropyrimidin-1(2H)-yl)piperidin-1-yl]methyl}thieno[3,2-d]pyrimidin-4 (3H)-one In the same manner as in Example 42 except that a 0.57M 1-(piperidin-4-yl)tetrahydropyrimidin-2 (1H)-one/N,N-dimethylacetamide solution (0.7 mL) was used instead of the 0.57M diethylamine/N,N-dimethylacetamide solution (0.7 mL), the title compound (10.6 mg) was obtained.
MS(ESI+): [M+H]$^+$428.
MS(ESI+), found: 428.

Example 68

Production of 6-(5-methyl-1H-pyrazol-4-yl)-2-{[(1-(thiophen-2-yl)cyclopropyl)methyl]amino}methyl)thieno[3,2-d]pyrimidin-4 (3H)-one A) Production of 1-(thiophen-2-yl)cyclopropanecarbonitrile To a suspension of sodium hydride (19.1 g) in DMSO (200 mL) was added dropwise a solution of thiophen-2-ylacetonitrile (25 g) in DMSO (20 mL) at 0° C. under a nitrogen atmosphere, and the mixture was stirred for 0.5 hr. To the obtained reaction mixture was added dropwise a solution of 1-bromo-2-chloroethane (25 mL) in DMSO (20 mL) at 0° C. under a nitrogen atmosphere, and the mixture was stirred at room temperature for 3 days. Water was added to the reaction mixture, and the mixture was extracted with ethyl acetate. The organic layer was dried over anhydrous magnesium sulfate, and the solvent was evaporated under reduced pressure. The obtained residue was purified by silica gel column chromatography (ethyl acetate/hexane) to give the title compound as a pale-brown oil (29.2 g).

$^1$H-NMR (CDCl$_3$) δ 1.39-1.46 (2H, m), 1.71-1.78 (2H, m), 6.94 (1H, dd, J=5.1, 3.6 Hz), 7.06 (1H, dd, J=3.6, 1.1 Hz), 7.19 (1H, dd, J=5.2, 1.2 Hz).

B) 1-[1-(thiophen-2-yl)cyclopropyl]methanamine monohydrochloride

To a solution of 1-(thiophen-2-yl)cyclopropanecarbonitrile (14.9 g) in tetrahydrofuran (100 mL) was added 1.1M borane•tetrahydrofuran complex (100 mL) at room temperature, and the mixture was stirred at 60° C. overnight. 6M Aqueous hydrochloric acid solution (20 mL) was carefully added to the reaction mixture, and the mixture was stirred at 60° C. for 0.5 hr. The reaction mixture was allowed to cool to room temperature, and tetrahydrofuran was evaporated under reduced pressure. The obtained residue was diluted with water, and washed with ethyl acetate. The aqueous layer was basified with 8M aqueous sodium hydroxide solution, and the mixture was extracted with ethyl acetate. The extract was dried over anhydrous magnesium sulfate, and the solvent was evaporated under reduced pressure. The obtained residue was dissolved in ethyl acetate, 4M hydrochloric acid/ethyl acetate solution (30 mL) was added, and the solvent was evaporated under reduced pressure. The obtained solid was recrystallized from ethanol-ethyl acetate to give the title compound (10.5 g) as white needle crystals.

$^1$H-NMR (DMSO-d$_6$) δ 0.92-1.00 (2H, m), 1.11-1.22 (2H, m), 3.08 (2H, s), 6.98 (1H, dd, J=5.1, 3.4 Hz), 7.08 (1H, dd, J=3.5, 1.2 Hz), 7.40 (1H, dd, J=5.1, 1.3 Hz), 8.05 (3H, s).

C) Production of 6-(5-methyl-1H-pyrazol-4-yl)-2-[({[1-(thiophen-2-yl)cyclopropyl]methyl}amino)methyl]thieno[3,2-c]pyrimidin-4 (3H)-one In the same manner as in Example 42 except that a 0.57M 1-[1-(thiophen-2-yl)cyclopropyl]methanamine monohydrochloride/N,N-dimethylacetamide solution (0.7 mL) was used instead of the 0.57M diethylamine/N,N-dimethylacetamide solution (0.7 mL), the title compound (1.9 mg) was obtained.

MS(ESI+): [M+H]$^+$397.
MS(ESI+), found: 397.

Example 69

Production of 7-methyl-1'-{[6-(5-methyl-1H-pyrazol-4-yl)-4-oxo-3,4-dihydrothieno[3,2-d]pyrimidin-2-yl]methyl}tetrahydro-5H-spiro[1,3-oxazolo[3,4-a]pyrazine-1,4'-piperidin]-3-one A) Production of tert-butyl 4-methylpiperazine-1-carboxylate A mixture of 1-methylpiperazine (15 g), triethylamine (22.7 mL) and tetrahydrofuran (300 mL) was cooled to 0° C., and di-tert-butyl dicarbonate (22 g) was added with stirring. Thereafter, the reaction system was stirred at room temperature for 3 hr. The reaction mixture was concentrated under reduced pressure, 4M aqueous sodium hydroxide solution (100 mL) was added to the residue, and the mixture was extracted with ethyl acetate (300 mL). The extract was washed with water (200 mL) and dried over anhydrous sodium sulfate. Insoluble material was removed by filtration, and the filtrate was concentrated under reduced pressure. The residue was purified by silica gel column chromatography to give the title compound (25.5 g) as a yellow oil.

$^1$H-NMR (CDCl$_3$) δ 1.40 (9H, s), 2.25 (3H, s), 2.31 (4H, t, J=4.8 Hz), 3.40 (4H, t, J=4.8 Hz).

B) Production of 1'-benzyl-7-methyltetrahydro-5H-spiro[1,3-oxazolo[3,4-a]pyrazine-1,4'-piperidin]-3-one A mixture of tert-butyl 4-methylpiperazine-1-carboxylate (24.2 g), N,N,N',N'-tetramethylethane-1,2-diamine (21 g) and tetrahydrofuran (500 mL) was cooled to −78° C. under a nitrogen atmosphere, and sec-butyllithium (184 mL, 1.3M cyclohexane solution) was added dropwise over 1.5 hr while stirring. Furthermore, the mixture was stirred at the same temperature for 2 hr, the reaction system was heated to 30° C., and the mixture was stirred for 1.5 hr. Thereafter, the reaction system was cooled again to −78° C., and a solution of 1-benzylpiperidin-4-one (28.3 g) in tetrahydrofuran (50 mL) was added dropwise over 1 hr. The reaction system was stirred at room temperature overnight, and the mixture was cooled to 0° C. Saturated aqueous ammonium chloride solution (100 mL) was added, and the mixture was stirred at room temperature for 30 min. The mixture was extracted with ethyl acetate (300 mL), and the extract was washed with water (300 mL) and dried over anhydrous sodium sulfate. Insoluble material was removed by filtration, and the filtrate was concentrated under reduced pressure. The residue was purified by silica gel column chromatography to give the title compound (17.6 g) as a brown oil.

$^1$H-NMR (CDCl$_3$) δ 1.62-1.89 (6H, m), 2.21 (3H, s), 2.31-2.40 (2H, m), 2.62 (1H, m), 2.96 (1H, m), 3.31 (1H, m), 3.42 (2H, m), 3.67 (1H, m), 7.20-7.28 (5H, m).

C) Production of 7-methyltetrahydro-5H-spiro[1,3-oxazolo[3,4-a]pyrazine-1,4'-piperidin]-3-one monohydrochloride A mixture of 1'-benzyl-7-methyltetrahydro-5H-spiro[1,3-oxazolo[3,4-a]pyrazine-1,4'-piperidin]-3-one (14.6 g), 10% Pd/C (2 g) and ethanol (100 mL) was stirred at room temperature for 72 hr under a hydrogen atmosphere. Insoluble material was removed by filtration, and the filtrate was concentrated under reduced pressure. The residue was dissolved in ethyl acetate (75 mL), 4M hydrochloric acid/ethyl acetate solution (15 mL) was added, and the mixture was treated for 4 hr. The title compound (10.45 g) was collected by filtration as a white solid.

$^1$H-NMR (CD$_3$OD) δ 2.14-2.18 (2H, m), 2.19-2.31 (2H, m), 3.03 (3H, s), 3.19-3.37 (4H, m), 3.48-3.59 (4H, m), 3.75 (1H, m), 4.03-4.13 (2H, m).

D) Production of 7-methyl-1'-{[6-(5-methyl-1H-pyrazol-4-yl)-4-oxo-3,4-dihydrothieno[3,2-d]pyrimidin-2-yl]methyl}tetrahydro-5H-spiro[1,3-oxazolo[3,4-a]pyrazine-1,4'-piperidin]-3-one In the same manner as in Example 42 except that a 0.57M 7-methyltetrahydro-5H-spiro[1,3-oxazolo[3,4-a]pyrazine-1,4'-piperidin]-3-one monohydrochloride/N,N-dimethylacetamide solution (0.7 mL) was used instead of the 0.57M diethylamine/N,N-dimethylacetamide solution (0.7 mL), the title compound (4.1 mg) was obtained.

MS(ESI+): [M+H]$^+$470.
MS(ESI+), found: 470.

Example 70

Production of 6-(5-methyl-1H-pyrazol-4-yl)-2-{[3-(phenylsulfonyl)pyrrolidin-1-yl]methyl}thieno[3,2-d]pyrimidin-4 (3H)-one In the same manner as in Example 42 except that a 0.57M 3-(phenylsulfonyl)pyrrolidine/N,N-dimethylacetamide solution (0.7 mL) was used instead of the 0.57M diethylamine/N,N-dimethylacetamide solution (0.7 mL), the title compound (11.8 mg) was obtained.
MS(ESI+): [M+H]$^+$456.
MS(ESI+), found: 456.

Example 71

Production of 6-(5-methyl-1H-pyrazol-4-yl)-2-(piperidin-2-yl)thieno[3,2-d]pyrimidin-4 (3H)-one dihydrochloride

A) Production of tert-butyl 2-(6-bromo-4-oxo-3,4-dihydrothieno[3,2-d]pyrimidin-2-yl)piperidine-1-carboxylate To a solution of (2S)-1-(tert-butoxycarbonyl)piperidine-2-carboxylic acid (518 mg) and triethylamine (0.392 mL) in tetrahydrofuran (5 ml) was added 2-methylpropyl chlorocarbonate (0.309 mL) at 0° C., and the mixture was stirred at room temperature for 30 min. To the reaction mixture was added a solution of 3-amino-5-bromothiophene-2-carboxamide (250 mg) produced in Example 1, step D, in tetrahydrofuran (5 mL), and the mixture was stirred at 60° C. for 15 hr. Ethyl acetate (20 mL) and aqueous sodium hydrogen carbonate (10 mL) were added to the reaction mixture, and the separated aqueous layer was extracted with ethyl acetate (5 mL). The combined organic layers were washed with brine (5 mL) and dried over anhydrous sodium sulfate. Insoluble material was filtered off, and the filtrate was concentrated under reduced pressure to give tert-butyl 2-[(5-bromo-2-carbamoylthiophen-3-yl)carbamoyl]piperidine-1-carboxylate as a pale-yellow oil. To a solution of tert-butyl 2-[(5-bromo-2-carbamoylthiophen-3-yl)carbamoyl]piperidine-1-carboxylate produced above in ethanol (5 mL) was added 2M aqueous sodium hydroxide solution (1.70 mL), and the mixture was stirred at 70° C. for 4 hr. The reaction mixture was neutralized with 6M hydrochloric acid (0.6 mL) under ice-cooling, and water (5 mL) was added dropwise at room temperature. The precipitated solid was collected by filtration to give the title compound (240 mg) as a pale-yellow solid.
*The optical purity was 2.9% ee. The analysis was performed by high performance liquid chromatography (column: CHIRALPAK AD-H (4.6 mm i.d.×250 mm L, manufactured by DAICEL CHEMICAL INDUSTRIES, LTD.), mobile phase: hexane/2-propanol/diethylamine (700/300/1), flow rate: 1 mL/min, column temperature: 30° C., detection 220 nm).
$^1$H-NMR (DMSO-d$_6$) δ 1.16-1.58 (3H, m), 1.30 (9H, brs), 1.59-1.86 (2H, m), 1.98-2.13 (1H, m), 3.36-3.53 (1H, m), 3.76-3.88 (1H, m), 4.90-5.07 (1H, m), 7.57 (1H, s), 12.64 (1H, brs).

B) Production of 6-(5-methyl-1H-pyrazol-4-yl)-2-(piperidin-2-yl)thieno[3,2-d]pyrimidin-4 (3H)-one dihydrochloride In the same manner as in the below-mentioned Example 83, step C, the title compound (97.4 mg) was obtained as a colorless solid from tert-butyl 2-(6-bromo-4-oxo-3,4-dihydrothieno[3,2-d]pyrimidin-2-yl)piperidine-1-carboxylate (232 mg) produced above, tert-butyl 3-methyl-4-(4,4,5,5-tetramethyl-1,3,2-dioxaborolan-2-yl)-1H-pyrazole-1-carboxylate (345 mg), cesium carbonate (395 mg), [1,1'-bis(diphenylphosphino)ferrocene]palladium(II) dichloride-dichloromethane complex (1:1) (91.5 mg), 1,2-dimethoxyethane (5 mL), water (0.5 mL), 4M hydrochloric acid/ethyl acetate solution (1 mL) and methanol (8 mL).
$^1$H-NMR (DMSO-d$_6$) δ 1.47-1.94 (5H, m), 2.23-2.35 (1H, m), 2.46 (3H, s), 2.96-3.12 (1H, m), 3.28-3.41 (1H, m), 4.16-4.28 (1H, m), 7.34 (1H, s), 8.12 (1H, s), 9.07-9.26 (1H, m), 9.34-9.46 (1H, m), 12.82 (1H, brs).

Example 72

Production of 6-(5-methyl-1H-pyrazol-4-yl)-2-(morpholin-3-yl)thieno[3,2-d]pyrimidin-4 (3H)-one dihydrochloride

A) Production of tert-butyl 3-(6-bromo-4-oxo-3,4-dihydrothieno[3,2-d]pyrimidin-2-yl)morpholine-4-carboxylate In the same manner as in Example 71, step A, the title compound (271 mg) was obtained as a colorless solid from 3-amino-5-bromothiophene-2-carboxamide (250 mg) produced in Example 1, step D, (3S)-4-(tert-butoxycarbonyl)morpholine-3-carboxylic acid (548 mg), 2-methylpropyl chlorocarbonate (0.309 mL), triethylamine (0.392 mL) and tetrahydrofuran (5 mL), 2M aqueous sodium hydroxide solution (1.70 mL) and ethanol (5 mL).
$^1$H-NMR (DMSO-d$_6$) δ 1.12-1.55 (9H, m), 3.39-3.52 (1H, m), 3.53-3.95 (3H, m), 3.76 (1H, dd, J=12.3, 4.2 Hz), 4.09-4.29 (1H, m), 4.72 (1H, brs), 7.58 (1H, s), 12.74 (1H, brs).

B) Production of 6-(5-methyl-1H-pyrazol-4-yl)-2-(morpholin-3-yl)thieno[3,2-d]pyrimidin-4 (3H)-one dihydrochloride In the same manner as in the below-mentioned Example 83, step C, the title compound (103 mg) was obtained as a colorless solid from tert-butyl 3-(6-bromo-4-oxo-3,4-dihydrothieno[3,2-d]pyrimidin-2-yl)morpholine-4-carboxylate (268 mg) produced above, tert-butyl 3-methyl-4-(4,4,5,5-tetramethyl-1,3,2-dioxaborolan-2-yl)-1H-pyrazole-1-carboxylate (397 mg), cesium carbonate (420 mg), [1,1'-bis(diphenylphosphino)ferrocene]palladium(II) dichloride-dichloromethane complex (1:1) (105 mg), 1,2-dimethoxyethane (5 mL), water (0.5 mL), 4M hydrochloric acid/ethyl acetate solution (1 mL) and methanol (3 mL).
$^1$H-NMR (DMSO-d$_6$) δ 2.46 (3H, s), 3.17-3.42 (2H, m), 3.68 (1H, dd, J=12.1, 10.2 Hz), 3.72-3.85 (1H, m), 3.93-4.04 (1H, m), 4.33 (1H, dd, J=12.4, 3.3 Hz), 4.44-4.56 (1H, m), 7.37 (1H, s), 8.12 (1H, s), 9.69 (1H, brs), 10.00 (1H, brs), 12.92 (1H, brs).

Example 73

Production of 6-(5-methyl-1H-pyrazol-4-yl)-2-[(3-oxopyrrolidin-1-yl)methyl]thieno[3,2-d]pyrimidin-4 (3H)-one A mixture of 2-(1,4-dioxa-7-azaspiro[4.4]non-7-ylmethyl)-6-(5-methyl-1H-pyrazol-4-yl)thieno[3,2-d]pyrimidin-4 (3H)-one (150 mg) produced in Example 39, step D, 6M hydrochloric acid (3 mL) and propan-2-ol (3 mL) was stirred with heating at 90° C. for 5 hr. Saturated aqueous sodium hydrogen carbonate (20 mL) was added to the reaction mixture, and the precipitated solid was collected by filtration, and washed successively with ethyl acetate (3 mL) and water (3 mL). The obtained pale-brown solid was crystallized from methanol/propan-2-ol/hexane to give the title compound (115 mg) as a pale-brown solid.

$^1$H-NMR (DMSO-d$_6$) δ 2.37 (2H, t, J=6.9 Hz), 2.46 (3H, brs), 3.01 (2H, t, J=6.9 Hz), 3.08 (2H, s), 3.71 (2H, s), 7.39 (1H, s), 7.89 (0.6H, brs), 8.26 (0.4H, brs), 12.22 (1H, brs), 12.99 (1H, brs).

Example 74

Production of 6-(5-methyl-1H-pyrazol-4-yl)-2-[phenyl(pyrrolidin-1-yl)methyl]thieno[3,2-d]pyrimidin-4 (3H)-one A) Production of 5-bromo-3-{[phenyl(pyrrolidin-1-yl)acetyl]amino}thiophene-2-carboxamide To a mixture of 3-amino-5-bromothiophene-2-carboxamide (221 mg) produced in Example 1, step D, triethylamine (0.153 mL) and tetrahydrofuran (5.0 mL) was added chloro(phenyl)acetylchloride (0.174 mL) with stirring at room temperature. The reaction mixture was stirred for 10 min, and pyrrolidine (0.42 mL) was added. The reaction mixture was stirred with heating at 70° C. for 1 hr, and the reaction system was concentrated under reduced pressure. To the residue was added 2M aqueous sodium hydroxide solution (1.5 mL), and the mixture was stirred with heating at 120° C. for 2 hr. The mixture was extracted with ethyl acetate and dried over anhydrous sodium sulfate. Insoluble material was removed by filtration, and the filtrate was concentrated under reduced pressure. The residue was purified by basic silica gel column chromatography (ethyl acetate/hexane). The obtained yellow solid was washed with ethyl acetate (2 mL) to give the title compound (330 mg) as a yellow solid.

$^1$H-NMR (DMSO-d$_6$) δ 1.67-1.80 (4H, m), 2.32-2.44 (2H, m), 2.44-2.49 (2H, m), 3.96 (1H, s), 7.26-7.45 (5H, m), 7.70 (2H, brs), 7.99 (1H, s), 12.24 (1H, s).

B) Production of 6-bromo-2-[phenyl(pyrrolidin-1-yl)methyl]thieno[3,2-d]pyrimidin-4 (3H)-one A mixture of 5-bromo-3-{[phenyl(pyrrolidin-1-yl)acetyl]amino}thiophene-2-carboxamide (320 mg), 2M aqueous sodium hydroxide solution (3 mL) and 1,2-dimethoxyethane (1 mL) was stirred with heating in a microwave reactor at 150° C. for 30 min. The mixture was extracted with ethyl acetate and dried over anhydrous sodium sulfate. Insoluble material was removed by filtration, and the filtrate was concentrated under reduced pressure. The residue was purified by basic silica gel column chromatography (ethyl acetate/hexane and methanol/ethyl acetate) to give the title compound (292 mg) as a pale-yellow solid.

$^1$H-NMR (DMSO-d$_6$) δ 1.65-1.85 (4H, m), 2.34-2.47 (4H, m), 4.35 (1H, s), 7.22-7.40 (3H, m), 7.55-7.65 (3H, m), 12.47 (1H, brs).

C) Production of 6-(5-methyl-1H-pyrazol-4-yl)-2-[phenyl(pyrrolidin-1-yl)methyl]thieno[3,2-d]pyrimidin-4 (3H)-one In the same manner as in Example 2, step C, the title compound (235 mg) was obtained as a pale-brown solid from 6-bromo-2-[phenyl(pyrrolidin-1-yl)methyl]thieno[3,2-d]pyrimidin-4 (3H)-one (320 mg) and tert-butyl 3-methyl-4-(4,4,5,5-tetramethyl-1,3,2-dioxaborolan-2-yl)-1H-pyrazole-1-carboxylate (758 mg), sodium carbonate (197 mg), 1,2-dimethoxyethane (4.0 mL), water (2.0 mL) and [1,1'-bis(diphenylphosphino)ferrocene]palladium(II) dichloride-dichloromethane complex (1:1) (67 mg).

$^1$H-NMR (DMSO-d$_6$) δ 1.65-1.85 (4H, m), 2.34-2.48 (7H, m), 4.34 (1H, s), 7.20-7.46 (4H, m), 7.62 (2H, d, J=7.2 Hz), 7.78-8.26 (1H, m), 12.26 (1H, brs), 12.94 (1H, brs).

Example 75

Production of 2-(3,6-dihydropyridin-1(2H)-ylmethyl)-6-(5-methyl-1H-pyrazol-4-yl)thieno[3,2-d]pyrimidin-4 (3H)-one A) Production of 6-bromo-2-(3,6-dihydropyridin-1(2H)-ylmethyl)thieno[3,2-d]pyrimidin-4 (3H)-one In the same manner as in Example 2, step B, the title compound (169 mg) was obtained as a pale-yellow solid from 6-bromo-2-(chloromethyl)thieno[3,2-d]pyrimidin-4 (3H)-one (180 mg) produced in Example 2, step A, 1,2,3,6-tetrahydropyridine (0.18 mL), potassium carbonate (178 mg), sodium iodide (9.7 mg) and N,N-dimethylformamide (3.0 mL).

$^1$H-NMR (DMSO-d$_6$) δ 2.04-2.16 (2H, m), 2.57-2.65 (2H, m), 2.96-3.04 (2H, m), 3.51 (2H, s), 5.54-5.78 (2H, m), 7.61 (1H, s), 12.36 (1H, brs).

B) Production of 2-(3,6-dihydropyridin-1(2H)-ylmethyl)-6-(5-methyl-1H-pyrazol-4-yl)thieno[3,2-d]pyrimidin-4 (3H)-one In the same manner as in Example 2, step C, the title compound (81 mg) was obtained as a pale-brown solid from 6-bromo-2-(3,6-dihydropyridin-1(2H)-ylmethyl)thieno[3,2-d]pyrimidin-4 (3H)-one (169 mg), tert-butyl 3-methyl-4-(4,4,5,5-tetramethyl-1,3,2-dioxaborolan-2-yl)-1H-pyrazole-1-carboxylate (479 mg), sodium carbonate (124 mg), 1,2-dimethoxyethane (3.0 mL), water (1.5 mL) and [1,1'-bis(diphenylphosphino)ferrocene]palladium(II) dichloride-dichloromethane complex (1:1) (42 mg).

$^1$H-NMR (DMSO-d$_6$) δ 2.03-2.18 (2H, m), 2.45 (3H, brs), 2.63 (2H, t, J=5.7 Hz), 2.97-3.09 (2H, m), 3.52 (2H, s), 5.47-5.90 (2H, m), 7.38 (1H, s), 8.02 (1H, brs), 12.18 (1H, brs), 12.91 (1H, brs).

Example 76

Production of 2-[(2S)-5,5-dimethylpyrrolidin-2-yl]-6-(5-methyl-1H-pyrazol-4-yl)thieno[3,2-d]pyrimidin-4 (3H)-one A) Production of tert-butyl(5S)-5-(6-bromo-4-oxo-3,4-dihydrothieno[3,2-d]pyrimidin-2-yl)-2,2-dimethylpyrrolidine-1-carboxylate In the same manner as in Example 71, step A, the title compound (431 mg) was obtained as a colorless solid from 3-amino-5-bromothiophene-2-carboxamide (250 mg) produced in Example 1, step D, 1-(tert-butoxycarbonyl)-5,5-dimethyl-L-proline (577 mg), 2-methylpropyl chlorocarbonate (0.324 mL), triethylamine (0.392 mL), tetrahydrofuran (5 mL), 2M aqueous sodium hydroxide solution (2.83 mL) and ethanol (5 mL).

$^1$H-NMR (DMSO-d$_6$) δ 1.11 (9H, s, major), 1.30-1.43 (6H, m), 1.57 (9H, s, minor), 1.66-1.88 (2H, m), 1.90-2.25 (2H, m), 4.67 (1H, dd, J=8.3, 3.6 Hz, major), 4.70-4.77 (1H, m, minor), 7.54 (1H, s, minor), 7.57 (1H, s, major), 12.68 (1H, brs).
* Observed as a 7:4 mixture of rotamers.
** Only a single peak was observed under chiral analysis conditions. The analysis was performed by high performance liquid chromatography (column: CHIRALPAK AD-H (4.6 mm i.d.×250 mm L, manufactured by DAICEL CHEMICAL INDUSTRIES, LTD.), mobile phase: hexane/2-propanol/diethylamine (800/200/1), flow rate: 1 mL/min, column temperature: 30° C., detection 220 nm).

B) Production of 2-[(2S)-5,5-dimethylpyrrolidin-2-yl]-6-(5-methyl-1H-pyrazol-4-yl)thieno[3,2-d]pyrimidin-4 (3H)-one In the same manner as in Example 83, step C, tert-butyl 4-{2-[(2S)-1-(tert-butoxycarbonyl)-5,5-dimethylpyrrolidin-2-yl]-4-oxo-3,4-dihydrothieno[3,2-d]pyrimidin-6-yl}-3-methyl-1H-pyrazole-1-carboxylate was obtained as a pale-yellow amorphous solid from tert-butyl(5S)-5-(6-bromo-4-oxo-3,4-dihydrothieno[3,2-d]pyrimidin-2-yl)-2,2-dimethylpyrrolidine-1-carboxylate (423 mg) produced above, tert-butyl 3-methyl-4-(4,4,5,5-tetramethyl-1,3,2-dioxaborolan-2-yl)-1H-pyrazole-1-carboxylate (610 mg), cesium carbonate (644 mg), [1,1'-bis(diphenylphosphino)ferrocene]palladium(II) dichloride-dichloromethane complex (1:1) (162 mg), 1,2-dimethoxyethane (5 mL) and water (0.5 mL). To a solution of tert-butyl 4-{2-[(2S)-1-(tert-butoxycarbonyl)-5,5-dimethylpyrrolidin-2-yl]-4-oxo-3,4-dihydrothieno[3,2-d]pyrimidin-6-yl}-3-methyl-1H-pyrazole-1-carboxylate produced above in methanol (4 mL) was added 4M hydrochloric acid/ethyl acetate solution (1 mL), and the mixture was stirred at 50° C. for 2 hr. Ethyl acetate (50 mL) and aqueous sodium hydrogen carbonate (10 mL) were added to the reaction mixture, and the separated aqueous layer was extracted with ethyl acetate (10 mL). The combined organic layers were washed with brine (5 mL) and dried over anhydrous sodium sulfate. Insoluble material was filtered off, the filtrate was concentrated under reduced pressure, and the obtained residue was crystallized from methanol/ethyl acetate (0.5 mL/4 mL) to give the title compound (176 mg) as a colorless solid.
$^1$H-NMR (DMSO-d$_6$) δ 1.17 (3H, s), 1.19 (3H, s), 1.60 (2H, t, J=7.4 Hz), 1.92-2.05 (1H, m), 2.23-2.38 (1H, m), 2.45 (3H, s), 4.24 (1H, dd, J=8.6, 6.3 Hz), 7.37 (1H, s), 8.02 (1H, brs).

Example 77

Production of 2-[(2S)-azetidin-2-yl]-6-(5-methyl-1H-pyrazol-4-yl)thieno[3,2-d]pyrimidin-4 (3H)-one A) Production of tert-butyl(2S)-2-(6-bromo-4-oxo-3,4-dihydrothieno[3,2-d]pyrimidin-2-yl)azetidine-1-carboxylate In the same manner as in Example 71, step A, the title compound (335 mg) was obtained as a colorless solid from 3-amino-5-bromothiophene-2-carboxamide (267 mg) produced in Example 1, step D, (2S)-1-(tert-butoxycarbonyl)azetidine-2-carboxylic acid (510 mg), 2-methylpropyl chlorocarbonate (0.346 mL), triethylamine (0.419 mL), tetrahydrofuran (5 mL), 2M aqueous sodium hydroxide solution (2.83 mL) and ethanol (5 mL).
$^1$H-NMR (DMSO-d$_6$) δ 1.04-1.51 (9H, m), 2.20-2.35 (1H, m), 2.44-2.57 (1H, m), 3.84 (1H, brs), 3.91-4.02 (1H, m), 5.01 (1H, dd, J=8.6, 5.6 Hz), 7.64 (1H, s), 12.74 (1H, brs).
* Only a single peak was observed under chiral analysis conditions. The analysis was performed by high performance liquid chromatography (column: CHIRALPAK AD-3 (4.6 mm i.d.×250 mm L, manufactured by DAICEL CHEMICAL INDUSTRIES, LTD.), mobile phase: hexane/ethanol/diethylamine (700/300/1), flow rate: 1 mL/min, column temperature: 30° C., detection 220 nm).

B) Production of 2-[(2S)-azetidin-2-yl]-6-(5-methyl-1H-pyrazol-4-yl)thieno[3,2-d]pyrimidin-4 (3H)-one In the same manner as in Example 76, step B, the title compound (42.1 mg) was obtained as a colorless solid from tert-butyl(2S)-2-(6-bromo-4-oxo-3,4-dihydrothieno[3,2-d]pyrimidin-2-yl)azetidine-1-carboxylate (328 mg) produced above, tert-butyl 3-methyl-4-(4,4,5,5-tetramethyl-1,3,2-dioxaborolan-2-yl)-1H-pyrazole-1-carboxylate (523 mg), cesium carbonate (554 mg), [1,1'-bis(diphenylphosphino)ferrocene]palladium(II) dichloride-dichloromethane complex (1:1) (139 mg), 1,2-dimethoxyethane (10 mL), water (1 mL), 4M hydrochloric acid/ethyl acetate solution (1 mL) and methanol (5 mL).
$^1$H-NMR (DMSO-d$_6$) δ 2.41-2.61 (2H, m), 2.45 (3H, s), 3.30-3.38 (1H, m), 3.61 (1H, q, J=7.9 Hz), 4.73 (1H, t, J=7.8 Hz), 7.38 (1H, s), 8.03 (1H, brs).

Example 78

Production of 6-(5-methyl-1H-pyrazol-4-yl)-2-[(2S, 3aS,7aS)-octahydro-1H-indol-2-yl]thieno[3,2-d]pyrimidin-4 (3H)-one A) Production of tert-butyl(2S,3aS,7aS)-2-[(5-bromo-2-carbamoylthiophen-3-yl)carbamoyl]octahydro-1H-indole-1-carboxylate To a solution of (2S,3aS,7aS)-1-(tert-butoxycarbonyl)octahydro-1H-indole-2-carboxylic acid (638 mg) and triethylamine (0.392 mL) in tetrahydrofuran (5 mL) was added 2-methylpropyl chlorocarbonate (0.324 mL) at 0° C., and the mixture was stirred at room temperature for 30 min. Thereafter, to the reaction system was added a solution of 3-amino-5-bromothiophene-2-carboxamide (250 mg) produced in Example 1, step D, in tetrahydrofuran (5 mL), and the mixture was stirred at 60° C. for 26 hr. Ethyl acetate (20 mL) and aqueous sodium hydrogen carbonate (10 mL) were added to the reaction mixture, and the separated aqueous layer was extracted with ethyl acetate (5 mL). The combined organic layers were washed with brine (5 mL) and dried over anhydrous sodium sulfate. Insoluble material was filtered off, and the filtrate was concentrated under reduced pressure. The residue was purified by silica gel column chromatography (ethyl acetate/hexane), and the object fraction was concentrated under reduced pressure to give the title compound (345 mg) as a pale-yellow amorphous solid.
$^1$H-NMR (DMSO-d$_6$) δ 1.07-1.49 (13H, m), 1.53-1.67 (3H, m), 1.85-2.06 (2H, m), 2.07-2.20 (1H, m), 2.22-2.36 (1H, m), 3.70-3.81 (1H, m), 4.14 (1H, dd, J=9.7, 7.5 Hz), 7.72 (2H, brs), 8.11 (1H, s), 11.61 (1H, brs).

B) Production of tert-butyl(2S,3aS,7aS)-2-(6-bromo-4-oxo-3,4-dihydrothieno[3,2-d]pyrimidin-2-yl)octahydro-1H-indole-1-carboxylate In the same manner as in Example 40, step B, the title compound (273 mg) was obtained as a colorless solid from tert-butyl(2S,3aS,7aS)-2-[(5-bromo-2-carbamoylthiophen-3-yl)carbamoyl]octahydro-1H-indole-1-carboxylate (340 mg) produced above, 2M aqueous sodium hydroxide solution (2.83 mL) and ethanol (5 mL).

$^1$H-NMR (DMSO-d$_6$) δ 1.06-1.48 (3H, m), 1.09 (9H, s, major), 1.34 (9H, s, minor), 1.53-1.78 (4H, m), 1.92-2.18 (2H, m), 2.29-2.41 (1H, m), 3.40-3.49 (1H, m, major), 3.67-3.79 (1H, m), 4.35 (1H, t, J=5.0 Hz, minor), 4.50-4.62 (1H, m), 7.55 (1H, s, minor), 7.60 (1H, s, major), 12.71 (1H, brs).
* Observed as a 2:1 mixture of rotamers.

C) Production of 6-(5-methyl-1H-pyrazol-4-yl)-2-[(2S,3aS,7aS)-octahydro-1H-indol-2-yl]thieno[3,2-d]pyrimidin-4 (3H)-one In the same manner as in Example 76, step B, the title compound (84.0 mg) was obtained as a colorless solid from tert-butyl(2S,3aS,7aS)-2-(6-bromo-4-oxo-3,4-dihydrothieno[3,2-d]pyrimidin-2-yl)octahydro-1H-indole-1-carboxylate (263 mg) produced above, tert-butyl 3-methyl-4-(4,4,5,5-tetramethyl-1,3,2-dioxaborolan-2-yl)-1H-pyrazole-1-carboxylate (357 mg), cesium carbonate (377 mg), [1,1'-bis(diphenylphosphino)ferrocene]palladium(II) dichloride-dichloromethane complex (1:1) (94.7 mg), 1,2-dimethoxyethane (10 mL), water (1 mL), 4M hydrochloric acid/ethyl acetate solution (1 mL) and methanol (5 mL).

$^1$H-NMR (DMSO-d$_6$) δ 51.10-1.66 (8H, m), 1.76-1.88 (1H, m), 1.95-2.10 (1H, m), 2.25-2.39 (1H, m), 2.45 (3H, s), 3.23 (1H, q, J=5.2 Hz), 4.19 (1H, dd, J=10.0, 5.5 Hz), 7.38 (1H, s), 7.89-8.29 (1H, m).

Example 79

Production of 2-(azepan-2-yl)-6-(5-methyl-1H-pyrazol-4-yl)thieno[3,2-d]pyrimidin-4 (3H)-one A) Production of tert-butyl 2-(6-bromo-4-oxo-3,4-dihydrothieno[3,2-d]pyrimidin-2-yl)azepane-1-carboxylate In the same manner as in Example 71, step A, tert-butyl 2-[(5-bromo-2-carbamoylthiophen-3-yl)carbamoyl]azepane-1-carboxylate was obtained as a yellow oil from 3-amino-5-bromothiophene-2-carboxamide (237 mg) produced in Example 1, step D, 1-(tert-butoxycarbonyl)azepane-2-carboxylic acid (547 mg), 2-methylpropyl chlorocarbonate (0.306 mL), triethylamine (0.371 mL) and tetrahydrofuran (5 mL). To a solution of tert-butyl 2-[(5-bromo-2-carbamoylthiophen-3-yl)carbamoyl]azepane-1-carboxylate produced above in ethanol (5 mL) was added 2M aqueous sodium hydroxide solution (2.68 mL), and the mixture was stirred at 70° C. for 3 hr. Ethyl acetate (20 mL), 6M hydrochloric acid (1 mL) and water (5 mL) were added to the reaction mixture, and the separated aqueous layer was extracted with ethyl acetate (5 mL). The combined organic layers were washed with brine (5 mL) and dried over anhydrous sodium sulfate. Insoluble material was filtered off, and the filtrate was concentrated under reduced pressure. The residue was purified by silica gel column chromatography (ethyl acetate/hexane), and the object fraction was concentrated under reduced pressure to give the title compound (438 mg) as a pale-yellow amorphous solid.

$^1$H-NMR (DMSO-d$_6$) δ 1.12-1.46 (12H, m), 1.58-1.99 (4H, m), 2.11-2.35 (1H, m), 3.16-3.29 (1H, m), 3.77-3.88 (1H, m, minor), 3.97 (1H, dd, J=14.8, 5.2 Hz, major), 4.65 (1H, dd, J=12.0, 4.8 Hz, major), 4.83 (1H, dd, J=12.1, 5.9 Hz, minor), 7.58 (1H, s, minor), 7.60 (1H, s, major), 12.61 (1H, brs).
* Observed as a 5:4 mixture of rotamers.

B) Production of 2-(azepan-2-yl)-6-(5-methyl-1H-pyrazol-4-yl)thieno[3,2-d]pyrimidin-4 (3H)-one In the same manner as in Example 76, step B, the title compound (21.8 mg) was obtained as a colorless solid from tert-butyl 2-(6-bromo-4-oxo-3,4-dihydrothieno[3,2-d]pyrimidin-2-yl)azepane-1-carboxylate (150 mg) produced above, tert-butyl 3-methyl-4-(4,4,5,5-tetramethyl-1,3,2-dioxaborolan-2-yl)-1H-pyrazole-1-carboxylate (215 mg), cesium carbonate (228 mg), [1,1'-bis(diphenylphosphino)ferrocene]palladium(II) dichloride-dichloromethane complex (1:1) (57.2 mg), 1,2-dimethoxyethane (5 mL), water (0.5 mL), 4M hydrochloric acid/ethyl acetate solution (1 mL) and methanol (3 mL).

$^1$H-NMR (DMSO-d$_6$) δ 1.41-1.89 (7H, m), 2.07-2.20 (1H, m), 2.45 (3H, s), 2.75-2.97 (2H, m), 3.74-3.87 (1H, m), 7.34 (1H, s), 8.00 (1H, brs).

Example 80

Production of 6-(5-methyl-1H-pyrazol-4-yl)-2-[(3-phenylpyrrolidin-1-yl)methyl]thieno[3,2-d]pyrimidin-4 (3H)-one A) Production of 6-bromo-2-[(3-phenylpyrrolidin-1-yl)methyl]thieno[3,2-d]pyrimidin-4 (3H)-one In the same manner as in Example 2, step B, the title compound (182 mg) was obtained as a yellow solid from 6-bromo-2-(chloromethyl)thieno[3,2-d]pyrimidin-4 (3H)-one (180 mg) produced in Example 2, step A, 3-phenylpyrrolidine hydrochloride (355 mg), potassium carbonate (445 mg), sodium iodide (9.7 mg) and N,N-dimethylformamide (3.0 mL).

$^1$H-NMR (DMSO-d$_6$) δ 1.71-1.85 (1H, m), 2.18-2.32 (1H, m), 2.55-2.63 (1H, m), 2.75-2.85 (2H, m), 3.04 (1H, t, J=8.4 Hz), 3.26-3.40 (1H, m), 3.65 (2H, s), 7.14-7.22 (1H, m), 7.24-7.34 (4H, m), 7.61 (1H, s), 12.39 (1H, brs).

B) Production of 6-(5-methyl-1H-pyrazol-4-yl)-2-[(3-phenylpyrrolidin-1-yl)methyl]thieno[3,2-d]pyrimidin-4 (3H)-one In the same manner as in Example 2, step C, the title compound (106 mg) was obtained as yellow crystals from 6-bromo-2-[(3-phenylpyrrolidin-1-yl)methyl]thieno[3,2-d]pyrimidin-4 (3H)-one (182 mg), tert-butyl 3-methyl-4-(4,4,5,5-tetramethyl-1,3,2-dioxaborolan-2-yl)-1H-pyrazole-1-carboxylate (431 mg), sodium carbonate (112 mg), 1,2-dimethoxyethane (4.0 mL), water (2.0 mL) and [1,1'-bis(diphenylphosphino)ferrocene]palladium(II) dichloride-dichloromethane complex (1:1) (38 mg).

$^1$H-NMR (DMSO-d$_6$) δ 1.72-1.87 (1H, m), 2.19-2.33 (1H, m), 2.45 (3H, brs), 2.55-2.64 (1H, m), 2.76-2.87 (2H, m), 3.02-3.11 (1H, m), 3.27-3.41 (1H, m), 3.65 (2H, s), 7.13-7.22 (1H, m), 7.25-7.34 (4H, m), 7.38 (1H, s), 8.03 (1H, brs), 11.92-13.34 (2H, m).

Example 81

Production of 2-{[3-hydroxy-3-(trifluoromethyl) pyrrolidin-1-yl]methyl}-6-(5-methyl-1H-pyrazol-4-yl)thieno[3,2-d]pyrimidin-4 (3H)-one

A) Production of 3-(trifluoromethyl)pyrrolidin-3-ol

A mixture of tert-butyl 3-oxopyrrolidine-1-carboxylate (600 mg), trimethyl(trifluoromethyl)silane (0.57 mL), 1M N,N,N-tributylbutane-1-aminium fluoride/tetrahydrofuran solution (0.50 mL) and tetrahydrofuran (6 mL) was stirred at room temperature for 30 min. Saturated aqueous ammonium chloride solution (2 mL) and 1M N,N,N-tributylbutane-1-aminium fluoride/tetrahydrofuran solution (1 mL) were added, and the reaction mixture was stirred at room temperature for 1 hr. The mixture was extracted with ethyl acetate, washed successively with water and brine, and dried over anhydrous sodium sulfate. Insoluble material was removed by filtration, and the filtrate was concentrated under reduced pressure. The residue was purified by silica gel column chromatography (ethyl acetate/hexane) to give a pale-brown solid. The obtained solid was dissolved in methanol (1 mL), and 4M hydrochloric acid/ethyl acetate solution (2 mL) was added at room temperature. The reaction mixture was stirred at room temperature for 4 hr, and the reaction system was concentrated under reduced pressure. Saturated aqueous sodium hydrogen carbonate (1 mL) was added to the residue, and the mixture was extracted with ethyl acetate/tetrahydrofuran and dried over anhydrous sodium sulfate. Insoluble material was removed by filtration, and the filtrate was concentrated under reduced pressure to give the title compound (260 mg) as a brown solid.

$^1$H-NMR (CDCl$_3$) δ 1.80-1.91 (1H, m), 2.14-2.25 (1H, m), 2.93-3.10 (2H, m), 3.12-3.29 (2H, m).

B) Production of 6-bromo-2-{[3-hydroxy-3-(trifluoromethyl)pyrrolidin-1-yl]methyl}thieno[3,2-d]pyrimidin-4 (3H)-one In the same manner as in Example 2, step B, the title compound (163 mg) was obtained as a brown solid from 6-bromo-2-(chloromethyl)thieno[3,2-d]pyrimidin-4 (3H)-one (180 mg) produced in Example 2, step A, 3-(trifluoromethyl)pyrrolidin-3-ol (260 mg), potassium carbonate (356 mg), sodium iodide (9.7 mg) and N,N-dimethylformamide (3.0 mL).

$^1$H-NMR (DMSO-d$_6$) δ 1.77-1.93 (1H, m), 2.04-2.17 (1H, m), 2.59-2.69 (1H, m), 2.71-2.80 (1H, m), 2.81-2.99 (2H, m), 3.62 (2H, s), 6.28 (1H, brs), 7.61 (1H, s), 12.35 (1H, brs).

C) Production of 2-{[3-hydroxy-3-(trifluoromethyl) pyrrolidin-1-yl]methyl}-6-(5-methyl-1H-pyrazol-4-yl)thieno[3,2-d]pyrimidin-4 (3H)-one In the same manner as in Example 2, step C, the title compound (102 mg) was obtained as pale-yellow crystals from 6-bromo-2-{[3-hydroxy-3-(trifluoromethyl)pyrrolidin-1-yl]methyl}thieno[3,2-d]pyrimidin-4 (3H)-one (160 mg) and tert-butyl 3-methyl-4-(4,4,5,5-tetramethyl-1,3,2-dioxaborolan-2-yl)-1H-pyrazole-1-carboxylate (371 mg), sodium carbonate (96 mg), 1,2-dimethoxyethane (4.0 mL) and water (2.0 mL) and [1,1'-bis(diphenylphosphino)ferrocene]palladium(II) dichloride-dichloromethane complex (1:1) (33 mg).

$^1$H-NMR (DMSO-d$_6$) δ 1.79-1.93 (1H, m), 2.05-2.20 (1H, m), 2.46 (3H, brs), 2.60-2.71 (1H, m), 2.72-2.83 (1H, m), 2.83-3.00 (2H, m), 3.63 (2H, s), 6.28 (1H, brs), 7.38 (1H, s), 7.90 (0.6H, brs), 8.26 (0.4H, brs), 12.16 (1H, brs), 12.99 (1H, brs).

Example 82

Production of 6-(5-methyl-1H-pyrazol-4-yl)-2-(2-methylpyrrolidin-2-yl)thieno[3,2-d]pyrimidin-4 (3H)-one dihydrochloride

A) Production of tert-butyl 2-(6-bromo-4-oxo-3,4-dihydrothieno[3,2-d]pyrimidin-2-yl)-2-methylpyrrolidine-1-carboxylate To a mixture of 1-(tert-butoxycarbonyl)-2-methylproline (425 mg), triethylamine (0.425 mL) and tetrahydrofuran (10 mL) was added 2-methylpropyl chlorocarbonate (0.2 mL) with stirring at room temperature. After 1 hr, 3-amino-5-bromothiophene-2-carboxamide (337 mg) produced in Example 1, step D, was added, and the mixture was stirred at 60° C. overnight. Thereafter, the mixture was stirred in a microwave reactor at 120° C. for 4 hr. The reaction mixture was allowed to cool to room temperature, and poured into saturated aqueous sodium hydrogen carbonate. The mixture was extracted with ethyl acetate, and the extract was dried over anhydrous magnesium sulfate. Insoluble material was removed by filtration, and the filtrate was concentrated under reduced pressure. The residue was dissolved in methanol (5 mL), 2M aqueous sodium hydroxide solution (2.04 mL) was added, and the mixture was stirred at 60° C. for 1 hr and at 80° C. for 1 hr. Ethanol (4 mL) was added to the reaction mixture, and the mixture was stirred at 100° C. for 4 hr. The reaction mixture was allowed to cool to room temperature, and poured into saturated aqueous sodium hydrogen carbonate, and the mixture was extracted with ethyl acetate/tetrahydrofuran mixture. The extract was dried over anhydrous magnesium sulfate. Insoluble material was removed by filtration, and the filtrate was concentrated under reduced pressure. The residue was purified by basic silica gel column chromatography (ethyl acetate/hexane and methanol/ethyl acetate) to give the title compound (109 mg) as a yellow solid.

MS(ESI+): [M+H]$^+$414.

MS(ESI+), found: 414.

B) Production of 6-(5-methyl-1H-pyrazol-4-yl)-2-(2-methylpyrrolidin-2-yl)thieno[3,2-d]pyrimidin-4 (3H)-one dihydrochloride In the same manner as in Example 11, step B, the title compound (64 mg) was obtained as a white solid from tert-butyl 2-(6-bromo-4-oxo-3,4-dihydrothieno[3,2-d]pyrimidin-2-yl)-2-methylpyrrolidine-1-carboxylate (109 mg), tert-butyl 3-methyl-4-(4,4,5,5-tetramethyl-1,3,2-dioxaborolan-2-yl)-1H-pyrazole-1-carboxylate (162 mg), cesium carbonate (400 mg), 1,2-dimethoxyethane (4 mL), water (0.5 mL) and [1,1'-bis(diphenylphosphino)ferrocene]palladium(II) dichloride-dichloromethane complex (1:1) (21 mg).

$^1$H-NMR (DMSO-d$_6$) δ 1.75 (3H, s), 1.84-2.40 (4H, m), 2.46 (3H, s), 3.30-3.42 (2H, m), 7.37 (1H, s), 8.10 (1H, brs), 9.21 (1H, brs), 9.75 (1H, brs), 12.82 (1H, brs).

Example 83

Production of 6-(5-methyl-1H-pyrazol-4-yl)-2-[(2S)-piperidin-2-yl]thieno[3,2-d]pyrimidin-4 (3H)-one dihydrochloride

A) Production of tert-butyl(2S)-2-(6-bromo-4-oxo-3,4-dihydrothieno[3,2-d]pyrimidin-2-yl)piperidine-1-carboxylate To a solution of (2S)-1-(tert-butoxycarbonyl)piperidine-2-carboxylic acid (5.00 g) and triethylamine (3.16 mL) in tetrahydrofuran (45 mL) was added 2-methylpropyl chlorocarbonate (2.84 mL) at 10° C., and the mixture was stirred at room temperature for 1 hr. Thereafter, to the reaction mixture was added a solution of 3-amino-5-bromothiophene-2-carboxamide (2.19 g) produced in Example 1, step D, in tetrahydrofuran (5 mL), and the mixture was stirred at room temperature for 7 days. Ethyl acetate (50 mL) and aqueous sodium hydrogen carbonate (50 mL) were added to the reaction mixture, and the separated aqueous layer was extracted with ethyl acetate (20 mL). The combined organic layers were washed with brine (10 mL) and dried over anhydrous sodium sulfate. Insoluble material was filtered off, and the filtrate was concentrated under reduced pressure to give tert-butyl(2S)-2-[(5-bromo-2-carbamoylthiophen-3-yl)carbamoyl]piperidine-1-carboxylate as a pale-yellow oil. To a solution of tert-butyl(2S)-2-[(5-bromo-2-carbamoylthiophen-3-yl)carbamoyl]piperidine-1-carboxylate produced above in ethanol (50 mL) was added 2M aqueous sodium hydroxide solution (24.8 mL), and the mixture was stirred at 70° C. for 3 hr. The reaction mixture was neutralized with 6M hydrochloric acid (8.5 mL) under ice-cooling, and water (10 mL) was added dropwise at room temperature. The precipitated solid was collected by filtration to give the title compound (3.03 g) as a pale-yellow solid. The optical purity was 73.8% ee. The analysis was performed by high performance liquid chromatography (column: CHIRALPAK AD-H (4.6 mm i.d.×250 mm L, manufactured by DAICEL CHEMICAL INDUSTRIES, LTD.), mobile phase: hexane/2-propanol/diethylamine (700/300/1), flow rate: 1 mL/min, column temperature: 30° C., detection 220 nm).

$^1$H-NMR (DMSO-$d_6$) δ 1.09-1.45 (11H, m), 1.46-1.58 (1H, m), 1.60-1.86 (2H, m), 1.98-2.14 (1H, m), 3.38-3.53 (1H, m), 3.75-3.89 (1H, m), 4.89-5.10 (1H, m), 7.58 (1H, s), 12.64 (1H, brs).

B) Optical resolution of tert-butyl(2S)-2-(6-bromo-4-oxo-3,4-dihydrothieno[3,2-d]pyrimidin-2-yl)piperidine-1-carboxylate tert-Butyl(2S)-2-(6-bromo-4-oxo-3,4-dihydrothieno[3,2-d]pyrimidin-2-yl)piperidine-1-carboxylate (3.03 g, 75.5% ee) was fractionated by high performance liquid chromatography (column: CHIRALPAK AD (50 mm i.d.×500 mm L, manufactured by DAICEL CHEMICAL INDUSTRIES, LTD.), mobile phase: hexane/2-propanol/diethylamine (700/300/1), flow rate: 80 mL/min, column temperature: 30° C.). tert-Butyl(2S)-2-(6-bromo-4-oxo-3,4-dihydrothieno[3,2-d]pyrimidin-2-yl)piperidine-1-carboxylate (2.55 g, >99.9% ee, retention time 6.1 min) and tert-butyl(2R)-2-(6-bromo-4-oxo-3,4-dihydrothieno[3,2-d]pyrimidin-2-yl)piperidine-1-carboxylate (330 mg, 99.2% ee, retention time 8.1 min) were obtained under the above-mentioned high performance liquid chromatography conditions. The analysis was performed by high performance liquid chromatography (column: CHIRALPAK AD-H (4.6 mm i.d.×250 mm L, manufactured by DAICEL CHEMICAL INDUSTRIES, LTD.), mobile phase: hexane/2-propanol/diethylamine (700/300/1), flow rate: 1 mL/min, column temperature: 30° C., detection 220 nm).

C) Production of 6-(5-methyl-1H-pyrazol-4-yl)-2-[(2S)-piperidin-2-yl]thieno[3,2-d]pyrimidin-4 (3H)-one dihydrochloride tert-Butyl(2S)-2-(6-bromo-4-oxo-3,4-dihydrothieno[3,2-d]pyrimidin-2-yl)piperidine-1-carboxylate (2.55 g) produced above, tert-butyl 3-methyl-4-(4,4,5,5-tetramethyl-1,3,2-dioxaborolan-2-yl)-1H-pyrazole-1-carboxylate (3.79 g), cesium carbonate (4.01 g), 1,2-dimethoxyethane (50 mL) and water (5 mL) were placed in a flask, and the atmosphere in the flask was purged with argon. [1,1'-Bis(diphenylphosphino)ferrocene]palladium(II) dichloride-dichloromethane complex (1:1) (502 mg) was added, the atmosphere in the flask was purged again with argon, and the mixture was stirred at 80° C. for 1.5 hr. Ethyl acetate (75 mL) and water (50 mL) were added to the reaction mixture, and the separated aqueous layer was extracted with ethyl acetate (20 mL×2). The combined organic layers were washed with brine (20 mL) and dried over anhydrous sodium sulfate. Insoluble material was filtered off, and the filtrate was concentrated under reduced pressure. The residue was purified by silica gel column chromatography (ethyl acetate/hexane), and the object fraction was concentrated under reduced pressure to give tert-butyl(2S)-2-{6-[1-(tert-butoxycarbonyl)-3-methyl-1H-pyrazol-4-yl]-4-oxo-3,4-dihydrothieno[3,2-d]pyrimidin-2-yl}piperidine-1-carboxylate as a pale-yellow solid. To a solution of tert-butyl(2S)-2-{6-[1-(tert-butoxycarbonyl)-3-methyl-1H-pyrazol-4-yl]-4-oxo-3,4-dihydrothieno[3,2-d]pyrimidin-2-yl}piperidine-1-carboxylate produced above in methanol (50 mL) was added 4M hydrochloric acid/ethyl acetate solution (10 mL), and the mixture was stirred at 50° C. for 4 hr and at room temperature for 1 hr. The precipitated solid was collected by filtration to give the title compound (1.18 g) as a pale-yellow solid.

$^1$H-NMR (DMSO-$d_6$) δ 1.48-1.92 (5H, m), 2.23-2.35 (1H, m), 2.46 (3H, s), 2.94-3.12 (1H, m), 3.29-3.41 (1H, m), 4.16-4.29 (1H, m), 7.34 (1H, s), 8.12 (1H, s), 9.07-9.25 (1H, m), 9.46-9.60 (1H, m), 12.84 (1H, brs).

MS(ESI+): [M+H]$^+$316.

MS(ESI+), found: 316.

D) Production of 6-(5-methyl-1H-pyrazol-4-yl)-2-[(2S)-piperidin-2-yl]thieno[3,2-d]pyrimidin-4 (3H)-one dihydrochloride tert-Butyl(2S)-2-(6-bromo-4-oxo-3,4-dihydrothieno[3,2-d]pyrimidin-2-yl)piperidine-1-carboxylate (3.25 g) produced in the below-mentioned Example 172, step B, tert-butyl 3-methyl-4-(4,4,5,5-tetramethyl-1,3,2-dioxaborolan-2-yl)-1H-pyrazole-1-carboxylate (4.83 g), cesium carbonate (5.11 g), 1,2-dimethoxyethane (88 mL) and water (8.8 mL) were placed in a flask, and the atmosphere in the flask was purged with argon. [1,1'-Bis(diphenylphosphino)ferrocene]palladium(II) dichloride-dichloromethane complex (1:1) (574 mg) was added, the atmosphere in the flask was purged again with argon, and the mixture was stirred at 80° C. for 1 hr. Ethyl acetate (100 mL) and water (100 mL) were added to the reaction mixture, and the separated aqueous layer was extracted with ethyl acetate (20 mL×2). The combined organic layers were dried over anhydrous magnesium sulfate. Insoluble material was filtered off, and the filtrate was concentrated under reduced pressure. The residue was purified by silica gel column chromatography (ethyl acetate/hexane), and the object fraction was concentrated under reduced pressure to give tert-butyl(2S)-2-{6-[1-(tert-butoxycarbonyl)-3-methyl-1H-pyrazol-4-yl]-4-oxo-3,4-dihydrothieno[3,2-d]pyrimidin-2-yl}piperidine-1-carboxylate as a white solid. To tert-butyl(2S)-2-{6-[1-(tert-butoxycarbonyl)-3-methyl-1H-pyrazol-4-yl]-4-oxo-3,4-dihydrothieno[3,2-d]pyrimidin-2-yl}piperidine-1-carboxylate produced above were added methanol (50 mL) and 4M hydrochloric acid/ethyl acetate solution (17 mL), and the mixture was stirred at 50° C. for 1 hr. Methanol (17 mL) and ethyl acetate (85 mL) were added, and the mixture was further stirred at 50° C. for 1 hr, and further at room temperature for 2 hr. The mixture was concentrated under reduced pressure. Methanol (50 mL) was added to the residue, and the mixture was stirred at 50° C. for 1 hr, and further at room temperature for 1 hr. The precipitated solid was collected by filtration to give the title compound (1.77 g) as a white solid.

$^1$H-NMR (DMSO-$d_6$) δ 1.48-1.91 (5H, m), 2.24-2.32 (1H, m), 2.46 (3H, s), 2.97-3.12 (1H, m), 3.29-3.41 (1H, m), 4.14-4.29 (1H, m), 7.34 (1H, s), 8.11 (1H, s), 9.07-9.23 (1H, m), 9.36-9.48 (1H, m), 12.81 (1H, brs).

The mother liquor was concentrated under reduced pressure, to the residue was added methanol (20 mL), and the mixture was stirred at 50° C. for 1 hr, and further at room temperature for 1 hr. Ethyl acetate (20 mL) was added, and the precipitated solid was collected by filtration to give the title compound (215 mg) as a white solid.

$^1$H-NMR (DMSO-$d_6$) δ 1.51-1.91 (5H, m), 2.25-2.33 (1H, m), 2.46 (3H, s), 2.97-3.10 (1H, m), 3.29-3.40 (1H, m), 4.16-4.28 (1H, m), 7.34 (1H, s), 8.11 (1H, s), 9.07-9.22 (1H, m), 9.45-9.56 (1H, m), 12.83 (1H, brs).

Example 84

Production of 6-(5-methyl-1H-pyrazol-4-yl)-2-(pyrrolidin-3-yl)thieno[3,2-d]pyrimidin-4 (3H)-one dihydrochloride A) Production of tert-butyl 3-(6-bromo-4-oxo-3,4-dihydrothieno[3,2-d]pyrimidin-2-yl)pyrrolidine-1-carboxylate In the same manner as in Example 71, step A, the title compound (396 mg) was obtained as a colorless solid from 3-amino-5-bromothiophene-2-carboxamide (250 mg) produced in Example 1, step D, 1-(tert-butoxycarbonyl)pyrrolidine-3-carboxylic acid (511 mg), 2-methylpropyl chlorocarbonate (0.323 mL), triethylamine (0.392 mL), tetrahydrofuran (5 mL), 2M aqueous sodium hydroxide solution (2.83 mL) and ethanol (5 mL).

$^1$H-NMR (DMSO-$d_6$) δ 1.40 (9H, s), 2.12-2.30 (2H, m), 3.39-3.56 (4H, m), 3.59-3.69 (1H, m), 7.60 (1H, s).

B) Production of 6-(5-methyl-1H-pyrazol-4-yl)-2-(pyrrolidin-3-yl)thieno[3,2-d]pyrimidin-4 (3H)-one dihydrochloride In the same manner as in Example 83, step C, the title compound (228 mg) was obtained as a pale-yellow solid from tert-butyl 3-(6-bromo-4-oxo-3,4-dihydrothieno[3,2-d]pyrimidin-2-yl)pyrrolidine-1-carboxylate (390 mg) produced above, tert-butyl 3-methyl-4-(4,4,5,5-tetramethyl-1,3,2-dioxaborolan-2-yl)-1H-pyrazole-1-carboxylate (601 mg), cesium carbonate (635 mg), [1,1'-bis(diphenylphosphino)ferrocene]palladium(II) dichloride-dichloromethane complex (1:1) (159 mg), 1,2-dimethoxyethane (10 mL), water (1 mL), 4M hydrochloric acid/ethyl acetate solution (1 mL) and methanol (5 mL).

$^1$H-NMR (DMSO-$d_6$) δ 2.09-2.24 (1H, m), 2.29-2.43 (1H, m), 2.45 (3H, s), 3.20-3.40 (2H, m), 3.47-3.66 (3H, m), 7.36 (1H, s), 8.05 (1H, s), 9.18 (1H, brs), 9.30 (1H, brs), 12.54 (1H, brs).

Example 85

Production of 6-(5-methyl-1H-pyrazol-4-yl)-2-[(2R)-piperidin-2-yl]thieno[3,2-d]pyrimidin-4 (3H)-one dihydrochloride In the same manner as in Example 83, step C, the title compound (60.8 mg) was obtained as a colorless solid from tert-butyl(2R)-2-(6-bromo-4-oxo-3,4-dihydrothieno[3,2-d]pyrimidin-2-yl)piperidine-1-carboxylate (120 mg) produced in Example 81, step B, tert-butyl 3-methyl-4-(4,4,5,5-tetramethyl-1,3,2-dioxaborolan-2-yl)-1H-pyrazole-1-carboxylate (179 mg), cesium carbonate (189 mg), [1,1'-bis(diphenylphosphino)ferrocene]palladium(II) dichloride-dichloromethane complex (1:1) (47.3 mg), 1,2-dimethoxyethane (5 mL), water (0.5 mL), 4M hydrochloric acid/ethyl acetate solution (1 mL) and methanol (3 mL).

$^1$H-NMR (DMSO-$d_6$) δ 1.48-1.94 (5H, m), 2.24-2.35 (1H, m), 2.46 (3H, s), 2.96-3.13 (1H, m), 3.29-3.41 (1H, m), 4.16-4.27 (1H, m), 7.34 (1H, s), 8.12 (1H, s), 9.07-9.25 (1H, m), 9.35-9.50 (1H, m), 12.82 (1H, brs).

Example 86

Production of 6-(5-methyl-1H-pyrazol-4-yl)-2-{1-[4-(methylsulfonyl)phenyl]pyrrolidin-2-yl}thieno[3,2-d]pyrimidin-4 (3H)-one A) Production of 6-bromo-2-{1-[4-(methylsulfonyl)phenyl]pyrrolidin-2-yl}thieno[3,2-d]pyrimidin-4 (3H)-one To a solution of 1-[4-(methylsulfonyl)phenyl]proline (512 mg) and triethylamine (0.314 mL) in tetrahydrofuran (10 mL) was added 2-methylpropyl chlorocarbonate (0.259 mL) at 0° C., and the mixture was stirred at room temperature for 30 min. Thereafter, to the reaction system was added 3-amino-5-bromothiophene-2-carboxamide (200 mg) produced in Example 1, step D, and the mixture was stirred at 60° C. for 19 hr. Ethyl acetate (20 mL) and aqueous sodium hydrogen carbonate (10 mL) were added to the reaction mixture, and the separated organic layer was washed with brine (5 mL), and dried over anhydrous sodium sulfate. Insoluble material was filtered off, and the filtrate was concentrated under reduced pressure. The residue was purified by silica gel column chromatography (ethyl acetate/hexane), and the object fraction was concentrated under reduced pressure to give N-(5-bromo-2-carbamoylthiophen-3-yl)-1-[4-(methylsulfonyl)phenyl]prolinamide as a pale-yellow amorphous solid. To a solution of N-(5-bromo-2-carbamoylthiophen-3-yl)-1-[4-(methylsulfonyl)phenyl]prolinamide produced above in ethanol (5 mL) was added 2M aqueous sodium hydroxide solution (2.83 mL), and the mixture was stirred at 70° C. for 10 hr. The reaction mixture was neutralized with 6M hydrochloric acid (0.6 mL) under ice-cooling, and water (2 mL) was added dropwise at room temperature. The precipitated solid was collected by filtration to give the title compound (208 mg) as a pale-yellow solid.

¹H-NMR (DMSO-d₆) δ 1.96-2.19 (3H, m), 2.35-2.48 (1H, m), 3.03 (3H, s), 3.36-3.47 (1H, m), 3.73-3.83 (1H, m), 4.76 (1H, dd, J=8.4, 2.0 Hz), 6.60 (2H, d, J=8.9 Hz), 7.59 (1H, s), 7.62 (2H, d, J=8.9 Hz), 12.69 (1H, brs).

B) Production of 6-(5-methyl-1H-pyrazol-4-yl)-2-{1-[4-(methylsulfonyl)phenyl]pyrrolidin-2-yl}thieno[3,2-d]pyrimidin-4 (3H)-one 6-Bromo-2-{1-[4-(methylsulfonyl)phenyl]pyrrolidin-2-yl}thieno[3,2-d]pyrimidin-4 (3H)-one (203 mg) produced above, tert-butyl 3-methyl-4-(4,4,5,5-tetramethyl-1,3,2-dioxaborolan-2-yl)-1H-pyrazole-1-carboxylate (275 mg), cesium carbonate (291 mg), 1,2-dimethoxyethane (5 mL) and water (0.5 mL) were placed in a flask, and the atmosphere in the flask was purged with argon. [1,1'-Bis(diphenylphosphino)ferrocene]palladium(II) dichloride-dichloromethane complex (1:1)(73.0 mg) was added, the atmosphere in the flask was purged again with argon, and the mixture was stirred at 80° C. for 1.5 hr. 2M Aqueous sodium hydroxide solution (1 mL) was added to the reaction mixture, and the mixture was further stirred at 80° C. for 2 hr. Ethyl acetate (20 mL) and 1M hydrochloric acid (3 mL) were added to the reaction mixture, and the separated aqueous layer was extracted with ethyl acetate (5 mL). The combined organic layers were washed with brine (5 mL) and dried over anhydrous sodium sulfate. Insoluble material was filtered off, and the filtrate was concentrated under reduced pressure. The residue was purified by silica gel column chromatography (methanol/ethyl acetate), and the object fraction was concentrated under reduced pressure. The obtained residue was washed with methanol (5 mL) to give the title compound (130 mg) as a pale-yellow solid.

¹H-NMR (DMSO-d₆) δ 1.96-2.22 (3H, m), 2.33-2.47 (4H, m), 3.03 (3H, s), 3.37-3.48 (1H, m), 3.73-3.85 (1H, m), 4.77 (1H, dd, J=8.4, 1.6 Hz), 6.61 (2H, d, J=8.9 Hz), 7.34 (1H, s), 7.63 (2H, d, J=8.9 Hz), 7.80-8.34 (1H, m), 12.47 (1H, brs), 12.83-13.09 (1H, m).

Example 87

Production of 2-[(1R*,2S*,5S*)-3-azabicyclo[3.1.0]hex-2-yl]-6-(5-methyl-1H-pyrazol-4-yl)thieno[3,2-d]pyrimidin-4 (3H)-one dihydrochloride A) Production of tert-butyl(1R*,2S*,5S*)-2-(6-bromo-4-oxo-3,4-dihydrothieno[3,2-d]pyrimidin-2-yl)-3-azabicyclo[3.1.0]hexane-3-carboxylate In the same manner as in Example 86, step A, the title compound (354 mg) was obtained as a colorless solid from 3-amino-5-bromothiophene-2-carboxamide (450 mg) produced in Example 1, step D, (1R*,2S*,5S*)-3-(tert-butoxycarbonyl)-3-azabicyclo[3.1.0]hexane-2-carboxylic acid (974 mg), 2-methylpropyl chlorocarbonate (0.584 mL), triethylamine (0.707 mL), tetrahydrofuran (10 mL), 2M aqueous sodium hydroxide solution (3.06 mL) and ethanol (5 mL).

¹H-NMR (DMSO-d₆) δ 0.47-0.62 (1H, m), 0.76-0.92 (1H, m), 1.07 (9H, s, major), 1.35 (9H, s, minor), 1.62-1.76 (1H, m), 1.86-1.99 (1H, m), 3.47-3.59 (2H, m), 4.27 (1H, d, J=5.1 Hz, minor), 4.77 (1H, d, J=5.1 Hz, major), 7.61 (1H, s, minor), 7.65 (1H, s, major), 12.44-12.80 (1H, m).
* Observed as a 3:2 mixture of rotamers.

B) Production of 2-[(1R*,2S*,5S*)-3-azabicyclo[3.1.0]hex-2-yl]-6-(5-methyl-1H-pyrazol-4-yl)thieno[3,2-d]pyrimidin-4 (3H)-one dihydrochloride In the same manner as in Example 83, step C, the title compound (36.5 mg) was obtained as a colorless solid from tert-butyl(1R*,2S*,5S*)-2-(6-bromo-4-oxo-3,4-dihydrothieno[3,2-d]pyrimidin-2-yl)-3-azabicyclo[3.1.0]hexane-3-carboxylate (200 mg) produced above, tert-butyl 3-methyl-4-(4,4,5,5-tetramethyl-1,3,2-dioxaborolan-2-yl)-1H-pyrazole-1-carboxylate (299 mg), cesium carbonate (316 mg), [1,1'-bis(diphenylphosphino)ferrocene]palladium(II) dichloride-dichloromethane complex (1:1) (79.2 mg), 1,2-dimethoxyethane (8 mL), water (0.8 mL), 4M hydrochloric acid/ethyl acetate solution (1 mL) and methanol (4 mL).

¹H-NMR (DMSO-d₆) δ 0.57-0.73 (2H, m), 1.83-1.93 (1H, m), 2.25-2.36 (1H, m), 2.46 (3H, s), 3.38-3.47 (2H, m), 4.92 (1H, brs), 7.32 (1H, s), 8.10 (1H, s), 8.74 (1H, brs), 10.25 (1H, brs), 13.03 (1H, brs).

Example 88

Production of 6-(5-methyl-1H-pyrazol-4-yl)-2-[(2S)-1-methylpyrrolidin-2-yl]thieno[3,2-d]pyrimidin-4 (3H)-one dihydrochloride A) Production of tert-butyl(2S)-2-[(5-bromo-2-carbamoylthiophen-3-yl)carbamoyl]pyrrolidine-1-carboxylate In the same manner as in Example 78, step A, the title compound (1.67 g) was obtained as a pale-yellow solid from 3-amino-5-bromothiophene-2-carboxamide (1.00 g) produced in Example 1, step D, 1-(tert-butoxycarbonyl)-L-proline (2.04 g), 2-methylpropyl chlorocarbonate (1.29 mL), triethylamine (1.57 mL) and tetrahydrofuran (25 mL).

¹H-NMR (DMSO-d₆) δ 1.25 (9H, s, major), 1.40 (9H, s, minor), 1.79-1.97 (3H, m), 2.12-2.30 (1H, m), 3.35-3.55 (2H, m), 4.09-4.21 (1H, m), 7.72 (2H, brs), 8.05 (1H, s), 11.66 (1H, s, major), 11.68 (1H, s, minor).
* Observed as a 8:7 mixture of rotamers.

B) Production of N-(5-bromo-2-carbamoylthiophen-3-yl)-L-prolinamide hydrochloride To a solution of tert-butyl(2S)-2-[(5-bromo-2-carbamoylthiophen-3-yl)carbamoyl]pyrrolidine-1-carboxylate (1.66 g) produced above in methanol/tetrahydrofuran (20 mL/10 mL) was added 4M hydrochloric acid/ethyl acetate (10 mL), and the mixture was stirred at 50° C. for 1 hr. Ethyl acetate (10 mL) was added to the reaction mixture, and the precipitated solid was collected by filtration to give the title compound (1.26 g) as a pale-yellow solid.

¹H-NMR (DMSO-d₆) δ 1.86-2.07 (3H, m), 2.28-2.41 (1H, m), 3.17-3.29 (2H, m), 4.52 (1H, t, J=7.5 Hz), 7.84 (2H, brs), 7.88 (1H, s), 9.15 (2H, brs), 11.46 (1H, brs).

C) Production of 6-bromo-2-[(2S)-1-methylpyrrolidin-2-yl]thieno[3,2-d]pyrimidin-4 (3H)-one To a solution of N-(5-bromo-2-carbamoylthiophen-3-yl)-L-prolinamide hydrochloride (1.05 g) produced above in methanol (25 mL) were added formalin (1.10 mL) and sodium cyanoborohydride (558 mg), and the mixture was stirred at room temperature for 1 hr. 2M Aqueous sodium hydroxide solution (7.40 mL) was added to the reaction mixture, and the mixture was further stirred at 50° C. for 5 hr. The reaction mixture was neutralized with 6M hydrochloric acid (2.5 mL) under ice-cooling, and concentrated under reduced pressure to a half volume. Ethyl acetate (50 mL) and brine (10 mL) were added to the residue, and the separated aqueous layer was extracted with ethyl acetate (2×10 mL). The combined organic layers were washed with brine (10 mL) and dried over anhydrous sodium sulfate. Insoluble material was filtered off, and the filtrate was concentrated under reduced pressure. The residue was purified by silica gel column chromatography (ethyl acetate/hexane), and the object fraction was concentrated under reduced pressure. The obtained residue was washed with diethylether (20 mL) to give the title compound (892 mg) as a colorless solid.

$^1$H-NMR (DMSO-$d_6$) δ 1.68-1.99 (3H, m), 2.10-2.39 (2H, m), 2.24 (3H, s), 3.08-3.18 (1H, m), 3.25-3.32 (1H, m), 7.57 (1H, s), 11.90 (1H, brs).

D) Production of 6-bromo-2-[(2S)-1-methylpyrrolidin-2-yl]-3-{[2-(trimethylsilyl)ethoxy]methyl}thieno[3,2-d]pyrimidin-4 (3H)-one To a solution of 6-bromo-2-[(2S)-1-methylpyrrolidin-2-yl]thieno[3,2-d]pyrimidin-4 (3H)-one (250 mg) produced above in tetrahydrofuran (5 mL) was added sodium hydride (60% in oil, 38.2 mg) under ice-cooling, and the mixture was stirred at 0° C. for 15 min. [2-(Chloromethoxy)ethyl](trimethyl)silane (0.169 mL) was added to the reaction mixture, and the mixture was stirred at room temperature for 1 hr. Ethyl acetate (15 mL) and aqueous ammonium chloride solution (5 mL) were added to the reaction mixture, and the separated aqueous layer was extracted with ethyl acetate (5 mL). The combined organic layers were washed with brine (10 mL) and dried over anhydrous sodium sulfate. Insoluble material was filtered off, and the filtrate was concentrated under reduced pressure. The residue was purified by basic silica gel column chromatography (ethyl acetate/hexane), and the object fraction was concentrated under reduced pressure to give the title compound (180 mg) as a colorless oil.

$^1$H-NMR (DMSO-$d_6$) δ −0.03 (9H, s), 0.82-0.91 (2H, m), 1.73-2.06 (3H, m), 2.17-2.29 (1H, m), 2.21 (3H, s), 2.35 (1H, q, J=8.4 Hz), 3.05-3.15 (1H, m), 3.64 (2H, t, J=8.1 Hz), 3.72 (1H, dd, J=8.4, 7.1 Hz), 5.62 (1H, d, J=10.5 Hz), 5.72 (1H, d, J=10.5 Hz), 7.65 (1H, s).

E) Production of 6-(5-methyl-1H-pyrazol-4-yl)-2-[(2S)-1-methylpyrrolidin-2-yl]thieno[3,2-d]pyrimidin-4 (3H)-one dihydrochloride In the same manner as in Example 83, step C, tert-butyl 3-methyl-4-(2-[(2S)-1-methylpyrrolidin-2-yl]-4-oxo-3-{[2-(trimethylsilyl)ethoxy]methyl}-3,4-dihydrothieno[3,2-d]pyrimidin-6-yl)-1H-pyrazole-1-carboxylate was obtained as a pale-yellow oil from 6-bromo-2-[(2S)-1-methylpyrrolidin-2-yl]-3-{[2-(trimethylsilyl)ethoxy]methyl}thieno[3,2-d]pyrimidin-4 (3H)-one (160 mg) produced above, tert-butyl 3-methyl-4-(4,4,5,5-tetramethyl-1,3,2-dioxaborolan-2-yl)-1H-pyrazole-1-carboxylate (222 mg), cesium carbonate (234 mg), [1,1'-bis(diphenylphosphino)ferrocene]palladium(II) dichloride-dichloromethane complex (1:1) (58.8 mg), 1,2-dimethoxyethane (5 mL) and water (0.5 mL). To a solution of tert-butyl 3-methyl-4-(2-[(2S)-1-methylpyrrolidin-2-yl]-4-oxo-3-{[2-(trimethylsilyl)ethoxy]methyl}-3,4-dihydrothieno[3,2-d]pyrimidin-6-yl)-1H-pyrazole-1-carboxylate produced above in N,N-dimethylformamide (2 mL) was added 1M tetrabutylammonium fluoride/tetrahydrofuran solution (1.44 mL), and the mixture was stirred at 90° C. for 4 hr. Ethyl acetate (20 mL) and brine (10 mL) were added to the reaction mixture, and the separated aqueous layer was extracted with ethyl acetate (2×10 mL). The combined organic layers were washed with brine (5 mL) and dried over anhydrous sodium sulfate. Insoluble material was filtered off, and the filtrate was concentrated under reduced pressure. The residue was purified by basic silica gel column chromatography (methanol/ethyl acetate), and the object fraction was concentrated under reduced pressure. To a solution of the residue in methanol (1 mL) were added 4M hydrochloric acid/ethyl acetate solution (2 mL) and ethyl acetate (1.5 mL), and the precipitate was collected by filtration to give the title compound (15.6 mg) as a pale-yellow solid.

$^1$H-NMR (DMSO-$d_6$) δ 1.92-2.21 (3H, m), 2.46 (3H, s), 2.60-2.71 (1H, m), 2.96 (3H, s), 3.24-3.38 (1H, m), 3.67-3.75 (1H, m), 4.45-4.57 (1H, m), 7.37 (1H, s), 8.10 (1H, brs), 10.08 (1H, brs), 12.92 (1H, brs).

Example 89

Production of 2-[2-(4-fluorobenzyl)pyrrolidin-2-yl]-6-(5-methyl-1H-pyrazol-4-yl)thieno[3,2-d]pyrimidin-4 (3H)-one dihydrochloride A) Production of tert-butyl 2-(6-bromo-4-oxo-3,4-dihydrothieno[3,2-d]pyrimidin-2-yl)-2-(4-fluorobenzyl)pyrrolidine-1-carboxylate In the same manner as in Example 82, step A, the title compound (53 mg) was obtained as a pale-yellow solid from 1-(tert-butoxycarbonyl)-2-(4-fluorobenzyl)proline (466 mg), triethylamine (0.335 mL), tetrahydrofuran (10 mL), 2-methylpropyl chlorocarbonate (0.158 mL), 3-amino-5-bromothiophene-2-carboxamide (265 mg) produced in Example 1, step D, 2M aqueous sodium hydroxide solution (3 mL) and ethanol (5 mL).

MS(ESI+): [M+H]$^+$508.
MS(ESI+), found: 508.

B) Production of 2-[2-(4-fluorobenzyl)pyrrolidin-2-yl]-6-(5-methyl-1H-pyrazol-4-yl)thieno[3,2-d]pyrimidin-4 (3H)-one dihydrochloride In the same manner as in Example 11, step B, the title compound (13 mg) was obtained as a white solid from tert-butyl 2-(6-bromo-4-oxo-3,4-dihydrothieno[3,2-d]pyrimidin-2-yl)-2-(4-fluorobenzyl)pyrrolidine-1-carboxylate (53 mg), tert-butyl 3-methyl-4-(4,4,5,5-tetramethyl-1,3,2-dioxaborolan-2-yl)-1H-pyrazole-1-carboxylate (64 mg), cesium carbonate (200 mg), 1,2-dimethoxyethane (3 mL), water (0.25 mL) and [1,1'-bis(diphenylphosphino)ferrocene]palladium (II) dichloride-dichloromethane complex (1:1) (8 mg).

$^1$H-NMR (DMSO-$d_6$) δ 1.75-2.73 (7H, m), 3.36-3.79 (4H, m), 7.09-7.12 (4H, m), 7.19 (1H, s), 8.07 (1H, brs), 9.26 (1H, brs), 9.70 (1H, brs), 13.05 (1H, brs).

Example 90

Production of 2-[(benzylamino)methyl]-6-(5-methyl-1H-pyrazol-4-yl)thieno[3,2-d]pyrimidin-4 (3H)-one monotrifluoroacetate A) Production of 2-[(benzylamino)methyl]-6-bromothieno[3,2-d]pyrimidin-4 (3H)-one In the same manner as in Example 2, step B, a crude product (234 mg) of the title compound was obtained as a colorless solid from 6-bromo-2-(chloromethyl)thieno[3,2-d]pyrimidin-4 (3H)-one (500 mg) produced in Example 2, step A, 1-phenylmethanamine (0.58 ml), potassium carbonate (495 mg), sodium iodide (27 mg) and N,N-dimethylformamide (5.0 ml).

B) Production of 6-benzyl-2-bromo-6,7-dihydroimidazo[1,5-a]thieno[3,2-d]pyrimidin-9(5H)-one A mixture of a crude product (185 mg) of 2-[(benzylamino)methyl]-6-bromothieno[3,2-d]pyrimidin-4 (3H)-one, 37% aqueous formaldehyde solution (1 ml) and tetrahydrofuran (2 mL) was stirred at room temperature for 1 hr. The precipitate was collected by filtration, and washed successively with water and ethyl acetate to give a crude product (104 mg) of the title compound as a pale-yellow solid.

C) Production of 6-benzyl-2-(5-methyl-1H-pyrazol-4-yl)-6,7-dihydroimidazo[1,5-a]thieno[3,2-d]pyrimidin-9(5H)-one In the same manner as in Example 2, step C, a crude product (89 mg) of the title compound was obtained as pale-yellow crystals from a crude product (100 mg) of 6-benzyl-2-bromo-6,7-dihydroimidazo[1,5-a]thieno[3,2-d]pyrimidin-9(5H)-one and tert-butyl 3-methyl-4-(4,4,5,5-tetramethyl-1,3,2-dioxaborolan-2-yl)-1H-pyrazole-1-carboxylate (255 mg), sodium carbonate (66 mg), 1,2-dimethoxyethane (3.0 mL) and water (1.5 mL) and [1,1'-bis(diphenylphosphino)ferrocene]palladium(II) dichloride-dichloromethane complex (1:1) (23 mg).

D) Production of 2-[(benzylamino)methyl]-6-(5-methyl-1H-pyrazol-4-yl)thieno[3,2-d]pyrimidin-4 (3H)-one monotrifluoroacetate A mixture of a crude product (80 mg) of 6-benzyl-2-(5-methyl-1H-pyrazol-4-yl)-6,7-dihydroimidazo[1,5-a]thieno[3,2-d]pyrimidin-9(5H)-one, methanol (2 mL) and trifluoroacetic acid (2 mL) was stirred with heating at 70° C. for 5 hr. The reaction system was concentrated under reduced pressure, and the residue was crystallized from methanol/ethyl acetate to give the title compound (43 mg) as a yellow solid.
$^1$H-NMR (DMSO-$d_6$) δ 2.46 (3H, brs), 4.20 (2H, s), 4.31 (2H, s), 7.40 (1H, s), 7.42-7.58 (5H, m), 8.05 (1H, brs), 9.15-10.22 (2H, m), 13.04 (1H, brs).

Example 91

Production of 2-[(1R,3S,4S)-2-azabicyclo[2.2.1]heptan-3-yl]-6-(5-methyl-1H-pyrazol-4-yl)thieno[3,2-d]pyrimidin-4 (3H)-one A) Production of tert-butyl(1R,3S,4S)-3-(6-bromo-4-oxo-3,4-dihydrothieno[3,2-d]pyrimidin-2-yl)-2-azabicyclo[2.2.1]heptane-2-carboxylate To a solution (15 mL) of (1R,3S,4S)-2-(tert-butoxycarbonyl)-2-azabicyclo[2.2.1]heptane-3-carboxylic acid (0.894 g) and triethylamine (0.541 mL) in tetrahydrofuran was added with stirring isobutyl chloroformate (0.487 mL) under ice-cooling. After stirring at room temperature for 30 min, a solution of 3-amino-5-bromothiophene-2-carboxamide (0.78 g) produced in Example 1, step D, in tetrahydrofuran (3 mL) was added. The reaction system was stirred with heating at 60° C. for 40 hr. Water was poured into the reaction system, and the mixture was extracted with ethyl acetate, washed with brine, and dried over anhydrous sodium sulfate. Insoluble material was removed by filtration, and the filtrate was concentrated under reduced pressure. 2M Aqueous sodium hydroxide solution (7.06 mL) and ethanol (14 mL) were added to the residue, and the mixture was stirred with heating at 70° C. for 5 hr. The reaction system was neutralized with 1M hydrochloric acid (4 mL) while stirring under ice-cooling. Insoluble material was removed by filtration. The mixture was extracted with ethyl acetate, washed with brine, and dried over anhydrous sodium sulfate. Insoluble material was removed by filtration, and the filtrate was concentrated under reduced pressure. The residue was purified by basic silica gel column chromatography (ethyl acetate/hexane) to give the title compound (1.06 g) as a pale-yellow solid.
$^1$H-NMR (DMSO-$d_6$) δ 1.07-1.83 (14H, m), 2.00-2.12 (1H, m), 2.58-2.67 (1H, m), 4.14 (1H, brs), 4.17-4.25 (1H, m), 7.56-7.81 (1H, m), 12.45-12.79 (1H, m).

B) Production of tert-butyl(1R,3S,4S)-3-[6-(5-methyl-1H-pyrazol-4-yl)-4-oxo-3,4-dihydrothieno[3,2-d]pyrimidin-2-yl]-2-azabicyclo[2.2.1]heptane-2-carboxylate tert-Butyl(1R,3S,4S)-3-(6-bromo-4-oxo-3,4-dihydrothieno[3,2-d]pyrimidin-2-yl)-2-azabicyclo[2.2.1]heptane-2-carboxylate (1.03 g) and tert-butyl 3-methyl-4-(4,4,5,5-tetramethyl-1,3,2-dioxaborolan-2-yl)-1H-pyrazole-1-carboxylate (1.49 g), sodium carbonate (768 mg), 1,2-dimethoxyethane (8.0 mL) and water (4.0 mL) were placed in a flask, and the atmosphere in the flask was purged with argon. [1,1'-Bis(diphenylphosphino)ferrocene]palladium(II) dichloride-dichloromethane complex (1:1) (197 mg) was added, and the atmosphere in the flask was purged again with argon. The reaction system was stirred at 100° C. for 3 hr, and the mixture was extracted with ethyl acetate and dried over anhydrous sodium sulfate. Insoluble material was removed by filtration, and the extract was concentrated under reduced pressure. The residue was purified by silica gel column chromatography (ethyl acetate/hexane) to give the title compound (690 mg) as a pale-yellow solid.
$^1$H-NMR (DMSO-$d_6$) δ 1.04-1.86 (14H, m), 2.04-2.20 (1H, m), 2.33-2.48 (3H, m), 2.60-2.67 (1H, m), 4.11-4.17 (1H, m), 4.18-4.26 (1H, m), 7.34-7.54 (1H, m), 7.88 (0.6H, brs), 8.23 (0.4H, brs), 12.23-12.48 (1H, m), 12.82-13.09 (1H, m).

C) Production of 2-[(1R,3S,4S)-2-azabicyclo[2.2.1]hept-3-yl]-6-(5-methyl-1H-pyrazol-4-yl)thieno[3,2-d]pyrimidin-4 (3H)-one To a solution of tert-butyl(1R,3S,4S)-3-[6-(5-methyl-1H-pyrazol-4-yl)-4-oxo-3,4-dihydrothieno[3,2-d]pyrimidin-2-yl]-2-azabicyclo[2.2.1]heptane-2-carboxylate (690 mg) in methanol (10 mL) was added 4M hydrochloric acid/ethyl acetate solution (2.0 mL) with stirring at room temperature. The reaction system was stirred with heating at 50° C. for 30 min, and the mixture was concentrated under reduced pressure. The residue was neutralized with saturated aqueous sodium hydrogen carbonate. Insoluble material was removed by filtration. The mixture was extracted with ethyl acetate, and dried over anhydrous sodium sulfate. Insoluble material was removed by filtration, and the filtrate was concentrated under reduced pressure. The residue was purified by basic silica gel column chromatography (ethyl acetate/hexane and methanol/ethyl acetate), and the obtained colorless solid was crystallized from methanol/ethyl acetate to give the title compound (220 mg) as a colorless solid. The optical purity was 86% ee. The analysis was performed by high performance liquid chromatography (column: CHIRALPAK OD-H (4.6 mm i.d.×250 mm L, manufactured by DAICEL CHEMICAL INDUSTRIES, LTD.), mobile phase: methanol, flow rate: 0.5 mL/min, column temperature: 30° C., detection 254 nm).

$^1$H-NMR (DMSO-d$_6$) δ 1.17 (1H, s), 1.27-1.38 (1H, m), 1.45-1.73 (4H, m), 2.45 (3H, s), 2.66-2.72 (1H, m), 3.57 (1H, s), 3.73 (1H, s), 7.35 (1H, s), 8.01 (1H, brs).
MS(ESI+): [M+H]$^+$328.
MS(ESI+), found: 328.

Example 92

Production of 6-(5-methyl-1H-pyrazol-4-yl)-2-[(2S, 4S)-4-methylpyrrolidin-2-yl]thieno[3,2-d]pyrimidin-4 (3H)-one dihydrochloride A) Production of tert-butyl(2S,4S)-2-[(5-bromo-2-carbamoylthiophen-3-yl)carbamoyl]-4-methylpyrrolidine-1-carboxylate To a solution of (4S)-1-(tert-butoxycarbonyl)-4-methyl-L-proline (491 mg) and triethylamine (0.353 mL) in tetrahydrofuran (5 mL) was added 2-methylpropyl chlorocarbonate (0.292 mL) at 0° C., and the mixture was stirred at room temperature for 1 hr. Thereafter, to the reaction system was added 3-amino-5-bromothiophene-2-carboxamide (225 mg) produced in Example 1, step D, and the mixture was stirred at 60° C. for 24 hr. Ethyl acetate (20 mL) and aqueous sodium hydrogen carbonate (10 mL) were added to the reaction mixture, and the separated aqueous layer was extracted with ethyl acetate (5 mL). The combined organic layers were washed with brine (5 mL) and dried over anhydrous sodium sulfate. Insoluble material was filtered off, the filtrate was concentrated under reduced pressure, and the residue was crystallized from ethanol (5 mL). The obtained colorless solid was fractionated by high performance liquid chromatography (column: CHIRALPAK AD (50 mm i.d.×500 mm L, manufactured by DAICEL CHEMICAL INDUSTRIES, LTD.), mobile phase: hexane/ethanol (850/150), flow rate: 80 mL/min, column temperature: 30° C.) to give the title compound (302 mg) as a colorless solid.
$^1$H-NMR (DMSO-d$_6$) δ 0.94-1.03 (3H, m), 1.22 (9H, s, major), 1.39 (9H, s, minor), 1.41-1.56 (1H, m), 2.13-2.33 (1H, m), 2.35-2.48 (1H, m), 2.82-3.00 (1H, m), 3.70 (1H, dd, J=10.1, 7.5 Hz), 4.13 (1H, t, J=8.1 Hz), 7.71 (2H, brs), 8.03 (1H, s, minor), 8.05 (1H, s, major), 11.65 (1H, s).
* Observed as a 3:2 mixture of rotamers.

B) Production of tert-butyl(2S,4S)-2-(6-bromo-4-oxo-3,4-dihydrothieno[3,2-d]pyrimidin-2-yl)-4-methylpyrrolidine-1-carboxylate In the same manner as in Example 40, step B, the title compound (240 mg) was obtained as a colorless solid from tert-butyl(2S,4S)-2-[(5-bromo-2-carbamoylthiophen-3-yl)carbamoyl]-4-methylpyrrolidine-1-carboxylate (300 mg) produced above, 2M aqueous sodium hydroxide solution (1.73 mL) and ethanol (5 mL).
$^1$H-NMR (DMSO-d$_6$) δ 0.98-1.05 (3H, m), 1.08 (9H, s, major), 1.35 (9H, s, minor), 1.45-1.66 (1H, m), 2.18-2.33 (1H, m), 2.34-2.46 (1H, m), 2.97-3.13 (1H, m), 3.57-3.71 (1H, m), 4.49-4.60 (1H, m), 7.61 (1H, s, minor), 7.64 (1H, s, major), 12.73 (1H, brs).
* Observed as a 2:1 mixture of rotamers.

C) Production of 6-(5-methyl-1H-pyrazol-4-yl)-2-[(2S,4S)-4-methylpyrrolidin-2-yl]thieno[3,2-d]pyrimidin-4 (3H)-one dihydrochloride In the same manner as in Example 83, step C, the title compound (137 mg) was obtained as a colorless solid from tert-butyl(2S,4S)-2-(6-bromo-4-oxo-3,4-dihydrothieno[3,2-d]pyrimidin-2-yl)-4-methylpyrrolidine-1-carboxylate (238 mg) produced above, tert-butyl 3-methyl-4-(4,4,5,5-tetramethyl-1,3,2-dioxaborolan-2-yl)-1H-pyrazole-1-carboxylate (354 mg), cesium carbonate (374 mg), [1,1'-bis(diphenylphosphino)ferrocene]palladium(II) dichloride-dichloromethane complex (1:1) (93.9 mg), 1,2-dimethoxyethane (5 mL), water (0.5 mL), 4M hydrochloric acid/ethyl acetate solution (1 mL) and methanol (4 mL).
$^1$H-NMR (DMSO-d$_6$) δ 1.07 (3H, d, J=6.6 Hz), 1.59-1.75 (1H, m), 2.34-2.50 (1H, m), 2.46 (3H, s), 2.60-2.76 (1H, m), 2.82-2.99 (1H, m), 3.40-3.53 (1H, m), 4.59-4.76 (1H, m), 7.37 (1H, s), 8.10 (1H, s), 9.04 (1H, brs), 10.02 (1H, brs), 12.85 (1H, brs).

Example 93

Production of 6-(5-methyl-1H-pyrazol-4-yl)-2-pyridin-2-ylthieno[3,2-d]pyrimidin-4 (3H)-one A) Production of 6-bromo-2-pyridin-2-ylthieno[3,2-d]pyrimidin-4 (3H)-one To a mixture of 3-amino-5-bromothiophene-2-carboxamide (221 mg) produced in Example 1, step D, triethylamine (0.42 mL) and tetrahydrofuran (15 mL) was added pyridine-2-carbonylchloride hydrochloride (214 mg) with stirring at room temperature. The mixture was stirred at room temperature for 30 min and at 50° C. overnight. Triethylamine (0.42 mL) and pyridine-2-carbonylchloride hydrochloride (214 mg) were added to the reaction mixture. 2 hr later, aqueous sodium hydrogen carbonate was added to the reaction mixture, and the mixture was extracted with ethyl acetate. The separated organic layer was washed with water and brine (5 mL), and dried over anhydrous magnesium sulfate. Insoluble material was filtered off, and the filtrate was concentrated under reduced pressure. Ethanol (10 mL) and 2M aqueous sodium hydroxide solution (3.0 mL) were added to the residue, and the mixture was stirred at 80° C. for 1 hr. The reaction mixture was neutralized with 6M hydrochloric acid under ice-cooling, and the mixture was extracted with ethyl acetate. The organic layer was washed with brine (10 mL), and dried over anhydrous magnesium sulfate. Insoluble material was filtered off, and the filtrate was concentrated under reduced pressure to give a crude product (300 mg) of the title compound as a pale-orange solid.
MS(ESI+): [M+H]$^+$309.
MS(ESI+), found: 308, 310.

B) Production of 6-bromo-2-pyridin-2-yl-3-{[2-(trimethylsilyl)ethoxy]methyl}thieno[3,2-d]pyrimidin-4 (3H)-one In the same manner as in Example 88, step D, a crude product (302 mg) of the title compound was obtained as a yellow oil from 6-bromo-2-pyridin-2-ylthieno[3,2-d]pyrimidin-4 (3H)-one (223 mg) produced above, tetrahydrofuran (10 mL), sodium hydride (60% in oil, 70 mg), and [2-(chloromethoxy)ethyl](trimethyl)silane (0.31 mL).
MS(ESI+): [M+H]$^+$439.
MS(ESI+), found: 438, 410.

C) Production of 6-(5-methyl-1H-pyrazol-4-yl)-2-pyridin-2-ylthieno[3,2-d]pyrimidin-4 (3H)-one In the same manner as in Example 83, step C, tert-butyl 3-methyl-4-(4-oxo-2-pyridin-2-yl-3-{[2-(trimethylsilyl)

ethoxy]methyl}-3,4-dihydrothieno[3,2-d]pyrimidin-6-yl)-1H-pyrazole-1-carboxylate was obtained as a pale-orange oil from 6-bromo-2-pyridin-2-yl-3-{[2-(trimethylsilyl)ethoxy]methyl}thieno[3,2-d]pyrimidin-4 (3H)-one (302 mg) produced above, tert-butyl 3-methyl-4-(4,4,5,5-tetramethyl-1,3,2-dioxaborolan-2-yl)-1H-pyrazole-1-carboxylate (425 mg), cesium carbonate (1.35 g), [1,1'-bis(diphenylphosphino)ferrocene]palladium(II) dichloride-dichloromethane complex (1:1) (25.2 mg), 1,2-dimethoxyethane (6 mL) and water (2 mL). To tert-butyl 3-methyl-4-(4-oxo-2-pyridin-2-yl-3-{[2-(trimethylsilyl)ethoxy]methyl}-3,4-dihydrothieno[3,2-d]pyrimidin-6-yl)-1H-pyrazole-1-carboxylate produced above was added 1M tetrabutylammonium fluoride/tetrahydrofuran solution (3.0 mL), and the mixture was stirred at 50° C. for 1 hr. Water was added to the reaction mixture, and the mixture was extracted with ethyl acetate/tetrahydrofuran (3:1). The organic layer was dried over anhydrous magnesium sulfate. Insoluble material was filtered off, and the filtrate was concentrated under reduced pressure. Trifluoroacetic acid (3 mL) was added to the residue, and the mixture was stirred at room temperature for 1 hr. The reaction mixture was concentrated under reduced pressure, aqueous sodium hydrogen carbonate was added to the residue, and the mixture was extracted with ethyl acetate/tetrahydrofuran (3:1). The organic layer was dried over anhydrous magnesium sulfate. Insoluble material was filtered off, and the filtrate was concentrated under reduced pressure. The residue was purified by basic silica gel column chromatography (methanol/ethyl acetate), and the object fraction was concentrated under reduced pressure to give the title compound (18.6 mg) as a pale-yellow solid.

$^1$H-NMR (DMSO-d$_6$) δ 2.41-2.47 (3H, m), 7.54 (1H, s), 7.66 (1H, ddd, J=7.6, 4.7, 1.1 Hz), 7.95 (0.67H, brs), 8.08 (1H, td, J=7.7, 1.5 Hz), 8.29-8.35 (0.33H, m), 8.40 (1H, d, J=7.9 Hz), 8.77 (1H, d, J=4.2 Hz), 11.94 (1H, brs), 13.05 (1H, brs).

Example 94

Production of 6-(5-methyl-1H-pyrazol-4-yl)-2-(2-phenyl-1-pyrrolidin-1-ylethyl)thieno[3,2-d]pyrimidin-4 (3H)-one A) Production of 2-chloro-3-phenylpropanoyl chloride To a mixture of 2-hydroxy-3-phenylpropanoic acid (1.0 g) and toluene (10 mL) was added thionyl chloride (1.3 mL) by small portions. The reaction system was stirred with heating at 40° C. for 2 hr, and N,N-dimethylformamide (0.093 mL) was added. The reaction system was stirred with heating at 40° C. for 20 hr, and concentrated under reduced pressure, and toluene (20 mL) was added. The mixture was concentrated under reduced pressure, and toluene (20 mL) was added. The mixture was concentrated again under reduced pressure to give a crude product (1.2 g) of the title compound as a pale-yellow liquid.

$^1$H-NMR (CDCl$_3$) δ 3.19-3.31 (1H, m), 3.39-3.57 (1H, m), 4.65-4.80 (1H, m), 7.04-7.46 (5H, m).

B) Production of 6-(5-methyl-1H-pyrazol-4-yl)-2-(2-phenyl-1-pyrrolidin-1-ylethyl)thieno[3,2-d]pyrimidin-4 (3H)-one To a mixture of 3-amino-5-bromothiophene-2-carboxamide (221 mg) produced in Example 1, step D, triethylamine (0.21 mL) and tetrahydrofuran (5.0 mL) was added 2-chloro-3-phenylpropanoyl chloride (305 mg) with stirring at room temperature. The reaction mixture was stirred for 10 min, and pyrrolidine (0.42 mL) was added. The reaction mixture was stirred with heating at 70° C. for 2 hr, sodium iodide (2.0 mg) was added, and the reaction mixture was stirred with heating at 70° C. for 18 hr. The mixture was extracted with ethyl acetate, and dried over anhydrous sodium sulfate. Insoluble material was removed by filtration, and the filtrate was concentrated under reduced pressure. The residue was purified by basic silica gel column chromatography (ethyl acetate/hexane) to give a pale-yellow solid (285 mg). The obtained pale-yellow solid (285 mg) and tert-butyl 3-methyl-4-(4,4,5,5-tetramethyl-1,3,2-dioxaborolan-2-yl)-1H-pyrazole-1-carboxylate (435 mg), sodium carbonate (126 mg), 1,2-dimethoxyethane (4.0 mL) and water (2.0 mL) were placed in a flask, and the atmosphere in the flask was purged with argon. [1,1'-Bis(diphenylphosphino)ferrocene]palladium(II) dichloride-dichloromethane complex (1:1) (57 mg) was added, and the atmosphere in the flask was purged again with argon. The reaction system was stirred at 100° C. for 30 min, extracted with ethyl acetate and dried over anhydrous sodium sulfate. Insoluble material was removed by filtration, and the extract was concentrated under reduced pressure. The residue was purified by basic silica gel column chromatography (ethyl acetate/hexane and methanol/ethyl acetate) to give two kinds of pale-yellow solids. The solid eluted earlier was purified by silica gel column chromatography (ethyl acetate/hexane) to give a crude product (5.0 mg) of tert-butyl 3-methyl-4-{4-oxo-2-[(E)-2-phenylethenyl]-3,4-dihydrothieno[3,2-d]pyrimidin-6-yl}-1H-pyrazole-1-carboxylate as a yellow solid. The solid eluted later was purified by silica gel column chromatography (ethyl acetate/hexane and methanol/ethyl acetate), and the obtained pale-yellow solid was crystallized from methanol/ethyl acetate to give the title compound (18 mg) as a colorless solid.

$^1$H-NMR (DMSO-d$_6$) δ 1.54-1.72 (4H, m), 2.24-2.49 (7H, m), 2.85-3.03 (1H, m), 3.33-3.40 (1H, m), 3.91-4.00 (1H, m), 7.14-7.30 (5H, m), 7.32 (1H, s), 7.77-8.38 (1H, m), 12.21 (1H, brs), 12.96 (1H, brs).

Example 95

Production of 6-(5-methyl-1H-pyrazol-4-yl)-2-[(E)-2-phenylethenyl]thieno[3,2-d]pyrimidin-4 (3H)-one monohydrochloride To a solution of a crude product (5.0 mg) of tert-butyl 3-methyl-4-{4-oxo-2-[(E)-2-phenylethenyl]-3,4-dihydrothieno[3,2-d]pyrimidin-6-yl}-1H-pyrazole-1-carboxylate produced in Example 94, step B, in methanol (1.0 mL) was added 4M hydrochloric acid/ethyl acetate solution (0.50 mL). The reaction system was stirred at room temperature for 30 min, and the mixture was concentrated under reduced pressure. The residue was crystallized from methanol/ethyl acetate to give the title compound (1.7 mg) as a yellow solid.

$^1$H-NMR (DMSO-d$_6$) δ 2.47 (3H, s), 7.04 (1H, d, J=16.1 Hz), 7.41 (1H, s), 7.42-7.51 (3H, m), 7.63-7.70 (2H, m), 7.93 (1H, d, J=16.1 Hz), 8.06 (1H, s).

Example 96

Production of 2-(1H-imidazol-1-ylmethyl)-6-(5-methyl-1H-pyrazol-4-yl)thieno[3,2-d]pyrimidin-4 (3H)-one A) Production of 6-bromo-2-(1H-imidazol-1-ylmethyl)thieno[3,2-d]pyrimidin-4 (3H)-one In the same manner as in Example 2, step B, the title compound (88 mg) was obtained as a yellow solid from 6-bromo-2-(chloromethyl)thieno[3,2-d]pyrimidin-4 (3H)-one (180 mg) produced in Example 2, step A, 1H-imidazole (131 mg), potassium carbonate (178 mg), sodium iodide (9.7 mg) and N,N-dimethylformamide (3.0 mL).

$^1$H-NMR (DMSO-$d_6$) δ 5.19 (2H, s), 6.91 (1H, brs), 7.21 (1H, brs), 7.59 (1H, s), 7.71 (1H, brs), 12.92 (1H, brs).

B) Production of 2-(1H-imidazol-1-ylmethyl)-6-(5-methyl-1H-pyrazol-4-yl)thieno[3,2-d]pyrimidin-4 (3H)-one In the same manner as in Example 2, step C, the title compound (1.8 mg) was obtained as a colorless solid from 6-bromo-2-(1H-imidazol-1-ylmethyl)thieno[3,2-d]pyrimidin-4 (3H)-one (88 mg) and tert-butyl 3-methyl-4-(4,4,5,5-tetramethyl-1,3,2-dioxaborolan-2-yl)-1H-pyrazole-1-carboxylate (174 mg), sodium carbonate (51 mg), 1,2-dimethoxyethane (2.0 mL) and water (1.0 mL) and [1,1'-bis (diphenylphosphino)ferrocene]palladium(II) dichloride-dichloromethane complex (1:1) (23 mg).

$^1$H-NMR (DMSO-$d_6$) δ 2.37-2.47 (3H, m), 5.19 (2H, s), 6.92 (1H, s), 7.23 (1H, s), 7.36 (1H, s), 7.73 (1H, s), 7.88 (0.6H, brs), 8.25 (0.4H, brs), 12.68 (1H, brs), 12.88-13.04 (1H, m).

Example 97

Production of 2-[(2,2-dimethylpyrrolidin-1-yl)methyl]-6-(5-methyl-1H-pyrazol-4-yl)thieno[3,2-d]pyrimidin-4 (3H)-one A) Production of 6-bromo-2-[(2,2-dimethylpyrrolidin-1-yl)methyl]thieno[3,2-d]pyrimidin-4 (3H)-one In the same manner as in Example 2, step B, the title compound (109 mg) was obtained as a pale-yellow solid from 6-bromo-2-(chloromethyl)thieno[3,2-d]pyrimidin-4 (3H)-one (180 mg) produced in Example 2, step A, 2,2-dimethylpyrrolidine monohydrochloride (261 mg), potassium carbonate (445 mg), sodium iodide (9.7 mg) and N,N-dimethylformamide (3.0 mL).

$^1$H-NMR (DMSO-$d_6$) δ 1.02 (6H, s), 1.56-1.76 (4H, m), 2.65-2.72 (2H, m), 3.52 (2H, s), 7.60 (1H, s), 11.91 (1H, brs).

B) Production of 2-[(2,2-dimethylpyrrolidin-1-yl) methyl]-6-(5-methyl-1H-pyrazol-4-yl)thieno[3,2-d] pyrimidin-4 (3H)-one In the same manner as in Example 2, step C, the title compound (22 mg) was obtained as brown crystals from 6-bromo-2-[(2,2-dimethylpyrrolidin-1-yl)methyl]thieno[3,2-d]pyrimidin-4 (3H)-one (109 mg) and tert-butyl 3-methyl-4-(4,4,5,5-tetramethyl-1,3,2-dioxaborolan-2-yl)-1H-pyrazole-1-carboxylate (196 mg), sodium carbonate (57 mg), 1,2-dimethoxyethane (3.0 mL) and water (1.5 mL) and [1,1'-bis (diphenylphosphino)ferrocene]palladium(II) dichloride-dichloromethane complex (1:1) (26 mg).

$^1$H-NMR (DMSO-$d_6$) δ 1.03 (6H, s), 1.65 (4H, s), 2.45 (3H, s), 2.71 (2H, brs), 3.53 (2H, s), 7.37 (1H, s), 8.02 (1H, brs), 11.52-13.00 (2H, m).

Example 98

Production of 6-(5-methyl-1H-pyrazol-4-yl)-2-(2-propylpyrrolidin-2-yl)thieno[3,2-d]pyrimidin-4 (3H)-one dihydrochloride A) Production of tert-butyl 2-(6-bromo-4-oxo-3,4-dihydrothieno[3,2-d]pyrimidin-2-yl)-2-propylpyrrolidine-1-carboxylate In the same manner as in Example 82, step A, the title compound (33 mg) was obtained as a pale-yellow solid from 1-(tert-butoxycarbonyl)-2-propylproline (503 mg) and triethylamine (0.454 mL) and tetrahydrofuran (10 mL) and 2-methylpropyl chlorocarbonate (0.211 mL) and 3-amino-5-bromothiophene-2-carboxamide (360 mg) produced in Example 1, step D and 2M aqueous sodium hydroxide solution (4 mL) and ethanol (10 mL).
MS(ESI+): [M+H]$^+$442.
MS(ESI+), found: 442.

B) Production of 6-(5-methyl-1H-pyrazol-4-yl)-2-(2-propylpyrrolidin-2-yl)thieno[3,2-d]pyrimidin-4 (3H)-one dihydrochloride In the same manner as in Example 11, step B, the title compound (13 mg) was obtained as a white solid from tert-butyl 2-(6-bromo-4-oxo-3,4-dihydrothieno[3,2-d]pyrimidin-2-yl)-2-propylpyrrolidine-1-carboxylate (33 mg) and tert-butyl 3-methyl-4-(4,4,5,5-tetramethyl-1,3,2-dioxaborolan-2-yl)-1H-pyrazole-1-carboxylate (46 mg) and cesium carbonate (146 mg) and 1,2-dimethoxyethane (3 mL) and water (0.2 mL) and [1,1'-bis(diphenylphosphino)ferrocene] palladium(II) dichloride-dichloromethane complex (1:1) (3 mg).

$^1$H-NMR (DMSO-$d_6$) δ 0.77-0.89 (3H, m), 0.90-1.02 (1H, m), 1.23-1.38 (1H, m), 1.74-1.89 (1H, m), 1.93-2.43 (5H, m), 2.46 (3H, s), 3.25-3.44 (2H, m), 7.34 (1H, s), 8.09 (1H, brs), 9.32 (1H, brs), 9.55 (1H, brs), 12.83 (1H, brs).

Example 99

Production of 6-(5-methyl-1H-pyrazol-4-yl)-2-[(8aR)-octahydropyrrolo[1,2-a]pyrazin-3-yl]thieno [3,2-d]pyrimidin-4 (3H)-one dihydrochloride A) Production of N-benzyl-5-oxo-D-prolinamide 5-Oxo-D-proline (5.0 g), benzylamine (4.65 mL), 1-ethyl-3-(3-dimethylaminopropyl)carbodiimide hydrochloride (8.5 g) and 1-hydroxybenzotriazole (6.3 g) were mixed in acetonitrile (100 mL) under ice-cooling, and the mixture was allowed to warm to room temperature and stirred for 3 hr. The mixture was diluted with ethyl acetate (200 mL), and washed successively with 1M hydrochloric acid (50 mL), saturated aqueous sodium hydrogen carbonate solution (50 mL) and brine (50 mL). The organic layer was dried over anhydrous magnesium sulfate, and concentrated under reduced pressure. The precipitated solid was collected by filtration, washed with diethyl ether, and dried under reduced pressure to give the title compound (4.02 g) as a white powder.

$^1$H-NMR (DMSO-$d_6$) δ 1.82-1.96 (1H, m), 2.02-2.36 (3H, m), 3.99-4.09 (1H, m), 4.29 (2H, d, J=5.9 Hz), 7.18-7.38 (5H, m), 7.85 (1H, s), 8.50 (1H, t, J=5.9 Hz).

B) Production of 1-phenyl-N-[(2R)-pyrrolidin-2-ylmethyl]methanamine

To a suspension of lithium aluminum hydride (5.40 g) in tetrahydrofuran (150 mL) was added dropwise a suspension (350 mL) of N-benzyl-5-oxo-D-prolinamide (11.0 g) in tetrahydrofuran under ice-cooling, and the mixture was stirred with heating at 60° C. for 14 hr. The reaction mixture was cooled to 0° C., water (10.8 mL), 1M aqueous sodium hydroxide solution (5.4 mL) and water (5.4 mL) were added, and the resultant insoluble material was filtered off. The filtrate was concentrated under reduced pressure to give the title compound (8.95 g) as a pale-yellow oil. This compound was used for the next reaction without further purification.

$^1$H-NMR (DMSO-d$_6$) δ 1.18-1.33 (1H, m), 1.48-1.81 (3H, m), 2.09 (2H, m), 2.30-2.44 (2H, m), 2.63-2.80 (2H, m), 3.00-3.12 (1H, m), 3.68 (2H, s), 7.13-7.37 (5H, m).

C) Production of methyl(3S,8aR)-2-benzyloctahydropyrrolo[1,2-a]pyrazine-3-carboxylate To a suspension of 1-phenyl-N-[(2R)-pyrrolidin-2-ylmethyl]methanamine (13.6 g) in toluene (120 mL) were added triethylamine (22.9 mL) and methyl 2,3-dibromopropanoate (13.4 g) under ice-cooling, and the mixture was stirred with heating at 90° C. for 5 hr. The reaction mixture was allowed to cool to room temperature, and diluted with diethyl ether (200 mL) and brine (200 mL). The organic layer was dried over anhydrous magnesium sulfate, and the insoluble material was filtered off. The filtrate was concentrated under reduced pressure, and purified by silica gel column chromatography (ethyl acetate/hexane=10/80→50/50) to give the title compound (6.86 g) as a pale-yellow oil.

$^1$H-NMR (DMSO-d$_6$) δ 1.14-1.28 (1H, m), 1.53-1.77 (3H, m), 1.83-2.00 (2H, m), 2.31 (1H, dd, J=10.7, 3.9 Hz), 2.61-2.95 (3H, m), 3.29 (1H, dd, J=10.7, 2.0 Hz), 3.53 (1H, dd, J=3.7, 1.8 Hz), 3.62 (3H, s), 3.89 (2H, s), 7.17-7.37 (5H, m).

D) Production of 2-tert-butyl 3-methyl(3S,8aR)-hexahydropyrrolo[1,2-a]pyrazine-2,3(1H)-dicarboxylate To a solution of methyl(3S,8aR)-2-benzyloctahydropyrrolo[1,2-a]pyrazine-3-carboxylate (6.80 g) in 5-10% hydrogen chloride-methanol was added 10% palladium-carbon (680 mg, 50% wet), and the mixture was stirred at room temperature for 10 hr under a hydrogen atmosphere (1 atm). Insoluble material was filtered off through a celite pat, and the filtrate was concentrated to give a pale-yellow oil. The obtained methyl(3S,8aR)-octahydropyrrolo[1,2-a]pyrazine-3-carboxylate dihydrochloride was dissolved in saturated aqueous sodium hydrogen carbonate solution (25 mL) and tetrahydrofuran (50 mL), di-tert-butyl dicarbonate (5.68 g) was added, and the mixture was stirred at room temperature for 1 hr. The mixture was diluted with ethyl acetate (300 mL), and washed with water (100 mL) and brine (100 mL). The organic layer was dried over anhydrous magnesium sulfate and concentrated under reduced pressure. The residue was purified by silica gel column chromatography (ethyl acetate/hexane=10/90→20/80) to give the title compound (6.50 g) as a colorless oil.

$^1$H-NMR (CDCl$_3$) δ 1.18-1.39 (1H, m), 1.42-1.51 (9H, m), 1.61-1.94 (4H, m), 1.97-2.12 (1H, m), 1.99-2.11 (1H, m), 2.22-2.33 (1H, m), 2.69-2.91 (1H, m), 2.99-3.09 (1H, m), 3.48-3.58 (1H, m), 3.72-3.78 (2H, m), 3.93-4.13 (1H, m), 4.56-4.82 (1H, m).

E) Production of tert-butyl(8aR)-3-(6-bromo-4-oxo-3,4-dihydrothieno[3,2-d]pyrimidin-2-yl)hexahydropyrrolo[1,2-a]pyrazine-2 (1H)-carboxylate To a mixture of (8aR)-2-(tert-butoxycarbonyl)octahydropyrrolo[1,2-a]pyrazine-3-carboxylic acid (270 mg), triethylamine (0.18 mL) and tetrahydrofuran (10 mL) was added 2-methylpropyl chlorocarbonate (0.13 mL) with stirring at room temperature. After 2 hr, 3-amino-5-bromothiophene-2-carboxamide (221 mg) produced in Example 1, step D, was added and the mixture was stirred at 50° C. for 2 hr. The reaction mixture was poured into saturated aqueous sodium hydrogen carbonate, and extracted with ethyl acetate. The extract was dried over anhydrous magnesium sulfate. Insoluble material was removed by filtration, and the filtrate was concentrated under reduced pressure. The residue was dissolved in ethanol (10 mL), 2M aqueous sodium hydroxide solution (2 mL) was added, and the mixture was stirred at 80° C. for 2 hr. The reaction mixture was allowed to cool to room temperature, and poured into saturated aqueous sodium hydrogen carbonate. The mixture was extracted with ethyl acetate/tetrahydrofuran mixture, and the extract was dried over anhydrous magnesium sulfate. Insoluble material was removed by filtration, and the filtrate was concentrated under reduced pressure. The residue was purified by basic silica gel column chromatography (methanol/ethyl acetate) to give the title compound (65 mg) as a yellow solid.

MS(ESI+): [M+H]$^+$455.

MS(ESI+), found: 455.

F) Production of 6-(5-methyl-1H-pyrazol-4-yl)-2-[(8aR)-octahydropyrrolo[1,2-a]pyrazin-3-yl]thieno[3,2-d]pyrimidin-4 (3H)-one dihydrochloride In the same manner as in Example 11, step B, the title compound (36 mg) was obtained as a white solid from tert-butyl(8aR)-3-(6-bromo-4-oxo-3,4-dihydrothieno[3,2-d]pyrimidin-2-yl)hexahydropyrrolo[1,2-a]pyrazine-2 (1H)-carboxylate (65 mg) and tert-butyl 3-methyl-4-(4,4,5,5-tetramethyl-1,3,2-dioxaborolan-2-yl)-1H-pyrazole-1-carboxylate (88 mg) and cesium carbonate (279 mg) and 1,2-dimethoxyethane (10 mL) and water (1 mL) and [1,1'-bis(diphenylphosphino)ferrocene]palladium(II) dichloride-dichloromethane complex (1:1) (5 mg).

$^1$H-NMR (DMSO-d$_6$) δ 1.55-4.06 (14H, m), 4.57-4.85 (1H, m), 7.40 (1H, s), 8.11 (1H, s), 12.01 (1H, brs).

Example 100

Production of tert-butyl(2S)-2-[6-(5-methyl-1H-pyrazol-4-yl)-4-oxo-3,4-dihydrothieno[3,2-d]pyrimidin-2-yl]piperidine-1-carboxylate To a suspension of 6-(5-methyl-1H-pyrazol-4-yl)-2-[(2S)-piperidin-2-yl]thieno[3,2-d]pyrimidin-4 (3H)-one dihydrochloride (1.05 g) produced in Example 83, step C, in tetrahydrofuran (35 mL) were added triethylamine (1.87 mL) and di-tert-butyl dicarbonate (0.932 mL), and the mixture was stirred at 50° C. for 1.5 hr. To the mixture were added ethyl acetate (50 mL) and aqueous ammonium chloride solution (30 mL), and the separated aqueous layer was extracted with ethyl acetate (10 mL). The combined organic layers were washed with brine (10 mL) and dried over anhydrous sodium sulfate. Insoluble material was filtered off, and the filtrate was concentrated under reduced pressure. The residue was purified by silica gel column chromatography (ethyl acetate/hexane), and the object fraction was concentrated under reduced pressure to give the title compound (560 mg) as a colorless solid.

$^1$H-NMR (DMSO-d$_6$) δ 1.15-1.60 (12H, m), 1.60-1.89 (2H, m), 1.99-2.16 (1H, m), 2.37-2.48 (3H, m), 3.41-3.59

(1H, m), 3.80-3.91 (1H, m), 5.01 (1H, brs), 7.37 (1H, s), 7.84-8.37 (1H, m), 12.36 (1H, brs), 12.97 (1H, brs).

Example 101

Production of 2-[(2R)-azepan-2-yl]-6-(5-methyl-1H-pyrazol-4-yl)thieno[3,2-d]pyrimidin-4 (3H)-one A) Optical resolution of tert-butyl 2-(6-bromo-4-oxo-3,4-dihydrothieno[3,2-d]pyrimidin-2-yl) azepane-1-carboxylate tert-Butyl 2-(6-bromo-4-oxo-3,4-dihydrothieno[3,2-d]pyrimidin-2-yl)azepane-1-carboxylate (772 mg) produced in Example 79, step A, was fractionated by high performance liquid chromatography (column: CHIRALPAK AD (50 mm i.d.×500 mm L, manufactured by DAICEL CHEMICAL INDUSTRIES, LTD.), mobile phase: hexane/ethanol (500/500), flow rate: 60 mL/min, column temperature: 30° C.). tert-Butyl(2R)-2-(6-bromo-4-oxo-3,4-dihydrothieno[3,2-d]pyrimidin-2-yl)azepane-1-carboxylate (325 mg, >99.9% ee, retention time 11.2 min) and tert-butyl(2S)-2-(6-bromo-4-oxo-3,4-dihydrothieno[3,2-d]pyrimidin-2-yl)azepane-1-carboxylate (326 mg, >99.9% ee, retention time 13.7 min) were obtained under the above-mentioned high performance liquid chromatography conditions. The analysis was performed by high performance liquid chromatography (column: CHIRALPAK AD-H (4.6 mm i.d.×250 mm L, manufactured by DAICEL CHEMICAL INDUSTRIES, LTD.), mobile phase: hexane/ethanol (500/500), flow rate: 0.5 mL/min, column temperature: 30° C., detection 220 nm). The absolute steric configuration after optical resolution was determined by an X-ray crystal structural analysis of the fraction at retention time 13.7 min.

B) Production of 2-[(2R)-azepan-2-yl]-6-(5-methyl-1H-pyrazol-4-yl)thieno[3,2-d]pyrimidin-4 (3H)-one In the same manner as in Example 76, step B, the title compound (68.8 mg) was obtained as a colorless solid from tert-butyl(2R)-2-(6-bromo-4-oxo-3,4-dihydrothieno[3,2-d]pyrimidin-2-yl)azepane-1-carboxylate (325 mg) produced above, tert-butyl 3-methyl-4-(4,4,5,5-tetramethyl-1,3,2-dioxaborolan-2-yl)-1H-pyrazole-1-carboxylate (468 mg), cesium carbonate (495 mg), [1,1'-bis(diphenylphosphino)ferrocene]palladium(II) dichloride-dichloromethane complex (1:1) (31.0 mg), 1,2-dimethoxyethane (8 mL), water (0.8 mL), 4M hydrochloric acid/ethyl acetate solution (1 mL) and methanol (5 mL).
$^1$H-NMR (DMSO-$d_6$) δ 1.42-1.89 (7H, m), 2.07-2.21 (1H, m), 2.45 (3H, s), 2.74-2.96 (2H, m), 3.82 (1H, dd, J=9.5, 4.4 Hz), 7.34 (1H, s), 8.01 (1H, brs).

Example 102

Production of 2-[(2S)-azepan-2-yl]-6-(5-methyl-1H-pyrazol-4-yl)thieno[3,2-d]pyrimidin-4 (3H)-one In the same manner as in Example 76, step B, the title compound (92.7 mg) was obtained as a colorless solid from tert-butyl(2S)-2-(6-bromo-4-oxo-3,4-dihydrothieno[3,2-d]pyrimidin-2-yl)azepane-1-carboxylate (310 mg) produced in Example 101, step A, tert-butyl 3-methyl-4-(4,4,5,5-tetramethyl-1,3,2-dioxaborolan-2-yl)-1H-pyrazole-1-carboxylate (446 mg), cesium carbonate (472 mg), [1,1'-bis(diphenylphosphino)ferrocene]palladium(II) dichloride-dichloromethane complex (1:1) (29.6 mg), 1,2-dimethoxyethane (8 mL), water (0.8 mL), 4M hydrochloric acid/ethyl acetate solution (1 mL) and methanol (5 mL).
$^1$H-NMR (DMSO-$d_6$) δ 1.40-1.89 (7H, m), 2.05-2.21 (1H, m), 2.45 (3H, s), 2.74-2.97 (2H, m), 3.76-3.86 (1H, m), 7.34 (1H, s), 8.01 (1H, brs).

Example 103

Production of 6-(5-methyl-1H-pyrazol-4-yl)-2-[(2S)-2-methylpyrrolidin-2-yl]thieno[3,2-d]pyrimidin-4 (3H)-one dihydrochloride A) Production of tert-butyl(2S)-2-(6-bromo-4-oxo-3,4-dihydrothieno[3,2-d]pyrimidin-2-yl)-2-methylpyrrolidine-1-carboxylate In the same manner as in Example 82, step A, a crude product (244 mg) of the title compound was obtained as a pale-yellow solid from 1-(tert-butoxycarbonyl)-2-methyl-L-proline (1.2 g) and triethylamine (1.21 mL) and tetrahydrofuran (20 mL) and 2-methylpropyl chlorocarbonate (0.566 mL) and 3-amino-5-bromothiophene-2-carboxamide (964 mg) produced in Example 1, step D and 2M aqueous sodium hydroxide solution (10.9 mL) and ethanol (20 mL).
MS(ESI+): [M+H]$^+$414.
MS(ESI+), found: 414.
Optical purity (19.5 min, >99.9% ee): The analysis was performed by high performance liquid chromatography (column: CHIRALPAK AD (4.6 mm i.d.×250 mm L, manufactured by DAICEL CHEMICAL INDUSTRIES, LTD.), mobile phase: hexane/ethanol (900/100), flow rate: 1.0 mL/min, column temperature: 30° C., detection 220 nm).

B) Production of 6-(5-methyl-1H-pyrazol-4-yl)-2-[(2S)-2-methylpyrrolidin-2-yl]thieno[3,2-d]pyrimidin-4 (3H)-one dihydrochloride In the same manner as in Example 11, step B, the title compound (54 mg) was obtained as a white solid from tert-butyl(2S)-2-(6-bromo-4-oxo-3,4-dihydrothieno[3,2-d]pyrimidin-2-yl)-2-methylpyrrolidine-1-carboxylate (239 mg) and tert-butyl 3-methyl-4-(4,4,5,5-tetramethyl-1,3,2-dioxaborolan-2-yl)-1H-pyrazole-1-carboxylate (356 mg) and cesium carbonate (1.13 g) and 1,2-dimethoxyethane (6 mL) and water (1.5 mL) and [1,1'-bis(diphenylphosphino)ferrocene]palladium(II) dichloride-dichloromethane complex (1:1) (21 mg).
$^1$H-NMR (DMSO-$d_6$) δ 1.74 (3H, s), 1.83-2.40 (4H, m), 2.46 (3H, brs), 3.27-3.44 (2H, m), 7.37 (1H, s), 8.10 (1H, brs), 9.18 (1H, brs), 9.62 (1H, brs), 12.81 (1H, brs).

Example 104

Production of 2-(3-azabicyclo[3.1.0]hex-3-ylmethyl)-6-(5-methyl-1H-pyrazol-4-yl)thieno[3,2-d]pyrimidin-4 (3H)-one A) Production of 2-(3-azabicyclo[3.1.0]hex-3-ylmethyl)-6-bromothieno[3,2-d]pyrimidin-4 (3H)-one In the same manner as in Example 2, step B, the title compound (90 mg) was obtained as a pale-yellow solid from 6-bromo-2-(chloromethyl)thieno[3,2-d]pyrimidin-4 (3H)-one (180 mg) produced in Example 2, step A, 3-azabicyclo[3.1.0]hexane monohydrochloride (231 mg), potassium carbonate (445 mg), sodium iodide (9.7 mg) and N,N-dimethylformamide (3.0 mL).

$^1$H-NMR (DMSO-d$_6$) δ 0.24-0.38 (1H, m), 0.66-0.75 (1H, m), 1.31-1.41 (2H, m), 2.43-2.48 (2H, m), 2.90 (2H, d, J=8.5 Hz), 3.55 (2H, s), 7.60 (1H, s), 12.27 (1H, brs).

B) Production of 2-(3-azabicyclo[3.1.0]hex-3-ylmethyl)-6-(5-methyl-1H-pyrazol-4-yl)thieno[3,2-d]pyrimidin-4 (3H)-one In the same manner as in Example 2, step C, the title compound (16 mg) was obtained as brown crystals from 2-(3-azabicyclo[3.1.0]hex-3-ylmethyl)-6-bromothieno[3,2-d]pyrimidin-4 (3H)-one (90 mg) and tert-butyl 3-methyl-4-(4,4,5,5-tetramethyl-1,3,2-dioxaborolan-2-yl)-1H-pyrazole-1-carboxylate (170 mg), sodium carbonate (50 mg), 1,2-dimethoxyethane (2.0 mL) and water (1.0 mL) and [1,1'-bis(diphenylphosphino)ferrocene]palladium(II) dichloride-dichloromethane complex (1:1) (23 mg).

$^1$H-NMR (DMSO-d$_6$) δ 0.26-0.41 (1H, m), 0.65-0.78 (1H, m), 1.31-1.46 (2H, m), 2.38-2.49 (5H, m), 2.92 (2H, d, J=8.5 Hz), 3.56 (2H, s), 7.37 (1H, s), 7.80-8.42 (1H, m), 12.01 (1H, brs), 12.99 (1H, brs).

Example 105

Production of 2-{[(4-methoxybenzyl)(1-methylethyl)amino]methyl}-6-(5-methyl-1H-pyrazol-4-yl)thieno[3,2-d]pyrimidin-4 (3H)-one In the same manner as in Example 2, step B, 6-bromo-2-{[(4-methoxybenzyl)(1-methylethyl)amino]methyl}thieno[3,2-d]pyrimidin-4 (3H)-one (120 mg) was obtained as a yellow solid from 6-bromo-2-(chloromethyl)thieno[3,2-d]pyrimidin-4 (3H)-one (180 mg) produced in Example 2, step A, N-(4-methoxybenzyl)propan-2-amine monohydrochloride (416 mg), potassium carbonate (445 mg), sodium iodide (9.7 mg) and N,N-dimethylformamide (3.0 mL). In the same manner as in Example 2, step C, the title compound (86 mg) was obtained as a yellow solid from the obtained 6-bromo-2-{[(4-methoxybenzyl) (1-methylethyl)amino]methyl}thieno[3,2-d]pyrimidin-4 (3H)-one (120 mg) and tert-butyl 3-methyl-4-(4,4,5,5-tetramethyl-1,3,2-dioxaborolan-2-yl)-1H-pyrazole-1-carboxylate (175 mg), sodium carbonate (51 mg), 1,2-dimethoxyethane (3.0 mL) and water (1.5 mL) and [1,1'-bis(diphenylphosphino)ferrocene]palladium(II) dichloride-dichloromethane complex (1:1) (23 mg).

$^1$H-NMR (DMSO-d$_6$) δ 1.05 (6H, d, J=6.6 Hz), 2.44 (3H, brs), 2.91-3.03 (1H, m), 3.55-3.64 (4H, m), 3.66 (3H, s), 6.79 (2H, d, J=8.6 Hz), 7.27 (2H, d, J=8.6 Hz), 7.32 (1H, s), 7.73-8.42 (1H, m), 11.42 (1H, brs), 12.96 (1H, brs).

Example 106

Production of tert-butyl(3S)-3-[6-(5-methyl-1H-pyrazol-4-yl)-4-oxo-3,4-dihydrothieno[3,2-d]pyrimidin-2-yl]-2-azabicyclo[2.2.2]octane-2-carboxylate A) Production of tert-butyl(3S)-3-(6-bromo-4-oxo-3,4-dihydrothieno[3,2-d]pyrimidin-2-yl)-2-azabicyclo[2.2.2]octane-2-carboxylate To a solution of (3S)-2-(tert-butoxycarbonyl)-2-azabicyclo[2.2.2]octane-3-carboxylic acid (0.511 g) and triethylamine (0.348 mL) in tetrahydrofuran (5 mL) was added isobutyl chloroformate (0.26 mL) while stirring under ice-cooling. After stirring at room temperature for 30 min, a solution of 3-amino-5-bromothiophene-2-carboxamide (0.221 g) produced in Example 1, step D, in tetrahydrofuran (1 mL) was added. The reaction system was stirred with heating at 60° C. for 4 days. Water was poured into the reaction system, and the mixture was extracted with ethyl acetate, and dried over anhydrous sodium sulfate. Insoluble material was removed by filtration, and the filtrate was concentrated under reduced pressure. 2M Aqueous sodium hydroxide solution (3.0 mL) and 1,2-dimethoxyethane (6.0 mL) were added to the residue, and the mixture was stirred with heating in a microwave reactor at 150° C. for 1 hr. Insoluble material was removed by filtration, and the mixture was extracted with ethyl acetate, and dried over anhydrous sodium sulfate. Insoluble material was removed by filtration, and the filtrate was concentrated under reduced pressure. The residue was purified by basic silica gel column chromatography (ethyl acetate/hexane) to give the title compound (193 mg) as a colorless solid. The optical purity was 70% ee. The analysis was performed by high performance liquid chromatography (column: CHIRALPAK AD-H (4.6 mm i.d.×250 mm L, manufactured by DAICEL CHEMICAL INDUSTRIES, LTD.), mobile phase: hexane/ethanol (800/200), flow rate: 1.0 mL/min, column temperature: 30° C., detection 220 nm).

$^1$H-NMR (DMSO-d$_6$) δ 1.07-1.83 (16H, m), 2.03-2.23 (2H, m), 3.95-4.08 (1H, m), 4.51-4.56 (1H, m), 7.63 (1H, s), 12.50-12.77 (1H, m).

B) Production of tert-butyl(3S)-3-[6-(5-methyl-1H-pyrazol-4-yl)-4-oxo-3,4-dihydrothieno[3,2-d]pyrimidin-2-yl]-2-azabicyclo[2.2.2]octane-2-carboxylate tert-Butyl(3S)-3-(6-Bromo-4-oxo-3,4-dihydrothieno[3,2-d]pyrimidin-2-yl)-2-azabicyclo[2.2.2]octane-2-carboxylate (190 mg), tert-butyl 3-methyl-4-(4,4,5,5-tetramethyl-1,3,2-dioxaborolan-2-yl)-1H-pyrazole-1-carboxylate (266 mg), sodium carbonate (78 mg), 1,2-dimethoxyethane (3.0 mL) and water (1.5 mL) were placed in a flask, and the atmosphere in the flask was purged with argon. [1,1'-Bis(diphenylphosphino)ferrocene]palladium(II) dichloride-dichloromethane complex (1:1) (35 mg) was added, and the atmosphere in the flask was purged again with argon. The reaction system was stirred at 100° C. for 3 hr, and the mixture was extracted with ethyl acetate and dried over anhydrous sodium sulfate. Insoluble material was removed by filtration, and the extract was concentrated under reduced pressure. The residue was purified by silica gel column chromatography (ethyl acetate/hexane), and the obtained pale-yellow solid was crystallized from methanol/ethyl acetate to give the title compound (146 mg) as a pale-yellow solid.

$^1$H-NMR (DMSO-d$_6$) δ 1.08-1.85 (16H, m), 2.06-2.22 (2H, m), 2.39-2.48 (3H, m), 3.97-4.09 (1H, m), 4.52-4.56 (1H, m), 7.39 (0.4H, s), 7.42 (0.6H, s), 7.92 (0.6H, brs), 8.27 (0.4H, brs), 12.24-12.46 (1H, m), 12.96 (1H, brs).

Example 107

Production of 6-(5-methyl-1H-pyrazol-4-yl)-2-[(2S*,5R*)-5-phenylpiperidin-2-yl]thieno[3,2-d]pyrimidin-4 (3H)-one monohydrochloride In the same manner as in Example 86, step A, tert-butyl (2S*,5R*)-2-(6-bromo-4-oxo-3,4-dihydrothieno[3,2-d]pyrimidin-2-yl)-5-phenylpiperidine-1-carboxylate was obtained as a pale-yellow amorphous solid from 3-amino-5-bromothiophene-2-carboxamide (323 mg) produced in Example 1, step D, 1-(tert-butoxycarbonyl)-5-phenylpiperidine-2-carboxylic acid (511 mg, purchased from ChemImpex, diastereomer ratio unknown), 2-methylpropyl chlorocarbonate (0.418 mL), triethylamine (0.506 mL) and tetrahydrofuran (8 mL), 2M aqueous sodium hydroxide solution (2 mL) and ethanol (5 mL). In the same manner as in Example 76, step B, the title compound (119 mg) was obtained as a colorless solid from tert-butyl(2S*,5R*)-2-(6-bromo-4-oxo-3,4-dihydrothieno[3,2-d]pyrimidin-2-yl)-5-phenylpiperidine-1-carboxylate produced above, tert-butyl 3-methyl-4-(4,4,5,5-tetramethyl-1,3,2-dioxaborolan-2-yl)-1H-pyrazole-1-carboxylate (321 mg), cesium carbonate (339 mg), [1,1'-bis(diphenylphosphino)ferrocene]palladium(II) dichloride-dichloromethane complex (1:1) (21.2 mg), 1,2-dimethoxyethane (5 mL), water (0.5 mL), 4M hydrochloric acid/ethyl acetate solution (1 mL) and methanol (5 mL).

$^1$H-NMR (DMSO-d$_6$) δ 1.66-1.89 (2H, m), 2.15-2.32 (1H, m), 2.47 (3H, s), 2.99-3.13 (1H, m), 3.34-3.44 (2H, m), 3.85-4.01 (1H, m), 4.72 (1H, brs), 7.23-7.31 (3H, m), 7.31-7.40 (2H, m), 7.49 (1H, s), 8.11 (1H, brs), 9.29-9.43 (1H, m), 9.78-9.93 (1H, m), 12.67 (1H, brs).

Example 108

Production of 2-[(3S)-2-azabicyclo[2.2.2]oct-3-yl]-6-(5-methyl-1H-pyrazol-4-yl)thieno[3,2-d]pyrimidin-4 (3H)-one dihydrochloride To a solution of tert-butyl(3S)-3-[6-(5-methyl-1H-pyrazol-4-yl)-4-oxo-3,4-dihydrothieno[3,2-d]pyrimidin-2-yl]-2-azabicyclo[2.2.2]octane-2-carboxylate (143 mg) produced in Example 106, step B, in methanol (3.0 mL) was added 4M hydrochloric acid/ethyl acetate solution (1.0 mL) with stirring at room temperature. The reaction system was stirred with heating at 50° C. for 1 hr, and the precipitate was collected by filtration, and washed with ethyl acetate to give the title compound (128 mg) as a colorless solid.

$^1$H-NMR (DMSO-d$_6$) δ 1.31-2.16 (8H, m), 2.31-2.38 (1H, m), 2.47 (3H, s), 3.51-3.64 (1H, m), 4.39-4.58 (1H, m), 7.38 (1H, s), 8.12 (1H, s), 8.19-8.40 (1H, m), 10.08-10.32 (1H, m), 12.87 (1H, brs).

Example 109

Production of 6-(5-methyl-1H-pyrazol-4-yl)-2-[(2R)-2-methylpyrrolidin-2-yl]thieno[3,2-d]pyrimidin-4 (3H)-one dihydrochloride A) Production of tert-butyl 2-(6-bromo-4-oxo-3,4-dihydrothieno[3,2-d]pyrimidin-2-yl)-2-methylpyrrolidine-1-carboxylate In the same manner as in Example 82, step A, the title compound (199 mg) was obtained as a pale-brown oil from 1-(tert-butoxycarbonyl)-2-methyl-L-proline (1.5 g) and triethylamine (3.0 mL) and tetrahydrofuran (20 mL) and 2-methylpropyl chlorocarbonate (0.707 mL) and 3-amino-5-bromothiophene-2-carboxamide (1.21 g) produced in Example 1, step D and 2M aqueous sodium hydroxide solution (13.6 mL) and ethanol (20 mL).

MS(ESI+): [M+H]$^+$414.
MS(ESI+), found: 414.

B) Optical resolution of tert-butyl 2-(6-bromo-4-oxo-3,4-dihydrothieno[3,2-d]pyrimidin-2-yl)-2-methylpyrrolidine-1-carboxylate tert-Butyl 2-(6-bromo-4-oxo-3,4-dihydrothieno[3,2-d]pyrimidin-2-yl)-2-methylpyrrolidine-1-carboxylate (180 mg) was fractionated by high performance liquid chromatography (column: CHIRALPAK AD (50 mm i.d.×500 mm L, manufactured by DAICEL CHEMICAL INDUSTRIES, LTD.), mobile phase: hexane/ethanol (900/100), flow rate: 80 mL/min, column temperature: 30° C.). Under the above-mentioned high performance liquid chromatography conditions, the fraction solution containing an optically active form having a shorter retention time was concentrated to give tert-butyl (2R)-2-(6-bromo-4-oxo-3,4-dihydrothieno[3,2-d]pyrimidin-2-yl)-2-methylpyrrolidine-1-carboxylate (88 mg, 9.25 min, >99.9% ee). In addition, the fraction solution containing an optically active form having a longer retention time was concentrated to give tert-butyl(2S)-2-(6-bromo-4-oxo-3,4-dihydrothieno[3,2-d]pyrimidin-2-yl)-2-methylpyrrolidine-1-carboxylate (85 mg, 19.3 min, >99.9% ee). The analysis was performed by high performance liquid chromatography (column: CHIRALPAK AD (4.6 mm i.d.×250 mm L, manufactured by DAICEL CHEMICAL INDUSTRIES, LTD.), mobile phase: hexane/ethanol (900/100), flow rate: 1.0 mL/min, column temperature: 30° C., detection 220 nm). The absolute configuration was determined by comparison to tert-butyl(2S)-2-(6-bromo-4-oxo-3,4-dihydrothieno[3,2-d]pyrimidin-2-yl)-2-methylpyrrolidine-1-carboxylate produced in Example 103, step A.

C) Production of 6-(5-methyl-1H-pyrazol-4-yl)-2-[(2R)-2-methylpyrrolidin-2-yl]thieno[3,2-d]pyrimidin-4 (3H)-one dihydrochloride In the same manner as in Example 11, step B, the title compound (56 mg) was obtained as a white solid from tert-butyl(2R)-2-(6-bromo-4-oxo-3,4-dihydrothieno[3,2-d]pyrimidin-2-yl)-2-methylpyrrolidine-1-carboxylate (88 mg) and tert-butyl 3-methyl-4-(4,4,5,5-tetramethyl-1,3,2-dioxaborolan-2-yl)-1H-pyrazole-1-carboxylate (131 mg) and cesium carbonate (415 mg) and 1,2-dimethoxyethane (2 mL) and water (0.5 mL) and [1,1'-bis(diphenylphosphino)ferrocene] palladium(II) dichloride-dichloromethane complex (1:1) (7.8 mg).

$^1$H-NMR (DMSO-d$_6$) δ 1.75 (3H, s), 1.81-2.40 (4H, m), 2.46 (3H, s), 3.30-3.43 (2H, m), 7.37 (1H, s), 8.10 (1H, brs), 9.23 (1H, brs), 9.77 (1H, brs), 12.81 (1H, brs).

Example 110

Production of 2-[(1S*,2S*,5R*)-3-azabicyclo[3.1.0]hex-2-yl]-6-(5-methyl-1H-pyrazol-4-yl)thieno[3,2-d]pyrimidin-4 (3H)-one dihydrochloride A) Production of tert-butyl(1S*,2S*,5R*)-2-[(5-bromo-2-carbamoylthiophen-3-yl)carbamoyl]-3-azabicyclo[3.1.0]hexane-3-carboxylate In the same manner as in Example 78, step A, the title compound (400 mg) was obtained as a pale-yellow amorphous solid from 3-amino-5-bromothiophene-2-carboxamide (338 mg) produced in Example 1, step D, (1S*,2S*,5R*)-3-(tert-butoxycarbonyl)-3-azabicyclo[3.1.0]hexane-2-carboxylic acid (695 mg), 2-methylpropyl chlorocarbonate (0.398 mL), triethylamine (0.424 mL) and tetrahydrofuran (5 mL). $^1$H-NMR (DMSO-d$_6$) δ 0.46-0.60 (1H, m), 0.60-0.72 (1H, m), 1.11-1.48 (9H, m), 1.63-1.73 (1H, m), 1.86-1.97 (1H, m), 3.40-3.47 (1H, m), 3.48-3.57 (1H, m), 4.27 (1H, d, J=4.9 Hz), 7.69 (2H, brs), 8.05 (1H, s), 11.51 (1H, brs).

B) Production of 2-[(1S*,2S*,5R*)-3-azabicyclo[3.1.0]hex-2-yl]-6-(5-methyl-1H-pyrazol-4-yl)thieno[3,2-d]pyrimidin-4 (3H)-one dihydrochloride To a solution of tert-butyl(1S*,2S*,5R*)-2-[(5-bromo-2-carbamoylthiophen-3-yl)carbamoyl]-3-azabicyclo[3.1.0]

hexane-3-carboxylate (400 mg) produced above in ethanol (4 mL) was added 2M aqueous sodium hydroxide solution (4.62 mL), and the mixture was stirred at 70° C. for 54 hr. The reaction mixture was neutralized with 6M hydrochloric acid (1.5 mL) under ice-cooling, and ethyl acetate (30 mL) was added. The separated organic layer was washed with brine (5 mL), and dried over anhydrous sodium sulfate. Insoluble material was filtered off, and the filtrate was concentrated under reduced pressure to give tert-butyl(1S,2S,5R)-2-(6-bromo-4-oxo-3,4-dihydrothieno[3,2-d]pyrimidin-2-yl)-3-azabicyclo[3.1.0]hexane-3-carboxylate as a pale-yellow solid. In the same manner as in Example 83, step C, the title compound (130 mg) was obtained as a colorless solid from tert-butyl(1S*,2S*,5R*)-2-(6-bromo-4-oxo-3,4-dihydrothieno[3,2-d]pyrimidin-2-yl)-3-azabicyclo[3.1.0]hexane-3-carboxylate produced above, tert-butyl 3-methyl-4-(4,4,5,5-tetramethyl-1,3,2-dioxaborolan-2-yl)-1H-pyrazole-1-carboxylate (572 mg), cesium carbonate (605 mg), [1,1'-bis(diphenylphosphino)ferrocene]palladium(II) dichloride-dichloromethane complex (1:1) (38.0 mg), 1,2-dimethoxyethane (7 mL), water (0.7 mL), 4M hydrochloric acid/ethyl acetate solution (1 mL) and methanol (4 mL).

$^1$H-NMR (DMSO-d$_6$) δ 0.56-0.73 (2H, m), 1.82-1.93 (1H, m), 2.25-2.36 (1H, m), 2.46 (3H, s), 3.38-3.54 (2H, m), 4.91 (1H, brs), 7.33 (1H, s), 8.11 (1H, s), 8.73 (1H, brs), 10.50 (1H, brs), 13.06 (1H, brs).

Example 111

Production of 6-(5-methyl-1H-pyrazol-4-yl)-2-[(4R)-1,3-thiazolidin-4-yl]thieno[3,2-d]pyrimidin-4 (3H)-one A) Production of tert-butyl(4R)-4-(6-bromo-4-oxo-3,4-dihydrothieno[3,2-d]pyrimidin-2-yl)-1,3-thiazolidine-3-carboxylate In the same manner as in Example 71, step A, the title compound (774 mg) was obtained as a pale-brown solid from 3-amino-5-bromothiophene-2-carboxamide (500 mg) produced in Example 1, step D, (4R)-3-(tert-butoxycarbonyl)-1,3-thiazolidine-4-carboxylic acid (1.16 g), 2-methylpropyl chlorocarbonate (0.647 mL), triethylamine (0.694 mL) and tetrahydrofuran (10 mL), 2M aqueous sodium hydroxide solution (5.65 mL) and ethanol (10 mL).

$^1$H-NMR (DMSO-d$_6$) δ 1.17 (9H, brs, major), 1.41 (9H, brs, minor), 3.18 (1H, brs), 3.51 (1H, brs), 4.60 (2H, q, J=8.7 Hz), 4.90 (1H, brs, major), 5.05 (1H, brs, minor), 7.61 (1H, brs), 12.77 (1H, brs).
* Observed as a 3:2 mixture of rotamers.

B) 6-(5-methyl-1H-pyrazol-4-yl)-2-[(4R)-1,3-thiazolidin-4-yl]thieno[3,2-d]pyrimidin-4 (3H)-one In the same manner as in Example 76, step B, the title compound (94 mg) was obtained as a colorless solid from tert-butyl(4R)-4-(6-bromo-4-oxo-3,4-dihydrothieno[3,2-d]pyrimidin-2-yl)-1,3-thiazolidine-3-carboxylate (250 mg) produced above, tert-butyl 3-methyl-4-(4,4,5,5-tetramethyl-1,3,2-dioxaborolan-2-yl)-1H-pyrazole-1-carboxylate (369 mg), cesium carbonate (389 mg), [1,1'-bis(diphenylphosphino)ferrocene]palladium(II) dichloride-dichloromethane complex (1:1) (24.4 mg), 1,2-dimethoxyethane (5 mL), water (0.5 mL), 4M hydrochloric acid/ethyl acetate solution (1 mL) and methanol (3 mL).

$^1$H-NMR (DMSO-d$_6$) δ 2.47 (3H, brs), 3.03 (1H, dd, J=10.0, 7.0 Hz), 3.21 (1H, dd, J=10.0, 6.6 Hz), 3.58 (1H, brs), 4.11 (1H, d, J=8.7 Hz), 4.19-4.33 (2H, m), 7.37 (1H, s), 7.90 (1H, brs, major), 8.26 (1H, brs, minor), 12.28 (1H, brs), 13.01 (1H, brs).
* Observed as a 3:2 mixture of tautomers.

Example 112

Production of 2-[(1S,2R,5R)-3-azabicyclo[3.1.0]hex-2-yl]-6-(5-methyl-1H-pyrazol-4-yl)thieno[3,2-d]pyrimidin-4 (3H)-one dihydrochloride A) Production of tert-butyl(1R*,2S*,5S*)-2-[6-(5-methyl-1H-pyrazol-4-yl)-4-oxo-3,4-dihydrothieno[3,2-d]pyrimidin-2-yl]-3-azabicyclo[3.1.0]hexane-3-carboxylate In the same manner as in Example 83, step C, tert-butyl (1R*,2S*,5S*)-2-{6-[1-(tert-butoxycarbonyl)-3-methyl-1H-pyrazol-4-yl]-4-oxo-3,4-dihydrothieno[3,2-d]pyrimidin-2-yl}-3-azabicyclo[3.1.0]hexane-3-carboxylate was obtained as a pale-yellow amorphous solid from tert-butyl(1R*,2S*,5S*)-2-(6-bromo-4-oxo-3,4-dihydrothieno[3,2-d]pyrimidin-2-yl)-3-azabicyclo[3.1.0]hexane-3-carboxylate (293 mg) produced in Example 87, step A, tert-butyl 3-methyl-4-(4,4,5,5-tetramethyl-1,3,2-dioxaborolan-2-yl)-1H-pyrazole-1-carboxylate (437 mg), cesium carbonate (463 mg), [1,1'-bis(diphenylphosphino)ferrocene]palladium(II) dichloride-dichloromethane complex (1:1) (29.0 mg), 1,2-dimethoxyethane (7 mL) and water (0.7 mL). To a solution of tert-butyl(1R*,2S*,5S*)-2-{6-[1-(tert-butoxycarbonyl)-3-methyl-1H-pyrazol-4-yl]-4-oxo-3,4-dihydrothieno[3,2-d]pyrimidin-2-yl}-3-azabicyclo[3.1.0]hexane-3-carboxylate produced above in tetrahydrofuran (5 mL) was added 2M aqueous sodium hydroxide solution (1 mL), and the mixture was stirred at 60° C. for 2 hr. Ethyl acetate (20 mL) and 1M hydrochloric acid (2 mL) were added to the reaction mixture, and the separated organic layer was washed with brine (5 mL), and dried over anhydrous sodium sulfate. Insoluble material was filtered off, and the filtrate was concentrated under reduced pressure to give the title compound (156 mg) as a colorless solid.

$^1$H-NMR (DMSO-d$_6$) δ 0.50-0.63 (1H, m), 0.79-0.96 (1H, m), 1.07 (9H, s, major), 1.36 (9H, s, minor), 1.63-1.76 (1H, m), 1.89-2.02 (1H, m), 2.45 (3H, s), 3.47-3.63 (2H, m), 4.77 (1H, d, J=5.1 Hz), 7.38 (1H, brs, minor), 7.42 (1H, s, major), 7.77-8.43 (1H, m), 12.36 (1H, brs), 12.96 (1H, brs).
* Observed as a 5:2 mixture of rotamers.

B) Optical resolution of tert-butyl(1R*,2S*,5S*)-2-[6-(5-methyl-1H-pyrazol-4-yl)-4-oxo-3,4-dihydrothieno[3,2-d]pyrimidin-2-yl]-3-azabicyclo[3.1.0]hexane-3-carboxylate tert-Butyl(1R*,2S*,5S*)-2-[6-(5-methyl-1H-pyrazol-4-yl)-4-oxo-3,4-dihydrothieno[3,2-d]pyrimidin-2-yl]-3-azabicyclo[3.1.0]hexane-3-carboxylate (205 mg) was fractionated by high performance liquid chromatography (column: CHIRALPAK AD (50 mm i.d.×500 mm L, manufactured by DAICEL CHEMICAL INDUSTRIES, LTD.), mobile phase: hexane/ethanol (900/100), flow rate: 80 mL/min, column temperature: 30° C.). tert-Butyl(1S,2R,5R)-2-[6-(5-methyl-1H-pyrazol-4-yl)-4-oxo-3,4-dihydrothieno[3,2-d]pyrimidin-2-yl]-3-azabicyclo[3.1.0]hexane-3-carboxylate (80 mg, >99.9% ee, retention time 20.2 min) and tert-butyl(1R,2S,5S)-2-[6-(5-methyl-1H-pyrazol-4-yl)-4-oxo-3,4-dihydrothieno[3,2-d]pyrimidin-2-yl]-3-azabicyclo[3.1.0]hexane-3-carboxylate (77 mg, 99.8% ee, retention time 30.2 min)

were obtained under the above-mentioned high performance liquid chromatography conditions. The analysis was performed by high performance liquid chromatography (column: CHIRALPAK AD-3 (4.6 mm i.d.×250 mm L, manufactured by DAICEL CHEMICAL INDUSTRIES, LTD.), mobile phase: hexane/ethanol (850/150), flow rate: 1 mL/min, column temperature: 30° C., detection 220 nm). The absolute steric configuration after optical resolution was determined by an X-ray crystallography of the fraction at retention time 20.2 min.

C) Production of 2-[(1S,2R,5R)-3-azabicyclo[3.1.0] hex-2-yl]-6-(5-methyl-1H-pyrazol-4-yl)thieno[3,2-d] pyrimidin-4 (3H)-one dihydrochloride To a solution of tert-butyl(1S,2R,5R)-2-[6-(5-methyl-1H-pyrazol-4-yl)-4-oxo-3,4-dihydrothieno[3,2-d]pyrimidin-2-yl]-3-azabicyclo[3.1.0]hexane-3-carboxylate (75.0 mg) produced above in methanol (5 mL) was added 4M hydrochloric acid/ethyl acetate solution (1 mL), and the mixture was stirred at 50° C. for 2 hr. Ethyl acetate (4 mL) was added, and the precipitated solid was collected by filtration to give the title compound (53.9 mg) as a colorless solid.

$^1$H-NMR (DMSO-$d_6$) δ 0.55-0.74 (2H, m), 1.82-1.94 (1H, m), 2.25-2.36 (1H, m), 2.46 (3H, s), 3.37-3.56 (2H, m), 4.91 (1H, brs), 7.33 (1H, s), 8.10 (1H, s), 8.73 (1H, brs), 10.43 (1H, brs), 13.04 (1H, brs).

Example 113

Production of 2-[(1R,2S,5S)-3-azabicyclo[3.1.0]hex-2-yl]-6-(5-methyl-1H-pyrazol-4-yl)thieno[3,2-d] pyrimidin-4 (3H)-one dihydrochloride In the same manner as in Example 110, step C, the title compound (56.9 mg) was obtained as a colorless solid from tert-butyl(1R,2S,5S)-2-[6-(5-methyl-1H-pyrazol-4-yl)-4-oxo-3,4-dihydrothieno[3,2-d]pyrimidin-2-yl]-3-azabicyclo[3.1.0]hexane-3-carboxylate (75.0 mg) produced in Example 112, step B, 4M hydrochloric acid/ethyl acetate solution (1 mL) and methanol (5 mL).

$^1$H-NMR (DMSO-$d_6$) δ 0.57-0.73 (2H, m), 1.82-1.93 (1H, m), 2.25-2.36 (1H, m), 2.46 (3H, s), 3.36-3.56 (2H, m), 4.91 (1H, brs), 7.32 (1H, s), 8.10 (1H, s), 8.73 (1H, brs), 10.40 (1H, brs), 13.04 (1H, brs).

Example 114

Production of 2-[(2,5-dimethylpyrrolidin-1-yl)methyl]-6-(5-methyl-1H-pyrazol-4-yl)thieno[3,2-d] pyrimidin-4 (3H)-one In the same manner as in Example 2, step B and step C, the title compound (45 mg) was obtained as a pale-yellow solid from 6-bromo-2-(chloromethyl)thieno[3,2-d]pyrimidin-4 (3H)-one (180 mg) produced in Example 2, step A, 2,5-dimethylpyrrolidine (0.170 mL) and potassium carbonate (178 mg) and sodium iodide (9.7 mg) and N,N-dimethylformamide (3.0 mL) and tert-butyl 3-methyl-4-(4,4,5,5-tetramethyl-1,3,2-dioxaborolan-2-yl)-1H-pyrazole-1-carboxylate (252 mg) and sodium carbonate (130 mg) and 1,2-dimethoxyethane (3.0 mL) and water (1.5 mL) and [1,1'-bis(diphenylphosphino)ferrocene]palladium(II) dichloride-dichloromethane complex (1:1) (33 mg).

$^1$H-NMR (DMSO-$d_6$) δ 0.96-1.06 (6H, m), 1.28-1.43 (2H, m), 1.75-1.91 (2H, m), 2.45 (3H, s), 2.72-2.85 (2H, m), 3.67 (2H, s), 7.37 (1H, s), 7.84-8.19 (1H, m), 11.48-12.21 (1H, m), 12.58-13.18 (1H, m).

Example 115

Production of 6-(5-methyl-1H-pyrazol-4-yl)-2-(1,2,3,4-tetrahydroisoquinolin-3-yl)thieno[3,2-d]pyrimidin-4 (3H)-one dihydrochloride A) Production of tert-butyl 3-(6-bromo-4-oxo-3,4-dihydrothieno[3,2-d]pyrimidin-2-yl)-3,4-dihydroisoquinoline-2 (1H)-carboxylate In the same manner as in Example 71, step A, the title compound (182 mg) was obtained as a colorless solid from 3-amino-5-bromothiophene-2-carboxamide (265 mg) produced in Example 1, step D, (3S)-2-(tert-butoxycarbonyl)-1,2,3,4-tetrahydroisoquinoline-3-carboxylic acid (699 mg), 2-methylpropyl chlorocarbonate (0.327 mL), triethylamine (0.416 mL) and tetrahydrofuran (5 mL), 2M aqueous sodium hydroxide solution (3.00 mL) and ethanol (5 mL).

$^1$H-NMR (DMSO-$d_6$) δ 1.07-1.53 (9H, m), 2.97-3.28 (2H, m), 4.43-5.18 (3H, m), 7.06-7.32 (4H, m), 7.43-7.66 (1H, m), 12.77 (1H, brs).

B) Production of 6-(5-methyl-1H-pyrazol-4-yl)-2-(1,2,3,4-tetrahydroisoquinolin-3-yl)thieno[3,2-d]pyrimidin-4 (3H)-one dihydrochloride In the same manner as in Example 83, step C, the title compound (65 mg) was obtained as a colorless solid from tert-butyl 3-(6-bromo-4-oxo-3,4-dihydrothieno[3,2-d]pyrimidin-2-yl)-3,4-dihydroisoquinoline-2 (1H)-carboxylate (150 mg) produced above, tert-butyl 3-methyl-4-(4,4,5,5-tetramethyl-1,3,2-dioxaborolan-2-yl)-1H-pyrazole-1-carboxylate (200 mg), cesium carbonate (211 mg), [1,1'-bis(diphenylphosphino)ferrocene]palladium(II) dichloride-dichloromethane complex (1:1)(13.3 mg), 1,2-dimethoxyethane (5 mL), water (0.5 mL), 4M hydrochloric acid/ethyl acetate solution (1 mL) and methanol (4 mL).

$^1$H-NMR (DMSO-$d_6$) δ 2.48 (3H, s), 3.20 (1H, dd, J=16.8, 11.9 Hz), 3.48-3.62 (1H, m), 4.35-4.52 (2H, m), 4.62-4.78 (1H, m), 5.95-7.55 (7H, m), 8.14 (1H, s), 9.92-10.17 (1H, m), 10.40 (1H, brs), 13.02 (1H, brs).

Example 116

Production of 2-(7-azabicyclo[2.2.1]hept-1-yl)-6-(5-methyl-1H-pyrazol-4-yl)thieno[3,2-d]pyrimidin-4 (3H)-one monohydrochloride A) Production of methyl 2-[(phenylcarbonyl)amino]prop-2-enoate To dichloromethane (400 mL) were added methyl serinate hydrochloride (45.0 g) and triethylamine (132 mL), and benzoyl chloride (77.0 mL) was added dropwise. After stirring at room temperature overnight, the reaction system was washed twice with saturated aqueous sodium hydrogen carbonate, and dried over anhydrous sodium sulfate. Insoluble material was removed by filtration, and the filtrate was concentrated under reduced pressure. The residue was dissolved in dichloromethane (300 mL), and 2,3,4,6,7,8,9,10-octahydroprimido [1,2-a]azepine(52.0 g) was added. The mixture was stirred at room temperature for 4 hr, and the reaction system was washed twice with water and saturated aqueous sodium hydrogen carbonate, and dried over anhydrous sodium sulfate. Insoluble material was removed by filtration, and the filtrate was concentrated under reduced pressure to give a crude product (67.0 g) of the title compound as a brown oil.
$^1$H-NMR (CDCl$_3$) δ 3.88 (3H, s), 5.99 (1H, s), 6.79 (1H, s), 7.45-7.56 (3H, m), 7.83 (2H, d, J=7.2 Hz), 8.53 (1H, s).

B) Production of methyl 4-oxo-1-[(phenylcarbonyl)amino]cyclohexanecarboxylate

To a solution of the crude product (67.0 g) of methyl 2-[(phenylcarbonyl)amino]prop-2-enoate produced above in dichloromethane (300 mL) was added zinc iodide (104 g). To the mixture was added trimethyl[(1-methylideneprop-2-en-1-yl)oxy]silane (173 mL), and the mixture was heated under reflux for 24 hr. The reaction system was allowed to cool to room temperature, washed with water, and dried over anhydrous sodium sulfate. Insoluble material was removed by filtration. To the filtrate were added a mixture (1:4, 40 mL) of 1M hydrochloric acid and tetrahydrofuran, and the mixture was stirred at room temperature for 5 hr. The reaction mixture was washed with brine, dried over anhydrous sodium sulfate, and concentrated under reduced pressure. The residue was purified by silica gel column chromatography (ethyl acetate/petroleum ether) to give the title compound (56.0 g).
$^1$H-NMR (CDCl$_3$) δ 2.49-2.57 (8H, m), 3.79 (3H, s), 6.43 (1H, s), 7.44-7.48 (2H, m), 7.53-7.57 (1H, m), 7.78-7.80 (2H, m).

C) Production of N-(3-oxo-2-oxabicyclo[2.2.2]oct-4-yl)benzamide

A solution of methyl 4-oxo-1-[(phenylcarbonyl)amino]cyclohexanecarboxylate (56.0 g) produced above in tetrahydrofuran (300 mL) was cooled to −78° C., 1M lithium tri(sec-butyl)borohydride/tetrahydrofuran solution was added dropwise, and the mixture was stirred at the same temperature for 15 hr and allowed to warm to room temperature overnight. The reaction was quenched with an aqueous ammonium chloride solution, and tetrahydrofuran was mostly evaporated under reduced pressure. An organic product was extracted from the residue with ethyl acetate, and the extract was washed with brine, dried over anhydrous sodium sulfate, and concentrated under reduced pressure. The residue was purified by silica gel column chromatography (ethyl acetate/petroleum ether) to give the title compound (26.0 g).
$^1$H-NMR (CDCl$_3$) δ 1.72-1.81 (2H, m), 1.93-2.00 (2H, m), 2.14-2.20 (2H, m), 3.25-3.33 (2H, m), 4.80 (1H, t, J=4.0 Hz), 7.43-7.54 (4H, m), 7.80-7.82 (2H, m).

D) Production of methyl trans-4-hydroxy-1-[(phenylcarbonyl)amino]cyclohexanecarboxylate To a solution of N-(3-oxo-2-oxabicyclo[2.2.2]oct-4-yl)benzamide (26.0 g) produced above in methanol (200 mL) was added 4-methylbenzenesulfonic acid (1.90 g), and the mixture was heated under reflux overnight. The reaction mixture was concentrated to give the title compound (27.0 g). The obtained compound was used for the next reaction without further purification.
$^1$H-NMR (CDCl$_3$) δ 1.73-1.85 (4H, m), 1.94-2.00 (2H, m), 2.39-2.47 (2H, m), 3.76 (3H, s), 3.98 (1H, d, J=2.8 Hz), 6.30 (1H, s), 7.42-7.54 (4H, m), 7.72-7.80 (2H, m).

E) Production of methyl 7-(phenylcarbonyl)-7-azabicyclo[2.2.1]heptane-1-carboxylate To a solution of methyl trans-4-hydroxy-1-[(phenylcarbonyl)amino]cyclohexanecarboxylate (27.0 g) produced above in dichloromethane (200 mL) was added N-ethyl-N-(1-methylethyl)propan-2-amine (33.8 mL). Methanesulfonyl chloride (15.2 mL) was added dropwise, and the mixture was stirred at room temperature overnight. The reaction system was successively washed with saturated aqueous sodium hydrogen carbonate and brine, dried over anhydrous sodium sulfate, and concentrated under reduced pressure. The residue was dissolved in tetrahydrofuran (300 mL), and cooled to −78° C. 1M Potassium 2-methylpropan-2-olate/tetrahydrofuran solution (150 mL) was added dropwise, and the mixture was stirred at the same temperature for 1 hr, and the reaction system was allowed to warm to room temperature. After stirring overnight, the mixture was acidified with 1M hydrochloric acid, and the organic product was extracted with ethyl acetate. The extract was washed with brine, dried over anhydrous sodium sulfate, and concentrated under reduced pressure. The residue was purified by silica gel column chromatography (ethyl acetate/petroleum ether) to give the title compound (4.0 g) as a white solid.
$^1$H-NMR (CDCl$_3$) δ 1.53-1.62 (2H, m), 1.78-1.85 (2H, m), 1.89-1.96 (2H, m), 2.32-2.39 (2H, m), 3.81 (3H, s), 4.27 (1H, t, J=4.8 Hz), 7.38-7.50 (3H, m), 7.02-7.23 (2H, m).

F) Production of 7-[(benzyloxy)carbonyl]-7-azabicyclo[2.2.1]heptane-1-carboxylic acid A mixture of methyl 7-(phenylcarbonyl)-7-azabicyclo[2.2.1]heptane-1-carboxylate (8.0 g) produced above and concentrated hydrochloric acid (100 mL) was heated under reflux for 24 hr, and concentrated under reduced pressure. To the residue was added water (50 mL), and the mixture was washed twice with ethyl acetate. To the obtained aqueous layer was basified with sodium carbonate, a solution of sodium carbonate (9.80 g) and benzylchlorocarbonate (5.40 mL) in 1,4-dioxane (30 mL), and the mixture was stirred at room temperature overnight. The reaction mixture was washed twice with ethyl acetate, and the aqueous layer was adjusted to pH3 with 2M hydrochloric acid. The organic product was extracted 3 times with ethyl acetate (150 mL), and the combined organic layers were washed with brine, dried over anhydrous sodium sulfate, and concentrated under reduced pressure to give the title compound (2.45 g) as a yellow solid.
$^1$H-NMR (CDCl$_3$) δ 1.49-1.56 (2H, m), 1.85-1.95 (4H, m), 2.16-2.20 (2H, m), 4.47 (1H, t, J=4.4 Hz), 5.14 (2H, s), 7.32-7.37 (5H, m).

G) Production of benzyl 1-(chlorocarbonyl)-7-azabicyclo[2.2.1]heptane-7-carboxylate To a mixture of 7-[(benzyloxy)carbonyl]-7-azabicyclo[2.2.1]heptane-1-carboxylic acid (550 mg) produced above, N,N-dimethylformamide (0.02 mL) and tetrahydrofuran (10 mL) was added dropwise ethanedioyl dichloride (0.80 mL) at room temperature. The mixture was stirred at room temperature for 30 min, and the reaction system was concentrated under reduced pressure. To the residue was added a small amount of tetrahydrofuran, and the mixture was concentrated again under reduced pressure to give a crude product (2.0 mmol) of the title compound. The obtained crude product of the title compound was used for the next reaction without further purification.

H) Production of benzyl 1-(6-bromo-4-oxo-3,4-dihydrothieno[3,2-d]pyrimidin-2-yl)-7-azabicyclo[2.2.1]heptane-7-carboxylate To a mixture of 3-amino-5-bromothiophene-2-carboxamide (221 mg) produced in Example 1, step D, the crude product (2.0 mmol) of benzyl 1-(chlorocarbonyl)-7-azabicyclo [2.2.1]heptane-7-carboxylate produced above and tetrahydrofuran (10 mL) was added N-ethyl-N-(1-methylethyl)propan-2-amine (0.70 mL) at room temperature. After stirring for 1 hr, the reaction system was poured into saturated aqueous sodium hydrogen carbonate, and the mixture was extracted with ethyl acetate. The extract was dried over anhydrous magnesium sulfate, and concentrated under reduced pressure. To the residue were added ethanol (10 mL) and 2M sodium hydroxide (2.5 mL), and the mixture was stirred at 100° C. overnight. The reaction system was cooled to room temperature, poured into saturated aqueous sodium hydrogen carbonate, and the mixture was extracted with ethyl acetate. The extract was dried over anhydrous magnesium sulfate, and concentrated under reduced pressure. The residue was purified by basic silica gel column chromatography (ethyl acetate/hexane and methanol/ethyl acetate) to give the title compound (313 mg) as a white solid.

$^1$H-NMR (DMSO-$d_6$) δ 1.50-1.64 (2H, m), 1.78-1.93 (4H, m), 2.16-2.29 (2H, m), 4.37-4.42 (1H, m), 4.90 (2H, s), 7.06-7.27 (5H, m), 7.57 (1H, s), 12.52 (1H, s).

I) Production of 2-(7-azabicyclo[2.2.1]hept-1-yl)-6-(5-methyl-1H-pyrazol-4-yl)thieno[3,2-d]pyrimidin-4 (3H)-one monohydrochloride Benzyl 1-(6-bromo-4-oxo-3,4-dihydrothieno[3,2-d]pyrimidin-2-yl)-7-azabicyclo[2.2.1]heptane-7-carboxylate (313 mg) produced above, tert-butyl 3-methyl-4-(4,4,5,5-tetramethyl-1,3,2-dioxaborolan-2-yl)-1H-pyrazole-1-carboxylate (419 mg), cesium carbonate (1.33 g), 1,2-dimethoxyethane (8 mL) and water (2.0 mL) were placed in a flask, and the atmosphere in the flask was purged with argon. [1,1'-Bis (diphenylphosphino)ferrocene]palladium(II) dichloride-dichloromethane complex (1:1) (25 mg) was added, the atmosphere in the flask was purged again with argon, and the mixture was stirred at 100° C. for 1 hr. The reaction mixture was poured into saturated aqueous sodium hydrogen carbonate, and the mixture was extracted with 3:1 ethyl acetate/tetrahydrofuran mixture. The obtained organic layer was dried over anhydrous magnesium sulfate. Insoluble material was filtered off, and the filtrate was concentrated under reduced pressure. The residue was purified by silica gel column chromatography (ethyl acetate/hexane), and the object fraction was concentrated under reduced pressure to give benzyl 1-{6-[1-(tert-butoxycarbonyl)-3-methyl-1H-pyrazol-4-yl]-4-oxo-3,4-dihydrothieno[3,2-d]pyrimidin-2-yl}-7-azabicyclo[2.2.1]heptane-7-carboxylate (240 mg). The benzyl 1-{6-[1-(tert-butoxycarbonyl)-3-methyl-1H-pyrazol-4-yl]-4-oxo-3,4-dihydrothieno[3,2-d]pyrimidin-2-yl}-7-azabicyclo[2.2.1]heptane-7-carboxylate (240 mg) produced above was dissolved in methanol (10 mL), 10% palladium-carbon (100 mg, 50% wet) was added, and the mixture was stirred at room temperature under a hydrogen atmosphere (1 atm) for 2 hr. The reaction system was filtered through a celite pat, and formic acid was passed through the celite pat until the compound was sufficiently eluted. The filtrate was concentrated under reduced pressure, to the residue was added saturated aqueous sodium hydrogen carbonate, and the mixture was extracted with 3:1 ethyl acetate/tetrahydrofuran mixture. The organic layer was dried over anhydrous magnesium sulfate. Insoluble material was filtered off, and the filtrate was concentrated under reduced pressure. To the residue was added 10% hydrochloric acid/methanol solution (5.0 mL), and the mixture was stirred at 50° C. for 1 hr. The mixture was concentrated under reduced pressure, to the residue was added heated 20:1 ethanol/water (15 mL), and the insoluble material was filtered off. The filtrate was left standing at room temperature for 1 hr, and the precipitate was collected by filtration to give the title compound (103 mg) as a white solid.

$^1$H-NMR (DMSO-$d_6$) δ 1.79-2.14 (6H, m), 2.37-2.47 (5H, m), 4.16-4.25 (1H, m), 7.38 (1H, s), 7.91-8.40 (1H, m), 9.71 (2H, brs), 12.66-13.15 (2H, m).
MS(ESI+): [M+H]$^+$328.
MS(ESI+), found: 328.

Example 117

Production of 6-(5-methyl-1H-pyrazol-4-yl)-2-[(2S, 4S)-4-phenylpyrrolidin-2-yl]thieno[3,2-d]pyrimidin-4 (3H)-one dihydrochloride A) Production of tert-butyl(2S,4S)-2-(6-bromo-4-oxo-3,4-dihydrothieno[3,2-d]pyrimidin-2-yl)-4-phenylpyrrolidine-1-carboxylate In the same manner as in Example 71, step A, the title compound (515 mg) was obtained as a white solid from 3-amino-5-bromothiophene-2-carboxamide (361 mg) produced in Example 1, step D, (4S)-1-(tert-butoxycarbonyl)-4-phenyl-L-proline (500 mg) and 2-methylpropyl chlorocarbonate (0.225 mL) and triethylamine (0.239 mL) and tetrahydrofuran (10 mL) and ethanol (5 mL) and 2M aqueous sodium hydroxide solution (3.27 mL).

$^1$H-NMR (DMSO-$d_6$) δ 1.15 (5.5H, s), 1.39 (3.5H, s), 2.22-2.48 (2H, m), 3.33-3.39 (1H, m), 3.54-3.74 (1H, m), 3.89-4.08 (1H, m), 4.71-4.87 (1H, m), 7.18-7.38 (5H, m), 7.56-7.65 (1H, m), 12.72 (1H, brs).

B) Production of tert-butyl(2S,4S)-2-[6-(5-methyl-1H-pyrazol-4-yl)-4-oxo-3,4-dihydrothieno[3,2-d] pyrimidin-2-yl]-4-phenylpyrrolidine-1-carboxylate In the same manner as in Example 2, step C, the title compound (231 mg) was obtained as a pale-yellow solid from tert-butyl(2S,4S)-2-(6-bromo-4-oxo-3,4-dihydrothieno[3,2-c]pyrimidin-2-yl)-4-phenylpyrrolidine-1-carboxylate (250 mg) and tert-butyl 3-methyl-4-(4,4,5,5-tetramethyl-1,3,2-dioxaborolan-2-yl)-1H-pyrazole-1-carboxylate (323 mg), sodium carbonate (167 mg), 1,2-dimethoxyethane (3.0 mL) and water (1.5 mL) and [1,1'-bis(diphenylphosphino)ferrocene]palladium(II) dichloride-dichloromethane complex (1:1)(43 mg).

$^1$H-NMR (DMSO-$d_6$) δ 1.17 (6H, s), 1.40 (3H, s), 2.21-2.48 (5H, m), 3.33-3.41 (1H, m), 3.62-3.79 (1H, m), 3.93-4.06 (1H, m), 4.76-4.91 (1H, m), 7.18-7.38 (5H, m), 7.43-7.53 (1H, m), 7.79-8.45 (1H, m), 12.32-12.59 (1H, m), 12.84-13.09 (1H, m).

C) Production of 6-(5-methyl-1H-pyrazol-4-yl)-2-[(2S,4S)-4-phenylpyrrolidin-2-yl]thieno[3,2-d]pyrimidin-4 (3H)-one dihydrochloride In the same manner as in Example 108, the title compound (186 mg) was obtained as a pale-yellow solid from tert-butyl (2S,4S)-2-[6-(5-methyl-1H-pyrazol-4-yl)-4-oxo-3,4-dihydrothieno[3,2-d]pyrimidin-2-yl]-4-phenylpyrrolidine-1-carboxylate (230 mg) and methanol (3.0 mL), 4M hydrochloric acid/ethyl acetate solution (1.0 mL).

$^1$H-NMR (DMSO-$d_6$) δ 2.42-2.57 (4H, m), 2.58-2.70 (1H, m), 3.26-3.44 (1H, m), 3.55-3.71 (1H, m), 3.83-3.97 (1H, m), 4.93-5.05 (1H, m), 7.24-7.45 (6H, m), 8.11 (1H, s), 9.21 (1H, brs), 10.59 (1H, brs), 12.66-13.09 (1H, m).

Example 118

Production of 2-(6,6-dimethylmorpholin-3-yl)-6-(5-methyl-1H-pyrazol-4-yl)thieno[3,2-d]pyrimidin-4 (3H)-one dihydrochloride

A) Production of tert-butyl 5-(6-bromo-4-oxo-3,4-dihydrothieno[3,2-d]pyrimidin-2-yl)-2,2-dimethyl-morpholine-4-carboxylate To a solution of 4-(tert-butoxycarbonyl)-6,6-dimethylmorpholine-3-carboxylic acid (1.00 g) and triethylamine (1.08 mL) in tetrahydrofuran (20 mL) was added, while stirring under ice-cooling, 2-methylpropyl chlorocarbonate (0.50 mL). After stirring at room temperature for 30 min, a solution of 3-amino-5-bromothiophene-2-carboxamide (568 mg) produced in Example 1, step D, in tetrahydrofuran (3 mL) was added. The reaction system was stirred with heating at 60° C. for 3 hr. Water was poured into the reaction system, and the mixture was extracted with ethyl acetate, washed with brine, and dried over anhydrous magnesium sulfate. Insoluble material was removed by filtration, and the filtrate was concentrated under reduced pressure. To the residue were added 2M aqueous sodium hydroxide solution (7.7 mL) and ethanol (20 mL), and the mixture was stirred with heating at 80° C. for 5 hr. Brine was poured into the reaction system, the mixture was extracted with 3:1 ethyl acetate/tetrahydrofuran mixture, and the extract was washed with brine, and dried over anhydrous magnesium sulfate. Insoluble material was removed by filtration, and the filtrate was concentrated under reduced pressure. The residue was purified by basic silica gel column chromatography (methanol/ethyl acetate) to give the title compound (630 mg) as a white solid.

$^1$H-NMR (DMSO-d$_6$) δ 1.05-1.50 (15H, m), 3.30-3.59 (2H, m), 3.86-4.03 (2H, m), 4.68-4.87 (1H, m), 7.61 (1H, brs), 12.72 (1H, brs).

B) Production of 2-(6,6-dimethylmorpholin-3-yl)-6-(5-methyl-1H-pyrazol-4-yl)thieno[3,2-d]pyrimidin-4 (3H)-one dihydrochloride In the same manner as in Example 83, step C, the title compound (75 mg) was obtained as a white solid from tert-butyl 5-(6-bromo-4-oxo-3,4-dihydrothieno[3,2-d]pyrimidin-2-yl)-2,2-dimethylmorpholine-4-carboxylate (111 mg) produced above, tert-butyl 3-methyl-4-(4,4,5,5-tetramethyl-1,3,2-dioxaborolan-2-yl)-1H-pyrazole-1-carboxylate (154 mg), cesium carbonate (489 mg), [1,1'-bis(diphenylphosphino)ferrocene]palladium(II) dichloride-dichloromethane complex (1:1)(9.1 mg), 1,2-dimethoxyethane (3 mL), water (0.75 mL), 10% hydrochloric acid/methanol solution (2 mL) and methanol (2 mL).

$^1$H-NMR (DMSO-d$_6$) δ 1.28 (3H, s), 1.34 (3H, s), 2.46 (3H, s), 2.96-3.08 (1H, m), 3.25-3.36 (1H, m), 3.87 (1H, dd, J=12.8, 9.4 Hz), 4.12-4.24 (1H, m), 4.32-4.44 (1H, m), 7.38 (1H, s), 8.11 (1H, s), 9.42 (1H, brs), 10.43 (1H, brs), 12.88 (1H, brs).

Example 119

Production of 2-[(1S,3S,5S)-2-azabicyclo[3.1.0]hex-3-yl]-6-(5-methyl-1H-pyrazol-4-yl)thieno[3,2-d]pyrimidin-4 (3H)-one dihydrochloride

A) Production of tert-butyl(1S,3S,5S)-3-(6-bromo-4-oxo-3,4-dihydrothieno[3,2-d]pyrimidin-2-yl)-2-azabicyclo[3.1.0]hexane-2-carboxylate In the same manner as in Example 71, step A, the title compound (215 mg) was obtained as a colorless solid from 3-amino-5-bromothiophene-2-carboxamide (255 mg) produced in Example 1, step D, (1S,3S,5S)-2-(tert-butoxycarbonyl)-2-azabicyclo[3.1.0]hexane-3-carboxylic acid (550 mg), 2-methylpropyl chlorocarbonate (0.315 mL), triethylamine (0.399 mL) and tetrahydrofuran (5 mL), 2M aqueous sodium hydroxide solution (2.88 mL) and ethanol (5 mL).

$^1$H-NMR (DMSO-d$_6$) δ 0.64-0.92 (2H, m), 1.06-1.43 (9H, m), 1.49-1.63 (1H, m), 1.92-2.04 (1H, m), 2.55-2.77 (1H, m), 3.37-3.52 (1H, m), 4.88-5.08 (1H, m), 7.54-7.67 (1H, m), 12.63 (1H, brs).

B) Production of 2-[(1S,3S,5S)-2-azabicyclo[3.1.0]hex-3-yl]-6-(5-methyl-1H-pyrazol-4-yl)thieno[3,2-d]pyrimidin-4 (3H)-one dihydrochloride In the same manner as in Example 83, step C, the title compound (56 mg) was obtained as a colorless solid from tert-butyl(1S,3S,5S)-3-(6-bromo-4-oxo-3,4-dihydrothieno[3,2-d]pyrimidin-2-yl)-2-azabicyclo[3.1.0]hexane-2-carboxylate (200 mg) produced above, tert-butyl 3-methyl-4-(4,4,5,5-tetramethyl-1,3,2-dioxaborolan-2-yl)-1H-pyrazole-1-carboxylate (149 mg), cesium carbonate (316 mg), [1,1'-bis(diphenylphosphino)ferrocene]palladium(II) dichloride-dichloromethane complex (1:1)(20.0 mg), 1,2-dimethoxyethane (5 mL), water (0.5 mL), 4M hydrochloric acid/ethyl acetate solution (1 mL) and methanol (5 mL).

$^1$H-NMR (DMSO-d$_6$) δ 0.83-1.13 (2H, m), 1.77-1.90 (1H, m), 2.34 (1H, dd, J=13.6, 3.8 Hz), 2.47 (3H, s), 2.61-2.76 (1H, m), 3.35-3.44 (1H, m), 4.97-5.16 (1H, m), 7.30-7.46 (1H, m), 8.11 (1H, s), 9.22 (1H, brs), 10.64-11.11 (1H, m), 12.86 (1H, brs).

Example 120

Production of 6-(5-methyl-1H-pyrazol-4-yl)-2-[(2S,4R)-4-phenylpyrrolidin-2-yl]thieno[3,2-d]pyrimidin-4 (3H)-one dihydrochloride

A) Production of tert-butyl(2S,4R)-2-(6-bromo-4-oxo-3,4-dihydrothieno[3,2-d]pyrimidin-2-yl)-4-phenylpyrrolidine-1-carboxylate In the same manner as in Example 71, step A, the title compound (314 mg) was obtained as a white solid from 3-amino-5-bromothiophene-2-carboxamide (361 mg) produced in Example 1, step D and (4R)-1-(tert-butoxycarbonyl)-4-phenyl-L-proline (500 mg) and 2-methylpropyl chlorocarbonate (0.225 mL) and triethylamine (0.239 mL) and tetrahydrofuran (10 mL) and ethanol (5 mL) and 2M aqueous sodium hydroxide solution (3.27 mL).

$^1$H-NMR (DMSO-d$_6$) δ 1.15 (6H, s), 1.37 (3H, s), 2.01-2.21 (1H, m), 2.58-2.71 (1H, m), 3.41-3.61 (2H, m), 3.85-3.98 (1H, m), 4.64-4.75 (1H, m), 7.19-7.40 (5H, m), 7.60-7.67 (1H, m), 12.81 (1H, brs).

B) Production of tert-butyl(2S,4R)-2-[6-(5-methyl-1H-pyrazol-4-yl)-4-oxo-3,4-dihydrothieno[3,2-d]pyrimidin-2-yl]-4-phenylpyrrolidine-1-carboxylate In the same manner as in Example 2, step C, the title compound (218 mg) was obtained as a pale-yellow solid from tert-butyl(2S,4R)-2-(6-bromo-4-oxo-3,4-dihydrothieno[3,2-d]pyrimidin-2-yl)-4-phenylpyrrolidine-1-carboxylate (250 mg) and tert-butyl 3-methyl-4-(4,4,5,5-tetramethyl-1,3,2-dioxaborolan-2-yl)-1H-pyrazole-1-carboxylate (323 mg), sodium carbonate (167 mg), 1,2-dimethoxyethane (3.0 mL)

and water (1.5 mL) and [1,1'-bis(diphenylphosphino)ferrocene]palladium(II) dichloride-dichloromethane complex (1:1)(43 mg).

$^1$H-NMR (DMSO-d$_6$) δ 1.12 (6H, s), 1.38 (3H, s), 2.06-2.23 (1H, m), 2.38-2.48 (3H, m), 2.60-2.77 (1H, m), 3.42-3.62 (2H, m), 3.87-3.98 (1H, m), 4.64-4.79 (1H, m), 7.18-7.47 (6H, m), 7.79-8.33 (1H, m), 12.40-12.65 (1H, m), 12.83-13.09 (1H, m).

C) Production of 6-(5-methyl-1H-pyrazol-4-yl)-2-[(2S,4R)-4-phenylpyrrolidin-2-yl]thieno[3,2-d]pyrimidin-4 (3H)-one dihydrochloride In the same manner as in Example 108, the title compound (172 mg) was obtained as a pale-yellow solid from tert-butyl (2S,4R)-2-[6-(5-methyl-1H-pyrazol-4-yl)-4-oxo-3,4-dihydrothieno[3,2-d]pyrimidin-2-yl]-4-phenylpyrrolidine-1-carboxylate (210 mg) and methanol (3.0 mL), and 4M hydrochloric acid/ethyl acetate solution (1.0 mL).

$^1$H-NMR (DMSO-d$_6$) δ 2.16-2.30 (1H, m), 2.47 (3H, s), 2.89-3.04 (1H, m), 3.28-3.45 (1H, m), 3.59-3.86 (2H, m), 4.78-4.93 (1H, m), 7.24-7.44 (6H, m), 8.11 (1H, s), 9.36 (1H, brs), 10.48 (1H, brs), 12.90 (1H, brs).

Example 121

Production of 2-[amino(cyclohexyl)methyl]-6-(5-methyl-1H-pyrazol-4-yl)thieno[3,2-d]pyrimidin-4 (3H)-one dihydrochloride

A) Production of tert-butyl [(6-bromo-4-oxo-3,4-dihydrothieno[3,2-d]pyrimidin-2-yl)(cyclohexyl)methyl]carbamate In the same manner as in Example 71, step A, the title compound (620 mg) was obtained as a colorless solid from 3-amino-5-bromothiophene-2-carboxamide (265 mg) produced in Example 1, step D, (2S)-[(tert-butoxycarbonyl)amino](cyclohexyl)ethanoic acid (648 mg), 2-methylpropyl chlorocarbonate (0.327 mL), triethylamine (0.416 mL) and tetrahydrofuran (5 mL), 2M aqueous sodium hydroxide solution (3.00 mL) and ethanol (5 mL).

$^1$H-NMR (DMSO-d$_6$) δ 0.73-1.88 (21H, m), 3.71-4.34 (1H, m), 6.80-7.16 (1H, m), 12.49 (1H, brs).

B) Production of 2-[amino(cyclohexyl)methyl]-6-(5-methyl-1H-pyrazol-4-yl)thieno[3,2-d]pyrimidin-4 (3H)-one dihydrochloride In the same manner as in Example 83, step C, the title compound (125 mg) was obtained as a colorless solid from tert-butyl [(6-bromo-4-oxo-3,4-dihydrothieno[3,2-d]pyrimidin-2-yl)(cyclohexyl)methyl]carbamate (499 mg) produced above, tert-butyl 3-methyl-4-(4,4,5,5-tetramethyl-1,3,2-dioxaborolan-2-yl)-1H-pyrazole-1-carboxylate (697 mg), cesium carbonate (737 mg), [1,1'-bis(diphenylphosphino)ferrocene]palladium(II) dichloride-dichloromethane complex (1:1)(46.5 mg), 1,2-dimethoxyethane (5 mL), water (0.5 mL), 4M hydrochloric acid/ethyl acetate solution (1 mL) and methanol (4 mL).

$^1$H-NMR (DMSO-d$_6$) δ 0.91-2.03 (11H, m), 2.47 (3H, s), 3.98-4.18 (1H, m), 5.99 (2H, brs), 7.31-7.39 (1H, m), 8.11 (1H, s), 8.71 (3H, s), 12.80 (1H, brs).

Example 122

Production of 6-(5-methyl-1H-pyrazol-4-yl)-2-(1,2,3,4-tetrahydroquinolin-2-yl)thieno[3,2-d]pyrimidin-4 (3H)-one dihydrochloride

A) Production of tert-butyl 2-(6-bromo-4-oxo-3,4-dihydrothieno[3,2-d]pyrimidin-2-yl)-3,4-dihydroquinoline-1 (2H)-carboxylate In the same manner as in Example 71, step A, the title compound (245 mg) was obtained as a colorless solid from 3-amino-5-bromothiophene-2-carboxamide (265 mg) produced in Example 1, step D, (2S)-1-(tert-butoxycarbonyl)-1,2,3,4-tetrahydroquinoline-2-carboxylic acid (699 mg), 2-methylpropyl chlorocarbonate (0.327 mL), triethylamine (0.416 mL) and tetrahydrofuran (5 mL), 2M aqueous sodium hydroxide solution (3.00 mL) and ethanol (5 mL).

$^1$H-NMR (DMSO-d$_6$) δ 1.22-1.33 (9H, m), 1.73-1.90 (1H, m), 2.24-2.40 (1H, m), 2.55-2.77 (2H, m), 5.10 (1H, t, J=7.3 Hz), 6.92-7.03 (1H, m), 7.08-7.24 (2H, m), 7.56 (1H, s), 7.79 (1H, d, J=8.1 Hz), 12.85 (1H, brs).

B) Production of 6-(5-methyl-1H-pyrazol-4-yl)-2-(1,2,3,4-tetrahydroquinolin-2-yl)thieno[3,2-d]pyrimidin-4 (3H)-one dihydrochloride In the same manner as in Example 83, step C, the title compound (86 mg) was obtained as a colorless solid from tert-butyl 2-(6-bromo-4-oxo-3,4-dihydrothieno[3,2-d]pyrimidin-2-yl)-3,4-dihydroquinoline-1(2H)-carboxylate (200 mg) produced above, tert-butyl 3-methyl-4-(4,4,5,5-tetramethyl-1,3,2-dioxaborolan-2-yl)-1H-pyrazole-1-carboxylate (267 mg), cesium carbonate (282 mg), [1,1'-bis(diphenylphosphino)ferrocene]palladium(II) dichloride-dichloromethane complex (1:1)(17.8 mg), 1,2-dimethoxyethane (5 mL), water (0.5 mL), 4M hydrochloric acid/ethyl acetate solution (1 mL) and methanol (4 mL).

$^1$H-NMR (DMSO-d$_6$) δ 2.09-2.24 (2H, m), 2.46 (3H, s), 2.63-2.86 (2H, m), 4.54 (1H, t, J=5.8 Hz), 6.48-7.83 (10H, m), 8.09 (1H, s).

Example 123

Production of 6-(5-methyl-1H-pyrazol-4-yl)-2-[(3aS,6aS)-octahydrocyclopenta[b]pyrrol-2-yl]thieno[3,2-d]pyrimidin-4 (3H)-one

A) Production of 1-(1-benzyl-3-methyl-1H-pyrazol-4-yl)ethanone

A mixture of pentane-2,4-dione (10.01 g) and 1,1-dimethoxy-N,N-dimethylmethanamine (12.51 g) was stirred at 80° C. for 1 hr. Tetrahydrofuran (20 mL) was added to the reaction mixture, hydrazine hydrate (7.51 g) was added by small portions under ice-cooling, and the mixture was stirred at room temperature for 30 min. The reaction mixture was allowed to warm to room temperature, ethyl acetate (100 mL) and water (100 mL) were added, and the separated aqueous layer was extracted with ethyl acetate (50 mL×2). The combined organic layers were washed with brine (20 mL) and dried over anhydrous magnesium sulfate. Insoluble material was removed by filtration, and the filtrate was concentrated under reduced pressure to give 1-(5-methyl-1H-pyrazol-4-yl) ethanone (12.40 g) as a colorless oil. This was dissolved in N,N-dimethylformamide (10 mL), bromomethylbenzene (18.80 g) and potassium carbonate (15.20 g) were added and the mixture was stirred at 60° C. for 18 hr. The reaction mixture was allowed to warm to room temperature, ethyl acetate (100 mL) and water (100 mL) were added, and the separated aqueous layer was extracted with ethyl acetate (50 mL×2). The combined organic layers were washed with brine (20 mL) and dried over anhydrous magnesium sulfate. Insoluble material was removed by filtration, and the filtrate was concentrated under reduced pressure. The residue was purified by silica gel column chromatography (ethyl acetate/hexane) to give the title compound (9.80 g) as a pale-yellow solid.

$^1$H-NMR (DMSO-$d_6$) δ 2.36 (3H, s), 2.49 (3H, s), 5.24 (2H, s), 7.04-7.44 (5H, m), 7.73 (1H, s).

B) Production of (2Z)-3-(1-benzyl-3-methyl-1H-pyrazol-4-yl)-3-chloroprop-2-enenitrile To N,N-dimethylformamide (13.4 g) was added phosphorus oxychloride (28.1 g) by small portions under ice-cooling, and the mixture was stirred at room temperature for 15 min. Thereto was added 1-(1-benzyl-3-methyl-1H-pyrazol-4-yl) ethanone (9.80 g) produced above by small portions under ice-cooling, and the reaction mixture was stirred at 50° C. for 30 min. Thereto was added hydroxylamine hydrochloride in a powder (25.4 g) at 50° C. by small portions, and the reaction mixture was stirred at 50° C. for 30 min. Ice water (200 mL) was added to the reaction mixture, and the mixture was neutralized with 1M aqueous sodium hydroxide solution, and extracted with ethyl acetate (100 mL×2). The combined organic layers were washed with brine (20 mL) and dried over anhydrous magnesium sulfate. Insoluble material was removed by filtration, the filtrate was concentrated under reduced pressure, and the residue was purified by silica gel column chromatography (ethyl acetate/hexane) and crystallized from diethyl ether to give the title compound (5.73 g) as a pale-yellow powder.

$^1$H-NMR (DMSO-$d_6$) δ 2.39 (3H, s), 5.22 (2H, s), 5.65 (1H, s), 7.02-7.48 (5H, m), 7.64 (1H, s).

C) Production of methyl 3-amino-5-(1-benzyl-3-methyl-1H-pyrazol-4-yl)thiophene-2-carboxylate A mixture of (2Z)-3-(1-benzyl-3-methyl-1H-pyrazol-4-yl)-3-chloroprop-2-enenitrile (5.73 g) produced above, methylsulfanyl acetate (2.95 g), sodium hydride (0.80 g) and N,N-dimethylformamide (10 mL) was stirred at 60° C. for 2 hr. Ethyl acetate (20 mL) and water (10 mL) were added to the reaction mixture, and the separated aqueous layer was extracted with ethyl acetate (10 mL×2). The combined organic layers were washed with brine (20 mL) and dried over anhydrous magnesium sulfate. Insoluble material was removed by filtration, the filtrate was concentrated under reduced pressure, and the residue was purified by silica gel column chromatography (ethyl acetate/hexane) to give the title compound (6.55 g) as a colorless solid.

$^1$H-NMR (DMSO-$d_6$) δ 2.33 (3H, s), 3.65 (3H, s), 5.23 (2H, s), 7.04-7.44 (6H, m), 7.49 (1H, s).

D) Production of 2-benzyl 1-tert-butyl(2S,3aS,6aS)-hexahydrocyclopenta[b]pyrrole-1,2(2H)-dicarboxylate A mixture of benzyl(2S,3aS,6aS)-octahydrocyclopenta[b] pyrrole-2-carboxylate hydrochloride (1.00 g), di-tert-butyl dicarbonate (1.16 g), triethylamine (0.72 g) and tetrahydrofuran (10 mL) was stirred at room temperature for 18 hr. Ethyl acetate (20 mL) and water (20 mL) were added to the reaction mixture, and the separated aqueous layer was extracted with ethyl acetate (10 mL×2). The combined organic layers were washed with brine (20 mL) and dried over anhydrous magnesium sulfate. Insoluble material was removed by filtration, the filtrate was concentrated under reduced pressure, and the residue was purified by silica gel column chromatography (ethyl acetate/hexane) to give the title compound (1.23 g) as a colorless oil.

$^1$H-NMR (DMSO-$d_6$) δ 1.20-1.57 (11H, m), 1.57-2.05 (5H, m), 2.30-2.50 (1H, m), 2.58-2.73 (1H, m), 4.08-4.53 (2H, m), 5.00-5.30 (2H, m), 7.25-7.45 (5H, m).

E) Production of (2S,3aS,6aS)-1-(tert-butoxycarbonyl)octahydrocyclopenta[b]pyrrole-2-carboxylic acid A mixture of 2-benzyl 1-tert-butyl(2S,3aS,6aS)-hexahydrocyclopenta[b]pyrrole-1,2(2H)-dicarboxylate (1.23 g) produced above, 20% palladium hydroxide-carbon (200 mg) and methanol (5 mL) was stirred under a hydrogen atmosphere at room temperature for 1 hr. Insoluble material was removed by filtration, the filtrate was concentrated under reduced pressure, to the residue were added ethyl acetate (50 mL) and water (50 mL), and the separated aqueous layer was extracted with ethyl acetate (10 mL×2). The combined organic layers were washed with brine (50 mL) and dried over anhydrous magnesium sulfate. Insoluble material was removed by filtration, and the filtrate was concentrated under reduced pressure to give the title compound (0.91 g) as a colorless solid.

$^1$H-NMR (DMSO-$d_6$) δ 1.40-1.65 (13H, m), 1.65-2.00 (3H, m), 2.15-2.25 (1H, m), 2.35-2.45 (1H, m), 2.60-2.75 (1H, m), 4.12-4.23 (1H, m), 4.37-4.48 (1H, m).

F) Production of tert-butyl(3aS,6aS)-2-{[5-(1-benzyl-3-methyl-1H-pyrazol-4-yl)-2-(methoxycarbonyl) thiophen-3-yl]carbamoyl}hexahydrocyclopenta[b] pyrrole-1(2H)-carboxylate A mixture of (2S,3aS,6aS)-1-(tert-butoxycarbonyl)octahydrocyclopenta[b]pyrrole-2-carboxylic acid (766 mg) produced above, 2-methylpropyl chlorocarbonate (410 mg), triethylamine (304 mg) and tetrahydrofuran (10 mL) was stirred for 1 hr under ice-cooling, to the obtained reaction mixture was added methyl 3-amino-5-(1-benzyl-3-methyl-1H-pyrazol-4-yl)thiophene-2-carboxylate (327 mg) produced in Example 123, step C, under ice-cooling, and the mixture was stirred at 60° C. for 18 hr. Ethyl acetate (20 mL) and water (20 mL) were added to the reaction mixture, and the separated aqueous layer was extracted with ethyl acetate (10 mL×2). The combined organic layers were washed with brine (20 mL) and dried over anhydrous magnesium sulfate. Insoluble material was removed by filtration, the filtrate was concentrated under reduced pressure, and the residue was purified by basic silica gel column chromatography (ethyl acetate/hexane) to give the title compound (340 mg) as a pale-yellow oil.

$^1$H-NMR (DMSO-$d_6$) δ 1.20-1.65 (12H, m), 1.65-1.85 (2H, m), 1.90-2.20 (4H, m), 2.48 (3H, s), 2.60-3.80 (1H, m), 3.85 (3H, s), 4.20-4.35 (1H, m), 5.24 (2H, s), 7.10-7.40 (6H, m), 7.60 (1H, s), 8.10 (1H, s).

G) Production of tert-butyl(3aS,6aS)-2-[6-(1-benzyl-3-methyl-1H-pyrazol-4-yl)-4-oxo-3,4-dihydrothieno [3,2-d]pyrimidin-2-yl]hexahydrocyclopenta[b]pyrrole-1(2H)-carboxylate A mixture of tert-butyl(3aS,6aS)-2-{[5-(1-benzyl-3-methyl-1H-pyrazol-4-yl)-2-(methoxycarbonyl)thiophen-3-yl]

carbamoyl}hexahydrocyclopenta[b]pyrrole-1(2H)-carboxylate (340 mg) produced above, 2M aqueous sodium hydroxide solution (2 mL) and methanol (10 mL) was stirred at 60° C. for 1 hr. The reaction mixture was neutralized with 2M hydrochloric acid (2 mL) under ice-cooling, ethyl acetate (20 mL) and water (20 mL) were added, and the separated aqueous layer was extracted with ethyl acetate (10 mL×2). The combined organic layers were washed with brine (20 mL) and dried over anhydrous magnesium sulfate. Insoluble material was removed by filtration, and the filtrate was concentrated under reduced pressure. The residue was dissolved in N,N-dimethylformamide (2 mL), 1-ethyl-3-(3-dimethylaminopropyl)carbodiimide hydrochloride (1.15 g), 1-hydroxybenzotriazole (810 mg), ammonium chloride (1.28 g) and triethylamine (0.705 mL) were added, and the mixture was stirred at 80° C. for 18 hr. Ethyl acetate (20 mL) and water (20 mL) were added to the reaction mixture, and the separated aqueous layer was extracted with ethyl acetate (10 mL×2). The combined organic layers were washed with brine (20 mL) and dried over anhydrous magnesium sulfate. Insoluble material was removed by filtration, and the filtrate was concentrated under reduced pressure. The residue was dissolved in methanol (10 mL), 2M aqueous sodium hydroxide solution (1 mL) was added, and the mixture was stirred at 60° C. for 1 hr. The reaction mixture was neutralized with 1M hydrochloric acid under ice-cooling, ethyl acetate (20 mL) and water (20 mL) were added, and the separated aqueous layer was extracted with ethyl acetate (10 mL×2). The combined organic layers were washed with brine (20 mL) and dried over anhydrous magnesium sulfate. Insoluble material was removed by filtration, the filtrate was concentrated under reduced pressure, and the residue was purified by basic silica gel column chromatography (ethyl acetate/hexane) to give the title compound (220 mg) as a colorless solid.

$^1$H-NMR (DMSO-$d_6$) δ 1.35-1.55 (12H, m), 1.60-1.80 (4H, m), 2.00-2.10 (2H, m), 2.50 (3H, s), 2.70-2.85 (1H, m), 4.20-4.85 (1H, m), 5.27 (2H, s), 7.17 (1H, s), 7.23-7.47 (5H, m), 7.38 (1H, s).

H) Production of 6-(5-methyl-1H-pyrazol-4-yl)-2-[(3aS,6aS)-octahydrocyclopenta[b]pyrrol-2-yl]thieno[3,2-d]pyrimidin-4 (3H)-one tert-Butyl(3aS,6aS)-2-[6-(1-benzyl-3-methyl-1H-pyrazol-4-yl)-4-oxo-3,4-dihydrothieno[3,2-d]pyrimidin-2-yl]hexahydrocyclopenta[b]pyrrole-1(2H)-carboxylate (220 mg) produced above, formic acid (5 mL), and 20% palladium hydroxide-carbon (20 mg) were stirred under a hydrogen atmosphere at 60° C. for 18 hr. Insoluble material was removed by filtration, the filtrate was concentrated under reduced pressure, and the residue was purified by basic silica gel column chromatography (methanol/ethyl acetate) to give the title compound (62 mg) as a colorless solid.

$^1$H-NMR (DMSO-$d_6$) δ 1.45-1.80 (6H, m), 1.95-2.05 (1H, m), 2.46 (3H, s), 2.62-2.78 (1H, m), 2.80-2.95 (1H, m), 4.02 (1H, brs), 4.41-4.58 (1H, m), 7.39 (1H, s), 8.08 (1H, brs).

Example 124

Production of 2-(1-acetylpyrrolidin-2-yl)-6-(5-methyl-1H-pyrazol-4-yl)thieno[3,2-d]pyrimidin-4 (3H)-one

A) Production of tert-butyl 2-[5-(1-benzyl-3-methyl-1H-pyrazol-4-yl)-2-(methoxycarbonyl)thiophen-3-ylcarbamoyl)pyrrolidine-1-carboxylate In the same manner as in Example 123, step F, the title compound (1.20 g) was obtained as a colorless solid from methyl 3-amino-5-(1-benzyl-3-methyl-1H-pyrazol-4-yl)thiophene-2-carboxylate (1.00 g) produced in Example 123, step C, 1-(tert-butoxycarbonyl)proline (1.97 g), 2-methylpropyl chlorocarbonate (1.25 g), triethylamine (0.93 g) and tetrahydrofuran (20 mL).

$^1$H-NMR (DMSO-$d_6$) δ 1.25-1.55 (10H, m), 1.85-2.05 (2H, m), 2.10-2.35 (2H, m), 2.48 (3H, s), 3.55-3.70 (1H, m), 3.87 (3H, s), 4.25-4.35 (1H, m), 5.24 (2H, s), 7.10-7.40 (6H, m), 7.59 (1H, s), 8.08 (1H, s).

B) Production of tert-butyl 2-[6-(1-benzyl-3-methyl-1H-pyrazol-4-yl)-4-oxo-3,4-dihydrothieno[3,2-d]pyrimidin-2-yl]pyrrolidine-1-carboxylate In the same manner as in Example 123, step G, the title compound (0.85 g) was obtained as a colorless solid from tert-butyl 2-[5-(1-benzyl-3-methyl-1H-pyrazol-4-yl)-2-(methoxycarbonyl)thiophen-3-ylcarbamoyl)pyrrolidine-1-carboxylate (1.20 g) produced above, 2M aqueous sodium hydroxide solution (2 mL), methanol (10 mL), and 1-ethyl-3-(3-dimethylaminopropyl)carbodiimide hydrochloride (4.39 g), 1-hydroxybenzotriazole (3.10 g), ammonium chloride (4.90 g), triethylamine (9.27 g), N,N-dimethylformamide (10 mL), and 2M aqueous sodium hydroxide solution (1 mL), and methanol (10 mL).

$^1$H-NMR (DMSO-$d_6$) δ 1.30-1.55 (13H, m), 1.90-2.10 (2H, m), 2.50 (3H, s), 3.15-3.25 (1H, m), 5.27 (1H, s), 5.32-5.38 (1H, m), 7.18 (1H, s), 7.26-7.38 (5H, m), 7.61 (1H, s).

C) Production of 6-(1-benzyl-3-methyl-1H-pyrazol-4-yl)-2-(pyrrolidin-2-yl)thieno[3,2-d]pyrimidin-4 (3H)-one A mixture of tert-butyl 2-[6-(1-benzyl-3-methyl-1H-pyrazol-4-yl)-4-oxo-3,4-dihydrothieno[3,2-d]pyrimidin-2-yl]pyrrolidine-1-carboxylate (0.85 g) produced above and trifluoroacetic acid (5 mL) was stirred for 1 hr under ice-cooling. The reaction mixture was concentrated under reduced pressure, to the residue were added ethyl acetate (20 mL) and water (20 mL), and the separated aqueous layer was extracted with ethyl acetate (10 mL×2). The combined organic layers were washed with brine (20 mL) and dried over anhydrous magnesium sulfate. Insoluble material was removed by filtration, and the filtrate was concentrated under reduced pressure to give the title compound (0.67 g) as a colorless solid.

$^1$H-NMR (DMSO-$d_6$) δ 1.45-1.90 (4H, m), 2.49 (3H, s), 3.05-3.20 (2H, m), 4.30-4.40 (1H, m), 5.27 (2H, s), 5.35-5.40 (1H, m), 7.10-7.20 (1H, m), 7.17 (1H, s), 7.26-7.38 (5H, m), 7.61 (1H, s).

D) Production of 2-(1-acetylpyrrolidin-2-yl)-6-(1-benzyl-3-methyl-1H-pyrazol-4-yl)thieno[3,2-d]pyrimidin-4 (3H)-one A mixture of 6-(1-benzyl-3-methyl-1H-pyrazol-4-yl)-2-(pyrrolidin-2-yl)thieno[3,2-d]pyrimidin-4 (3H)-one (196 mg) produced above, acetic anhydride (255 mg) and pyridine (5 mL) was stirred at 60° C. for 18 hr. Ethyl acetate (50 ml) and water (50 mL) were added to the reaction mixture, and the separated aqueous layer was extracted with ethyl acetate (10 mL×2). The combined organic layers were washed with brine (20 mL) and dried over anhydrous magnesium sulfate. Insoluble material was removed by filtration, the filtrate was concentrated under reduced pressure, and the residue was purified by silica gel column chromatography (ethyl acetate/hexane) to give the title compound (216 mg) as a colorless solid.

$^1$H-NMR (DMSO-d$_6$) δ 1.90-2.20 (4H, m), 2.17 (3H, s), 2.50 (3H, s), 2.75-2.90 (1H, m), 3.50-3.70 (2H, m), 5.15-5.40 (2H, m), 7.17 (1H, s), 7.26-7.40 (5H, m), 7.60 (1H, s).

E) Production of 2-(1-acetylpyrrolidin-2-yl)-6-(5-methyl-1H-pyrazol-4-yl)thieno[3,2-d]pyrimidin-4 (3H)-one In the same manner as in Example 123, step H, the title compound (65 mg) was obtained as a colorless solid from 2-(1-acetylpyrrolidin-2-yl)-6-(1-benzyl-3-methyl-1H-pyrazol-4-yl)thieno[3,2-d]pyrimidin-4 (3H)-one (216 mg) produced above, formic acid (5 mL), and 20% palladium hydroxide-carbon (20 mg).
$^1$H-NMR (DMSO-d$_6$) δ 1.90-2.10 (4H, m), 2.20 (3H, brs), 2.45 (3H, brs), 3.50-3.65 (1H, m), 3.65-3.80 (1H, m), 4.77 (1H, dd, J=8.3, 3.6 Hz), 7.34 (1H, s), 7.89 (1H, brs).

Example 125

Production of 2-[(1R*,2S*)-2-aminocyclohexyl]-6-(5-methyl-1H-pyrazol-4-yl)thieno[3,2-d]pyrimidin-4 (3H)-one dihydrochloride A) Production of tert-butyl [(1R*,2S*)-2-(6-bromo-4-oxo-3,4-dihydrothieno[3,2-d]pyrimidin-2-yl)cyclohexyl]carbamate In the same manner as in Example 82, step A, a crude product (63 mg) of the title compound was obtained as a white solid from (1R*,2S*)-2-[(tert-butoxycarbonyl)amino]cyclohexanecarboxylic acid (365 mg) and triethylamine (0.418 mL) and tetrahydrofuran (10 mL) and 2-methylpropyl chlorocarbonate (0.195 mL) and 3-amino-5-bromothiophene-2-carboxamide (221 mg) produced in Example 1, step D and 2M aqueous sodium hydroxide solution (3 mL) and ethanol (10 mL).
MS(ESI+): [M+H]$^+$428.
MS(ESI+), found: 428.

B) Production of 2-[(1R*,2S*)-2-aminocyclohexyl]-6-(5-methyl-1H-pyrazol-4-yl)thieno[3,2-d]pyrimidin-4 (3H)-one dihydrochloride In the same manner as in Example 83, step C, the title compound (20 mg) was obtained as a white solid from the crude product (63 mg) of tert-butyl [(1R*,2S*)-2-(6-bromo-4-oxo-3,4-dihydrothieno[3,2-d]pyrimidin-2-yl)cyclohexyl] carbamate produced above, tert-butyl 3-methyl-4-(4,4,5,5-tetramethyl-1,3,2-dioxaborolan-2-yl)-1H-pyrazole-1-carboxylate (91 mg), cesium carbonate (288 mg), [1,1'-bis(diphenylphosphino)ferrocene]palladium(II) dichloride-dichloromethane complex (1:1)(5.4 mg), 1,2-dimethoxyethane (3 mL), water (0.50 mL), 10% hydrochloric acid/methanol solution (2 mL) and methanol (2 mL).
$^1$H-NMR (DMSO-d$_6$) δ 1.28-1.88 (6H, m), 1.93-2.19 (2H, m), 2.46 (3H, s), 3.04-3.14 (1H, m), 3.72 (1H, brs), 7.38 (1H, s), 7.99 (3H, brs), 8.04 (1H, brs), 12.40 (1H, brs).

Example 126

Production of 2-(6-(5-methyl-1H-pyrazol-4-yl)-4-oxo-3,4-dihydrothieno[3,2-d]pyrimidin-2-yl)pyrrolidine-1-carboxamide A) Production of 2-(6-(1-benzyl-3-methyl-1H-pyrazol-4-yl)-4-oxo-3,4-dihydrothieno[3,2-d]pyrimidin-2-yl)pyrrolidine-1-carboxamide A mixture of 6-(1-benzyl-3-methyl-1H-pyrazol-4-yl)-2-(pyrrolidin-2-yl)thieno[3,2-d]pyrimidin-4 (3H)-one (196 mg) produced in Example 124, step C, N,N'-carbonyldiimidazole (162 mg) and pyridine (5 mL) was stirred at room temperature for 18 hr. The reaction mixture was concentrated under reduced pressure, the residue was dissolved in 8M ammonia/methanol solution, and the mixture was stirred at room temperature for 18 hr. Ethyl acetate (50 mL) and water (50 mL) were added to the reaction mixture, and the separated aqueous layer was extracted with ethyl acetate (10 mL×2). The combined organic layers were washed with brine (20 mL) and dried over anhydrous magnesium sulfate. Insoluble material was removed by filtration, the filtrate was concentrated under reduced pressure, and the residue was purified by silica gel column chromatography (ethyl acetate/hexane) to give the title compound (110 mg) as a colorless solid.
$^1$H-NMR (DMSO-d$_6$) δ 1.80-2.25 (4H, m), 2.25-2.35 (1H, m), 2.38 (3H, s), 3.45-3.55 (1H, m), 4.73 (1H, dd, J=7.9, 3.2 Hz), 5.28 (2H, s), 5.98 (2H, s), 7.15-7.48 (6H, m), 8.37 (1H, s).

B) Production of 2-(6-(5-methyl-1H-pyrazol-4-yl)-4-oxo-3,4-dihydrothieno[3,2-d]pyrimidin-2-yl)pyrrolidine-1-carboxamide In the same manner as in Example 123, step H, the title compound (23 mg) was obtained as a colorless solid from 2-(6-(1-benzyl-3-methyl-1H-pyrazol-4-yl)-4-oxo-3,4-dihydrothieno[3,2-d]pyrimidin-2-yl)pyrrolidine-1-carboxamide (60 mg) produced above, formic acid (5 mL), and 20% palladium hydroxide-carbon (20 mg).
$^1$H-NMR (DMSO-d$_6$) δ 1.90-2.10 (3H, m), 2.15-2.30 (1H, m), 2.45 (3H, brs), 3.50-3.65 (1H, m), 3.65-3.80 (1H, m), 4.77 (1H, dd, J=8.3, 3.6 Hz), 7.34 (1H, s), 7.89 (1H, brs).

Example 127

Production of 6-(5-methyl-1H-pyrazol-4-yl)-2-(pyrrolidin-1-ylcarbonyl)thieno[3,2-d]pyrimidin-4 (3H)-one In the same manner as in Example 11, step A, 6-bromo-2-(pyrrolidin-1-ylcarbonyl)thieno[3,2-d]pyrimidin-4 (3H)-one was obtained as a yellow solid from 3-amino-5-bromothiophene-2-carboxamide (100 mg) produced in Example 1, step D, and oxo(pyrrolidin-1-yl)acetic acid (68 mg) and O-(7-azabenzotriazol-1-yl)-N,N,N',N'-tetramethyluronium hexafluorophosphate (206 mg) and N-ethyl-N-(1-methylethyl)propan-2-amine (0.158 mL) and N,N-dimethylformamide (2 mL) and ethanol (1 mL) and 2M aqueous sodium hydroxide solution (0.91 mL). In the same manner as in Example 2, step C, the title compound (30 mg) was obtained as a white solid from 6-bromo-2-(pyrrolidin-1-ylcarbonyl)thieno[3,2-d]pyrimidin-4 (3H)-one produced above and tert-butyl 3-methyl-4-(4,4,5,5-tetramethyl-1,3,2-dioxaborolan-2-yl)-1H-pyrazole-1-carboxylate (263 mg), sodium carbonate (136 mg), 1,2-dimethoxyethane (2.0 mL) and water (1.0 mL) and [1,1'-bis(diphenylphosphino) ferrocene] palladium(II) dichloride-dichloromethane complex (1:1)(35 mg).
$^1$H-NMR (DMSO-d$_6$) δ 1.82-1.95 (4H, m), 2.39-2.48 (3H, m), 3.44-3.57 (2H, m), 3.64-3.78 (2H, m), 7.43 (1H, s), 7.85-8.45 (1H, m), 12.47-12.67 (1H, m), 12.87-13.11 (1H, m).

Example 128

Production of 2-[(1R*,3S,4R*,5S)-5-fluoro-2-azabicyclo[2.2.1]hept-3-yl]-6-(5-methyl-1H-pyrazol-4-yl)thieno[3,2-d]pyrimidin-4 (3H)-one dihydrochloride

A) Production of tert-butyl(1R*,3S,4R*,5S)-3-(6-bromo-4-oxo-3,4-dihydrothieno[3,2-d]pyrimidin-2-yl)-5-fluoro-2-azabicyclo[2.2.1]heptane-2-carboxylate In the same manner as in Example 71, step A, the title compound (303 mg) was obtained as a white solid from 3-amino-5-bromothiophene-2-carboxamide (200 mg) produced in Example 1, step D and (1R*,3S,4R*,5S)-2-(tert-butoxycarbonyl)-5-fluoro-2-azabicyclo[2.2.1]heptane-3-carboxylic acid (352 mg) and 2-methylpropyl chlorocarbonate (0.178 mL) and triethylamine (0.190 mL) and tetrahydrofuran (6 mL) and ethanol (4 mL) and 2M aqueous sodium hydroxide solution (1.81 mL).

$^1$H-NMR (DMSO-d$_6$) δ 1.07-1.67 (11H, m), 2.00-2.33 (2H, m), 2.93-3.06 (1H, m), 4.05-4.24 (1H, m), 4.63-4.77 (1H, m), 5.18-5.51 (1H, m), 7.54-7.79 (1H, m), 12.59-12.98 (1H, m).

B) Production of tert-butyl(1R*,3S,4R*,5S)-5-fluoro-3-[6-(5-methyl-1H-pyrazol-4-yl)-4-oxo-3,4-dihydrothieno[3,2-d]pyrimidin-2-yl]-2-azabicyclo[2.2.1]heptane-2-carboxylate tert-Butyl(1R*,3S,4R*,5S)-3-(6-bromo-4-oxo-3,4-dihydrothieno[3,2-d]pyrimidin-2-yl)-5-fluoro-2-azabicyclo[2.2.1]heptane-2-carboxylate (300 mg) and tert-butyl 3-methyl-4-(4,4,5,5-tetramethyl-1,3,2-dioxaborolan-2-yl)-1H-pyrazole-1-carboxylate (416 mg), sodium carbonate (215 mg), 1,2-dimethoxyethane (3.0 mL) and water (1.5 mL) were placed in a flask, and the atmosphere in the flask was purged with argon. [1,1'-Bis(diphenylphosphino)ferrocene]palladium(II) dichloride-dichloromethane complex (1:1)(55 mg) was added, and the atmosphere in the flask was purged again with argon. The reaction system was stirred at 100° C. for 3 hr, and concentrated under reduced pressure. The residue was purified by silica gel column chromatography (ethyl acetate/hexane), and the obtained pale-yellow solid was purified by high performance liquid chromatography {column: L-column 2 ODS (20 mm i.d.×50 mm L), mobile phase: 0.1% aqueous trifluoroacetic acid solution/0.1% trifluoroacetic acid-acetonitrile solution}. The object fraction was neutralized with saturated aqueous sodium hydrogen carbonate, and the mixture was concentrated under reduced pressure. The residue was collected by filtration and washed with water (3 mL) to give the title compound (106 mg) as a colorless solid.

$^1$H-NMR (DMSO-d$_6$) δ 1.12-1.61 (11H, m), 2.05-2.34 (2H, m), 2.36-2.48 (3H, m), 2.93-3.07 (1H, m), 4.04-4.28 (1H, m), 4.58-4.83 (1H, m), 5.17-5.53 (1H, m), 7.33-7.54 (1H, m), 7.81-8.34 (1H, m), 12.31-12.61 (1H, m), 12.82-13.13 (1H, m).

C) Production of 2-[(1R*,3S,4R*,5S)-5-fluoro-2-azabicyclo[2.2.1]hept-3-yl]-6-(5-methyl-1H-pyrazol-4-yl)thieno[3,2-d]pyrimidin-4 (3H)-one dihydrochloride In the same manner as in Example 108, the title compound (71 mg) was obtained as a white solid from tert-butyl(1R*,3S,4R*,5S)-5-fluoro-3-[6-(5-methyl-1H-pyrazol-4-yl)-4-oxo-3,4-dihydrothieno[3,2-d]pyrimidin-2-yl]-2-azabicyclo[2.2.1]heptane-2-carboxylate (80 mg) and methanol (1.5 mL), and 4M hydrochloric acid/ethyl acetate solution (0.18 mL).

$^1$H-NMR (DMSO-d$_6$) δ 1.66-1.77 (1H, m), 1.81-2.02 (2H, m), 2.16-2.34 (1H, m), 2.46 (3H, s), 3.25-3.31 (1H, m), 4.13-4.25 (1H, m), 4.77-4.87 (1H, m), 5.23-5.54 (1H, m), 7.37 (1H, s), 8.10 (1H, s), 8.79 (1H, brs), 10.23 (1H, brs), 13.09 (1H, brs).

Example 129

Production of 2-[(1R*,2R*)-2-aminocyclohexyl]-6-(5-methyl-1H-pyrazol-4-yl)thieno[3,2-d]pyrimidin-4 (3H)-one dihydrochloride

A) Production of tert-butyl [(1R*,2R*)-2-(6-bromo-4-oxo-3,4-dihydrothieno[3,2-d]pyrimidin-2-yl)cyclohexyl]carbamate In the same manner as in Example 82, step A, a crude product (61 mg) of the title compound was obtained as a white solid from (1R*,2R*)-2-[(tert-butoxycarbonyl)amino]cyclohexanecarboxylic acid (365 mg) and triethylamine (0.418 mL) and tetrahydrofuran (10 mL) and 2-methylpropyl chlorocarbonate (0.195 mL) and 3-amino-5-bromothiophene-2-carboxamide (221 mg) produced in Example 1, step D and 2M aqueous sodium hydroxide solution (3 mL) and ethanol (10 mL).

MS(ESI+): [M+H]$^+$428.
MS(ESI+), found: 428.

B) Production of 2-[(1R*,2R*)-2-aminocyclohexyl]-6-(5-methyl-1H-pyrazol-4-yl)thieno[3,2-d]pyrimidin-4 (3H)-one dihydrochloride In the same manner as in Example 83, step C, the title compound (27 mg) was obtained as a white solid from the crude product (61 mg) of tert-butyl [(1R*,2R*)-2-(6-bromo-4-oxo-3,4-dihydrothieno[3,2-d]pyrimidin-2-yl)cyclohexyl]carbamate produced above, tert-butyl 3-methyl-4-(4,4,5,5-tetramethyl-1,3,2-dioxaborolan-2-yl)-1H-pyrazole-1-carboxylate (87 mg), cesium carbonate (277 mg), [1,1'-bis(diphenylphosphino)ferrocene]palladium(II) dichloride-dichloromethane complex (1:1)(5.2 mg), 1,2-dimethoxyethane (3 mL), water (0.50 mL), 10% hydrochloric acid/methanol solution (2 mL) and methanol (2 mL).

$^1$H-NMR (DMSO-d$_6$) δ 1.16-1.55 (4H, m), 1.69-1.84 (2H, m), 2.01-2.15 (2H, m), 2.45 (3H, s), 2.75-2.87 (1H, m), 3.50-3.64 (1H, m), 7.36 (1H, s), 7.94 (3H, brs), 8.05 (1H, s), 12.45 (1H, brs).

Example 130

Production of 6-(5-methyl-1H-pyrazol-4-yl)-2-(1H-pyrrol-1-ylmethyl)thieno[3,2-d]pyrimidin-4 (3H)-one In the same manner as in Example 2, step B and step C, the title compound (46 mg) was obtained as a pale-yellow solid from 6-bromo-2-(chloromethyl)thieno[3,2-d]pyrimidin-4 (3H)-one (180 mg) produced in Example 2, step A and 2,5-dihydro-1H-pyrrole (0.150 mL) and potassium carbonate (178 mg) and sodium iodide (9.7 mg) and N,N-dimethylformamide (3.0 mL) and tert-butyl 3-methyl-4-(4,4,5,5-tetramethyl-1,3,2-dioxaborolan-2-yl)-1H-pyrazole-1-carboxylate (248 mg) and sodium carbonate (128 mg) and 1,2-dimethoxyethane (3.0 mL) and water (1.5 mL) and [1,1'-bis(diphenylphosphino)ferrocene]palladium(II) dichloride-dichloromethane complex (1:1)(33 mg).

$^1$H-NMR (DMSO-d$_6$) δ 2.37-2.48 (3H, m), 5.03 (2H, s), 6.02 (2H, t, J=2.1 Hz), 6.87 (2H, t, J=2.1 Hz), 7.38 (1H, s), 7.79-8.31 (1H, m), 12.63 (1H, brs), 12.87-13.06 (1H, m).

Example 131

Production of 6-(5-methyl-1H-pyrazol-4-yl)-2-morpholin-2-ylthieno[3,2-d]pyrimidin-4 (3H)-one dihydrochloride A) Production of tert-butyl 2-(6-bromo-4-oxo-3,4-dihydrothieno[3,2-d]pyrimidin-2-yl)morpholine-4-carboxylate In the same manner as in Example 118, step A, the title compound (290 mg) was obtained as a white solid from 3-amino-5-bromothiophene-2-carboxamide (221 mg) produced in Example 1, step D, 4-(tert-butoxycarbonyl)morpholine-2-carboxylic acid (347 mg), 2-methylpropyl chlorocarbonate (0.195 mL), triethylamine (0.418 mL) and tetrahydrofuran (10 mL), 2M aqueous sodium hydroxide solution (3.0 mL) and ethanol (10 mL).

$^1$H-NMR (DMSO-d$_6$) δ 1.42 (9H, s), 2.91-3.06 (1H, m), 3.09-3.25 (1H, m), 3.53 (1H, td, J=11.4, 2.7 Hz), 3.72-3.80 (1H, m), 3.92-4.00 (1H, m), 4.00-4.13 (1H, m), 4.38 (1H, dd, J=10.2, 3.0 Hz), 7.65 (1H, s), 12.57 (1H, brs).

B) Production of 6-(5-methyl-1H-pyrazol-4-yl)-2-morpholin-2-ylthieno[3,2-d]pyrimidin-4 (3H)-one dihydrochloride In the same manner as in Example 83, step C, the title compound (102 mg) was obtained as a white solid from tert-butyl 2-(6-bromo-4-oxo-3,4-dihydrothieno[3,2-d]pyrimidin-2-yl)morpholine-4-carboxylate (290 mg) produced above, tert-butyl 3-methyl-4-(4,4,5,5-tetramethyl-1,3,2-dioxaborolan-2-yl)-1H-pyrazole-1-carboxylate (429 mg), cesium carbonate (1.34 g), [1,1'-bis(diphenylphosphino)ferrocene]palladium(II) dichloride-dichloromethane complex (1:1)(26 mg), 1,2-dimethoxyethane (6 mL), water (2 mL), 10% hydrochloric acid/methanol solution (4 mL) and methanol (4 mL).

$^1$H-NMR (DMSO-d$_6$) δ 2.46 (3H, s), 3.04-3.60 (4H, m), 3.83-4.13 (2H, m), 4.81 (1H, dd, J=10.1, 2.7 Hz), 7.43 (1H, s), 8.05 (1H, s), 9.29-9.53 (2H, m), 12.55 (1H, brs).

Example 132

Production of 6-(5-methyl-1H-pyrazol-4-yl)-2-[(2R*,3R*)-3-phenylpyrrolidin-2-yl]thieno[3,2-d]pyrimidin-4 (3H)-one dihydrochloride A) Production of tert-butyl(2R*,3R*)-2-(6-bromo-4-oxo-3,4-dihydrothieno[3,2-d]pyrimidin-2-yl)-3-phenylpyrrolidine-1-carboxylate In the same manner as in Example 82, step A, the title compound (27 mg) was obtained as a white solid from ((2R*,3R*)-1-(tert-butoxycarbonyl)-3-phenylproline (437 mg) and triethylamine (0.418 mL) and tetrahydrofuran (10 mL) and 2-methylpropyl chlorocarbonate (0.195 mL) and 3-amino-5-bromothiophene-2-carboxamide (221 mg) produced in Example 1, step D and 2M aqueous sodium hydroxide solution (3 mL) and ethanol (10 mL).

MS(ESI+): [M+H]$^+$476.

MS(ESI+), found: 476.

B) Production of 6-(5-methyl-1H-pyrazol-4-yl)-2-[(2R*,3R*)-3-phenylpyrrolidin-2-yl]thieno[3,2-d]pyrimidin-4 (3H)-one dihydrochloride In the same manner as in Example 83, step C, the title compound (11 mg) was obtained as a white solid from tert-butyl(2R*,3R*)-2-(6-bromo-4-oxo-3,4-dihydrothieno[3,2-d]pyrimidin-2-yl)-3-phenylpyrrolidine-1-carboxylate (27 mg) produced above, tert-butyl 3-methyl-4-(4,4,5,5-tetramethyl-1,3,2-dioxaborolan-2-yl)-1H-pyrazole-1-carboxylate (35 mg), cesium carbonate (111 mg), [1,1'-bis(diphenylphosphino)ferrocene]palladium(II) dichloride-dichloromethane complex (1:1)(2.1 mg), 1,2-dimethoxyethane (2 mL), water (0.17 mL), 10% hydrochloric acid/methanol solution (1 mL) and methanol (1 mL).

$^1$H-NMR (DMSO-d$_6$) δ 2.41-2.56 (5H, m), 3.36-3.52 (1H, m), 3.71-3.83 (1H, m), 3.95-4.08 (1H, m), 4.88-4.98 (1H, m), 7.07-7.23 (5H, m), 7.36 (1H, s), 8.09 (1H, s), 9.20 (1H, brs), 10.34 (1H, brs), 12.39 (1H, brs).

Example 133

Production of 2-[(methylamino)methyl]-6-(5-methyl-1H-pyrazol-4-yl)thieno[3,2-d]pyrimidin-4 (3H)-one dihydrochloride A) Production of tert-butyl [(6-bromo-4-oxo-3,4-dihydrothieno[3,2-d]pyrimidin-2-yl)methyl]methylcarbamate In the same manner as in Example 71, step A, the title compound (780 mg) was obtained as a colorless solid from 3-amino-5-bromothiophene-2-carboxamide (473 mg) produced in Example 1, step D, N-(tert-butoxycarbonyl)-N-methylglycine (850 mg), 2-methylpropyl chlorocarbonate (0.583 mL), triethylamine (0.741 mL) and tetrahydrofuran (5 mL), 2M aqueous sodium hydroxide solution (5.35 mL) and ethanol (10 mL).

$^1$H-NMR (DMSO-d$_6$) δ 1.31-1.49 (9H, m), 2.77-2.87 (3H, m), 3.79-3.90 (2H, m), 7.60 (1H, s), 12.63 (1H, brs).

B) Production of 2-[(methylamino)methyl]-6-(5-methyl-1H-pyrazol-4-yl)thieno[3,2-d]pyrimidin-4 (3H)-one dihydrochloride In the same manner as in Example 83, step C, the title compound (50 mg) was obtained as a colorless solid from tert-butyl [(6-bromo-4-oxo-3,4-dihydrothieno[3,2-d]pyrimidin-2-yl)methyl]methylcarbamate (400 mg) produced above, tert-butyl 3-methyl-4-(4,4,5,5-tetramethyl-1,3,2-dioxaborolan-2-yl)-1H-pyrazole-1-carboxylate (659 mg), cesium carbonate (696 mg), [1,1'-bis(diphenylphosphino)ferrocene]palladium(II) dichloride-dichloromethane complex (1:1)(44.0 mg), 1,2-dimethoxyethane (5 mL), water (0.5 mL), 4M hydrochloric acid/ethyl acetate solution (1 mL) and methanol (5 mL).

$^1$H-NMR (DMSO-d$_6$) δ 2.47 (3H, s), 2.69 (3H, brs), 4.23 (2H, brs), 7.31-8.30 (5H, m), 9.54 (2H, brs).

Example 134

Production of 2-(2-amino-2-methylpropyl)-6-(5-methyl-1H-pyrazol-4-yl)thieno[3,2-d]pyrimidin-4 (3H)-one dihydrochloride A) Production of tert-butyl [2-(6-bromo-4-oxo-3,4-dihydrothieno[3,2-d]pyrimidin-2-yl)-1,1-dimethyl-ethyl]carbamate In the same manner as in Example 71, step A, the title compound (780 mg) was obtained as a colorless solid from 3-amino-5-bromothiophene-2-carboxamide (412 mg) produced in Example 1, step D, 3-[(tert-butoxycarbonyl)amino]-3-methylbutanoic acid (850 mg), 2-methylpropyl chlorocarbonate (0.507 mL), triethylamine (0.646 mL) and tetrahydrofuran (5 mL), 2M aqueous sodium hydroxide solution (4.66 mL) and ethanol (10 mL).

$^1$H-NMR (DMSO-$d_6$) δ 1.24-1.43 (15H, m), 2.92 (2H, s), 7.51 (1H, s), 11.77-12.47 (2H, m).

B) Production of 2-(2-amino-2-methylpropyl)-6-(5-methyl-1H-pyrazol-4-yl)thieno[3,2-d]pyrimidin-4 (3H)-one dihydrochloride In the same manner as in Example 83, step C, the title compound (63 mg) was obtained as a colorless solid from tert-butyl [2-(6-bromo-4-oxo-3,4-dihydrothieno[3,2-d]pyrimidin-2-yl)-1,1-dimethylethyl]carbamate (700 mg) produced above, tert-butyl 3-methyl-4-(4,4,5,5-tetramethyl-1,3,2-dioxaborolan-2-yl)-1H-pyrazole-1-carboxylate (1072 mg), cesium carbonate (1134 mg), [1,1'-bis(diphenylphosphino)ferrocene]palladium(II) dichloride-dichloromethane complex (1:1)(71.6 mg), 1,2-dimethoxyethane (5 mL), water (0.5 mL), 4M hydrochloric acid/ethyl acetate solution (1 mL) and methanol (4 mL).

$^1$H-NMR (DMSO-$d_6$) δ 1.39 (6H, s), 2.48 (3H, s), 3.02 (2H, s), 6.95 (3H, brs), 7.39-7.44 (1H, m), 8.09 (1H, s), 8.37 (3H, brs).

Example 135

Production of 2-(1-amino-1-methylethyl)-6-(5-methyl-1H-pyrazol-4-yl)thieno[3,2-d]pyrimidin-4 (3H)-one dihydrochloride To a solution of N-[(9H-fluoren-9-ylmethoxy)carbonyl]-2-methylalanine (3.00 g) in toluene (20 mL) was added thionyl dichloride (0.673 mL) at 0° C., and the mixture was stirred at room temperature for 3 hr. The reaction mixture was concentrated under reduced pressure, to the residue were added 3-amino-5-bromothiophene-2-carboxamide (1.70 g) produced in Example 1, step D, pyridine (729 mg), and tetrahydrofuran (5 mL), and the mixture was stirred at 100° C. for 15 hr. Ethyl acetate (20 mL) and water (10 mL) were added to the reaction mixture, and the separated aqueous layer was extracted with ethyl acetate (5 mL). The combined organic layers were washed with brine (5 mL) and dried over anhydrous magnesium sulfate. Insoluble material was filtered off, and the filtrate was concentrated under reduced pressure to give 9H-fluoren-9-ylmethyl {2-[(5-bromo-2-carbamoylthiophen-3-yl)amino]-1,1-dimethyl-2-oxoethyl}carbamate as a pale-yellow oil.

To a solution of 9H-fluoren-9-ylmethyl {2-[(5-bromo-2-carbamoylthiophen-3-yl)amino]-1,1-dimethyl-2-oxoethyl}carbamate produced above in ethanol (50 mL) was added 2M aqueous sodium hydroxide solution (19.2 mL), and the mixture was stirred at 70° C. for 15 hr. The reaction mixture was neutralized with 1M hydrochloric acid (38.4 mL) under ice-cooling, and concentrated under reduced pressure. The residue was dissolved in tetrahydrofuran (20 mL), di-tert-butyl dicarbonate (1.78 mL) was added, and the mixture was stirred at room temperature for 15 hr. Ethyl acetate (20 mL) and water (10 mL) were added to the reaction mixture, and the separated aqueous layer was extracted with ethyl acetate (5 mL). The combined organic layers were washed with brine (5 mL) and dried over anhydrous magnesium sulfate. Insoluble material was filtered off, and the filtrate was concentrated under reduced pressure to give tert-butyl [1-(6-bromo-4-oxo-3,4-dihydrothieno[3,2-d]pyrimidin-2-yl)-1-methylethyl]carbamate as a colorless solid. In the same manner as in Example 83, step C, the title compound (240 mg) was obtained as a colorless solid from tert-butyl [1-(6-bromo-4-oxo-3,4-dihydrothieno[3,2-d]pyrimidin-2-yl)-1-methyl-ethyl]carbamate produced above, tert-butyl 3-methyl-4-(4,4,5,5-tetramethyl-1,3,2-dioxaborolan-2-yl)-1H-pyrazole-1-carboxylate (1.03 g), cesium carbonate (1.09 g), [1,1'-bis(diphenylphosphino)ferrocene]palladium(II) dichloride-dichloromethane complex (1:1)(68.9 mg), 1,2-dimethoxyethane (5 mL), water (0.5 mL), 4M hydrochloric acid/ethyl acetate solution (1 mL) and methanol (4 mL).

$^1$H-NMR (DMSO-$d_6$) δ 1.74 (6H, s), 2.49 (3H, s), 7.41 (1H, s), 7.59-8.99 (7H, m).

Example 136

Production of 6-(5-methyl-1H-pyrazol-4-yl)-2-(1,2,3,6-tetrahydropyridin-2-yl)thieno[3,2-d]pyrimidin-4 (3H)-one dihydrochloride A) Production of tert-butyl 2-(6-bromo-4-oxo-3,4-dihydrothieno[3,2-d]pyrimidin-2-yl)-3,6-dihydropyridine-1(2H)-carboxylate In the same manner as in Example 82, step A, the title compound (663 mg) was obtained as a pale-yellow solid from 3-amino-5-bromothiophene-2-carboxamide (636 mg) produced in Example 1, step D, (2S)-1-(tert-butoxycarbonyl)-1,2,3,6-tetrahydropyridine-2-carboxylic acid (980 mg), 2-methylpropyl chlorocarbonate (0.559 mL), triethylamine (1.20 mL) and tetrahydrofuran (30 mL), 2M aqueous sodium hydroxide solution (8.6 mL) and ethanol (30 mL).

$^1$H-NMR (DMSO-$d_6$) δ 1.19-1.48 (9H, m), 2.53-2.68 (2H, m), 3.93-4.18 (2H, m), 5.06-5.32 (1H, m), 5.61-5.83 (2H, m), 7.54 (1H, s), 12.65 (1H, brs).

B) Production of 6-(5-methyl-1H-pyrazol-4-yl)-2-(1,2,3,6-tetrahydropyridin-2-yl)thieno[3,2-d]pyrimidin-4 (3H)-one dihydrochloride In the same manner as in Example 83, step C, the title compound (54 mg) was obtained as a white solid from tert-butyl 2-(6-bromo-4-oxo-3,4-dihydrothieno[3,2-d]pyrimidin-2-yl)-3,6-dihydropyridine-1(2H)-carboxylate (100 mg) produced above, tert-butyl 3-methyl-4-(4,4,5,5-tetramethyl-1,3,2-dioxaborolan-2-yl)-1H-pyrazole-1-carboxylate (149 mg), cesium carbonate (474 mg), [1,1'-bis(diphenylphosphino)ferrocene]palladium(II) dichloride-dichloromethane complex (1:1)(8.9 mg), 1,2-dimethoxyethane (3 mL), water (0.5 mL), 10% hydrochloric acid/methanol solution (2 mL) and methanol (3 mL).

$^1$H-NMR (DMSO-$d_6$) δ 2.35-2.47 (4H, m), 2.70-2.86 (1H, m), 3.62-3.84 (2H, m), 4.35-6.05 (3H, m), 7.37 (1H, s), 8.12 (1H, s), 9.71 (2H, brs), 12.86 (1H, brs).

Example 137

Production of 2-(2-aminocyclopentyl)-6-(5-methyl-1H-pyrazol-4-yl)thieno[3,2-d]pyrimidin-4 (3H)-one dihydrochloride

A) Production of tert-butyl [2-(6-bromo-4-oxo-3,4-dihydrothieno[3,2-d]pyrimidin-2-yl)cyclopentyl] carbamate In the same manner as in Example 82, step A, a crude product (51 mg) of the title compound was obtained as a white solid from 3-amino-5-bromothiophene-2-carboxamide (116 mg) produced in Example 1, step D, (1R*,2S*)-2-[(tert-butoxycarbonyl)amino]cyclopentanecarboxylic acid (180 mg), 2-methylpropyl chlorocarbonate (0.102 mL), triethylamine (0.219 mL) and tetrahydrofuran (6 mL), 2M aqueous sodium hydroxide solution (1.57 mL) and ethanol (6 mL).

MS(ESI+): [M+H]$^+$414.
MS(ESI+), found: 414.

B) Production of 2-(2-aminocyclopentyl)-6-(5-methyl-1H-pyrazol-4-yl)thieno[3,2-d]pyrimidin-4 (3H)-one dihydrochloride In the same manner as in Example 83, step C, the title compound (21 mg) was obtained as a white solid from tert-butyl [2-(6-bromo-4-oxo-3,4-dihydrothieno[3,2-d]pyrimidin-2-yl)cyclopentyl]carbamate (51 mg) produced above, tert-butyl methyl-4-(4,4,5,5-tetramethyl-1,3,2-dioxaborolan-2-yl)-1H-pyrazole-1-carboxylate (76 mg), cesium carbonate (241 mg), [1,1'-bis(diphenylphosphino)ferrocene]palladium(II) dichloride-dichloromethane complex (1:1)(4.5 mg), 1,2-dimethoxyethane (3 mL), water (0.3 mL), 10% hydrochloric acid/methanol solution (2 mL) and methanol (2 mL).

$^1$H-NMR (DMSO-d$_6$) δ 1.61-2.34 (6H of major, 6H of minor, m), 2.45 (3H of major, 3H of minor, s), 3.13-3.26 (1H of major, m), 3.26-3.37 (1H of minor, m), 3.82-3.92 (1H of minor, m), 4.02-4.15 (1H of major, m), 7.35 (1H of minor, s), 7.38 (1H of major, s), 7.93 (3H of minor, brs), 8.04 (1H of major, 1H of minor, brs), 8.13 (3H of major, brs), 12.47 (1H of major, 1H of minor, brs). * The ratio of the observed isomers was 2.5:1.

Example 138

Production of 6-(5-methyl-1H-pyrazol-4-yl)-2-(1,3-thiazol-2-yl)thieno[3,2-d]pyrimidin-4 (3H)-one

A) Production of 6-bromo-2-(1,3-thiazol-2-yl)thieno[3,2-d]pyrimidin-4 (3H)-one To a mixture of 3-amino-5-bromothiophene-2-carboxamide (200 mg) produced in Example 1, step D, triethylamine (0.19 mL) and tetrahydrofuran (4.0 mL) was added 1,3-thiazole-2-carbonyl chloride (0.22 g) at 0° C., and the mixture was stirred at room temperature for 2 hr. Water was poured into the reaction system, and the precipitate was collected by filtration to give N-(5-bromo-2-carbamoylthiophen-3-yl)-1,3-thiazole-2-carboxamide (290 mg) as a pale-yellow solid. To N-(5-bromo-2-carbamoylthiophen-3-yl)-1,3-thiazole-2-carboxamide produced above were added 2M aqueous sodium hydroxide solution (1.75 mL) and 1,2-dimethoxyethane (4.0 mL), and the mixture was stirred at 100° C. for 18 hr. The reaction system was neutralized with 1M hydrochloric acid at 0° C. The precipitate was collected by filtration to give the title compound (236 mg) as a white solid.

$^1$H-NMR (DMSO-d$_6$) δ 7.73 (1H, s), 8.03-8.18 (2H, m), 13.01 (1H, brs).

B) Production of 6-(5-methyl-1H-pyrazol-4-yl)-2-(1,3-thiazol-2-yl)thieno[3,2-d]pyrimidin-4 (3H)-one In the same manner as in Example 2, step C, the title compound (6 mg) was obtained as a pale-yellow solid from 6-bromo-2-(1,3-thiazol-2-yl)thieno[3,2-d]pyrimidin-4 (3H)-one (230 mg) and tert-butyl 3-methyl-4-(4,4,5,5-tetramethyl-1,3,2-dioxaborolan-2-yl)-1H-pyrazole-1-carboxylate (451 mg), sodium carbonate (233 mg), 1,2-dimethoxyethane (3.0 mL) and water (1.5 mL) and [1,1'-bis(diphenylphosphino)ferrocene]palladium(II) dichloride-dichloromethane complex (1:1)(60 mg).

$^1$H-NMR (DMSO-d$_6$) δ 2.43-2.49 (3H, m), 7.53 (1H, s), 7.81-8.52 (3H, m), 12.61-13.20 (2H, m).

Example 139

Production of 2-(2-aminocyclopentyl)-6-(5-methyl-1H-pyrazol-4-yl)thieno[3,2-d]pyrimidin-4 (3H)-one dihydrochloride

A) Production of tert-butyl [2-(6-bromo-4-oxo-3,4-dihydrothieno[3,2-d]pyrimidin-2-yl)cyclopentyl] carbamate In the same manner as in Example 82, step A, a crude product (610 mg) of the title compound was obtained as a white solid from 3-amino-5-bromothiophene-2-carboxamide (663 mg) produced in Example 1, step D, (1R*,2R*)-2-[(tert-butoxycarbonyl)amino]cyclopentanecarboxylic acid (1.03 g), 2-methylpropyl chlorocarbonate (0.584 mL), triethylamine (1.25 mL) and tetrahydrofuran (30 mL), 2M aqueous sodium hydroxide solution (9.0 mL) and ethanol (30 mL).

MS(ESI+): [M+H]$^+$414.
MS(ESI+), found: 414.

B) Production of 2-(2-aminocyclopentyl)-6-(5-methyl-1H-pyrazol-4-yl)thieno[3,2-d]pyrimidin-4 (3H)-one dihydrochloride In the same manner as in Example 83, step C, the title compound (242 mg) was obtained as a white solid from tert-butyl [2-(6-bromo-4-oxo-3,4-dihydrothieno[3,2-d]pyrimidin-2-yl)cyclopentyl]carbamate (610 mg) produced above, tert-butyl 3-methyl-4-(4,4,5,5-tetramethyl-1,3,2-dioxaborolan-2-yl)-1H-pyrazole-1-carboxylate (907 mg), cesium carbonate (2.88 g), [1,1'-bis(diphenylphosphino)ferrocene]palladium(II) dichloride-dichloromethane complex (1:1)(54 mg), 1,2-dimethoxyethane (7 mL), water (3 mL), 10% hydrochloric acid/methanol solution (6 mL) and methanol (6 mL).

$^1$H-NMR (DMSO-d$_6$) δ 1.66-1.89 (4H, m), 2.07-2.32 (2H, m), 2.46 (3H, s), 3.20-3.30 (1H, m), 4.03-4.15 (1H, m), 7.39 (1H, s), 8.05 (1H, s), 8.28 (3H, brs).

Example 140

Production of 6-(5-methyl-1H-pyrazol-4-yl)-2-[(2S,3S)-3-methylpyrrolidin-2-yl]thieno[3,2-d]pyrimidin-4 (3H)-one dihydrochloride

A) Production of (3S)-1-(tert-butoxycarbonyl)-3-methyl-L-proline

To a mixture of (3S)-3-methyl-L-proline (250 mg), tetrahydrofuran (10 mL) and 1M aqueous sodium hydroxide solution (2.9 mL) was added, while stirring at room temperature, di-tert-butyl dicarbonate (0.67 mL). After stirring overnight, the reaction mixture was ice-cooled, and adjusted to pH 4 by adding 1M hydrochloric acid (2.9 mL) dropwise. The organic product was extracted with ethyl acetate (80 mL), and the obtained organic layer was washed with water, and dried over anhydrous magnesium sulfate. Insoluble material was filtered off, and the filtrate was concentrated under reduced pressure. To the residue were added ethyl acetate/hexane and the precipitated solid was collected by filtration to give the title compound (323 mg) as a white solid.

$^1$H-NMR (DMSO-$d_6$) δ 1.06-1.11 (3H, m), 1.33 (9H of major, s), 1.39 (9H of minor, s), 1.41-1.56 (1H, m), 1.87-2.01 (1H, m), 2.13-2.25 (1H, m), 3.20-3.29 (1H, m), 3.37-3.47 (1H, m), 3.55-3.62 (1H, m), 12.49 (1H, brs). The ratio of the observed rotamers was 2:1.

B) Production of tert-butyl(2S,3S)-2-(6-bromo-4-oxo-3,4-dihydrothieno[3,2-d]pyrimidin-2-yl)-3-methylpyrrolidine-1-carboxylate In the same manner as in Example 82, step A, a crude product (276 mg) of the title compound was obtained as a pale-yellow oil from 3-amino-5-bromothiophene-2-carboxamide (208 mg) produced in Example 1, step D, (3S)-1-(tert-butoxycarbonyl)-3-methyl-L-proline (323 mg) produced above, 2-methylpropyl chlorocarbonate (0.183 mL), triethylamine (0.393 mL) and tetrahydrofuran (10 mL), 2M aqueous sodium hydroxide solution (2.8 mL) and ethanol (10 mL).

MS(ESI+): [M+H]$^+$414.
MS(ESI+), found: 414.
$^1$H-NMR (DMSO-$d_6$) δ 1.03-1.07 (3H, m), 1.09 (9H of major, s), 1.33-1.38 (9H of minor, m), 1.47-1.62 (1H, m), 1.99-2.11 (1H, m), 2.24-2.38 (1H, m), 3.42-3.57 (2H, m), 4.05-4.15 (1H, m), 7.61 (1H of minor, s), 7.63 (1H of major, s), 12.77 (1H, brs). The ratio of the observed rotamers was 5:2.

C) Production of 6-(5-methyl-1H-pyrazol-4-yl)-2-[(2S,3S)-3-methylpyrrolidin-2-yl]thieno[3,2-d]pyrimidin-4 (3H)-one dihydrochloride In the same manner as in Example 83, step C, the title compound (127 mg) was obtained as a white solid from tert-butyl(2S,3S)-2-(6-bromo-4-oxo-3,4-dihydrothieno[3,2-d]pyrimidin-2-yl)-3-methylpyrrolidine-1-carboxylate (272 mg) produced above, tert-butyl 3-methyl-4-(4,4,5,5-tetramethyl-1,3,2-dioxaborolan-2-yl)-1H-pyrazole-1-carboxylate (405 mg), cesium carbonate (1.28 g), [1,1'-bis(diphenylphosphino)ferrocene]palladium(II) dichloride-dichloromethane complex (1:1)(24 mg), 1,2-dimethoxyethane (5 mL), water (2 mL), 10% hydrochloric acid/methanol solution (2 mL) and methanol (3 mL).

$^1$H-NMR (DMSO-$d_6$) δ 1.17 (3H, d, J=6.8 Hz), 1.60-1.75 (1H, m), 2.14-2.28 (1H, m), 2.46 (3H, s), 2.50-2.59 (1H, m), 3.36-3.48 (2H, m), 4.17-4.25 (1H, m), 7.37 (1H, s), 8.09 (1H, s), 9.00 (1H, brs), 10.25 (1H, brs), 12.94 (1H, brs).

Example 141

Production of 2-(4-hydroxy-4-phenylpyrrolidin-2-yl)-6-(5-methyl-1H-pyrazol-4-yl)thieno[3,2-d]pyrimidin-4 (3H)-one dihydrochloride A) Production of tert-butyl 2-(6-bromo-4-oxo-3,4-dihydrothieno[3,2-d]pyrimidin-2-yl)-4-hydroxy-4-phenylpyrrolidine-1-carboxylate To a solution of methyl 3-amino-5-bromothiophene-2-carboxylate (1.14 g) produced in Example 1, step C in tetrahydrofuran (20 mL) was added 1M lithium hexamethyldisilazide-tetrahydrofuran solution (4.84 mL) at 0° C., and the mixture was stirred for 30 min. To the reaction mixture was added a solution of tert-butyl(1S,4R)-3-oxo-1-phenyl-2-oxa-5-azabicyclo[2.2.1]heptane-5-carboxylate (700 mg) in tetrahydrofuran (5 mL), and the mixture was stirred at room temperature for 15 hr. The reaction mixture was neutralized with 1M hydrochloric acid under ice-cooling, and extracted with ethyl acetate (20 mL). The organic layer was washed with brine (5 mL), and dried over anhydrous magnesium sulfate. Insoluble material was filtered off, and the filtrate was concentrated under reduced pressure to give tert-butyl 2-{[5-bromo-2-(methoxycarbonyl)thiophen-3-yl]carbamoyl}-4-hydroxy-4-phenylpyrrolidine-1-carboxylate as a pale-yellow oil. To a solution of tert-butyl 2-{[5-bromo-2-(methoxycarbonyl)thiophen-3-yl]carbamoyl}-4-hydroxy-4-phenylpyrrolidine-1-carboxylate produced above in ethanol (15 mL) was added 2M aqueous sodium hydroxide solution (5.00 mL), and the mixture was stirred at 60° C. for 2 hr. The reaction mixture was neutralized with 6M hydrochloric acid (1.7 mL) under ice-cooling, and concentrated under reduced pressure. To the residue were added ammonium chloride (137 mg), triethylamine (0.520 mL) and N,N-dimethylformamide (5 mL), and the mixture was stirred at room temperature for 5 min. To the reaction system were added 1-ethyl-3-(3-dimethylaminopropyl)carbodiimide hydrochloride (399 mg) and 1-hydroxybenzotriazole (278 mg), and the mixture was stirred at room temperature for 15 hr. The reaction system was poured into water (10 mL), and the mixture was extracted with ethyl acetate (10 mL). The organic layer was washed with saturated aqueous sodium hydrogen carbonate, and dried over anhydrous magnesium sulfate. Insoluble material was filtered off, and the filtrate was concentrated under reduced pressure to give tert-butyl 2-[(5-bromo-2-carbamoylthiophen-3-yl)carbamoyl]-4-hydroxy-4-phenylpyrrolidine-1-carboxylate as a pale-yellow oil. To a solution of tert-butyl 2-[(5-bromo-2-carbamoylthiophen-3-yl)carbamoyl]-4-hydroxy-4-phenylpyrrolidine-1-carboxylate produced above in ethanol (5 mL) was added 2M aqueous sodium hydroxide solution (1.71 mL), and the mixture was stirred at 70° C. for 3 hr. The reaction mixture was neutralized with 1M hydrochloric acid (3.4 mL) under ice-cooling, and extracted with ethyl acetate (10 mL). The organic layer was washed with water, and dried over anhydrous magnesium sulfate. Insoluble material was removed by filtration, the filtrate was concentrated under reduced pressure, and the residue was purified by silica gel column chromatography (ethyl acetate/hexane) to give the title compound (62 mg) as a brown solid.

$^1$H-NMR (DMSO-$d_6$) δ 1.11-1.43 (9H, m), 2.25-2.41 (1H, m), 2.76-2.91 (1H, m), 3.70-3.85 (2H, m), 4.72-4.89 (1H, m), 6.18-6.44 (1H, m), 7.21-7.43 (3H, m), 7.49-7.58 (2H, m), 7.62-7.70 (1H, m), 12.28-12.52 (1H, m).

B) Production of 2-(4-hydroxy-4-phenylpyrrolidin-2-yl)-6-(5-methyl-1H-pyrazol-4-yl)thieno[3,2-d]pyrimidin-4 (3H)-one dihydrochloride In the same manner as in Example 83, step C, the title compound (21 mg) was obtained as a colorless solid from tert-butyl 2-(6-bromo-4-oxo-3,4-dihydrothieno[3,2-d]pyrimidin-2-yl)-4-hydroxy-4-phenylpyrrolidine-1-carboxylate (58 mg) produced above, tert-butyl 3-methyl-4-(4,4,5,5-tetramethyl-1,3,2-dioxaborolan-2-yl)-1H-pyrazole-1-carboxylate (72.6 mg), cesium carbonate (77.0 mg), [1,1'-bis(diphenylphosphino)ferrocene]palladium(II) dichloride-dichloromethane complex (1:1)(4.85 mg), 1,2- dimethoxyethane (5 mL), water (0.5 mL), 4M hydrochloric acid/ethyl acetate solution (1 mL) and methanol (4 mL).

¹H-NMR (DMSO-$d_6$) δ 2.48 (3H, s), 2.56-5.15 (6H, m), 7.27-7.60 (7H, m), 8.12 (1H, s), 9.12 (1H, brs), 10.66 (1H, brs), 12.90 (1H, brs).

Example 142

Production of 2-[(1R,3S,4R,5S) or (1S,3S,4S,5S)-5-hydroxy-2-azabicyclo[2.2.1]hept-3-yl]-6-(5-methyl-1H-pyrazol-4-yl)thieno[3,2-d]pyrimidin-4 (3H)-one dihydrochloride A) Production of tert-butyl(1R*,3S,4R*,5S)-3-(6-bromo-4-oxo-3,4-dihydrothieno[3,2-d]pyrimidin-2-yl)-5-hydroxy-2-azabicyclo[2.2.1]heptane-2-carboxylate To a solution of (1R*,3S,4R*,5S)-2-(tert-butoxycarbonyl)-5-hydroxy-2-azabicyclo[2.2.1]heptane-3-carboxylic acid (349 mg) and triethylamine (0.190 mL) in tetrahydrofuran (4 mL) was added 2-methylpropyl chlorocarbonate (0.178 mL) at 0° C., and the mixture was stirred at room temperature for 30 min. To the reaction system was added a solution of 3-amino-5-bromothiophene-2-carboxamide (200 mg) produced in Example 1, step D, in tetrahydrofuran (2 mL), and the mixture was stirred at 60° C. for 18 hr. Water was added to the reaction mixture, and the separated aqueous layer was extracted with ethyl acetate. The organic layer was washed with brine, and dried over anhydrous sodium sulfate. Insoluble material was filtered off, the filtrate was concentrated under reduced pressure, and the residue was purified by basic silica gel column chromatography (ethyl acetate/hexane). To the obtained pale-yellow amorphous solid (307 mg) were added 2M aqueous sodium hydroxide solution (1.81 mL) and ethanol (4.0 mL), and the mixture was stirred at 70° C. for 5 hr. The reaction system was neutralized with 1M hydrochloric acid at 0° C. To the reaction system was added water (2 mL), and the mixture was extracted with ethyl acetate. The organic layer was washed with brine, and dried over anhydrous sodium sulfate. Insoluble material was filtered off, and the filtrate was concentrated under reduced pressure. The residue was washed with ethyl acetate (2 mL) to give the title compound (211 mg) as a colorless solid.

¹H-NMR (DMSO-$d_6$) δ 1.13-1.47 (11H, m), 1.88-2.15 (2H, m), 2.56-2.63 (1H, m), 3.97-4.10 (1H, m), 4.23-4.34 (1H, m), 4.79-4.88 (1H, m), 5.05-5.14 (1H, m), 7.47-7.74 (1H, m), 12.25-12.70 (1H, m).

B) Optical resolution of tert-butyl(1R*,3S,4R*,5S)-3-(6-bromo-4-oxo-3,4-dihydrothieno[3,2-d]pyrimidin-2-yl)-5-hydroxy-2-azabicyclo[2.2.1]heptane-2-carboxylate tert-Butyl(1R*,3S,4R*,5S)-3-(6-bromo-4-oxo-3,4-dihydrothieno[3,2-d]pyrimidin-2-yl)-5-hydroxy-2-azabicyclo[2.2.1]heptane-2-carboxylate (211 mg) was fractionated by high performance liquid chromatography (column: CHIRALPAK AD (50 mm i.d.×500 mm L, manufactured by DAICEL CHEMICAL INDUSTRIES, LTD.), mobile phase: hexane/ethanol (800/200) and hexane/ethanol (200/800), flow rate: 80 mL/min, column temperature: 30° C.). tert-Butyl(1R,3S,4R,5S) or (1S,3S,4S,5S)-3-(6-bromo-4-oxo-3,4-dihydrothieno[3,2-d]pyrimidin-2-yl)-5-hydroxy-2-azabicyclo[2.2.1]heptane-2-carboxylate (101 mg, >99.9% ee, fraction eluted with hexane/ethanol (800/200), retention time 6.3 min) and tert-butyl(1R,3S,4R,5S) or (1S,3S,4S,5S)-3-(6-bromo-4-oxo-3,4-dihydrothieno[3,2-d]pyrimidin-2-yl)-5-hydroxy-2-azabicyclo[2.2.1]heptane-2-carboxylate (100 mg, >99.9% ee, fraction eluted with hexane/ethanol (200/800), retention time 8.9 min) were obtained under the above-mentioned high performance liquid chromatography conditions. The analysis was performed by high performance liquid chromatography (column: CHIRALPAK AS-H (4.6 mm i.d.×250 mm L, manufactured by DAICEL CHEMICAL INDUSTRIES, LTD.), mobile phase: hexane/ethanol (850/150), flow rate: 1 mL/min, column temperature: 30° C., detection 220 nm).

C) Production of tert-butyl(1R,3S,4R,5S) or (1S,3S,4S,5S)-5-hydroxy-3-[6-(5-methyl-1H-pyrazol-4-yl)-4-oxo-3,4-dihydrothieno[3,2-d]pyrimidin-2-yl]-2-azabicyclo[2.2.1]heptane-2-carboxylate In the same manner as in Example 2, step C, the title compound (91 mg) was obtained as a white solid from tert-butyl(1R,3S,4R,5S) or (1S,3S,4S,5S)-3-(6-bromo-4-oxo-3,4-dihydrothieno[3,2-d]pyrimidin-2-yl)-5-hydroxy-2-azabicyclo[2.2.1]heptane-2-carboxylate (100 mg, >99.9% ee, fraction eluted with hexane/ethanol (800/200), retention time 6.3 min) and tert-butyl 3-methyl-4-(4,4,5,5-tetramethyl-1,3,2-dioxaborolan-2-yl)-1H-pyrazole-1-carboxylate (139 mg), sodium carbonate (72 mg), 1,2-dimethoxyethane (3.0 mL) and water (1.5 mL) and [1,1'-bis(diphenylphosphino)ferrocene]palladium(II) dichloride-dichloromethane complex (1:1)(18 mg).

¹H-NMR (CDCl₃) δ 1.32-2.01 (11H, m), 2.05-2.23 (2H, m), 2.42-2.64 (3H, m), 2.95-3.20 (1H, m), 4.14-4.39 (1H, m), 4.51-4.63 (1H, m), 5.08-5.25 (1H, m), 7.11-7.23 (1H, m), 7.73-7.89 (1H, m).

D) Production of 2-[(1R,3S,4R,5S) or (1S,3S,4S,5S)-5-hydroxy-2-azabicyclo[2.2.1]hept-3-yl]-6-(5-methyl-1H-pyrazol-4-yl)thieno[3,2-d]pyrimidin-4 (3H)-one dihydrochloride In the same manner as in Example 108, the title compound (59 mg) was obtained as a white solid from tert-butyl(1R,3S,4R,5S) or (1S,3S,4S,5S)-5-hydroxy-3-[6-(5-methyl-1H-pyrazol-4-yl)-4-oxo-3,4-dihydrothieno[3,2-d]pyrimidin-2-yl]-2-azabicyclo[2.2.1]heptane-2-carboxylate (90 mg) produced in Example 142, step C, and methanol (2.0 mL), 4M hydrochloric acid/ethyl acetate solution (0.457 mL).

¹H-NMR (DMSO-$d_6$) δ 1.41-1.52 (1H, m), 1.62-1.72 (1H, m), 1.77-1.86 (1H, m), 2.01-2.15 (1H, m), 2.46 (3H, s), 2.91-3.01 (1H, m), 4.01-4.14 (1H, m), 4.28-4.42 (1H, m), 4.92-5.02 (1H, m), 7.35 (1H, s), 8.08 (1H, s), 8.57-8.68 (1H, m), 9.60-9.72 (1H, m), 12.97 (1H, brs).

Example 143

Production of 2-(pyrrolidin-1-ylmethyl)-6-[5-(trifluoromethyl)-1H-pyrazol-4-yl]thieno[3,2-d]pyrimidin-4 (3H)-one 6-Bromo-2-(pyrrolidin-1-ylmethyl)thieno[3,2-d]pyrimidin-4 (3H)-one (372 mg) produced in Example 2, step B, [3-(trifluoromethyl)-1-trityl-1H-pyrazol-4-yl]boronic acid (600 mg), sodium carbonate (314 mg), ethanol (10 mL) and water (1.5 mL) were placed in a flask, and the atmosphere in the flask was purged with argon.

Tetrakis(triphenylphosphine)palladium(0) (68.4 mg) was added, the atmosphere in the flask was purged again with argon, and the mixture was stirred at 80° C. for 5 hr. Ethyl acetate (20 mL) and water (10 mL) were added to the reaction mixture, and the separated aqueous layer was extracted with ethyl acetate (10 mL×2). The combined organic layers were washed with brine (20 mL) and dried over anhydrous sodium sulfate. Insoluble material was filtered off, and the filtrate was concentrated under reduced pressure. The residue was purified by silica gel column chromatography (ethyl acetate/hexane), and the object fraction was concentrated under reduced pressure to give 2-(pyrrolidin-1-ylmethyl)-6-[3-(trifluoromethyl)-1-trityl-1H-pyrazol-4-yl]thieno[3,2-d]pyrimidin-4 (3H)-one as a colorless oil. To 2-(pyrrolidin-1-ylmethyl)-6-[3-(trifluoromethyl)-1-trityl-1H-pyrazol-4-yl]thieno[3,2-d]pyrimidin-4 (3H)-one produced above was added hydrochloric acid/methanol solution (5 mL), and the mixture was stirred at 60° C. for 6 hr. Ethyl acetate (20 mL) and saturated aqueous sodium hydrogen carbonate (10 mL) were added to the reaction mixture, and the separated aqueous layer was extracted with ethyl acetate (10 mL×2). The combined organic layers were washed with brine (20 mL) and dried over anhydrous sodium sulfate. Insoluble material was filtered off, and the filtrate was concentrated under reduced pressure. The residue was purified by basic silica gel column chromatography (ethyl acetate/methanol), and the object fraction was concentrated under reduced pressure to give the title compound (3.8 mg) as a colorless solid.

$^1$H-NMR (DMSO-$d_6$) δ 1.66-1.78 (4H, m), 2.54-2.60 (4H, m), 3.58 (2H, s), 7.37 (1H, s), 8.53 (1H, s).

Example 144

Production of 6-(5-methyl-1H-pyrazol-4-yl)-2-[(2R*,3S*)-3-phenylpyrrolidin-2-yl]thieno[3,2-d]pyrimidin-4 (3H)-one hydrochloride A) Production of tert-butyl(2R*,3S*)-2-(6-bromo-4-oxo-3,4-dihydrothieno[3,2-d]pyrimidin-2-yl)-3-phenylpyrrolidine-1-carboxylate In the same manner as in Example 82, step A, a crude product (345 mg) of the title compound was obtained as a white solid from 3-amino-5-bromothiophene-2-carboxamide (221 mg) produced in Example 1, step D, (2R*,3S*)-1-(tert-butoxycarbonyl)-3-phenylproline (437 mg), 2-methylpropyl chlorocarbonate (0.195 mL), triethylamine (0.418 mL) and tetrahydrofuran (10 mL), 2M aqueous sodium hydroxide solution (3 mL) and ethanol (10 mL).

$^1$H-NMR (DMSO-$d_6$) δ 1.09 (9H of major, s), 1.38 (9H of minor, s), 2.03-2.35 (2H of major, 2H of minor, m), 3.46-3.70 (3H of major, 2H of minor, m), 4.00-4.13 (1H of minor, m), 4.54-4.67 (1H of major, 1H of minor, m), 7.19-7.36 (5H of major, 5H of minor, m), 7.59-7.65 (1H of major, 1H of minor, m), 12.78 (1H of major, 1H of minor, brs). The ratio of the observed rotamers was 5:2.

B) Production of 6-(5-methyl-1H-pyrazol-4-yl)-2-[(2*, 3S*)-3-phenylpyrrolidin-2-yl]thieno[3,2-d]pyrimidin-4 (3H)-one hydrochloride In the same manner as in Example 83, step C, the title compound (185 mg) was obtained as a white solid from tert-butyl(2R*,3S*)-2-(6-bromo-4-oxo-3,4-dihydrothieno[3,2-d]pyrimidin-2-yl)-3-phenylpyrrolidine-1-carboxylate (345 mg) produced above, tert-butyl 3-methyl-4-(4,4,5,5-tetramethyl-1,3,2-dioxaborolan-2-yl)-1H-pyrazole-1-carboxylate (446 mg), cesium carbonate (1.42 g), [1,1'-bis(diphenylphosphino)ferrocene]palladium(II) dichloride-dichloromethane complex (1:1)(27 mg), 1,2-dimethoxyethane (6 mL), water (2 mL), 10% hydrochloric acid/methanol solution (4 mL) and methanol (5 mL).

$^1$H-NMR (DMSO-$d_6$) δ 2.15-2.29 (1H, m), 2.43-2.60 (4H, m), 3.45-3.66 (2H, m), 3.76-3.90 (1H, m), 4.62 (1H, d, J=8.9 Hz), 7.28-7.38 (5H, m), 7.43 (1H, s), 7.86-8.39 (1H, m), 9.12-10.47 (1H, m), 13.05 (1H, brs).

Example 145

Production of 6-(5-methyl-1H-pyrazol-4-yl)-2-[(2S)-1,2,3,6-tetrahydropyridin-2-yl]thieno[3,2-d]pyrimidin-4 (3H)-one dihydrochloride A) Production of tert-butyl(2S)-2-(6-bromo-4-oxo-3,4-dihydrothieno[3,2-d]pyrimidin-2-yl)-3,6-dihydropyridine-1(2H)-carboxylate To a mixture of (2S)-1-(tert-butoxycarbonyl)-1,2,3,6-tetrahydropyridine-2-carboxylic acid (1.16 g), triethylamine (1.42 mL) and tetrahydrofuran (12 mL) was added 2-methylpropyl chlorocarbonate (0.662 mL) with stirring at room temperature. After 1 hr, 3-amino-5-bromothiophene-2-carboxamide (752 mg) produced in Example 1, step D, was added, and the mixture was stirred in a microwave reactor at 100° C. for 2 hr. The reaction mixture was allowed to cool to room temperature, and poured into saturated aqueous sodium hydrogen carbonate. The mixture was extracted with ethyl acetate, and the extract was dried over anhydrous magnesium sulfate. Insoluble material was removed by filtration, and the filtrate was concentrated under reduced pressure. The residue was dissolved in ethanol (10 mL), 2M aqueous sodium hydroxide solution (10.2 mL) was added, and the mixture was stirred at 90° C. for 2 hr. The reaction mixture was ice-cooled, and 6M hydrochloric acid (3.33 mL) was added dropwise. The reaction mixture was poured into brine, and extracted with 3:1 ethyl acetate/tetrahydrofuran mixture. The extract was dried over anhydrous magnesium sulfate. Insoluble material was removed by filtration, and the filtrate was concentrated under reduced pressure. The residue was purified by basic silica gel column chromatography (ethyl acetate/hexane and methanol/ethyl acetate) to give the title compound (851 mg) as a white solid. The optical purity was 51.1% ee. The analysis was performed by high performance liquid chromatography (column: CHIRALPAK IC (4.6 mm i.d.×250 mm L, manufactured by DAICEL CHEMICAL INDUSTRIES, LTD.), mobile phase: hexane/ethanol (900/100), flow rate: 1 mL/min, column temperature: 30° C., detection 220 nm).

$^1$H-NMR (DMSO-$d_6$) δ 1.21-1.47 (9H, m), 2.53-2.65 (2H, m), 3.92-4.19 (2H, m), 5.09-5.31 (1H, m), 5.62-5.81 (2H, m), 7.54 (1H, s), 12.65 (1H, brs).

B) Optical resolution of tert-butyl(2S)-2-(6-bromo-4-oxo-3,4-dihydrothieno[3,2-d]pyrimidin-2-yl)-3,6-dihydropyridine-1(2H)-carboxylate tert-Butyl(2S)-2-(6-bromo-4-oxo-3,4-dihydrothieno[3,2-d]pyrimidin-2-yl)-3,6-dihydropyridine-1(2H)-carboxylate (0.86 g, 51.1% ee) was fractionated by high performance liquid chromatography (column: CHIRALPAK IC (50 mm i.d.×500 mm L, manufactured by DAICEL CHEMICAL INDUSTRIES, LTD.), mobile phase: hexane/ethanol (900/100), flow rate: 80 mL/min, column temperature: 30° C.). tert-Butyl(2S)-2-(6-bromo-4-oxo-3,4-dihydrothieno[3,2-d]pyrimidin-2-yl)piperidine-1-carboxylate (0.54 g, 99.8% ee, retention time 10.16 min) and tert-butyl(2R)-2-(6-bromo-4-oxo-3,4-dihydrothieno[3,2-d]pyrimidin-2-yl)piperidine-1- carboxylate (0.20 g, >99.9% ee, retention time 7.31 min) were obtained under the above-mentioned high performance liquid chromatography conditions. The analysis was performed by high performance liquid chromatography (column: CHIRALPAK IC (4.6 mm i.d.×250 mm L, manufactured by DAICEL CHEMICAL INDUSTRIES, LTD.), mobile phase: hexane/ethanol (900/100), flow rate: 1 mL/min, column temperature: 30° C., detection 220 nm).

C) Production of 6-(5-methyl-1H-pyrazol-4-yl)-2-[(2S)-1,2,3,6-tetrahydropyridin-2-yl]thieno[3,2-d]pyrimidin-4 (3H)-one dihydrochloride tert-Butyl(2S)-2-(6-bromo-4-oxo-3,4-dihydrothieno[3,2-d]pyrimidin-2-yl)-3,6-dihydropyridine-1(2H)-carboxylate (900 mg) produced above, tert-butyl 3-methyl-4-(4,4,5,5-tetramethyl-1,3,2-dioxaborolan-2-yl)-1H-pyrazole-1-carboxylate (1.35 g), cesium carbonate (4.27 g), 1,2-dimethoxyethane (12 mL) and water (4 mL) were placed in a flask, and the atmosphere in the flask was purged with argon. [1,1'-Bis(diphenylphosphino)ferrocene]palladium(II) dichloride-dichloromethane complex (1:1)(80 mg) was added, the atmosphere in the flask was purged again with argon, and the mixture was stirred at 90° C. for 1 hr. The reaction mixture was poured into saturated aqueous sodium hydrogen carbonate, and the mixture was extracted with 3:1 ethyl acetate/tetrahydrofuran mixture. The obtained organic layer was successively washed with saturated aqueous sodium hydrogen carbonate and brine (20 mL), and dried over anhydrous magnesium sulfate. Insoluble material was filtered off, and the filtrate was concentrated under reduced pressure. The residue was purified by silica gel column chromatography (ethyl acetate/hexane), and the object fraction was concentrated under reduced pressure to give tert-butyl(2S)-2-{6-[1-(tert-butoxycarbonyl)-3-methyl-1H-pyrazol-4-yl]-4-oxo-3,4-dihydrothieno[3,2-d]pyrimidin-2-yl}-3,6-dihydropyridine-1(2H)-carboxylate as a white solid. To a solution of tert-butyl (2S)-2-{6-[1-(tert-butoxycarbonyl)-3-methyl-1H-pyrazol-4-yl]-4-oxo-3,4-dihydrothieno[3,2-d]pyrimidin-2-yl}-3,6-dihydropyridine-1(2H)-carboxylate produced above in methanol (15 mL) was added 10% hydrochloric acid/methanol solution (14 mL), and the mixture was stirred at 50° C. for 1 hr. After cooling to room temperature, the precipitated solid was collected by filtration to give the title compound (620 mg) as a white solid.

$^{1}$H-NMR (DMSO-$d_6$) δ 2.37-2.53 (4H, m), 2.71-2.86 (1H, m), 3.61-3.83 (2H, m), 4.34-4.51 (1H, m), 5.74-6.02 (2H, m), 7.36 (1H, s), 8.13 (1H, brs), 9.74 (1H, brs), 9.85-9.96 (1H, m), 12.89 (1H, brs).
MS(ESI+): [M+H]$^{+}$314.
MS(ESI+), found: 314.

Example 146

Production of 6-(5-methyl-1H-pyrazol-4-yl)-2-[(2R)-1,2,3,6-tetrahydropyridin-2-yl]thieno[3,2-d]pyrimidin-4 (3H)-one dihydrochloride In the same manner as in Example 145, step C, the title compound (88 mg) was obtained as a white solid from tert-butyl(2R)-2-(6-bromo-4-oxo-3,4-dihydrothieno[3,2-d]pyrimidin-2-yl)piperidine-1-carboxylate (117 mg) produced in Example 145, step B, tert-butyl 3-methyl-4-(4,4,5,5-tetramethyl-1,3,2-dioxaborolan-2-yl)-1H-pyrazole-1-carboxylate (175 mg), cesium carbonate (555 mg), [1,1'-bis(diphenylphosphino)ferrocene]palladium(II) dichloride-dichloromethane complex (1:1)(10 mg), 1,2-dimethoxyethane (3 mL), water (1 mL), 10% hydrochloric acid/methanol solution (2 mL) and methanol (3 mL).

$^{1}$H-NMR (DMSO-$d_6$) δ 2.38-2.48 (4H, m), 2.72-2.87 (1H, m), 3.61-3.85 (2H, m), 4.36-4.49 (1H, m), 5.76-6.02 (2H, m), 7.37 (1H, s), 8.12 (1H, s), 9.62-9.94 (2H, m), 12.88 (1H, brs).

Example 147

Production of 6-(5-methyl-1H-pyrazol-4-yl)-2-(piperazin-2-yl)thieno[3,2-d]pyrimidin-4 (3H)-one ditrifluoroacetate A) Production of di-tert-butyl 2-{[5-(1-benzyl-3-methyl-1H-pyrazol-4-yl)-2-(methoxycarbonyl)thiophen-3-yl]carbamoyl}piperazine-1,4-dicarboxylate In the same manner as in Example 123, step F, the title compound (250 mg) was obtained as a colorless solid from methyl 3-amino-5-(1-benzyl-3-methyl-1H-pyrazol-4-yl)thiophene-2-carboxylate (327 mg) produced in Example 123, step C, 1,4-bis(tert-butoxycarbonyl)piperazine-2-carboxylic acid (496 mg), 2-methylpropyl chlorocarbonate (205 mg), triethylamine (304 mg) and tetrahydrofuran (10 mL).

$^{1}$H-NMR (DMSO-$d_6$) δ 1.41 (9H, s), 1.57 (9H, s), 2.47 (3H, s), 2.92-3.10 (2H, m), 3.30-3.45 (4H, m), 3.80-3.90 (1H, m), 3.85 (3H, s), 5.24 (2H, s), 7.10-7.20 (1H, m), 7.26-7.40 (4H, m), 7.59 (1H, s), 8.07 (1H, s), 10.76 (1H, brs).

B) Production of di-tert-butyl 2-[6-(1-benzyl-3-methyl-1H-pyrazol-4-yl)-4-oxo-3,4-dihydrothieno[3,2-d]pyrimidin-2-yl]piperazine-1,4-dicarboxylate In the same manner as in Example 123, step G, the title compound (150 mg) was obtained as a colorless solid from di-tert-butyl 2-{[5-(1-benzyl-3-methyl-1H-pyrazol-4-yl)-2-(methoxycarbonyl)thiophen-3-yl]carbamoyl}piperazine-1,4-dicarboxylate (250 mg) produced above, 2M aqueous sodium hydroxide solution (1 mL), methanol (5 mL), and 1-ethyl-3-(3-dimethylaminopropyl)carbodiimide hydrochloride (1.92 g), 1-hydroxybenzotriazole (1.35 g), ammonium chloride (2.14 g), triethylamine (4.05 g), N,N-dimethylformamide (5 mL), and 2M aqueous sodium hydroxide solution (1 mL), and methanol (10 mL).

$^{1}$H-NMR (DMSO-$d_6$) δ 1.41 (9H, s), 1.58 (9H, s), 2.49 (3H, s), 3.20-3.50 (4H, m), 3.85-4.00 (2H, m), 5.07-5.17 (1H, m), 5.27 (2H, s), 7.12-7.20 (2H, m), 7.25-7.40 (4H, m), 7.61 (1H, s), 10.00 (1H, brs).

C) Production of 6-(5-methyl-1H-pyrazol-4-yl)-2-piperazin-2-ylthieno[3,2-d]pyrimidin-4 (3H)-one ditrifluoroacetate In the same manner as in Example 123, step H, 6-(5-methyl-1H-pyrazol-4-yl)-2-(piperazin-2-yl)thieno[3,2-d]pyrimidin-4 (3H)-one (90 mg) was obtained as a colorless solid from di-tert-butyl 2-[6-(1-benzyl-3-methyl-1H-pyrazol-4-yl)-4-oxo-3,4-dihydrothieno[3,2-d]pyrimidin-2-yl]piperazine-1,4-dicarboxylate (150 mg) produced above, formic acid (5 mL), and 20% palladium hydroxide-carbon (20 mg). This was dissolved in trifluoroacetic acid (5 mL), the mixture was concentrated under reduced pressure, and the residue was crystallized from diethyl ether to give the title compound (35 mg) as a colorless solid.

¹H-NMR (DMSO-d₆) δ 2.47 (3H, s), 3.05-3.12 (1H, m), 3.90-4.01 (4H, m), 4.22-4.32 (1H, m), 5.20-5.25 (1H, m), 7.44 (1H, s), 8.26 (1H, s).

Example 148

Production of 2-(2-azabicyclo[2.1.1]hex-1-yl)-6-(5-methyl-1H-pyrazol-4-yl)thieno[3,2-d]pyrimidin-4(3H)-one hydrochloride A) Production of tert-butyl 1-(6-bromo-4-oxo-3,4-dihydrothieno[3,2-d]pyrimidin-2-yl)-2-azabicyclo[2.1.1]hexane-2-carboxylate In the same manner as in Example 71, step A, the title compound (180 mg) was obtained as a colorless solid from 3-amino-5-bromothiophene-2-carboxamide (327 mg) produced in Example 1, step D, 2-(tert-butoxycarbonyl)-2-azabicyclo[2.1.1]hexane-1-carboxylic acid (455 mg), 2-methylpropyl chlorocarbonate (273 mg), triethylamine (202 mg) and tetrahydrofuran (10 mL), and 2M aqueous sodium hydroxide solution (1 mL) and methanol (5 mL).

¹H-NMR (DMSO-d₆) δ 1.02 (9H, brs), 1.70 (2H, dd, J=4.5, 1.7 Hz), 1.97 (2H, brs), 2.64 (1H, t, J=2.9 Hz), 3.34-3.38 (2H, m), 7.19 (1H, s).

B) Production of 2-(2-azabicyclo[2.1.1]hexan-1-yl)-6-(5-methyl-1H-pyrazol-4-yl)thieno[3,2-d]pyrimidin-4(3H)-one hydrochloride In the same manner as in Example 83, step C, the title compound (98 mg) was obtained as a colorless solid from tert-butyl 1-(6-bromo-4-oxo-3,4-dihydrothieno[3,2-d]pyrimidin-2-yl)-2-azabicyclo[2.1.1]hexane-2-carboxylate (150 mg) produced above, tert-butyl 3-methyl-4-(4,4,5,5-tetramethyl-1,3,2-dioxaborolan-2-yl)-1H-pyrazole-1-carboxylate (270 mg), cesium carbonate (290 mg), [1,1'-bis(diphenylphosphino)ferrocene]palladium(II) dichloride-dichloromethane complex (1:1)(18 mg), 1,2-dimethoxyethane (10 mL), water (1 mL), and 4M hydrochloric acid/ethyl acetate solution (2 mL) and methanol (10 mL).

¹H-NMR (DMSO-d₆) δ 1.80-1.92 (2H, m), 2.47 (3H, s), 2.68-2.82 (2H, m), 2.92-3.02 (1H, m), 3.28-3.40 (2H, m), 7.42 (1H, s), 8.12 (1H, s), 9.95 (2H, brs).

Example 149

Production of 2-[(cyclopentylamino)methyl]-6-(5-methyl-1H-pyrazol-4-yl)thieno[3,2-d]pyrimidin-4(3H)-one dihydrochloride A) Production of tert-butyl [(6-bromo-4-oxo-3,4-dihydrothieno[3,2-d]pyrimidin-2-yl)methyl]cyclopentylcarbamate In the same manner as in Example 71, step A, the title compound (620 mg) was obtained as a colorless solid from 3-amino-5-bromothiophene-2-carboxamide (431 mg) produced in Example 1, step D, N-(tert-butoxycarbonyl)-N-cyclopentylglycine (996 mg), 2-methylpropyl chlorocarbonate (0.531 mL), triethylamine (0.676 mL) and tetrahydrofuran (5 mL), 2M aqueous sodium hydroxide solution (4.88 mL) and ethanol (5 mL).

¹H-NMR (DMSO-d₆) δ 1.05-2.00 (17H, m), 3.63-4.52 (3H, m), 7.57 (1H, s), 12.42 (1H, brs).

B) Production of 2-[(cyclopentylamino)methyl]-6-(5-methyl-1H-pyrazol-4-yl)thieno[3,2-d]pyrimidin-4(3H)-one dihydrochloride In the same manner as in Example 83, step C, the title compound (242 mg) was obtained as a colorless solid from tert-butyl [(6-bromo-4-oxo-3,4-dihydrothieno[3,2-d]pyrimidin-2-yl)methyl]cyclopentylcarbamate (700 mg) produced above, tert-butyl 3-methyl-4-(4,4,5,5-tetramethyl-1,3,2-dioxaborolan-2-yl)-1H-pyrazole-1-carboxylate (1.01 g), cesium carbonate (1.07 g), [1,1'-bis(diphenylphosphino)ferrocene]palladium(II) dichloride-dichloromethane complex (1:1)(67.2 mg), 1,2-dimethoxyethane (5 mL), water (0.5 mL), 4M hydrochloric acid/ethyl acetate solution (1 mL) and methanol (4 mL).

¹H-NMR (DMSO-d₆) δ 1.46-1.61 (2H, m), 1.66-1.82 (4H, m), 1.91-2.06 (2H, m), 2.47 (3H, s), 3.56-3.73 (1H, m), 4.24 (2H, qd), 7.39 (1H, s), 8.11 (1H, s), 9.63 (2H, brs).

Example 150

Production of 2-[(1R,3S,4R,5S) or (1S,3S,4S,5S)-5-hydroxy-2-azabicyclo[2.2.1]hept-3-yl]-6-(5-methyl-1H-pyrazol-4-yl)thieno[3,2-d]pyrimidin-4(3H)-one dihydrochloride A) Production of tert-butyl(1R,3S,4R,5S) or (1S,3S,4S,5S)-5-hydroxy-3-[6-(5-methyl-1H-pyrazol-4-yl)-4-oxo-3,4-dihydrothieno[3,2-d]pyrimidin-2-yl]-2-azabicyclo[2.2.1]heptane-2-carboxylate In the same manner as in Example 2, step C, the title compound (87 mg) was obtained as a pale-brown solid from tert-butyl(1R,3S,4R,5S) or (1S,3S,4S,5S)-3-(6-bromo-4-oxo-3,4-dihydrothieno[3,2-d]pyrimidin-2-yl)-5-hydroxy-2-azabicyclo[2.2.1]heptane-2-carboxylate produced in Example 142, step B (100 mg), >99.9% ee, fraction eluted with hexane/ethanol (200/800), retention time 8.9 min) and tert-butyl 3-methyl-4-(4,4,5,5-tetramethyl-1,3,2-dioxaborolan-2-yl)-1H-pyrazole-1-carboxylate (139 mg), sodium carbonate (72 mg), 1,2-dimethoxyethane (3.0 mL) and water (1.5 mL) and [1,1'-bis(diphenylphosphino)ferrocene]palladium(II) dichloride-dichloromethane complex (1:1)(18 mg).

¹H-NMR (DMSO-d₆) δ 1.10-1.49 (11H, m), 1.88-2.23 (2H, m), 2.37-2.48 (3H, m), 2.57-2.67 (1H, m), 4.00-4.12 (1H, m), 4.24-4.40 (1H, m), 4.78-4.93 (1H, m), 5.01-5.17 (1H, m), 7.32-7.55 (1H, m), 7.77-8.36 (1H, m), 11.98-12.43 (1H, m), 12.80-13.12 (1H, m).

B) Production of 2-[(1R,3S,4R,5S) or (1S,3S,4S,5S)-5-hydroxy-2-azabicyclo[2.2.1]hept-3-yl]-6-(5-methyl-1H-pyrazol-4-yl)thieno[3,2-d]pyrimidin-4(3H)-one dihydrochloride In the same manner as in Example 108, the title compound (50 mg) was obtained as a white solid from tert-butyl(1R,3S,4R,5S) or (1S,3S,4S,5S)-5-hydroxy-3-[6-(5-methyl-1H-pyrazol-4-yl)-4-oxo-3,4-dihydrothieno[3,2-d]pyrimidin-2-yl]-2-azabicyclo[2.2.1]heptane-2-carboxylate (86 mg) produced in Example 150, step A and methanol (2.0 mL), 4M hydrochloric acid/ethyl acetate solution (0.436 mL).

¹H-NMR (DMSO-d₆) δ 1.39-1.51 (1H, m), 1.62-1.72 (1H, m), 1.78-1.88 (1H, m), 2.01-2.15 (1H, m), 2.46 (3H, s), 2.89-2.99 (1H, m), 4.00-4.13 (1H, m), 4.29-4.42 (1H, m), 4.93-5.01 (1H, m), 7.35 (1H, s), 8.08 (1H, s), 8.53-8.71 (1H, m), 9.46-9.65 (1H, m), 12.91-13.04 (1H, m).

Example 151

Production of 2-(cyclopentylmethyl)-6-(5-methyl-1H-pyrazol-4-yl)thieno[3,2-d]pyrimidin-4 (3H)-one

A) Production of 5-bromo-3-[(cyclopentylacetyl)amino]thiophene-2-carboxamide In the same manner as in Example 11, step A, the title compound (290 mg) was obtained as a yellow oil from 3-amino-5-bromothiophene-2-carboxamide (200 mg) produced in Example 1, step D and cyclopentylacetic acid (0.113 mL) and O-(7-azabenzotriazol-1-yl)-N,N,N',N'-tetramethyluronium hexafluorophosphate (413 mg) and N-ethyl-N-(1-methylethyl)propan-2-amine (0.316 mL) and N,N-dimethylformamide (2.0 mL).

$^1$H-NMR (CDCl$_3$) δ 1.13-1.30 (2H, m), 1.60 (4H, s), 1.81-1.94 (2H, m), 2.24-2.38 (1H, m), 2.39-2.45 (2H, m), 5.42 (2H, brs), 8.28 (1H, s), 10.86 (1H, brs).

B) Production of 6-bromo-2-(cyclopentylmethyl)thieno[3,2-d]pyrimidin-4 (3H)-one To 5-bromo-3-[(cyclopentylacetyl)amino]thiophene-2-carboxamide (290 mg) were added 2M aqueous sodium hydroxide solution (1.75 mL) and ethanol (3.0 mL), and the mixture was stirred at 70° C. for 2 hr. The reaction system was neutralized with 1M hydrochloric acid at 0° C. Water (2 mL) was added, and the precipitate was collected by filtration to give the title compound (165 mg) as a white solid.

$^1$H-NMR (DMSO-d$_6$) δ 1.12-1.28 (2H, m), 1.42-1.75 (6H, m), 2.24-2.35 (1H, m), 2.60 (2H, d, J=7.6 Hz), 7.57 (1H, s), 12.52 (1H, brs).

C) Production of 2-(cyclopentylmethyl)-6-(5-methyl-1H-pyrazol-4-yl)thieno[3,2-d]pyrimidin-4 (3H)-one In the same manner as in Example 2, step C, the title compound (57 mg) was obtained as a white solid from 6-bromo-2-(cyclopentylmethyl)thieno[3,2-d]pyrimidin-4 (3H)-one (160 mg) and tert-butyl 3-methyl-4-(4,4,5,5-tetramethyl-1,3,2-dioxaborolan-2-yl)-1H-pyrazole-1-carboxylate (315 mg), sodium carbonate (162 mg), 1,2-dimethoxyethane (3.0 mL) and water (1.5 mL) and [1,1'-bis(diphenylphosphino)ferrocene]palladium(II) dichloride-dichloromethane complex (1:1)(42 mg).

$^1$H-NMR (DMSO-d$_6$) δ 1.09-1.32 (2H, m), 1.40-1.78 (6H, m), 2.25-2.40 (1H, m), 2.45 (3H, brs), 2.61 (2H, d, J=7.4 Hz), 7.34 (1H, s), 7.73-8.37 (1H, m), 12.26 (1H, brs), 12.95 (1H, brs).

Example 152

Production of ethyl {2-[6-(5-methyl-1H-pyrazol-4-yl)-4-oxo-3,4-dihydrothieno[3,2-d]pyrimidin-2-yl]pyrrolidin-1-yl}acetate

A) Production of ethyl {2-[6-(1-benzyl-3-methyl-1H-pyrazol-4-yl)-4-oxo-3,4-dihydrothieno[3,2-d]pyrimidin-2-yl]pyrrolidin-1-yl}acetate A mixture of 6-(1-benzyl-3-methyl-1H-pyrazol-4-yl)-2-(pyrrolidin-2-yl)thieno[3,2-d]pyrimidin-4 (3H)-one (391 mg) produced in Example 124, step C, ethyl 2-bromoacetate (184 mg), N-ethyl-N-(1-methylethyl)propan-2-amine (258 mg) and N,N-dimethylformamide (5 mL) was stirred at 60° C. for 2 hr. Ethyl acetate (50 mL) and water (50 mL) were added, and the separated aqueous layer was extracted with ethyl acetate (10 mL×2). The combined organic layers were washed with brine (20 mL) and dried over anhydrous magnesium sulfate. Insoluble material was removed by filtration, the filtrate was concentrated under reduced pressure, and the residue was purified by basic silica gel column chromatography (ethyl acetate/hexane) to give the title compound (140 mg) as a colorless solid.

$^1$H-NMR (DMSO-d$_6$) δ 1.26 (3H, t, J=7.2 Hz), 1.73-2.12 (3H, m), 2.35-2.57 (1H, m), 2.49 (3H, s), 2.84 (1H, td, J=9.2, 6.6 Hz), 3.28-3.41 (1H, m), 3.41-3.64 (2H, m), 4.04 (1H, dd, J=9.5, 4.1 Hz), 4.18 (2H, q, J=7.2 Hz), 5.27 (2H, s), 7.16 (1H, s), 7.24-7.47 (5H, m), 7.62 (1H, s), 10.52 (1H, brs).

B) Production of ethyl {2-[6-(5-methyl-1H-pyrazol-4-yl)-4-oxo-3,4-dihydrothieno[3,2-d]pyrimidin-2-yl]pyrrolidin-1-yl}acetate In the same manner as in Example 123, step H, the title compound (13 mg) was obtained as a colorless solid from ethyl {2-[6-(1-benzyl-3-methyl-1H-pyrazol-4-yl)-4-oxo-3,4-dihydrothieno[3,2-d]pyrimidin-2-yl]pyrrolidin-1-yl}acetate (40 mg) produced above, palladium hydroxide (10 mg), and formic acid (5 mL).

$^1$H-NMR (DMSO-d$_6$) δ 1.27 (3H, t, J=6.9 Hz), 1.73-2.14 (3H, m), 2.39-2.54 (1H, m), 2.55 (3H, s), 2.84 (1H, td, J=9.2, 6.6 Hz), 3.36 (1H, ddd, J=8.9, 6.7, 2.5 Hz), 3.42-3.64 (2H, m), 4.05 (1H, dd, J=9.4, 4.1 Hz), 4.19 (2H, q, J=7.1 Hz), 7.22 (1H, s), 7.83 (1H, s).

Example 153

Production of 2-(decahydroisoquinolin-1-yl)-6-(5-methyl-1H-pyrazol-4-yl)thieno[3,2-d]pyrimidin-4 (3H)-one In the same manner as in Example 71, step A, tert-butyl 1-(6-bromo-4-oxo-3,4-dihydrothieno[3,2-d]pyrimidin-2-yl)octahydroisoquinoline-2 (1H)-carboxylate (180 mg) as a colorless solid from 3-amino-5-bromothiophene-2-carboxamide (0.22 g) produced in Example 1, step D, 2-(tert-butoxycarbonyl)-2-azabicyclo[2.1.1]hexane-1-carboxylic acid (0.57 g), 2-methylpropyl chlorocarbonate (0.27 g), triethylamine (0.20 g) and tetrahydrofuran (10 mL), and 2M aqueous sodium hydroxide solution (1 mL) and methanol (5 mL). In the same manner as in Example 83, step C, 2-(decahydroisoquinolin-1-yl)-6-(5-methyl-1H-pyrazol-4-yl)thieno[3,2-d]pyrimidin-4 (3H)-one hydrochloride was obtained from the compound obtained above, tert-butyl 3-methyl-4-(4,4,5,5-tetramethyl-1,3,2-dioxaborolan-2-yl)-1H-pyrazole-1-carboxylate (270 mg), cesium carbonate (290 mg), [1,1'-bis(diphenylphosphino)ferrocene]palladium(II) dichloride-dichloromethane complex (1:1)(18 mg), 1,2-dimethoxyethane (10 mL), water (1 mL), and 4M hydrochloric acid/ethyl acetate solution (2 mL) and methanol (10 mL). This was purified by basic silica gel column chromatography (methanol/ethyl acetate) to give the title compound (36 mg) as a colorless solid.

$^1$H-NMR (DMSO-d$_6$) δ 1.21-1.46 (8H, m), 1.48-1.70 (2H, m), 1.83-1.93 (1H, m), 2.13-2.23 (1H, m), 2.45 (3H, s), 2.65-2.85 (2H, m), 3.80-3.90 (1H, m), 7.36 (1H, s), 8.02 (1H, s).

Example 154

Production of 2-[2-(1-aminocyclopropyl)ethyl]-6-(5-methyl-1H-pyrazol-4-yl)thieno[3,2-d]pyrimidin-4 (3H)-one dihydrochloride In the same manner as in the below-mentioned Example 155, step G, the title compound (18 mg) was obtained as a white solid from 2-(trimethylsilyl)ethyl {1-[2-(6-bromo-4-oxo-3,4-dihydrothieno[3,2-d]pyrimidin-2-yl)ethyl]cyclopropyl}carbamate (57 mg) produced in Example 155, step F, tert-butyl 3-methyl-4-(4,4,5,5-tetramethyl-1,3,2-dioxaborolan-2-yl)-1H-pyrazole-1-carboxylate (77 mg), cesium carbonate (243 mg), [1,1'-bis(diphenylphosphino)ferrocene]palladium(II) dichloride-dichloromethane complex (1:1)(4.6 mg), 1,2-dimethoxyethane (3 mL), water (0.3 mL) and 10% hydrochloric acid/methanol solution (5 mL).

$^1$H-NMR (DMSO-$d_6$) δ 0.71-0.79 (2H, m), 0.88-0.96 (2H, m), 2.00-2.11 (2H, m), 2.45 (3H, s), 2.77-2.87 (2H, m), 7.33 (1H, s), 8.03 (1H, brs), 8.34 (3H, brs), 12.34 (1H, brs).

Example 155

Production of 2-(4-azaspiro[2.4]hept-5-yl)-6-(5-methyl-1H-pyrazol-4-yl)thieno[3,2-d]pyrimidin-4 (3H)-one dihydrochloride A) Production of ethyl 2-(diethoxyphosphoryl)hex-5-enoate Sodium hydride (60% in oil, 65.0 g) was suspended in tetrahydrofuran (800 mL) under a nitrogen atmosphere, and ethyl(diethoxyphosphoryl)acetate (200 g) was added dropwise at room temperature over 30 min. After the completion of the dropwise addition, the mixture was further stirred by a mechanical stirrer for 30 min. 4-Bromobut-1-ene (217 g) was added dropwise to the reaction mixture over 30 min. The reaction mixture was heated under reflux for 5 hr, allowed to cool to room temperature, and quenched by adding 1M aqueous ammonium chloride solution (300 mL). The mixture was concentrated under reduced pressure, to the residue were added water (500 mL) and diethylether (500 mL), and the mixture was partitioned. The aqueous layer was saturated with sodium chloride, and the mixture was extracted with diethylether (500 mL×2). The combined extracts were washed with brine, and dried over anhydrous sodium sulfate. Insoluble material was filtered off, and the filtrate was concentrated under reduced pressure to give a crude product (241.6 g) of the title compound as a yellow oil. This was used for the next reaction without further purification.

$^1$H-NMR (CDCl$_3$) δ 1.21-1.30 (9H, m), 1.80-2.15 (4H, m), 2.88-2.97 (1H, m), 4.05-4.20 (6H, m), 4.91-5.01 (2H, m), 5.65-5.73 (1H, m).

B) Production of 1-but-3-en-1-ylcyclopropanecarboxylic acid

Sodium hydride (60% in oil, 42 g) was suspended in toluene (500 mL) under a nitrogen atmosphere, and a solution of ethyl 2-(diethoxyphosphoryl)hex-5-enoate (241.6 g) produced above in toluene (200 mL) was added dropwise at room temperature over 1 hr. A catalytic amount of ethanol (0.6 mL) was added, and the reaction mixture was cooled to 0° C. in an ice bath. To the reaction mixture was added oxirane (176.6 g) in a flask cooled by dry ice/ethanol with a cannula. The ice bath was removed, and the reaction mixture was mildly heated under reflux for 6 hr. The reaction mixture was quenched by carefully adding 1M ammonium chloride (500 mL) at 0° C., and the mixture was extracted 3 times with diethyl ether (600 mL). The combined extracts were washed with saturated aqueous sodium hydrogen carbonate (400 mL), water (400 mL) and brine (400 mL), and dried over anhydrous sodium sulfate. Insoluble material was filtered off, and the filtrate was concentrated under reduced pressure. The obtained oil was dissolved in ethanol (500 mL), and an aqueous solution (500 mL) of sodium hydroxide (90.3 g) was added. The mixture was stirred, and heated under reflux for 12 hr. After cooling to room temperature, ethanol was evaporated under reduced pressure. The residue was cooled, and adjusted to pH 1 by adding dropwise concentrated hydrochloric acid while maintaining at 0° C. From the obtained suspension, the organic product was extracted 3 times with ethyl acetate (400 mL), and the combined extracts were washed with brine, and dried over anhydrous sodium sulfate. Insoluble material was filtered off, and the filtrate was concentrated under reduced pressure to give a crude product (88 g) of the title compound as a yellow oil. This was used for the next reaction without further purification.

$^1$H-NMR(CDCl$_3$) δ 1.92-2.37 (4H, m), 3.53-4.22 (4H, m), 5.02-5.06 (2H, m), 5.75-5.87 (1H, m), 7.81 (1H, brs).

C) Production of 2-(trimethylsilyl)ethyl(1-but-3-en-1-ylcyclopropyl) carbamate

The crude product (130.5 g) of 1-but-3-en-1-ylcyclopropanecarboxylic acid produced above was dissolved in tetrahydrofuran (1300 mL), and the mixture was cooled to 0° C. under a nitrogen atmosphere. Triethylamine (263 mL) and ethyl chlorocarbonate (152.0 g) were successively added, and the mixture was stirred at 0° C. for 1 hr. To the reaction mixture was added an aqueous solution (500 mL) of sodium azide (152 g), and the mixture was stirred at 0° C. for 2 hr. Ethyl acetate (500 mL) and water (300 mL) were added to the reaction mixture, and the mixture was partitioned. The organic layer was separated, and dried over anhydrous sodium sulfate. Insoluble material was filtered off, and the filtrate was concentrated under reduced pressure. The residue was dissolved in toluene (1000 mL), and the mixture was heated under reflux for 1 hr. 2-(Trimethylsilyl)ethanol (118 g) was added to the reaction mixture, and the mixture was further heated under reflux for 6 hr. The reaction mixture was diluted with ethyl acetate (600 mL), and the mixture was successively washed with saturated aqueous sodium hydrogen carbonate, water and brine, and dried over anhydrous sodium sulfate. Insoluble material was filtered off, and the filtrate was concentrated under reduced pressure. The residue was purified by silica gel column chromatography (ethyl acetate/petroleum ether) to give the title compound (148.0 g) as a yellow oil.

$^1$H-NMR (CDCl$_3$) δ 0.09 (9H, m), 0.65-1.00 (6H, m), 1.66-1.68 (2H, m), 2.18-2.24 (2H, m), 4.14 (2H, t, J=7.2 Hz), 4.96-5.07 (3H, m), 5.83-5.87 (1H, m).

D) Production of 2-(trimethylsilyl)ethyl 5-(hydroxymethyl)-4-azaspiro[2.4]heptane-4-carboxylate To a solution of 2-(trimethylsilyl)ethyl(1-but-3-en-1-ylcyclopropyl)carbamate (120.0 g) produced above in dichloromethane (1000 mL) was added 3-chlorobenzenecarboperoxoic acid (122.0 g), and the mixture was stirred at room temperature for 3 hr. The reaction mixture was diluted with dichloromethane (500 mL), and the mixture was washed successively with aqueous sodium thiosulfate solution (500 mL) and saturated aqueous sodium hydrogen carbonate (500 mL), and dried over anhydrous sodium sulfate. Insoluble material was filtered off, and the filtrate was concentrated under reduced pressure. The residue was dissolved in acetic acid, and the mixture was stirred at room temperature for 24 hr. The solvent was evaporated under reduced pressure, and the residue was purified by silica gel column chromatography (ethyl acetate/petroleum ether) to give the title compound (127.0 g) as a colorless oil.

$^1$H-NMR (CDCl$_3$) δ 0.01 (9H, s), 0.46-1.71 (11H, m), 3.64-3.69 (1H, m), 4.06-4.10 (3H, m).

E) Production of 4-{[2-(trimethylsilyl)ethoxy]carbonyl}-4-azaspiro[2.4]heptane-5-carboxylic acid To a solution of 2-(trimethylsilyl)ethyl 5-(hydroxymethyl)-4-azaspiro[2.4]heptane-4-carboxylate (42.0 g) produced above in acetone (600 mL) was added Jones reagent (257 mL). The obtained suspension was stirred at room temperature for 30 min and quenched by adding 2-propanol (30 mL). Insoluble material was filtered off. The organic layer was separated from the filtrate, and diluted with ethyl acetate, and the mixture was washed with water and brine and dried over anhydrous sodium sulfate. Insoluble material was filtered off, and the filtrate was concentrated under reduced pressure. The residue was purified by silica gel column chromatography (ethyl acetate/petroleum ether) to give a crude product (21.0 g) of the title compound as a yellow oil.

$^1$H-NMR (CDCl$_3$) δ 0.01-0.05 (9H, m), 0.47-0.96 (4H, m), 1.74-1.87 (2H, m), 2.03-2.51 (4H, m), 4.06-4.50 (3H, m), 9.60 (1H, s).

F) Production of 2-(trimethylsilyl)ethyl 5-(6-bromo-4-oxo-3,4-dihydrothieno[3,2-d]pyrimidin-2-yl)-4-azaspiro[2.4]heptane-4-carboxylate In the same manner as in Example 82, step A, the title compound (133 mg) was obtained was obtained as a white solid from 3-amino-5-bromothiophene-2-carboxamide (221 mg) produced in Example 1, step D, the crude product (571 mg) of 4-{[2-(trimethylsilyl)ethoxy]carbonyl}-4-azaspiro[2.4]heptane-5-carboxylic acid produced above, 2-methylpropyl chlorocarbonate (0.259 mL), triethylamine (0.418 mL) and tetrahydrofuran (10 mL), 2M aqueous sodium hydroxide solution (3 mL) and ethanol (10 mL).

$^1$H-NMR (DMSO-d$_6$) δ –0.15 (9H, s), 0.44-0.68 (4H, m), 1.20-2.37 (6H, m), 3.79-3.95 (2H, m), 4.84 (1H, dd, J=8.3 Hz, 3.6 Hz), 7.61 (1H, s), 12.70 (1H, brs).

In addition, 2-(trimethylsilyl)ethyl {1-[2-(6-bromo-4-oxo-3,4-dihydrothieno[3,2-d]pyrimidin-2-yl)ethyl]cyclopropyl}carbamate (57 mg) was obtained. It is considered that the crude product of 4-{[2-(trimethylsilyl)ethoxy]carbonyl}-4-azaspiro[2.4]heptane-5-carboxylic acid produced above contained 3-[1-({[2-(trimethylsilyl)ethoxy]carbonyl}amino)cyclopropyl]propanoic acid.

$^1$H-NMR (DMSO-d$_6$) δ –0.01 (9H, s), 0.58 (4H, d, J=14.4 Hz), 0.80-0.92 (2H, m), 1.79-1.91 (2H, m), 2.62-2.75 (2H, m), 3.91-4.02 (2H, m), 7.33 (1H, brs), 7.53 (1H, s), 12.52 (1H, brs).

G) Production of 2-(4-azaspiro[2.4]hept-5-yl)-6-(5-methyl-1H-pyrazol-4-yl)thieno[3,2-d]pyrimidin-4 (3H)-one dihydrochloride 2-(Trimethylsilyl)ethyl 5-(6-bromo-4-oxo-3,4-dihydrothieno[3,2-d]pyrimidin-2-yl)-4-azaspiro[2.4]heptane-4-carboxylate (133 mg) produced above, tert-butyl 3-methyl-4-(4,4,5,5-tetramethyl-1,3,2-dioxaborolan-2-yl)-1H-pyrazole-1-carboxylate (174 mg), cesium carbonate (553 mg), 1,2-dimethoxyethane (5 mL) and water (0.8 mL) were placed in a flask, and the atmosphere in the flask was purged with argon. [1,1'-Bis(diphenylphosphino)ferrocene]palladium(II) dichloride-dichloromethane complex (1:1)(10 mg) was added, the atmosphere in the flask was purged again with argon, and the mixture was stirred at 90° C. for 30 min. The reaction mixture was poured into saturated aqueous sodium hydrogen carbonate, and the mixture was extracted with ethyl acetate. The obtained organic layer was dried over anhydrous magnesium sulfate. Insoluble material was filtered off, and the filtrate was concentrated under reduced pressure. The residue was purified by silica gel column chromatography (ethyl acetate/hexane), and the object fraction was concentrated under reduced pressure to give 2-(trimethylsilyl)ethyl 5-{6-[1-(tert-butoxycarbonyl)-3-methyl-1H-pyrazol-4-yl]-4-oxo-3,4-dihydrothieno[3,2-d]pyrimidin-2-yl}-4-azaspiro[2.4]heptane-4-carboxylate as a pale-yellow white solid. To a solution of 2-(trimethylsilyl)ethyl 5-{6-[1-(tert-butoxycarbonyl)-3-methyl-1H-pyrazol-4-yl]-4-oxo-3,4-dihydrothieno[3,2-d]pyrimidin-2-yl}-4-azaspiro[2.4]heptane-4-carboxylate produced above in methanol (5 mL) was added 10% hydrochloric acid/methanol solution (5 mL), and the mixture was stirred at 60° C. overnight. The reaction mixture was concentrated under reduced pressure, 2-propanol (5 mL) was added to the residue, and the mixture was stirred at 80° C. for 30 min. After cooling to room temperature, a precipitated solid was collected by filtration to give the title compound (55 mg) as a white solid.

$^1$H-NMR (DMSO-d$_6$) δ 0.82-0.95 (2H, m), 1.19-1.36 (2H, m), 1.98-2.32 (3H, m), 2.46-4.89 (5H, m), 7.38 (1H, s), 8.10 (1H, s), 9.22 (1H, brs), 10.22 (1H, brs), 12.86 (1H, brs).

Example 156

Production of 6-(5-methyl-1H-pyrazol-4-yl)-2-[(2S)-4-piperidin-1-ylpyrrolidin-2-yl]thieno[3,2-d]pyrimidin-4 (3H)-one A) Production of tert-butyl(2S)-2-(6-bromo-4-oxo-3,4-dihydrothieno[3,2-d]pyrimidin-2-yl)-4-piperidin-1-ylpyrrolidine-1-carboxylate In the same manner as in Example 11, step A, tert-butyl (2S)-2-[(5-bromo-2-carbamoylthiophen-3-yl)carbamoyl]-4-piperidin-1-ylpyrrolidine-1-carboxylate was obtained as a pale-brown amorphous solid (132 mg) from 3-amino-5-bromothiophene-2-carboxamide (200 mg) produced in Example 1, step D and 1-(tert-butoxycarbonyl)-4-piperidin-1-yl-L-proline (270 mg) and O-(7-azabenzotriazol-1-yl)-N,N,N',N'-tetramethyluronium hexafluorophosphate (413 mg) and N-ethyl-N-(1-methylethyl)propan-2-amine (0.316 mL) and N,N-dimethylformamide (5.0 mL). To tert-butyl(2S)-2-[(5-bromo-2-carbamoylthiophen-3-yl)carbamoyl]-4-piperidin-1-ylpyrrolidine-1-carboxylate produced above were added 2M aqueous sodium hydroxide solution (0.52 mL) and ethanol (1.0 mL), and the mixture was stirred at 70° C. for 2 hr. The reaction system was neutralized with 1M hydrochloric acid at 0° C. The mixture was extracted with ethyl acetate, and the mixture was washed with brine, and dried over anhydrous sodium sulfate. Insoluble material was removed by filtration, and the filtrate was concentrated under reduced pressure. The residue was purified by silica gel column chromatography (ethyl acetate/hexane) to give the title compound (63 mg) as a pale-brown amorphous solid.

$^1$H-NMR (CDCl$_3$) δ 1.23-2.01 (16H, m), 2.21-2.43 (1H, m), 2.49-2.74 (4H, m), 3.18-3.32 (1H, m), 3.88-4.25 (3H, m), 7.27 (1H, s).

B) Production of 6-(5-methyl-1H-pyrazol-4-yl)-2-[(2S)-4-piperidin-1-ylpyrrolidin-2-yl]thieno[3,2-d]pyrimidin-4 (3H)-one In the same manner as in Example 2, step C, tert-butyl(2S)-2-[6-(5-methyl-1H-pyrazol-4-yl)-4-oxo-3,4-dihydrothieno

[3,2-d]pyrimidin-2-yl]-4-piperidin-1-ylpyrrolidine-1-carboxylate was obtained as a pale-brown solid (57 mg) from tert-butyl(2S)-2-(6-bromo-4-oxo-3,4-dihydrothieno[3,2-d]pyrimidin-2-yl)-4-piperidin-1-ylpyrrolidine-1-carboxylate (60 mg) and tert-butyl 3-methyl-4-(4,4,5,5-tetramethyl-1,3,2-dioxaborolan-2-yl)-1H-pyrazole-1-carboxylate (76 mg), sodium carbonate (40 mg), 1,2-dimethoxyethane (1.5 mL) and water (0.75 mL) and [1,1'-bis(diphenylphosphino)ferrocene]palladium(II) dichloride-dichloromethane complex (1:1)(10 mg). To a solution of tert-butyl(2S)-2-[6-(5-methyl-1H-pyrazol-4-yl)-4-oxo-3,4-dihydrothieno[3,2-d]pyrimidin-2-yl]-4-piperidin-1-ylpyrrolidine-1-carboxylate produced above in methanol (1.0 mL) was added, while stirring at room temperature, 4M hydrochloric acid/ethyl acetate solution (0.26 mL). After stirring the reaction system with heating at 50° C. for 3 hr, the reaction mixture was concentrated under reduced pressure, and to the residue were added ethyl acetate (1 mL) and saturated aqueous sodium hydrogen carbonate (0.5 mL). Insoluble material was filtered off, the filtrate was concentrated under reduced pressure, and the residue was purified by basic silica gel column chromatography (ethyl acetate/hexane and methanol/ethyl acetate). The obtained pale-yellow solid was crystallized from methanol/ethyl acetate/hexane to give the title compound (19 mg) as a white solid.

$^1$H-NMR (DMSO-$d_6$) δ 1.02-1.37 (2H, m), 1.51-1.64 (1H, m), 1.66-1.91 (4H, m), 2.09-2.25 (1H, m), 2.25-2.48 (6H, m), 2.53-2.64 (1H, m), 2.78-2.98 (2H, m), 3.16-3.25 (1H, m), 3.79-3.91 (1H, m), 7.34 (1H, s), 8.01 (1H, s).

Example 157

Production of 2-[(1S,5R)-2-azabicyclo[3.1.0]hex-1-yl]-6-(5-methyl-1H-pyrazol-4-yl)thieno[3,2-d]pyrimidin-4 (3H)-one dihydrochloride A) Production of (4S)-4-(2-chloroethyl)-1,3,2-dioxathiolane 2,2-dioxide To a solution of (2S)-butane-1,2,4-triol (10.0 g) and pyridine (15.2 mL) in acetonitrile (100 mL) was added thionyl chloride (34.4 mL) at 0° C., and the mixture was stirred at room temperature for 15 hr. Ethyl acetate (20 mL) and 0.1M hydrochloric acid (10 mL) were added to the reaction mixture, and the separated aqueous layer was extracted with ethyl acetate (10 mL×2). The combined organic layers were washed with brine (20 mL) and dried over anhydrous magnesium sulfate. Insoluble material was filtered off, and the filtrate was concentrated under reduced pressure. The residue was purified by silica gel column chromatography (ethyl acetate/hexane), and the object fraction was concentrated under reduced pressure to give (4S)-4-(2-chloroethyl)-1,3,2-dioxathiolane 2-oxide as a brown oil. A mixture of (4S)-4-(2-chloroethyl)-1,3,2-dioxathiolane 2-oxide produced above, sodium periodate (19.6 g), ruthenium chloride monohydrate (172 mg), acetonitrile (200 mL) and water (40 mL) was stirred at room temperature for 15 hr. Acetonitrile was evaporated under reduced pressure, and the aqueous layer was extracted with ethyl acetate (10 mL×2). The combined organic layers were washed with brine (20 mL) and dried over anhydrous magnesium sulfate. Insoluble material was filtered off, and the filtrate was concentrated under reduced pressure. The residue was purified by silica gel column chromatography (ethyl acetate/hexane), and the object fraction was concentrated under reduced pressure to give the title compound (14.2 g) as a colorless oil.

$^1$H-NMR (DMSO-$d_6$) δ 1.87-2.43 (2H, m), 3.62-3.87 (2H, m), 4.26-5.40 (3H, m).

B) Production of ethyl(1S,5R)-2-azabicyclo[3.1.0] hexane-1-carboxylate hydrochloride To a suspension of sodium hydride (3.21 g) in 1,2-dimethoxyethane (100 ml) were added (4S)-4-(2-chloroethyl)-1,3,2-dioxathiolane 2,2-dioxide (7.50 g) produced above and ethyl N-(diphenylmethylidene)glycinate (10.7 g) at 0° C., and the mixture was stirred for 15 hr under refluxing conditions. Water (100 ml) was added to the reaction mixture, and the mixture was extracted with ethyl acetate (100 ml). The organic layer was dried over anhydrous magnesium sulfate and the solvent was evaporated under reduced pressure. The residue was dissolved in diethylether (100 ml), 1M hydrochloric acid (48.2 mL) was added, and the mixture was stirred at room temperature for 15 hr. The separated aqueous layer was washed with ethyl acetate (100 mL), and the solvent was evaporated under reduced pressure. The residue was dissolved in ethanol (50 mL), potassium carbonate (5.55 g) was added, and the mixture was stirred at room temperature for 15 hr. Insoluble material was removed by filtration, and 4M hydrochloric acid/ethyl acetate solution (10 mL) was added to the filtrate. The solvent was evaporated under reduced pressure. To the residue were added ethyl acetate (8 mL) and ethanol (2 mL), and the precipitated solid was collected by filtration and washed with ethyl acetate to give the title compound (2.51 g) as a brown solid.

$^1$H-NMR (DMSO-$d_6$) δ 1.23 (3H, t, J=7.1 Hz), 1.48-1.73 (2H, m), 1.90-2.37 (3H, m), 2.87-3.02 (1H, m), 3.26-3.40 (1H, m), 4.13-4.26 (2H, m), 10.22 (2H, brs).

C) Production of (1S,5R)-2-(tert-butoxycarbonyl)-2-azabicyclo[3.1.0]hexane-1-carboxylic acid A solution of ethyl(1S,5R)-2-azabicyclo[3.1.0]hexane-1-carboxylate hydrochloride (1.50 g), di-tert-butyl dicarbonate (1.91 mL) and triethylamine (2.18 mL) in tetrahydrofuran (15 mL) was stirred at room temperature for 15 hr. Water (10 ml) was added to the reaction mixture, and the mixture was extracted with ethyl acetate (20 mL). The organic layer was dried over anhydrous magnesium sulfate. The solvent was evaporated under reduced pressure. The residue was dissolved in ethanol (7 mL), 8M aqueous sodium hydroxide solution (1 mL) was added, and the mixture was stirred at room temperature for 2 hr. The reaction mixture was acidified with 6M hydrochloric acid (1.5 mL) under ice-cooling, and the precipitated solid was collected by filtration to give the title compound (1.20 g) as a colorless solid.

$^1$H-NMR (DMSO-$d_6$) δ 0.99 (1H, t, J=5.3 Hz), 1.40 (9H, s), 1.72 (1H, dd, J=8.9, 4.7 Hz), 1.77-1.90 (1H, m), 1.95-2.06 (1H, m), 2.10-2.24 (1H, m), 3.22-3.46 (1H, m), 3.60 (1H, ddd, J=11.0, 9.4, 6.2 Hz), 12.35 (1H, brs).

D) Production of tert-butyl(1S,5R)-1-(6-bromo-4-oxo-3,4-dihydrothieno[3,2-d]pyrimidin-2-yl)-2-azabicyclo[3.1.0]hexane-2-carboxylate In the same manner as in Example 71, step A, the title compound (330 mg) was obtained as a colorless oil from 3-amino-5-bromothiophene-2-carboxamide (321 mg) produced in Example 1, step D, (1S,5R)-2-(tert-butoxycarbonyl)-2-azabicyclo[3.1.0]hexane-1-carboxylic acid (495 mg) produced above, 2-methylpropyl chlorocarbonate (0.283 mL), triethylamine (0.503 mL) and tetrahydrofuran (10 mL), 8M aqueous sodium hydroxide solution (1.00 mL) and ethanol (10 mL).

$^1$H-NMR (DMSO-$d_6$) δ 1.00-1.51 (10H, m), 1.87-2.05 (3H, m), 2.17-2.35 (1H, m), 3.22-3.31 (1H, m), 3.77 (1H, td, J=10.4, 4.0 Hz), 7.54 (1H, s), 12.65 (1H, brs).

E) Production of 2-[(1S,5R)-2-azabicyclo[3.1.0]hex-1-yl]-6-(5-methyl-1H-pyrazol-4-yl)thieno[3,2-d]pyrimidin-4 (3H)-one dihydrochloride In the same manner as in Example 83, step C, the title compound (145 mg) was obtained as a colorless solid from tert-butyl(1S,5R)-1-(6-bromo-4-oxo-3,4-dihydrothieno[3,2-d]pyrimidin-2-yl)-2-azabicyclo[3.1.0]hexane-2-carboxylate (301 mg) produced above, tert-butyl 3-methyl-4-(4,4,5,5-tetramethyl-1,3,2-dioxaborolan-2-yl)-1H-pyrazole-1-carboxylate (448 mg), cesium carbonate (474 mg), [1,1'-bis(diphenylphosphino)ferrocene]palladium(II) dichloride-dichloromethane complex (1:1)(29.9 mg), 1,2-dimethoxyethane (5 mL), water (0.5 mL), 4M hydrochloric acid/ethyl acetate solution (1 mL) and methanol (5 mL).

$^1$H-NMR (DMSO-$d_6$) δ 1.77 (2H, d, J=7.7 Hz), 2.05-2.30 (2H, m), 2.46 (3H, s), 2.64-2.76 (1H, m), 2.94-3.14 (1H, m), 3.33-3.48 (1H, m), 7.38 (1H, s), 8.12 (1H, s), 9.82 (1H, brs), 10.53 (1H, brs).

Example 158

Production of 2-[1-(2-hydroxyethyl)pyrrolidin-2-yl]-6-(5-methyl-1H-pyrazol-4-yl)thieno[3,2-d]pyrimidin-4 (3H)-one A) Production of 6-(1-benzyl-3-methyl-1H-pyrazol-4-yl)-2-[1-(2-hydroxyethyl)pyrrolidin-2-yl]thieno[3,2-d]pyrimidin-4 (3H)-one A mixture of ethyl {2-[6-(1-benzyl-3-methyl-1H-pyrazol-4-yl)-4-oxo-3,4-dihydrothieno[3,2-d]pyrimidin-2-yl]pyrrolidin-1-yl}acetate (80 mg) produced in Example 152, step A, sodium borohydride (63 mg), tetrahydrofuran (5 mL) and ethanol (5 mL) was stirred at room temperature for 2 hr. 1M Hydrochloric acid (2 mL) was added to the reaction mixture under ice-cooling, and the mixture was neutralized with 1M aqueous sodium hydroxide solution (2 mL), ethyl acetate (20 mL) and water (20 mL) were added, and the separated aqueous layer was extracted with ethyl acetate (10 mL×2). The combined organic layers were washed with brine (20 mL) and dried over anhydrous magnesium sulfate. Insoluble material was removed by filtration, the filtrate was concentrated under reduced pressure and the mixture was crystallized from diethylether to give the title compound (73 mg) as a white powder.

$^1$H-NMR (DMSO-$d_6$) δ 1.55-1.74 (2H, m), 1.82-2.06 (1H, m), 2.07-2.26 (1H, m), 2.27-2.47 (5H, m), 2.74-2.90 (1H, m), 3.17-3.35 (1H, m), 3.39-3.59 (3H, m), 5.20 (2H, s), 7.08 (1H, s), 7.18-7.39 (5H, m), 7.49 (1H, s).

B) Production of 2-[1-(2-hydroxyethyl)pyrrolidin-2-yl]-6-(5-methyl-1H-pyrazol-4-yl)thieno[3,2-d]pyrimidin-4 (3H)-one In the same manner as in Example 123, step H, the title compound (40 mg) was obtained as a colorless solid from 6-[1-benzyl-3-methyl-1H-pyrazol-4-yl]-2-[1-(2-hydroxyethyl)pyrrolidin-2-yl]thieno[3,2-d]pyrimidin-4 (3H)-one (73 mg) produced above, 20% palladium hydroxide-carbon (20 mg), and formic acid (5 mL).

$^1$H-NMR (DMSO-$d_6$) δ 1.69-1.98 (3H, m), 2.15-2.33 (1H, m), 2.58 (3H, s), 3.41 (1H, brs), 3.45-3.59 (1H, m), 3.65 (1H, dd, J=9.2, 5.1 Hz), 3.98-4.17 (4H, m), 4.75 (1H, brs), 7.34 (2H, s).

Example 159

Production of 2-[(1R,3S,4R,5R) or (1S,3S,4S,5R)-5-fluoro-2-azabicyclo[2.2.1]hept-3-yl]-6-(5-methyl-1H-pyrazol-4-yl)thieno[3,2-d]pyrimidin-4 (3H)-one dihydrochloride A) Production of tert-butyl(1R*,3S,4R*,5R)-3-(6-bromo-4-oxo-3,4-dihydrothieno[3,2-d]pyrimidin-2-yl)-5-fluoro-2-azabicyclo[2.2.1]heptane-2-carboxylate To a solution of (1R*,3S,4R*,5R)-2-(tert-butoxycarbonyl)-5-fluoro-2-azabicyclo[2.2.1]heptane-3-carboxylic acid (352 mg) and triethylamine (0.190 mL) in tetrahydrofuran (4 mL) was added 2-methylpropyl chlorocarbonate (0.178 mL) at 0° C., and the mixture was stirred at room temperature for 30 min. To the reaction system was added a solution of 3-amino-5-bromothiophene-2-carboxamide (200 mg) produced in Example 1, step D, in tetrahydrofuran (2 mL), and the mixture was stirred at 60° C. for 18 hr. Water was added to the reaction mixture, and the separated aqueous layer was extracted with ethyl acetate. The organic layer was washed with brine, and dried over anhydrous sodium sulfate. Insoluble material was filtered off, the filtrate was concentrated under reduced pressure, and the residue was purified by basic silica gel column chromatography (ethyl acetate/hexane). To the obtained pale-yellow solid (328 mg) were added 2M aqueous sodium hydroxide solution (1.81 mL) and ethanol (4.0 mL), and the mixture was stirred at 70° C. for 5 hr. The reaction system was neutralized with 1M hydrochloric acid at 0° C. To the reaction system was added water (2 mL), and the precipitate was collected by filtration to give the title compound (274 mg) as a colorless solid.

$^1$H-NMR (DMSO-$d_6$) δ 1.13 (5H, s), 1.39 (4H, s), 1.47-1.90 (2H, m), 2.01-2.21 (2H, m), 2.84-2.94 (1H, m), 4.02-4.11 (1H, m), 4.16-4.30 (1H, m), 4.91-5.20 (1H, m), 7.64-7.71 (1H, m), 12.67 (1H, brs).

B) Optical resolution of tert-butyl(1R*,3S,4R*,5R)-3-(6-bromo-4-oxo-3,4-dihydrothieno[3,2-d]pyrimidin-2-yl)-5-fluoro-2-azabicyclo[2.2.1]heptane-2-carboxylate tert-Butyl(1R*,3S,4R*,5R)-3-(6-bromo-4-oxo-3,4-dihydrothieno[3,2-d]pyrimidin-2-yl)-5-fluoro-2-azabicyclo[2.2.1]heptane-2-carboxylate (274 mg) was fractionated by high performance liquid chromatography (column: CHIRALPAK AD (50 mm i.d.×500 mm L, manufactured by DAICEL CHEMICAL INDUSTRIES, LTD.), mobile phase: hexane/ethanol (800/200), flow rate: 80 mL/min, column temperature: 30° C.). tert-Butyl(1R,3S,4R,5R) or (1S,3S,4S,5R)-3-(6-bromo-4-oxo-3,4-dihydrothieno[3,2-d]pyrimidin-2-yl)-5-fluoro-2-azabicyclo[2.2.1]heptane-2-carboxylate (130 mg, >99.9% ee, retention time 5.4 min) and tert-butyl (1R,3S,4R,5R) or (1S,3S,4S,5R)-3-(6-bromo-4-oxo-3,4-dihydrothieno[3,2-d]pyrimidin-2-yl)-5-fluoro-2-azabicyclo[2.2.1]heptane-2-carboxylate (127 mg, >99.9% ee, retention time 7.5 min) were obtained under the above-mentioned high performance liquid chromatography conditions. The analysis was performed by high performance liquid chromatography (column: CHIRALPAK AS-H (4.6 mm i.d.×250 mm L, C) Production of tert-butyl(1R,3S,4R,5R) or (1S,3S,
4S,5R)-5-fluoro-3-[6-(5-methyl-1H-pyrazol-4-yl)-4-
oxo-3,4-dihydrothieno[3,2-d]pyrimidin-2-yl]-2-
azabicyclo[2.2.1]heptane-2-carboxylate In the same manner as in Example 2, step C, the title compound (116 mg) was obtained as a pale-yellow solid from tert-butyl(1R,3S,4R,5R) or (1S,3S,4S,5R)-3-(6-bromo-4-oxo-3,4-dihydrothieno[3,2-d]pyrimidin-2-yl)-5-fluoro-2-azabicyclo[2.2.1]heptane-2-carboxylate (125 mg, >99.9% ee, retention time 5.4 min) produced in Example 159, step B and tert-butyl 3-methyl-4-(4,4,5,5-tetramethyl-1,3,2-dioxaborolan-2-yl)-1H-pyrazole-1-carboxylate (173 mg), sodium carbonate (89 mg), 1,2-dimethoxyethane (3.0 mL) and water (1.5 mL) and [1,1'-bis(diphenylphosphino)ferrocene]palladium(II) dichloride-dichloromethane complex (1:1)(23 mg).
$^1$H-NMR (DMSO-d$_6$) δ 1.14 (5H, s), 1.40 (4H, s), 1.48-1.87 (2H, m), 2.04-2.23 (2H, m), 2.46 (3H, brs), 2.83-2.95 (1H, m), 4.02-4.14 (1H, m), 4.16-4.32 (1H, m), 4.89-5.21 (1H, m), 7.39-7.51 (1H, m), 7.77-8.37 (1H, m), 12.38 (1H, brs), 12.96 (1H, brs).

D) Production of 2-[(1R,3S,4R,5R) or (1S,3S,4S,
5R)-5-fluoro-2-azabicyclo[2.2.1]hept-3-yl]-6-(5-
methyl-1H-pyrazol-4-yl)thieno[3,2-d]pyrimidin-4
(3H)-one dihydrochloride In the same manner as in Example 108, the title compound (66 mg) was obtained as a white solid from tert-butyl(1R,3S,4R,5R) or (1S,3S,4S,5R)-5-fluoro-3-[6-(5-methyl-1H-pyrazol-4-yl)-4-oxo-3,4-dihydrothieno[3,2-d]pyrimidin-2-yl]-2-azabicyclo[2.2.1]heptane-2-carboxylate (115 mg) produced in Example 159, step C and methanol (2.0 mL), 4M hydrochloric acid/ethyl acetate solution (0.581 mL).
$^1$H-NMR (DMSO-d$_6$) δ 1.75-1.98 (3H, m), 2.46 (3H, s), 2.53-2.64 (1H, m), 3.18-3.25 (1H, m), 4.20-4.33 (2H, m), 4.93-5.19 (1H, m), 7.35 (1H, s), 8.09 (1H, s), 8.62 (1H, brs), 10.04 (1H, brs), 12.95 (1H, brs).

Example 160

Production of 2-[(1R,3S,4R,5R) or (1S,3S,4S,5R)-5-
fluoro-2-azabicyclo[2.2.1]hept-3-yl]-6-(5-methyl-
1H-pyrazol-4-yl)thieno[3,2-d]pyrimidin-4 (3H)-one
dihydrochloride A) Production of tert-butyl(1R,3S,4R,5R) or (1S,3S,
4S,5R)-5-fluoro-3-[6-(5-methyl-1H-pyrazol-4-yl)-4-
oxo-3,4-dihydrothieno[3,2-d]pyrimidin-2-yl]-2-
azabicyclo[2.2.1]heptane-2-carboxylate tert-Butyl(1R,3S,4R,5R) or (1S,3S,4S,5R)-3-(6-bromo-4-oxo-3,4-dihydrothieno[3,2-d]pyrimidin-2-yl)-5-fluoro-2-azabicyclo[2.2.1]heptane-2-carboxylate (125 mg, >99.9% ee, retention time 7.5 min) produced in Example 159, step B and tert-butyl 3-methyl-4-(4,4,5,5-tetramethyl-1,3,2-dioxaborolan-2-yl)-1H-pyrazole-1-carboxylate (173 mg), sodium carbonate (89 mg), 1,2-dimethoxyethane (3.0 mL) and water (1.5 mL) were placed in a flask, and the atmosphere in the flask was purged with argon. [1,1'-Bis(diphenylphosphino)ferrocene]palladium(II) dichloride-dichloromethane complex (1:1)(23 mg) was added, and the atmosphere in the flask was purged again with argon. The reaction system was stirred at 100° C. for 3 hr, and water was added. The mixture was extracted with ethyl acetate, and the extract was concentrated under reduced pressure. The residue was purified by silica gel column chromatography (ethyl acetate/hexane) to give the title compound (108 mg) as a pale-yellow solid.
$^1$H-NMR (DMSO-d$_6$) δ 1.14 (5H, s), 1.40 (4H, s), 1.50-1.87 (2H, m), 2.04-2.23 (2H, m), 2.39-2.48 (3H, m), 2.86-2.95 (1H, m), 4.03-4.12 (1H, m), 4.18-4.32 (1H, m), 4.92-5.18 (1H, m), 7.37-7.49 (1H, m), 7.82-8.33 (1H, m), 12.29-12.47 (1H, m), 12.88-13.02 (1H, m).

B) Production of 2-[(1R,3S,4R,5R) or (1S,3S,4S,
5R)-5-fluoro-2-azabicyclo[2.2.1]hept-3-yl]-6-(5-
methyl-1H-pyrazol-4-yl)thieno[3,2-d]pyrimidin-4
(3H)-one dihydrochloride To a solution of tert-butyl(1R,3S,4R,5R) or (1S,3S,4S,5R)-5-fluoro-3-[6-(5-methyl-1H-pyrazol-4-yl)-4-oxo-3,4-dihydrothieno[3,2-d]pyrimidin-2-yl]-2-azabicyclo[2.2.1]heptane-2-carboxylate (105 mg) produced in Example 160, step A, in methanol (2.0 mL) was added 4M hydrochloric acid/ethyl acetate solution (0.53 mL) at room temperature with stirring. The reaction system was stirred with heating at 50° C. for 30 min, and the precipitate was collected by filtration and washed with ethyl acetate to give the title compound (65 mg) as a colorless solid.
$^1$H-NMR (DMSO-d$_6$) δ 1.71-2.00 (3H, m), 2.46 (3H, s), 2.51-2.61 (1H, m), 3.18-3.27 (1H, m), 4.17-4.33 (2H, m), 4.93-5.19 (1H, m), 7.35 (1H, s), 8.09 (1H, s), 8.63 (1H, brs), 9.88 (1H, brs), 12.92 (1H, brs).
MS(ESI+): [M+H]$^+$346.
MS(ESI+), found: 346.

Example 161

Production of 2-[(2S)-piperidin-2-yl]-6-[5-(trifluo-
romethyl)-1H-pyrazol-4-yl]thieno[3,2-d]pyrimidin-4
(3H)-one hydrochloride tert-butyl(2S)-2-(6-bromo-4-oxo-3,4-dihydrothieno[3,2-d]pyrimidin-2-yl)piperidine-1-carboxylate (1.41 g) produced in Example 83, step B, [3-(trifluoromethyl)-1-trityl-1H-pyrazol-4-yl]boronic acid (1.72 g), sodium carbonate (902 mg), ethanol (15 mL) and water (3 mL) were placed in a flask, and the atmosphere in the flask was purged with argon. Tetrakis(triphenylphosphine)palladium(0) (197 mg) was added, the atmosphere in the flask was purged again with argon, and the mixture was stirred at 80° C. for 15 hr. Ethyl acetate (20 mL) and water (10 mL) were added to the reaction mixture, and the separated aqueous layer was extracted with ethyl acetate (10 mL×2). The combined organic layers were washed with brine (20 mL) and dried over anhydrous magnesium sulfate. Insoluble material was filtered off, and the filtrate was concentrated under reduced pressure. The residue was purified by basic silica gel column chromatography (ethyl acetate/hexane), and the object fraction was concentrated under reduced pressure to give tert-butyl(2S)-2-{4-oxo-6-[3-(trifluoromethyl)-1-trityl-1H-pyrazol-4-yl]-3,4-dihydrothieno[3,2-d]pyrimidin-2-yl}piperidine-1-carboxylate as a colorless oil. To a solution of tert-butyl(2S)-2-{4-oxo-6-[3-(trifluoromethyl)-1-trityl-1H-pyrazol-4-yl]-3,4-dihydrothieno[3,2-d]pyrimidin-2-yl}piperidine-1-carboxylate produced above in methanol (4 mL) was added 4M hydrochloric acid/ethyl acetate solution (1 mL), and the mixture was stirred at 60° C. for 15 hr. The precipitated solid was collected by filtration to give the title compound (530 mg) as a colorless solid.

$^1$H-NMR (DMSO-d$_6$) δ 1.47-1.93 (5H, m), 2.23-2.36 (1H, m), 2.95-3.11 (1H, m), 3.28-3.34 (1H, m), 4.22-4.34 (1H, m), 7.39 (1H, s), 8.64 (1H, s), 9.13 (1H, brs), 9.78 (1H, brs), 13.04 (1H, brs), 14.30 (1H, brs).

MS(ESI+): [M+H]$^+$370.
MS(ESI+), found: 370.

Example 162

Production of 6-(5-ethyl-1H-pyrazol-4-yl)-2-[(2S)-piperidin-2-yl]thieno[3,2-d]pyrimidin-4 (3H)-one dihydrochloride A) Production of N,N-dimethyl-1H-pyrazole-1-sulfonamide Pyrazole (12 g) was dissolved in tetrahydrofuran (200 mL), sodium hydride (60% in oil, 8.46 g) was added at 0° C. with stirring under a nitrogen atmosphere. After 20 min, dimethylsulfamoyl chloride (17 mL) was added dropwise, and the mixture was further stirred at the same temperature for 1 hr, and at room temperature for 1 hr. The reaction mixture was poured into saturated aqueous sodium hydrogen carbonate (400 mL), the mixture was extracted with ethyl acetate (400 mL), and the extract was dried over anhydrous magnesium sulfate. Insoluble material was filtered off, and the filtrate was concentrated under reduced pressure. The residue was purified by silica gel column chromatography (ethyl acetate/hexane), and the object fraction was concentrated under reduced pressure to give the title compound (25.3 g) as a colorless oil.

$^1$H-NMR (CDCl$_3$) δ 2.95 (6H, s), 6.40 (1H, m), 7.75 (1H, m), 7.99 (1H, d, J=2.7 Hz).

B) Production of 5-ethyl-N,N-dimethyl-1H-pyrazole-1-sulfonamide

N,N-dimethyl-1H-pyrazole-1-sulfonamide (25.3 g) produced above was dissolved in tetrahydrofuran (200 mL), and the mixture was cooled to −78° C. 1.6M n-Butyllithium/hexane solution (99 mL) was added dropwise with stirring. After the completion of the dropwise addition, the mixture was stirred for 30 min and iodoethane (12.8 mL) was added dropwise. The reaction mixture was further stirred for 30 min, and allowed to warm to room temperature. After 1 hr, since stirring became difficult due to precipitation, tetrahydrofuran (200 mL) was added to dissolve the precipitate. After stirring for 2 hr, the reaction mixture was poured into saturated aqueous sodium hydrogen carbonate (600 mL), and the mixture was extracted twice with ethyl acetate (400 mL), and the combined extracts were dried over anhydrous magnesium sulfate. Insoluble material was filtered off, and the filtrate was concentrated under reduced pressure. The residue was purified by silica gel column chromatography (ethyl acetate/hexane), and the object fraction was concentrated under reduced pressure to give the title compound (19.8 g) as a colorless oil.

$^1$H-NMR (CDCl$_3$) δ 1.30 (3H, t, J=7.8 Hz), 2.94 (2H, dd, J=15.0 Hz, 7.5 Hz), 3.03 (6H, s), 6.13 (1H, brs), 7.55 (1H, brs).

C) Production of 4-bromo-5-ethyl-N,N-dimethyl-1H-pyrazole-1-sulfonamide

5-Ethyl-N,N-dimethyl-1H-pyrazole-1-sulfonamide (19.8 g) produced above was dissolved in tetrahydrofuran (300 mL), and 1-bromopyrrolidine-2,5-dione (20.8 g) was added. The mixture was stirred at 50° C. for 2 hr. The reaction mixture was concentrated under reduced pressure, and the residue was poured into saturated aqueous sodium hydrogen carbonate, and the mixture was extracted with ethyl acetate (400 mL). The extract was washed with brine, and dried over anhydrous magnesium sulfate. Insoluble material was filtered off, and the filtrate was concentrated under reduced pressure. The residue was purified by silica gel column chromatography (ethyl acetate/hexane), and the object fraction was concentrated under reduced pressure to give the title compound (26.2 g) as a yellow oil.

$^1$H-NMR (CDCl$_3$) δ 1.24 (3H, t, J=7.5 Hz), 2.97 (2H, dd, J=15.0 Hz, 7.8 Hz), 3.06 (6H, s), 7.54 (1H, s).

D) Production of 5-ethyl-N,N-dimethyl-4-(4,4,5,5-tetramethyl-1,3,2-dioxaborolan-2-yl)-1H-pyrazole-1-sulfonamide 4-Bromo-5-ethyl-N,N-dimethyl-1H-pyrazole-1-sulfonamide (13.0 g) produced above, 4,4,4',4',5,5,5',5'-octamethyl-2,2'-bi-1,3,2-dioxaborolane (12.3 g), potassium acetate (13.6 g) and 1,2-dimethoxyethane (300 mL) were placed in a flask, and the atmosphere in the flask was purged with argon. [1,1'-Bis(diphenylphosphino)ferrocene]palladium(II) dichloride-dichloromethane complex (1:1)(3.76 g) was added, the atmosphere in the flask was purged again with argon, and the mixture was stirred at 90° C. overnight. The reaction mixture was allowed to cool to room temperature, and the insoluble material was filtered off. The filtrate was concentrated under reduced pressure, to the residue was added 1:1 ethyl acetate/hexane solution, and the insoluble material was filtered off. The filtrate was concentrated under reduced pressure, and the residue was purified by silica gel column chromatography (ethyl acetate/hexane). The object fraction was concentrated under reduced pressure, and the obtained residue was left standing at room temperature overnight. The precipitate was collected by filtration, and washed with hexane to give the title compound (6.32 g) as a white solid.

$^1$H-NMR (CDCl$_3$) δ 1.25 (3H, t, J=7.5 Hz), 1.31 (12H, s), 3.03 (6H, s), 3.17 (2H, dd, J=15.0, 7.5 Hz), 7.75 (1H, s).

E) Production of 6-(5-ethyl-1H-pyrazol-4-yl)-2-[(2S)-piperidin-2-yl]thieno[3,2-d]pyrimidin-4 (3H)-one dihydrochloride 5-Ethyl-N,N-dimethyl-4-(4,4,5,5-tetramethyl-1,3,2-dioxaborolan-2-yl)-1H-pyrazole-1-sulfonamide (658 mg) produced above, tert-butyl(2S)-2-(6-bromo-4-oxo-3,4-dihydrothieno[3,2-d]pyrimidin-2-yl)piperidine-1-carboxylate (414 mg) produced in Example 83, step B, cesium carbonate (1.96 g), 1,2-dimethoxyethane (6 mL) and water (2 mL) were placed in a flask, and the atmosphere in the flask was purged with argon. [1,1'-Bis(diphenylphosphino)ferrocene]palladium(II) dichloride-dichloromethane complex (1:1)(37 mg) was added, the atmosphere in the flask was purged again with argon, and the mixture was stirred at 90° C. for 1 hr. The reaction mixture was poured into saturated aqueous sodium hydrogen carbonate, and the mixture was extracted with 3:1 ethyl acetate/tetrahydrofuran. The obtained organic layer was successively washed with saturated aqueous sodium hydrogen carbonate and brine, and dried over anhydrous magnesium sulfate. Insoluble material was filtered off, and the filtrate was concentrated under reduced pressure. The residue was purified by basic silica gel column chromatography (methanol/ethyl acetate), and the object fraction was concentrated under reduced pressure to give tert-butyl(2S)-2-{6-[1-

(dimethylsulfamoyl)-5-ethyl-1H-pyrazol-4-yl]-4-oxo-3,4-dihydrothieno[3,2-d]pyrimidin-2-yl}piperidine-1-carboxylate as a white solid. To a solution of tert-butyl(2S)-2-{6-[1-(dimethylsulfamoyl)-5-ethyl-1H-pyrazol-4-yl]-4-oxo-3,4-dihydrothieno[3,2-d]pyrimidin-2-yl}piperidine-1-carboxylate produced above in methanol (10 mL) was added 10% hydrochloric acid/methanol solution (8 mL), and the mixture was stirred at 50° C. for 1 hr. The reaction mixture was allowed to cool to room temperature, and ethyl acetate (10 mL) was added. The precipitated solid was collected by filtration to give the title compound (136 mg) as a white solid.

$^1$H-NMR (DMSO-d$_6$) δ 1.25 (3H, t, J=7.6 Hz), 1.50-1.92 (5H, m), 2.24-2.33 (1H, m), 2.87 (2H, q, J=7.6 Hz), 2.96-3.11 (1H, m), 3.29-3.40 (1H, m), 4.15-4.29 (1H, m), 7.32 (1H, s), 8.09 (1H, s), 9.06-9.22 (1H, m), 9.40-9.52 (1H, m), 12.82 (1H, brs).

Example 163

Production of 2-{2-[6-(5-methyl-1H-pyrazol-4-yl)-4-oxo-3,4-dihydrothieno[3,2-d]pyrimidin-2-yl]pyrrolidin-1-yl}acetamide A) Production of 2-{2-[6-(1-benzyl-3-methyl-1H-pyrazol-4-yl)-4-oxo-3,4-dihydrothieno[3,2-d]pyrimidin-2-yl]pyrrolidin-1-yl}acetamide A mixture of ethyl {2-[6-(1-benzyl-3-methyl-1H-pyrazol-4-yl)-4-oxo-3,4-dihydrothieno[3,2-d]pyrimidin-2-yl]pyrrolidin-1-yl}acetate (80 mg) produced in Example 152, step A, 2M aqueous sodium hydroxide solution (1 mL) and methanol (5 mL) was stirred at 60° C. for 2 hr. 1M Hydrochloric acid (2 mL) was added to the reaction mixture under ice-cooling, ethyl acetate (20 mL) and water (20 mL) were added, and the separated aqueous layer was extracted with ethyl acetate (10 mL×2). The combined organic layers were washed with brine (20 mL) and dried over anhydrous magnesium sulfate. Insoluble material was removed by filtration, and the filtrate was concentrated under reduced pressure. The residue was dissolved in N,N-dimethylformamide (2 mL), 1-ethyl-3-(3-dimethylaminopropyl)carbodiimide hydrochloride (675 mg), 1-hydroxybenzotriazole (397 mg), ammonium chloride (628 mg) and triethylamine (1.19 g) were added, and the mixture was stirred at 80° C. for 18 hr. Ethyl acetate (20 mL) and water (20 mL) were added to the reaction mixture, and the separated aqueous layer was extracted with ethyl acetate (10 mL×2). The combined organic layers were washed with brine (20 mL) and dried over anhydrous magnesium sulfate. Insoluble material was removed by filtration, and the filtrate was concentrated under reduced pressure. The residue was purified by basic silica gel column chromatography (methanol/ethyl acetate) to give the title compound (60 mg) as a colorless solid.

$^1$H-NMR (DMSO-d$_6$) δ 1.81-2.04 (2H, m), 2.26-2.69 (2H, m), 2.50 (3H, s), 2.91-3.04 (1H, m), 3.19 (1H, d, J=16.4 Hz), 3.48 (1H, d, J=16.4 Hz), 3.62 (1H, brs), 3.84 (1H, dd, J=9.0, 6.2 Hz), 5.28 (2H, s), 5.58 (2H, brs), 7.12-7.24 (2H, m), 7.24-7.47 (4H, m), 7.65 (1H, s), 8.13 (1H, brs).

B) Production of 2-{2-[6-(5-methyl-1H-pyrazol-4-yl)-4-oxo-3,4-dihydrothieno[3,2-d]pyrimidin-2-yl]pyrrolidin-1-yl}acetamido In the same manner as in Example 123, step H, the title compound (22 mg) was obtained as a colorless solid from 2-{2-[6-(1-benzyl-3-methyl-1H-pyrazol-4-yl)-4-oxo-3,4-dihydrothieno[3,2-d]pyrimidin-2-yl]pyrrolidin-1-yl}acetamide (60 mg) produced above, 20% palladium hydroxide-carbon (20 mg), and formic acid (5 mL).

$^1$H-NMR (DMSO-d$_6$) δ 1.75-2.07 (4H, m), 2.43 (3H, s), 2.56-2.70 (1H, m), 2.88-3.05 (1H, m), 3.15-3.25 (2H, m), 3.72 (1H, brs), 7.19 (1H, brs), 7.32-7.41 (2H, m), 7.84 (1H, brs).

Example 164

Production of 2-[(2R)-1-azabicyclo[2.2.2]oct-2-yl]-6-(5-methyl-1H-pyrazol-4-yl)thieno[3,2-d]pyrimidin-4 (3H)-one trifluoroacetate A) Production of tert-butyl 4-(2-hydroxyethyl)piperidine-1-carboxylate To a mixed solution of 2-piperidin-4-ylethanol (5.0 g), water (12 mL) and 2-methylpropan-2-ol (9 mL) was added sodium hydroxide (1.6 g) at 0° C., and the reaction system was stirred for 30 min. di-tert-Butyl dicarbonate (8.5 g) was added by small portions, and the reaction system was stirred overnight at room temperature. The reaction system was poured into water (100 mL), and the mixture was extracted with ethyl acetate (200 mL). The extract was washed with water and brine, and concentrated to give the title compound (8.8 g).

$^1$H-NMR (CDCl$_3$) δ 1.19-1.23 (2H, m), 1.50 (9H, s), 1.59-1.61 (6H, m), 2.68-2.72 (2H, m), 3.68-3.73 (2H, m), 4.08 (2H, s).

B) Production of tert-butyl 4-(2-oxoethyl)piperidine-1-carboxylate

To a solution of pyridinium chlorochromate (125.0 g) and sodium acetate (48.0 g) in dichloromethane (300 mL) was added a solution of tert-butyl 4-(2-hydroxyethyl)piperidine-1-carboxylate (89.0 g) in dichloromethane (150 mL) at 0° C. The reaction system was stirred at 25° C. for 3 hr, diethyl ether (300 mL) was added, and insoluble material was collected by filtration by silica gel column chromatography, and washed with diethyl ether (1000 mL) and dichloromethane/diethyl ether (1000 mL). The filtrate was concentrated to give the title compound (60.0 g).

$^1$H-NMR (CDCl$_3$) δ 1.18-1.22 (2H, m), 1.46 (9H, s), 1.68-1.72 (2H, m), 2.08-2.10 (1H, m), 2.38-2.42 (2H, m), 2.73-2.77 (2H, m), 4.06-4.10 (2H, m), 9.78 (1H, s).

C) Production of tert-butyl 4-(2-cyano-2-hydroxyethyl)piperidine-1-carboxylate

To a solution of tert-butyl 4-(2-oxoethyl)piperidine-1-carboxylate (60 g) in diethylether (150 mL) were added a solution of sodium cyanide (32.4 g) in water (100 mL) and concentrated hydrochloric acid (55 mL) by small portions at 0° C. The reaction system was stirred for 4 hr, and the organic layer was washed with brine, dried, and concentrated to give the title compound (67.0 g).

$^1$H-NMR (CDCl$_3$) δ 1.20-1.24 (2H, m), 1.50 (9H, s), 1.79-1.83 (5H, m), 2.70-2.74 (2H, m), 3.50-3.54 (1H, m), 4.11-4.15 (2H, m), 4.56-4.60 (1H, m).

D) Production of tert-butyl 4-{2-cyano-2-[(methylsulfonyl)oxy]ethyl}piperidine-1-carboxylate To a solution of tert-butyl 4-(2-cyano-2-hydroxyethyl)piperidine-1-carboxylate (67.0 g) and triethylamine (35.0 g) in dichloromethane (500 mL) was slowly added a solution of methanesulfonyl chloride (36.3 g) in dichloromethane (200 mL). The reaction system was stirred at room temperature for 2 hr, and added to ice water (300 mL). The organic layer was dried over anhydrous sodium sulfate, insoluble material was removed by filtration, and the filtrate was concentrated to give the title compound (80.0 g).

$^1$H-NMR (CDCl$_3$) δ 1.18-1.22 (2H, m), 1.48 (9H, s), 1.73-1.77 (3H, m), 1.93-1.97 (1H, m), 2.03-2.07 (1H, m), 2.72-2.76 (2H, m), 3.23 (3H, s), 4.13-4.15 (2H, m), 5.27-5.29 (1H, m).

E) Production of 1-azabicyclo[2.2.2]octane-2-carbonitrile

To a solution of tert-butyl 4-{2-cyano-2-[(methylsulfonyl)oxy]ethyl}piperidine-1-carboxylate (80.0 g) in dichloromethane (200 mL) was added a solution of trifluoroacetic acid (137.0 g) in dichloromethane (200 mL), and the reaction system was stirred at room temperature overnight. The reaction system was concentrated, acetonitrile (200 mL) was added to the residue, and triethylamine (98.0 g) was slowly added at 0° C. The mixture was concentrated, the residue was diluted with dichloromethane, and the mixture was washed with brine, and dried over anhydrous sodium sulfate. Insoluble material was removed by filtration, and the filtrate was concentrated. The residue was purified by flash silica gel column chromatography (ethyl acetate/petroleum ether) to give the title compound (13.0 g) as a yellow oil.

$^1$H-NMR (CDCl$_3$) δ 1.58-1.62 (3H, m), 1.80-1.84 (3H, m), 2.00-2.02 (1H, m), 2.88-2.92 (3H, m), 3.23-3.27 (1H, m), 3.86-3.90 (1H, m).

F) Production of (2R)-1-azabicyclo[2.2.2]octane-2-carboxylic acid hydrochloride In the same manner as in a document (Mi, Y.; Corey, E. J. Tetrahedron Lett. 2006, 47, 2515-2516), optical resolution by a diastereomer salt method was performed to synthesis the title compound. That is, to a solution of 1-azabicyclo[2.2.2]octane-2-carbonitrile (20.0 g) in methanol (100 mL) was slowly added a solution of (+)-tartaric acid (22.0 g) in methanol (100 mL) at 0° C. The reaction system was stirred for 90 min, and concentrated, and the obtained solid was crystallized 4 times from methanol. The precipitate was filtered off, and the filtrate was concentrated. To the residue was added water (150 mL), and sodium hydrogen carbonate was added to reach pH 8. The mixture was extracted with dichloromethane (200 mL×3), and the extract was washed with brine, dried, and concentrated. The obtained white solid (15.0 g) was dissolved in methanol (100 mL), and a solution of (−)-tartaric acid (16.5 g) in methanol (100 mL) was slowly added at 0° C. The reaction system was stirred for 90 min, and concentrated, and the obtained solid was crystallized 4 times from methanol to give (−)-tartrate of (2R)-1-azabicyclo[2.2.2]octane-2-carbonitrile (4.0 g, >90% ee). To the obtained solid was added water (50 mL), and sodium hydrogen carbonate was added to reach pH 8. The mixture was extracted with dichloromethane (100 mL×3), and the extract was washed with brine, dried, and concentrated. The obtained white solid (1.75 g) was dissolved in concentrated hydrochloric acid (50 mL), and the reaction mixture was heated under reflux overnight. After concentration, to the residue was slowly added a solution of sodium hydroxide (1.04 g) in water (10 mL) at 0° C. The mixture was concentrated, concentrated hydrochloric acid (5 mL) was added, and the mixture was concentrated again. The obtained white solid was extracted with methanol (10 mL). Insoluble material was filtered off, and the filtrate was concentrated to give the title compound (0.80 g).

$^1$H-NMR (CDCl$_3$) δ 1.68-1.72 (4H, m), 1.88-1.92 (1H, m), 2.13-2.17 (2H, m), 3.32-3.36 (4H, m), 4.43 (1H, t, J=9.6 Hz), 9.89 (1H, s), 14.15 (1H, brs).

G) Production of 2-[(2R)-1-azabicyclo[2.2.2]oct-2-yl]-6-bromothieno[3,2-d]pyrimidin-4 (3H)-one To a solution of 3-amino-5-bromothiophene-2-carboxamide (200 mg) produced in Example 1, step D, (2R)-1-azabicyclo[2.2.2]octane-2-carboxylic acid hydrochloride (173 mg), and N-ethyl-N-(1-methylethyl)propan-2-amine (0.395 mL) in N,N-dimethylformamide (4.0 mL) was added O-(7-azabenzotriazol-1-yl)-N,N,N',N'-tetramethyluronium hexafluorophosphate (413 mg) at 0° C., and the reaction system was stirred at 70° C. for 20 hr. Water was added to the reaction mixture, and the mixture was extracted with ethyl acetate. The organic layer was washed with water and brine, and dried over anhydrous sodium sulfate. Insoluble material was filtered off, and the filtrate was concentrated under reduced pressure to give a mixture of (2R)—N-(5-bromo-2-carbamoylthiophen-3-yl)-1-azabicyclo[2.2.2]octane-2-carboxamide and the title compound. A mixed solution of (2R)—N-(5-bromo-2-carbamoylthiophen-3-yl)-1-azabicyclo[2.2.2]octane-2-carboxamide and the title compound produced above, and ethanol (2.0 mL) and 2M aqueous sodium hydroxide solution (1.8 mL) was stirred at 70° C. for 2 hr. The reaction mixture was neutralized with 1M hydrochloric acid at 0° C., and the mixture was extracted with ethyl acetate. The organic layer was washed with brine, and dried over anhydrous sodium sulfate. Insoluble material was filtered off, and the filtrate was concentrated under reduced pressure. The residue was purified by basic silica gel column chromatography (ethyl acetate/hexane and methanol/ethyl acetate) to give the title compound (114 mg) as a yellow solid.

$^1$H-NMR (DMSO-d$_6$) δ 1.39-1.52 (2H, m), 1.52-1.66 (2H, m), 1.73-1.85 (1H, m), 1.85-1.94 (1H, m), 2.19-2.32 (1H, m), 2.59-2.77 (2H, m), 2.83-2.97 (1H, m), 3.03-3.16 (1H, m), 3.93-4.01 (1H, m), 7.60 (1H, s).

H) Production of 2-[(2R)-1-azabicyclo[2.2.2]oct-2-yl]-6-(5-methyl-1H-pyrazol-4-yl)thieno[3,2-d]pyrimidin-4 (3H)-one trifluoroacetate 2-[(2R)-1-Azabicyclo[2.2.2]oct-2-yl]-6-bromothieno[3,2-d]pyrimidin-4 (3H)-one (110 mg) and tert-butyl 3-methyl-4-(4,4,5,5-tetramethyl-1,3,2-dioxaborolan-2-yl)-1H-pyrazole-1-carboxylate (199 mg), sodium carbonate (103 mg), 1,2-dimethoxyethane (2.0 mL) and water (1.0 mL) were placed in a flask, and the atmosphere in the flask was purged with argon. [1,1'-Bis(diphenylphosphino)ferrocene]palladium(II) dichloride-dichloromethane complex (1:1)(26 mg) was added, and the atmosphere in the flask was purged again with argon. The reaction system was stirred at 100° C. for 2 hr, brine was added, and the mixture was extracted with ethyl acetate. The extract was dried over anhydrous sodium sulfate, insoluble material was removed by filtration, and the filtrate was concentrated under reduced pressure. The residue was purified by silica gel column chromatography (ethyl acetate/hexane and methanol/ethyl acetate), and the obtained pale-brown solid (96 mg) was crystallized from ethyl acetate/hexane to give a crude product (50 mg) of 2-[(2R)-1-azabicyclo[2.2.2]oct-2-yl]-6-(5-methyl-1H-pyrazol-4-yl)thieno[3,2-d]pyrimidin-4 (3H)-one as a pale-brown solid. To a suspension of the crude product (50 mg) of 2-[(2R)-1- azabicyclo[2.2.2]oct-2-yl)-6-(5-methyl-1H-pyrazol-4-yl)thieno[3,2-d]pyrimidin-4 (3H)-one produced above in N,N-dimethylformamide (1.0 mL) were added triethylamine (0.020 mL) and di-tert-butyl dicarbonate (0.034 mL). The reaction mixture was stirred at room temperature for 18 hr, water was added, and the mixture was extracted with ethyl acetate. The extract was dried over anhydrous sodium sulfate, insoluble material was removed by filtration, and the filtrate was concentrated under reduced pressure. The residue was purified by silica gel column chromatography (ethyl acetate/hexane) to give tert-butyl 4-{2-[(2R)-1-azabicyclo[2.2.2]oct-2-yl]-4-oxo-3,4-dihydrothieno[3,2-d]pyrimidin-6-yl}-3-methyl-1H-pyrazole-1-carboxylate (position of Boc on pyrazole ring is unidentified) as a pale-yellow solid (22 mg). To tert-butyl 4-{2-[(2R)-1-azabicyclo[2.2.2]oct-2-yl]-4-oxo-3,4-dihydrothieno[3,2-d]pyrimidin-6-yl}-3-methyl-1H-pyrazole-1-carboxylate produced above were added water (0.50 mL) and trifluoroacetic acid (51.6 mg), and the reaction system was stirred at 90° C. for 30 min. The reaction system was concentrated under reduced pressure, and the residue was washed with methanol (2 mL) and ethyl acetate (2 mL) to give the title compound (4.0 mg) as an orange solid.

$^1$H-NMR (DMSO-d$_6$) δ 1.74-1.97 (4H, m), 2.06-2.29 (2H, m), 2.36-2.48 (4H, m), 3.22-3.29 (2H, m), 3.42-3.79 (2H, m), 4.67-4.81 (1H, m), 7.44 (1H, s), 7.86-8.29 (1H, m), 9.83 (1H, brs), 12.68 (1H, brs).

Example 165

Production of 2-(2-azabicyclo[2.1.1]hex-1-yl)-6-[5-(trifluoromethyl)-1H-pyrazol-4-yl]thieno[3,2-d]pyrimidin-4 (3H)-one dihydrochloride In the same manner as in Example 161, the title compound (12 mg) was obtained as a colorless solid from tert-butyl 1-(6-bromo-4-oxo-3,4-dihydrothieno[3,2-d]pyrimidin-2-yl)-2-azabicyclo[2.1.1]hexane-2-carboxylate (35.0 mg) produced in Example 148, step A, [3-(trifluoromethyl)-1-trityl-1H-pyrazol-4-yl]boronic acid (71.7 mg), sodium carbonate (22.5 mg), ethanol (5 mL), water (0.5 mL), tetrakis(triphenylphosphine)palladium(0) (4.90 mg), methanol (4 mL) and 4M hydrochloric acid/ethyl acetate solution (1 mL).

$^1$H-NMR (DMSO-d$_6$) δ 1.84-1.90 (2H, m), 2.72-2.81 (2H, m), 2.94-2.99 (1H, m), 3.30-3.38 (2H, m), 7.43 (1H, s), 8.63 (1H, s), 9.88-10.26 (3H, m), 13.03 (1H, brs), 14.26 (1H, brs).

Example 166

Production of 2-cyclohexyl-6-(5-methyl-1H-pyrazol-4-yl)thieno[3,2-d]pyrimidin-4 (3H)-one A) Production of 6-bromo-2-cyclohexylthieno[3,2-d]pyrimidin-4 (3H)-one To a mixed solution of 3-amino-5-bromothiophene-2-carboxamide (200 mg) produced in Example 1, step D, triethylamine (0.19 mL) and tetrahydrofuran (4.0 mL) was added cyclohexanecarbonyl chloride (0.18 mL) at 0° C., and the mixture was stirred at room temperature for 30 min. Water was poured into the reaction system, the mixture was extracted with ethyl acetate, and the extract was washed with brine, and dried over anhydrous sodium sulfate. Insoluble material was removed by filtration, and the filtrate was concentrated under reduced pressure to give 5-bromo-3-[(cyclohexylcarbonyl)amino]thiophene-2-carboxamide. To 5-bromo-3-[(cyclohexylcarbonyl)amino]thiophene-2-carboxamide produced above were added 2M aqueous sodium hydroxide solution (0.90 mL) and ethanol (2.0 mL), and the mixture was stirred at 70° C. for 2 hr. The reaction system was neutralized with 1M hydrochloric acid at 0° C. Water (2 mL)) was added, and the precipitate was collected by filtration to give the title compound (252 mg) as a white solid.

$^1$H-NMR (DMSO-d$_6$) δ 1.14-1.38 (3H, m), 1.44-1.62 (2H, m), 1.63-1.95 (5H, m), 2.55-2.67 (1H, m), 7.57 (1H, s), 12.45 (1H, brs).

B) Production of 2-cyclohexyl-6-(5-methyl-1H-pyrazol-4-yl)thieno[3,2-d]pyrimidin-4 (3H)-one In the same manner as in Example 2, step C, the title compound (158 mg) was obtained as a pale-yellow solid from 6-bromo-2-cyclohexylthieno[3,2-d]pyrimidin-4 (3H)-one (250 mg) and tert-butyl 3-methyl-4-(4,4,5,5-tetramethyl-1,3,2-dioxaborolan-2-yl)-1H-pyrazole-1-carboxylate (492 mg), sodium carbonate (254 mg), 1,2-dimethoxyethane (4.0 mL) and water (2.0 mL) and [1,1'-bis(diphenylphosphino)ferrocene]palladium(II) dichloride-dichloromethane complex (1:1)(65 mg).

$^1$H-NMR (DMSO-d$_6$) δ 1.11-1.97 (10H, m), 2.45 (3H, s), 2.54-2.68 (1H, m), 7.35 (1H, s), 7.95 (1H, brs), 12.20 (1H, brs), 12.96 (1H, brs).

Example 167

Production of 2-methyl-6-(5-methyl-1H-pyrazol-4-yl)thieno[3,2-d]pyrimidin-4 (3H)-one A) Production of 6-bromo-2-methylthieno[3,2-d]pyrimidin-4 (3H)-one In the same manner as in Example 166, step A, the title compound (131 mg) was obtained as a white solid from 3-amino-5-bromothiophene-2-carboxamide (200 mg) produced in Example 1, step D, triethylamine (0.19 mL), tetrahydrofuran (4.0 mL) and acetyl chloride (0.096 mL) and 2M aqueous sodium hydroxide solution (0.45 mL) and ethanol (2.0 mL).

$^1$H-NMR (DMSO-d$_6$) δ 2.36 (3H, s), 7.54 (1H, s), 12.55 (1H, brs).

B) Production of 2-methyl-6-(5-methyl-1H-pyrazol-4-yl)thieno[3,2-d]pyrimidin-4 (3H)-one In the same manner as in Example 2, step C, the title compound (74 mg) was obtained as a white solid from 6-bromo-2-methylthieno[3,2-d]pyrimidin-4 (3H)-one (130 mg) and tert-butyl 3-methyl-4-(4,4,5,5-tetramethyl-1,3,2-dioxaborolan-2-yl)-1H-pyrazole-1-carboxylate (327 mg), sodium carbonate (169 mg), 1,2-dimethoxyethane (3.0 mL) and water (1.5 mL) and [1,1'-bis(diphenylphosphino)ferrocene]palladium(II) dichloride-dichloromethane complex (1:1)(43 mg).

$^1$H-NMR (DMSO-d$_6$) δ 2.36 (3H, s), 2.44 (3H, s), 7.31 (1H, s), 7.98 (1H, brs), 12.30 (1H, brs), 12.96 (1H, brs).

Example 168

Production of 2-{[(2-hydroxy-2-methylpropyl)amino]methyl}-6-(5-methyl-1H-pyrazol-4-yl)thieno[3,2-d]pyrimidin-4 (3H)-one In the same manner as in Example 2, step B, 6-bromo-2-{[(2-hydroxy-2-methylpropyl)amino]methyl}thieno[3,2-d]

pyrimidin-4 (3H)-one (160 mg) was obtained as a white solid from 6-bromo-2-(chloromethyl)thieno[3,2-d]pyrimidin-4 (3H)-one (300 mg) produced in Example 2, step A, and 1-amino-2-methylpropan-2-ol (191 mg) and potassium carbonate (445 mg) and sodium iodide (16 mg) and N,N-dimethylformamide (5.0 mL). A mixture of 6-bromo-2-{[(2-hydroxy-2-methylpropyl)amino]methyl}thieno[3,2-d]pyrimidin-4 (3H)-one (130 mg) produced above, triethylamine (0.060 mL), di-tert-butyl dicarbonate (0.100 mL), N,N-dimethylpyridin-4-amine (4.78 mg) and N,N-dimethylformamide (2.0 mL) was stirred at 50° C. for 2 hr. The mixture was purified by basic silica gel column chromatography (ethyl acetate/hexane and methanol/ethyl acetate) to give tert-butyl [(6-bromo-4-oxo-3,4-dihydrothieno[3,2-d]pyrimidin-2-yl)methyl](2-hydroxy-2-methylpropyl)carbamate (position of Boc on pyrazole ring is unidentified) (96 mg) as a white solid. In the same manner as in Example 2, step C, tert-butyl(2-hydroxy-2-methylpropyl){[6-(5-methyl-1H-pyrazol-4-yl)-4-oxo-3,4-dihydrothieno[3,2-d]pyrimidin-2-yl]methyl}carbamate (30 mg) was obtained as a pale-yellow solid from tert-butyl [(6-bromo-4-oxo-3,4-dihydrothieno[3,2-d]pyrimidin-2-yl)methyl](2-hydroxy-2-methylpropyl)carbamate (95 mg) produced above and tert-butyl 3-methyl-4-(4,4,5,5-tetramethyl-1,3,2-dioxaborolan-2-yl)-1H-pyrazole-1-carboxylate (135 mg), sodium carbonate (70 mg), 1,2-dimethoxyethane (2.0 mL) and water (1.0 mL) and [1,1'-bis(diphenylphosphino)ferrocene]palladium(II) dichloride-dichloromethane complex (1:1)(18 mg). To a solution of tert-butyl(2-hydroxy-2-methylpropyl){[6-(5-methyl-1H-pyrazol-4-yl)-4-oxo-3,4-dihydrothieno[3,2-d]pyrimidin-2-yl]methyl}carbamate (30 mg) produced above in methanol (3.0 mL) was added, while stirring at room temperature, 4M hydrochloric acid/ethyl acetate solution (1.0 mL). The reaction system was stirred with heating at 50° C. for 5 hr, and concentrated under reduced pressure. The residue was purified by basic silica gel column chromatography (ethyl acetate/hexane and methanol/ethyl acetate), and the obtained pale-yellow solid was crystallized from methanol/ethyl acetate to give the title compound (13 mg) as a colorless solid.

$^1$H-NMR (DMSO-d$_6$) δ 1.09 (6H, s), 2.41 (2H, s), 2.45 (3H, s), 3.70 (2H, s), 4.38 (1H, brs), 7.36 (1H, s), 8.01 (1H, brs).

Example 169

Production of 2-{[(2-hydroxyethyl)(methyl)amino]methyl}-6-(5-methyl-1H-pyrazol-4-yl)thieno[3,2-d]pyrimidin-4 (3H)-one A) Production of 6-bromo-2-{[(2-hydroxyethyl)(methyl)amino]methyl}thieno[3,2-d]pyrimidin-4 (3H)-one In the same manner as in Example 2, step B, the title compound (128 mg) was obtained as a pale-brown solid from 6-bromo-2-(chloromethyl)thieno[3,2-d]pyrimidin-4 (3H)-one (300 mg) produced in Example 2, step A, and 2-(methylamino)ethanol (0.172 mL) and potassium carbonate (445 mg) and sodium iodide (16 mg) and N,N-dimethylformamide (5.0 mL).

$^1$H-NMR (DMSO-d$_6$) δ 2.22 (3H, s), 2.52-2.57 (2H, m), 3.50 (2H, t, J=5.5 Hz), 3.55 (2H, s), 4.63 (1H, s), 7.60 (1H, s), 12.10 (1H, brs).

B) Production of 2-{[(2-hydroxyethyl)(methyl)amino]methyl}-6-(5-methyl-1H-pyrazol-4-yl)thieno[3,2-d]pyrimidin-4 (3H)-one In the same manner as in Example 2, step C, the title compound (10 mg) was obtained as a pale-brown solid from 6-bromo-2-{[(2-hydroxyethyl)(methyl)amino]methyl}thieno[3,2-d]pyrimidin-4 (3H)-one (28 mg) and tert-butyl 3-methyl-4-(4,4,5,5-tetramethyl-1,3,2-dioxaborolan-2-yl)-1H-pyrazole-1-carboxylate (54 mg), sodium carbonate (28 mg), 1,2-dimethoxyethane (1.0 mL) and water (0.5 mL) and [1,1'-bis(diphenylphosphino)ferrocene]palladium(II) dichloride-dichloromethane complex (1:1)(7 mg).

$^1$H-NMR (DMSO-d$_6$) δ 2.24 (3H, s), 2.45 (3H, s), 2.55 (2H, t, J=5.6 Hz), 3.51 (2H, t, J=5.6 Hz), 3.55 (2H, s), 7.36 (1H, s), 7.92 (1H, brs), 12.98 (1H, brs).

Example 170

Production of 2-[(2S)-1-azabicyclo[2.2.2]oct-2-yl]-6-(5-methyl-1H-pyrazol-4-yl)thieno[3,2-d]pyrimidin-4 (3H)-one trifluoroacetate A) Production of (2S)-1-azabicyclo[2.2.2]octane-2-carboxylic acid hydrochloride In the same manner as in a document (Mi, Y.; Corey, E. J. Tetrahedron Lett. 2006, 47, 2515-2516), optical resolution by a diastereomer salt method was performed to synthesis the title compound. That is, to a solution of 1-azabicyclo[2.2.2]octane-2-carbonitrile (20.0 g) produced in Example 164, step E, in methanol (100 mL) was slowly added a solution of (+)-tartaric acid (22.0 g) in methanol (100 mL) at 0° C. The reaction system was stirred for 90 min, and concentrated, and the obtained solid was crystallized 4 times from methanol to give (+)-tartrate of (2S)-1-azabicyclo[2.2.2]octane-2-carbonitrile (3.0 g, >90% ee). To the obtained solid was added water (50 mL), and sodium hydrogen carbonate was added to reach pH 8. The mixture was extracted with dichloromethane (100 mL×3), and the extract was washed with brine, dried, and concentrated. The obtained white solid (1.4 g) was dissolved in concentrated hydrochloric acid (50 mL), and the reaction mixture was heated under reflux overnight. After concentration, to the residue was slowly added a solution of sodium hydroxide (0.83 g) in water (10 mL) at 0° C. The mixture was concentrated, concentrated hydrochloric acid (5 mL) was added, and the mixture was concentrated again. The obtained white solid was extracted with methanol (10 mL). Insoluble material was filtered off, and the filtrate was concentrated to give the title compound (1.7 g).

$^1$H-NMR (DMSO-d$_6$) δ 1.88-1.92 (5H, m), 2.13-2.17 (2H, m), 3.32-3.36 (4H, m), 4.43 (1H, t, J=9.6 Hz), 10.01 (1H, s), 14.10 (1H, brs).

B) Production of 2-[(2S)-1-azabicyclo[2.2.2]oct-2-yl]-6-bromothieno[3,2-d]pyrimidin-4 (3H)-one To a solution of 3-amino-5-bromothiophene-2-carboxamide (600 mg) produced in Example 1, step D, (2S)-1-azabicyclo[2.2.2]octane-2-carboxylic acid hydrochloride (520 mg), and N-ethyl-N-(1-methylethyl)propan-2-amine (1.19 mL) in N,N-dimethylformamide (10 mL) was added O-(7-azabenzotriazol-1-yl)-N,N,N',N'-tetramethyluronium hexafluorophosphate (1.24 g) at 0° C., and the reaction system was stirred at 70° C. for 20 hr. Water was added to the reaction mixture, and the separated aqueous layer was extracted with ethyl acetate. The organic layer was washed with water and brine, and dried over anhydrous sodium sulfate. Insoluble material was filtered off, and the filtrate was concentrated under reduced pressure to give a mixture of (2S)—N-(5-bromo-2-carbamoylthiophen-3-yl)-1-azabicyclo[2.2.2]octane-2-carboxamide and the title compound. A mixed solution of (2S)—N-(5-bromo-2-carbamoylthiophen-3-yl)-1-azabicyclo[2.2.2]octane-2-carboxamide and the title compound produced above in ethanol (4.0 mL) and 2M aqueous sodium hydroxide solution (2.7 mL) was stirred at 70° C. for 2 hr. The reaction mixture was neutralized with 1M hydrochloric acid at 0° C., and the mixture was extracted with ethyl acetate. The organic layer was washed with brine, and dried over anhydrous sodium sulfate. Insoluble material was filtered off, and the filtrate was concentrated under reduced pressure. The residue was purified by basic silica gel column chromatography (ethyl acetate/hexane and methanol/ethyl acetate) to give the title compound (220 mg) as a yellow solid.

$^1$H-NMR (DMSO-$d_6$) δ 1.40-1.63 (4H, m), 1.73-1.94 (2H, m), 2.18-2.30 (1H, m), 2.60-2.71 (2H, m), 2.83-2.97 (1H, m), 3.04-3.17 (1H, m), 3.89-4.01 (1H, m), 7.60 (1H, s).

C) Production of 2-[(2S)-1-azabicyclo[2.2.2]oct-2-yl]-6-(5-methyl-1H-pyrazol-4-yl)thieno[3,2-d]pyrimidin-4 (3H)-one trifluoroacetate 2-[(2S)-1-Azabicyclo[2.2.2]oct-2-yl]-6-bromothieno[3,2-d]pyrimidin-4 (3H)-one (210 mg) and tert-butyl 3-methyl-4-(4,4,5,5-tetramethyl-1,3,2-dioxaborolan-2-yl)-1H-pyrazole-1-carboxylate (571 mg), sodium carbonate (196 mg), 1,2-dimethoxyethane (4.0 mL) and water (2.0 mL) were placed in a flask, and the atmosphere in the flask was purged with argon. [1,1'-Bis(diphenylphosphino)ferrocene]palladium(II) dichloride-dichloromethane complex (1:1)(252 mg) was added, and the atmosphere in the flask was purged again with argon. The reaction system was stirred at 100° C. for 2 hr, brine was added, and the mixture was extracted with ethyl acetate. The extract was concentrated under reduced pressure. The residue was purified by silica gel column chromatography (ethyl acetate/hexane and methanol/ethyl acetate) to give a crude product (96 mg) of 2-[(2S)-1-azabicyclo[2.2.2]oct-2-yl]-6-(5-methyl-1H-pyrazol-4-yl)thieno[3,2-d]pyrimidin-4 (3H)-one as a pale-brown solid. To a suspension of the crude product (96 mg) of 2-[(2S)-1-azabicyclo[2.2.2]oct-2-yl]-6-(5-methyl-1H-pyrazol-4-yl)thieno[3,2-d]pyrimidin-4 (3H)-one produced above in N,N-dimethylformamide (1.0 mL) were added triethylamine (0.039 mL) and di-tert-butyl dicarbonate (0.065 mL). The reaction mixture was stirred at 50° C. for 18 hr, water was added, and the mixture was extracted with ethyl acetate. The extract was dried over anhydrous sodium sulfate, insoluble material was removed by filtration, and the filtrate was concentrated under reduced pressure. The residue was purified by silica gel column chromatography (ethyl acetate/hexane) to give tert-butyl 4-{2-[(2S)-1-azabicyclo[2.2.2]oct-2-yl]-4-oxo-3,4-dihydrothieno[3,2-d]pyrimidin-6-yl}-3-methyl-1H-pyrazole-1-carboxylate (position of Boc on pyrazole ring is unidentified) as a pale-yellow solid (49 mg). To tert-butyl 4-{2-[(2S)-1-azabicyclo[2.2.2]oct-2-yl]-4-oxo-3,4-dihydrothieno[3,2-d]pyrimidin-6-yl}-3-methyl-1H-pyrazole-1-carboxylate produced above were added water (0.50 mL) and trifluoroacetic acid (50.6 mg), and the reaction system was stirred at 90° C. for 30 min. The reaction system was concentrated under reduced pressure, and the residue was purified by basic silica gel column chromatography (ethyl acetate/hexane and methanol/ethyl acetate) to give a pale-yellow solid. The obtained pale-yellow solid was purified by high performance liquid chromatography {column: L-column 2 ODS (20 mm i.d.×50 mm L), mobile phase: 0.1% aqueous trifluoroacetic acid solution/0.1% trifluoroacetic acid acetonitrile solution}. The object fraction was concentrated under reduced pressure, and the residue was crystallized from ethyl acetate/hexane to give the title compound (6 mg) as a colorless solid.

$^1$H-NMR (DMSO-$d_6$) δ 1.70-1.95 (4H, m), 2.05-2.25 (2H, m), 2.36-2.48 (4H, m), 3.21-3.31 (2H, m), 3.42-3.56 (1H, m), 3.59-3.78 (1H, m), 4.57-4.84 (1H, m), 7.44 (1H, s), 7.81-8.44 (1H, m), 9.81 (1H, brs), 12.43-13.20 (2H, m).

MS(ESI+): [M+H]$^+$342.

MS(ESI+), found: 342.

Example 171

Production of 2-[(1R*,6R*)-3-azabicyclo[4.1.0]hept-4-yl]-6-(5-methyl-1H-pyrazol-4-yl)thieno[3,2-d]pyrimidin-4 (3H)-one dihydrochloride A) Production of methyl 2-[(tert-butoxycarbonyl)amino]pent-4-enoate A mixture of 2-[(tert-butoxycarbonyl)amino]pent-4-enoic acid (20.0 g), potassium carbonate (13.2 g) and N,N-dimethylformamide (100 mL) was stirred for 15 min. The mixture was cooled to 0° C., iodomethane (9.2 g) was added, and the mixture was stirred at room temperature for 2 hr. The reaction mixture was filtered, and the residue was washed with ethyl acetate. The filtrate was successively washed with 5% hydrochloric acid and brine, and dried over anhydrous sodium sulfate. Insoluble material was filtered off, and the filtrate was concentrated under reduced pressure to give the title compound (21.0 g).

$^1$H-NMR (CDCl$_3$) δ 1.45 (9H, s), 2.47-2.58 (2H, m), 3.75 (3H, s), 4.40 (1H, q, J=6.4 Hz), 5.07 (1H, d, J=5.6 Hz), 5.13-5.16 (2H, m), 5.66-5.74 (1H, m).

B) Production of methyl 2-[(tert-butoxycarbonyl)(prop-2-en-1-yl)amino]pent-4-enoate A solution of methyl 2-[(tert-butoxycarbonyl)amino]pent-4-enoate (10.5 g) produced above in ethanol (50 mL) was cooled to −20° C., 3-bromoprop-1-ene (6.1 g) and sodium hydride (60% in oil, 2.0 g) were added, and the mixture was stirred at −20° C. for 1.5 hr and quenched by adding a saturated aqueous ammonium chloride solution (20 mL). The organic product was extracted with diethylether, and the extract was dried over anhydrous sodium sulfate. Insoluble material was filtered off, and the filtrate was concentrated under reduced pressure to give the title compound (9.9 g).

$^1$H-NMR (CDCl$_3$) δ 1.47 (9H, s), 2.59-2.75 (2H, m), 3.72 (3H, s), 3.79-4.15 (3H, m), 5.08-5.36 (4H, m), 5.74-5.84 (2H, m).

C) Production of tert-butyl [1-(hydroxymethyl)but-3-en-1-yl]prop-2-en-1-ylcarbamate To a mixture of methyl 2-[(tert-butoxycarbonyl)(prop-2-en-1-yl)amino]pent-4-enoate (5.0 g) produced above and tetrahydrofuran (100 mL) was added 1M diisobutylaluminum hydride/toluene solution (60 mL) at 0° C., and the mixture was stirred at the same temperature for 15 min. The reaction mixture was diluted with aqueous potassium sodium tartrate solution, and the mixture was extracted with ethyl acetate. The extract was dried over anhydrous sodium sulfate. Insoluble material was filtered off, and the filtrate was concentrated under reduced pressure to give the title compound (3.76 g).

$^1$H-NMR (CDCl$_3$) δ 1.45 (9H, s), 2.35-2.37 (2H, m), 3.49-3.84 (5H, m), 5.01-5.18 (4H, m), 5.69-5.87 (2H, m).

D) Production of 2-[(tert-butoxycarbonyl)(prop-2-en-1-yl)amino]pent-4-en-1-yl 4-nitrobenzoate To a mixture of tert-butyl [1-(hydroxymethyl)but-3-en-1-yl]prop-2-en-1-ylcarbamate (15.0 g) produced above, triethylamine (19.0 g) and dichloromethane (150 mL) was added N,N-dimethylpyridin-4-amine (0.7 g). To the mixture was added dropwise a solution of 4-nitrobenzoyl chloride (14.2 g) in dichloromethane (30 mL), and the mixture was stirred at 0° C. for 30 min. The reaction mixture was diluted with saturated aqueous sodium hydrogen carbonate, the mixture was extracted with dichloromethane, and the extract was dried over anhydrous sodium sulfate. Insoluble material was filtered off, and the filtrate was concentrated under reduced pressure. The residue was purified by silica gel column chromatography (ethyl acetate/petroleum ether) to give the title compound (14.1 g).

$^1$H-NMR (CDCl$_3$) δ 1.45 (9H, s) 2.33-2.38 (1H, m) 2.42-2.47 (1H, m), 3.73 (1H, s), 3.84 (1H, s), 4.38-4.52 (3H, m), 5.01-5.16 (4H, m), 5.72-5.79 (2H, m), 8.19 (2H, d, J=8.0 Hz), 8.26-8.28 (2H, m).

E) Production of tert-butyl 2-({[(4-nitrophenyl)carbonyl]oxy}methyl)-3,6-dihydropyridine-1(2H)-carboxylate A solution of 2-[(tert-butoxycarbonyl)(prop-2-en-1-yl)amino]pent-4-en-1-yl 4-nitrobenzoate (14.0 g) produced above in benzene (300 mL) was heated under reflux under a nitrogen atmosphere for 15 min and cooled to 10° C. Grubbs reagent (1.9 g) was added at 10° C., and the reaction mixture was stirred for 3 hr. Dimethyl sulfoxide (8.6 mL) was added, and the mixture was concentrated under reduced pressure. The residue was purified by silica gel column chromatography (ethyl acetate/petroleum ether) to give the title compound (11.3 g).

$^1$H-NMR (CDCl$_3$) δ 1.25-1.33 (9H, m), 2.01-2.09 (1H, m), 2.51-2.56 (1H, m), 3.60-3.64 (1H, m), 4.14-4.44 (3H, m), 4.75-4.79 (1H, m), 5.69-5.77 (2H, m), 8.20 (2H, d, J=8.4 Hz), 8.25 (2H, s).

F) Production of tert-butyl(1R*,4S*,6R*)-4-({[(4-nitrophenyl)carbonyl]oxy}methyl)-3-azabicyclo[4.1.0]heptane-3-carboxylate tert-Butyl 2-{[(4-nitrophenyl)carbonyl]oxy}methyl)-3,6-dihydropyridine-1(2H)-carboxylate (10.0 g) produced above was dissolved in 5% diazomethane/diethyl ether (1.4 L), palladium acetate (689 mg) was added at 10° C., and the mixture was stirred at the same temperature for 40 min. The reaction mixture was purified by silica gel column chromatography (ethyl acetate/petroleum ether) to give a mixture of tert-butyl 2-({[(4-nitrophenyl)carbonyl]oxy}methyl)-3,6-dihydropyridine-1(2H)-carboxylate and the title compound. The obtained mixture was subjected to 3 repeats of a similar reaction operation to give the title compound (8.4 g).

$^1$H-NMR (CDCl$_3$) δ 0.12-0.15 (1H, m), 0.69-0.74 (1H, m), 0.95-1.02 (2H, m), 1.40 (9H, s), 1.80-1.97 (2H, m), 3.39-3.43 (1H, m), 3.82-3.91 (1H, m), 4.24-4.48 (3H, m), 8.16-8.20 (2H, m), 8.27-8.29 (2H, m).

G) Production of tert-butyl(1R*,4S*,6R*)-4-(hydroxymethyl)-3-azabicyclo[4.1.0]heptane-3-carboxylate To a mixture of tert-butyl(1R*,4S*,6R*)-4-{[(4-nitrophenyl)carbonyl]oxy}methyl)-3-azabicyclo[4.1.0]heptane-3-carboxylate (8.2 g) produced above, tetrahydrofuran (70 mL), methanol (70 mL) and water (35 mL) was added lithium hydroxide monohydrate (2.7 g). The mixture was stirred at room temperature for 1 hr. The reaction mixture was diluted with brine, and the mixture was extracted with ethyl acetate. The extract was dried over anhydrous sodium sulfate. Insoluble material was filtered off, and the filtrate was concentrated under reduced pressure. The residue was purified by silica gel column chromatography (ethyl acetate/petroleum ether) to give the title compound (3.5 g).

$^1$H-NMR (CDCl$_3$) δ 0.24 (1H, brs), 0.61-0.64 (1H, m), 0.88-0.92 (2H, m), 1.24-1.29 (1H, m), 1.45 (9H, m), 1.73 (2H, brs), 1.88 (1H, brs), 3.47 (1H, brs), 3.58-3.61 (1H, m), 3.67-3.72 (1H, m), 4.00-4.13 (1H, m).

H) Production of tert-butyl(1R*,4S*,6R*)-4-formyl-3-azabicyclo[4.1.0]heptane-3-carboxylate A solution of tert-butyl(1R*,4S*,6R*)-4-(hydroxymethyl)-3-azabicyclo[4.1.0]heptane-3-carboxylate (200 mg) produced above and Dess-Martin periodinane (450 mg) in dichloromethane (10 mL) was stirred at 0° C. for 3 hr. Water (10 mL) was added, and the mixture was extracted with dichloromethane. The extract was dried over anhydrous sodium sulfate. Insoluble material was filtered off, and the filtrate was concentrated under reduced pressure. The residue was purified by silica gel column chromatography (ethyl acetate/petroleum ether) to give the title compound (160 mg).

$^1$H-NMR (CDCl$_3$) δ 0.17-0.27 (1H, m), 0.67-0.72 (1H, m), 0.85-1.14 (2H, m), 1.42-1.48 (9H, m), 1.66-1.77 (1H, m), 2.27-2.39 (1H, m), 3.49-3.89 (2H, m), 3.97-4.25 (1H, m), 9.52 (1H, s).

I) Production of (1R*,4S*,6R*)-3-(tert-butoxycarbonyl)-3-azabicyclo[4.1.0]heptane-4-carboxylic acid To a solution of tert-butyl(1R*,4S*,6R*)-4-formyl-3-azabicyclo[4.1.0]heptane-3-carboxylate (700 mg) produced above in t-butanol (20 mL) were added 2-methylbut-2-ene (0.5 mL), sodium chlorite (367 mg) and 1.67M aqueous sodium dihydrogen phosphate solution (1.67 mL). The oxidation reaction proceeded at room temperature for 2 hr and quenched with water. The mixture was adjusted to pH 4 with 5% hydrochloric acid, and extracted with diethylether. The extract was dried over anhydrous sodium sulfate. Insoluble material was filtered off, and the filtrate was concentrated under reduced pressure. The residue was purified by silica gel column chromatography (ethyl acetate/petroleum ether) to give the title compound (562 mg).

$^1$H-NMR (CDCl$_3$) δ 0.07-0.17 (1H, m), 0.56-0.62 (1H, m), 0.88-0.97 (1H, m), 1.31-1.39 (9H, m), 1.72-1.76 (1H, m), 2.16-2.31 (1H, m), 3.33-3.38 (2H, m), 3.52-3.63 (1H, m), 4.02-4.21 (1H, m).

J) Production of tert-butyl(1R*,6R*)-4-(6-bromo-4-oxo-3,4-dihydrothieno[3,2-d]pyrimidin-2-yl)-3-azabicyclo[4.1.0]heptane-3-carboxylate In the same manner as in Example 82, step A, the title compound (310 mg) was obtained as a white solid from 3-amino-5-bromothiophene-2-carboxamide (663 mg) produced in Example 1, step D, (1R*,4S*,6R*)-3-(tert-butoxycarbonyl)-3-azabicyclo[4.1.0]heptane-4-carboxylic acid (1.09 g) produced above, 2-methylpropyl chlorocarbonate (0.584 mL), triethylamine (1.25 mL) and tetrahydrofuran (12 mL), 2M aqueous sodium hydroxide solution (9 mL) and ethanol (12 mL).

$^1$H-NMR (DMSO-d$_6$) δ 0.18-1.37 (13H, m), 1.87-2.39 (2H, m), 3.52-4.59 (3H, m), 7.57-7.63 (1H, m), 12.63 (1H, brs).

K) Production of 2-[(1R*,6R*)-3-azabicyclo[4.1.0]
hept-4-yl]-6-(5-methyl-1H-pyrazol-4-yl)thieno[3,2-
d]pyrimidin-4 (3H)-one dihydrochloride In the same manner as in Example 83, step C, the title compound (148 mg) was obtained as a white solid from tert-butyl(1R*,6R*)-4-(6-bromo-4-oxo-3,4-dihydrothieno [3,2-d]pyrimidin-2-yl)-3-azabicyclo[4.1.0]heptane-3-carboxylate (310 mg) produced above, tert-butyl 3-methyl-4-(4,4,5,5-tetramethyl-1,3,2-dioxaborolan-2-yl)-1H-pyrazole-1-carboxylate (448 mg), cesium carbonate (711 mg), [1,1'-bis(diphenylphosphino)ferrocene]palladium(II) dichloride-dichloromethane complex (1:1)(53 mg), 1,2-dimethoxyethane (7.5 mL), water (0.75 mL), 4M hydrochloric acid/cyclopentylmethylether solution (2 mL) and methanol (3 mL).

$^1$H-NMR (DMSO-$d_6$) δ 0.51-2.27 (6H of major, 6H of minor, m), 2.42-2.47 (3H of major, 3H of minor, m), 3.02-4.03 (3H of major, 3H of minor, m), 7.32 (1H of minor, s), 7.34 (1H of major, s), 8.11-8.12 (1H of major, 1H of minor, m), 8.99-9.72 (2H of major, 2H of minor, m), 12.71-12.91 (1H of major, 1H of minor, m). The ratio of the observed diastereomers was 3:2.

Example 172

Production of 6-(5-methyl-1H-pyrazol-4-yl)-2-[(2S)-
piperidin-2-yl]thieno[3,2-d]pyrimidin-4 (3H)-one
hydrochloride A) Production of tert-butyl(2S)-2-(6-bromo-4-oxo-3,
4-dihydrothieno[3,2-d]pyrimidin-2-yl)piperidine-1-
carboxylate A solution of (2S)-1-(tert-butoxycarbonyl)piperidine-2-carboxylic acid (37.8 g) in tetrahydrofuran (375 mL) was cooled to an inside temperature of 10° C. in an ice bath. Triethylamine (23.0 mL) was added, and the mixture was stirred at the same temperature for 10 min. To the mixture was added dropwise 2-methylpropyl chlorocarbonate (21.4 mL) over 30 min (inside temperature 8-13° C.). The ice bath was removed, and the mixture was stirred at room temperature for 1 hr. Then, to the reaction mixture was added 3-amino-5-bromothiophene-2-carboxamide (16.6 g) produced in Example 1, step D, and the mixture was stirred at 60° C. for 12 hr. The reaction mixture was stirred at room temperature for 8 hr, and ethyl acetate (750 mL) and aqueous sodium hydrogen carbonate (750 mL) were added. The precipitate was collected by filtration, and washed with water to give a crude product (18.6 g) of tert-butyl(2S)-2-[(5-bromo-2-carbamoylthiophen-3-yl)carbamoyl]piperidine-1-carboxylate as a white solid. The organic layer was separated from the mother liquor, and dried over anhydrous magnesium sulfate. Insoluble material was filtered off, and the filtrate was concentrated under reduced pressure. The obtained yellow oily residue (38 g) and the crude product (18.6 g) of tert-butyl(2S)-2-[(5-bromo-2-carbamoylthiophen-3-yl)carbamoyl]piperidine-1-carboxylate produced above were combined, and ethanol (375 mL) and 2M aqueous sodium hydroxide solution (188 mL) were added. The mixture was stirred at 75° C. for 2 hr, and cooled in an ice bath, and water (125 mL) was added. The mixture was adjusted to pH 7 by 6M hydrochloric acid (117 mL) while maintaining the inside temperature at 4-8° C. The reaction mixture was stirred in an ice bath for 30 min. and the precipitate was collected by filtration to give the title compound (24.8 g) as a white solid. The optical purity was 38.7% ee. The analysis was performed by high performance liquid chromatography (column: CHIRALPAK AD-H (4.6 mm i.d.×250 mm L, manufactured by DAICEL CHEMICAL INDUSTRIES, LTD.), mobile phase: hexane/2-propanol/diethylamine (700/300/1), flow rate: 1 mL/min, column temperature: 30° C., detection 220 nm).

$^1$H-NMR (DMSO-$d_6$) δ 1.09-1.45 (11H, m), 1.46-1.58 (1H, m), 1.60-1.86 (2H, m), 1.98-2.14 (1H, m), 3.38-3.53 (1H, m), 3.75-3.89 (1H, m), 4.89-5.10 (1H, m), 7.58 (1H, s), 12.64 (1H, brs).

B) Optical resolution of tert-butyl(2S)-2-(6-bromo-4-
oxo-3,4-dihydrothieno[3,2-d]pyrimidin-2-yl)piperi-
dine-1-carboxylate tert-Butyl(2S)-2-(6-bromo-4-oxo-3,4-dihydrothieno[3,2-d]pyrimidin-2-yl)piperidine-1-carboxylate (10.1 g, 38.7% ee) was fractionated by high performance liquid chromatography (column: CHIRALPAK AD (50 mm i.d.×500 mm L, manufactured by DAICEL CHEMICAL INDUSTRIES, LTD.), mobile phase: hexane/2-propanol/diethylamine (700/300/1), flow rate: 80 mL/min, column temperature: 30° C.). tert-Butyl(2S)-2-(6-bromo-4-oxo-3,4-dihydrothieno[3,2-d]pyrimidin-2-yl)piperidine-1-carboxylate (6.59 g, >99.9% ee, retention time 6.32 min) and tert-butyl(2R)-2-(6-bromo-4-oxo-3,4-dihydrothieno[3,2-d]pyrimidin-2-yl)piperidine-1-carboxylate (2.71 g, >99.9% ee, retention time 8.6 min) were obtained under the above-mentioned high performance liquid chromatography conditions. The analysis was performed by high performance liquid chromatography (column: CHIRALPAK AD-H (4.6 mm i.d.×250 mm L, manufactured by DAICEL CHEMICAL INDUSTRIES, LTD.), mobile phase: hexane/2-propanol/diethylamine (700/300/1), flow rate: 1 mL/min, column temperature: 30° C., detection 220 nm).

C) Production of 6-(5-methyl-1H-pyrazol-4-yl)-2-
[(2S)-piperidin-2-yl]thieno[3,2-d]pyrimidin-4 (3H)-
one hydrochloride The mother liquor finally obtained by the crystallization step in Example 83, step D, was concentrated under reduced pressure. To the residue was added ethanol (7 mL), and the mixture was heated with stirring at 80° C. Water (0.5 mL) was added, and the obtained solution was gradually cooled to room temperature while stirring. After 2 hr, the precipitated solid was collected by filtration to give the title compound (75 mg) as a white solid.

$^1$H-NMR (DMSO-$d_6$) δ 1.51-1.92 (5H, m), 2.25-2.33 (1H, m), 2.46 (3H, s), 2.97-3.10 (1H, m), 3.35-3.39 (1H, m), 4.16-4.25 (1H, m), 7.34 (1H, s), 8.00 (1H, brs), 9.23 (1H, brs), 13.02 (1H, brs).
MS(ESI+): [M+H]$^+$316.
MS(ESI+), found: 316.

Example 173

Production of 2-{2-[(2-hydroxyethyl)(methyl)amino]
ethyl}-6-(5-methyl-1H-pyrazol-4-yl)thieno[3,2-d]
pyrimidin-4 (3H)-one To a mixture of 3-amino-5-bromothiophene-2-carboxamide (300 mg) produced in Example 1, step D, triethylamine (0.208 mL) and tetrahydrofuran (7.0 mL) was added 3-chloropropanoyl chloride (0.143 mL) while stirring at 0° C. The reaction mixture was stirred at room temperature for 30 min, and 2-(methylamino)ethanol (0.542 mL) was added. The reaction mixture was stirred with heating at 70° C. for 18 hr.

The reaction mixture was neutralized with 1M aqueous hydrochloric acid solution at 0° C., and concentrated under reduced pressure. The residue was purified by basic silica gel column chromatography (ethyl acetate/hexane and methanol/ethyl acetate) to give 6-bromo-2-{2-[(2-hydroxyethyl)(methyl)amino]ethyl}thieno[3,2-d]pyrimidin-4 (3H)-one (405 mg) as a pale-yellow solid. In the same manner as in Example 2, step C, the title compound (22 mg) was obtained as a pale-brown solid from 6-bromo-2-{2-[(2-hydroxyethyl)(methyl)amino]ethyl}thieno[3,2-d]pyrimidin-4 (3H)-one (50 mg) produced above and tert-butyl 3-methyl-4-(4,4,5,5-tetramethyl-1,3,2-dioxaborolan-2-yl)-1H-pyrazole-1-carboxylate (93 mg), sodium carbonate (48 mg), 1,2-dimethoxyethane (1.0 mL) and water (0.5 mL) and [1,1'-bis(diphenylphosphino)ferrocene]palladium(II) dichloride-dichloromethane complex (1:1)(12 mg).

$^1$H-NMR (DMSO-d$_6$) δ 2.24 (3H, s), 2.39-2.48 (5H, m), 2.70-2.84 (4H, m), 3.46 (2H, t, J=6.2 Hz), 4.42 (1H, brs), 7.33 (1H, s), 7.67-8.32 (1H, m), 12.15-13.16 (2H, m).

Example 174

Production of 6-(5-methyl-1H-pyrazol-4-yl)-2-[(2S)-piperidin-2-yl]thieno[3,2-d]pyrimidin-4 (3H)-one 6-(5-Methyl-1H-pyrazol-4-yl)-2-[(2S)-piperidin-2-yl]thieno[3,2-d]pyrimidin-4 (3H)-one dihydrochloride (255 mg) produced in Example 83, step D, was suspended in methanol (7 mL), and triethylamine (0.28 mL) was added to give a solution. To the mixture was added basic silica gel (5 g), and they were mixed. The solvent was evaporated under reduced pressure. The residue was purified by basic silica gel column chromatography (methanol/ethyl acetate). The object fraction was concentrated under reduced pressure, and ethyl acetate (10 mL) was added the obtained residue. The precipitate was collected by filtration to give the title compound (183 mg) as a white solid.

$^1$H-NMR (DMSO-d$_6$) δ 1.36-1.62 (4H, m), 1.77-1.94 (2H, m), 2.44 (3H, s), 2.59-2.69 (1H, m), 2.98-3.08 (1H, m), 3.60-3.68 (1H, m), 7.31 (1H, s), 8.00 (1H, brs).

MS(ESI+): [M+H]$^+$316.
MS(ESI+), found: 316.

Example 175

Production of 2-[(1R,3S,4R,5R) or (1S,3S,4S,5R)-5-fluoro-2-azabicyclo[2.2.1]hept-3-yl]-6-(5-methyl-1H-pyrazol-4-yl)thieno[3,2-d]pyrimidin-4 (3H)-one hydrochloride A) Production of tert-butyl(1R*,3S,4R*,5R)-3-(6-bromo-4-oxo-3,4-dihydrothieno[3,2-d]pyrimidin-2-yl)-5-fluoro-2-azabicyclo[2.2.1]heptane-2-carboxylate To a solution of (1R*,3S,4R*,5R)-2-(tert-butoxycarbonyl)-5-fluoro-2-azabicyclo[2.2.1]heptane-3-carboxylic acid (2.65 g) and triethylamine (1.42 mL) in tetrahydrofuran (35 mL) was added 2-methylpropyl chlorocarbonate (1.34 mL) at 0° C., and the mixture was stirred at room temperature for 30 min. To the reaction system was added a solution of 3-amino-5-bromothiophene-2-carboxamide (1.88 g) produced in Example 1, step D, in tetrahydrofuran (10 mL), and the mixture was stirred at 60° C. for 18 hr. Water was added to the reaction mixture, and the separated aqueous layer was extracted with ethyl acetate. The organic layer was washed with brine, and dried over anhydrous sodium sulfate. Insoluble material was filtered off, the filtrate was concentrated under reduced pressure, and the residue was purified by basic silica gel column chromatography (ethyl acetate/hexane). To the obtained pale-yellow solid were added 2M aqueous sodium hydroxide solution (34 mL) and ethanol (200 mL), and the mixture was stirred at 80° C. for 8 hr. The reaction system was neutralized with 1M hydrochloric acid at 0° C. To the reaction system was added water (20 mL), and the precipitate was collected by filtration to give the title compound (2.82 g) as a colorless solid.

$^1$H-NMR (DMSO-d$_6$) δ 1.06-1.45 (9H, m), 1.50-1.86 (2H, m), 2.01-2.22 (2H, m), 2.83-2.95 (1H, m), 4.03-4.13 (1H, m), 4.15-4.32 (1H, m), 4.91-5.20 (1H, m), 7.57-7.75 (1H, m), 12.58-12.76 (1H, m).

B) Optical resolution of tert-butyl(1R*,3S,4R*,5R)-3-(6-bromo-4-oxo-3,4-dihydrothieno[3,2-d]pyrimidin-2-yl)-5-fluoro-2-azabicyclo[2.2.1]heptane-2-carboxylate tert-Butyl(1R*,3S,4R*,5R)-3-(6-bromo-4-oxo-3,4-dihydrothieno[3,2-d]pyrimidin-2-yl)-5-fluoro-2-azabicyclo[2.2.1]heptane-2-carboxylate (274 mg) was fractionated by high performance liquid chromatography (column: CHIRALPAK AD (50 mm i.d.×500 mm L, manufactured by DAICEL CHEMICAL INDUSTRIES, LTD.), mobile phase: hexane/ethanol (800/200), flow rate: 80 mL/min, column temperature: 30° C.). tert-Butyl(1R,3S,4R,5R) or (1S,3S,4S,5R)-3-(6-bromo-4-oxo-3,4-dihydrothieno[3,2-d]pyrimidin-2-yl)-5-fluoro-2-azabicyclo[2.2.1]heptane-2-carboxylate (1.39 g, >99.9% ee, retention time 7.1 min) and tert-butyl(1R,3S,4R,5R) or (1S,3S,4S,5R)-3-(6-bromo-4-oxo-3,4-dihydrothieno[3,2-d]pyrimidin-2-yl)-5-fluoro-2-azabicyclo[2.2.1]heptane-2-carboxylate (1.40 g, 99.8% ee, retention time 14.2 min) were obtained under the above-mentioned high performance liquid chromatography conditions. The analysis was performed by high performance liquid chromatography (column: CHIRALPAK AD-H (4.6 mm i.d.×250 mm L, manufactured by DAICEL CHEMICAL INDUSTRIES, LTD.), mobile phase: hexane/ethanol (800/200), flow rate: 1 mL/min, column temperature: 30° C., detection 220 nm).

C) Production of 2-[(1R,3S,4R,5R) or (1S,3S,4S,5R)-5-fluoro-2-azabicyclo[2.2.1]hept-3-yl]-6-(5-methyl-1H-pyrazol-4-yl)thieno[3,2-d]pyrimidin-4 (3H)-one hydrochloride tert-Butyl(1R,3S,4R,5R) or (1S,3S,4S,5R)-3-(6-bromo-4-oxo-3,4-dihydrothieno[3,2-d]pyrimidin-2-yl)-5-fluoro-2-azabicyclo[2.2.1]heptane-2-carboxylate (1.40 g, 99.8% ee, retention time 14.2 min) produced in Example 175, step B, and tert-butyl 3-methyl-4-(4,4,5,5-tetramethyl-1,3,2-dioxaborolan-2-yl)-1H-pyrazole-1-carboxylate (1.94 g), sodium carbonate (1.00 g), 1,2-dimethoxyethane (30 mL) and water (15 mL) were placed in a flask, and the atmosphere in the flask was purged with argon. [1,1'-Bis(diphenylphosphino)ferrocene]palladium(II) dichloride-dichloromethane complex (1:1)(257 mg) was added, and the atmosphere in the flask was purged again with argon. The reaction system was stirred at 100° C. for 1 hr, and water was added. The mixture was extracted with ethyl acetate, and the extract was dried over anhydrous sodium sulfate, insoluble material was removed by filtration, and the filtrate was concentrated under reduced pressure. The residue was purified by silica gel column chromatography (ethyl acetate/hexane) to give tert-butyl(1R,3S, 4R,5R) or (1S,3S,4S,5R)-5-fluoro-3-[6-(5-methyl-1H-pyrazol-4-yl)-4-oxo-3,4-dihydrothieno[3,2-d]pyrimidin-2-yl]-2-azabicyclo[2.2.1]heptane-2-carboxylate (1.39 g) as a pale-yellow solid. To a solution of tert-butyl(1R,3S,4R,5R) or (1S,3S,4S,5R)-5-fluoro-3-[6-(5-methyl-1H-pyrazol-4-yl)-4-oxo-3,4-dihydrothieno[3,2-d]pyrimidin-2-yl]-2-azabicyclo[2.2.1]heptane-2-carboxylate (1.39 g) produced above in methanol (15 mL) was added, while stirring at room temperature, 5% hydrochloric acid/methanol solution (15 mL). The reaction system was stirred with heating at 50° C. for 3 hr and the reaction mixture was concentrated under reduced pressure. To the residue was added ethanol (15 mL), and water (2 mL) was slowly added at 100° C. The solution was cooled to room temperature, and the precipitate was collected by filtration to give the title compound (826 mg) as a colorless solid.

$^1$H-NMR (DMSO-$d_6$) δ 1.75-1.96 (3H, m), 2.46 (3H, s), 2.53-2.62 (1H, m), 3.18-3.26 (1H, m), 4.19-4.31 (2H, m), 4.93-5.18 (1H, m), 7.35 (1H, s), 8.09 (1H, s), 8.64 (1H, brs), 9.98 (1H, brs), 12.94 (1H, brs).

MS(ESI+): [M+H]$^+$346.

MS(ESI+), found: 346.

Example 176

Production of 2-(1-azabicyclo[2.2.2]oct-2-yl)-6-(5-methyl-1H-pyrazol-4-yl)thieno[3,2-d]pyrimidin-4(3H)-one A) Production of 1-(1-tert-butyl-5-methyl-1H-pyrazol-4-yl)ethanone A mixture of pentane-2,4-dione (5.01 g) and 1,1-dimethoxy-N,N-dimethylmethanamine (6.26 g) was stirred at 80° C. for 1 hr. Tetrahydrofuran (10 mL) was added to the reaction mixture, tert-butylhydrazine hydrochloride was added by small portions under ice-cooling, and the mixture was stirred at 60° C. for 30 min. The reaction mixture was allowed to cool to room temperature, ethyl acetate (100 mL) and water (100 mL) were added, and the separated aqueous layer was extracted with ethyl acetate (50 mL×2). The combined organic layers were washed with brine (20 mL) and dried over anhydrous magnesium sulfate. Insoluble material was removed by filtration, the filtrate was concentrated under reduced pressure, and the residue was purified by silica gel column chromatography (ethyl acetate/hexane) to give the title compound (7.47 g) as a colorless oil.

$^1$H-NMR (DMSO-$d_6$) δ 1.67 (9H, s), 2.42 (3H, s), 2.77 (3H, s), 7.76 (1H, s).

B) Production of (2Z)-3-chloro-3-(5-methyl-1H-pyrazol-4-yl)prop-2-enenitrile

To N,N-dimethylformamide (12.1 g) was added phosphorus oxychloride (25.4 g) by small portions under ice-cooling, and the mixture was stirred at room temperature for 15 min. Thereto was added 1-(1-tert-butyl-5-methyl-1H-pyrazol-4-yl)ethanone (7.47 g) produced above by small portions under ice-cooling, and the reaction mixture was stirred at 50° C. for 30 min. Thereto was added a powder (11.5 g) of hydroxylamine hydrochloride by small portions at 50° C., and the reaction mixture was stirred at 50° C. for 30 min. Ice water (200 mL) was added to the reaction mixture, and the mixture was neutralized with 1M aqueous sodium hydroxide solution, and extracted with ethyl acetate (100 mL×2). The combined organic layers were washed with brine (20 mL) and dried over anhydrous magnesium sulfate. Insoluble material was removed by filtration, the filtrate was concentrated under reduced pressure, and the residue was purified by silica gel column chromatography (ethyl acetate/hexane), and crystallized from diethylether to give the title compound (3.02 g) as a pale-yellow powder.

$^1$H-NMR (DMSO-$d_6$) δ 2.48 (3H, s), 5.68 (1H, s), 7.82 (1H, s).

C) Production of methyl 3-amino-5-(5-methyl-1H-pyrazol-4-yl)thiophene-2-carboxylate A mixture of (2Z)-3-chloro-3-(5-methyl-1H-pyrazol-4-yl)prop-2-enenitrile (3.08 g) produced above, methylsulfanyl acetate (2.15 g), sodium hydride (1.47 g) and N,N-dimethylacetamide (10 mL) was stirred at 60° C. for 2 hr. Ethyl acetate (20 mL) and water (10 mL) were added to the reaction mixture, and the separated aqueous layer was extracted with ethyl acetate (10 mL×2). The combined organic layers were washed with brine (20 mL) and dried over anhydrous magnesium sulfate. Insoluble material was removed by filtration, the filtrate was concentrated under reduced pressure, and the residue was purified by silica gel column chromatography (ethyl acetate/hexane) to give the title compound (3.57 g) as a colorless solid.

$^1$H-NMR (DMSO-$d_6$) δ 2.39 (3H, s), 3.68 (3H, s), 6.53 (2H, s), 6.65 (1H, s), 7.46-8.26 (1H, m), 12.83 (1H, brs).

D) Production of methyl 3-amino-5-[1-(4-methoxybenzyl)-3-methyl-1H-pyrazol-4-yl]thiophene-2-carboxylate and methyl 3-amino-5-[1-(4-methoxybenzyl)-5-methyl-1H-pyrazol-4-yl]thiophene-2-carboxylate A mixture of methyl 3-amino-5-(5-methyl-1H-pyrazol-4-yl)thiophene-2-carboxylate (3.50 g) produced above, potassium carbonate (2.45 g), 1-(chloromethyl)-4-methoxybenzene (2.43 g) and N,N-dimethylformamide (30 mL) was stirred at 100° C. for 15 hr. Ethyl acetate (20 mL) and water (10 mL) were added to the reaction mixture, and the separated aqueous layer was extracted with ethyl acetate (10 mL×2). The combined organic layers were washed with brine (20 mL) and dried over anhydrous magnesium sulfate. Insoluble material was filtered off, the filtrate was concentrated under reduced pressure, and the precipitated solid was collected by filtration to give the title compound (4.98 g) as a colorless solid.

$^1$H-NMR (DMSO-$d_6$) δ 2.29 (2H, s), 2.39 (1H, s), 3.68-3.75 (6H, m), 5.16 (1.33H, s), 5.29 (0.67H, s), 6.54 (2H, s), 6.61-6.67 (1H, m), 6.86-6.94 (2H, m), 7.10-7.17 (0.67H, m), 7.21-7.29 (1.33H, m), 7.72 (0.33H, s), 8.15 (0.67H, s).

E) Production of methyl 3-[(1-azabicyclo[2.2.2]oct-2-ylcarbonyl)amino]-5-[1-(4-methoxybenzyl)-3-methyl-1H-pyrazol-4-yl]thiophene-2-carboxylate and methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate A mixture of 1-azabicyclo[2.2.2]octane-2-carboxylic acid (488 mg), thionyl chloride (5 mL) and N,N-dimethylformamide (23 mg) was stirred at room temperature for 15 hr. The reaction mixture was concentrated under reduced pressure, and the residue was dissolved in tetrahydrofuran (5 mL). A mixture of methyl 3-amino-5-[1-(4-methoxybenzyl)-3-methyl-1H-pyrazol-4-yl]thiophene-2-carboxylate and methyl 3-amino-5-[1-(4-methoxybenzyl)-5-methyl-1H-pyrazol-4-yl]thiophene-2-carboxylate (750 mg) produced above, and N-ethyl-N-(1-methylethyl)propan-2-amine (0.916 mL) were added, and the mixture was stirred at 60° C. for 2 hr. Ethyl acetate (20 mL) and water (10 mL) were added to the reaction mixture, and the separated aqueous layer was extracted with ethyl acetate (10 mL×2). The combined organic layers were washed with brine (20 mL) and dried over anhydrous magnesium sulfate. Insoluble material was removed by filtration, the filtrate was concentrated under reduced pressure, and the residue was purified by basic silica gel column chromatography (ethyl acetate/hexane) to give the title compound (534 mg) as a colorless oil.

$^1$H-NMR (DMSO-$d_6$) δ 1.31-1.59 (4H, m), 1.73-1.87 (3H, m), 2.33 (2H, s), 2.43 (1H, s), 2.55-3.11 (4H, m), 3.54-3.66 (1H, m), 3.70-3.85 (6H, m), 5.18 (1.33H, s), 5.31 (0.67H, s), 6.84-6.95 (2H, m), 7.10-7.32 (2H, m), 7.82 (0.33H, s), 8.09-8.15 (1H, m), 8.32 (0.67H, s), 11.24 (1H, s).

F) Production of N-{2-carbamoyl-5-[1-(4-methoxybenzyl)-3-methyl-1H-pyrazol-4-yl]thiophen-3-yl}-1-azabicyclo[2.2.2]octane-2-carboxamide and N-{2-carbamoyl-5-[1-(4-methoxybenzyl)-5-methyl-1H-pyrazol-4-yl]thiophen-3-yl}-1-azabicyclo[2.2.2]octane-2-carboxamide A mixture of methyl 3-[(1-azabicyclo[2.2.2]oct-2-ylcarbonyl)amino]-5-[1-(4-methoxybenzyl)-3-methyl-1H-pyrazol-4-yl]thiophene-2-carboxylate and methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate (500 mg) produced above, 8M aqueous sodium hydroxide solution (1 mL), and ethanol (7 mL) was stirred at 60° C. for 2 hr. The reaction mixture was neutralized with 6M hydrochloric acid (1.4 mL) under ice-cooling, and concentrated under reduced pressure. To the residue were added ammonium chloride (162 mg), triethylamine (0.705 mL) and N,N-dimethylformamide (5 mL), and the mixture was stirred at room temperature for 5 min. To the reaction system were added 1-ethyl-3-(3-dimethylaminopropyl)carbodiimide hydrochloride (235 mg) and 1-hydroxybenzotriazole (205 mg), and the mixture was stirred at room temperature for 15 hr. The reaction system was poured into water (10 mL), and the mixture was extracted with ethyl acetate (10 mL). The organic layer was washed with saturated aqueous sodium hydrogen carbonate, and dried over anhydrous magnesium sulfate. Insoluble material was filtered off, and the filtrate was concentrated under reduced pressure to give the title compound (316 mg) as a colorless solid.

$^1$H-NMR (DMSO-$d_6$) δ 1.31-1.55 (4H, m), 1.71-1.86 (3H, m), 2.33 (1H, s), 2.41-2.45 (2H, m), 2.55-3.05 (4H, m), 3.50-3.59 (1H, m), 3.70-3.76 (3H, m), 5.18 (0.67H, s), 5.30 (1.33H, s), 6.87-6.96 (2H, m), 7.10-7.50 (4H, m), 7.72 (0.67H, s), 8.06-8.11 (1H, m), 8.17 (0.33H, s), 11.85 (1H, s).

G) Production of 2-(1-azabicyclo[2.2.2]oct-2-yl)-6-[1-(4-methoxybenzyl)-3-methyl-1H-pyrazol-4-yl]thieno[3,2-d]pyrimidin-4 (3H)-one and 2-(1-azabicyclo[2.2.2]oct-2-yl)-6-[1-(4-methoxybenzyl)-5-methyl-1H-pyrazol-4-yl]thieno[3,2-d]pyrimidin-4 (3H)-one A mixture of N-{2-carbamoyl-5-[1-(4-methoxybenzyl)-3-methyl-1H-pyrazol-4-yl]thiophen-3-yl}-1-azabicyclo[2.2.2] octane-2-carboxamide and N-{2-carbamoyl-5-[1-(4-methoxybenzyl)-5-methyl-1H-pyrazol-4-yl]thiophen-3-yl}-1-azabicyclo[2.2.2]octane-2-carboxamide (200 mg) produced above, 2M aqueous sodium hydroxide solution (1 mL), and ethanol (3 mL) were stirred at 80° C. for 3 hr. The reaction mixture was neutralized with 1M hydrochloric acid under ice-cooling, and the mixture was extracted with ethyl acetate (20 mL). The organic layer was washed with brine (5 mL), and dried over anhydrous magnesium sulfate. Insoluble material was filtered off, the filtrate was concentrated under reduced pressure, and the solid was collected by filtration to give the title compound (142 mg) as a colorless solid.

$^1$H-NMR (DMSO-$d_6$) δ 1.38-3.14 (14H, m), 3.72-3.75 (3H, m), 3.92 (1H, t, J=8.9 Hz), 5.19 (1.8H, s), 5.32 (0.2H, s), 6.88-6.96 (1.8H, m), 7.17 (0.2H, d, J=8.5 Hz), 7.27 (2H, d, J=8.5 Hz), 7.38 (0.9H, s), 7.45 (0.1H, s), 7.92 (0.1H, s), 8.32 (0.9H, s).

H) Production of 2-(1-azabicyclo[2.2.2]oct-2-yl)-6-(5-methyl-1H-pyrazol-4-yl)thieno[3,2-d]pyrimidin-4 (3H)-one A mixture of 2-(1-azabicyclo[2.2.2]oct-2-yl)-6-[1-(4-methoxybenzyl)-3-methyl-1H-pyrazol-4-yl]thieno[3,2-d]pyrimidin-4 (3H)-one and 2-(1-azabicyclo[2.2.2]oct-2-yl)-6-[1-(4-methoxybenzyl)-5-methyl-1H-pyrazol-4-yl]thieno[3, 2-d]pyrimidin-4 (3H)-one (120 mg) produced above, trifluoroacetic acid (3 mL), and methoxybenzene (0.3 mL) were stirred at 70° C. for 24 hr. The reaction mixture was concentrated under reduced pressure, neutralized with saturated aqueous sodium hydrogen carbonate, and extracted with a mixed solvent of ethyl acetate/tetrahydrofuran (20 mL×3). The organic layer was washed with water, and dried over anhydrous magnesium sulfate. Insoluble material was removed by filtration, the filtrate was concentrated under reduced pressure, and the residue was purified by basic silica gel column chromatography (ethyl acetate/methanol) to give the title compound (52 mg) as a colorless solid.

$^1$H-NMR (DMSO-$d_6$) δ 1.35-1.63 (4H, m), 1.69-1.81 (1H, m), 1.83-1.92 (1H, m), 2.22-2.34 (1H, m), 2.46 (3H, s), 2.55-2.67 (2H, m), 2.79-2.93 (1H, m), 3.01-3.15 (1H, m), 3.86-3.97 (1H, m), 7.44 (1H, s), 8.04 (1H, s), 12.21 (1H, brs).

MS(ESI+): [M+H]$^+$342.

MS(ESI+), found: 342.

Example 177

Production of 6-(5-methyl-1H-pyrazol-4-yl)-2-[(2S)-1,2,3,6-tetrahydropyridin-2-yl]thieno[3,2-d]pyrimidin-4 (3H)-one hydrochloride 6-(5-Methyl-1H-pyrazol-4-yl)-2-[(2S)-1,2,3,6-tetrahydropyridin-2-yl]thieno[3,2-d]pyrimidin-4 (3H)-one dihydrochloride (350 mg) produced in Example 145, step C, was suspended in ethanol (12 mL), and the mixture was stirred with heating at 90° C. Water (1.6 mL) was added to give a solution, and the solution was allowed to cool to room temperature. The mixture was concentrated under reduced pressure, methanol (8 mL) was added to the residue, and the mixture was stirred with heating at 65° C. Water (0.8 mL) was added, and the mixture was allowed to cool to room temperature. The precipitate was collected by filtration to give the title compound (169 mg) as a white solid.

$^1$H-NMR (DMSO-$d_6$) δ 2.37-2.53 (4H, m), 2.71-2.86 (1H, m), 3.62-3.84 (2H, m), 4.41 (1H, dd, J=11.1, 4.5 Hz), 5.77-5.85 (1H, m), 5.92-6.01 (1H, m), 7.37 (1H, s), 7.98 (0.6H, brs), 8.31 (0.4H, brs), 9.75 (1H, brs), 13.06 (1H, brs).

MS(ESI+): [M+H]$^+$314.

MS(ESI+), found: 314.

Example 178

Production of 2-[(2S)-1-azabicyclo[2.2.2]oct-2-yl]-6-(5-methyl-1H-pyrazol-4-yl)thieno[3,2-d]pyrimidin-4 (3H)-one dihydrochloride

A) Production of 1-(1-benzyl-5-methyl-1H-pyrazol-4-yl)ethanone

A mixture of pentane-2,4-dione (10.01 g) and 1,1-dimethoxy-N,N-dimethylmethanamine (12.51 g) was stirred at 80° C. for 1 hr. Tetrahydrofuran (20 mL) was added to the reaction mixture, benzylhydrazine dihydrochloride (21.46 g) was added by small portions under ice-cooling, and the mixture was stirred at 60° C. for 30 min. The reaction mixture was allowed to cool to room temperature, ethyl acetate (100 mL) and water (100 mL) were added, and the separated aqueous layer was extracted with ethyl acetate (50 mL×2). The combined organic layers were washed with brine (20 mL) and dried over anhydrous magnesium sulfate. Insoluble material was removed by filtration, the filtrate was concentrated under reduced pressure, and the residue was purified by silica gel column chromatography (ethyl acetate/hexane) to give the title compound (13.53 g) as a colorless oil.

$^1$H-NMR (DMSO-$d_6$) δ 2.44 (3H, s), 2.51 (3H, s), 5.31 (2H, s), 7.05-7.15 (2H, m), 7.18-7.40 (3H, m), 7.89 (1H, s).

B) Production of (2Z)-3-(1-benzyl-5-methyl-1H-pyrazol-4-yl)-3-chloroprop-2-enenitrile To N,N-dimethylformamide (17.55 g) was added phosphorus oxychloride (36.8 g) by small portions under ice-cooling, the mixture was stirred at room temperature for 15 min. Thereto was added 1-(1-benzyl-5-methyl-1H-pyrazol-4-yl)ethanone (12.86 g) produced above by small portions under ice-cooling, and the reaction mixture was stirred at 50° C. for 30 min. Thereto was added a powder (33.40 g) of hydroxylamine hydrochloride at 50° C. by small portions, and the reaction mixture was stirred at 50° C. for 30 min. Ice water (200 mL) was added to the reaction mixture, and the mixture was neutralized with 1M aqueous sodium hydroxide solution, and extracted with ethyl acetate (100 mL×2). The combined organic layers were washed with brine (20 mL) and dried over anhydrous magnesium sulfate. Insoluble material was removed by filtration, the filtrate was concentrated under reduced pressure, and the residue was purified by silica gel column chromatography (ethyl acetate/hexane), and crystallized from diethylether to give the title compound (6.71 g) as a pale-yellow powder.

$^1$H-NMR (DMSO-$d_6$) δ 2.37 (3H, s), 5.33 (2H, s), 5.57 (1H, s), 7.03-7.19 (5H, m), 7.73 (1H, s).

C) Production of methyl 3-amino-5-(1-benzyl-5-methyl-1H-pyrazol-4-yl)thiophene-2-carboxylate A mixture of (2Z)-3-(1-benzyl-5-methyl-1H-pyrazol-4-yl)-3-chloroprop-2-enenitrile (5.73 g) produced above, methylsulfanyl acetate (2.95 g), sodium hydride (0.80 g) and N,N-dimethylformamide (10 mL) was stirred at 60° C. for 2 hr. Ethyl acetate (20 mL) and water (10 mL) were added to the reaction mixture, and the separated aqueous layer was extracted with ethyl acetate (10 mL×2). The combined organic layers were washed with brine (20 mL) and dried over anhydrous magnesium sulfate. Insoluble material was removed by filtration, the filtrate was concentrated under reduced pressure, and the residue was purified by silica gel column chromatography (ethyl acetate/hexane) to give the title compound (6.55 g) as a colorless solid.

$^1$H-NMR (DMSO-$d_6$) δ 2.33 (3H, s), 3.65 (3H, s), 5.23 (2H, s), 7.04-7.44 (6H, m), 7.49 (1H, s).

D) Production of methyl 3-{[(2S)-1-azabicyclo[2.2.2]oct-2-ylcarbonyl]amino}-5-(1-benzyl-5-methyl-1H-pyrazol-4-yl)thiophene-2-carboxylate To a solution of (2S)-1-azabicyclo[2.2.2]octane-2-carboxylic acid hydrochloride (0.62 g) produced in Example 170, step A in thionyl chloride (4.93 mL) was added N,N-dimethylformamide (0.038 mL), and the mixture was stirred at room temperature for 24 hr. The reaction system was concentrated under reduced pressure, and to the residue were added methyl 3-amino-5-(1-benzyl-5-methyl-1H-pyrazol-4-yl)thiophene-2-carboxylate (704 mg) produced in Example 178, step C, and tetrahydrofuran (7.0 mL). To the reaction mixture was added N-ethyl-N-(1-methylethyl)propan-2-amine (0.939 mL) at 0° C., the mixture was stirred at 80° C. for 1 day, and water was added. The mixture was extracted with ethyl acetate, and the extract was washed with brine, and dried over anhydrous sodium sulfate. Insoluble material was removed by filtration, and the filtrate was concentrated under reduced pressure. The residue was purified by silica gel column chromatography (ethyl acetate/hexane) to give the title compound (481 mg) as an orange amorphous solid.

$^1$H-NMR (CDCl$_3$) δ 1.43-1.61 (4H, m), 1.86-1.99 (3H, m), 2.42 (3H, s), 2.71-3.18 (4H, m), 3.47-3.58 (1H, m), 3.88 (3H, s), 5.34 (2H, s), 7.09-7.16 (2H, m), 7.27-7.38 (3H, m), 7.75 (1H, s), 8.18 (1H, s), 11.35 (1H, brs).

E) Production of 2-[(2S)-1-azabicyclo[2.2.2]oct-2-yl]-6-(5-methyl-1H-pyrazol-4-yl)thieno[3,2-d]pyrimidin-4 (3H)-one dihydrochloride A mixed solvent of methyl 3-{[(2S)-1-azabicyclo[2.2.2]oct-2-ylcarbonyl]amino}-5-(1-benzyl-5-methyl-1H-pyrazol-4-yl)thiophene-2-carboxylate (480 mg), methanol (15 mL) and 2M aqueous sodium hydroxide solution (3.1 mL) was stirred at 60° C. for 4 hr. The reaction mixture was neutralized with 1M hydrochloric acid at 0° C., and concentrated under reduced pressure. To the residue were added ammonium chloride (2.2 g), triethylamine (5.74 mL) and N,N-dimethylformamide (15 mL), and the mixture was stirred at room temperature for 5 min. To the reaction system were added 1-ethyl-3-(3-dimethylaminopropyl)carbodiimide hydrochloride (1.98 g) and 1-hydroxybenzotriazole (1.39 g), and the mixture was stirred at room temperature for 18 hr. Water was poured into the reaction system, the mixture was extracted with ethyl acetate, and the extract was washed with water and brine, and dried over anhydrous sodium sulfate. Insoluble material was removed by filtration, and the filtrate was concentrated under reduced pressure. The residue was purified by silica gel column chromatography (ethyl acetate/hexane) to give a crude product (226 mg) of (2S)—N-[5-(1-benzyl-3-methyl-1H-pyrazol-4-yl)-2-carbamoylthiophen-3-yl]-1-azabicyclo[2.2.2]octane-2-carboxamide as a yellow solid. To the crude product of (2S)—N-[5-(1-benzyl-3-methyl-1H-pyrazol-4-yl)-2-carbamoylthiophen-3-yl]-1-azabicyclo[2.2.2]octane-2-carboxamide were added formic acid (10 mL) and 20% palladium hydroxide-carbon (50 mg), and the mixture was stirred at 80° C. for 3 hr under a hydrogen atmosphere. An operation of adding 20% palladium hydroxide-carbon (50 mg) and stirring the mixture at 80° C. for 3 hr was repeated 8 times under a hydrogen atmosphere (total reaction time: 27 hr, total palladium hydroxide-carbon used:

450 mg). The palladium hydroxide-carbon was removed by filtration, and the filtrate was concentrated under reduced pressure. The residue was purified by silica gel column chromatography (ethyl acetate/hexane and methanol/ethyl acetate) to give a pale-yellow solid. The obtained pale-yellow solid was purified by high performance liquid chromatography {column: L-column 2 ODS (20 mm i.d.×50 mm L), mobile phase: 0.1% aqueous trifluoroacetic acid solution/ 0.1% trifluoroacetic acid-acetonitrile solution}, and the object fraction was concentrated under reduced pressure. To the residue (91 mg) were added ethanol (1.0 mL) and 2M aqueous sodium hydroxide solution (0.38 mL), and the mixture was stirred at 70° C. for 30 min. The reaction mixture was concentrated under reduced pressure, and the residue was purified by basic silica gel column chromatography (ethyl acetate/hexane and methanol/ethyl acetate) to give a white solid. To the obtained solid were added methanol (2 mL) and 4M hydrochloric acid/ethyl acetate solution (2 mL) and the mixture was stirred at room temperature for 30 min. The precipitate was collected by filtration to give the title compound (57 mg) as a white solid.

$^1$H-NMR (DMSO-d$_6$) δ 1.73-1.92 (4H, m), 2.09-2.29 (2H, m), 2.37-2.47 (4H, m), 3.23-3.39 (2H, m), 3.44-3.56 (1H, m), 3.61-3.76 (1H, m), 4.70-4.81 (1H, m), 7.44 (1H, s), 8.10 (1H, brs), 9.99 (1H, brs), 12.72 (1H, brs).

MS(ESI+): [M+H]$^+$342.

MS(ESI+), found: 342.

Example 179

Production of 2-(1-azabicyclo[2.2.2]oct-2-yl)-6-[5-(trifluoromethyl)-1H-pyrazol-4-yl]thieno[3,2-d]pyrimidin-4 (3H)-one A) Production of 4-(4,4,5,5-tetramethyl-1,3,2-dioxaborolan-2-yl)-3-(trifluoromethyl)-1-trityl-1H-pyrazole 4-Bromo-3-(trifluoromethyl)-1-trityl-1H-pyrazole (3.45 g), 4,4,4',4',5,5,5',5'-octamethyl-2,2'-bi-1,3,2-dioxaborolane (5.75 g), potassium acetate (3.70 g) and N,N-dimethylformamide (30 mL) were placed in a flask, and the atmosphere in the flask was purged with argon. [1,1'-Bis(diphenylphosphino)ferrocene]palladium(II) dichloride-dichloromethane complex (1:1)(621 mg) was added, the atmosphere in the flask was purged again with argon, and the mixture was stirred at 80° C. for 15 hr. Ethyl acetate (50 mL) and water (50 mL) were added to the reaction mixture, and the separated aqueous layer was extracted with ethyl acetate (30 mL×2). The combined organic layers were washed with brine (50 mL) and dried over anhydrous magnesium sulfate. Insoluble material was filtered off, and the filtrate was concentrated under reduced pressure. The residue was purified by silica gel column chromatography (ethyl acetate/hexane), and the object fraction was concentrated under reduced pressure to give the title compound (3.81 g) as a colorless solid.

$^1$H-NMR (DMSO-d$_6$) δ 1.23 (12H, s), 6.99-7.07 (6H, m), 7.36-7.46 (9H, m), 7.60 (1H, d, J=0.9 Hz).

B) Production of 2-(1-azabicyclo[2.2.2]oct-2-yl)-6-bromothieno[3,2-d]pyrimidin-4 (3H)-one A mixture of 1-azabicyclo[2.2.2]octane-2-carboxylic acid hydrochloride (2.57 g), thionyl chloride (10 mL) and N,N-dimethylformamide (100 mg) was stirred at room temperature for 15 hr. The reaction mixture was concentrated under reduced pressure, the residue was dissolved in tetrahydrofuran (30 mL), 3-amino-5-bromothiophene-2-carboxamide (2.00 g) produced in Example 1, step D, and N-ethyl-N-(1-methylethyl)propan-2-amine (4.74 mL) were added, and the mixture was stirred at 60° C. for 2 hr. Ethyl acetate (50 mL) and water (50 mL) were added to the reaction mixture, and the separated aqueous layer was extracted with ethyl acetate (30 mL×2). The combined organic layers were washed with brine (50 mL) and dried over anhydrous magnesium sulfate. Insoluble material was removed by filtration, the filtrate was concentrated under reduced pressure, and the residue was purified by silica gel column chromatography (ethyl acetate/hexane) to give N-(5-bromo-2-carbamoylthiophen-3-yl)-1-azabicyclo[2.2.2]octane-2-carboxamide. A mixture of N-(5-bromo-2-carbamoylthiophen-3-yl)-1-azabicyclo[2.2.2] octane-2-carboxamide produced above in ethanol (10 mL) and 8M aqueous sodium hydroxide solution (3 mL) was stirred at 80° C. for 3 hr. The reaction mixture was neutralized with 1M hydrochloric acid at 0° C., and concentrated. To the residue was added methanol (5 mL), insoluble material was filtered off, and the filtrate was purified by basic silica gel column chromatography (ethyl acetate/methanol) to give the title compound (430 mg) as a colorless solid.

$^1$H-NMR (DMSO-d$_6$) δ 1.40-1.65 (4H, m), 1.73-1.94 (2H, m), 2.24 (1H, dd, J=12.9, 7.8 Hz), 2.56-2.74 (2H, m), 2.83-2.97 (1H, m), 3.05-3.17 (1H, m), 3.97 (1H, t, J=8.8 Hz), 7.60 (1H, s).

C) Production of 2-(1-azabicyclo[2.2.2]oct-2-yl)-6-[5-(trifluoromethyl)-1H-pyrazol-4-yl]thieno[3,2-d] pyrimidin-4 (3H)-one 2-(1-Azabicyclo[2.2.2]oct-2-yl)-6-bromothieno[3,2-d] pyrimidin-4 (3H)-one (400 mg) produced above, 4-(4,4,5,5-tetramethyl-1,3,2-dioxaborolan-2-yl)-3-(trifluoromethyl)-1-trityl-1H-pyrazole (889 mg), cesium carbonate (766 mg), 1,2-dimethoxyethane (10 mL) and water (1 mL) were placed in a flask, and the atmosphere in the flask was purged with argon. [1,1'-Bis(diphenylphosphino)ferrocene]palladium(II) dichloride-dichloromethane complex (1:1)(48.4 mg) was added, the atmosphere in the flask was purged again with argon, and the mixture was stirred at 80° C. for 15 hr. Ethyl acetate (20 mL) and water (10 mL) were added to the reaction mixture, and the separated aqueous layer was extracted with ethyl acetate (10 mL×2). The combined organic layers were washed with brine (20 mL) and dried over anhydrous magnesium sulfate. Insoluble material was filtered off, and the filtrate was concentrated under reduced pressure. The residue was purified by basic silica gel column chromatography (ethyl acetate/methanol) and silica gel column chromatography (ethyl acetate/methanol), and the object fraction was concentrated under reduced pressure to give 2-(1-azabicyclo [2.2.2]oct-2-yl)-6-[3-(trifluoromethyl)-1-trityl-1H-pyrazol-4-yl]thieno[3,2-d]pyrimidin-4 (3H)-one as a colorless oil. To a solution of 2-(1-azabicyclo[2.2.2]oct-2-yl)-6-[3-(trifluoromethyl)-1-trityl-1H-pyrazol-4-yl]thieno[3,2-d]pyrimidin-4 (3H)-one produced above in methanol (4 mL) was added 4M hydrochloric acid/ethyl acetate solution (4 mL), and the mixture was stirred at 60° C. for 15 hr. The reaction mixture was concentrated under reduced pressure, to the residue were added ethyl acetate (10 mL) and water (10 mL), and the separated aqueous layer was washed with ethyl acetate (10 mL). The obtained aqueous layer was basified with saturated aqueous sodium hydrogen carbonate, and extracted with ethyl acetate (10 mL×2). The combined organic layers were washed with brine (10 mL) and dried over anhydrous magnesium sulfate. Insoluble material was filtered off, and the filtrate was concentrated under reduced pressure. The residue was purified by basic silica gel column chromatography (ethyl acetate/methanol), and the object fraction was concentrated under reduced pressure to give the title compound (3.0 mg) as a colorless solid.

$^1$H-NMR (CDCl$_3$) δ 0.72-2.20 (7H, m), 2.46-2.64 (1H, m), 2.74-3.18 (3H, m), 3.80-3.92 (1H, m), 7.42-7.48 (1H, m), 7.92 (1H, s).

The structural formulas of the compounds described in Examples 1-179 are shown in the following.

TABLE 1

| Ex. No. | IUPAC name | structure | salt |
|---|---|---|---|
| 1 | 2-(2-chlorophenyl)-6-(5-methyl-1H-pyrazol-4-yl)thieno[3,2-d]pyrimidin-4(3H)-one | 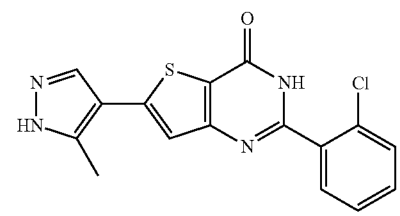 [SMILES: Cc1[nH]ncc1-c1cc2nc(-c3ccccc3Cl)[nH]c(=O)c2s1] | |
| 2 | 6-(5-methyl-1H-pyrazol-4-yl)-2-(pyrrolidin-1-ylmethyl)thieno[3,2-d]pyrimidin-4(3H)-one | 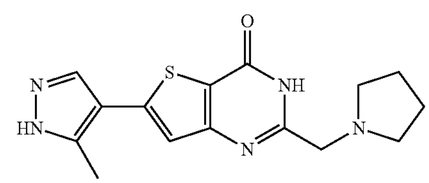 [SMILES: Cc1[nH]ncc1-c1cc2nc(CN3CCCC3)[nH]c(=O)c2s1] | |
| 3 | 6-(5-methyl-1H-pyrazol-4-yl)-2-phenylthieno[3,2-d]pyrimidin-4(3H)-one | 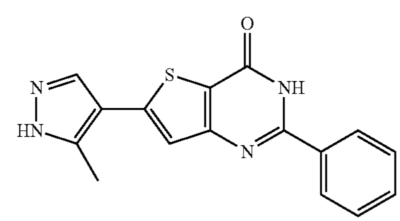 | |
| 4 | 2-{[(3S)-3-fluoro-pyrrolidin-1-yl]methyl}-6-(5-methyl-1H-pyrazol-4-yl)-thieno[3,2-d]pyrimidin-4(3H)-one | 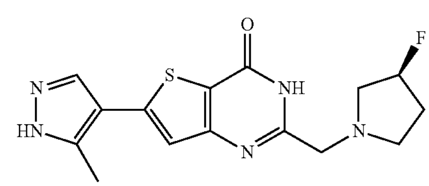 | |
| 5 | 2-{[(3R)-3-fluoro-pyrrolidin-1-yl]methyl}-6-(5-methyl-1H-pyrazol-4-yl)thieno[3,2-d]pyrimidin-4(3H)-one | 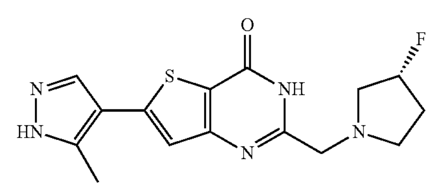 [SMILES: Cc1[nH]ncc1-c1cc2nc(CN3CC[C@@H](F)C3)[nH]c(=O)c2s1] | |
| 6 | 2-{[(3R)-3-hydroxy-pyrrolidin-1-yl]methyl}-6-(5-methyl-1H-pyrazol-4-yl)thieno[3,2-d]pyrimidin-4(3H)-one | 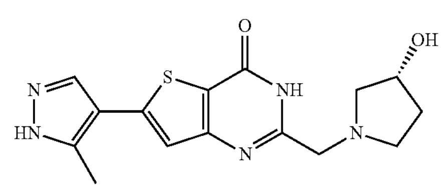 [SMILES: Cc1[nH]ncc1-c1cc2nc(CN3CC[C@@H](O)C3)[nH]c(=O)c2s1] | |
| 7 | 2-{[(3S)-3-hydroxy-pyrrolidin-1-yl]methyl}-6-(5-methyl-1H-pyrazol-4-yl)thieno[3,2-d]pyrimidin-4(3H)-one | 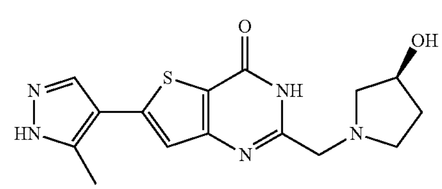 [SMILES: Cc1[nH]ncc1-c1cc2nc(CN3CC[C@H](O)C3)[nH]c(=O)c2s1] | |

TABLE 1-continued

| Ex. No. | IUPAC name | structure | salt |
|---|---|---|---|
| 8 | 2-[(3,3-difluoropyrrolidin-1-yl)methyl]-6-(5-methyl-1H-pyrazol-4-yl)thieno[3,2-d]pyrimidin-4(3H)-one | 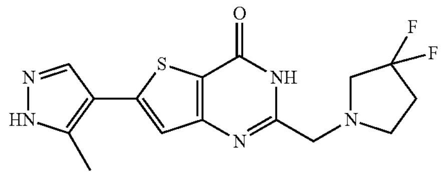 [SMILES: Cc1[nH]ncc1-c1cc2nc(CN3CCC(F)(F)C3)[nH]c(=O)c2s1] | |
| 9 | 6-(5-methyl-1H-pyrazol-4-yl)-2-(piperidin-1-ylmethyl)thieno[3,2-d]pyrimidin-4(3H)-one | 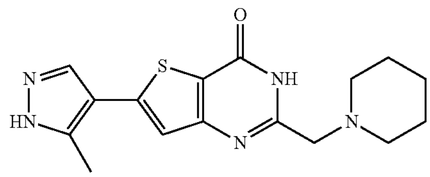 [SMILES: Cc1[nH]ncc1-c1cc2nc(CN3CCCCC3)[nH]c(=O)c2s1] | |
| 10 | 6-(5-methyl-1H-pyrazol-4-yl)-2-(morpholin-4-ylmethyl)thieno[3,2-d]pyrimidin-4(3H)-one | 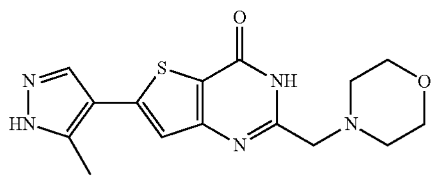 [SMILES: Cc1[nH]ncc1-c1cc2nc(CN3CCOCC3)[nH]c(=O)c2s1] | |
| 11 | 6-(5-methyl-1H-pyrazol-4-yl)-2-[(2S)-pyrrolidin-2-yl]thieno[3,2-d]pyrimidin-4(3H)-one | 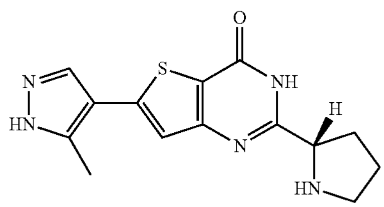 [SMILES: Cc1[nH]ncc1-c1cc2nc([C@@H]3CCCN3)[nH]c(=O)c2s1] | mono-trifluoro-acetate |
| 12 | 6-(5-methyl-1H-pyrazol-4-yl)-2-[(2R)-pyrrolidin-2-yl]thieno[3,2-d]pyrimidin-4(3H)-one | 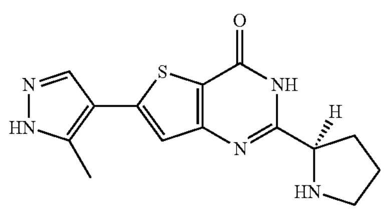 [SMILES: Cc1[nH]ncc1-c1cc2nc([C@H]3CCCN3)[nH]c(=O)c2s1] | mono-trifluoro-acetate |
| 13 | 6-(5-methyl-1H-pyrazol-4-yl)-2-(2-pyrrolidin-1-ylethyl)thieno[3,2-d]pyrimidin-4(3H)-one | 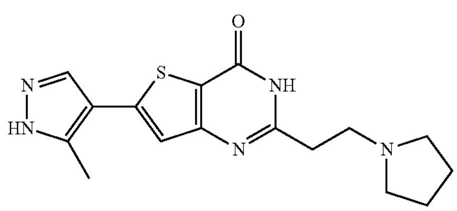 [SMILES: Cc1[nH]ncc1-c1cc2nc(CCN3CCCC3)[nH]c(=O)c2s1] | |
| 14 | 6-(5-methyl-1H-pyrazol-4-yl)-2-[(4-phenylpiperazin-1-yl)methyl]thieno[3,2-d]pyrimidin-4(3H)-one | 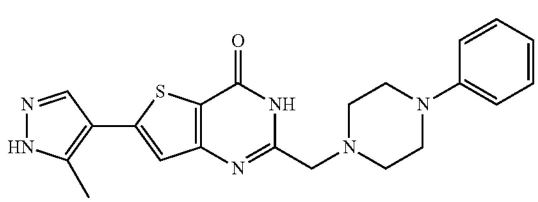 [SMILES: Cc1[nH]ncc1-c1cc2nc(CN3CCN(c4ccccc4)CC3)[nH]c(=O)c2s1] | |
| 15 | 6-(5-methyl-1H-pyrazol-4-yl)-2-[(4-phenylpiperidin-1-yl)methyl]thieno[3,2-d]pyrimidin-4(3H)-one | 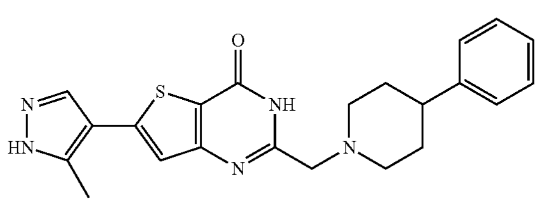 [SMILES: Cc1[nH]ncc1-c1cc2nc(CN3CCC(c4ccccc4)CC3)[nH]c(=O)c2s1] | |

TABLE 1-continued

| Ex. No. | IUPAC name | structure | salt |
|---|---|---|---|
| 16 | 2-{[(2S)-2-(hydroxymethyl)pyrrolidin-1-yl]methyl}-6-(5-methyl-1H-pyrazol-4-yl)thieno[3,2-d]pyrimidin-4(3H)-one | 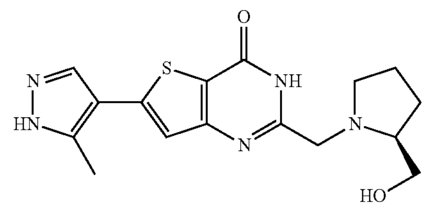 [SMILES: Cc1[nH]ncc1-c1cc2nc(CN3CCC[C@H]3CO)[nH]c(=O)c2s1] | dihydrochloride |
| 17 | 2-{[(2R)-2-(hydroxymethyl)pyrrolidin-1-yl]methyl}-6-(5-methyl-1H-pyrazol-4-yl)thieno[3,2-d]pyrimidin-4(3H)-one | 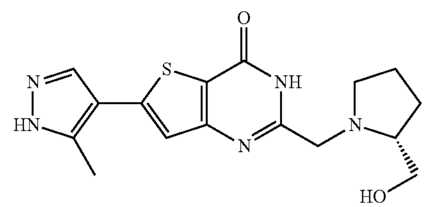 [SMILES: Cc1[nH]ncc1-c1cc2nc(CN3CCC[C@@H]3CO)[nH]c(=O)c2s1] | dihydrochloride |
| 18 | 2-{[(3S)-3-methoxypyrrolidin-1-yl]methyl}-6-(5-methyl-1H-pyrazol-4-yl)thieno[3,2-d]pyrimidin-4(3H)-one | 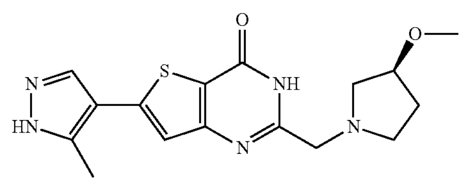 [SMILES: CO[C@H]1CCN(Cc2nc3cc(-c4cn[nH]c4C)sc3c(=O)[nH]2)C1] | |
| 19 | 2-{[(3R)-3-methoxypyrrolidin-1-yl]methyl}-6-(5-methyl-1H-pyrazol-4-yl)thieno[3,2-d]pyrimidin-4(3H)-one | 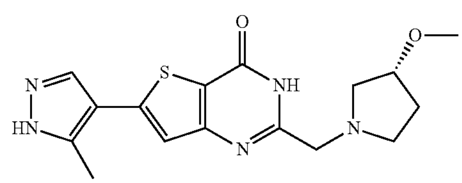 [SMILES: CO[C@@H]1CCN(Cc2nc3cc(-c4cn[nH]c4C)sc3c(=O)[nH]2)C1] | |
| 20 | 6-(5-methyl-1H-pyrazol-4-yl)-2-(1-pyrrolidin-1-ylethyl)thieno[3,2-d]pyrimidin-4(3H)-one | 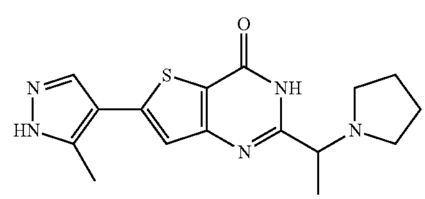 [SMILES: Cc1[nH]ncc1-c1cc2nc(C(C)N3CCCC3)[nH]c(=O)c2s1] | |
| 21 | 6-(5-ethyl-1H-pyrazol-4-yl)-2-(pyrrolidin-1-ylmethyl)thieno[3,2-d]pyrimidin-4(3H)-one | 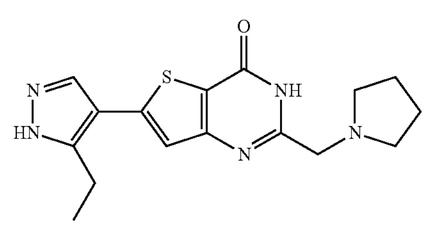 [SMILES: CCc1[nH]ncc1-c1cc2nc(CN3CCCC3)[nH]c(=O)c2s1] | dihydrochloride |
| 22 | 2-[(2S)-4,4-difluoropyrrolidin-2-yl]-6-(5-methyl-1H-pyrazol-4-yl)thieno[3,2-d]pyrimidin-4(3H)-one | 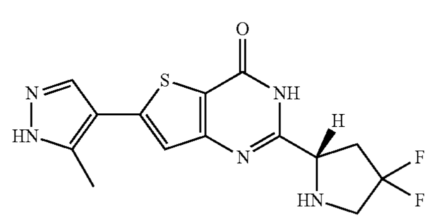 [SMILES: Cc1[nH]ncc1-c1cc2nc([C@@H]3CC(F)(F)CN3)[nH]c(=O)c2s1] | dihydrochloride |

TABLE 1-continued

| Ex. No. | IUPAC name | structure | salt |
|---|---|---|---|
| 23 | 2-[(2S,4R)-4-fluoropyrrolidin-2-yl]-6-(5-methyl-1H-pyrazol-4-yl)thieno[3,2-d]pyrimidin-4(3H)-one | 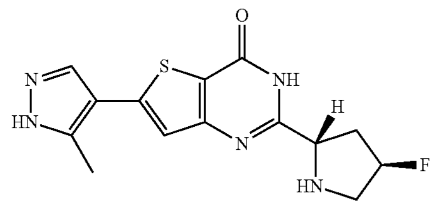 [SMILES: Cc1[nH]ncc1-c1cc2nc([C@@H]3C[C@@H](F)CN3)[nH]c(=O)c2s1] | dihydrochloride |
| 24 | 2-[(2S,4S)-4-fluoropyrrolidin-2-yl]-6-(5-methyl-1H-pyrazol-4-yl)thieno[3,2-d]pyrimidin-4(3H)-one | 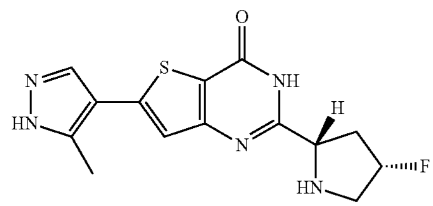 [SMILES: Cc1[nH]ncc1-c1cc2nc([C@@H]3C[C@H](F)CN3)[nH]c(=O)c2s1] | dihydrochloride |
| 25 | 2-[(3,3-difluoroazetidin-1-yl)methyl]-6-(5-methyl-1H-pyrazol-4-yl)thieno[3,2-d]pyrimidin-4(3H)-one | 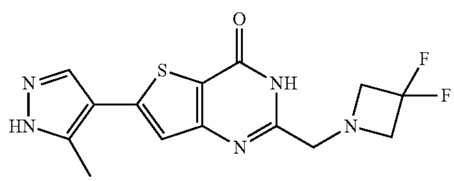 [SMILES: Cc1[nH]ncc1-c1cc2nc(CN3CC(F)(F)C3)[nH]c(=O)c2s1] | |
| 26 | 6-(5-methyl-1H-pyrazol-4-yl)-2-{[(3R)-3-methylpyrrolidin-1-yl]methyl}thieno[3,2-d]pyrimidin-4(3H)-one | 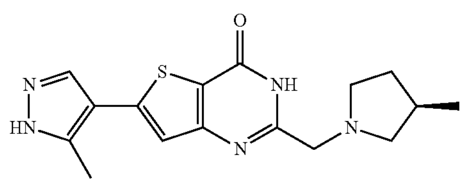 [SMILES: Cc1[nH]ncc1-c1cc2nc(CN3CC[C@@H](C)C3)[nH]c(=O)c2s1] | |
| 27 | 6-(5-methyl-1H-pyrazol-4-yl)-2-{[(3S)-3-methylpyrrolidin-1-yl]methyl}thieno[3,2-d]pyrimidin-4(3H)-one | 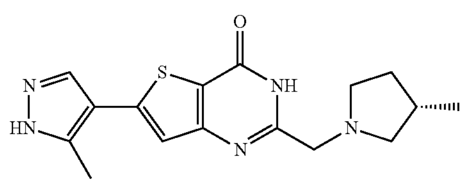 [SMILES: Cc1[nH]ncc1-c1cc2nc(CN3CC[C@H](C)C3)[nH]c(=O)c2s1] | |
| 28 | 6-(5-methyl-1H-pyrazol-4-yl)-2-{[3-(trifluoromethyl)pyrrolidin-1-yl]methyl}thieno[3,2-d]pyrimidin-4(3H)-one | 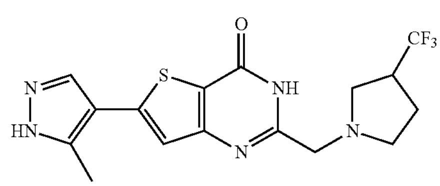 [SMILES: Cc1[nH]ncc1-c1cc2nc(CN3CCC(C(F)(F)F)C3)[nH]c(=O)c2s1] | |
| 29 | 6-(5-methyl-1H-pyrazol-4-yl)-2-{[2-(trifluoromethyl)pyrrolidin-1-yl]methyl}thieno[3,2-d]pyrimidin-4(3H)-one | 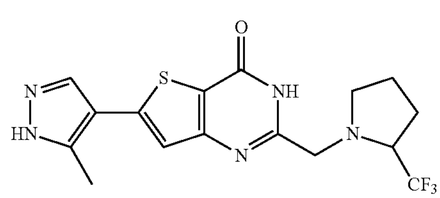 [SMILES: Cc1[nH]ncc1-c1cc2nc(CN3CCCC3C(F)(F)F)[nH]c(=O)c2s1] | |
| 30 | 6-(5-methyl-1H-pyrazol-4-yl)-2-[(2S,4R)-4-phenoxypyrrolidin-2-yl]thieno[3,2-d]pyrimidin-4(3H)-one | 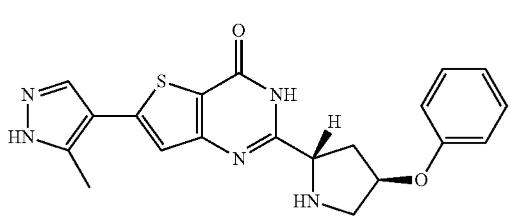 [SMILES: Cc1[nH]ncc1-c1cc2nc([C@@H]3C[C@@H](Oc4ccccc4)CN3)[nH]c(=O)c2s1] | dihydrochloride |

TABLE 1-continued

| Ex. No. | IUPAC name | structure | salt |
|---|---|---|---|
| 31 | 6-(5-methyl-1H-pyrazol-4-yl)-2-morpholin-4-ylthieno[3,2-d]pyrimidin-4(3H)-one | 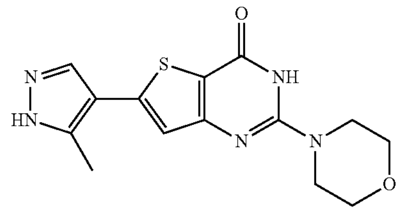 [SMILES: Cc1[nH]ncc1-c1cc2nc(N3CCOCC3)[nH]c(=O)c2s1] | |
| 32 | 6-(5-methyl-1H-pyrazol-4-yl)-2-(tetrahydrofuran-2-yl)thieno[3,2-d]pyrimidin-4(3H)-one | 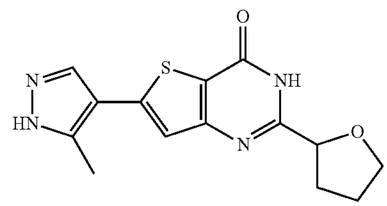 [SMILES: Cc1[nH]ncc1-c1cc2nc(C3CCCO3)[nH]c(=O)c2s1] | |
| 33 | 6-(5-methyl-1H-pyrazol-4-yl)-2-{[(2R)-2-methylpyrrolidin-1-yl]methyl}thieno[3,2-d]pyrimidin-4(3H)-one | 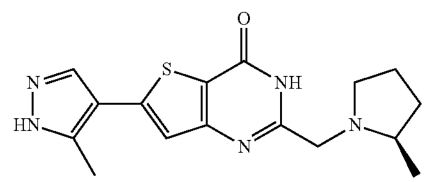 [SMILES: Cc1[nH]ncc1-c1cc2nc(CN3CCC[C@H]3C)[nH]c(=O)c2s1] | |
| 34 | 2-(ethoxymethyl)-6-(5-methyl-1H-pyrazol-4-yl)thieno[3,2-d]pyrimidin-4(3H)-one | 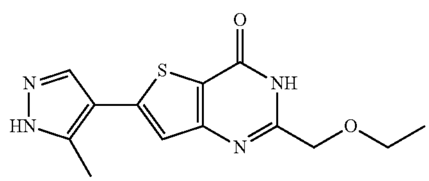 [SMILES: CCOCc1nc2cc(-c3cn[nH]c3C)sc2c(=O)[nH]1] | |
| 35 | 6-(5-methyl-1H-pyrazol-4-yl)-2-{[(2S)-2-methylpyrrolidin-1-yl]methyl}thieno[3,2-d]pyrimidin-4(3H)-one | 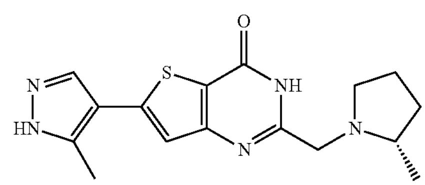 [SMILES: Cc1[nH]ncc1-c1cc2nc(CN3CCC[C@@H]3C)[nH]c(=O)c2s1] | dihydro-chloride |
| 36 | 6-(5-methyl-1H-pyrazol-4-yl)-2-(1-pyrrolidin-1-ylethyl)thieno[3,2-d]pyrimidin-4(3H)-one | 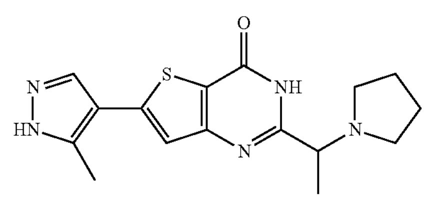 [SMILES: Cc1[nH]ncc1-c1cc2nc(C(C)N3CCCC3)[nH]c(=O)c2s1] | |
| 37 | 6-(5-methyl-1H-pyrazol-4-yl)-2-[(2S)-pyrrolidin-2-yl]thieno[3,2-d]pyrimidin-4(3H)-one | 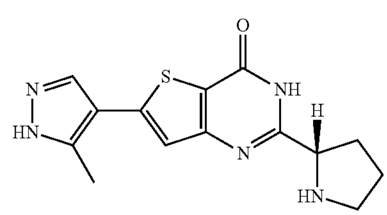 [SMILES: Cc1[nH]ncc1-c1cc2nc([C@@H]3CCCN3)[nH]c(=O)c2s1] | dihydro-chloride |

TABLE 1-continued

| Ex. No. | IUPAC name | structure | salt |
|---|---|---|---|
| 38 | 6-(5-methyl-1H-pyrazol-4-yl)-2-[(3-phenoxypyrrolidin-1-yl)methyl]thieno[3,2-d]pyrimidin-4(3H)-one | 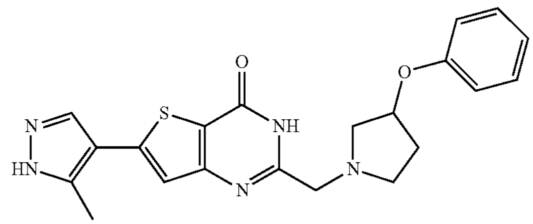 [SMILES: Cc1[nH]ncc1-c1cc2nc(CN3CCC(Oc4ccccc4)C3)[nH]c(=O)c2s1] | |
| 39 | 2-(1,4-dioxa-7-azaspiro[4.4]non-7-ylmethyl)-6-(5-methyl-1H-pyrazol-4-yl)thieno[3,2-d]pyrimidin-4(3H)-one | 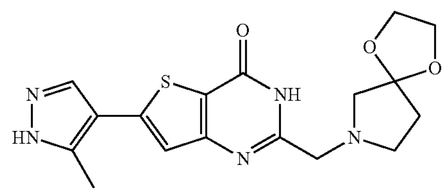 [SMILES: Cc1[nH]ncc1-c1cc2nc(CN3CCC4(C3)OCCO4)[nH]c(=O)c2s1] | |
| 40 | 6-(5-methyl-1H-pyrazol-4-yl)-2-[(2S,5R)-5-phenylpyrrolidin-2-yl]thieno[3,2-d]pyrimidin-4(3H)-one | 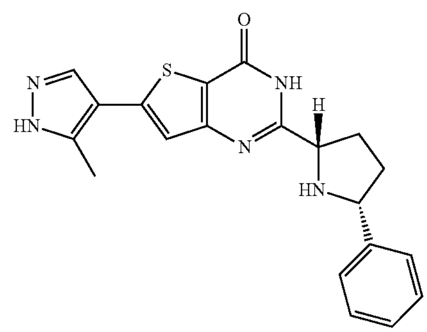 [SMILES: Cc1[nH]ncc1-c1cc2nc([C@@H]3CC[C@H](c4ccccc4)N3)[nH]c(=O)c2s1] | non-hydro-chloride |
| 41 | 2-[(dimethylamino)methyl]-6-(5-methyl-1H-pyrazol-4-yl)thieno[3,2-d]pyrimidin-4(3H)-one | 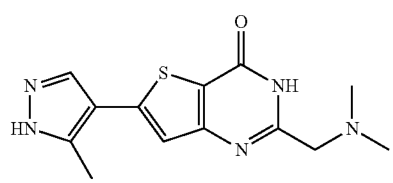 [SMILES: Cc1[nH]ncc1-c1cc2nc(CN(C)C)[nH]c(=O)c2s1] | dihydro-chloride |
| 42 | 2-[(diethylamino)methyl]-6-(5-methyl-1H-pyrazol-4-yl)thieno[3,2-d]pyrimidin-4(3H)-one | 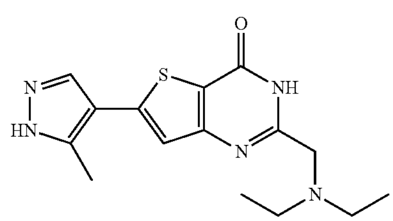 [SMILES: CCN(CC)Cc1nc2cc(-c3cn[nH]c3C)sc2c(=O)[nH]1] | |
| 43 | 2-[(4-hydroxypiperidin-1-yl)methyl]-6-(5-methyl-1H-pyrazol-4-yl)thieno[3,2-d]pyrimidin-4(3H)-one | 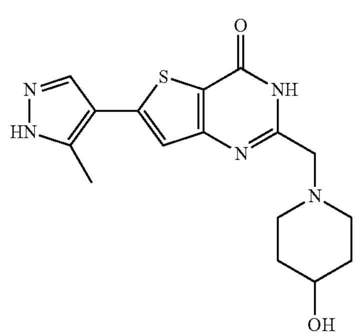 [SMILES: Cc1[nH]ncc1-c1cc2nc(CN3CCC(O)CC3)[nH]c(=O)c2s1] | |

TABLE 1-continued

| Ex. No. | IUPAC name | structure | salt |
|---|---|---|---|
| 44 | 2-[(3-hydroxypiperidin-1-yl)methyl]-6-(5-methyl-1H-pyrazol-4-yl)thieno[3,2-d]pyrimidin-4(3H)-one | 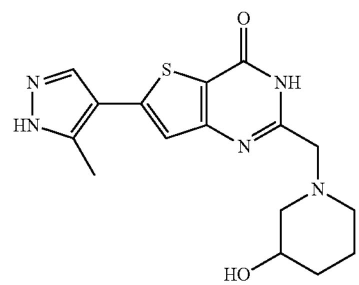 [SMILES: Cc1[nH]ncc1-c1cc2nc(CN3CCCC(O)C3)[nH]c(=O)c2s1] | |
| 45 | 6-(5-methyl-1H-pyrazol-4-yl)-2-(thiomorpholin-4-ylmethyl)thieno[3,2-d]pyrimidin-4(3H)-one | 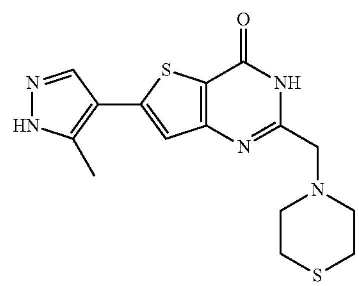 [SMILES: Cc1[nH]ncc1-c1cc2nc(CN3CCSCC3)[nH]c(=O)c2s1] | |
| 46 | 2-{[(2R)-2-(methoxymethyl)pyrrolidin-1-yl]methyl}-6-(5-methyl-1H-pyrazol-4-yl)thieno[3,2-d]pyrimidin-4(3H)-one | 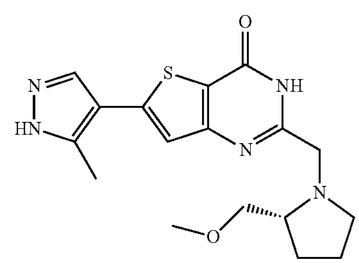 [SMILES: COC[C@H]1CCCN1Cc1nc2cc(-c3cn[nH]c3C)sc2c(=O)[nH]1] | |
| 47 | 2-{[(2S)-2-(methoxymethyl)pyrrolidin-1-yl]methyl}-6-(5-methyl-1H-pyrazol-4-yl)thieno[3,2-d]pyrimidin-4(3H)-one | 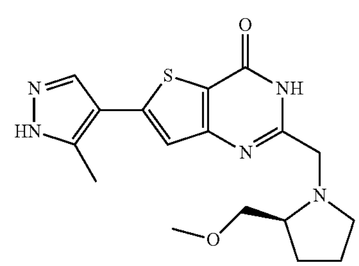 [SMILES: COC[C@@H]1CCCN1Cc1nc2cc(-c3cn[nH]c3C)sc2c(=O)[nH]1] | |
| 48 | 2-(1,3-dihydro-2H-isoindol-2-ylmethyl)-6-(5-methyl-1H-pyrazol-4-yl)thieno[3,2-d]pyrimidin-4(3H)-one | 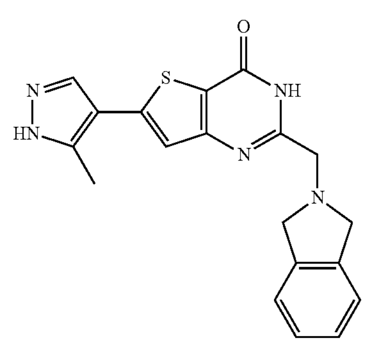 [SMILES: Cc1[nH]ncc1-c1cc2nc(CN3Cc4ccccc4C3)[nH]c(=O)c2s1] | |

TABLE 1-continued

| Ex. No. | IUPAC name | structure | salt |
|---|---|---|---|
| 49 | 2-{[benzyl(methyl)-amino]methyl}-6-(5-methyl-1H-pyrazol-4-yl)thieno[3,2-d]pyrimidin-4(3H)-one | 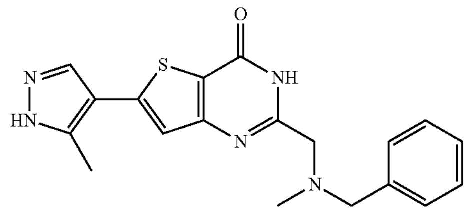 [SMILES: Cc1[nH]ncc1-c1cc2nc(CN(C)Cc3ccccc3)[nH]c(=O)c2s1] | |
| 50 | 2-(3,4-dihydroisoquinoline-2(1H)-ylmethyl)-6-(5-methyl-1H-pyrazol-4-yl)thieno[3,2-d]pyrimidin-4(3H)-one | 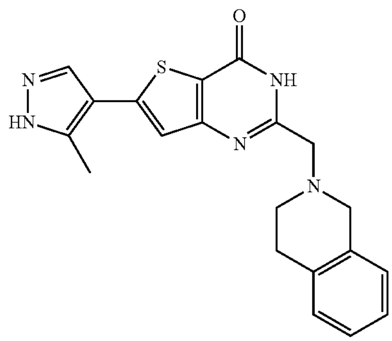 [SMILES: Cc1[nH]ncc1-c1cc2nc(CN3CCc4ccccc4C3)[nH]c(=O)c2s1] | |
| 51 | ethyl 1-{[6-(5-methyl-1H-pyrazol-4-yl)-4-oxo-3,4-dihydrothieno[3,2-d]-pyrimidin-2-yl]methyl}-piperidine-3-carboxylate | 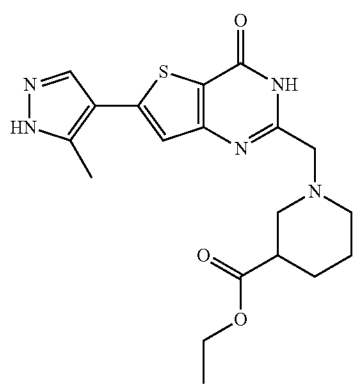 [SMILES: CCOC(=O)C1CCCN(Cc2nc3cc(-c4cn[nH]c4C)sc3c(=O)[nH]2)C1] | |
| 52 | 1-{[6-(5-methyl-1H-pyrazol-4-yl)-4-oxo-3,4-dihydrothieno-[3,2-d]pyrimidin-2-yl]methyl}-4-phenylpiperidine-4-carbonitrile | 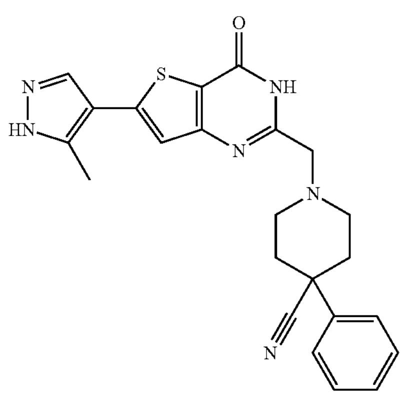 [SMILES: Cc1[nH]ncc1-c1cc2nc(CN3CCC(C#N)(c4ccccc4)CC3)[nH]c(=O)c2s1] | |

TABLE 1-continued

| Ex. No. | IUPAC name | structure | salt |
|---|---|---|---|
| 53 | 2-[(4-acetyl-4-phenylpiperidin-1-yl)methyl]-6-(5-methyl-1H-pyrazol-4-yl)thieno[3,2-d]pyrimidin-4(3H)-one | 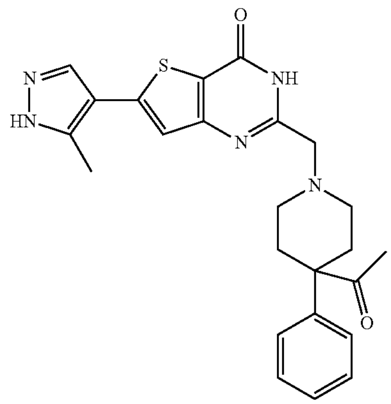 [SMILES: CC(=O)C1(c2ccccc2)CCN(Cc2nc3cc(-c4cn[nH]c4C)sc3c(=O)[nH]2)CC1] | |
| 54 | 1-{[6-(5-methyl-1H-pyrazol-4-yl)-4-oxo-3,4-dihydrothieno[3,2-d]pyrimidin-2-yl]methyl}-L-proline | 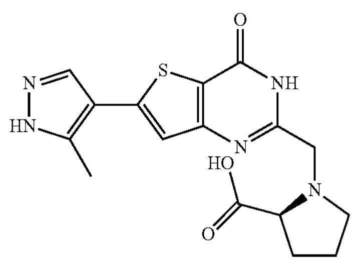 [SMILES: Cc1[nH]ncc1-c1cc2nc(CN3CCC[C@H]3C(=O)O)[nH]c(=O)c2s1] | |
| 55 | 2-{[3-(dimethylamino)-pyrrolidin-1-yl]methyl}-6-(5-methyl-1H-pyrazol-4-yl)thieno[3,2-d]pyrimidin-4(3H)-one | 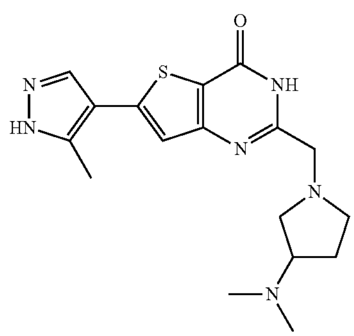 [SMILES: Cc1[nH]ncc1-c1cc2nc(CN3CCC(N(C)C)C3)[nH]c(=O)c2s1] | |
| 56 | 6-(5-methyl-1H-pyrazol-4-yl)-2-[(4-(pyrrolidin-1-yl)piperidin-1-yl)methyl]thino[3,2-d]pyrimidin-4(3H)-one | 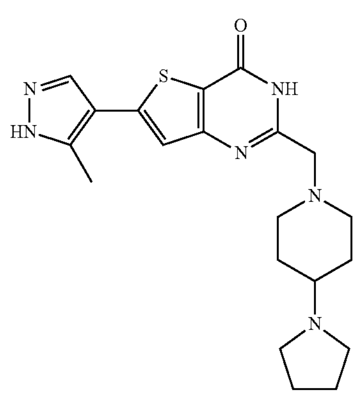 [SMILES: Cc1[nH]ncc1-c1cc2nc(CN3CCC(N4CCCC4)CC3)[nH]c(=O)c2s1] | |

TABLE 1-continued

| Ex. No. | IUPAC name | structure | salt |
|---|---|---|---|
| 57 | 2-{[(1-benzylpyrrolidin-3-yl)(methyl)amino]methyl}-6-(5-methyl-1H-pyrazol-4-yl)thieno[3,2-d]pyrimidin-4(3H)-one | 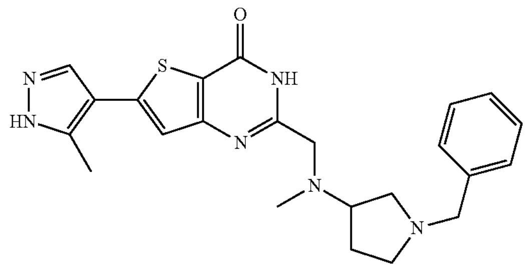 [SMILES: Cc1[nH]ncc1-c1cc2nc(CN(C)C3CCN(Cc4ccccc4)C3)[nH]c(=O)c2s1] | |
| 58 | 2-{[4-(2-fluorophenyl)-piperazin-1-yl]methyl}-6-(5-methyl-1H-pyrazol-4-yl)thieno[3,2-d]pyrimidin-4(3H)-one | 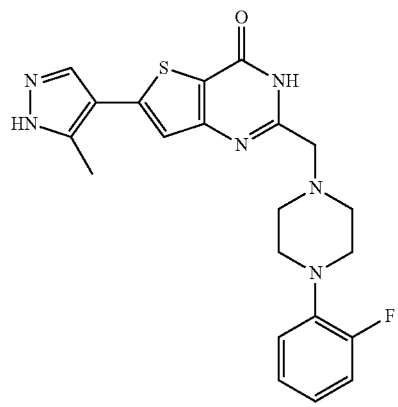 [SMILES: Cc1[nH]ncc1-c1cc2nc(CN3CCN(c4ccccc4F)CC3)[nH]c(=O)c2s1] | |
| 59 | ethyl N-{[6-(5-methyl-1H-pyrazol-4-yl)-4-oxo-3,4-dihydrothieno[3,2-d]pyrimidin-2-yl]methyl}-N-pyridin-2-ylmethyl)glycinate | 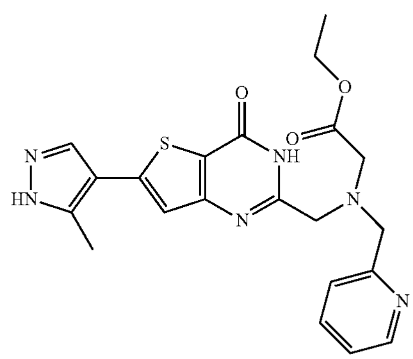 [SMILES: CCOC(=O)CN(Cc1ccccn1)Cc1nc2cc(-c3cn[nH]c3C)sc2c(=O)[nH]1] | |
| 60 | 2-{[bis(pyridin-3-ylmethyl)amino]methyl}-6-(5-methyl-1H-pyrazol-4-yl)thieno[3,2-d]pyrimidin-4(3H)-one | 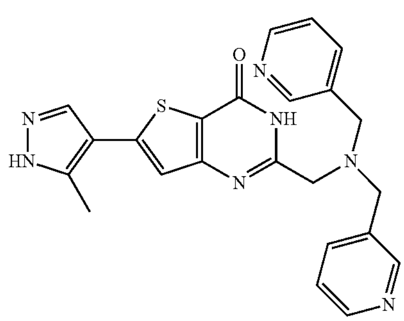 [SMILES: Cc1[nH]ncc1-c1cc2nc(CN(Cc3cccnc3)Cc3cccnc3)[nH]c(=O)c2s1] | |

| Ex. No. | IUPAC name | structure | salt |
|---|---|---|---|
| 61 | 2-{[4-(diphenylmethyl)-piperazin-1-yl]methyl}-6-(5-methyl-1H-pyrazol-4-yl)thieno[3,2-d]pyrimidin-4(3H)-one | 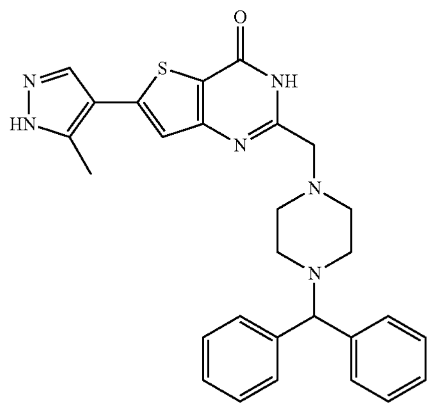 [SMILES: Cc1[nH]ncc1-c1cc2nc(CN3CCN(C(c4ccccc4)c4ccccc4)CC3)[nH]c(=O)c2s1] | |
| 62 | 2-{[(3,5-dimethoxyphenyl)-amino]methyl}-6-(5-methyl-1H-pyrazol-4-yl)thieno[3,2-d]pyrimidin-4(3H)-one | 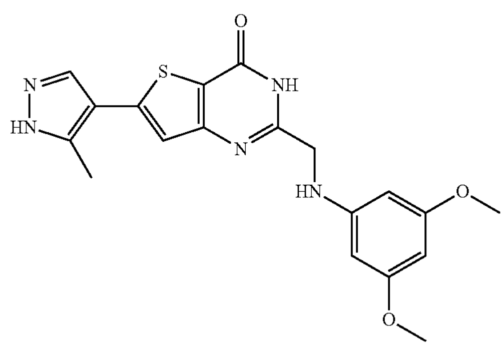 [SMILES: COc1cc(NCc2nc3cc(-c4cn[nH]c4C)sc3c(=O)[nH]2)cc(OC)c1] | |
| 63 | 2-{[(2,4-dimethoxyphenyl)-amino]methyl}-6-(5-methyl-1H-pyrazol-4-yl)thieno[3,2-d]pyrimidin-4(3H)-one | 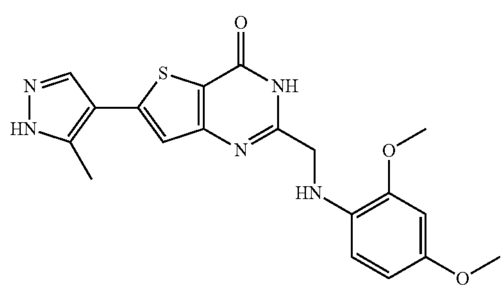 [SMILES: COc1ccc(NCc2nc3cc(-c4cn[nH]c4C)sc3c(=O)[nH]2)c(OC)c1] | |
| 64 | 6-(5-methyl-1H-pyrazol-4-yl)-2-[(2-phenylthiomorpholin-4-yl)methyl]thieno[3,2-d]pyrimidin-4(3H)-one | 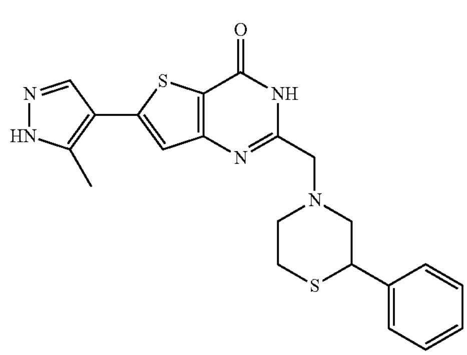 [SMILES: Cc1[nH]ncc1-c1cc2nc(CN3CCSC(c4ccccc4)C3)[nH]c(=O)c2s1] | |

TABLE 1-continued

| Ex. No. | IUPAC name | structure | salt |
|---|---|---|---|
| 65 | 6-(5-methyl-1H-pyrazol-4-yl)-2-[(2-phenylpyrrolidin-1-yl)methyl]thieno[3,2-d]pyrimidin-4(3H)-one | 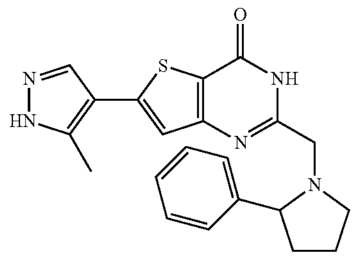 [SMILES: Cc1[nH]ncc1-c1cc2nc(CN3CCCC3c3ccccc3)[nH]c(=O)c2s1] | |
| 66 | 2-{[3-(4-methylbenzyl)-pyrrolidin-1-yl]methyl}-6-(5-methyl-1H-pyrazol-4-yl)thieno[3,2-d]pyrimidin-4(3H)-one | 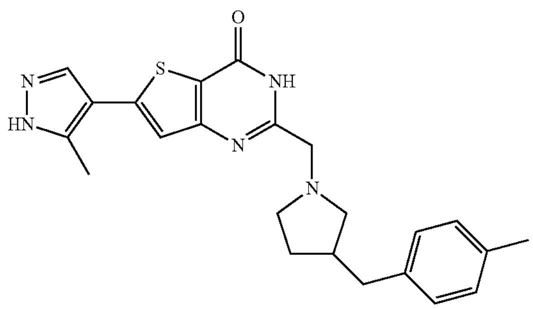 [SMILES: Cc1ccc(CC2CCN(Cc3nc4cc(-c5cn[nH]c5C)sc4c(=O)[nH]3)C2)cc1] | |
| 67 | 6-(5-methyl-1H-pyrazol-4-yl)-2-{[4-(2-oxotetrahydropyrimidin-1(2H)-yl)piperidin-1-yl]methyl}thieno[3,2-d]pyrimidin-4(3H)-one | 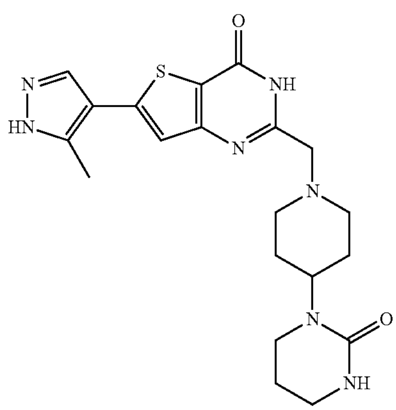 [SMILES: Cc1[nH]ncc1-c1cc2nc(CN3CCC(N4CCCNC4=O)CC3)[nH]c(=O)c2s1] | |
| 68 | 6-(5-methyl-1H-pyrazol-4-yl)-2-({[(1-(thiophen-2-yl)-cyclopropyl)methyl]amino}methyl)thieno[3,2-d]pyrimidin-4(3H)-one | 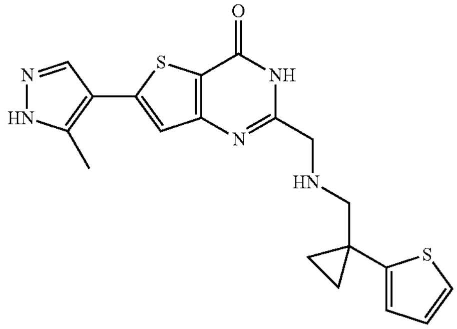 [SMILES: Cc1[nH]ncc1-c1cc2nc(CNCC3(c4cccs4)CC3)[nH]c(=O)c2s1] | |

TABLE 1-continued

| Ex. No. | IUPAC name | structure | salt |
|---|---|---|---|
| 69 | 7-methyl-1'-{[6-(5-methyl-1H-pyrazol-4-yl)-4-oxo-3,4-dihydrothieno[3,2-d]pyrimidin-2-yl]methyl}tetrahydro-5H-spiro[1,3-oxazolo[3,4-a]pyrazine-1,4'-piperidin]-3-one | 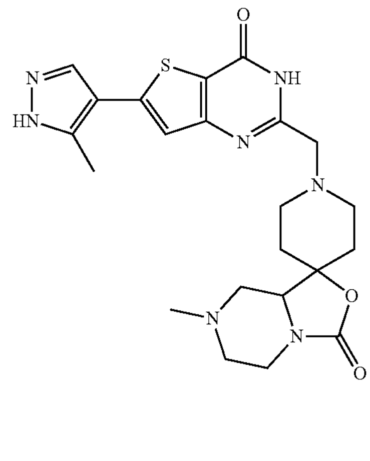 [SMILES: Cc1[nH]ncc1-c1cc2nc(CN3CCC4(CC3)OC(=O)N3CCN(C)CC34)[nH]c(=O)c2s1] | |
| 70 | 6-(5-methyl-1H-pyrazol-4-yl)-2-{[3-(phenylsulfonyl)pyrrolidin-1-yl]methyl}thieno[3,2-d]pyrimidin-4(3H)-one | 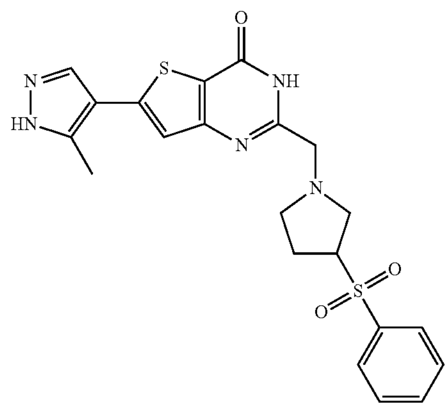 [SMILES: Cc1[nH]ncc1-c1cc2nc(CN3CCC(S(=O)(=O)c4ccccc4)C3)[nH]c(=O)c2s1] | |
| 71 | 6-(5-methyl-1H-pyrazol-4-yl)-2-piperidin-2-ylthieno[3,2-d]pyrimidin-4(3H)-one | 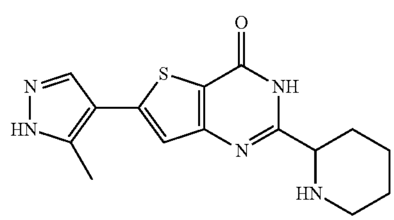 [SMILES: Cc1[nH]ncc1-c1cc2nc(C3CCCCN3)[nH]c(=O)c2s1] | dihydrochloride |
| 72 | 6-(5-methyl-1H-pyrazol-4-yl)-2-(morpholin-3-yl)thieno[3,2-d]pyrimidin-4(3H)-one | 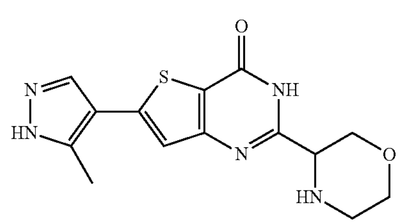 [SMILES: Cc1[nH]ncc1-c1cc2nc(C3COCCN3)[nH]c(=O)c2s1] | dihydrochloride |
| 73 | 6-(5-methyl-1H-pyrazol-4-yl)-2-[(3-oxopyrrolidin-1-yl)methyl]thieno[3,2-d]pyrimidin-4(3H)-one | 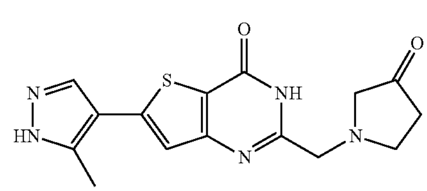 [SMILES: Cc1[nH]ncc1-c1cc2nc(CN3CCC(=O)C3)[nH]c(=O)c2s1] | |

TABLE 1-continued

| Ex. No. | IUPAC name | structure | salt |
|---|---|---|---|
| 74 | 6-(5-methyl-1H-pyrazol-4-yl)-2-[phenyl(pyrrolidin-1-yl)methyl]thieno[3,2-d]pyrimidin-4(3H)-one | 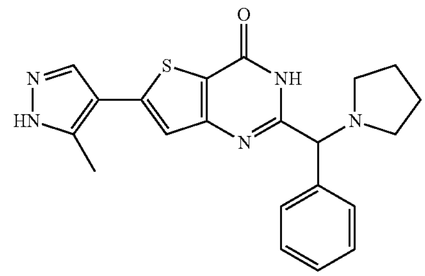 [SMILES: Cc1[nH]ncc1-c1cc2nc(C(c3ccccc3)N3CCCC3)[nH]c(=O)c2s1] | |
| 75 | 2-(3,6-dihydropyridin-1(2H)-ylmethyl)-6-(5-methyl-1H-pyrazol-4-yl)thieno[3,2-d]pyrimidin-4(3H)-one | 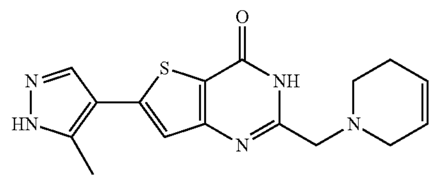 [SMILES: Cc1[nH]ncc1-c1cc2nc(CN3CC=CCC3)[nH]c(=O)c2s1] | |
| 76 | 2-[(2S)-5,5-dimethylpyrrolidin-2-yl]-6-(5-methyl-1H-pyrazol-4-yl)thieno[3,2-d]pyrimidin-4(3H)-one | 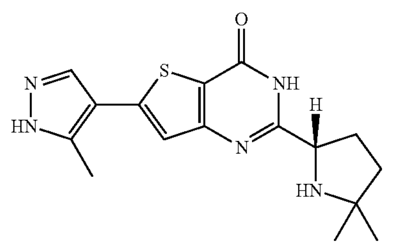 [SMILES: Cc1[nH]ncc1-c1cc2nc([C@@H]3CCC(C)(C)N3)[nH]c(=O)c2s1] | |
| 77 | 2-[(2S)-azetidin-2-yl]-6-(5-methyl-1H-pyrazol-4-yl)thieno[3,2-d]pyrimidin-4(3H)-one | 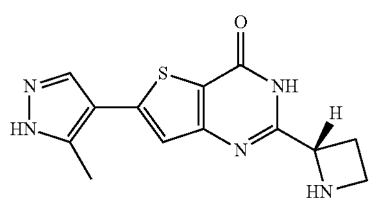 [SMILES: Cc1[nH]ncc1-c1cc2nc([C@@H]3CCN3)[nH]c(=O)c2s1] | |
| 78 | 6-(5-methyl-1H-pyrazol-4-yl)-2-[(2S,3aS,7aS)-octahydro-1H-indol-2-yl]thieno[3,2-d]pyrimidin-4(3H)-one | 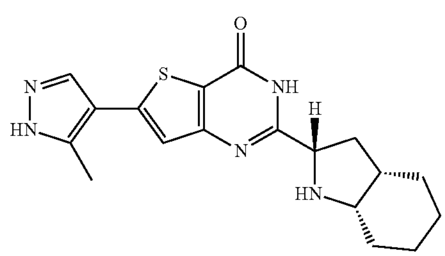 [SMILES: Cc1[nH]ncc1-c1cc2nc([C@@H]3C[C@@H]4CCCC[C@@H]4N3)[nH]c(=O)c2s1] | |
| 79 | 2-azepan-2-yl-6-(5-methyl-1H-pyrazol-4-yl)thieno[3,2-d]pyrimidin-4(3H)-one | 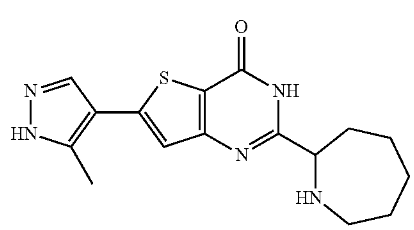 [SMILES: Cc1[nH]ncc1-c1cc2nc(C3CCCCCN3)[nH]c(=O)c2s1] | |

TABLE 1-continued

| Ex. No. | IUPAC name | structure | salt |
|---|---|---|---|
| 80 | 6-(5-methyl-1H-pyrazol-4-yl)-2-[(3-phenylpyrrolidin-1-yl)methyl]thieno[3,2-d]pyrimidin-4(3H)-one | 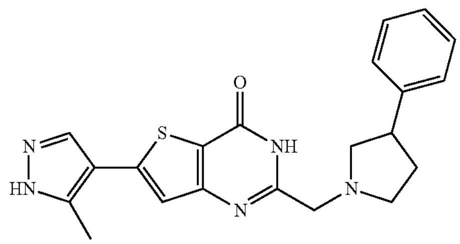 [SMILES: Cc1[nH]ncc1-c1cc2nc(CN3CCC(c4ccccc4)C3)[nH]c(=O)c2s1] | |
| 81 | 2-{[3-hydroxy-3-(tyrifluoromethyl)pyrrolidin-1-yl]methyl}-6-(5-methyl-1H-pyrazol-4-yl)thieno[3,2-d]pyrimidin-4(3H)-one | 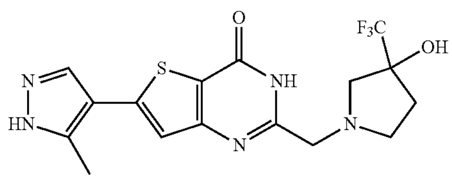 [SMILES: Cc1[nH]ncc1-c1cc2nc(CN3CCC(O)(C(F)(F)F)C3)[nH]c(=O)c2s1] | |
| 82 | 6-(5-methyl-1H-pyrazol-4-yl)-2-(2-methylpyrrolidin-2-yl)thieno[3,2-d]pyrimidin-4(3H)-one | 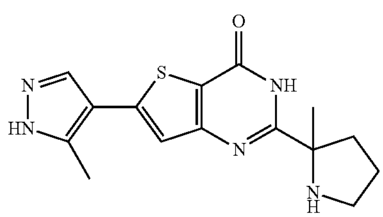 [SMILES: Cc1[nH]ncc1-c1cc2nc(C3(C)CCCN3)[nH]c(=O)c2s1] | dihydro-chloride |
| 83 | 6-(5-methyl-1H-pyrazol-4-yl)-2-[(2S)-piperidin-2-yl]thieno[3,2-d]pyrimidin-4(3H)-one | 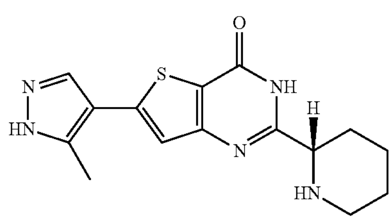 [SMILES: Cc1[nH]ncc1-c1cc2nc([C@@H]3CCCCN3)[nH]c(=O)c2s1] | dihydro-chloride |
| 84 | 6-(5-methyl-1H-pyrazol-4-yl)-2-(pyrrolidin-3-yl)thieno[3,2-d]pyrimidin-4(3H)-one | 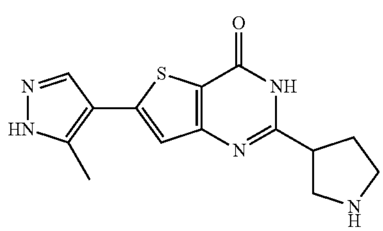 [SMILES: Cc1[nH]ncc1-c1cc2nc(C3CCNC3)[nH]c(=O)c2s1] | dihydro-chloride |
| 85 | 6-(5-methyl-1H-pyrazol-4-yl)-2-[(2R)-piperidin-2-yl]thieno[3,2-d]pyrimidin-4(3H)-one | 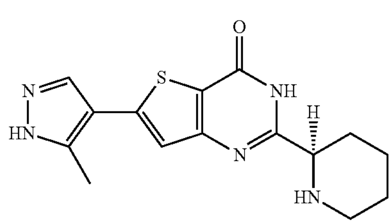 [SMILES: Cc1[nH]ncc1-c1cc2nc([C@H]3CCCCN3)[nH]c(=O)c2s1] | dihydro-chloride |

TABLE 1-continued

| Ex. No. | IUPAC name | structure | salt |
|---|---|---|---|
| 86 | 6-(5-methyl-1H-pyrazol-4-yl)-2-{1-[4-(methylsulfonyl)phenyl]pyrrolidin-2-yl}thieno[3,2-d]pyrimidin-4(3H)-one | 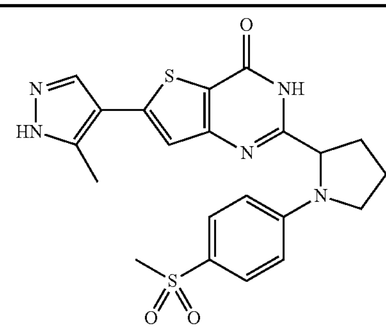 | |
| 87 | 2-[(1R*,2S*,5S*)-3-azabicyclo[3.1.0]hex-2-yl]-6-(5-methyl-1H-pyrazol-4-yl)thieno[3,2-d]pyrimidin-4(3H)-one | 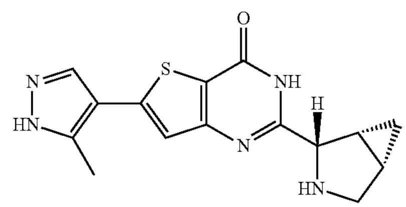 [SMILES: Cc1[nH]ncc1-c1cc2nc([C@H]3NC[C@H]4C[C@H]43)[nH]c(=O)c2s1] | dihydrochloride |
| 88 | 6-(5-methyl-1H-pyrazol-4-yl)-2-[(2S)-1-methylpyrrolidin-2-yl]thieno[3,2-d]pyimidin-4(3H)-one | 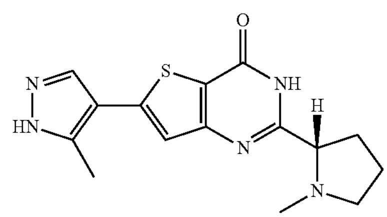 [SMILES: Cc1[nH]ncc1-c1cc2nc([C@@H]3CCCN3C)[nH]c(=O)c2s1] | dihydrochloride |
| 89 | 2-[2-(4-fluorobenzyl)pyrrolidin-2-yl]-6-(5-methyl-1H-pyrazol-4-yl)thieno[3,2-d]pyrimidin-4(3H)-one | 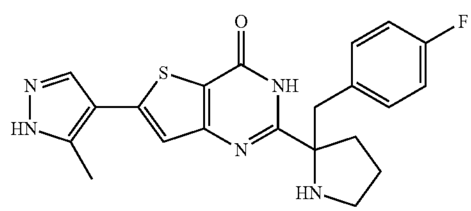 [SMILES: Cc1[nH]ncc1-c1cc2nc(C3(Cc4ccc(F)cc4)CCCN3)[nH]c(=O)c2s1] | dihydrochloride |
| 90 | 2-[(benzylamino)methyl]-6-(5-methyl-1H-pyrazol-4-yl)thieno[3,2-d]pyrimidin-4(3H)-one | 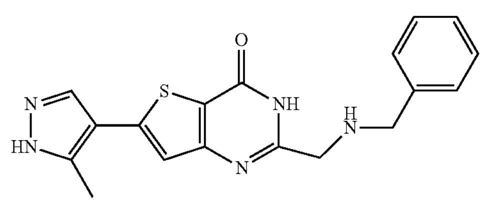 [SMILES: Cc1[nH]ncc1-c1cc2nc(CNCc3ccccc3)[nH]c(=O)c2s1] | monotrifluoroacetate |
| 91 | 2-[(1R,3S,4S)-2-azabicyclo[2.2.1]hept-3-yl]-6-(5-methyl-1H-pyrazol-4-yl)thieno[3,2-d]pyrimidin-4(3H)-one | 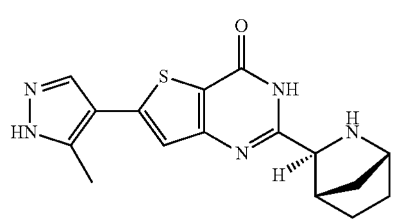 [SMILES: Cc1[nH]ncc1-c1cc2nc([C@H]3N[C@@H]4CC[C@H]3C4)[nH]c(=O)c2s1] | |
| 92 | 6-(5-methyl-1H-pyrazol-4-yl)-2-[(2S,4S)-4-methylpyrrolidin-2-yl]thieno[3,2-d]pyrimidin-4(3H)-one | 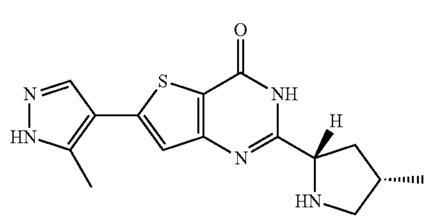 [SMILES: Cc1[nH]ncc1-c1cc2nc([C@@H]3C[C@H](C)CN3)[nH]c(=O)c2s1] | dihydrochloride |

TABLE 1-continued

| Ex. No. | IUPAC name | structure | salt |
|---|---|---|---|
| 93 | 6-(5-methyl-1H-pyrazol-4-yl)-2-pyridin-2-ylthieno[3,2-d]pyrimidin-4(3H)-one | 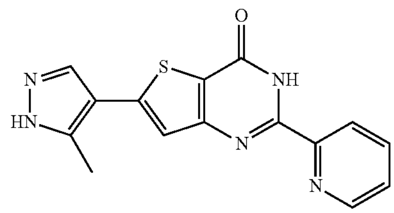 [SMILES: Cc1[nH]ncc1-c1cc2nc(-c3ccccn3)[nH]c(=O)c2s1] | |
| 94 | 6-(5-methyl-1H-pyrazol-4-yl)-2-(2-phenyl-1-pyrrolidin-1-ylethyl)thieno[3,2-d]pyrimidin-4(3H)-one | 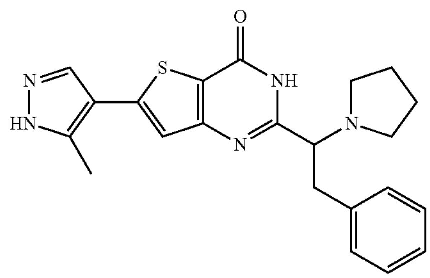 [SMILES: Cc1[nH]ncc1-c1cc2nc(C(Cc3ccccc3)N3CCCC3)[nH]c(=O)c2s1] | |
| 95 | 6-(5-methyl-1H-pyrazol-4-yl)-2-[(E)-2-phenylethenyl]thieno[3,2-d]pyrimidin-4(3H)-one | 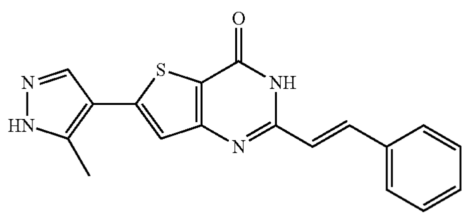 [SMILES: Cc1[nH]ncc1-c1cc2nc(/C=C/c3ccccc3)[nH]c(=O)c2s1] | monohydrochloride |
| 96 | 2-(1H-imidazol-1-ylmethyl)-6-(5-methyl-1H-pyrazol-4-yl)thieno[3,2-d]pyrimidin-4(3H)-one | 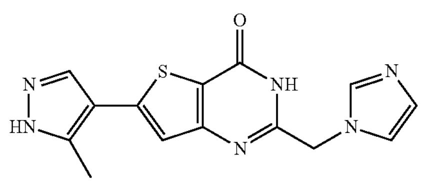 [SMILES: Cc1[nH]ncc1-c1cc2nc(Cn3ccnc3)[nH]c(=O)c2s1] | |
| 97 | 2-[(2,2-dimethylpyrrolidin-1-yl)methyl]-6-(5-methyl-1H-pyrazol-4-yl)thieno[3,2-d]pyrimidin-4(3H)-one | 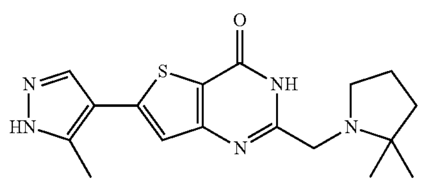 [SMILES: Cc1[nH]ncc1-c1cc2nc(CN3CCCC3(C)C)[nH]c(=O)c2s1] | |
| 98 | 6-(5-methyl-1H-pyrazol-4-yl)-2-(2-propylpyrrolidin-2-yl)thieno[3,2-d]pyrimidin-4(3H)-one | 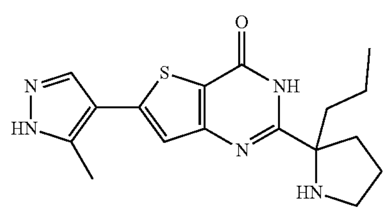 [SMILES: CCCC1(c2nc3cc(-c4cn[nH]c4C)sc3c(=O)[nH]2)CCCN1] | dihydrochloride |
| 99 | 6-(5-methyl-1H-pyrazol-4-yl)-2-[(8aR)-octahydropyrrolo[1,2-a]pyrazin-3-yl]thieno[3,2-d]pyrimidin-4(3H)-one | 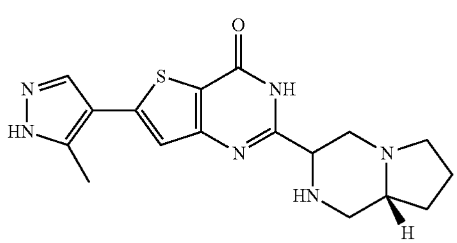 [SMILES: Cc1[nH]ncc1-c1cc2nc(C3CN4CCC[C@@H]4CN3)[nH]c(=O)c2s1] | dihydrochloride |

TABLE 1-continued

| Ex. No. | IUPAC name | structure | salt |
|---|---|---|---|
| 100 | tert-butyl (2S)-2-[6-(5-methyl-1H-pyrazol-4-yl)-4-oxo-3,4-dihydrothieno[3,2-d]pyrimidin-2-yl]piperidine-1-carboxylate | 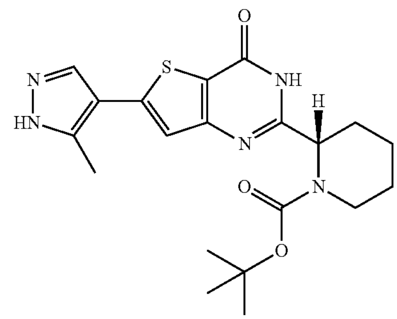 [SMILES: Cc1[nH]ncc1-c1cc2nc([C@@H]3CCCCN3C(=O)OC(C)(C)C)[nH]c(=O)c2s1] | |
| 101 | 2-[(2R)-azepan-2-yl]-6-(5-methyl-1H-pyrazol-4-yl)thieno[3,2-d]pyrimidin-4(3H)-one | 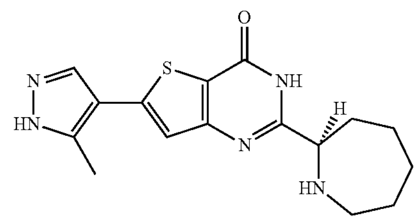 [SMILES: Cc1[nH]ncc1-c1cc2nc([C@H]3CCCCCN3)[nH]c(=O)c2s1] | |
| 102 | 2-[(2S)-azepan-2-yl]-6-(5-methyl-1H-pyrazol-4-yl)thieno[3,2-d]pyrimidin-4(3H)-one | 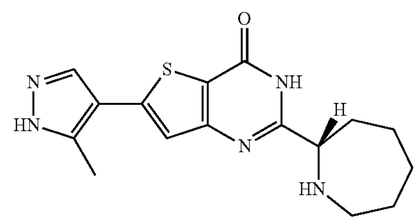 [SMILES: Cc1[nH]ncc1-c1cc2nc([C@@H]3CCCCCN3)[nH]c(=O)c2s1] | |
| 103 | 6-(5-methyl-1H-pyrazol-4-yl)-2-[(2S)-2-methylpyrrolidin-2-yl]thieno[3,2-d]pyrimidin-4(3H)-one | 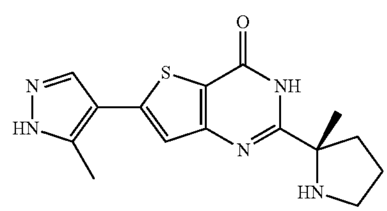 [SMILES: Cc1[nH]ncc1-c1cc2nc([C@]3(C)CCCN3)[nH]c(=O)c2s1] | dihydrochloride |
| 104 | 2-(3-azabicyclo[3.1.0]hex-3-ylmethyl)-6-(5-methyl-1H-pyrazol-4-yl)thieno[3,2-d]pyrimidin-4(3H)-one | 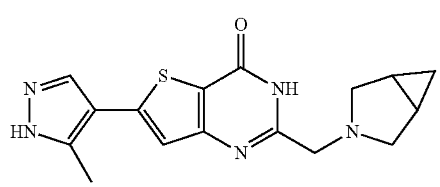 [SMILES: Cc1[nH]ncc1-c1cc2nc(CN3CC4CC4C3)[nH]c(=O)c2s1] | |
| 105 | 2-{[(4-methoxybenzyl)(1-methylethyl)amino]methyl}-6-(5-methyl-1H-pyrazol-4-yl)thieno[3,2-d]pyrimidin-4(3H)-one | 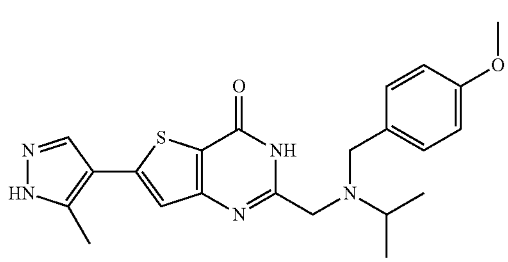 [SMILES: COc1ccc(CN(Cc2nc3cc(-c4cn[nH]c4C)sc3c(=O)[nH]2)C(C)C)cc1] | |

TABLE 1-continued

| Ex. No. | IUPAC name | structure | salt |
|---|---|---|---|
| 106 | tert-butyl (3S)-3-[6-(5-methyl-1H-pyrazol-4-yl)-4-oxo-3,4-dihydrothieno[3,2-d]pyrimidin-2-yl]-2-azabicyclo[2.2.2]octane-2-carboxylate | 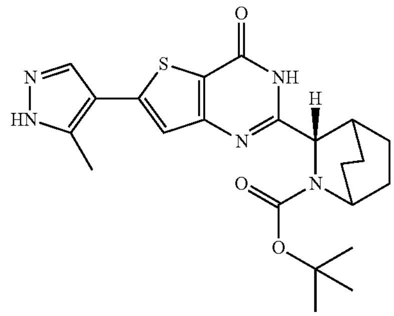 [SMILES: Cc1[nH]ncc1-c1cc2nc([C@@H]3C4CCC(CC4)N3C(=O)OC(C)(C)C)[nH]c(=O)c2s1] | |
| 107 | 6-(5-methyl-1H-pyrazol-4-yl)-2-[(2S*,5R*)-5-phenylpiperidin-2-yl]thieno[3,2-d]pyrimidin-4(3H)-one | 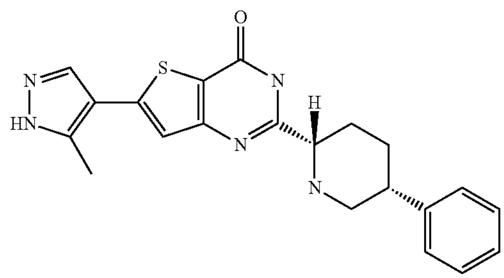 [SMILES: Cc1[nH]ncc1-c1cc2nc([C@@H]3CC[C@H](c4ccccc4)CN3)[nH]c(=O)c2s1] | mono-hydro-chloride |
| 108 | 2-[(3S)-2-azabicyclo[2.2.2]oct-3-yl]-6-(5-methyl-1H-pyrazol-4-yl)thieno[3,2-d]pyrimidin-4(3H)-one | 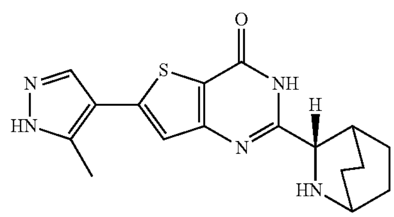 [SMILES: Cc1[nH]ncc1-c1cc2nc([C@H]3NC4CCC3CC4)[nH]c(=O)c2s1] | dihydro-chloride |
| 109 | 6-(5-methyl-1H-pyrazol-4-yl)-2-[(2R)-2-methylpyrrolidin-2-yl]thieno[3,2-d]pyrimidin-4(3H)-one | 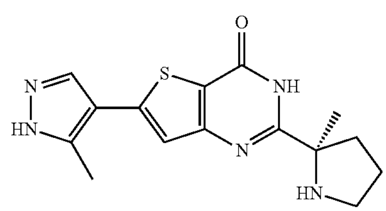 [SMILES: Cc1[nH]ncc1-c1cc2nc([C@@]3(C)CCCN3)[nH]c(=O)c2s1] | dihydro-chloride |
| 110 | 2-[(1S*,2S*,5R*)-3-azabicyclo[3.1.0]hex-2-yl]-6-(5-methyl-1H-pyrazol-4-yl)thieno[3,2-d]pyrimidin-4(3H)-one | 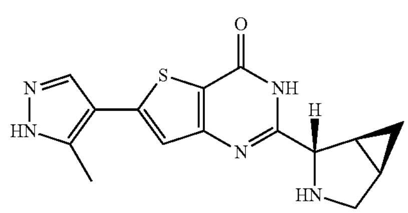 [SMILES: Cc1[nH]ncc1-c1cc2nc([C@H]3NC[C@@H]4C[C@@H]43)[nH]c(=O)c2s1] | dihydro-chloride |
| 111 | 6-(5-methyl-1H-pyrazol-4-yl)-2-[(4R)-1,3-thiazolidin-4-yl]thieno[3,2-d]pyrimidin-4(3H)-one | 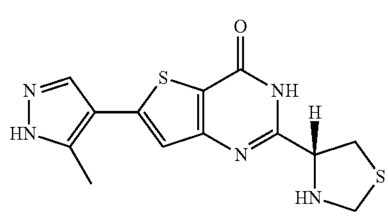 [SMILES: Cc1[nH]ncc1-c1cc2nc([C@@H]3CSCN3)[nH]c(=O)c2s1] | |

TABLE 1-continued

| Ex. No. | IUPAC name | structure | salt |
|---|---|---|---|
| 112 | 2-[(1S,2R,5R)-3-azabicyclo[3.1.0]hex-2-yl]-6-(5-methyl-1H-pyrazol-4-yl)thieno[3,2-d]pyrimidin-4(3H)-one | 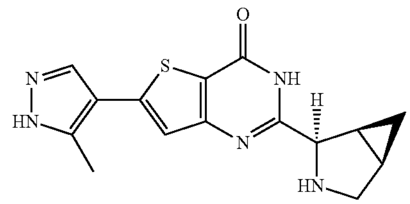 [SMILES: Cc1[nH]ncc1-c1cc2nc([C@@H]3NC[C@@H]4C[C@@H]43)[nH]c(=O)c2s1] | dihydrochloride |
| 113 | 2-[(1R,2S,5S)-3-azabicyclo[3.1.0]hex-2-yl]-6-(5-methyl-1H-pyrazol-4-yl)thieno[3,2-d]pyrimidin-4(3H)-one | 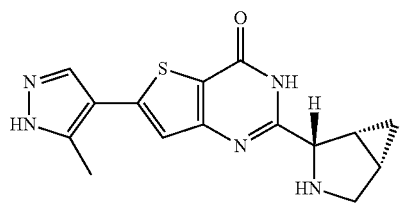 [SMILES: Cc1[nH]ncc1-c1cc2nc([C@H]3NC[C@H]4C[C@H]43)[nH]c(=O)c2s1] | dihydrochloride |
| 114 | 2-[(2,5-dimethylpyrrolidin-1-yl)methyl]-6-(5-methyl-1H-pyrazol-4-yl)thieno[3,2-d]pyrimidin-4(3H)-one | 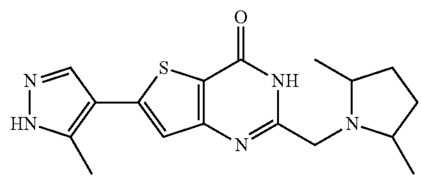 [SMILES: Cc1[nH]ncc1-c1cc2nc(CN3C(C)CCC3C)[nH]c(=O)c2s1] | |
| 115 | 6-(5-methyl-1H-pyrazol-4-yl)-2-(1,2,3,4-tetrahydroisoquinolin-3-yl)thieno[3,2-d]pyrimidin-4(3H)-one | 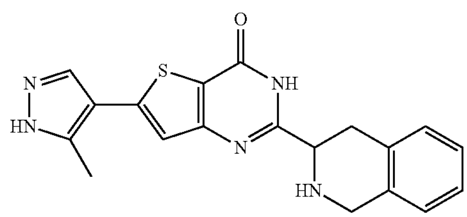 [SMILES: Cc1[nH]ncc1-c1cc2nc(C3Cc4ccccc4CN3)[nH]c(=O)c2s1] | dihydrochloride |
| 116 | 2-(7-azabicyclo[2.2.1]hept-1-yl)-6-(5-methyl-1H-pyrazol-4-yl)thieno[3,2-d]pyrimidin-4(3H)-one | 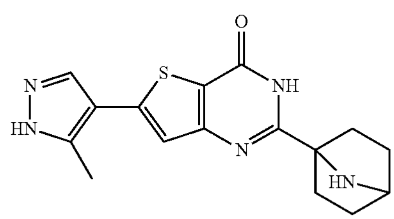 [SMILES: Cc1[nH]ncc1-c1cc2nc(C34CCC(CC3)N4)[nH]c(=O)c2s1] | monohydrochloride |
| 117 | 6-(5-methyl-1H-pyrazol-4-yl)-2-[(2S,4S)-4-phenylpyrrolidin-2-yl]thieno[3,2-d]pyrimidin-4(3H)-one | 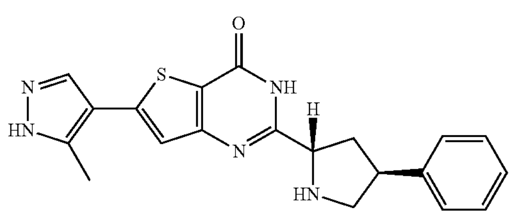 [SMILES: Cc1[nH]ncc1-c1cc2nc([C@@H]3C[C@@H](c4ccccc4)CN3)[nH]c(=O)c2s1] | dihydrochloride |
| 118 | 2-(6,6-dimethylmorpholin-3-yl)-6-(5-methyl-1H-pyrazol-4-yl)thieno[3,2-d]pyrimidin-4(3H)-one | 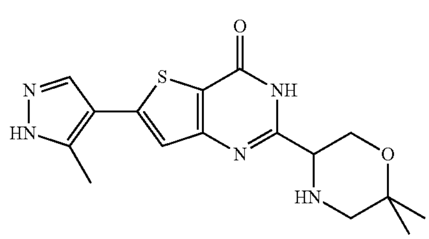 [SMILES: Cc1[nH]ncc1-c1cc2nc(C3COC(C)(C)CN3)[nH]c(=O)c2s1] | dihydrochloride |

TABLE 1-continued

| Ex. No. | IUPAC name | structure | salt |
|---|---|---|---|
| 119 | 2-[(1S,3S,5S)-2-azabicyclo[3.1.0]hex-3-yl]-6-(5-methyl-1H-pyrazol-4-yl)thieno[3,2-d]pyrimidin-4(3H)-one | 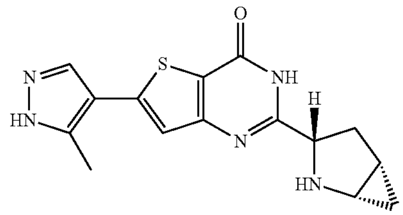 [SMILES: Cc1[nH]ncc1-c1cc2nc([C@@H]3C[C@@H]4C[C@@H]4N3)[nH]c(=O)c2s1] | dihydrochloride |
| 120 | 6-(5-methyl-1H-pyrazol-4-yl)-2-[(2S,4R)-4-phenylpyrrolidin-2-yl]thieno[3,2-d]pyrimidin-4(3H)-one | 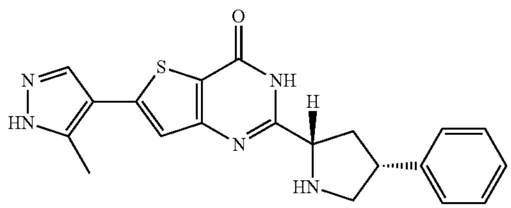 [SMILES: Cc1[nH]ncc1-c1cc2nc([C@@H]3C[C@H](c4ccccc4)CN3)[nH]c(=O)c2s1] | dihydrochloride |
| 121 | 2-[amino(cyclohexyl)methyl]-6-(5-methyl-1H-pyrazol-4-yl)thieno[3,2-d]pyrimidin-4(3H)-one | 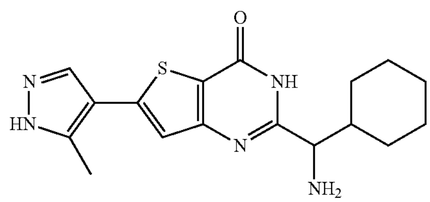 [SMILES: Cc1[nH]ncc1-c1cc2nc(C(N)C3CCCCC3)[nH]c(=O)c2s1] | dihydrochloride |
| 122 | 6-(5-methyl-1H-pyrazol-4-yl)-2-(1,2,3,4-tetrahydroquinolin-2-yl)thieno[3,2-d]pyrimidin-4(3H)-one | 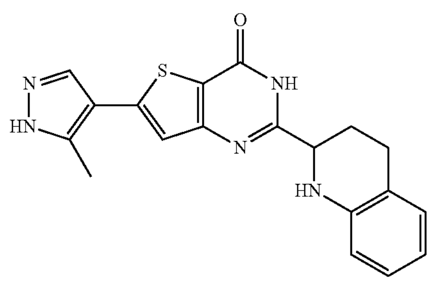 [SMILES: Cc1[nH]ncc1-c1cc2nc(C3CCc4ccccc4N3)[nH]c(=O)c2s1] | dihydrochloride |
| 123 | 6-(5-methyl-1H-pyrazol-4-yl)-2-[(3aS,6aS)-octahydrocyclopenta[b]pyrrol-2-yl]thieno[3,2-d]pyrimidin-4(3H)-one | 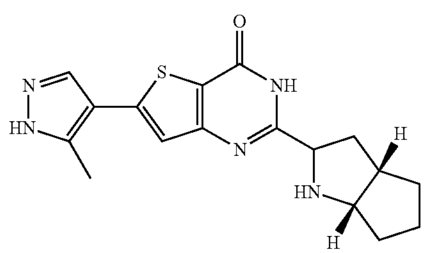 [SMILES: Cc1[nH]ncc1-c1cc2nc(C3C[C@@H]4CCC[C@@H]4N3)[nH]c(=O)c2s1] | |
| 124 | 2-(1-acetylpyrrolidin-2-yl)-6-(5-methyl-1H-pyrazol-4-yl)thieno[3,2-d]pyrimidin-4(3H)-one | 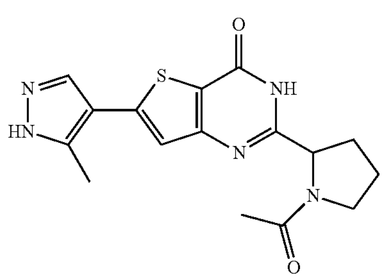 [SMILES: CC(=O)N1CCCC1c1nc2cc(-c3cn[nH]c3C)sc2c(=O)[nH]1] | |

TABLE 1-continued

| Ex. No. | IUPAC name | structure | salt |
|---|---|---|---|
| 125 | 2-[(1R*,2S*)-2-aminocyclohexyl]-6-(5-methyl-1H-pyrazol-4-yl)thieno[3,2-d]pyrimidin-4(3H)-one | 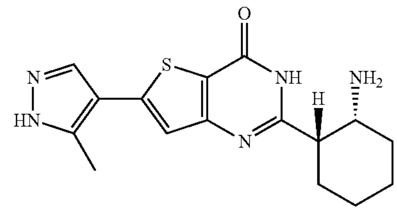 [SMILES: Cc1[nH]ncc1-c1cc2nc([C@H]3CCCC[C@H]3N)[nH]c(=O)c2s1] | dihydrochloride |
| 126 | 2-[6-(5-methyl-1H-pyrazol-4-yl)-4-oxo-3,4-dihydrothieno[3,2-d]pyrimidin-2-yl]pyrrolidine-1-carboxamide | 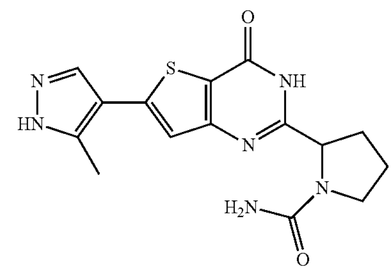 [SMILES: Cc1[nH]ncc1-c1cc2nc(C3CCCN3C(N)=O)[nH]c(=O)c2s1] | |
| 127 | 6-(5-methyl-1H-pyrazol-4-yl)-2-(pyrrolidin-1-ylcarbonyl)thieno[3,2-d]pyrimidin-4(3H)-one | 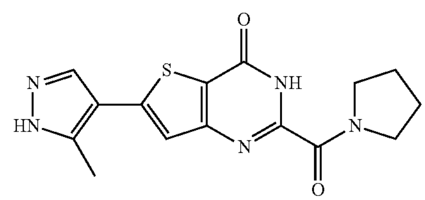 [SMILES: Cc1[nH]ncc1-c1cc2nc(C(=O)N3CCCC3)[nH]c(=O)c2s1] | |
| 128 | 2-[(1R*,3S,4R*,5S)-5-fluoro-2-azabicyclo[2.2.1]hept-3-yl]-6-(5-methyl-1H-pyrazol-4-yl)thieno[3,2-d]pyrimidin-4(3H)-one | 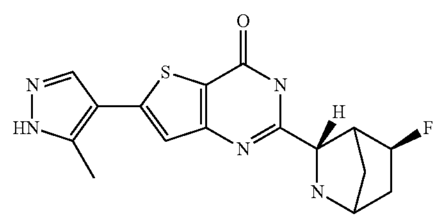 [SMILES: Cc1[nH]ncc1-c1cc2nc([C@H]3NC4CC3[C@@H](F)C4)[nH]c(=O)c2s1] | dihydrochloride |
| 129 | 2-[(1R*,2R*)-2-aminocyclohexyl]-6-(5-methyl-1H-pyrazol-4-yl)thieno[3,2-d]pyrimidin-4(3H)-one | 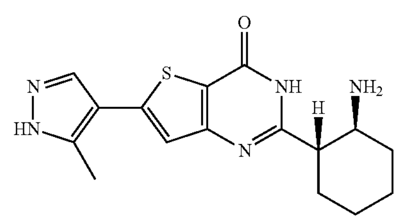 [SMILES: Cc1[nH]ncc1-c1cc2nc([C@H]3CCCC[C@@H]3N)[nH]c(=O)c2s1] | dihydrochloride |
| 130 | 6-(5-methyl-1H-pyrazol-4-yl)-2-(1H-pyrrol-1-ylmethyl)thieno[3,2-d]pyrimidin-4(3H)-one | 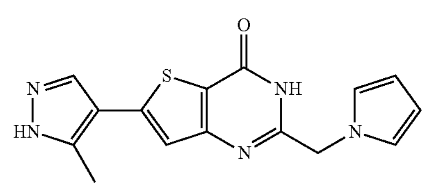 [SMILES: Cc1[nH]ncc1-c1cc2nc(Cn3cccc3)[nH]c(=O)c2s1] | |
| 131 | 6-(5-methyl-1H-pyrazol-4-yl)-2-morpholin-2-ylthieno[3,2-d]pyrimidin-4(3H)-one | 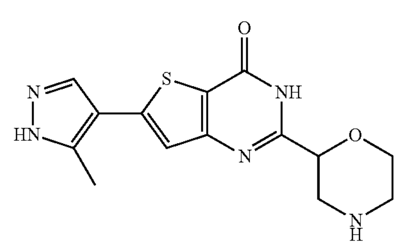 [SMILES: Cc1[nH]ncc1-c1cc2nc(C3CNCCO3)[nH]c(=O)c2s1] | dihydrochloride |

TABLE 1-continued

| Ex. No. | IUPAC name | structure | salt |
|---|---|---|---|
| 132 | 6-(5-methyl-1H-pyrazol-4-yl)-2-[(2R*,3R*)-3-phenylpyrrolidin-2-yl]thieno[3,2-d]pyrimidin-4(3H)-one | 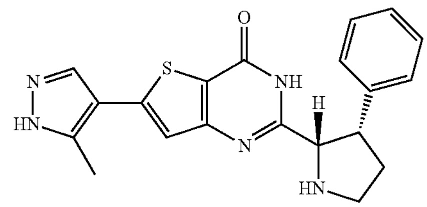 [SMILES: Cc1[nH]ncc1-c1cc2nc([C@H]3NCC[C@H]3c3ccccc3)[nH]c(=O)c2s1] | dihydrochloride |
| 133 | 2-[(methylamino)methyl]-6-(5-methyl-1H-pyrazol-4-yl)thieno[3,2-d]pyrimidin-4(3H)-one | 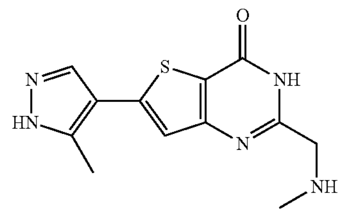 [SMILES: CNCc1nc2cc(-c3cn[nH]c3C)sc2c(=O)[nH]1] | dihydrochloride |
| 134 | 2-(2-amino-2-methylpropyl)-6-(5-methyl-1H-pyrazol-4-yl)thieno[3,2-d]pyrimidin-4(3H)-one | 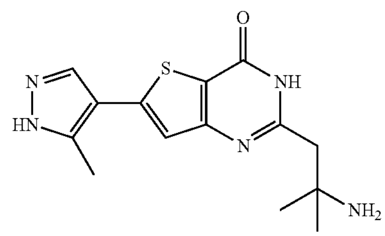 [SMILES: Cc1[nH]ncc1-c1cc2nc(CC(C)(C)N)[nH]c(=O)c2s1] | dihydrochloride |
| 135 | 2-(1-amino-1-methylethyl)-6-(5-methyl-1H-pyrazol-4-yl)thieno[3,2-d]pyrimidin-4(3H)-one | 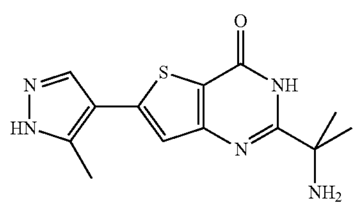 [SMILES: Cc1[nH]ncc1-c1cc2nc(C(C)(C)N)[nH]c(=O)c2s1] | dihydrochloride |
| 136 | 6-(5-methyl-1H-pyrazol-4-yl)-2-(1,2,3,6-tetrahydropyridin-2-yl)thieno[3,2-d]pyrimidin-4(3H)-one | 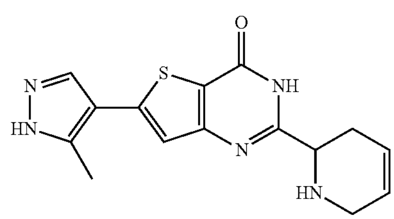 [SMILES: Cc1[nH]ncc1-c1cc2nc(C3CC=CCN3)[nH]c(=O)c2s1] | dihydrochloride |
| 137 | 2-(2-aminocyclopentyl)-6-(5-methyl-1H-pyrazol-4-yl)thieno[3,2-d]pyrimidin-4(3H)-one | 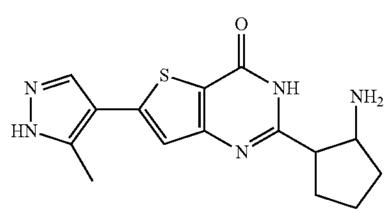 [SMILES: Cc1[nH]ncc1-c1cc2nc(C3CCCC3N)[nH]c(=O)c2s1] | dihydrochloride |
| 138 | 6-(5-methyl-1H-pyrazol-4-yl)-2-(1,3-thiazol-2-yl)thieno[3,2-d]pyrimidin-4(3H)-one | 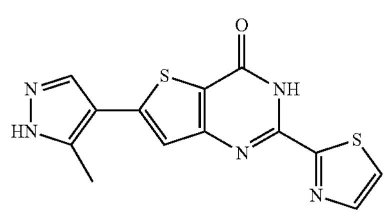 [SMILES: Cc1[nH]ncc1-c1cc2nc(-c3nccs3)[nH]c(=O)c2s1] | dihydrochloride |

TABLE 1-continued

| Ex. No. | IUPAC name | structure | salt |
|---|---|---|---|
| 139 | 2-(2-aminocyclopentyl)-6-(5-methyl-1H-pyrazol-4-yl)thieno[3,2-d]pyrimidin-4(3H)-one | 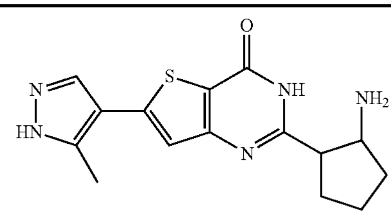 | dihydro-chloride |
| 140 | 6-(5-methyl-1H-pyrazol-4-yl)-2-[(2S,3S)-3-methylpyrrolidin-2-yl]thieno[3,2-d]pyrimidin-4(3H)-one | 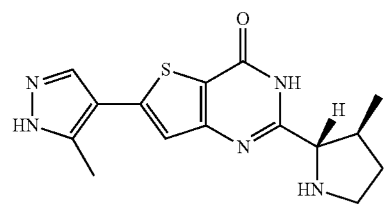 [SMILES: Cc1[nH]ncc1-c1cc2nc([C@H]3NCC[C@@H]3C)[nH]c(=O)c2s1] | dihydro-chloride |
| 141 | 2-(4-hydroxy-4-phenylpyrrolidin-2-yl)-6-(5-methyl-1H-pyrazol-4-yl)thieno[3,2-d]pyrimidin-4(3H)-one | 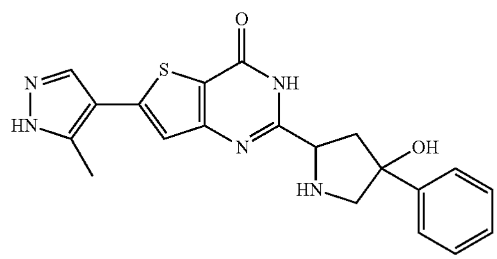 [SMILES: Cc1[nH]ncc1-c1cc2nc(C3CC(O)(c4ccccc4)CN3)[nH]c(=O)c2s1] | dihydro-chloride |
| 142 | 2-[(1R,3S,4R,5S) or (1S,3S,4S,5S)-5-hydroxy-2-azabicyclo[2.2.1]hept-3-yl]-6-(5-methyl-1H-pyrazol-4-yl)thieno[3,2-d]pyrimidin-4(3H)-one | 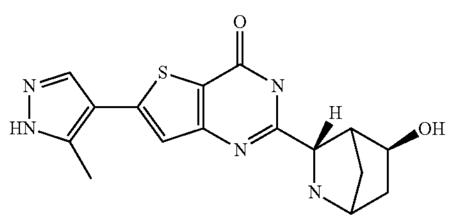 [SMILES: Cc1[nH]ncc1-c1cc2nc([C@H]3NC4CC3[C@@H](O)C4)[nH]c(=O)c2s1] | dihydro-chloride |
| 143 | 2-(pyrrolidin-1-ylmethyl)-6-[5-(trifluoromethyl)-1H-pyrazol-4-yl]thieno[3,2-d]pyrimidin-4(3H)-one | 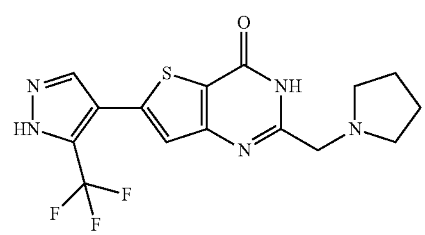 [SMILES: O=c1[nH]c(CN2CCCC2)nc2cc(-c3cn[nH]c3C(F)(F)F)sc12] | |
| 144 | 6-(5-methyl-1H-pyrazol-4-yl)-2-[(2R*,3S*)-3-phenylpyrrolidin-2-yl]thieno[3,2-d]pyrimidin-4(3H)-one | 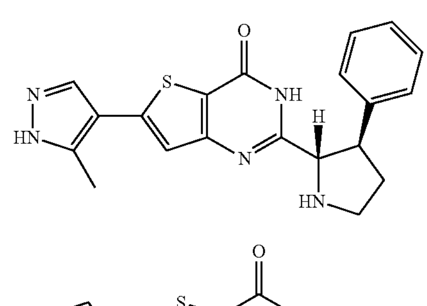 | mono-hydro-chloride |
| 145 | 6-(5-methyl-1H-pyrazol-4-yl)-2-[(2S)-1,2,3,6-tetrahydropyridin-2-yl]thieno[3,2-d]pyrimidin-4(3H)-one | 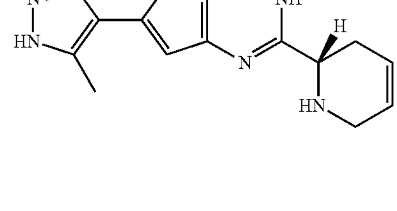 | dihydro-chloride |

TABLE 1-continued

| Ex. No. | IUPAC name | structure | salt |
|---|---|---|---|
| 146 | 6-(5-methyl-1H-pyrazol-4-yl)-2-[(2R)-1,2,3,6-tetrahydropyridin-2-yl]thieno[3,2-d]pyrimidin-4(3H)-one | 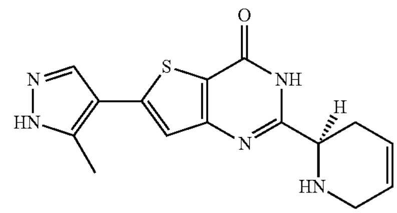 [SMILES: Cc1[nH]ncc1-c1cc2nc([C@H]3CC=CCN3)[nH]c(=O)c2s1] | dihydro-chloride |
| 147 | 6-(5-methyl-1H-pyrazol-4-yl)-2-piperazin-2-ylthieno[3,2-d]pyrimidin-4(3H)-one | 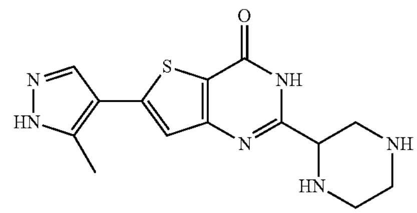 [SMILES: Cc1[nH]ncc1-c1cc2nc(C3CNCCN3)[nH]c(=O)c2s1] | ditri-fluoro-acetate |
| 148 | 2-(2-azabicyclo[2.2.1]hex-1-yl)-6-(5-methyl-1H-pyrazol-4-yl)thieno[3,2-d]pyrimidin-4(3H)-one | 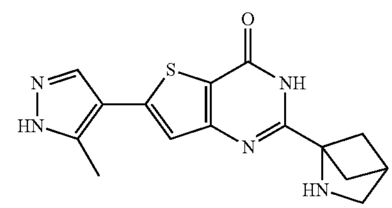 [SMILES: Cc1[nH]ncc1-c1cc2nc(C34CC(CN3)C4)[nH]c(=O)c2s1] | mono-hydro-chloride |
| 149 | 2-[(cyclopentylamino)methyl]-6-(5-methyl-1H-pyrazol-4-yl)thieno[3,2-d]pyrimidin-4(3H)-one | 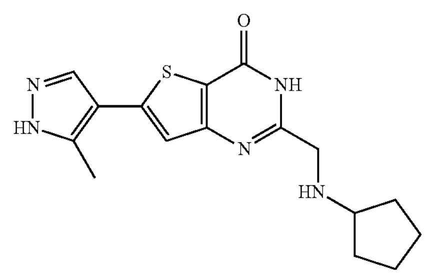 [SMILES: Cc1[nH]ncc1-c1cc2nc(CNC3CCCC3)[nH]c(=O)c2s1] | dihydro-chloride |
| 150 | 2-[(1R,3S,4R,5S) or (1S,3S,4S,5S)-5-hydroxy-2-azabicyclo[2.2.1]hept-3-yl]-6-(5-methyl-1H-pyrazol-4-yl)thieno[3,2-d]pyrimidin-4(3H)-one | 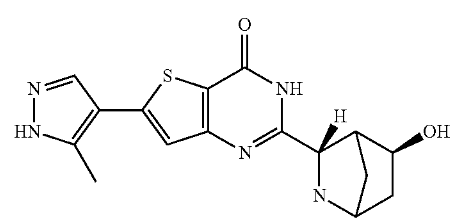 [SMILES: Cc1[nH]ncc1-c1cc2nc([C@H]3NC4CC3[C@@H](O)C4)[nH]c(=O)c2s1] | dihydro-chloride |
| 151 | 2-(cyclopentylmethyl)-6-(5-methyl-1H-pyrazol-4-yl)thieno[3,2-d]pyrimidin-4(3H)-one | 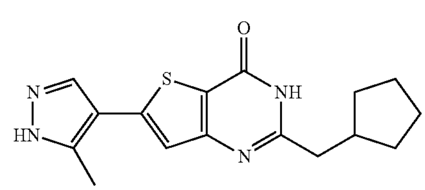 [SMILES: Cc1[nH]ncc1-c1cc2nc(CC3CCCC3)[nH]c(=O)c2s1] | |

TABLE 1-continued

| Ex. No. | IUPAC name | structure | salt |
|---|---|---|---|
| 152 | ethyl {2-[6-(5-methyl-1H-pyrazol-4-yl)-4-oxo-3,4-dihydrothieno[3,2-d]pyrimidin-2-yl]pyrrolidin-1-yl}acetate | 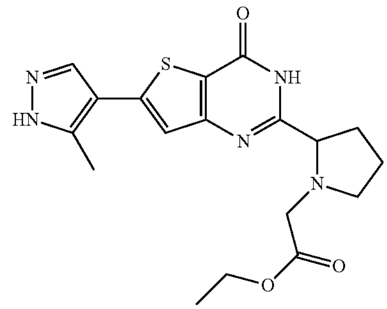 [SMILES: CCOC(=O)CN1CCCC1c1nc2cc(-c3cn[nH]c3C)sc2c(=O)[nH]1] | |
| 153 | 2-(decahydroisoquinolin-1-yl)-6-(5-methyl-1H-pyrazol-4-yl)thieno[3,2-d]pyrimidin-4(3H)-one | 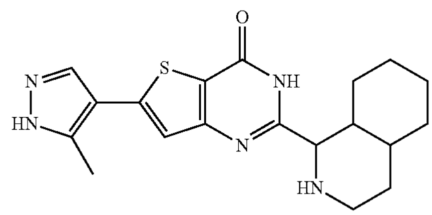 [SMILES: Cc1[nH]ncc1-c1cc2nc(C3NCCC4CCCCC43)[nH]c(=O)c2s1] | |
| 154 | 2-[2-(1-aminocyclopropyl)ethyl]-6-(5-methyl-1H-pyrazol-4-yl)thieno[3,2-d]pyrimidin-4(3H)-one | 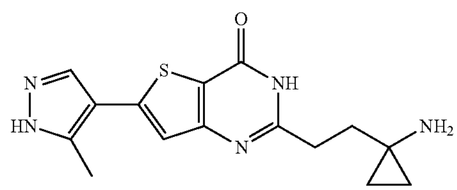 [SMILES: Cc1[nH]ncc1-c1cc2nc(CCC3(N)CC3)[nH]c(=O)c2s1] | dihydrochloride |
| 155 | 2-(4-azaspiro[2.4]hept-5-yl)-6-(5-methyl-1H-pyrazol-4-yl)thieno[3,2-d]pyrimidin-4(3H)-one | 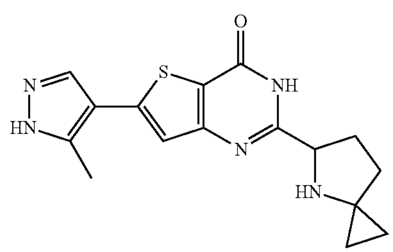 [SMILES: Cc1[nH]ncc1-c1cc2nc(C3CCC4(CC4)N3)[nH]c(=O)c2s1] | dihydrochloride |
| 156 | 6-(5-methyl-1H-pyrazol-4-yl)-2-[(2S)-4-piperidin-1-ylpyrrolidin-2-yl]thieno[3,2-d]pyrimidin-4(3H)-one | 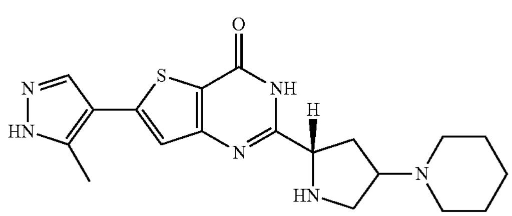 [SMILES: Cc1[nH]ncc1-c1cc2nc([C@@H]3CC(N4CCCCC4)CN3)[nH]c(=O)c2s1] | |
| 157 | 2-[(1S,5R)-2-azabicyclo[3.1.0]hex-1-yl]-6-(5-methyl-1H-pyrazol-4-yl)thieno[3,2-d]pyrimidin-4(3H)-one | 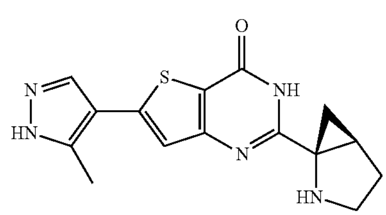 [SMILES: Cc1[nH]ncc1-c1cc2nc([C@]34C[C@H]3CCN4)[nH]c(=O)c2s1] | dihydrochloride |

TABLE 1-continued

| Ex. No. | IUPAC name | structure | salt |
|---|---|---|---|
| 158 | 2-[1-(2-hydroxyethyl)pyrrolidin-2-yl]-6-(5-methyl-1H-pyrazol-4-yl)thieno[3,2-d]pyrimidin-4(3H)-one | 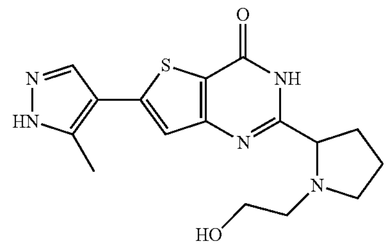 [SMILES: Cc1[nH]ncc1-c1cc2nc(C3CCCN3CCO)[nH]c(=O)c2s1] | |
| 159 | 2-[(1R,3S,4R,5R) or (1S,3S,4S,5R)-5-fluoro-2-azabicyclo[2.2.1]hept-3-yl]-6-(5-methyl-1H-pyrazol-4-yl)thieno[3,2-d]pyrimidin-4(3H)-one | 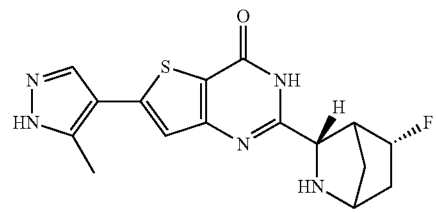 [SMILES: Cc1[nH]ncc1-c1cc2nc([C@H]3NC4CC3[C@H](F)C4)[nH]c(=O)c2s1] | dihydro-chloride |
| 160 | 2-[(1R,3S,4R,5R) or (1S,3S,4S,5R)-5-fluoro-2-azabicyclo[2.2.1]hept-3-yl]-6-(5-methyl-1H-pyrazol-4-yl)thieno[3,2-d]pyrimidin-4(3H)-one | 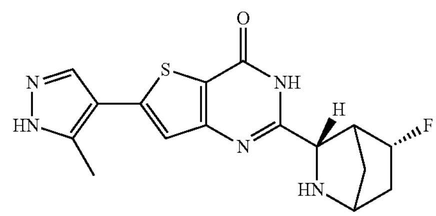 [SMILES: Cc1[nH]ncc1-c1cc2nc([C@H]3NC4CC3[C@H](F)C4)[nH]c(=O)c2s1] | dihydro-chloride |
| 161 | 2-[(2S)-piperidin-2-yl]-6-[5-(trifluoromethyl)-1H-pyrazol-4-yl]thieno[3,2-d]pyrimidin-4(3H)-one | 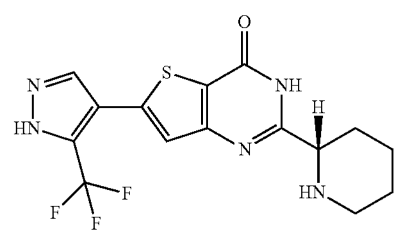 [SMILES: O=c1[nH]c([C@@H]2CCCCN2)nc2cc(-c3cn[nH]c3C(F)(F)F)sc12] | mono-hydro-chloride |
| 162 | 6-(5-ethyl-1H-pyrazol-4-yl)-2-[(2S)-piperidin-2-yl]thieno[3,2-d]pyrimidin-4(3H)-one | 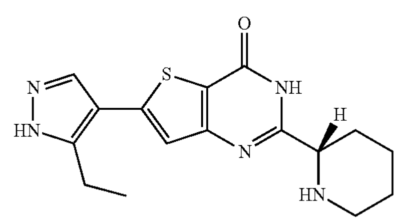 [SMILES: CCc1[nH]ncc1-c1cc2nc([C@@H]3CCCCN3)[nH]c(=O)c2s1] | dihydro-chloride |
| 163 | 2-{2-[6-(5-methyl-1H-pyrazol-4-yl)-4-oxo-3,4-dihydrothieno[3,2-d]pyrimidin-2-yl]pyrrolidin-1-yl}acetamide | 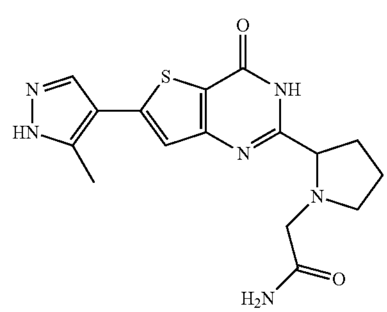 [SMILES: Cc1[nH]ncc1-c1cc2nc(C3CCCN3CC(N)=O)[nH]c(=O)c2s1] | |

TABLE 1-continued

| Ex. No. | IUPAC name | structure | salt |
|---|---|---|---|
| 164 | 2-[(2R)-1-azabicyclo[2.2.2]oct-2-yl]-6-(5-methyl-1H-pyrazol-4-yl)thieno[3,2-d]pyrimidin-4(3H)-one | 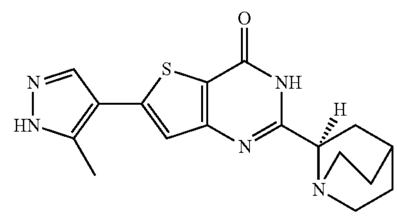 [SMILES: Cc1[nH]ncc1-c1cc2nc([C@H]3CC4CCN3CC4)[nH]c(=O)c2s1] | monotri-fluoro-acetate |
| 165 | 2-(2-azabicyclo[2.1.1]hex-1-yl)-6-[5-(trifluoromethyl)-1H-pyrazol-4-yl]thieno[3,2-d]pyrimidin-4(3H)-one | 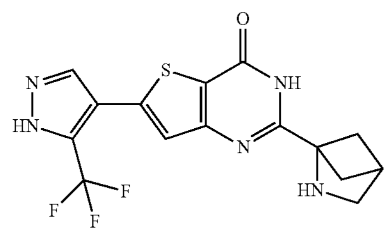 [SMILES: O=c1[nH]c(C23CC(CN2)C3)nc2cc(-c3cn[nH]c3C(F)(F)F)sc12] | dihydro-chloride |
| 166 | 2-cyclohexyl-6-(5-methyl-1H-pyrazol-4-yl)thieno[3,2-d]pyrimidin-4(3H)-one | 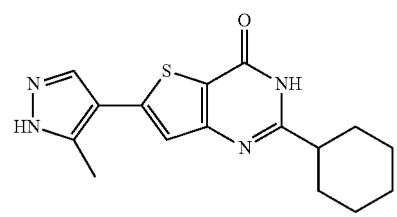 [SMILES: Cc1[nH]ncc1-c1cc2nc(C3CCCCC3)[nH]c(=O)c2s1] | |
| 167 | 2-methyl-6-(5-methyl-1H-pyrazol-4-yl)thieno[3,2-d]pyrimidin-4(3H)-one | 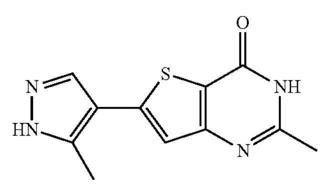 [SMILES: Cc1nc2cc(-c3cn[nH]c3C)sc2c(=O)[nH]1] | |
| 168 | 2-{[(2-hydroxy-2-methylpropyl)amino]methyl}-6-(5-methyl-1H-pyrazol-4-yl)thieno[3,2-d]pyrimidin-4(3H)-one | 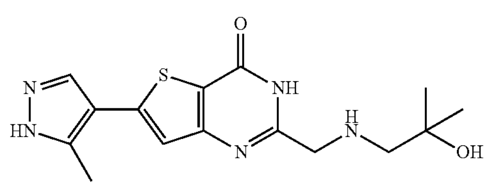 [SMILES: Cc1[nH]ncc1-c1cc2nc(CNCC(C)(C)O)[nH]c(=O)c2s1] | |
| 169 | 2-{[(2-hydroxyethyl)(methyl)amino]methyl}-6-(5-methyl-1H-pyrazol-4-yl)thieno[3,2-d]pyrimidin-4(3H)-one | 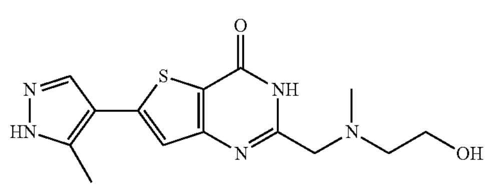 [SMILES: Cc1[nH]ncc1-c1cc2nc(CN(C)CCO)[nH]c(=O)c2s1] | |
| 170 | 2-[(2S)-1-azabicyclo[2.2.2]oct-2-yl]-6-(5-methyl-1H-pyrazol-4-yl)thieno[3,2-d]pyrimidin-4(3H)-one | 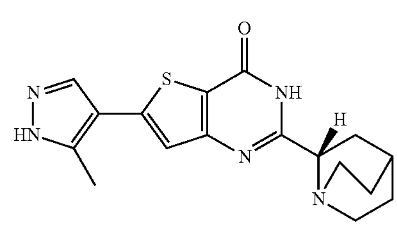 [SMILES: Cc1[nH]ncc1-c1cc2nc([C@@H]3CC4CCN3CC4)[nH]c(=O)c2s1] | monotri-fluoro-acetate |

TABLE 1-continued

| Ex. No. | IUPAC name | structure | salt |
|---|---|---|---|
| 171 | 2-[(1R*,6R*)-3-azabicyclo[4.1.0]hept-4-yl]-6-(5-methyl-1H-pyrazol-4-yl)thieno[3,2-d]pyrimidin-4(3H)-one | 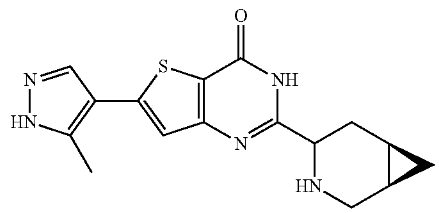 [SMILES: Cc1[nH]ncc1-c1cc2nc(C3C[C@H]4C[C@H]4CN3)[nH]c(=O)c2s1] | dihydrochloride |
| 172 | 6-(5-methyl-1H-pyrazol-4-yl)-2-[(2S)-piperidin-2-yl]thieno[3,2-d]pyrimidin-4(3H)-one | 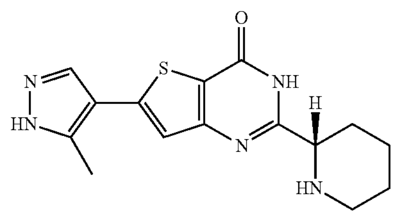 [SMILES: Cc1[nH]ncc1-c1cc2nc([C@@H]3CCCCN3)[nH]c(=O)c2s1] | monohydrochloride |
| 173 | 2-{2-[(2-hydroxyethyl)(methyl)amino]ethyl}-6-(5-methyl-1H-pyrazol-4-yl)thieno[3,2-d]pyrimidin-4(3H)-one | 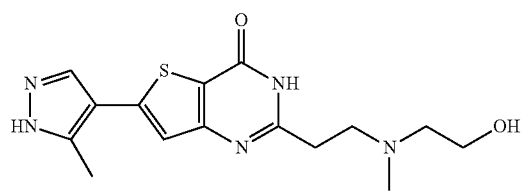 [SMILES: Cc1[nH]ncc1-c1cc2nc(CCN(C)CCO)[nH]c(=O)c2s1] | |
| 174 | 6-(5-methyl-1H-pyrazol-4-yl)-2-[(2S)-piperidin-2-yl]thieno[3,2-d]pyrimidin-4(3H)-one | 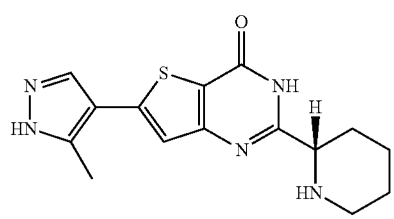 [SMILES: Cc1[nH]ncc1-c1cc2nc([C@@H]3CCCCN3)[nH]c(=O)c2s1] | |
| 175 | 2-[(1R,3S,4R,5R) or (1S,3S,4S,5R)-5-fluoro-2-azabicyclo[2.2.1]hept-3-yl]-6-(5-methyl-1H-pyrazol-4-yl)thieno[3,2-d]pyrimidin-4(3H)-one | 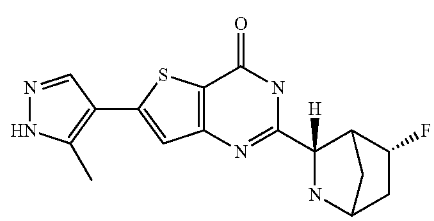 [SMILES: Cc1[nH]ncc1-c1cc2nc([C@H]3NC4CC3[C@H](F)C4)[nH]c(=O)c2s1] | monohydrochloride |
| 176 | 2-(1-azabicyclo[2.2.2]oct-2-yl)-6-(5-methyl-1H-pyrazol-4-yl)thieno[3,2-d]pyrimidin-4(3H)-one | 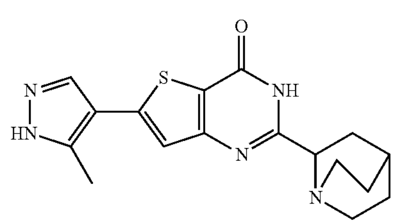 [SMILES: Cc1[nH]ncc1-c1cc2nc(C3CC4CCN3CC4)[nH]c(=O)c2s1] | |
| 177 | 6-(5-methyl-1H-pyrazol-4-yl)-2-[(2S)-1,2,3,6-tetrahydropyridin-2-yl]thieno[3,2-d]pyrimidin-4(3H)-one | 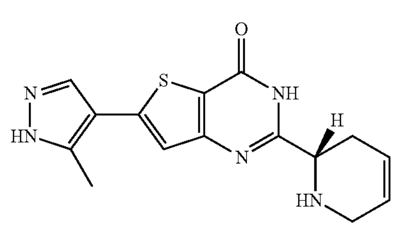 [SMILES: Cc1[nH]ncc1-c1cc2nc([C@@H]3CC=CCN3)[nH]c(=O)c2s1] | monohydrochloride |

TABLE 1-continued

| Ex. No. | IUPAC name | structure | salt |
|---|---|---|---|
| 178 | 2-[(2S)-1-azabicyclo[2.2.2]oct-2-yl]-6-(5-methyl-1H-pyrazol-4-yl)thieno[3,2-d]pyrimidin-4(3H)-one | 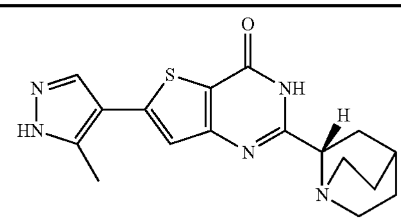 | dihydrochloride |
| 179 | 2-(1-azabicyclo[2.2.2]oct-2-yl)-6-[5-(trifluoromethyl)-1H-pyrazol-4-yl]thieno[3,2-d]pyrimidin-4(3H)-one | 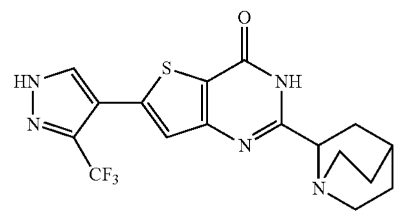 [SMILES: O=c1[nH]c(C2CC3CCN2CC3)nc2cc(-c3c[nH]nc3C(F)(F)F)sc12] | |

Experimental Example 1

Preparation of Human-Derived MCM2 Protein

The genetic engineering methods described below followed the method described in a book (Maniatis et al., Molecular Cloning, Cold Spring Harbor Laboratory, 1989) or a method described in the protocol attached to the reagent.

N terminal Histagged recombinant human MCM2 protein corresponding to the 10-294th amino acids from the N terminal was cloned to *Escherichia coli* expression vector pET-21. The vector pET21-HH was prepared by inserting the following 6×Histag synthetic DNA

```
                                      (SEQ ID NO: 1)
5'-TATGCATCATCATCATCATCACGGATCCCATCATCATCATCATCAC
TGAGC-3';
and
                                      (SEQ ID NO: 2)
5'-GGCCGCTCAGTGATGATGATGATGATGGGATCCGTGATGATGATGA
TGATGCA-3'
``` into the Nde I-Not I site of pET-21a(+) (Novagen).

The Mcm2(10-294 a.a.) gene encoding the 10-294th amino acids from the N terminal side of human MCM2 protein was cloned by PCR using synthetic DNA

```
                                      (SEQ ID NO: 3)
    5'-CGCGGATCCATGGCATCCAGCCCGGCCCA-3';
    and
                                      (SEQ ID NO: 4)
    5'-ATTCTTATGCGGCCGCTCACAGCTCCTCCACCAGAGGCA-3'
``` prepared by reference to the base sequence described in GenBank accession No.: NM_004526, as a primer set and human testis cDNA library (TAKARA BIO INC.) as a template. PCR reaction was performed according to the protocol attached to Pyrobest (TAKARA BIO INC.).

The obtained 883 bp fragment was digested with restriction enzymes BamHI and NotI, inserted into the BamHI-NotI site of pET21-HH, and the inserted base sequence was confirmed to give pET21-HHhMcm2 (10-294) plasmid. The pET21-HHhMcm2 (10-294) plasmid was introduced into *Escherichia coli* BL21 (DE3) cell line (American Type Culture Collection).

*Escherichia coli* cells introduced with the above-mentioned plasmid were cultured in LB medium (1% tripton, 0.5% yeast extract, 0.5% sodium chloride) containing 50 mg/L ampicillin, and MCM2 expression was induced by addition of 1 mM IPTG for 6 hr. *Escherichia coli* cells expressing MCM2 were recovered by centrifugation (6000 rpm, 10 min), washed with phosphate-buffered saline, and cryopreserved at −80° C. The above-mentioned cryopreserved *Escherichia coli* cells were thawed on ice, and suspended in Complete EDTA (Roche Diagnostics GmbH, Mannheim, Germany)-added buffer A (25 mM tris-hydrochloride (pH 7.4), 2.7 mM potassium chloride, 137 mM sodium chloride). The above-mentioned suspended *Escherichia coli* cells were lysed with 1 mg/mL lysozyme, and sonicated 4 times in Insonator 201M (Kubota) at 170 W for 30 sec while cooling with ice water. This extract was ultracentrifuged at 15000 rpm, 4° C. for 20 min, and the obtained supernatant was passed through a 0.22 μm filter to give an *Escherichia coli* cell-fee cell extract. The *Escherichia coli* cell-free cell extract was passed through nickel-NTA Superflow resin, and the resulting resin was washed with buffer A, and eluted with buffer B (25 mM tris-hydrochloride (pH 7.4), 2.7 mM potassium chloride, 137 mM sodium chloride, 10% glycerol, 200 mM imidazole). The eluate was concentrated using Amicon Ultra 4 (5K MWCO, Millipore, Mass., U.S.A.), and purified by gel filtration using HiLoad 16/60 Superdex 200 pg (GE healthcare, Chalfont St. Giles, UK) equilibrated with buffer C (25 mM tris-hydrochloride (pH 7.4), 2.7 mM potassium chloride, 137 mM sodium chloride, 10% glycerol, 200 mM imidazole). The fraction containing MCM2 protein was concentrated as a purified sample, and cryopreserved at −80° C.

Experimental Example 2

Measurement of Cdc7 Kinase Inhibitory Activity

Full-length Cdc7 co-expressed with full-length Dbf4 was purchased from Carna Biosciences (Kobe). The enzyme activity of Cdc7/Dbf4 complex was detected by homogeneous time-resolved fluorescence method Transcreener ADP assay (Cisbio Inc., MA, U.S.A.). The enzyme reaction was performed in a kinase buffer (20 mM HEPES pH 7.5, 10 mM magnesium acetate, 1 mM dithiothreitol) supplemented with 1.0 μm ATP, and 10 μg/ml MCM2 (prepared in Experimental Example 1) 0.1 μg/ml. Free ADP produced by ATP hydrolysis was detected by $Eu^{3+}$-Cryptate-labeled anti-ADP monoclonal antibody competitively with d2-labeled ADP, and the production amount thereof was measured. The obtained time-resolved fluorescence resonance energy transfer signal was measured by EnVision (Perkin Elmer Inc., MA, U.S.A.). The inhibitory rate (%) of the test compound to Cdc7 was calculated by the following formula.

Inhibitory rate(%)=(1−(count of test compound−blank)+(control−blank))×100

The count of the Cdc7/Dbf4 reaction mixture under compound-free conditions was taken as the control, and that under compound-free and Cdc7/Dbf4-free conditions was taken as the blank.

The Cdc7 kinase inhibitory rates of the compounds of the present invention are shown in Table 2.

TABLE 2

| test compound | inhibitory rate (%) at 1 μM |
| --- | --- |
| Example 1 | 97.0 |
| Example 2 | 93.8 |
| Example 4 | 102.5 |
| Example 11 | 103.0 |
| Example 23 | 98.4 |
| Example 37 | 102.6 |
| Example 71 | 108.7 |
| Example 72 | 102.2 |
| Example 75 | 107.4 |
| Example 76 | 105.8 |
| Example 77 | 107.6 |
| Example 78 | 86.2 |
| Example 79 | 93.3 |
| Example 82 | 104.7 |
| Example 83 | 125.5 |
| Example 85 | 103.2 |
| Example 87 | 106.8 |
| Example 88 | 100.8 |
| Example 91 | 105.6 |
| Example 92 | 108.0 |
| Example 101 | 96.2 |
| Example 102 | 95.9 |
| Example 103 | 96.7 |
| Example 108 | 103.4 |
| Example 110 | 100 |
| Example 112 | 105 |
| Example 113 | 124 |
| Example 116 | 102 |
| Example 123 | 97 |
| Example 129 | 108 |
| Example 133 | 107 |
| Example 135 | 111 |
| Example 136 | 91 |
| Example 137 | 97 |
| Example 139 | 106 |
| Example 140 | 100 |
| Example 143 | 122 |
| Example 145 | 126 |
| Example 146 | 108 |
| Example 148 | 102 |
| Example 157 | 92 |
| Example 160 | 104 |
| Example 161 | 102 |
| Example 162 | 104 |
| Example 164 | 101 |
| Example 165 | 105 |
| Example 170 | 95 |
| Example 172 | 102 |
| Example 174 | 104 |
| Example 175 | 105 |

The Experimental Example has shown that the compound of the present invention has a superior Cdc7 inhibitory activity.

Experimental Example 3: Measurement of growth inhibitory activity on human colorectal cancer cell Colo205

The growth inhibition of colorectal cancer cell Colo205 with the compound of the present invention can be measured as follows.

A cell suspension (100 μl) of human colorectal cancer cell Colo205 (purchased from ATCC) (3,000 cells/well) was plated in a 96 well plate, and cultured in a 5% carbon dioxide gas incubator at 37° C. for 1 day. Each 2 μM test compound solution was added by 100 μl and the cells were cultured for 3 days. CellTiter-Glo™ Luminescent Cell Viability Assay reagent (50 μl, Promega) was added to the 96 well plate, the luminescence level was measured by a luminometer and the residual ATP amount was taken as the cell amount. The luminescence level of a well free of cell plating was taken as a blank. The cell proliferation inhibitory rate (%) of the test compound was calculated by the following formula.

Inhibitory rate(%)=(1−(luminescence level of test compound—blank)+(luminescence level of control group—blank))×100

The inhibitory rate of each test compound is shown in Table 3.

TABLE 3

| test compound | inhibitory rate (%) at 1 μM |
| --- | --- |
| Example 2 | 44.1 |
| Example 37 | 75.3 |
| Example 83 | 76.6 |
| Example 91 | 71.7 |
| Example 116 | 60.5 |
| Example 145 | 78.5 |
| Example 160 | 73.3 |
| Example 161 | 78.6 |
| Example 170 | 69.7 |

The Experimental Example has shown that the compound of the present invention has a superior cancer (colorectal cancer) cell proliferation suppressive action.

Experimental Example 4

Measurement of MCM2 Phosphorylation Inhibitory Activity in Human Colorectal Cancer Cell Colo205

The MCM2 phosphorylation suppressive action of the compound of the present invention in human colorectal cancer cell Colo205 can be measured as follows.

A cell suspension (500 μl) of human colorectal cancer cell Colo205 (purchased from ATCC) (50,000 cells/well) was plated in a 24 well plate, and cultured in a 5% carbon dioxide gas incubator at 37° C. for 1 day. Each 2 μM test compound solution was added by 500 μl and the cells were cultured for 8 hr. The plate was washed with PBS, the cells were lysed in Laemmli Sample Buffer (BioRad), and cell lysate was treated at 95° C. for 5 min. Then, SDS-PAGE was performed and the protein was transferred onto a PVDF membrane by using iBlot™ gel transfer system (Invitrogen). The membrane was blocked with StartingBlock T20 (PBS) Blocking Buffer (Thermo Scientific), and reacted with anti-phosphorylated MCM2 (Ser40/Ser41) (Bethyl Laboratories, A300-788A) diluted 1000-fold with Can Get Signal Immunoreaction Enhancer Solution 1 (TOYOBO). The membrane was washed with tris-buffered saline (BioRad) containing 0.05% Tween 20 (Bio-Rad), and reacted for 1 hr at room temperature with HRP-labeled rabbit IgG polyclonal antibody (Amersham Biosciences, NA9340) diluted 10000-fold with Can Get Signal Immunoreaction Enhancer Solution 2 (TOYOBO). The membrane was washed in the same manner as above, chemical luminescence of antibody-labeled phosphorylated MCM2 protein using SuperSignal West FemtoMaximum Sensitivity Substrate (Pierce Biotechnology) was detected by lumino image analyzer LAS-1000 (Fuji Film).

Using the anti-MCM2 antibody (Santa Cruzu Biotechnology, sc-9839) and HRP-labeled goat IgG polyclonal antibody (Santa Cruzu Biotechnology, sc-2020) and in the same manner as above, the MCM2 protein was detected.

The phosphorylated MCM2 specific activity of each sample was calculated by the following formula.

Phosphorylated MCM2 specific activity=(phosphorylated MCM2 luminescence level-background)÷(MCM2 luminescence level-background)

The phosphorylated MCM2 protein inhibitory rate (%) of the test compound was calculated by the following formula and shown in Table.

Inhibitory rate(%)=(1−phosphorylated MCM2 specific activity of test compound phosphorylated MCM2 specific activity of control group)×100

The inhibitory rate of each test compound is shown in Table 4.

TABLE 4

| test compound | inhibitory rate (%) at 1 µM |
| --- | --- |
| Example 2 | 90.4 |
| Example 37 | 98.4 |
| Example 83 | 97.6 |
| Example 91 | 98.4 |
| Example 116 | 98.7 |
| Example 145 | 95.8 |
| Example 160 | 95.0 |
| Example 161 | 96.2 |
| Example 170 | 97.3 |

The Experimental Example has shown that the compound of the present invention has a superior MCM2 phosphorylation inhibitory action in cancer (colorectal cancer) cell, namely, that the compound of the present invention has a superior Cdc7 inhibitory action in a cancer (colorectal cancer) cell.

Experimental Example 5

Measurement of MCM2 Phosphorylation Inhibitory Activity in Tumor in Human Colorectal Cancer Cell Colo205 Cancer Bearing Mouse The MCM2 phosphorylation inhibitory activity of the compound of the present invention in tumor in human colorectal cancer cell Colo205 cancer bearing mouse can be measured as follows.

Human colorectal cancer cell Colo205 was suspended in 50% Matrigel solution, and transplanted into 6- to 7-week-old female BALB/c mice (CLEA Japan, Inc.) at $5.0 \times 10^6$ cells by subcutaneous injection. The diameter of the tumor engrafted in 7 to 14 days from the transplantation was measured, and the tumor volume was calculated by the following formula.

Tumor volume=long diameter×short diameter×short diameter×(½)

A suspension of the test compound in 0.5% methylcellulose solution (Wako Pure Chemical Industries, Ltd.) was orally administered at a dose shown in the Table to mice having a tumor volume of 150-600 mm³. The tumor was removed under ether anesthesia at 4 hr after administration of the test compound, and homogenized in Cell Lysis Buffer (Cell Signaling). Using BCA Protein assay kit (Thermo Scientific), the protein in the tumor lysate was quantified, and the protein amount was adjusted. The above-mentioned protein solution was treated with Laemmli Sample Buffer (BioRad) at 95° C. for 5 min.

Then, SDS-PAGE was performed and the protein was transferred onto a PVDF membrane by using iBlot™ gel transfer system (Invitrogen). The membrane was blocked with StartingBlock T20 (PBS) Blocking Buffer (Thermo Scientific), and reacted with anti-phosphorylated MCM2 (Ser40/Ser41) (Bethyl Laboratories, A300-788A) diluted 1000-fold with Can Get Signal Immunoreaction Enhancer Solution 1 (TOYOBO). The membrane was washed with tris-buffered saline (BioRad) containing 0.05% Tween 20 (Bio-Rad), and reacted for 1 hr at room temperature with HRP-labeled rabbit IgG polyclonal antibody (Amersham Biosciences, NA9340) diluted 10000-fold with Can Get Signal Immunoreaction Enhancer Solution 2 (TOYOBO). The membrane was washed in the same manner as above, chemical luminescence of antibody-labeled phosphorylated MCM2 protein using SuperSignal West FemtoMaximum Sensitivity Substrate (Pierce Biotechnology) was detected by lumino image analyzer LAS-1000 (Fuji Film).

Using the anti-MCM2 antibody (Santa Cruzu Biotechnology, sc-9839) and HRP-labeled goat IgG polyclonal antibody (Santa Cruzu Biotechnology, sc-2020) and in the same manner as above, the MCM2 protein was detected.

The phosphorylated MCM2 specific activity of each sample was calculated by the following formula.

Phosphorylated MCM2 specific activity=(phosphorylated MCM2 luminescence level-background)÷(MCM2 luminescence level-background)

The phosphorylated MCM2 protein inhibitory rate (%) of the test compound was calculated by the following formula and shown in Table.

Inhibitory rate(%)=(1−phosphorylated MCM2 specific activity of test compound=phosphorylated MCM2 specific activity of control group)×100

The inhibitory rate of each test compound is shown in Table 5.

TABLE 5

| test compound | dose (mg/kg) | inhibitory rate (%) |
| --- | --- | --- |
| Example 83 | 100 | 71.8 |
| Example 145 | 100 | 68.9 |
| Example 161 | 100 | 80.9 |

The Experimental Example has shown that the compound of the present invention has a superior MCM2 phosphorylation inhibitory action in cancer (colorectal cancer) cell cancer bearing mouse, and that the compound of the present invention has a superior Cdc7 inhibitory action in cancer (colorectal cancer) cell cancer bearing mouse.

Experimental Example 6

Measurement of Antitumor Activity in Human Colorectal Cancer Cell Colo205 Cancer Bearing Mouse The antitumor action of the compound of the present invention on human colorectal cancer cell Colo205 cancer bearing mouse can be measured as follows.

Human colorectal cancer cell Colo205 was suspended in 50% Matrigel solution, and transplanted into 6- to 7-week-old female BALE/c mice (CLEA Japan, Inc.) at 5.0×10⁶ cells by subcutaneous injection. The diameter of the tumor engrafted in 7 to 14 days from the transplantation was measured, and the tumor volume was calculated by the following formula.

Tumor volume=long diameter×short diameter×short diameter×(½)

Mice having an engrafted tumor volume of about 200 mm³ were selected, and 5 mice per group were used for the experiment. A suspension of the test compound in 0.5% methylcellulose solution (Wako Pure Chemical Industries, Ltd.) was orally administered at the dose of Table 1 twice a day for 14 days. The tumor diameter was measured one day before the start of the administration and the next day of the completion of the administration and the tumor volume was calculated.

The tumor growth ratio of the test compound administration group as compared to that of the control administration group was taken as T/C(%) and calculated by the following formula.

T/C(%)=(tumor volume of test compound administration group after completion of administration−tumor volume of test compound administration group one day before start of administration)/(tumor volume of control administration group after completion of administration−tumor volume of control administration group one day before start of administration))×100

T/C of each test compound is shown in Table 6.

TABLE 6

| test compound | dose (mg/kg) | T/C (%) |
|---|---|---|
| Example 83 | 100 | 5.7 |
| Example 145 | 100 | −4.7 |
| Example 161 | 100 | −3.6 |
| Example 175 | 50 | 40.3 |

The Experimental Example has shown that the compound of the present invention has a superior antitumor action.

Formulation Example 1

A medicament containing the compound of the present invention as an active ingredient can be produced according to, for example, the following formulation.
1. Capsule

| (1) compound obtained in Example 1 | 40 mg |
|---|---|
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. Thereto is added the rest of (4) and the whole amount is filled in a gelatin capsule.
2. Tablet

| (1) compound obtained in Example 1 | 40 mg |
|---|---|
| (2) lactose | 58 mg |
| (3) cornstarch | 18 mg |
| (4) microcrystalline cellulose | 3.5 mg |
| (5) magnesium stearate | 0.5 mg |
| 1 tablet | 120 mg |

(1), (2), (3), ⅔ of (4) and ½ of (5) are blended and granulated. The rest of (4) and (5) is added to the granules and the mixture is compression molded into a tablet.

Formulation Example 2

The compound (50 mg) obtained in Example 1 is dissolved in Japanese Pharmacopoeia distilled water for injection (50 ml), to which Japanese Pharmacopoeia distilled water for injection is added to make the volume 100 ml. Thus obtained solution is filtered under sterile conditions. The solution (1 ml) is taken, filled in a vial for injection under sterile conditions and freeze-dried, and the vial is sealed.

INDUSTRIAL APPLICABILITY

Since the compound of the present invention has a superior cdc7 inhibitory action, it is useful as an agent for the prophylaxis or treatment of cdc7-associated diseases (e.g., cancer etc.). In addition, since the compound of the present invention is superior in the efficacy expression, pharmacokinetics, solubility, interaction with other pharmaceutical products, safety and stability, it is useful as a pharmaceutical product.

While some of the embodiments of the present invention have been described in detail in the above, it is, however, possible for those of ordinary skill in the art to make various modifications and changes to the particular embodiments shown without substantially departing from the teaching and advantages of the present invention. Such modifications and changes are encompassed in the spirit and scope of the present invention as set forth in the appended claims.

This application is based on patent application Nos. 2010-031899 and 2010-131950 filed in Japan, the contents of which are incorporated in full herein.

The invention claimed is:

1. A compound of formula (I):

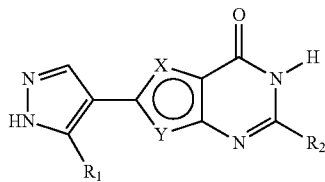

wherein
one of X and Y is a sulfur atom, and the other is CH,
$R_1$ is a $C_{1-6}$ alkyl group optionally substituted by halogen atom(s),
$R_2$ is
(1) a $C_{1-6}$ alkyl group optionally substituted by 1 to 3 substituents selected from
  (a) a non-aromatic heterocyclic group optionally substituted by 1 to 3 substituents selected from
    (i) a halogen atom,
    (ii) a hydroxy group,
    (iii) a $C_{1-6}$ alkyl group optionally substituted by 1 to 3 substituents selected from
      (aa) a halogen atom,
      (bb) a hydroxy group,
      (cc) a $C_{1-6}$ alkoxy group, and
      (dd) a $C_{6-14}$ aryl group optionally substituted by 1 to 3 $C_{1-6}$ alkyl groups,
    (iv) a $C_{1-6}$ alkoxy group,
    (v) a $C_{6-14}$ aryl group optionally substituted by 1 to 3 halogen atoms,
    (vi) a $C_{6-14}$ aryloxy group,
    (vii) a $C_{1-6}$ alkoxy-carbonyl group,
    (viii) a $C_{1-6}$ alkyl-carbonyl group,
    (ix) a cyano group,
    (x) a $C_{6-14}$ arylsulfonyl group,
    (xi) a carboxy group,
    (xii) an amino group optionally mono- or di-substituted by a $C_{1-6}$ alkyl group,
    (xiii) a non-aromatic heterocyclic group optionally substituted by an oxo group, and
    (xiv) an oxo group,
  (b) a $C_{1-6}$ alkoxy group,
  (c) an amino group optionally mono- or di-substituted by substituent(s) selected from
    (i) a $C_{1-6}$ alkyl group optionally substituted by 1 to 3 substituents selected from
      (aa) a $C_{6-14}$ aryl group optionally substituted by 1 to 3 $C_{1-6}$ alkoxy groups,
      (bb) a $C_{1-6}$ alkoxy-carbonyl group,
      (cc) an aromatic heterocyclic group,
      (dd) a $C_{3-8}$ cycloalkyl group optionally substituted by an aromatic heterocyclic group, and
      (ee) a hydroxy group,
    (ii) a non-aromatic heterocyclic group optionally substituted by 1 to 3 $C_{7-13}$ aralkyl groups,
    (iii) a $C_{6-14}$ aryl group optionally substituted by 1 to 3 $C_{1-6}$ alkoxy groups, and
    (iv) a $C_{3-8}$ cycloalkyl group,
  (d) a 5- or 6-membered aromatic heterocyclic group,
  (e) a $C_{6-14}$ aryl group, and
  (f) a $C_{3-8}$ cycloalkyl group optionally substituted by an amino group;
(2) a $C_{6-14}$ aryl group optionally substituted by 1 to 3 halogen atoms;
(3) a non-aromatic heterocyclic group optionally substituted by 1 to 3 substituents selected from (a) a halogen atom,
(b) a $C_{1-6}$ alkyl group optionally substituted by 1 to 3 substituents selected from
  (i) a hydroxy group,
  (ii) a $C_{1-6}$ alkoxy-carbonyl group, and
  (iii) a carbamoyl group,
(c) a $C_{6-14}$ aryloxy group,
(d) a $C_{1-6}$ alkoxy-carbonyl group,
(e) a $C_{1-6}$ alkyl-carbonyl group,
(f) a $C_{6-14}$ aryl group optionally substituted by a $C_{1-6}$ alkylsulfonyl group,
(g) a $C_{7-13}$ aralkyl group optionally substituted by 1 to 3 halogen atoms,
(h) a hydroxy group,
(i) a carbamoyl group, and
(j) a non-aromatic heterocyclic group;
(4) a $C_{2-6}$ alkenyl group optionally substituted by 1 to 3 $C_{6-14}$ aryl groups;
(5) a 5- or 6-membered aromatic heterocyclic group;
(6) a non-aromatic heterocyclyl-carbonyl group; or
(7) a $C_{3-8}$ cycloalkyl group optionally substituted by an amino group;
or a salt thereof.

2. The compound of claim 1, wherein X is a sulfur atom; and
Y is CH, or a salt thereof.

3. The compound of claim 1, wherein $R_2$ is
(1) a 4- to 6-membered non-aromatic heterocyclyl-$C_{1-6}$ alkyl group optionally substituted by 1 to 3 halogen atoms;
(2) a $C_{6-14}$ aryl group optionally substituted by 1 to 3 halogen atoms; or
(3) a non-aromatic heterocyclic group optionally substituted by 1 to 3 substituents selected from
  (a) a halogen atom, and
  (b) a $C_{1-6}$ alkyl group,
or a salt thereof.

4. The compound of claim 1, wherein X is a sulfur atom;
Y is CH; and
$R_1$ is a $C_{1-6}$ alkyl group,
or a salt thereof.

5. The compound of claim 1, wherein $R_1$ is a $C_{1-6}$ alkyl group, or a salt thereof.

6. The compound of claim 5, wherein $R_1$ is a methyl, or a salt thereof.

7. The compound of claim 1, wherein $R_2$ is a non-aromatic heterocyclic group optionally substituted by 1 to 3 substituents selected from
(a) a halogen atom,
(b) a $C_{1-6}$ alkyl group optionally substituted by 1 to 3 substituents selected from
  (i) a hydroxy group,
  (ii) a $C_{1-6}$ alkoxy-carbonyl group, and
  (iii) a carbamoyl group,
(c) a $C_{6-14}$ aryloxy group,
(d) a $C_{1-6}$ alkoxy-carbonyl group,
(e) a $C_{1-6}$ alkyl-carbonyl group,
(f) a $C_{6-14}$ aryl group optionally substituted by a $C_{1-6}$ alkylsulfonyl group,
(g) a $C_{7-13}$ aralkyl group optionally substituted by 1 to 3 halogen atoms,
(h) a hydroxy group,
(i) a carbamoyl group, and
(j) a non-aromatic heterocyclic group, or a salt thereof.

8. The compound of claim 7, wherein $R_2$ is a non-aromatic heterocyclic group optionally substituted by 1 to 3 substituents selected from
(a) a halogen atom, and
(b) a $C_{1-6}$ alkyl group, or a salt thereof.

9. The compound of claim 7, wherein $R_2$ is a 4- to 7-membered monocyclic non-aromatic heterocyclic group optionally substituted by 1 to 3 substituents selected from (a) a halogen atom, and (b) a $C_{1-6}$ alkyl group, or a salt thereof.

10. The compound of claim 9, wherein $R_2$ is selected from pyrrolidinyl, morpholinyl, piperidyl, piperazinyl, tetrahydrofuryl, tetrahydropyridyl, azetidinyl, azepanyl, and thiazolidinyl, or a salt thereof.

11. The compound of claim 7, wherein $R_2$ is a 8- to 10-membered fused non-aromatic heterocyclic group optionally substituted by 1 to 3 substituents selected from
(a) a halogen atom, and
(b) a $C_{1-6}$ alkyl group, or a salt thereof.

12. The compound according to claim 11, wherein $R_2$ is selected from an octahydroindolyl and an octahydrocyclopenta[b]pyrrolyl, or a salt thereof.

13. The compound of claim 7, wherein $R_2$ is a bridged non-aromatic heterocyclic group optionally substituted by 1 to 3 substituents selected from
(a) a halogen atom, and
(b) a $C_{1-6}$ alkyl group, or a salt thereof.

14. The compound of claim 13, wherein $R_2$ is selected from azabicyclo[3.1.0]hexanyl, azabicyclo[2.2.1]heptanyl, azabicyclo[2.2.1]hexanyl and azabicyclo[2.2.2]octanyl.

15. The compound of claim 14, wherein $R_2$ is selected from 3-azabicyclo[3.1.0]hex-2-yl, 2-azabicyclo[3.1.0]hex-3-yl, 2-azabicyclo[2.2.1]hept-3-yl, 7-azabicyclo [2.2.1]hept-l-yl, and 1-azabicyclo[2.2.2]oct-2-yl.

16. A medicament comprising the compound of claim 1, or a salt thereof.

* * * * *